US009315488B2

(12) United States Patent
Ding et al.

(10) Patent No.: US 9,315,488 B2
(45) Date of Patent: Apr. 19, 2016

(54) BCL-2-SELECTIVE APOPTOSIS-INDUCING AGENTS FOR THE TREATMENT OF CANCER AND IMMUNE DISEASES

(71) Applicant: AbbVie Inc., North Chicago, IL (US)

(72) Inventors: Hong Ding, Gurnee, IL (US); Steven W. Elmore, Northbrook, IL (US); Lisa Hasvold, Grayslake, IL (US); Laura A. Hexamer, Grayslake, IL (US); Aaron R. Kunzer, Arlington Heights, IL (US); William J. McClellan, Waukegan, IL (US); Andrew J. Souers, Evanston, IL (US); Gerard M. Sullivan, Lake Villa, IL (US); Zhi-Fu Tao, Gurnee, IL (US); Michael D. Wendt, Vernon Hills, IL (US)

(73) Assignee: ABBVIE INC., North Chicago, IL (US)

(*) Notice: Subject to any disclaimer, the term of this patent is extended or adjusted under 35 U.S.C. 154(b) by 0 days.

(21) Appl. No.: 14/726,337

(22) Filed: May 29, 2015

(65) Prior Publication Data
US 2016/0009687 A1  Jan. 14, 2016

Related U.S. Application Data

(63) Continuation of application No. 14/058,164, filed on Oct. 18, 2013, now Pat. No. 9,072,748, which is a continuation of application No. 12/631,404, filed on Dec. 4, 2009, now Pat. No. 8,563,735.

(60) Provisional application No. 61/120,275, filed on Dec. 5, 2008, provisional application No. 61/181,180, filed on May 26, 2009.

(51) Int. Cl.
C07D 295/155 (2006.01)
C07D 209/08 (2006.01)
C07D 211/58 (2006.01)
C07D 401/12 (2006.01)
C07D 309/04 (2006.01)

(52) U.S. Cl.
CPC ............ C07D 401/12 (2013.01); C07D 209/08 (2013.01); C07D 211/58 (2013.01); C07D 295/155 (2013.01); C07D 309/04 (2013.01)

(58) Field of Classification Search
CPC ............. C07D 295/155; C07D 209/08; C07D 211/58; C07D 401/12
See application file for complete search history.

(56) References Cited

U.S. PATENT DOCUMENTS

| 5,661,159 | A | 8/1997 | Matsuo et al. |
|---|---|---|---|
| 6,720,338 | B2 | 4/2004 | Augeri et al. |
| 7,390,799 | B2 | 6/2008 | Bruncko et al. |
| 7,504,512 | B2 | 3/2009 | Augeri et al. |
| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 7,642,260 | B2 | 1/2010 | Bruncko et al. |
| 7,709,467 | B2 | 5/2010 | Bruncko et al. |
| 7,754,886 | B2 | 7/2010 | Augeri et al. |
| 7,767,684 | B2 | 8/2010 | Bruncko et al. |
| 7,851,637 | B2 | 12/2010 | Castro et al. |
| 7,973,161 | B2 | 7/2011 | Bruncko et al. |
| 8,084,607 | B2 | 12/2011 | Bruncko et al. |
| 8,173,811 | B2 | 5/2012 | Bruncko et al. |
| 8,354,404 | B2 | 1/2013 | Bruncko et al. |
| 8,546,399 | B2 | 10/2013 | Bruncko et al. |
| 8,557,983 | B2 | 10/2013 | Doherty et al. |
| 8,563,735 | B2 | 10/2013 | Bruncko et al. |
| 8,580,794 | B2 | 11/2013 | Doherty et al. |
| 8,586,754 | B2 | 11/2013 | Bruncko et al. |
| 8,614,318 | B2 | 12/2013 | Bruncko et al. |
| 8,686,136 | B2 | 4/2014 | Bruncko et al. |
| 8,952,157 | B2 | 2/2015 | Ding et al. |
| 9,006,247 | B2 | 4/2015 | Tao et al. |
| 9,029,404 | B2 | 5/2015 | Doherty et al. |
| 9,034,875 | B2 | 5/2015 | Doherty et al. |
| 9,045,420 | B2 | 6/2015 | Doherty et al. |
| 9,045,475 | B2 | 6/2015 | Elmore et al. |
| 9,072,748 | B2 | 7/2015 | Bruncko et al. |
| 9,073,855 | B2 | 7/2015 | Doherty et al. |
| 2002/0055631 | A1 | 5/2002 | Augeri et al. |
| 2002/0086887 | A1 | 7/2002 | Augeri et al. |
| 2005/0159427 | A1 | 7/2005 | Bruncko et al. |
| 2006/0128706 | A1 | 6/2006 | Bruncko et al. |

(Continued)

FOREIGN PATENT DOCUMENTS

| CA | 2075586 C | 12/2002 |
|---|---|---|
| EA | 005373 B1 | 2/2005 |

(Continued)

OTHER PUBLICATIONS

Souers et al., "ABT-199, a potent and selective BCL-2 inhibitor, achieves antitumor activity while sparing platelets," Nature Medicine, (2013), pp. 202-208, vol. 19.
International Searching Authority, "Supplementary International Search Report for International Application No. PCT/US2009/066722," (Feb. 16, 2012), 4 pages.
International Searching Authority, "International Search Report for International Application No. PCT/US2010/036198," (Apr. 29, 2005), 3 pages.
International Searching Auhthority, "Supplementary International Search Report for Application No. PCT/US2009/066790," (mailed on Mar. 24, 2011), 2 paqes.

(Continued)

Primary Examiner — Shawquia Jackson
(74) Attorney, Agent, or Firm — Jones Day

(57) ABSTRACT

Disclosed are compounds which inhibit the activity of anti-apoptotic Bcl-2 or Bcl-xL proteins, compositions containing the compounds and methods of treating diseases during which are expressed anti-apoptotic Bcl-2 protein.

2 Claims, No Drawings

(56) References Cited

U.S. PATENT DOCUMENTS

| | | |
|---|---|---|
| 2006/0258657 A1 | 11/2006 | Bruncko et al. |
| 2007/0015787 A1 | 1/2007 | Bruncko et al. |
| 2007/0027135 A1 | 2/2007 | Bruncko et al. |
| 2007/0072860 A1 | 3/2007 | Bruncko et al. |
| 2008/0076779 A1 | 3/2008 | Elmore et al. |
| 2008/0182845 A1 | 7/2008 | Bardwell et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2010/0022773 A1 | 1/2010 | Bruncko et al. |
| 2010/0152183 A1 | 6/2010 | Bruncko et al. |
| 2010/0160322 A1 | 6/2010 | Bruncko et al. |
| 2010/0184750 A1 | 7/2010 | Hexamer et al. |
| 2010/0184766 A1 | 7/2010 | Kunzer et al. |
| 2010/0227838 A1 | 9/2010 | Shah |
| 2010/0240715 A1 | 9/2010 | Bruncko et al. |
| 2010/0298321 A1 | 11/2010 | Bruncko et al. |
| 2010/0298323 A1 | 11/2010 | Bruncko et al. |
| 2010/0305122 A1 | 12/2010 | Bruncko et al. |
| 2011/0124628 A1 | 5/2011 | Doherty et al. |
| 2011/0256129 A1 | 10/2011 | Bruncko et al. |
| 2013/0267514 A1 | 10/2013 | Bruncko et al. |
| 2013/0267534 A1 | 10/2013 | Bruncko et al. |
| 2013/0296295 A1 | 11/2013 | Bruncko et al. |
| 2014/0057889 A1 | 2/2014 | Bruncko et al. |
| 2014/0057890 A1 | 2/2014 | Bruncko et al. |
| 2014/0066621 A1 | 3/2014 | Bruncko et al. |
| 2014/0088106 A1 | 3/2014 | Bruncko et al. |
| 2014/0094471 A1 | 4/2014 | Bruncko et al. |
| 2014/0107119 A1 | 4/2014 | Bruncko et al. |
| 2014/0113910 A1 | 4/2014 | Bruncko et al. |
| 2015/0183775 A1 | 7/2015 | Bruncko et al. |

FOREIGN PATENT DOCUMENTS

| | | |
|---|---|---|
| EA | 006973 B1 | 6/2006 |
| EP | 0527378 B1 | 2/1993 |
| EP | 0569810 A | 3/1993 |
| RU | 2208609 | 7/2003 |
| RU | 2232751 C2 | 7/2004 |
| RU | 2245876 | 10/2005 |
| RU | 2263666 | 10/2005 |
| RU | 2007101276 A | 8/2008 |
| UA | 74889 C2 | 2/2004 |
| WO | 9304046 A1 | 3/1993 |
| WO | WO9507271 A1 | 3/1995 |
| WO | 9710223 | 3/1997 |
| WO | 9942443 A1 | 8/1999 |
| WO | 9906433 A1 | 11/1999 |
| WO | 0001389 A1 | 1/2000 |
| WO | 0112189 A1 | 2/2001 |
| WO | 0170693 A2 | 9/2001 |
| WO | 0224636 A2 | 3/2002 |
| WO | 0206470 A1 | 8/2002 |
| WO | 02098848 A1 | 12/2002 |
| WO | WO03007436 A2 | 1/2003 |
| WO | 03040107 A1 | 5/2003 |
| WO | 2004043950 A1 | 5/2004 |
| WO | 2004048329 A1 | 6/2004 |
| WO | 2005049593 A2 | 6/2005 |
| WO | 2005049594 A1 | 6/2005 |
| WO | 2005099353 A2 | 10/2005 |
| WO | 2006008754 A1 | 1/2006 |
| WO | 2006009869 A1 | 1/2006 |
| WO | 2007040650 A2 | 12/2007 |
| WO | 2008030836 A2 | 3/2008 |
| WO | 2010065824 A2 | 6/2010 |
| WO | 2010065865 A2 | 6/2010 |
| WO | 2010083441 A2 | 7/2010 |
| WO | 2010138588 A2 | 12/2010 |

OTHER PUBLICATIONS

Patel, N. B., et al., "Synthesis and antimicrobial activity of sulfonamides and 4-(p-nitrobenzoyl)piperazine incorporated fluoroquinolones," Indian Journal of Heterocyclic Chemistry, (2006), pp. 205-206, vol. 16, No. 2.

Lala et al, "Role of nitric oxide in tumor progression: Lessons from experimental tumors," Cancer and Metastasis Reviews (1998), pp. 91-106, vol. 17, Issue 1.

Golub et al, "Molecular Classification of Cancer: Class Discovery and Class Prediction by Gene Expression Monitoring," Science (1999), pp. 531-537, vol. 286.

Cross, L.C., et al., "IUPAC Commission on Nomenclature of Organic Chemistry: Rules for the Nomenclature of Organic Chemistry, Section E: Stereochemistry," Pure and Applied Chemistry, (1976), pp. 13-30, vol. 45.

Del Gaizo Moore, V., et al., "BCL-2 Dependence and ABT-737 Sensitivity in Acute Lymphoblastic Leukemia," Blood, (2008), pp. 2300-2309, vol. 111, No. 4.

Corbett, Thomas H. et al., "Discovery and Preliminal Antitumor efficacy evaluations of LY32262 and LY33169," Investigational New Drugs, (2003), pp. 33-45, vol. 21.

Prueksaritanont et al., "Toxicology and Applied Pharmacology," (2006), pp. 143-152, vol. 217.

Beylot M., et al., "In vivo studies of intrahepatic metabolic pathways," Diabetes Metabolism, (1997), pp. 251-257, vol. 23, Issue 3.

Blagojevic N., et al., "Role of heavy water in Boron Neutron Capture Therapy," in Topics in Dosimetry & Treatment Planning for Neutron Capture Therapy, Advanced Medical Publishing, Madison, WI, (1994), pp. 125-134.

Blake et al., "Studies with deuterated drugs," J. Pharm. Sci., (1975), pp. 367-391, vol. 64, Issue 3.

Brickner, S. J., et al., "Synthesis and antibacterial activity of U-100592 and U-100766, two oxazolidinone antibacterial agents for the potential treatment of multidrug-resistant gram-positive bacterial infections," J Med Chem., (1996), pp. 673-679, vol. 39, Issue 3.

Bruncko, M., et al., "Studies leading to potent, dual inhibitors of Bcl-2 and Bcl-xL" Journal of Medicinal Chemistry, (2007), pp. 641-662, vol. 50, Issue 4.

Certo, M., et al., "Mitochondria primed by death signals determine cellular addiction to antiapoptotic BCL-2 family members", Cancer Cell, (2006), pp. 351-365, vol. 9, Issue 5.

Czajka, D. M., "Effect of deuterium oxide on the reproductive potential of mice," Ann NY Acad Sci, (1960), pp. 770-779, vol. 84.

Czajka, D.M., et al., "Physiological effects of deuterium on dogs," Am. J. Physiol., (1961), pp. 357-362, vol. 201, Issue 2.

Eliel, E. L. et al., "Stereochemistry of Organic Compounds," (1994), pp. 119-120, vol. 1206, John Wiley & Sons, Inc. New York.

Foster, A.B., et al., "Deuterium Isotope Effects in the Metabolism of Drugs and Xenobiotics: Implications for Drug Design," Advances in Drug Research, (1985), pp. 2-36, vol. 14, Academic Press, London.

Harada, H., et al., "Survival factor-induced extracellular signal-regulated kinase phosphorylates BIM, inhibiting its association with BAX and proapoptotic activity", Proc Natl Acad Sci USA, (2004), pp. 15313-15317, vol. 101, Issue 43.

Holzelova et al., "Autoimmune Lymphoproliferative Syndrome with Somatic Fas Mutations," New England Journal of Medicine, (2004), pp. 1409-1418, vol. 351.

International Searching Authority, "International Search Report for International Application No. PCT/US2010/036919," (Aug. 19, 2010), 5 pages.

International Searching Authority, "International Search Report for International Application No. PCT/US2009/066722," (Aug. 4, 2010), 4 pages.

International Searching Authority, "International Search Report for International Application No. PCT/US2009/066790," (Jul. 28, 2010), 5 pages.

(56) References Cited

OTHER PUBLICATIONS

International Searching Authority, "International Search Report for International Application No. PCT/US2010/036844," (Aug. 16, 2010), 5 pages.
Becker D.P., et al., "Azaadamantane Benzamide 5-HT4 Agonists: Gastrointestinal Prokinetic SC-54750," Bioorganic and Medicinal Chemistry Letters, (2004), pp. 5509-5512, vol. 14, No. 22.
Jones, C.D et al., "Effects of Substituent Modification on Face Selection in Reduction," Journal Org. Chem, (1998), vol. 63., pp. 2758-2760.
Kato et al., "Synthesis of Deuterated Mosapride Citrate," J. Labelled Camp. Radiopharmaceut, (1995), pp. 927-932, vol. 36, Issue 10.
Korolkova, A., "Essentials of Medicinal Chemistry," John Wiley-Interscience Publications, John Wiley & Sons, New York, (1988), pp. 97-118.
Kushner et al., "Pharmacological uses and perspectives of heavy water and deuterated compounds," Can J Physiol Pharmacal, (1999), pp. 79-88, vol. 77.
Lizondo J., et al., "Linezolid: Oxazolidinone antibacterial," Drugs of the Future, (1996), pp. 1116-1123, vol. 21, Issue 11.
Mallesham, B., et al., "Highly efficient Cui-catalyzed coupling of aryl bromides with oxazolidinones using Buchwald's protocol: a short route to linezolid and toloxatone," Org. Lett., (2003), pp. 963-965, vol. 5, Issue 7.
Mason, K.D. et al, "Programmed a nuclear cell death delimits platelet life span," Cell, (2007), pp. 1173-1186, vol. 128.
Park, C.M., et al., "Discovery of an orally bioavailable small molecule inhibitor of prosurvival B-celllymphoma 2 proteins," Journal of Medicinal Chemistry, (2008), pp. 6902-6915, vol. 51, Issue 21.
Puck et al., "Immune Disorders Caused by Defects in the Caspase Cascade," Current Allergy and Asthma Reports, (2003), pp. 378-384, vol. 3.
Rengan. et al., "Actin cytoskeletal function is spared, but apoptosis is increased, in WAS patient hematopoietic cells," Blood, (2000), pp. 1283-1292, vol. 95, Issue 4.
Shimazaki et al., "Evaluation of apoptosis as a prognostic factor in myelodysplastic syndromes", British J Haematology, (2000), pp. 584-590, vol. 110, Issue 3.
Sutton, V.R., et al. "Bcl-2 prevents apoptosis induced by perforin and granzyme B, but not that mediated by whole cytotoxic lymphocytes", Journal of Immunology, (1997), pp. 5783-5790, vol. 158, Issue 12.
Thomson, J. F., "Physiological effects of D20 in mammals," Ann. New York Acad. Sci., (1960), pp. 736-744, vol. 84.
Tse et al., "ABT-263: A Potent and Orally Bioavailable Bcl-2 Family Inhibitor," Cancer Research, (2008), pp. 3421-3428, vol. 68, Issue 9.
Wang, Z. X., "An exact mathematical expression for describing competitive binding of two different ligands to a protein molecule", FEBS Lett, (1995), pp. 111-114, vol. 360, Issue 2.
Wendt, Michael, "Discovery of ABT-263, a Bcl-family protein inhibitor: observations on \v 080 targeting a large protein-protein interaction", Expert Opin Drug Discov (2008), pp. 1123-1143, vol. 3, Issue 9.
International Searching Authority, Written Opinion of the International Searching Authority for International Application No. PCT/US2010/036844, (Jun. 14, 2012), 10 pages.
International Searching Authority, "Written Opinion of the International Searching Authority for International Application No. PCT/US2010/036919," (Jun. 5, 2012.), 9 pages.
Zhang, H. et al., "Bcl-2 family proteins are essential for platelet survival," Cell Death and Differentiation, (2007), pp. 943-951, vol. 14, Issue 5.
Oltersdorf, T., et al., "An inhibitor of Bcl-2 family proteins induces regression of solid tumours," Nature, (2005), pp. 677-681, vol. 435.
Bardwell, P.D., et al., "The Bcl-2 family antagonist ABT-737 significantly inhibits multiple animal models of autoimmunity," J. Immunol., (2009), pp. 7482-7489, vol. 182, No. 12.
Humerickhouse, R., "Clinical Activity of the Potent and Selective Bcl-2 Inhibitor ABT-199: Proving the Concept," Symposium presentation, (Apr. 9, 2016), American Association for Cancer Research (AACR) Annual Meeting (Washington, D.C.), pp. 1-31.
Cancer [online], [retrieved on Jul. 6, 2007]. Retrieved from the Internet, URL http://www.nlm.nih.gov/medlineplus/cancer.html>.
Cancer [online], [retrieved on Jul. 6, 2007]. Retrieved from the Internet, URL; http://en.wikipedia.orglwikiiCancer.
Prodrug [online], [retrieved on Mar. 11, 2007]. Retrieved from the Internet, URL; http:llen.wikipedia.orglwikiiProdrug>.
File Registry (STN) [online], CAS Registry No. 745034-46-2, 378189-42-5.
File Registry (STN) [online], CAS Registry No. 753468-40-5, 745034-46-2, 745028-47-1, 716373-52-3, 380557-27-7, 378189-42-5.
File Registry (STN) [online], CAS Registry No. 739342-14-4, 395090-67-2, 328028-74-6, 303228-76-4.

BCL-2-SELECTIVE APOPTOSIS-INDUCING AGENTS FOR THE TREATMENT OF CANCER AND IMMUNE DISEASES

This application is a continuation of U.S. patent application Ser. No. 14/058,164, filed Oct. 18, 2013, which is a continuation of U.S. patent application Ser. No. 12/631,404, filed Dec. 4, 2009, which claims the benefit of U.S. Provisional Patent Application No. 61/120,275, filed Dec. 5, 2008, and U.S. Provisional Patent Application No. 61/181,180, filed May 26, 2009, each of which is hereby incorporated by reference in its entirety into this application.

FIELD OF THE INVENTION

This invention pertains to compounds which selectively inhibit the activity of anti-apoptotic Bcl-2 family proteins, compositions containing the compounds, and methods of treating diseases during which anti-apoptotic Bcl-2 proteins are expressed.

BACKGROUND OF THE INVENTION

Anti-apoptotic Bcl-2 family proteins are associated with a number of diseases and are under investigation as potential therapeutic drug targets. These targets for interventional therapy include, for example, the Bcl-2 family proteins Bcl-2, Bcl-$X_L$ and Bcl-w. Recently, inhibitors of Bcl-2 family proteins have been reported in commonly-owned PCT/US/2004/36770, published as WO 2005/049593 and PCT/US/2004/367911, published as WO 2005/049594. While this art teaches inhibitors having high binding to the target protein, compound binding affinity is only one of many parameters to be considered. One goal is to produce compounds that preferentially bind to, that is, are selective for, one protein over another protein. To exhibit this selectivity, it is well known that a compound not only displays a high binding affinity to a particular protein but a lower binding affinity for another member as well.

A typical measure of binding affinity of an anti-apoptotic protein inhibitor is the balance between the binding and dissociation processes between the protein and the inhibitor ($K_i$). The inhibition constant ($K_i$) is the dissociation constant of an enzyme-inhibitor complex or a protein/small molecule complex, wherein the small molecule is inhibiting binding of one protein to another protein. So a large $K_i$ value indicates a low binding affinity, and a small $K_i$ value indicates a high binding affinity.

A typical measure of cellular activity of an anti-apoptotic protein inhibitor is the concentration eliciting 50% cellular effect ($EC_{50}$).

Accordingly, the inventors have discovered that while compounds taught in the art have utility for the treatment of various cancers and immune diseases, they are not selective for anti-apoptotic Bcl-2 proteins over anti-apoptotic Bcl-$X_L$ proteins and thereby result in a higher probability of side effects characterized by inhibition of anti-apoptotic Bcl-$X_L$ proteins such as, thrombocytopenia.

This invention therefore comprises a series of compounds that demonstrate unexpected properties with respect to their selectivity for binding to, and inhibiting the activity of anti-apoptotic Bcl-2 protein over anti-apoptotic Bcl-$X_L$ protein as significantly higher than those of the compounds taught in PCT/US/2004/36770 and PCT/US/2004/367911.

SUMMARY OF THE INVENTION

One embodiment of this invention, therefore, pertains to compounds or therapeutically acceptable salts, prodrugs or salts of prodrugs thereof, which are useful as selective inhibitors one or more than one anti-apoptotic protein family member, the compounds having Formula (I)

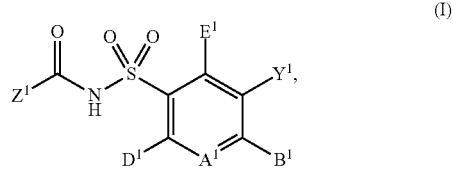

wherein $A^1$ is N or $C(A^2)$;

one or two or three or each of $A^2$, $B^1$, $D^1$ and $E^1$ are independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NR^1C(O)NHR^1$, $NR^1C(O)N(R^1)_2$, $SO_2NHR^1$, $SO_2N(R^1)_2$, $NHSO_2R^1$, $NHSO_2NHR^1$ or $N(CH_3)SO_2N(CH_3)R^1$, and the remainder are independently selected H, F, Cl, Br, I, CN, $CF_3$, C(O)OH, $C(O)NH_2$ or $C(O)OR^{1A}$; and $Y^1$ is H, CN, $NO_2$, C(O)OH, F, Cl, Br, 1, $CF_3$, $OCF_3$, $CF_2CF_3$, $OCF_2CF_3$, $R^{17}$, $OR^{17}$, $C(O)R^{17}$, $C(O)OR^{17}$, $SR^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, $NHS(O)R^{17}$ or $NHSO_2R^{17}$;

or $B^1$ and $Y^1$, together with the atoms to which they are attached, are imidazole or triazole; and one or two or each of $A^2$, $D^1$ and $E^1$ are independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NHC(O)NHR^1$, $N(CH_3)C(O)N(CH_3)R^1$, $SO_2NHR^1$, $SO_2N(R^1)_2$, $NHSO_2R^1$, $NHSO_7NHR^1$ or $N(CH_3)SO_2N(CH_3)R^1$, and the remainder are independently selected H, F, Cl, Br, I, $CF_3$, C(O)OH, $C(O)NH_2$ or $C(O)OR^{1A}$;

$R^1$ is $R^2$, $R^3$, $R^4$ or $R^5$;

$R^{1A}$ is $C_1$-$C_6$-alkyl, $C_3$-$C_6$-alkenyl or $C_3$-$C_6$-alkynyl;

$R^2$ is phenyl which is unfused or fused with arene, heteroarene or $R^{2A}$; $R^{2A}$ is cycloalkane or heterocycloalkane;

$R^3$ is heteroaryl which is unfused or fused with benzene, heteroarene or $R^{3A}$; $R^{3A}$ is cycloalkane or heterocycloalkane;

$R^4$ is cycloalkyl, cycloalkenyl, heterocycloalkyl or heterocycloalkenyl, each of which is unfused or fused with arene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $NHC(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, OH, (O), C(O)OH, (O), $N_3$, CN, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or $R^{11}$;

$R^8$ is phenyl which is unfused or fused with arene, heteroarene or $R^{8A}$;

$R^{8A}$ is cycloalkane, cycloalkene, heterocycloalkane or heterocycloalkene;

$R^9$ is heteroaryl which is unfused or fused with arene, heteroarene or $R^{9A}$; $R^{9A}$ is cycloalkane, cycloalkene, heterocycloalkane or heterocycloalkene;

$R^{10}$ is $C_3$-$C_{10}$-cycloalkyl or $C_4$-$C_{10}$-cycloalkenyl, each having one or two CH/moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $NHR^{12}$, $N(R^{12})_2$, $C(O)NH_2$, $C(O)NHR^{12}$, $C(O)N(R^{12})_2$, OH, (O), C(O)OH, $N_3$, CN, $NH_2$, $CF_3$, $CF_2CF_3$, F, Cl, Br or I substituents;

$R^{12}$ is $R^{13}$, $R^{14}$, $R^{15}$, or $R^{16}$;

$R^{13}$ is phenyl which is unfused or fused with arene, heteroarene or $R^{13A}$; $R^{13A}$ is cycloalkane, cycloalkene, heterocycloalkane or heterocycloalkene;

$R^{14}$ is heteroaryl, each of which is unfused or fused with arene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with arene, heteroarene or $R^{15A}$; $R^{15A}$ is cycloalkane, cycloalkene, heterocycloalkane or heterocycloalkene;

$R^{16}$ is alkyl, alkenyl or alkynyl;

$R^{17}$ is $R^{18}$, $R^{19}$, $R^{20}$ or $R^{21}$;

$R^{18}$ is phenyl which is unfused or fused with arene, heteroarene or $R^{18A}$; $R^{18A}$ is cycloalkane, cycloalkene, heterocycloalkane or heterocycloalkene;

$R^{19}$ is heteroaryl which is unfused or fused with arene, heteroarene or $R^{19A}$; $R^{19A}$ is cycloalkane, cycloalkene, heterocycloalkane or heterocycloalkene;

$R^{20}$ is $C_3$-$C_{10}$-cycloalkyl or $C_4$-$C_{10}$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{20A}$; $R^{20A}$ is cycloalkane, cycloalkene, heterocycloalkane or heterocycloalkene;

$R^{21}$ is alkyl, alkenyl or alkynyl, each of which is unsubstituted or substituted with one or two or three independently selected $R^{22}$, $OR^{22}$, $NHR^{22}$, $N(R^{22})_2$, $C(O)NH_2$, $C(O)NHR^{22}$, $C(O)N(R^{22})_2$, OH, (O), C(O)OH, $N_3$, CN, $NH_2$, $CF_3$, $CF_2CF_3$, F, Cl, Br or I substituents;

$R^{22}$ is $R^{23}$, $R^{24}$ or $R^{25}$;

$R^{23}$ is phenyl which is unfused or fused with arene, heteroarene or $R^{23A}$; $R^{23A}$ is cycloalkane, cycloalkene, heterocycloalkane or heterocycloalkene;

$R^{24}$ is heteroarene which is unfused or fused with arene, heteroarene or $R^{24A}$; $R^{24A}$ is cycloalkane, cycloalkene, heterocycloalkane or heterocycloalkene;

$R^{25}$ is $C_3$-$C_6$-cycloalkyl or $C_4$-$C_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{25A}$; $R^{25A}$ is cycloalkane, cycloalkene, heterocycloalkane or heterocycloalkene;

$Z^1$ is $R^{26}$ or $R^{27}$, each of which is substituted with $R^{28}$, $R^{29}$ or $R^{30}$, each of which is substituted with F, Cl, Br, I, $CH_2R^{37}$, $CH(R^{31})(R^{37})$, $C(R^{31})(R^{31A})(R^{37})$, $C(O)R^{37}$, $OR^{37}$, $SR^{37}$, $S(O)R^{37}$, $SO_2R^{37}$, $NHR^{37}$ or $N(R^{32})R^{37}$;

$R^{26}$ is phenyl which is unfused or fused with arene or heteroarene;

$R^{27}$ is heteroarene which is unfused or fused with arene or heteroarene;

$R^{28}$ is phenyl which is unfused or fused with arene, heteroarene or $R^{28A}$; $R^{28A}$ is cycloalkane, cycloalkene, heterocycloalkane or heterocycloalkene;

$R^{29}$ is heteroaryl or $R^{29A}$; $R^{29A}$ is cycloalkane, cycloalkene, heterocycloalkane or heterocycloalkene;

$R^{30}$ is cycloalkyl or cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{30A}$; $R^{30A}$ is cycloalkane, cycloalkene, heterocycloalkane or heterocycloalkene;

$R^{31}$ and $R^{31A}$ are independently F, Cl, Br or alkyl or are taken together and are $C_2$-$C_5$-spiroalkyl;

$R^{32}$ is $R^{33}$, $C(O)R^{33}$ or $C(O)OR^{33}$;

$R^{33}$ is $R^{34}$ or $R^{35}$;

$R^{34}$ is phenyl which is unfused or fused with aryl, heteroaryl or $R^{34A}$; $R^{34A}$ is cycloalkane, cycloalkene, heterocycloalkane or heterocycloalkene;

$R^{35}$ is alkyl which is unsubstituted or substituted with $R^{36}$;

$R^{36}$ is phenyl which is unfused or fused with arene, heteroarene or $R^{36A}$; $R^{36A}$ is cycloalkane, cycloalkene, heterocycloalkane or heterocycloalkene;

$R^{37}$ is $R^{38}$, $R^{39}$ or $R^{40}$, each of which is substituted with F, Cl, Br, I, $R^{41}$, $OR^{41}$, $NHR^{41}$, $N(R^{41})_2$, $NHC(O)OR^{41}$, $SR^{41}$, $S(O)R^{41}$ or $SO_2R^{41}$;

$R^{38}$ is phenyl which is unfused or fused with arene, heteroarene or $R^{38A}$; $R^{38A}$ is cycloalkane, cycloalkene, heterocycloalkane or heterocycloalkene;

$R^{39}$ is heteroaryl which is unfused or fused with arene, heteroarene or $R^{39A}$; $R^{39A}$ is cycloalkane, cycloalkene, heterocycloalkane or heterocycloalkene;

$R^{40}$ is $C_3$-$C_8$-cycloalkyl or $C_4$-$C_8$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{40A}$; $R^{40A}$ cycloalkane, cycloalkene, heterocycloalkane or heterocycloalkene;

$R^{41}$ is $R^{42}$, $R^{43}$, $R^{44}$ or $R^{45}$;

$R^{42}$ is phenyl which is unfused or fused with arene, heteroarene or $R^{42A}$; $R^{42A}$ is cycloalkane, cycloalkene, heterocycloalkane or heterocycloalkene;

$R^{43}$ is heteroaryl which is unfused or fused with arene, heteroarene or $R^{43A}$; $R^{43A}$ is cycloalkane, cycloalkene, heterocycloalkane or heterocycloalkene;

$R^{44}$ is $C_3$-$C_9$-cycloalkyl or $C_4$-$C_7$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, $OR^{46}$, $NHR^{46}$, $N(R^{46})_2$, $C(O)NH_2$, $C(O)NHR^{46}$, $C(O)N(R^{46})_2$, OH, (O), C(O)OH, $N_3$, CN, $NH_2$, $CF_3$, $CF_2CF_3$, F, Cl, Br or I substituents;

$R^{46}$ is $R^{47}$, $R^{48}$ or $R^{49}$;

$R^{47}$ is phenyl which is unfused or fused with arene, heteroarene or $R^{47A}$; $R^{47A}$ is cycloalkane, cycloalkene, heterocycloalkane or heterocycloalkene;

$R^{48}$ is heteroaryl or $R^{48A}$; $R^{48A}$ is cycloalkane, cycloalkene, heterocycloalkane or heterocycloalkene;

$R^{49}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{49A}$; $R^{49A}$ is cycloalkane, cycloalkene, heterocycloalkane or heterocycloalkene;

wherein the moieties represented by $R^{26}$ and $R^{27}$ are further substituted by one or two or three of independently selected $R^{50A}$, $OR^{50A}$, $SR^{50A}$, $S(O)R^{50A}$, $SO_2R^{50A}$ or $NHR^{50A}$;

$R^{50A}$ is $R^{51A}$, $R^{52A}$, $R^{53A}$ or $R^{54A}$;

$R^{51A}$ is phenyl which is unfused or fused with benzene, heteroarene or $R^{51AA}$;

wherein $R^{51AA}$ is cycloalkane, cycloalkene or heterocycloalkane heterocycloalkene, $R^{52A}$ is heteroaryl;

$R^{53A}$ is $C_3$-$C_6$-cycloalkyl or $C_4$-$C_6$-cycloalkenyl; each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{53\ AA}$ wherein $R^{53AA}$ is cycloalkane, cycloalkene, heterocycloalkane or heterocycloalkene;

$R^{54A}$ is alkyl, alkenyl or alkynyl, each of which is unsubstituted or substituted with one or two or three of independently selected $R^{55AA}$, $OR^{55AA}$, $SR^{55AA}$, $S(O)R^{55AA}$, $SO_2R^{55AA}$, $NHR^{55AA}$, $N(R^{55AA})_2$, $C(O)R^{55AA}$, $C(O)NH_2$, $C(O)NHR^{55AA}$, $NHC(O)R^{55AA}$, $NHSO_2R^{55AA}$, $NHC(O)OR^{55AA}$, $SO_2NH_2$, $SO_2NHR^{55AA}$, $SO_2N(R^{55AA})_2$, $NHC(O)NH_2$, $NHC(O)NHR^{55AA}$, OH, (O), C(O)OH, (O), $N_3$, CN, $NH_2$, $CF_3$, $OCF_3$, $CF_2CF_3$, $OCF_2CF_3$, F, Cl, Br or I substituents;

$R^{55AA}$ is alkyl, alkenyl, alkynyl, phenyl or heteroaryl, or $R^{56A}$;

$R^{56A}$ is $C_3$-$C_6$-cycloalkyl or $C_4$-$C_6$-cycloalkyl, each having one or two $CH_2$ moieties unreplaced or replaced with independently selected O, C(O), CNOH, CNOCH$_3$, S, S(O), SO$_2$ or NH and one or two CH moieties unreplaced or replaced with N;

wherein moieties represented by $R^2R^3R^4$, $R^6$, $R^{6C}$, $R^8$, $R^{8A}$, $R^9$, $R^{10}$, $R^{13}$, $R^{14}$, $R^{15}$, $R^{18}$, $R^{19}$, $R^{20}$, $R^{23}$, $R^{24}$, $R^{25}$, $R^{26}$, $R^{27}$, $R^{28}$, $R^{29}$, $R^{30}$, $R^{34}$, $R^{36}$, $R^{38}$, $R^{39}$, $R^{40}$, $R^{42}$, $R^{43}$, $R^{44}$, $R^{47}$, $R^{48}$, and $R^{49}$ are independently unsubstituted, further unsubstituted, substituted or further substituted with one or two or three or four or five independently selected $R^{50}$, $OR^{50}$, $SR^{50}$, $S(O)R^{50}$, $SO_2R^{50}$, $C(O)R^{50}$, $CO(O)R^{50}$, $OC(O)R^{50}$, $OC(O)OR^{50}$, $NH_2$, $NHR^{50}$, $N(R^{50})_2$, $C(O)NH_2$, $C(O)NHR^{50}$, $C(O)N(R^{50})_2$, $C(O)NHOH$, $C(O)NHOR^{50}$, $C(O)NHSO_2R^{50}$, $C(O)NR^{55}SO_2R^{50}$, $SO_2NH_2$, $SO_2NHR^{50}$, $SO_2N(R^{50})_2$, $CF_3$, $CF_2CF_3$, C(O)H, C(O)OH, $C(N)NH_2$, $C(N)NHR^{50}$, $C(N)N(R^{50})_2$, OH, (O), CN, $N_3$, $NO_2$, $CF_3$, $CF_2CF_3$, $OCF_3$, $OCF_2CF_3$, F, Cl, Br or I substituents;

$R^{50}$ is $R^{51}$, $R^{52}$, $R^{53}$ or $R^{54}$;

$R^{51}$ is phenyl which is unfused or fused with arene, heteroarene or $R^{51B}$; $R^{51B}$ is cycloalkane, cycloalkene, heterocycloalkane or heterocycloalkene;

$R^{52}$ is heteroaryl;

$R^{53}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{53B}$;

wherein $R^{53B}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, $OR^{55}$, $SR^{55}$, $S(O)R^{55}$, $SO_2R^{55}$, $NHR^{55}$, $N(R^{55})_2$, $C(O)R^{55}$, $C(O)NH_2$, $C(O)NHR^{55}$, $NHC(O)R^{55}$, $NHSO_2R^{55}$, $NHC(O)OR^{55}$, $SO_2NH_2$, $SO_2NHR^{55}$, $SO_2N(R^{55})_2$, $NHC(O)NH_2$, $NHC(O)NHR^{55}$, OH, (O), C(O)OH, (O), $N_3$, CN, $NH_2$, $CF_3$, $OCF_3$, $CF_2CF_3$, $OCF_2CF_3$, F, Cl, Br or I substituents;

$R^{55}$ is alkyl, alkenyl, alkynyl, phenyl, heteroaryl or $R^{56}$;

wherein the alkyl, alkenyl, alkynyl are unsubstituted or substituted with $OCH_3$; and $R^{56}$ is $C_3$-$C_8$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N.

Another embodiment of this invention pertains to compounds or therapeutically acceptable salts, prodrugs or salts of prodrugs thereof, which are useful as selective inhibitors of anti-apoptotic Bcl-2 proteins, the compounds having Formula (II)

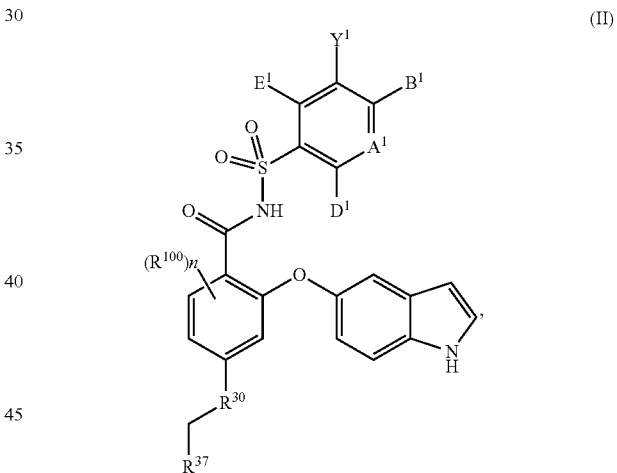

(II)

wherein
$R^{100}$ is as described for substituents on $R^{26}$;
n is 0, 1, 2, or 3;
$A^1$ is N or $C(A^2)$;
one or two or three or each of $A^2$, $B^1$, $D^1$ and $E^1$ are independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NR^1C(O)NHR^1$, $NR^1C(O)N(R^1)_2$, $SO_2NHR^1$, $SO_2N(R^1)_2$, $NHSO_2R^1$, $NHSO_2NHR^1$ or $N(CH_3)SO_2N(CH_3)R^1$, and the remainder are independently selected H, F, Cl, Br, I, CN, $CF_3$, C(O)OH, $C(O)NH_2$ or $C(O)OR^{14}$; and $Y^1$ is H, CN, $NO_2$, C(O)OH, F, Cl, Br, I, $CF_3$, $OCF_3$, $CF_2CF_3$, $OCF_2CF_3$, $R^{17}$, $OR^{17}$, $C(O)R^{17}$, $C(O)OR^{17}$, $SR^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, $NHS(O)R^{17}$ or $NHSO_2R^{17}$; or $B^1$ and $Y^1$, together with the atoms to which they are attached, are imidazole or triazole; and one or two or each of $A^2$, $D^1$ and $E^1$ are independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NHC(O)NHR^1$, $N(CH_3)C(O)N(CH_3)R^1$, $SO_2NHR^1$, $SO_2N(R^1)_2$, $NHSO_2R^1$, $NHSO_2NHR^1$ or $N(CH_3)SO_2N(CH_3)R^1$, and the remainder are independently selected H, F, Cl, Br, I, $CF_3$, $C(O)OH$, $C(O)NH_2$ or $C(O)OR^{1A}$;

$R^1$ is $R^2$, $R^3$, $R^4$ or $R^5$;

$R^{1A}$ is $C_1$-$C_6$-alkyl, $C_3$-$C_6$-alkenyl or $C_3$-$C_6$-alkynyl;

$R^2$ is phenyl which is unfused or fused with arene, heteroarene or $R^{2A}$; $R^{2A}$ is cycloalkane or heterocycloalkane;

$R^3$ is heteroaryl which is unfused or fused with benzene, heteroarene or $R^{3A}$; $R^{3A}$ is cycloalkane or heterocycloalkane;

$R^4$ is cycloalkyl, cycloalkenyl, heterocycloalkyl or heterocycloalkenyl, each of which is unfused or fused with arene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $NHC(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, OH, (O), $C(O)OH$, (O), $N_3$, CN, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, 1, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or $R^{11}$;

$R^8$ is phenyl which is unfused or fused with arene, heteroarene or $R^{8A}$;

$R^{8A}$ is cycloalkane, cycloalkene, heterocycloalkane or heterocycloalkene;

$R^9$ is heteroaryl which is unfused or fused with arene, heteroarene or $R^{9A}$; $R^{9A}$ is cycloalkane, cycloalkene, heterocycloalkane or heterocycloalkene;

$R^{10}$ is $C_3$-$C_{10}$-cycloalkyl or $C_4$-$C_{10}$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $NHR^{12}$, $N(R^{12})_2$, $C(O)NH_2$, $C(O)NHR^{12}$, $C(O)N(R^{12})_2$, OH, (O), $C(O)OH$, $N_3$, CN, $NH_2$, $CF_3$, $CF_2CF_3$, F, Cl, Br or I substituents;

$R^{12}$ is $R^{13}$, $R^{14}$, $R^{15}$ or $R^{16}$;

$R^{13}$ is phenyl which is unfused or fused with arene, heteroarene or $R^{13A}$; $R^{13A}$ is cycloalkane, cycloalkene, heterocycloalkane or heterocycloalkene;

$R^{14}$ is heteroaryl, each of which is unfused or fused with arene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with arene, heteroarene or $R^{15A}$; $R^{15A}$ is cycloalkane, cycloalkene, heterocycloalkane or heterocycloalkene;

$R^{16}$ is alkyl, alkenyl or alkynyl;

$R^{17}$ is $R^{18}$, $R^{19}$, $R^{20}$ or $R^{21}$;

$R^{18}$ is phenyl which is unfused or fused with arene, heteroarene or $R^{18A}$; $R^{18A}$ is cycloalkane, cycloalkene, heterocycloalkane or heterocycloalkene;

$R^{19}$ is heteroaryl which is unfused or fused with arene, heteroarene or $R^{19A}$; $R^{19A}$ is cycloalkane, cycloalkene, heterocycloalkane or heterocycloalkene;

$R^{20}$ is $C_3$-$C_{10}$-cycloalkyl or $C_4$-$C_{10}$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or $R^{20A}$; $R^{20A}$ is cycloalkane, cycloalkene, heterocycloalkane or heterocycloalkene;

$R^{21}$ is alkyl, alkenyl or alkynyl, each of which is unsubstituted or substituted with one or two or three independently selected $R^{22}$, $OR^{22}$, $NHR^{22}$, $N(R^{22})_2$, $C(O)NH_2$, $C(O)NHR^{22}$, $C(O)N(R^{22})_2$, OH, (O), $C(O)OH$, $N_3$, CN, $NH_2$, $CF_3$, $CF_2CF_3$, F, Cl, Br or I substituents;

$R^{22}$ is $R^{23}$, $R^{24}$ or $R^{25}$;

$R^{23}$ is phenyl which is unfused or fused with arene, heteroarene or $R^{23A}$; $R^{23A}$ is cycloalkane, cycloalkene, heterocycloalkane or heterocycloalkene;

$R^{24}$ is heteroarene which is unfused or fused with arene, heteroarene or $R^{24A}$; $R^{24A}$ is cycloalkane, cycloalkene, heterocycloalkane or heterocycloalkene;

$R^{25}$ is $C_3$-$C_6$-cycloalkyl or $C_4$-$C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or $R^{25A}$; $R^{25A}$ is cycloalkane, cycloalkene, heterocycloalkane or heterocycloalkene;

$R^{30}$ is cycloalkyl or cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or $R^{30A}$; $R^{30A}$ is cycloalkane, cycloalkene, heterocycloalkane or heterocycloalkene; each of which is substituted with F, Cl, Br, I, $CH_2R^{37}$, $CH(R^{31})(R^{37})$, $C(R^{31})(R^{31A})(R^{37})$, $C(O)R^{37}$, $OR^{37}$, $SR^{37}$, $S(O)R^{37}$, $SO_2R^{37}$, $NHR^{37}$ or $N(R^{32})R^{37}$;

$R^{31}$ and $R^{31A}$ are independently F, Cl, Br or alkyl or are taken together and are $C_2$-$C_5$-spiroalkyl;

$R^{32}$ is $R^{33}$, $C(O)R^{33}$ or $C(O)OR^{33}$;

$R^{33}$ is $R^{34}$ or $R^{35}$;

$R^{34}$ is phenyl which is unfused or fused with aryl, heteroaryl or $R^{34A}$; $R^{34A}$ is cycloalkane, cycloalkene, heterocycloalkane or heterocycloalkene;

$R^{35}$ is alkyl which is unsubstituted or substituted with $R^{36}$;

$R^{36}$ is phenyl which is unfused or fused with arene, heteroarene or $R^{36A}$; $R^{36A}$ is cycloalkane, cycloalkene, heterocycloalkane or heterocycloalkene;

$R^{37}$ is $R^{38}$, $R^{39}$ or $R^{40}$, each of which is substituted with F, Cl, Br, I, $R^{41}$, $OR^{41}$, $NHR^{41}$, $N(R^{41})_2$, $NHC(O)OR^{41}$, $SR^{41}$, $S(O)R^{41}$ or $SO_2R^{41}$;

$R^{38}$ is phenyl which is unfused or fused with arene, heteroarene or $R^{38A}$; $R^{38A}$ is cycloalkane, cycloalkene, heterocycloalkane or heterocycloalkene;

$R^{39}$ is heteroaryl which is unfused or fused with arene, heteroarene or $R^{39A}$; $R^{39A}$ is cycloalkane, cycloalkene, heterocycloalkane or heterocycloalkene;

$R^{40}$ is $C_3$-$C_8$-cycloalkyl or $C_4$-$C_8$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or $R^{40A}$; $R^{40A}$ cycloalkane, cycloalkene, heterocycloalkane or heterocycloalkene;

$R^{41}$ is $R^{42}$, $R^{43}$, $R^{44}$ or $R^{45}$;

$R^{42}$ is phenyl which is unfused or fused with arene, heteroarene or $R^{42A}$; $R^{42A}$ is cycloalkane, cycloalkene, heterocycloalkane or heterocycloalkene;

$R^{43}$ is heteroaryl which is unfused or fused with arene, heteroarene or $R^{43A}$; $R^{43A}$ is cycloalkane, cycloalkene, heterocycloalkane or heterocycloalkene;

$R^{44}$ is $C_3$-$C_9$-cycloalkyl or $C_4$-$C_7$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, OR$^{46}$, NHR$^{46}$, N(R$^{46}$)$_2$, C(O)NH$_2$, C(O)NHR$^{46}$, C(O)N (R$^{46}$)$_2$, OH, (O), C(O)OH, N$_3$, CN, NH$_2$, CF$_3$, CF$_2$CF$_3$, F, Cl, Br or I substituents;

$R^{46}$ is $R^{47}$, $R^{48}$ or $R^{49}$;

$R^{47}$ is phenyl which is unfused or fused with arene, heteroarene or $R^{47A}$; $R^{47A}$ is cycloalkane, cycloalkene, heterocycloalkane or heterocycloalkene;

$R^{48}$ is heteroaryl or $R^{48A}$; $R^{48A}$ is cycloalkane, cycloalkene, heterocycloalkane or heterocycloalkene;

$R^{49}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{49A}$; $R^{49A}$ is cycloalkane, cycloalkene, heterocycloalkane or heterocycloalkene;

wherein moieties represented by $R^2R^3R^4$, $R^6$, $R^{6C}$, $R^8$, $R^{8A}R^9$, $R^{10}$, $R^{13}$, $R^{14}$, $R^{15}$, $R^{18}$, $R^{19}$, $R^{20}$, $R^{23}$, $R^{24}$, $R^{25}$, $R^{26}$, $R^{27}$, $R^{28}$, $R^{29}$, $R^{30}$, $R^{34}$, $R^{36}$, $R^{38}$, $R^{39}$, $R^{40}$, $R^{42}$, $R^{43}$, $R^{44}$, $R^{47}$, $R^{48}$, and $R^{49}$ are independently unsubstituted, further unsubstituted, substituted or further substituted with one or two or three or four or five independently selected $R^{50}$, OR$^{50}$, SR$^{50}$, S(O)R$^{50}$, SO$_2$R$^{50}$, C(O)R$^{50}$, CO(O)R$^{50}$, OC(O)R$^{50}$, OC(O)OR$^{50}$, NH$_2$, NHR$^{50}$, N(R$^{50}$)$_2$, C(O)NH$_2$, C(O)NHR$^{50}$, C(O)N(R$^{50}$)$_2$, C(O)NHOH, C(O)NHOR$^{50}$, C(O)NHSO$_2$R$^{50}$, C(O)NR$^{55}$SO$_2$R$^{50}$, SO$_2$NH$_2$, SO$_2$NHR$^{50}$, SO$_2$N(R$^{50}$)$_2$, CF$_3$, CF$_2$CF$_3$, C(O)H, C(O)OH, C(N)NH$_2$, C(N)NHR$^{50}$, C(N)N(R$^{50}$)$_2$, OH, (O), CN, N$_3$, NO$_2$, CF$_3$, CF$_2$CF$_3$, OCF$_3$, OCF$_2$CF$_3$, F, Cl, Br or I substituents;

$R^{50}$ is $R^{51}$, $R^{52}$, $R^{53}$ or $R^{54}$;

$R^{51}$ is phenyl which is unfused or fused with arene, heteroarene or $R^{51B}$; $R^{51B}$ is cycloalkane, cycloalkene, heterocycloalkane or heterocycloalkene;

$R^{52}$ is heteroaryl;

$R^{53}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{53B}$;

wherein $R^{53B}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, OR$^{55}$, SR$^{55}$, S(O)R$^{55}$, SO$_2$R$^{55}$, NHR$^{55}$, N(R$^{55}$)$_2$, C(O)R$^{55}$, C(O)NH$_2$, C(O)NHR$^{55}$, NHC(O)R$^{55}$, NHSO$_2$R$^{55}$, NHC(O)R$^{55}$, SO$_2$NH$_2$, SO$_2$NHR$^{55}$, SO$_2$N (R$^{55}$)$_2$, NHC(O)NH$_2$, NHC(O)NHR$^{15}$, OH, (O), C(O)OH, (O), N$_3$, CN, NH$_2$, CF$_3$, OCF$_3$, CF$_2$CF$_3$, OCF$_2$CF$_3$, F, Cl, Br or I substituents;

$R^{55}$ is alkyl, alkenyl, alkynyl, phenyl, heteroaryl or $R^{56}$;

wherein the alkyl, alkenyl, alkynyl are unsubstituted or substituted with OCH$_3$; and $R^{56}$ is $C_3$-$C_8$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N.

Another embodiment of this invention pertains to compounds or therapeutically acceptable salts, prodrugs or salts of prodrugs thereof, which are useful as selective inhibitors of anti-apoptotic Bcl-2 proteins, the compounds having Formula (III)

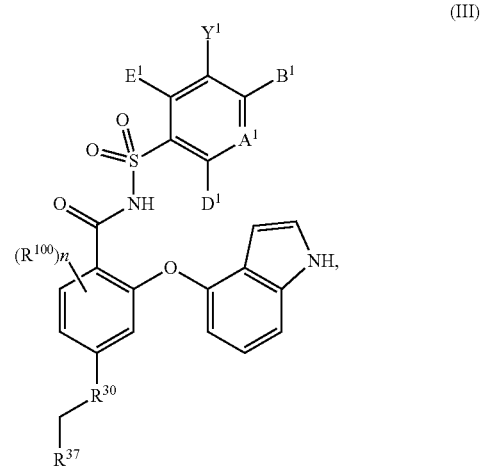

(III)

wherein $R^{10}$ is as described for substituents on $R^{26}$;

n is 0, 1, 2, or 3;

$A^1$ is N or C($A^2$);

one or two or three or each of $A^2$, $B^1$, $D^1$ and $E^1$ are independently selected $R^1$, OR$^1$, SR$^1$, S(O)R$^1$, SO$_2$R$^1$, C(O) R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NHC(O)OR$^1$, NR$^1$C(O)NHR$^1$, NR$^1$C (O)N(R$^1$)$_2$, SO$_2$NHR$^1$, SO$_2$N(R$^1$)$_2$, NHSO$_2$R$^1$, NHSO$_2$NHR$^1$ or N(CH$_3$)SO$_2$N(CH$_3$)R$^1$, and the remainder are independently selected H, F, Cl, Br, I, CN, CF$_3$, C(O)OH, C(O)NH$_2$ or C(O)OR$^{1A}$; and $Y^1$ is H, CN, NO$_2$, C(O)OH, F, Cl, Br, I, CF$_3$, OCF$_3$, CF$_2$CF$_3$, OCF$_2$CF$_3$, R$^{17}$, OR$^{17}$, C(O)R$^{17}$, C(O)OR$^{17}$, SR$^{17}$, NH$_2$, NHR$^{17}$, N(R$^1$)$_2$, NHC(O)R$^{17}$, C(O)NH$_2$, C(O)NHR$^{17}$, C(O)N(R$^{17}$)$_2$, NHS(O)R$^{17}$ or NHSO$_2$R$^{17}$;

or $B^1$ and $Y^1$, together with the atoms to which they are attached, are imidazole or triazole; and one or two or each of $A^2$, $D^1$ and $E^1$ are independently selected $R^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NHC(O)OR$^1$, NHC(O)NHR$^1$, N(CH$_3$)C(O)N(CH$_3$)R$^1$, SO$_2$NHR$^1$, SO$_2$N (R$^1$)$_2$, NHSO$_2$R$^1$, NHSO$_2$NHR$^1$ or N(CH$_3$)SO$_2$N(CH$_3$)R$^1$, and the remainder are independently selected H, F, Cl, Br, I, CF$_3$, C(O)OH, C(O)NH$_2$ or C(O)OR$^{1A}$, $R^1$ is $R^2$, $R^3$, $R^4$ or $R^5$;

$R^{1a}$ is $C_1$-$C_6$-alkyl, $C_3$-$C_6$-alkenyl or $C_3$-$C_6$-alkynyl;

R² is phenyl which is unfused or fused with arene, heteroarene or $R^{2A}$; $R^{2A}$ is cycloalkane or heterocycloalkane;

R³ is heteroaryl which is unfused or fused with benzene, heteroarene or $R^{3A}$; $R^{3A}$ is cycloalkane or heterocycloalkane;

R⁴ is cycloalkyl, cycloalkenyl, heterocycloalkyl or heterocycloalkenyl, each of which is unfused or fused with arene, heteroarene or $R^{4A}$; $R^{4A}$ is cycloalkane, cycloalkene, heterocycloalkane or heterocycloalkene;

R⁵ is alkyl, alkenyl or alkynyl, each of which is unsubstituted or substituted with one or two or three independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $NHC(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^7$, OH, (O), C(O)OH, (O), $N_3$, CN, $NH_2$, $CF_3$, $CF_2CF_3$, F, Cl, Br or I substituents;

R⁶ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

R⁷ is $R^8$, $R^9$, $R^{10}$ or $R^{11}$;

R⁸ is phenyl which is unfused or fused with arene, heteroarene or $R^{8A}$;

$R^{8A}$ is cycloalkane, cycloalkene, heterocycloalkane or heterocycloalkene;

R⁹ is heteroaryl which is unfused or fused with arene, heteroarene or $R^{9A}$; $R^{9A}$ is cycloalkane, cycloalkene, heterocycloalkane or heterocycloalkene;

R¹⁰ is $C_3$-$C_{10}$-cycloalkyl or $C_4$-$C_{10}$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or $R^{10A}$; $R^{10A}$ is cycloalkane, cycloalkene, heterocycloalkane or heterocycloalkene;

R¹¹ is alkyl, alkenyl or alkynyl, each of which is unsubstituted or substituted with one or two or three independently selected $R^{12}$, $OR^{12}$, $NHR^{12}$, $N(R^1)_2$, $C(O)NH_2$, $C(O)NHR^{12}$, $C(O)N(R^2)_2$, OH, (O), C(O)OH, $N_3$, CN, $NH_2$, $CF_3$, $CF_2CF_3$, F, Cl, Br or I substituents;

R¹² is $R^{13}$, $R^{14}$, $R^{15}$ or $R^{16}$;

R¹³ is phenyl which is unfused or fused with arene, heteroarene or $R^{13A}$; $R^{13A}$ is cycloalkane, cycloalkene, heterocycloalkane or heterocycloalkene;

R¹⁴ is heteroaryl, each of which is unfused or fused with arene, heteroarene or $R^{14A}$;

$R^{14A}$ is cycloalkane, cycloalkene, heterocycloalkane or heterocycloalkene;

R¹⁵ is cycloalkane, cycloalkene, heterocycloalkane or heterocycloalkene, each of which is unfused or fused with arene, heteroarene or $R^{15A}$; $R^{15A}$ is cycloalkane, cycloalkene, heterocycloalkane or heterocycloalkene;

R¹⁶ is alkyl, alkenyl or alkynyl;

R¹⁷ is $R^{18}$, $R^{19}$, $R^{20}$ or $R^{21}$;

R¹⁸ is phenyl which is unfused or fused with arene, heteroarene or $R^{18A}$; $R^{18A}$ is cycloalkane, cycloalkene, heterocycloalkane or heterocycloalkene;

R¹⁹ is heteroaryl which is unfused or fused with arene, heteroarene or $R^{19A}$; $R^{19A}$ is cycloalkane, cycloalkene, heterocycloalkane or heterocycloalkene;

R²⁰ is $C_3$-$C_{10}$-cycloalkyl or $C_4$-$C_{10}$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or $R^{20A}$; $R^{20A}$ is cycloalkane, cycloalkene, heterocycloalkane or heterocycloalkene;

R² is alkyl, alkenyl or alkynyl, each of which is unsubstituted or substituted with one or two or three independently selected $R^{22}$, $OR^{22}$, $NHR^{22}$, $N(R^{22})_2$, $C(O)NH_2$, $C(O)NHR^{22}$, $C(O)N(R^{22})_2$, OH, (O), C(O)OH, $N_3$, CN, $NH_2$, $CF_3$, $CF_2CF_3$, F, Cl, Br or I substituents;

R²² is $R^3$, $R^{24}$ or $R^{25}$;

R²³ is phenyl which is unfused or fused with arene, heteroarene or $R^{23A}$; $R^{23A}$ is cycloalkane, cycloalkene, heterocycloalkane or heterocycloalkene;

R²⁴ is heteroarene which is unfused or fused with arene, heteroarene or $R^{24A}$; $R^{24A}$ is cycloalkane, cycloalkene, heterocycloalkane or heterocycloalkene;

R²⁵ is $C_3$-$C_6$-cycloalkyl or $C_4$-$C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or $R^{25A}$; $R^{25A}$ is cycloalkane, cycloalkene, heterocycloalkane or heterocycloalkene;

R³⁰ is cycloalkyl or cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or $R^{30A}$; $R^{30A}$ is cycloalkane, cycloalkene, heterocycloalkane or heterocycloalkene; each of which is substituted with F, Cl, Br, I, $CH_2R^{37}$, $CH(R^{31})(R^{37})$, $C(R^{31})(R^{31A})(R^{37})$, $C(O)R^{37}$, $OR^{37}$, $SR^{37}$, $S(O)R^{37}$, $SO_2R^{37}$, $NHR^{37}$ or $N(R^{32})R^{37}$;

R³¹ and $R^{31A}$ are independently F, Cl, Br or alkyl or are taken together and are $C_2$-$C_5$-spiroalkyl;

R³² is $R^{33}$, $C(O)R^{33}$ or $C(O)OR^{33}$;

R³³ is $R^{34}$ or $R^{35}$;

R³⁴ is phenyl which is unfused or fused with aryl, heteroaryl or $R^{34A}$; $R^{34A}$ is cycloalkane, cycloalkene, heterocycloalkane or heterocycloalkene;

R³⁵ is alkyl which is unsubstituted or substituted with $R^{36}$;

R³⁶ is phenyl which is unfused or fused with arene, heteroarene or $R^{36A}$; $R^{36A}$ is cycloalkane, cycloalkene, heterocycloalkane or heterocycloalkene;

R³⁷ is $R^{38}$, $R^{39}$ or $R^{40}$, each of which is substituted with F, Cl, Br, I, $R^{41}$, $OR^{41}$, $NHR^{41}$, $N(R^{41})_2$, $NHC(O)OR^{41}$, $SR^{41}$, $S(O)R^{41}$ or $SO_2R^{41}$;

R³⁸ is phenyl which is unfused or fused with arene, heteroarene or $R^{38A}$; $R^{38A}$ is cycloalkane, cycloalkene, heterocycloalkane or heterocycloalkene;

R³⁹ is heteroaryl which is unfused or fused with arene, heteroarene or $R^{39A}$; $R^{39A}$ is cycloalkane, cycloalkene, heterocycloalkane or heterocycloalkene;

R⁴⁰ is $C_3$-$C_8$-cycloalkyl or $C_4$-$C_8$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or $R^{40A}$; $R^{40A}$ cycloalkane, cycloalkene, heterocycloalkane or heterocycloalkene;

R⁴¹ is $R^{42}$, $R^{43}$, $R^{44}$ or $R^{45}$;

R⁴² is phenyl which is unfused or fused with arene, heteroarene or $R^{42A}$; $R^{42A}$ is cycloalkane, cycloalkene, heterocycloalkane or heterocycloalkene;

$R^{43}$ is heteroaryl which is unfused or fused with arene, heteroarene or $R^{43A}$; $R^{43A}$ is cycloalkane, cycloalkene, heterocycloalkane or heterocycloalkene;

$R^{44}$ is $C_3$-$C_9$-cycloalkyl or $C_4$-$C_7$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, $OR^{46}$, $NHR^{46}$, $N(R^{46})_2$, $C(O)NH_2$, $C(O)NHR^{46}$, $C(O)N(R^{46})_2$, OH, (O), C(O)OH, $N_3$, CN, $NH_2$, $CF_3$, $CF_2CF_3$, F, Cl, Br or I substituents;

$R^{46}$ is $R^{47}$, $R^{48}$ or $R^{49}$;

$R^{47}$ is phenyl which is unfused or fused with arene, heteroarene or $R^{47A}$; $R^{47A}$ is cycloalkane, cycloalkene, heterocycloalkane or heterocycloalkene;

$R^{48}$ is heteroaryl or $R^{48A}$; $R^{48A}$ is cycloalkane, cycloalkene, heterocycloalkane or heterocycloalkene;

$R^{49}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{49A}$; $R^{49A}$ is cycloalkane, cycloalkene, heterocycloalkane or heterocycloalkene;

wherein moieties represented by $R^2R^3R^4$, $R^6$, $R^{6C}$, $R^8$, $R^{8A}R^9$, $R^{10}$, $R^{13}$, $R^{14}$, $R^{15}$, $R^{18}$, $R^{19}$, $R^{20}$, $R^{23}$, $R^{24}$, $R^2$, $R^{26}$, $R^{27}$, $R^{28}$, $R^{29}$, $R^{30}$, $R^{34}$, $R^{36}$, $R^{38}$, $R^{39}$, $R^{40}$, $R^{42}$, $R^{43}$, $R^{44}$, $R^{47}$, $R^{48}$, and $R^{49}$ are independently unsubstituted, further unsubstituted, substituted or further substituted with one or two or three or four or five independently selected $R^{50}$, $OR^{50}$, $SR^{50}$, $S(O)R^{50}$, $SO_2R^{50}$, $C(O)R^{50}$, $CO(O)R^{50}$, $OC(O)R^{50}$, $OC(O)OR^{50}$, $NH_2$, $NHR^{50}$, $N(R^{50})_2$, $C(O)NH_2$, $C(O)NHR^{50}$, $C(O)N(R^{50})_2$, C(O)NHOH, C(O)NHOR$^{50}$, C(O)NHSO$_2R^{50}$, C(O)NR$^{55}$SO$_2R^{50}$, $SO_2NH_2$, $SO_2NHR^{50}$, $SO_2N(R^{50})_2$, $CF_3$, $CF_2CF_3$, C(O)H, C(O)OH, $C(N)NH_2$, $C(N)NHR^{50}$, $C(N)N(R^{50})_2$, OH, (O), CN, $N_3$, $NO_2$, $CF_3$, $CF_2CF_3$, $OCF_3$, $OCF_2CF_3$, F, Cl, Br or I substituents;

$R^{50}$ is $R^{51}$, $R^{52}$, $R^{53}$ or $R^{54}$;

$R^{51}$ is phenyl which is unfused or fused with arene, heteroarene or $R^{51B}$; $R^{51B}$ is cycloalkane, cycloalkene, heterocycloalkane or heterocycloalkene;

$R^{52}$ is heteroaryl;

$R^{53}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{53B}$;

wherein $R^{53B}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, $OR^{55}$, $SR^{55}$, $S(O)R^{55}$, $SO_2R^{55}$, $NHR^{55}$, $N(R^{55})_2$, $C(O)R^{55}$, $C(O)NH_2$, $C(O)NHR^{55}$, $NHC(O)R^{55}$, $NHSO_2R^{55}$, $NHC(O)OR^{55}$, $SO_2NH_2$, $SO_2NHR^{55}$, $SO_2N(R^{55})_2$, $NHC(O)NH_2$, $NHC(O)NHR^{55}$, OH, (O), C(O)OH, (O), $N_3$, CN, $NH_2$, $CF_3$, $OCF_3$, $CF_2CF_3$, $OCF_2CF_3$, F, Cl, Br or I substituents;

$R^{55}$ is alkyl, alkenyl, alkynyl, phenyl, heteroaryl or $R^{56}$;
wherein the alkyl, alkenyl, alkynyl are unsubstituted or substituted with OCH$_3$; and $R^{56}$ is $C_3$-$C_8$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N.

Another embodiment of this invention pertains to compounds or therapeutically acceptable salts, prodrugs or salts of prodrugs thereof, which are useful as selective inhibitors of anti-apoptotic Bcl-2 proteins, the compounds having Formula (IV)

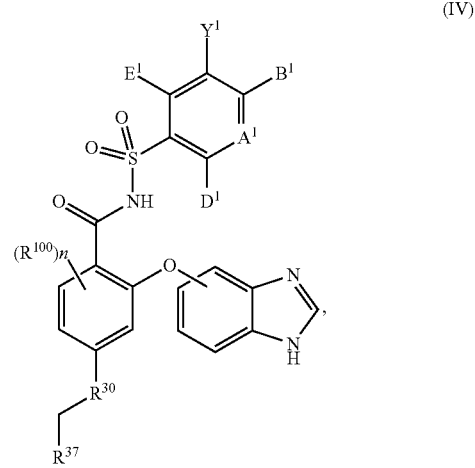

wherein
$R^{100}$ is as described for substituents on $R^{26}$;
n is 0, 1, 2, or 3;
$A^1$ is N or $C(A^2)$;
one or two or three or each of $A^2$, $B^1$, D and $E^1$ are independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NR^1C(O)NHR^1$, $NR^1C(O)N(R^1)_2$, $SO_2NHR^1$, $SO_2N(R^1)_2$, $NHSO_2R^1$, $NHSO_2NHR^1$ or $N(CH_3)SO_2N(CH_3)R^1$, and the remainder are independently selected H, F, Cl, Br, I, CN, $CF_3$, C(O)OH, $C(O)NH_2$ or $C(O)OR^{14}$; and $Y^1$ is H, CN, $NO_2$, C(O)OH, F, Cl, Br, I, $CF_3$, $OCF_3$, $CF_2CF_3$, $OCF_2CF_3$, $R^{17}$, $OR^{17}$, $C(O)R^{17}$, $C(O)OR^{17}$, $SR^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, NHS(O)$R^{17}$ or $NHSO_2R^{17}$;

or $B^1$ and $Y^1$, together with the atoms to which they are attached, are imidazole or triazole; and one or two or each of $A^2$, $D^1$ and $E^1$ are independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NHC(O)NHR^1$, $N(CH_3)C(O)N(CH_3)R^1$, $SO_2NHR^1$, $SO_2N(R^1)_2$, $NHSO_2R^1$, $NHSO_2NHR^1$ or $N(CH_3)SO_2N(CH_3)R^1$, and the remainder are independently selected H, F, Cl, Br, I, $CF_3$, C(O)OH, $C(O)NH_2$ or $C(O)OR^{14}$;

$R^1$ is $R^2$, $R^3$, $R^4$ or $R^5$;
$R^{1A}$ is $C_1$-$C_6$-alkyl, $C_3$-$C_6$-alkenyl or $C_3$-$C_6$-alkynyl;
$R^2$ is phenyl which is unfused or fused with arene, heteroarene or $R^{2A}$; $R^{2A}$ is cycloalkane or heterocycloalkane;
$R^3$ is heteroaryl which is unfused or fused with benzene, heteroarene or $R^{3A}$; $R^{3A}$ is cycloalkane or heterocycloalkane;
$R^4$ is cycloalkyl, cycloalkenyl, heterocycloalkyl or heterocycloalkenyl, each of which is unfused or fused with arene, heteroarene or $R^{4A}$; $R^{4A}$ is cycloalkane, cycloalkene, heterocycloalkane or heterocycloalkene;

R⁵ is alkyl, alkenyl or alkynyl, each of which is unsubstituted or substituted with one or two or three independently selected R⁶, NC(R⁶ᴬ)(R⁶ᴮ), R⁷, OR⁷, SR⁷, S(O)R⁷, SO₂R⁷, NHR⁷, N(R⁷)₂, C(O)R⁷, C(O)NH₂, C(O)NHR⁷, NHC(O)R⁷, NHSO₂R⁷, NHC(O)OR⁷, SO₂NH₂, SO₂NHR⁷, SO₂N(R⁷)₂, NHC(O)NH₂, NHC(O)NHR⁷, NHC(O)CH(CH₃)NHC(O)CH(CH₃)NH₂, NHC(O)CH(CH₃)NHC(O)CH(CH₃)NHR¹, OH, (O), C(O)OH, (O), N₃, CN, NH₂, CF₃, CF₂CF₃, F, Cl, Br or I substituents;

R⁶ is C₂-C₅-spiroalkyl, each of which is unsubstituted or substituted with OH, (O), N₃, CN, CF₃, CF₂CF₃, F, Cl, Br, I, NH₂, NH(CH₃) or N(CH₃)₂;

R⁶ᴬ and R⁶ᴮ are independently selected alkyl or, together with the N to which they are attached, R⁶ᶜ;

R⁶ᶜ is aziridin-1-yl, azetidin-1-yl, pyrrolidin-1-yl or piperidin-1-yl, each having one CH₂ moiety unreplaced or replaced with O, C(O), CNOH, CNOCH₃, S, S(O), SO₂ or NH;

R⁷ is R⁸, R⁹, R¹⁰ or R¹¹;

R⁸ is phenyl which is unfused or fused with arene, heteroarene or R⁸ᴬ;

R⁸ᴬ is cycloalkane, cycloalkene, heterocycloalkane or heterocycloalkene;

R⁹ is heteroaryl which is unfused or fused with arene, heteroarene or R⁹ᴬ; R⁹ᴬ is cycloalkane, cycloalkene, heterocycloalkane or heterocycloalkene;

R¹⁰ is C₃-C₁₀-cycloalkyl or C₄-C₁₀-cycloalkenyl, each having one or two CH₂ moieties unreplaced or replaced with independently selected O, C(O), CNOH, CNOCH₃, S, S(O), SO₂ or NH and one or two CH moieties unreplaced or replaced with N, and each of which is unfused or fused with arene, heteroarene or R¹⁰ᴬ; R¹⁰ᴬ is cycloalkane, cycloalkene, heterocycloalkane or heterocycloalkene;

R¹¹ is alkyl, alkenyl or alkynyl, each of which is unsubstituted or substituted with one or two or three independently selected R¹², OR¹², NHR¹², N(R¹²)₂, C(O)NH₂, C(O)NHR¹², C(O)N(R¹²)₂, OH, (O), C(O)OH, N₃, CN, NH₂, CF₃, CF₂CF₃, F, Cl, Br or I substituents;

R¹² is R¹³, R¹⁴, R¹⁵ or R¹⁶;

R¹³ is phenyl which is unfused or fused with arene, heteroarene or R¹³ᴬ; R¹³ᴬ is cycloalkane, cycloalkene, heterocycloalkane or heterocycloalkene;

R¹⁴ is heteroaryl, each of which is unfused or fused with arene, heteroarene or R¹⁴ᴬ; R¹⁴ᴬ is cycloalkane, cycloalkene, heterocycloalkane or heterocycloalkene;

R⁵ is cycloalkane, cycloalkene, heterocycloalkane or heterocycloalkene, each of which is unfused or fused with arene, heteroarene or R¹⁵ᴬ; R¹⁵ᴬ is cycloalkane, cycloalkene, heterocycloalkane or heterocycloalkene;

R¹⁶ is alkyl, alkenyl or alkynyl;

R¹⁷ is R¹⁸, R¹⁹, R²⁰ or R²¹;

R¹⁸ is phenyl which is unfused or fused with arene, heteroarene or R¹⁸ᴬ; R¹⁸ᴬ is cycloalkane, cycloalkene, heterocycloalkane or heterocycloalkene;

R¹⁹ is heteroaryl which is unfused or fused with arene, heteroarene or R¹⁹ᴬ; R¹⁹ᴬ is cycloalkane, cycloalkene, heterocycloalkane or heterocycloalkene;

R²⁰ is C₃-C₁₀-cycloalkyl or C₄-C₁₀-cycloalkenyl, each having one or two CH₂ moieties unreplaced or replaced with independently selected O, C(O), CNOH, CNOCH₃, S, S(O), SO₂ or NH and one or two CH moieties unreplaced or replaced with N, and each of which is unfused or fused with arene, heteroarene or R²⁰ᴬ; R²⁰ᴬ is cycloalkane, cycloalkene, heterocycloalkane or heterocycloalkene;

R²¹ is alkyl, alkenyl or alkynyl, each of which is unsubstituted or substituted with one or two or three independently selected R²², OR²², NHR²², N(R²²)₂, C(O)NH₂, C(O)NHR²², C(O)N(R²²)₂, OH, (O), C(O)OH, N₃, CN, NH₂, CF₃, CF₂CF₃, F, Cl, Br or I substituents;

R²² is R²³, R²⁴ or R²⁵;

R²³ is phenyl which is unfused or fused with arene, heteroarene or R²³ᴬ; R²³ᴬ is cycloalkane, cycloalkene, heterocycloalkane or heterocycloalkene;

R²⁴ is heteroarene which is unfused or fused with arene, heteroarene or R²⁴ᴬ; R²⁴ᴬ is cycloalkane, cycloalkene, heterocycloalkane or heterocycloalkene;

R²⁵ is C₃-C₆-cycloalkyl or C₄-C₆-cycloalkenyl, each having one or two CH₂ moieties unreplaced or replaced with independently selected O, C(O), CNOH, CNOCH₃, S, S(O), SO₂ or NH and one or two CH moieties unreplaced or replaced with N, and each of which is unfused or fused with arene, heteroarene or R²⁵ᴬ; R²⁵ᴬ is cycloalkane, cycloalkene, heterocycloalkane or heterocycloalkene;

R³⁰ is cycloalkyl or cycloalkenyl, each having one or two CH₂ moieties unreplaced or replaced with independently selected O, C(O), CNOH, CNOCH₃, S, S(O), SO₂ or NH and one or two CH moieties unreplaced or replaced with N, and each of which is unfused or fused with arene, heteroarene or R³⁰ᴬ; R³⁰ᴬ is cycloalkane, cycloalkene, heterocycloalkane or heterocycloalkene; each of which is substituted with F, Cl, Br, I, CH₂R³⁷, CH(R³¹)(R³⁷), C(R³¹)(R³¹ᴬ)(R³⁷), C(O)R³⁷, OR³⁷, SR³⁷, S(O)R³⁷, SO₂R³⁷, NHR³⁷ or N(R³²)R³⁷;

R³¹ and R³¹ᴬ are independently F, Cl, Br or alkyl or are taken together and are C₂-C₅-spiroalkyl;

R³² is R³³, C(O)R³³ or C(O)OR³³;

R³³ is R³⁴ or R³⁵;

R³⁴ is phenyl which is unfused or fused with aryl, heteroaryl or R³⁴ᴬ; R³⁴ᴬ is cycloalkane, cycloalkene, heterocycloalkane or heterocycloalkene;

R³⁵ is alkyl which is unsubstituted or substituted with R³⁶;

R³⁶ is phenyl which is unfused or fused with arene, heteroarene or R³⁶ᴬ; R³⁶ᴬ is cycloalkane, cycloalkene, heterocycloalkane or heterocycloalkene;

R³⁷ is R³⁸, R³⁹ or R⁴⁰, each of which is substituted with F, Cl, Br, I, R⁴¹, OR⁴¹, NHR⁴¹, N(R⁴¹)₂, NHC(O)OR⁴¹, SR⁴¹, S(O)R⁴¹ or SO₂R⁴¹;

R³⁸ is phenyl which is unfused or fused with arene, heteroarene or R³⁸ᴬ; R³⁸ᴬ is cycloalkane, cycloalkene, heterocycloalkane or heterocycloalkene;

R³⁹ is heteroaryl which is unfused or fused with arene, heteroarene or R³⁹ᴬ; R³⁹ᴬ is cycloalkane, cycloalkene, heterocycloalkane or heterocycloalkene;

R⁴⁰ is C₃-C₈-cycloalkyl or C₄-C₈-cycloalkenyl, each having one or two CH₂ moieties unreplaced or replaced with independently selected O, C(O), CNOH, CNOCH₃, S, S(O), SO₂ or NH and one or two CH moieties unreplaced or replaced with N, and each of which is unfused or fused with arene, heteroarene or R⁴⁰ᴬ; R⁴⁰ᴬ cycloalkane, cycloalkene, heterocycloalkane or heterocycloalkene;

R⁴¹ is R⁴², R⁴³, R⁴⁴ or R⁴⁵;

R⁴² is phenyl which is unfused or fused with arene, heteroarene or R⁴²ᴬ; R⁴²ᴬ is cycloalkane, cycloalkene, heterocycloalkane or heterocycloalkene;

R⁴³ is heteroaryl which is unfused or fused with arene, heteroarene or R⁴³ᴬ; R⁴³ᴬ is cycloalkane, cycloalkene, heterocycloalkane or heterocycloalkene;

R⁴⁴ is C₃-C₉-cycloalkyl or C₄-C₇-cycloalkenyl, each having one or two CH₂ moieties unreplaced or replaced with independently selected O, C(O), CNOH, CNOCH₃, S, S(O), SO₂ or NH and one or two CH moieties unreplaced or replaced with N, and each of which is unfused or fused with arene, heteroarene or R⁴⁴ᴬ; R⁴⁴ᴬ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, $OR^{46}$, $NHR^{46}$, $N(R^{46})_2$, $C(O)NH_2$, $C(O)NHR^{46}$, $C(O)N(R^{46})_2$, OH, (O), C(O)OH, $N_3$, CN, $NH_2$, $CF_3$, $CF_2CF_3$, F, Cl, Br or I substituents;

$R^{46}$ is $R^{47}$, $R^{48}$ or $R^{49}$;

$R^{47}$ is phenyl which is unfused or fused with arene, heteroarene or $R^{47A}$; $R^{47A}$ is cycloalkane, cycloalkene, heterocycloalkane or heterocycloalkene;

$R^{48}$ is heteroaryl or $R^{48A}$; $R^{48A}$ is cycloalkane, cycloalkene, heterocycloalkane or heterocycloalkene;

$R^{49}$ is $C_3$-$C_6$-cycloalkyl or $C_4$-$C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or $R^{49A}$; $R^{49A}$ is cycloalkane, cycloalkene, heterocycloalkane or heterocycloalkene;

wherein moieties represented by $R^2R^3R^4$, $R^6$, $R^{6C}$, $R^8$, $R^{8A}R^9$, $R^{10}$, $R^{13}$, $R^{14}$, $R^{15}$, $R^{18}$, $R^{19}$, $R^{20}$, $R^{23}$, $R^{24}$, $R^{25}$, $R^{26}$, $R^{27}$, $R^{28}$, $R^{29}$, $R^{30}$, $R^{34}$, $R^{36}$, $R^{38}$, $R^{39}$, $R^{40}$, $R^{42}$, $R^{43}$, $R^{44}$, $R^{47}$, $R^{48}$, and $R^{49}$ are independently unsubstituted, further unsubstituted, substituted or further substituted with one or two or three or four or five independently selected $R^{50}$, $OR^{50}$, $SR^{50}$, $S(O)R^{50}$, $SO_2R^{50}$, $C(O)R^{50}$, $CO(O)R^{50}$, $OC(O)R^{50}$, $OC(O)OR^{50}$, $NH_2$, $NHR^{50}$, $N(R^{50})_2$, $C(O)NH_2$, $C(O)NHR^{50}$, $C(O)N(R^{50})_2$, C(O)NHOH, $C(O)NHOR^{50}$, $C(O)NHSO_2R^{50}$, $C(O)NR^{55}SO_2R^{50}$, $SO_2NH_2$, $SO_2NHR^{50}$, $SO_2N(R^{50})_2$, $CF_3$, $CF_2CF_3$, C(O)H, C(O)OH, $C(N)NH_2$, $C(N)NHR^{50}$, $C(N)N(R^{50})_2$, OH, (O), CN, $N_3$, $NO_2$, $CF_3$, $CF_2CF_3$, $OCF_3$, $OCF_2CF_3$, F, Cl, Br or I substituents;

$R^{50}$ is $R^{51}$, $R^{52}$, $R^{53}$ or $R^{54}$;

$R^{51}$ is phenyl which is unfused or fused with arene, heteroarene or $R^{51B}$; $R^{51B}$ is cycloalkane, cycloalkene, heterocycloalkane or heterocycloalkene;

$R^{52}$ is heteroaryl;

$R^{53}$ is $C_3$-$C_6$-cycloalkyl or $C_4$-$C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or $R^{53B}$;

wherein $R^{53B}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, $OR^{55}$, $SR^{55}$, $S(O)R^{55}$, $SO_2R^{55}$, $NHR^{55}$, $N(R^{55})_2$, $C(O)R^{55}$, $C(O)NH_2$, $C(O)NHR^{55}$, $NHC(O)R^{15}$, $NHSO_2R^{55}$, $NHC(O)OR^{55}$, $SO_2NH_2$, $SO_2NHR^{55}$, $SO_2N(R^{55})_2$, $NHC(O)NH_2$, $NHC(O)NHR^{15}$, OH, (O), C(O)OH, (O), $N_3$, CN, $NH_2$, $CF_3$, $OCF_3$, $CF_2CF_3$, $OCF_2CF_3$, F, Cl, Br or I substituents;

$R^{55}$ is alkyl, alkenyl, alkynyl, phenyl, heteroaryl or $R^{56}$;

wherein the alkyl, alkenyl, alkynyl are unsubstituted or substituted with $OCH_3$; and $R^{56}$ is $C_3$-$C_8$-cycloalkyl or $C_4$-$C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N.

Another embodiment of this invention pertains to compounds or therapeutically acceptable salts, prodrugs or salts of prodrugs thereof, which are useful as selective inhibitors of anti-apoptotic Bcl-2 proteins, the compounds having Formula (V)

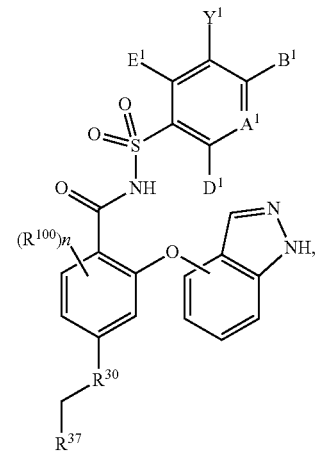

wherein $R^{10}$ is as described for substituents on $R^{26}$;

n is 0, 1, 2, or 3;

$A^1$ is N or $C(A^2)$;

one or two or three or each of $A^2$, $B^1$, $D^1$ and $E^1$ are independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, NHC(O)OR, $NR^1C(O)NHR^1$, $NR^1C(O)N(R^1)_2$, $SO_2NHR^1$, $SO_2N(R^1)_2$, $NHSO_2R^1$, $NHSO_2NHR^1$ or $N(CH_3)SO_2N(CH_3)R^1$, and the remainder are independently selected H, F, Cl, Br, I, CN, $CF_3$, C(O)OH, $C(O)NH_2$ or $C(O)OR^{1A}$; and $Y^1$ is H, CN, $NO_2$, C(O)OH, F, Cl, Br, I, $CF_3$, $OCF_3$, $CF_2CF_3$, $OCF_2CF_3$, $R^{17}$, $OR^{17}$, $C(O)R^{17}$, $C(O)OR^{17}$, $SR^{17}$, $NH_2$, $NHR^{17}$, $N(R^1)_2$, $NHC(O)R^{17}$, $C(O)NH_2$, $C(O)NHR^{17}$, $C(O)N(R^{17})_2$, $NHS(O)R^{17}$ or $NHSO_2R^{17}$;

or $B^1$ and $Y^1$, together with the atoms to which they are attached, are imidazole or triazole; and one or two or each of $A^2$, $D^1$ and $E^1$ are independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, NHC(O)$R^1$, NHC(O)$OR^1$, NHC(O)$NHR^1$, $N(CH_3)C(O)N(CH_3)R^1$, $SO_2NHR^1$, $SO_2N(R^1)_2$, $NHSO_2R^1$, $NHSO_2NHR^1$ or $N(CH_3)SO_2N(CH_3)R^1$, and the remainder are independently selected H, F, Cl, Br, I, $CF_3$, C(O)OH, $C(O)NH_2$ or $C(O)OR^{1A}$;

$R^1$ is $R^2$, $R^3$, $R^4$ or $R^5$;

$R^{1A}$ is $C_1$-$C_6$-alkyl, $C_3$-$C_6$-alkenyl or $C_3$-$C_6$-alkynyl;

$R^2$ is phenyl which is unfused or fused with arene, heteroarene or $R^{2A}$; $R^{2A}$ is cycloalkane or heterocycloalkane;

$R^3$ is heteroaryl which is unfused or fused with benzene, heteroarene or $R^{3A}$; $R^{3A}$ is cycloalkane or heterocycloalkane;

$R^4$ is cycloalkyl, cycloalkenyl, heterocycloalkyl or heterocycloalkenyl, each of which is unfused or fused with arene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $NHC(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)$ $CH(CH_3)NH_2$, $NHC(O)CH(CH_3)NHC(O)CH(CH_3)NHR^7$, OH, (O), C(O)OH, (O), $N_3$, CN, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, CNOCH$_3$, S, S(O), SO$_2$ or NH;

$R^7$ is $R^8$, $R^9$, $R^{10}$ or $R^{11}$;

$R^8$ is phenyl which is unfused or fused with arene, heteroarene or $R^{8A}$;

$R^{8A}$ is cycloalkane, cycloalkene, heterocycloalkane or heterocycloalkene;

$R^9$ is heteroaryl which is unfused or fused with arene, heteroarene or $R^{9A}$; $R^{9A}$ is cycloalkane, cycloalkene, heterocycloalkane or heterocycloalkene;

$R^{10}$ is $C_3$-$C_{10}$-cycloalkyl or $C_4$-$C_{10}$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^{12}$, $OR^{12}$, $NHR^{12}$, $N(R^{12})_2$, $C(O)NH_2$, $C(O)NHR^2$, $C(O)N(R^{12})_2$, OH, (O), C(O)OH, $N_3$, CN, $NH_2$, $CF_3$, $CF_2CF_3$, F, Cl, Br or I substituents;

$R^{12}$ is $R^{13}$, $R^{14}$, $R^{15}$ or $R^{16}$;

$R^{13}$ is phenyl which is unfused or fused with arene, heteroarene or $R^{13A}$; $R^{13A}$ is cycloalkane, cycloalkene, heterocycloalkane or heterocycloalkene;

$R^{14}$ is heteroaryl, each of which is unfused or fused with arene, heteroarene or $R^{14A}$;

$R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with arene, heteroarene or $R^{15A}$; $R^{15A}$ is cycloalkane, cycloalkene, heterocycloalkane or heterocycloalkene;

$R^{16}$ is alkyl, alkenyl or alkynyl;

$R^{17}$ is $R^{18}$, $R^{19}$, $R^{20}$ or $R^{21}$;

$R^{18}$ is phenyl which is unfused or fused with arene, heteroarene or $R^{18A}$; $R^{18A}$ is cycloalkane, cycloalkene, heterocycloalkane or heterocycloalkene;

$R^{19}$ is heteroaryl which is unfused or fused with arene, heteroarene or $R^{19A}$; $R^{9A}$ is cycloalkane, cycloalkene, heterocycloalkane or heterocycloalkene;

$R^{20}$ is $C_3$-$C_{10}$-cycloalkyl or $C_4$-$C_{10}$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{20A}$; $R^{20A}$ is cycloalkane, cycloalkene, heterocycloalkane or heterocycloalkene;

$R^{21}$ is alkyl, alkenyl or alkynyl, each of which is unsubstituted or substituted with one or two or three independently selected $R^{22}$, $OR^{21}$, $NHR^{22}$, $N(R^{22})_2$, $C(O)NH_2$, $C(O)NHR^{22}$, $C(O)N(R^{22})_2$, OH, (O), C(O)OH, $N_3$, CN, $NH_2$, $CF_3$, $CF_2CF_3$, F, Cl, Br or I substituents;

$R^{22}$ is $R^{23}$, $R^{24}$ or $R^{25}$;

$R^{23}$ is phenyl which is unfused or fused with arene, heteroarene or $R^{23A}$; $R^{23A}$ is cycloalkane, cycloalkene, heterocycloalkane or heterocycloalkene;

$R^{24}$ is heteroarene which is unfused or fused with arene, heteroarene or $R^{24A}$; $R^{24A}$ is cycloalkane, cycloalkene, heterocycloalkane or heterocycloalkene;

$R^{25}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{25A}$; $R^{25A}$ is cycloalkane, cycloalkene, heterocycloalkane or heterocycloalkene;

$R^{30}$ is cycloalkyl or cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{30A}$; $R^{30A}$ is cycloalkane, cycloalkene, heterocycloalkane or heterocycloalkene; each of which is substituted with F, Cl, Br, I, $CH_2R^{37}$, $CH(R^{31})(R^{37})$, $C(R^{31})(R^{31A})(R^{37})$, $C(O)R^{37}$, $OR^{37}$, $SR^{37}$, $S(O)R^{37}$, $SO_2R^{37}$, $NHR^{37}$ or $N(R^{32})R^{37}$;

$R^{31}$ and $R^{31A}$ are independently F, Cl, Br or alkyl or are taken together and are $C_2$-$C_5$-spiroalkyl;

$R^{32}$ is $R^{33}$, $C(O)R^{33}$ or $C(O)OR^{33}$;

$R^{33}$ is $R^{34}$ or $R^{35}$;

$R^{34}$ is phenyl which is unfused or fused with aryl, heteroaryl or $R^{34A}$; $R^{34A}$ is cycloalkane, cycloalkene, heterocycloalkane or heterocycloalkene;

$R^{35}$ is alkyl which is unsubstituted or substituted with $R^{36}$;

$R^{36}$ is phenyl which is unfused or fused with arene, heteroarene or $R^{36A}$; $R^{36A}$ is cycloalkane, cycloalkene, heterocycloalkane or heterocycloalkene;

$R^{37}$ is $R^{38}$, $R^{39}$ or $R^{40}$, each of which is substituted with F, Cl, Br, I, $R^{41}$, $OR^{41}$, $NHR^{41}$, $N(R^{41})_2$, $NHC(O)OR^{41}$, $SR^{41}$, $S(O)R^{41}$ or $SO_2R^{41}$;

$R^{38}$ is phenyl which is unfused or fused with arene, heteroarene or $R^{38A}$; $R^{38A}$ is cycloalkane, cycloalkene, heterocycloalkane or heterocycloalkene;

$R^{39}$ is heteroaryl which is unfused or fused with arene, heteroarene or $R^{39A}$; $R^{39A}$ is cycloalkane, cycloalkene, heterocycloalkane or heterocycloalkene;

$R^{40}$ is $C_3$-$C_8$-cycloalkyl or $C_4$-$C_8$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{40A}$; $R^{40A}$ cycloalkane, cycloalkene, heterocycloalkane or heterocycloalkene;

$R^{41}$ is $R^{42}$, $R^{43}$, $R^{44}$ or $R^{45}$;

$R^{42}$ is phenyl which is unfused or fused with arene, heteroarene or $R^{42A}$; $R^{42A}$ is cycloalkane, cycloalkene, heterocycloalkane or heterocycloalkene;

$R^{43}$ is heteroaryl which is unfused or fused with arene, heteroarene or $R^{43A}$; $R^{43A}$ is cycloalkane, cycloalkene, heterocycloalkane or heterocycloalkene;

$R^{44}$ is $C_3$-$C_9$-cycloalkyl or $C_4$-$C_7$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, $OR^{46}$, $NHR^{46}$, $N(R^{46})_2$, $C(O)NH_2$, $C(O)NHR^{46}$, $C(O)N(R^{46})_2$, OH, (O), C(O)OH, $N_3$, CN, $NH_2$, $CF_3$, $CF_2CF_3$, F, Cl, Br or I substituents;

$R^{46}$ is $R^{47}$, $R^{48}$ or $R^{49}$;

R⁴⁷ is phenyl which is unfused or fused with arene, heteroarene or R⁴⁷ᴬ; R⁴⁷ᴬ is cycloalkane, cycloalkene, heterocycloalkane or heterocycloalkene;

R⁴⁸ is heteroaryl or R⁴⁸ᴬ; R⁴⁸ᴬ is cycloalkane, cycloalkene, heterocycloalkane or heterocycloalkene;

R⁴⁹ is $C_3$-$C_6$-cycloalkyl or $C_4$-$C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or R⁴⁹ᴬ; R⁴⁹ᴬ is cycloalkane, cycloalkene, heterocycloalkane or heterocycloalkene;

wherein moieties represented by R²R³R⁴, R⁶, R⁶ᶜ, R⁸, R⁸ᴬR⁹, R¹⁰, R¹³, R¹⁴, R¹⁵, R¹⁸, R¹⁹, R²⁰, R²³, R²⁴, R²⁵, R²⁶, R²⁷, R²⁸, R²⁹, R³⁰, R³⁴, R³⁶, R³⁸, R³⁹, R⁴⁰, R⁴², R⁴³, R⁴⁴, R⁴⁷, R⁴⁸, and R⁴⁹ are independently unsubstituted, further unsubstituted, substituted or further substituted with one or two or three or four or five independently selected R⁵⁰, OR⁵⁰, SR⁵⁰, S(O)R⁵⁰, $SO_2R^{50}$, C(O)R⁵⁰, CO(O)R⁵⁰, OC(O)R⁵⁰, OC(O)OR⁵⁰, $NH_2$, NHR⁵⁰, N(R⁵⁰)₂, C(O)$NH_2$, C(O)NHR⁵⁰, C(O)N(R⁵⁰)₂, C(O)NHOH, C(O)NHOR⁵⁰, C(O)$NHSO_2R^{50}$, C(O)NR⁵⁵$SO_2R^{50}$, $SO_2NH_2$, $SO_2NHR^{50}$, $SO_2N(R^{50})_2$, $CF_3$, $CF_2CF_3$, C(O)H, C(O)OH, C(N)$NH_2$, C(N)NHR⁵⁰, C(N)N(R⁵⁰)₂, OH, (O), CN, $N_3$, $NO_2$, $CF_3$, $CF_2CF_3$, $OCF_3$, $OCF_2CF_3$, F, Cl, Br or I substituents;

R⁵⁰ is R⁵¹, R⁵², R⁵³ or R⁵⁴;

R⁵¹ is phenyl which is unfused or fused with arene, heteroarene or R⁵¹ᴮ; R⁵¹ᴮ is cycloalkane, cycloalkene, heterocycloalkane or heterocycloalkene;

R⁵² is heteroaryl;

R⁵³ is $C_3$-$C_6$-cycloalkyl or $C_4$-$C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or R⁵³ᴮ;

wherein R⁵³ᴮ is cycloalkane, cycloalkene, heterocycloalkane or heterocycloalkene;

R⁵⁴ is alkyl, alkenyl or alkynyl, each of which is unsubstituted or substituted with one or two or three independently selected R⁵⁵, OR⁵⁵, SR⁵⁵, S(O)R⁵⁵, $SO_2R^{55}$, NHR⁵⁵, N(R⁵⁵)₂, C(O)R⁵⁵, C(O)$NH_2$, C(O)NHR⁵⁵, NHC(O)R⁵⁵, $NHSO_2R^{55}$, NHC(O)OR⁵⁵, $SO_2NH_2$, $SO_2NHR^{55}$, $SO_2N(R^{55})_2$, NHC(O)$NH_2$, NHC(O)NHR⁵⁵, OH, (O), C(O)OH, (O), $N_3$, CN, $NH_2$, $CF_3$, $OCF_3$, $CF_2CF_3$, $OCF_2CF_3$, F, Cl, Br or I substituents;

R⁵⁵ is alkyl, alkenyl, alkynyl, phenyl, heteroaryl or R⁵⁶;

wherein the alkyl, alkenyl, alkynyl are unsubstituted or substituted with $OCH_3$; and R⁵⁶ is $C_3$-$C_8$-cycloalkyl or $C_4$-$C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N.

Another embodiment pertains to compounds of Formula (I), Formula (TI), Formula (III), Formula (IV), or Formula (V) wherein A¹ is C(A²); and A² is H.

Another embodiment pertains to compounds of Formula (I), Formula (II), Formula (III), Formula (IV), or Formula (V) wherein A¹ is C(A²); A² is H; and B¹ is NHR¹.

Another embodiment pertains to compounds of Formula (I), Formula (II), Formula (III), Formula (IV), or Formula (V) wherein A¹ is C(A²); A² is H; B¹ is NHR¹; and D¹ is H.

Another embodiment pertains to compounds of Formula (I), Formula (II), Formula (III), Formula (IV), or Formula (V) wherein A¹ is C(A²); A² is H; B¹ is NHR¹; D¹ is H; and E¹ is H.

Another embodiment pertains to compounds of Formula (I), Formula (II), Formula (III), Formula (IV), or Formula (V) wherein A¹ is C(A²); A² is H; B¹ is NHR¹; D¹ is H; E¹ is H; and Y¹ is $NO_2$.

Still another embodiment pertains to compounds having Formula I which are 4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;
benzamide;

4-(4-((4'-chloro-1,1'-biphenyl-2-yl)methyl)piperazin-1-yl)-2-phenoxy-N-((4-((tetrahydro-2H-pyran-4-ylmethyl)amino)phenyl)sulfonyl)benzamide;

2-(benzyloxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(2-phenylethoxy)benzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(phenylthio)benzamide;

4-(4-((4'-chloro-1,1'-biphenyl-2-yl)methyl)piperazin-1-yl)-2-(phenylthio)-N-((4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(phenylthio)benzamide;

4-(4-((4'-chloro-1,1-biphenyl-2-yl)methyl)piperazin-1-yl)-N-((3-nitro-4-((tetrahydro-2H-pyran-4-ylmethyl)amino)phenyl)sulfonyl)-2-(phenylsulfonyl)benzamide;

4-(4-((4'-chloro-1,1-biphenyl-2-yl)methyl)piperazin-1-yl)-N-((3-nitro-4-((tetrahydro-2H-pyran-4-ylmethyl)amino)phenyl)sulfonyl)-2-(phenylsulfinyl)benzamide;

2-benzyl-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

2-benzyl-4-(4-((4'-chloro-1,1'-biphenyl-2-yl)methyl)piperazin-1-yl)-N-((4-((tetrahydro-2H-pyran-4-ylmethyl)amino)phenyl)sulfonyl)benzamide;

2-(4-((4-chloro-1,1'-biphenyl-2-yl)methyl)piperazin-1-yl)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(2 phenylethyl)benzamide;

2-(benzylamino)-4-(4-((4'-chloro-1,1'-biphenyl-2-yl)methyl)piperazin-1-yl)-N-((3-nitro-4-2-anilino-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

2-anilino-4-(4-((4'-chloro-1,1'-biphenyl-2-yl)methyl)piperazin-1-yl)-N-((4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-methoxy-N-((3-nitro-4-((tetrahydro-2H-pyran-4-ylmethyl)amino)phenyl)sulfonyl)benzamide;

4-(4-((2-(4-chlorophenyl)-4,4-dimethylcyclohex-1-en-1-yl)methyl)piperazin-1-yl)-N-((4-((3-morpholin-4-ylpropyl)amino)-3-nitrophenyl)sulfonyl)-2-phenoxybenzamide;

4-(4-((2-(4-chlorophenyl)-5,5-dimethylcyclohex-1-en-1-yl)methyl)piperazin-1-yl)-N-((4-((3-morpholin-4-ylpropyl)amino)-3-nitrophenyl)sulfonyl)-2-phenoxybenzamide;

4-(4-((2-(4-chlorophenyl)-4,4-dimethylcyclohex-1-en-1-yl)methyl)piperazin-1-yl)-2-(1H-indazol-5-yloxy)-N-((4-((3-morpholin-4-ylpropyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indazol-5-yloxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-N-((4-((3-morpholin-4-ylpropyl)amino)-3-nitrophenyl)sulfonyl)-2-(1,2,3,4-tetrahydroquinolin-6-yloxy)benzamide;

4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)-2-(1,2,3,4-tetrahydroquinolin-6-yloxy)benzamide;

4-(4-((4'-chloro-4-(pyrrolidin-1-ylmethyl)-1,1-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((4'-chloro-4-(2-pyrrolidin-1-ylethyl)-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((2-(4-chlorophenyl)-4,4-dimethylcyclohex-1-en-1-yl)methyl)piperazin-1-yl)-N-((4-(((1-cyclopentylpiperidin-4-yl)amino)-3-nitrophenyl)sulfonyl)-2-(1H-indol-5-yloxy)benzamide 4-(4-((4'-chloro-1,1'-biphenyl-2-yl)methyl)-3-isobutylpiperazin-1-yl)-N-((3-nitro-4-((tetrahydro-2H-pyran-4-ylmethyl)amino)phenyl)sulfonyl)-2-phenoxybenzamide;

4-(4-((4'-chloro-1,1'-biphenyl-2-yl)methyl)piperazin-1-yl)-N-((4-(2,4-dioxo-3-azabicyclo(3.2.0)hept-3-yl)phenyl)sulfonyl)-2-phenoxybenzamide;

4-(4-((4'-chloro-1,1'-biphenyl-2-yl)methyl)piperazin-1-yl)-N-((4-(4-methyl-6-oxo-1,4,5,6-tetrahydropyridazin-3-yl)phenyl)sulfonyl)-2-phenoxybenzamide;

4-(4-((4'-chloro-1,1'-biphenyl-2-yl)methyl)piperazin-1-yl)-N-((4-(3,3-dimethyl-2-oxoazetidin-1-yl)phenyl)sulfonyl)-2-phenoxybenzamide;

4-(4-((4'-chloro-1,1-biphenyl-2-yl)methyl)piperazin-1-yl)-N-((4-(4-nitro-2H-1,2,3-triazol-2-yl)phenyl)sulfonyl)-2-phenoxybenzamide;

4-(4-((4'-chloro-1,1'-biphenyl-2-yl)methyl)piperazin-1-yl)-2-phenoxy-N-((2-(2-piperidin-1-ylethoxy)phenyl)sulfonyl)benzamide;

4-(4-((4'-chloro-1,1'-biphenyl-2-yl)methyl)piperazin-1-yl)-N-((3-(((((1-ethylpyrrolidin-2-yl)methyl)amino)carbonyl)-4-methoxyphenyl)sulfonyl)-2-phenoxybenzamide;

4-(4-((4'-chloro-1,1'-biphenyl-2-yl)methyl)piperazin-1-yl)-2-(1-naphthyloxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(2-naphthyloxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(2-naphthyloxy)benzamide;

4-(4-((4'-chloro-1,1-biphenyl-2-yl)methyl)piperazin-1-yl)-2-(2-naphthyloxy)-N-((4-((tetrahydro-2H-pyran-4-ylmethyl)amino)-3-((trifluoromethyl)sulfonyl)phenyl)sulfonyl)benzamide;

4-(4-((4'-chloro-1,1-biphenyl-2-yl)methyl)piperazin-1-yl)-N-((3-nitro-4-((tetrahydro-2H-pyran-4-ylmethyl)amino)phenyl)sulfonyl)-2-(quinolin-7-yloxy)benzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(quinolin-6-yloxy)benzamide;

4-(4-((4'-chloro-1,1'-biphenyl-2-yl)methyl)piperazin-1-yl)-2-(1H-indol-5-yloxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(isoquinolin-5-yloxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(isoquinolin-5-yloxy)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(quinolin-6-yloxy)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(1H-indol-5-yloxy)benzamide;

4-(4-((4'-chloro-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(1H-indol-4-yloxy)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(1H-indol-6-yloxy)benzamide;

4-(4-((4'-chloro-1,1'-biphenyl-2-yl)methyl)piperazin-1-yl)-2-(isoquinolin-7-yloxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(isoquinolin-7-yloxy)benzamide;

4-(4-((2-(4-chlorophenyl)-5,5-dimethylcyclohex-1-en-1-yl)methyl)piperazin-1-yl)-2-(1H-indol-5-yloxy)-N-((4-((3-morpholin-4-ylpropyl)amino)-3-nitrophenyl)sulfonyl)benzamide;

4-(4-((2-(4-chlorophenyl)-5,5-dimethylcyclohex-1-en-1-yl)methyl)piperazin-1-yl)-N-((4-((3-(dimethylamino)propyl)amino)-3-nitrophenyl)sulfonyl)-2-(1H-indol-5-yloxy)benzamide;

4-(4-((2-(4-chlorophenyl)-4,4-dimethylcyclohex-1-en-1-yl)methyl)piperazin-1-yl)-2-(1H-indol-5-yloxy)-N-((4-((3-morpholin-4-ylpropyl)amino)-3-nitrophenyl)sulfonyl)benzamide;

4-(4-((2-(4-chlorophenyl)-4,4-dimethylcyclohex-1-en-1-yl)methyl)piperazin-1-yl)-N-((4-((3-(dimethylamino)propyl)amino)-3-nitrophenyl)sulfonyl)-2-(1H-indol-5-yloxy)benzamide;

4-(4-((2-(4-chlorophenyl)-5,5-dimethylcyclohex-1-en-1-yl)methyl)piperazin-1-yl)-2-(1H-indol-4-yloxy)-N-((4-((3-morpholin-4-ylpropyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((4-((3-morpholin-4-ylpropyl)amino)-3-nitrophenyl)sulfonyl)benzamide;

4-(4-((2-(4-chlorophenyl)-5,5-dimethylcyclohex-1-en-1-yl)methyl)piperazin-1-yl)-N-((4-((3-(dimethylamino)propyl)amino)-3-nitrophenyl)sulfonyl)-2-(1H-indol-4-yloxy)benzamide;

4-(4-((2-(4-chlorophenyl)-4,4-dimethylcyclohex-1-en-1-yl)methyl)piperazin-1-yl)-N-((4-((3-(dimethylamino)propyl)amino)-3-nitrophenyl)sulfonyl)-2-(1H-indol-4-yloxy)benzamide;

4-(4-((4'-chloro-1,1'-biphenyl-2-yl)methyl)piperazin-1-yl)-2-(1H-indol-4-yloxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(1H-indol-5-yloxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-N-((4-methoxyphenyl)sulfonyl)-2-phenoxybenzamide;

4-(4-((4'-chloro-1,1'-biphenyl-2-yl)methyl)piperazin-1-yl)-N-((4-methylphenyl)sulfonyl)-2-phenoxybenzamide;

4-(4-((4'-chloro-1,1'-biphenyl-2-yl)methyl)piperazin-1-yl)-2-(1H-indol-5-yloxy)-N-((4-((tetrahydro-2H-pyran-4-ylmethyl)amino-3-((trifluoromethyl)sulfonyl)phenyl)sulfonyl)benzamide;

4-(4-((4'-chloro-1,1'-biphenyl-2-yl)methyl)piperazin-1-yl)-2-(1H-indol-4-yloxy)-N-((4-((tetrahydro-2H-pyran-4-ylmethyl)amino)-3-((trifluoromethyl)sulfonyl)phenyl)sulfonyl)benzamide;

4-(4-((4'-chloro-1,1'-biphenyl-2-yl)methyl)piperazin-1-yl)-N-((4-((3-(dimethylamino)propyl)amino)-3-((trifluoromethyl)sulfonyl)phenyl)sulfonyl)-2-(H-indol-5-yloxy)benzamide;

4-(4-((4'-chloro-1,1'-biphenyl-2-yl)methyl)piperazin-1-yl)-2-(1H-indol-4-yloxy)-N-((4-((3-morpholin-4-ylpropyl)amino)-3-((trifluoromethyl)sulfonyl)phenyl)sulfonyl)benzamide;

N-((3-((chloro(difluoro)methyl)sulfonyl)-4-((3-(dimethylamino)propyl)amino)phenyl)sulfonyl)-4-(4-((2-(4-chlorophenyl)-4,4-dimethylcyclohex-1-en-1-yl)methyl)piperazin-1-yl)-2-(1H-indol-5-yloxy)benzamide;

2-(1H-indol-4-yloxy)-4-(4-((2-(4-methoxyphenyl)-4,4-dimethylcyclohex-1-en-1-yl)methyl)piperazin-1-yl)-N-((3-nitro-4-((3-pyrrolidin-1-ylpropyl)amino)phenyl)sulfonyl)benzamide;

4-(4-((4,4-dimethyl-2-(4-(trifluoromethyl)phenyl)cyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((4,4-dimethyl-2-(4-(trifluoromethoxy)phenyl)cyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((4,4-dimethyl-2-(3-(trifluoromethyl)phenyl)cyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(3-fluorophenyl)-4,4-dimethylcyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-fluorophenyl)-4,4-dimethylcyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

N-((3-((chloro(difluoro)methyl)sulfonyl)-4-((1-methylpiperidin-4-yl)amino)phenyl)sulfonyl)-4-(4-((2-(4-chlorophenyl)-4,4-dimethylcyclohex-1-en-1-yl)methyl)piperazin-1-yl)-2-(1H-indol-5-yloxy)benzamide;

4-(4-((2-(4-chlorophenyl)cyclohex-1-en-1-yl)methyl)piperazin-1-yl)-2-(1H-indol-5-yloxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-5-yloxy)-N-((4-((I-methylpiperidin-4-yl)amino)-3-((trifluoromethyl)sulfonyl)phenyl)sulfonyl)benzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(phenoxymethyl)benzamide;

4-(4-((4'-chloro-1,1-biphenyl-2-yl)methyl)piperazin-1-yl)-N-((4-((3-morpholin-4-ylpropyl)amino)phenyl)sulfonyl)-2-phenoxybenzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(pyridin-3-yloxy)benzamide;

4-(4-((4'-chloro-1,1-biphenyl-2-yl)methyl)piperazin-1-yl)-2-(pyridin-3-yloxy)-N-((4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-((((1R)-3-(dimethylamino)-1-((phenylthio)methyl)propyl)amino)-3-nitrophenyl)sulfonyl)-2-phenoxybenzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(pyridin-4-yloxy)benzamide;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(pyridin-3-yloxy)benzamide;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(pyridin-4-yloxy)benzamide;

4-(4-((4'-chloro-1,1'-biphenyl-2-yl)methyl)piperazin-1-yl)-N-((4-((2-(4-methylpiperazin-1-yl)ethyl)amino)-3-nitrophenyl)sulfonyl)-2-phenoxybenzamide;

4-(4-((4'-chloro-1,1'-biphenyl-2-yl)methyl)piperazin-1-yl)-N-((4-((3-(4-methylpiperazin-1-yl)propyl)amino)-3-nitrophenyl)sulfonyl)-2-phenoxybenzamide;

4-(4-((4'-chloro-1,1'-biphenyl-2-yl)methyl)piperazin-1-yl)-N-((4-((3-(dimethylamino)propyl)(methyl)amino)-3-nitrophenyl)sulfonyl)-2-phenoxybenzamide;

4-(4-((4'-chloro-1,1'-biphenyl-2-yl)methyl)piperazin-1-yl)-N-((4-(((1-methylpiperidin-4-yl)methyl)amino)-3-nitrophenyl)sulfonyl)-2-phenoxybenzamide;

4-(4-((4'-chloro-1,1'-biphenyl-2-yl)methyl)piperazin-1-yl)-N-((4-(((1-methylpiperidin-4-yl)amino)-3-nitrophenyl)sulfonyl)-2-phenoxybenzamide;

4-(4-((4'-chloro-1,1'-biphenyl-2-yl)methyl)piperazin-1-yl)-N-((3-cyano-4-((3-(dimethylamino)propyl)amino)phenyl)sulfonyl)-2-phenoxybenzamide;

4-(4-((4'-chloro-1,1'-biphenyl-2-yl)methyl)piperazin-1-yl)-N-((3-nitro-4-((3-pyrrolidin-1-4-(4-((4'-chloro-1,1-biphenyl-2-yl)methyl)piperazin-1-yl)-N-((4-((3-(dimethylamino)propyl)amino)-3-(trifluoromethyl)phenyl)sulfonyl)-2-phenoxybenzamide;

4-(4-((4'-chloro-1,1'-biphenyl-2-yl)methyl)piperazin-1-yl)-N-((4-((3-(isopropyl(methyl)amino)propyl)amino)-3-nitrophenyl)sulfonyl)-2-phenoxybenzamide;

4-(4-((4'-chloro-1,1'-biphenyl-2-yl)methyl)piperazin-1-yl)-N-((4-(3-(dimethylamino)propoxy)-3-nitrophenyl)sulfonyl)-2-phenoxybenzamide;

4-(4-((2-(4-chlorophenyl)-4,4-dimethylcyclohex-1-en-1-yl)methyl)piperazin-1-yl)-2-(1H-indol-5-yloxy)-N-((4-((2-(4-methylpiperazin-1-yl)ethyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-5-yloxy)-N-((4-((3-(4-methylpiperazin-1-yl)propyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-5-yloxy)-N-((3-nitro-4-((3-pyrrolidin-1-ylpropyl)amino)phenyl)sulfonyl)benzamide 4-(4-((2-(4-chlorophenyl)-4,4-dimethylcyclohex-1-en-1-yl)methyl)piperazin-1-yl)-2-(1H-indol-5-yloxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((4-((3-(4-methylpiperazin-1-yl)propyl)amino)-3-nitrophenyl)sulfonyl)benzamide;

4-(4-((2-(4-chlorophenyl)-4,4-dimethylcyclohex-1-en-1-yl)methyl)piperazin-1-yl)-N-((4-(3-(dimethylamino)propoxy)-3-nitrophenyl)sulfonyl)-2-(1H-indol-5-yloxy)benzamide;

4-(4-((2-(4-chlorophenyl)-4,4-dimethylcyclohex-1-en-1-yl)methyl)piperazin-1-yl)-2-(1H-indol-4-yloxy)-N-((4-((2-(4-methylpiperazin-1-yl)ethyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-5-yloxy)-N-((4-(((1-methylpiperidin-4-yl)methyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((4-(((1-methylpiperidin-4-yl)methyl)amino-3-nitrophenyl)sulfonyl)benzamide;

4-(4-((2-(4-chlorophenyl)-4,4-dimethylcyclohex-1-en-1-yl)methyl)piperazin-1-yl)-N-((4-(3-(dimethylamino)propoxy)-3-nitrophenyl)sulfonyl)-2-(1H-indol-4-yloxy)benzamide;

4-(4-((2-(4-chlorophenyl)-4,4-dimethylcyclohex-1-en-1-yl)methyl)piperazin-1-yl)-2-(1H-indol-5-yloxy)-N-((4-(4-methylpiperazin-1-yl)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-4-yl oxy)-N-((3-nitro-4-((1-(2,2,2-trifluoroethyl)piperidin-4-yl)amino)phenyl)sulfonyl)benzamide;

4-(4-((2-(4-chlorophenyl)-4,4-dimethylcyclohex-1-en-1-yl)methyl)piperazin-1-yl)-N-((4-(((4-(dimethylamino)-1-methylpiperidin-4-yl)methyl)amino)-3-nitrophenyl)sulfonyl)-2-(1H-indol-5-yloxy)benzamide;

4-(4-((4'-chloro-1,1'-biphenyl-2-yl)methyl)piperazin-1-yl)-2-(2,3-dihydro-1,4-benzodioxin-5-yloxy)-N-((3-nitro-4-((tetrahydro-2H-pyran-4-ylmethyl)amino)phenyl)sulfonyl)benzamide;

5-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-1,1'-biphenyl-2-carboxamide;

5-(4-((4'-chloro-1,1'-biphenyl-2-yl)methyl)piperazin-1-yl)-N-((4-((3-(dimethylamino)propyl)amino)-3-nitrophenyl)sulfonyl)-1,1'-biphenyl-2-carboxamide;

4-(4-((4'-chloro-4-(2-(dimethylamino)ethoxy)-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;

4-(4-((4'-chloro-4-(3-piperidin-1-ylpropoxy)-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;

4-(4-((4'-chloro-4-(2-morpholin-4-ylethoxy)-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;

4-(4-((4'-chloro-4-(3-(dimethylamino)propoxy)-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;

4-(4-((4'-chloro-4-(2-morpholin-4-ylethoxy)-1,1'-biphenyl-2-yl)methyl)piperazin-1-yl)-2-phenoxy-N-((4-((tetrahydro-2H-pyran-4-ylmethyl)amino)-3-((trifluoromethyl)sulfonyl)phenyl)sulfonyl)benzamide;

4-(4-((4'-chloro-4-(3-(dimethylamino)propoxy)-1,1'-biphenyl-2-yl)methyl)piperazin-1-yl)-2-phenoxy-N-((4-((tetrahydro-2H-pyran-4-ylmethyl)amino)-3-((trifluoromethyl)sulfonyl)phenyl)sulfonyl)benzamide;

4-(4-((4'-chloro-4-(3-(dimethylamino)propoxy)-1,1'-biphenyl-2-yl)methyl)piperazin-1-yl)-2-phenoxy-N-((4-((tetrahydro-2H-pyran-4-ylmethyl)amino)-3-((trifluoromethyl)sulfonyl)phenyl)sulfonyl)benzamide;

4-(4-((4'-chloro-4-(2-(dimethylamino)ethoxy)-1,1'-biphenyl-2-yl)methyl)piperazin-1-yl)-2-phenoxy-N-((4-((tetrahydro-2H-pyran-4-ylmethyl)amino)-3-((trifluoromethyl)sulfonyl)phenyl)sulfonyl)benzamide;

4-(4-((4'-chloro-4-(2-(dimethyl amino)ethoxy)-1,1'-biphenyl-2-yl)methyl)piperazin-1-yl)-N-((3-nitro-4-((3-pyrrolidin-1-ylpropyl)amino)phenyl)sulfonyl)-2-phenoxybenzamide;

4-(4-((4'-chloro-3-(2-(dimethylamino)ethoxy)-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;

4-(4-((4'-chloro-3-(2-(dimethylamino)ethoxy)-1,1'-biphenyl-2-yl)methyl)piperazin-1-yl)-N-((3-nitro-4-((3-pyrrolidin-1-ylpropyl)amino)phenyl)sulfonyl)-2-phenoxybenzamide;

4-(4-((4'-chloro-3-(2-(dimethylamino)ethoxy)-1,1'-biphenyl-2-yl)methyl)piperazin-1-yl)-2-phenoxy-N-((4-((tetrahydro-2H-pyran-4-ylmethyl)amino)-3-((trifluoromethyl)sulfonyl)phenyl)sulfonyl)benzamide;

4-(4-((4'-chloro-4-(2-(dimethylamino)ethoxy)-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((4'-chloro-4-(2-(dimethyl amino)ethoxy)-1,1'-biphenyl-2-yl)methyl)piperazin-1-yl)-2-(1H-indol-5-yloxy)-N-((3-nitro-4-((tetrahydro-2H-pyran-4-ylmethyl)amino)phenyl)sulfonyl)benzamide;

4-(4-((4'-chloro-4-(2-morpholin-4-ylethoxy)-1,1'-biphenyl-2-yl)methyl)piperazin-1-yl)-2-(1H-indol-5-yloxy)-N-((3-nitro-4-((tetrahydro-2H-pyran-4-ylmethyl)amino)phenyl)sulfonyl)benzamide;

4-(4-((4'-chloro-3-(2-(dimethylamino)ethoxy)-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((4'-chloro-3-(2-(dimethylamino)ethoxy)-1,1'-biphenyl-2-yl)methyl)piperazin-1-yl)-2-(1H-indol-5-yloxy)-N-((3-nitro-4-((tetrahydro-2H-pyran-4-ylmethyl)amino)phenyl)sulfonyl)benzamide;

4-(4-((4'-chloro-4-(2-morpholin-4-ylethoxy)-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((4'-chloro-3-(2-morpholin-4-ylethoxy)-1,1'-biphenyl-2-yl)methyl)piperazin-1-yl)-2-ylmethyl)amino)phenyl)sulfonyl)benzamide;

4-(4-((4'-chloro-3-(2-morpholin-4-ylethoxy)-1,1'-biphenyl-2-yl)methyl)piperazin-1-yl)-2-(1H-indol-5-yloxy)-N-((3-nitro-4-((tetrahydro-2H-pyran-4-ylmethyl)amino)phenyl)sulfonyl)benzamide;

4-(4-((4'-chloro-4-(2-(dimethylamino)ethoxy)-1,1'-biphenyl-2-yl)methyl)piperazin-1-yl)-N-((4-((1-methylpiperidin-4-yl)amino)-3-nitrophenyl)sulfonyl)-2-phenoxybenzamide;

4-(4-((4'-chloro-3-(2-(dimethylamino)ethoxy)-1,1'-biphenyl-2-yl)methyl)piperazin-1-yl)-2-(1H-indol-5-yloxy)-N-((3-nitro-4-((3-pyrrolidin-1-ylpropyl)amino)phenyl)sulfonyl)benzamide;

4-(4-((4'-chloro-4-(2-(dimethylamino)ethoxy)-1,1'-biphenyl-2-yl)methyl)piperazin-1-yl)-2-(1H-indol-5-yloxy)-N-((3-nitro-4-((3-pyrrolidin-1-ylpropyl)amino)phenyl)sulfonyl)benzamide;

4-(4-((4'-chloro-4-(2-morpholin-4-ylethoxy)-1,1'-biphenyl-2-yl)methyl)piperazin-1-yl)-2-(1H-indol-5-yloxy)-N-((3-nitro-4-((3-pyrrolidin-1-ylpropyl)amino)phenyl)sulfonyl)benzamide;

4-(4-((4'-chloro-4-(2-(dimethylamino)ethoxy)-1,1'-biphenyl-2-yl)methyl)piperazin-1-yl)-N-((3-nitro-4-((1-(2,2,2-trifluoroethyl)piperidin-4-yl)amino)phenyl)sulfonyl)-2-phenoxybenzamide;

4-(4-((4'-chloro-4-(2-pyrrolidin-1-ylethoxy)-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;

4-(4-((4'-chloro-4-(2-(diisopropylamino)ethoxy)-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;

4-(4-((4'-chloro-1,1'-biphenyl-2-yl)methyl)piperazin-1-yl)-2-(2,3-dihydro-1H-indol-5-yloxy)-N-((3-nitro-4-((tetrahydro-2H-pyran-4-ylmethyl)amino)phenyl)sulfonyl)benzamide;

4-(4-((2-(4-chlorophenyl)cyclohept-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-chlorophenyl)cyclooct-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-chlorophenyl)cyclopent-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-chlorophenyl)-4,4-dimethylcyclopent-1-en-1-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((4-(4-chlorophenyl)-6,6-dimethyl-5,6-dihydro-2H-pyran-3-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((2-(4-chlorophenyl)cyclooct-1-en-1-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((2-(4-chlorophenyl)cyclohept-1-en-1-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((2-(4-chlorophenyl)cyclopent-1-en-1-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((2-(4-chlorophenyl)cyclohex-1-en-1-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((4-(4-chlorophenyl)-6,6-dimethyl-5,6-dihydro-2H-pyran-3-yl)methyl)piperazin-1-yl)-2-(1H-indol-5-yloxy)-N-((4-((1-methylpiperidin-4-yl)amino)-3-nitrophenyl)sulfonyl)benzamide;

4-(4-((2-(4-chlorophenyl)cyclohept-1-en-1-yl)methyl)piperazin-1-yl)-2-(1H-indol-5-yloxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)-2-phenoxybenzamide;

4-(4-((4'-chloro-1,1'-biphenyl-2-yl)methyl)piperazin-1-yl)-N-((4-((2-(dimethylamino)ethyl)amino)-3-nitrophenyl)sulfonyl)-2-phenoxybenzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-phenoxybenzamide;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-phenoxybenzamide;

4-(4-((4'-chloro-1,1'-biphenyl-2-yl)methyl)piperazin-1-yl)-N-((4-((4-(dimethylamino)butyl)amino)-3-nitrophenyl)sulfonyl)-2-phenoxybenzamide;

4-(4-((4'-chloro-1,1'-biphenyl-2-yl)methyl)piperazin-1-yl)-N-((3-nitro-4-((1-(phenylsulfonyl)piperidin-4-yl)amino)phenyl)sulfonyl)-2-phenoxybenzamide;

4-(4-((4'-chloro-1,1'-biphenyl-2-yl)methyl)piperazin-1-yl)-N-((3-nitro-4-((1-(quinolin-8-ylsulfonyl)piperidin-4-yl)amino)phenyl)sulfonyl)-2-phenoxybenzamide;

4-(4-((4'-chloro-1,1'-biphenyl-2-yl)methyl)piperazin-1-yl)-2-phenoxy-N-((4-((1-(phenylsulfonyl)piperidin-4-yl)amino)-3-((trifluoromethyl)sulfonyl)phenyl)sulfonyl)benzamide;

4-(4-((4'-chloro-1,1'-biphenyl-2-yl)methyl)piperazin-1-yl)-2-phenoxy-N-((4-((1-(quinolin-8-ylsulfonyl)piperidin-4-yl)amino)-3-((trifluoromethyl)sulfonyl)phenyl)sulfonyl)benzamide;

4-(4-((4'-chloro-1,1-biphenyl-2-yl)methyl)piperazin-1-yl)-N-((4-(((1S)-3-(dimethylamino)-1-thien-2-ylpropyl)amino)-3-nitrophenyl)sulfonyl)-2-phenoxybenzamide;

4-(4-((4'-chloro-1,1'-biphenyl-2-yl)methyl)piperazin-1-yl)-N-((3-nitro-4-((thien-2-ylmethyl)amino)phenyl)sulfonyl)-2-phenoxybenzamide;

4-(4-((4'-chloro-1,1'-biphenyl-2-yl)methyl)piperazin-1-yl)-2-phenoxy-N-((4-((tetrahydro-2-pyran-4-ylmethyl)amino)-3-((trifluoromethyl)sulfonyl)phenyl)sulfonyl)benzamide;

4-(4-((4'-chloro-1,1'-biphenyl-2-yl)methyl)piperazin-1-yl)-N-((3-nitro-4-((2-(1H-1,2,3-triazol-1-yl)ethyl)amino)phenyl)sulfonyl)-2-phenoxybenzamide;

4-(4-((4'-chloro-1,1'-biphenyl-2-yl)methyl)piperazin-1-yl)-N-((3-nitro-4-((2-(2H-1,2,3-triazol-2-yl)ethyl)amino)phenyl)sulfonyl)-2-phenoxybenzamide;

4-(4-((4'-chloro 1,1-biphenyl-2-yl)methyl)piperazin-1-yl)-N-((3-(dimethylamino)propyl)amino)-3-nitrophenyl)sulfonyl)-2-(2-naphthyloxy)benzamide;

4-(4-((4'-chloro-1,1'-biphenyl-2-yl)methyl)piperazin-1-yl)-N-((3-nitro-4-((2-(2-oxopyridin-1(2H)-yl)ethyl)amino)phenyl)sulfonyl)-2-phenoxybenzamide;

4-(4-((4'-chloro-1,1'-biphenyl-2-yl)methyl)piperazin-1-yl)-N-((3-nitro-4-((2-(pyridin-2-yloxy)ethyl)amino)phenyl)sulfonyl)-2-phenoxybenzamide;

4-(4-((4'-chloro-1,1'-biphenyl-2-yl)methyl)piperazin-1-yl)-N-((3-nitro-4-((2-(pyridin-4-ylethyl)amino)phenyl)sulfonyl)-2-phenoxybenzamide;

4-(4-((2-(4-chlorophenyl)-4,4-dimethylcyclohex-1-en-1-yl)methyl)piperazin-1-yl)-N-((4-((3-(dimethylamino)propyl)amino)-3-((trifluoromethyl)sulfonyl)phenyl)sulfonyl)-2-(1H-indol-5-yloxy)benzamide;

4-(4-((2-(4-chlorophenyl)-4,4-dimethylcyclohex-1-en-1-yl)methyl)piperazin-1-yl)-N-((4-((3-(dimethylamino)propyl)amino)-3-(trifluoromethyl)phenyl)sulfonyl)-2-(1H-indol-5-yloxy)benzamide;

4-(4-((2-(4-chlorophenyl)-4,4-dimethylcyclohex-1-en-1-yl)methyl)piperazin-1-yl)-N-((3-cyano-4-((3-(dimethylamino)propyl)amino)phenyl)sulfonyl)-2-(1H-indol-5-yloxy)benzamide;

4-(4-((2-(4-chlorophenyl)-4,4-dimethylcyclohex-1-en-1-yl)methyl)piperazin-1-yl)-2-(1H-indol-5-yloxy)-N-((3-nitro-4-((1-tetrahydro-2H-pyran-4-ylpiperidin-4-yl)amino)phenyl)sulfonyl)benzamide;

4-(4-((2-(4-chlorophenyl)-4,4-dimethylcyclohex-1-en-1-yl)methyl)piperazin-1-yl)-2-(1H-indol-5-yloxy)-N-((4-(4-methylpiperazin-1-yl)amino)-3-nitrophenyl)sulfonyl)benzamide;

4-(4-(1-(4'-chloro-1,1'-biphenyl-2-yl)ethyl)piperazin-1-yl)-2-(1H-indol-4-yloxy)-N-((3-nitro-4-((tetrahydro-2H-pyran-4-ylmethyl)amino)phenyl)sulfonyl)benzamide;

N-((4-(((4-aminotetrahydro-2H-pyran-4-yl)methyl)amino)-3-nitrophenyl)sulfonyl)-4-(4-((2-(4-chlorophenyl)-4,4-dimethylcyclohex-1-en-1-yl)methyl)piperazin-1-yl)-2-(H-indol-4-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

Trans-4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylcyclohexyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(H-indol-5-yloxy)-N-({4-[(2-methoxyethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3S)-tetrahydro-2H-pyran-3-ylmethyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3R)-tetrahydro-2H-pyran-3-ylmethyl]amino}phenyl)sulfonyl]benzamide;

4-(4-{[4-(4-chlorophenyl)-6,6-dimethyl-5,6-dihydro-2H-pyran-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-3-fluoro-2-(1H-indol-5-yloxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-3-fluoro-2-(1H-indol-5-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]-2-(1H-indol-4-yloxy)benzamide;

N-[(4-{[(3S,4R)-1-benzyl-3-hydroxypiperidin-4-yl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide;

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[1-(2-methoxyethyl)piperidin-4-yl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[1-(2-hydroxyethyl)piperidin-4-yl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[1-(2-methoxyethyl)piperidin-4-yl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-[(4-{[1-(3-hydroxypropyl)piperidin-4-yl]amino}-3-nitrophenyl)sulfonyl]-2-(1H-indol-4-yloxy)benzamide;

4-[4-({4'-chloro-3-[3-(dimethylamino)propyl]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-[(4-{[1-(3-hydroxypropyl)piperidin-4-yl]amino}-3-nitrophenyl)sulfonyl]-2-(1H-indol-5-yloxy)benzamide;

4-{4-[(4'-chloro-4-morpholin-4-yl-1,1'-biphenyl-2-yl)methyl]piperazin-1-yl}-2-(1H-indol-4-yloxy)-N-({3-nitro-4-[(tetrahydro-2H-pyran-4-ylmethyl)amino]phenyl}sulfonyl)benzamide;

4-[4-({4'-chloro-3-[2-(dimethylamino)ethoxy]-1,1'-biphenyl-2-yl}methyl)piperazin-1-yl]-2-(1H-indol-4-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[4-(dimethylamino)cyclohexyl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(4-morpholin-4-ylcyclohexyl)amino]-3-nitrophenyl}sulfonyl)benzamide;

4-[4-({4'-chloro-3-[2-(dimethylamino)ethoxy]-1,1'-biphenyl-2-yl}methyl)piperazin-1-yl]-2-(1H-indol-4-yloxy)-N-({4-[(1-methylpiperidin-4-yl)amino]-3-nitrophenyl}sulfonyl)benzamide;

4-{4-[1-(4'-chloro-1,1'-biphenyl-2-yl)ethyl]piperazin-1-yl}-2-(1H-indol-4-yloxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-{[4-({[4-(dimethylamino)tetrahydro-2H-pyran-4-yl]methyl}amino)-3-nitrophenyl]sulfonyl}-2-(1H-indol-5-yloxy)benzamide;

N-({4-[(2-aminocyclohexyl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide;

4-[4-({4'-chloro-4-[3-(dimethylamino)prop-1-ynyl]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[1-(4,4,4-trifluorobutyl)piperidin-4-yl]amino}phenyl)sulfonyl]benzamide;

4-(4-{[2-(4-chlorophenyl)-4,4-dimethylcyclohex-1-en-1-yl]methyl}piperazin-1-yl)-N-[(4-{[2-(4-hydroxy-1-methylpiperidin-4-yl)ethyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-2-yl)piperidin-4-yl]amino}phenyl)sulfonyl]benzamide;

4-(4-{[4'-chloro-4-(2-hydroxyethoxy)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(4-methylpiperazin-1-yl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(4,4,4-trifluorobutyl)piperidin-4-yl]amino}phenyl)sulfonyl]benzamide;

4-{4-[1-(4'-chloro-1,1'-biphenyl-2-yl)ethyl]piperazin-1-yl}-2-(1H-indol-4-yloxy)-N-({4-[(4-methylpiperazin-1-yl)amino]-3-nitrophenyl}sulfonyl)benzamide;

4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({4-[(1-methylpiperidin-4-yl)amino]-3-nitrophenyl}sulfonyl)benzamide;

4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(4-methylpiperazin-1-yl)amino]-3-[(trifluoromethyl)sulfonyl]phenyl}sulfonyl)benzamide;

4-(4-{[4'-chloro-4-(2-hydroxyethoxy)-1,1'-biphenyl-2-yl]methyl}piperazin-1-yl)-2-(1H-indol-4-yloxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[3-(3-oxopiperazin-1-yl)propyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[3-(3-oxopiperazin-1-yl)propyl]amino}phenyl)sulfonyl]benzamide;

4-(4-{[2-(4-chlorophenyl)-5-hydroxycyclohex-1-en-1-yl]methyl}piperazin-1-yl)-2-(1H-indol-5-yloxy)-N-({4-[(1-methylpiperidin-4-yl)amino]-3-nitrophenyl}sulfonyl)benzamide;

4-(4-{[2-(4-chlorophenyl)-5-hydroxycyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-5-hydroxycyclohex-1-en-1-yl]methyl}piperazin-1-yl)-2-(1H-indol-5-yloxy)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[1-(2,3-dihydro-1H-inden-2-yl)piperidin-4-yl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-N-[(4-{[1-(2,3-dihydro-1H-inden-2-yl)piperidin-4-yl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(1-morpholin-4-ylcyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-2-ylmethyl)piperidin-4-yl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-4-ylmethyl)piperidin-4-yl]amino}phenyl)sulfonyl]benzamide;

4-(4-{[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[4-(2-hydroxyethyl)piperazin-1-yl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(3S)-1-methylpyrrolidin-3-yl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-[(4-{[1-(3-fluoropropyl)piperidin-4-yl]amino}-3-nitrophenyl)sulfonyl]-2-(1H-indol-5-yloxy)benzamide;

4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({3-nitro-4-[(tetrahydro-2H-pyran-4-ylmethyl)amino]phenyl}sulfonyl)benzamide;

N-[(4-{[(4-aminotetrahydro-2H-pyran-4-yl)methyl]amino}-3-nitrophenyl)sulfonyl]-4-[4-{[2-(4-chlorophenyl)-4,4-dimethylcyclohex-1-en-1-yl]methyl}-3-(hydroxymethyl)piperazin-1-yl]-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[(1-hydroxycyclohexyl)methyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(2-methoxyethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[4-(hydroxymethyl)tetrahydro-2H-pyran-4-yl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[4-(hydroxymethyl)tetrahydro-2H-pyran-4-yl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-N-({4-[(2-hydroxy-1-tetrahydro-2H-pyran-4-ylethyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[3-nitro-4-({1-[2-(1H-pyrazol-1-yl)ethyl]piperidin-4-yl}amino)phenyl]sulfonyl}benzamide;

4-(4-{[2-(4-chlorophenyl)-4,4-dimethylcyclohex-1-en-1-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-{[4-(methylamino)-3-nitrophenyl]sulfonyl}benzamide;

4-(4-{[2-(4-chlorophenyl)-4,4-dimethylcyclohex-1-en-1-yl]methyl}piperazin-1-yl)-2-(1H-indol-4-yloxy)-N-{[4-(methylamino)-3-nitrophenyl]sulfonyl}benzamide;

4-{4-[1-(4'-chloro-1,1'-biphenyl-2-yl)ethyl]piperazin-1-yl}-2-(1H-indol-4-yloxy)-N-({4-[(3-morpholin-4-ylpropyl)amino]-3-nitrophenyl}sulfonyl)benzamide;

4-(4-{[2-(4-chlorophenyl)-5-hydroxycyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-5-morpholin-4-ylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

N-[(4-{[(1-aminocyclohexyl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(2-oxopyrrolidin-1-yl)ethyl]amino}phenyl)sulfonyl]benzamide;

4-{4-[1-(4'-chloro-1,1'-biphenyl-2-yl)ethyl]piperazin-1-yl}-2-(1H-indol-5-yloxy)-N-({3-nitro-4-[(tetrahydro-2H-pyran-4-ylmethyl)amino]phenyl}sulfonyl)benzamide;

4-(4-{1-[2-(4-chlorophenyl)-4,4-dimethylcyclohex-1-en-1-yl]ethyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{1-[2-(4-chlorophenyl)-4,4-dimethylcyclohex-1-en-1-yl]ethyl}piperazin-1-yl)-2-(1H-indol-5-yloxy)-N-({4-[(4-methylpiperazin-1-yl)amino]-3-nitrophenyl}sulfonyl)benzamide;

4-{4-[(1R)-1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide;

4-{4-[(1S)-1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide;

4-(4-{1-[2-(4-chlorophenyl)-4,4-dimethylcyclohex-1-en-1-yl]ethyl}piperazin-1-yl)-2-(1H-indol-5-yloxy)-N-({4-[(3-morpholin-4-ylpropyl)amino]-3-nitrophenyl}sulfonyl)benzamide;

4-(4-{1-[2-(4-chlorophenyl)-4,4-dimethylcyclohex-1-en-1-yl]ethyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-N-({4-[(cyclohexylmethyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[4-(morpholin-4-ylamino)-3-nitrophenyl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-3-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-{[4-(morpholin-4-ylamino)-3-nitrophenyl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(tetrahydro-2H-pyran-4-ylamino)phenyl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(3-methyloxetan-3-yl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-({4-[(4-methoxycyclohexyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[3-(1,1-dioxidothiomorpholin-4-yl)propyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(H-indol-5-yloxy)-N-[(3-nitro-4-{[2-(2-oxopiperidin-1-yl)ethyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(2-oxoimidazolidin-1-yl)ethyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2-pyridin-4-ylethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(4-morpholin-4-yl-3-nitrophenyl)sulfonyl]benzamide;

4-(4-{[2-(4-chlorophenyl)-4,4-dimethylcyclohex-1-en-1-yl]methyl}piperazin-1-yl)-2-(1 1H-indol-5-yloxy)-N-{[4-(4-methoxypiperidin-1-yl)-3-nitrophenyl]sulfonyl}benzamide;

4-(4-{[2-(4-chlorophenyl)-5-pyrrolidin-1-ylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(3-oxopiperazin-1-yl)ethyl]amino}phenyl)sulfonyl]benzamide;

4-[4-({4'-chloro-4-[2-(dimethylamino)ethoxy]-1,1'-biphenyl-2-yl}methyl)piperazin-1-yl]-2-(1H-indol-4-yloxy)-N-({4-[(4-methylpiperazin-1-yl)amino]-3-nitrophenyl}sulfonyl)benzamide;

4-(4-{[2-(4-chlorophenyl)-4,4-dimethylcyclohex-4-en-1-yl]methyl}piperazin-1-yl)-N-[(4-{[(1,1-dioxidotetrahydrothien-3-yl)methyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-N-({4-[(1,1-dioxidotetrahydrothien-3-yl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[4-[(tetrahydro-2H-pyran-4-ylmethyl)amino]-3-(trifluoromethyl)phenyl]sulfonyl}benzamide;

4-(4-{[2-(4-chlorophenyl)-4,4-dimethylcyclohex-1-en-1-yl]methyl}piperazin-1-yl)-N-({4-[2-(1,3-dioxolan-2-yl)ethyl]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(tetrahydro-2H-pyran-4-ylmethoxy)phenyl]sulfonyl}benzamide;

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[2-(3-oxopiperazin-1-yl)ethyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-({4-[(1-methyl-5-oxopyrrolidin-3-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(1 1H-indol-5-yloxy)-N-({4-[(1-methyl-6-oxopiperidin-3-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-{[3-nitro-4-(piperidin-1-ylamino)phenyl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(piperidin-1-ylamino)phenyl]sulfonyl}benzamide;

4-(4-{[4-(4-chlorophenyl)-1-methyl-1H-pyrazol-5-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(3-methyloxetan-3-yl)methoxy]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(1-oxidotetrahydro-2H-thiopyran-4-yl)methyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1,3-thiazol-5-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-{[3-nitro-4-(tetrahydro-2H-pyran-4-ylmethoxy)phenyl]sulfonyl}benzamide;

4-(4-{[2-(4-chlorophenyl)-5,5-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2-tetrahydro-2H-pyran-4-ylethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[2-(trifluoromethoxy)ethyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[2-(2-methoxyethoxy)ethyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[3-(methylsulfonyl)propyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-[(4-{[3-(1,1-dioxidothiomorpholin-4-yl)propyl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(2-tetrahydro-2H-pyran-4-ylethyl)phenyl]sulfonyl}benzamide;

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[2-(2-methoxyethoxy)ethyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-({4-[(1,1-dioxidotetrahydrothien-3-yl)amino]-3-nitrophenyl}sulfonyl)-2-(1H-indol-4-yloxy)benzamide;

4-(4-{[2-(4 chlorophenyl)-4,4-dimethylcyclohex-1-en-1-yl]methyl}piperazin-1-yl)-2-(1H-indol-5-yloxy)-N-[(3-nitro-4-{[2-(trifluoromethoxy)ethyl]amino}phenyl)sulfonyl]benzamide;

4-(4-{[2-(4-chlorophenyl)-4,4-dimethylcyclohex-1-en-1-yl]methyl}piperazin-1-yl)-N-[(4-{[(1,1-dioxidotetrahydro-2H-thiopyran-4-yl)methyl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-N-({4-[(2,2-difluoroethyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(tetrahydro-2H-pyran-4-ylmethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(tetrahydro-2H-pyran-4-ylmethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-N-({4-[(4,4-difluorocyclohexyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-indol-4-yloxy)benzamide;

4-(4-{[4-(4-chlorophenyl)-1-isopropyl-6-oxo-1,6-dihydropyridin-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(tetrahydro-2H-pyran-4-ylmethyl)amino]carbonyl}phenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-({4-[(2-methoxyethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-{[3-nitro-4-(2-tetrahydro-2H-pyran-4-ylethoxy)phenyl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-({4-[(2-methoxyethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-({4-[3-(methylsulfonyl)propoxy]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(3-methoxypropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(3-methoxypropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-indol-4-yloxy)benzamide;

4-(4-{[2-(4-chlorophenyl)-4,4-dimethylcyclohex-1-en-1-yl]methyl}piperazin-1-yl)-N-{[4-({[(3R)-4-hydroxy-1-adamantyl]methyl}amino)-3-nitrophenyl]sulfonyl}-2-(1H-indol-5-yloxy)benzamide;

4-(4-{[2-(4-chlorophenyl)-4,4-dimethylcyclohex-1-en-1-yl]methyl}piperazin-1-yl)-N-{[4-({[Cis-4-hydroxy-1-adamantyl]methyl}amino)-3-nitrophenyl]sulfonyl}-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({3-nitro-4-[(3,3,3-trifluoropropyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(3,3,3-trifluoropropyl)amino]phenyl}sulfonyl)benzamide;

N-({5-bromo-6-[(tetrahydro-2H-pyran-4-ylmethyl)amino]pyridin-3-yl}sulfonyl)-4-(4-{[2-(4-chlorophenyl)-4,4-dimethylcyclohex-1-en-1-yl]methyl}piperazin-1-yl)-2-(1H-indol-4-yloxy)benzamide;

4-(4-{[2-(4-chlorophenyl)-4,4-dimethylcyclohex-1-en-1-yl]methyl}piperazin-1-yl-N-[(4-{[(1,1-dioxidotetrahydrothien-3-yl)methyl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({4-(methylamino)-3-[(trifluoromethyl)sulfonyl]phenyl}sulfonyl)benzamide;

N-{[5-bromo-6-(tetrahydro-2H-pyran-4-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-indol-5-yloxy)benzamide;

4-(4-{[4-(4-chlorophenyl)-6-isopropoxypyridin-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-{[6-(tetrahydro-2H-pyran-4-ylmethoxy)-5-(1,3-thiazol-2-yl)pyridin-3-yl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(2-methoxyethyl)amino]carbonyl}phenyl)sulfonyl]benzamide;

4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-indol-5-yloxy)benzamide;

N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[1-(methylsulfonyl)piperidin-4-yl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-(1H-indol-5-yloxy)benzamide;

N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[1-(methylsulfonyl)piperidin-4-yl]amino}-3-nitrophenyl)sulfonyl]benzamide;

4-(4-{[4'-chloro-5-(trifluoromethyl)-1,1'-biphenyl-2-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[4'-chloro-5-(trifluoromethyl)-1,1'-biphenyl-2-yl]methyl}-piperazin-1-yl)-2-(1H-indol-5-yloxy)-N-{[3-nitro-4-(tetrahydro-2H-pyran-4-ylmethoxy)phenyl]sulfonyl}benzamide;

4-{4-[(5-tert-butyl-4'-chloro-1,1'-biphenyl-2-yl)methyl]piperazin-1-yl}-2-(1H-indol-5-yloxy)-N-({3-nitro-4-[(tetrahydro-2H-pyran-4-ylmethyl)amino]phenyl}sulfonyl)benzamide;

4-{4-[(5-tert-butyl-4'-chloro-1,1'-biphenyl-2-yl)methyl]piperazin-1-yl}-2-(1H-indol-5-yloxy)-N-{[3-nitro-4-(tetrahydro-2H-pyran-4-ylmethoxy)phenyl]sulfonyl}benzamide;

4-(4-{[2-(4-chlorophenyl)-4,4-dimethylcyclohex-1-en-1-yl]methyl}piperazin-1-yl)-2-(1H-indol-4-yloxy)-N-({3-nitro-4-[(2,2,2-trifluoroethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2,2,2-trifluoroethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-{[(tetrahydro-2H-pyran-4-ylmethyl)amino]carbonyl}phenyl)sulfonyl]benzamide;

4-(4-{[2-(4-chlorophenyl)-4,4-dimethylcyclohex-1-en-1-yl]methyl}piperazin-1-yl)-N-({4-[(2R)-1,4-dioxan-2-ylmethoxy]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-N-({4-[(2S)-1,4-dioxan-2-ylmethoxy]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(3-morpholin-4-ylpropyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(3-morpholin-4-ylpropyl)amino]-3-[(trifluoromethyl)sulfonyl]phenyl}sulfonyl)benzamide;

N-({5-bromo-6-[(tetrahydro-2H-pyran-4-ylmethyl)amino]pyridin-3-yl}sulfonyl)-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(2-morpholin-4-ylethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-N-({5-cyano-6-[(tetrahydro-2H-pyran-4-ylmethyl)amino]pyridin-3-yl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)oxy]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)methoxy]-3-nitrophenyl}sulfonyl)benzamide;

4-(4-{[4-(4-chlorophenyl)-1-(3-hydroxypropyl)-1,2,5,6-tetrahydropyridin-3-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide;

benzyl 4-({[4-({[4-(4-{[2-(4-chlorophenyl)-4,4-dimethylcyclohex-1-en-1-yl]methyl}piperazin-1-yl)-2-(1H-indol-5-yloxy)benzoyl]amino}sulfonyl)-2-nitrophenyl]amino}methyl)piperidine-1-carboxylate;

N-{[3-(aminocarbonyl)-4-(tetrahydro-2H-pyran-4-ylmethoxy)phenyl]sulfonyl}-4-(4-{[2-(4-chlorophenyl)-4,4-dimethylcyclohex-1-en-1-yl]methyl}piperazin-1-yl)-2-(1H-indol-5-yloxy)benzamide;

4-(4-{[4'-chloro-5-(trifluoromethyl)-1,1'-biphenyl-2-yl]methyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide;

4-{4-[(5-tert-butyl-4'-chloro-1,1'-biphenyl-2-yl)methyl]piperazin-1-yl}-2-(1H-indol-5-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(1-methyl-1H-imidazol-5-yl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-{[4-(morpholin-4-ylsulfonyl)phenyl]sulfonyl}benzamide;

4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(H-indol-5-yloxy)-N-({4-[(4-morpholin-4-ylcyclohexyl)amino]-3-nitrophenyl}sulfonyl)benzamide;

N-{[5-bromo-6-(tetrahydro-2H-pyran-4-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-{[6-[(tetrahydro-2H-pyran-4-ylmethyl)amino]-5-(1,3-thiazol-2-yl)pyridin-3-yl]sulfonyl}benzamide;

4-(4-{[2-(4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-indol-4-yloxy)benzamide;

4-(4-{[2-(4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-N-({4-[(3,3-dimethylbutyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[(1S)-1-(hydroxymethyl)-3-methylbutyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(2R)-tetrahydrofuran-2-ylmethyl]amino}phenyl)sulfonyl]benzamide;

4-(4-{[2-(4-chlorophenyl)-4,4-dimethylcyclohex-1-en-1-yl]methyl}piperazin-1-yl)-N-[(4-{[(1R)-1-(hydroxymethyl)-2-methylpropyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(4-methoxyphenyl)amino]-3-nitrophenyl}sulfonyl)benzamide;

N-[(4-{[2-(1,3-benzodioxol-5-yl)ethyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[3-(2-oxopyrrolidin-1-yl)propyl]amino}phenyl)sulfonyl]benzamide;

4-(4-{[2-(4-chlorophenyl)-4,4-dimethylcyclohex-1-en-1-yl]methyl}piperazin-1-yl)-N-({4-[(4-hydroxyphenyl)amino]-3-nitrophenyl}sulfonyl)-2-(1H-indol-5-yloxy)benzamide; N-{[4-({2-[4-(aminosulfonyl)phenyl]ethyl}amino)-3-nitrophenyl]sulfonyl}-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[3-(1H-imidazol-1-yl)propyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(1S)-1-phenylethyl]amino}phenyl)sulfonyl]benzamide;

N-({2-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[2-(2-methoxyethoxy)ethyl]thio}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[2-(2-methoxyethoxy)ethyl]thio}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-{[4-(methylsulfonyl)phenyl]sulfonyl}benzamide;

4-(4-{[2-(4-chlorophenyl)-4,4-dimethylcyclohex-1-en-1-yl]methyl}piperazin-1-yl)-2-(1H-indol-4-yloxy)-N-{[4-(methylsulfonyl)phenyl]sulfonyl}benzamide;

4-(4-{[2-(4-chlorophenyl)-4,4-dimethylcyclohex-1-en-1-yl]methyl}piperazin-1-yl)-N-({4-[(2,2-dimethyltetrahydro-2H-pyran-4-yl)methoxy]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-indol-4-yloxy)benzamide;

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-indol-4-yloxy)benzamide;

4-(4-{[2-(4-chlorophenyl)-4,4-dimethylcyclohex-1-en-1-yl]methyl}piperazin-1-yl)-N-{[5-cyano-6-(morpholin-4-ylethoxy)pyridin-3-yl]sulfonyl}-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)oxy]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylbut-2-ynyl)oxy]-3-nitrophenyl}sulfonyl)benzamide;

4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-(1H-indol-4-yloxy)benzamide;

4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-indol-4-yloxy)benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-4-yloxy)benzamide;

4-(4-{[2-(4-chlorophenyl)-4,4-dimethylcyclohex-1-en-1-yl]methyl}piperazin-1-yl)-N-({4-[(3-hydroxy-4-methoxyphenyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(2,3-dihydro-1H-indol-4-yloxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(pyridin-3-ylamino)benzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(pyridin-3-ylamino)benzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(pyridin-3-yloxy)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1,2,3,4-tetrahydroisoquinolin-5-yloxy)benzamide;

4-(4-{[2-(4-chlorophenyl)-4,4-dimethylcyclohex-1-en-1-yl]methyl}piperazin-1-yl)-2-(1H-indazol-4-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indazol-4-yloxy)-N-({3-nitro-4-[(1-tetrahydro-2H-pyran-4-ylpiperidin-4-yl)amino]phenyl}sulfonyl)benzamide;

Trans-4-(4-{[2-(4-chlorophenyl)-4,4-dimethylcyclohex-1-en-1-yl]methyl}piperazin-1-yl)-2-(1H-indazol-4-yloxy)-N-({4-[(4-morpholin-4-ylcyclohexyl)amino]-3-nitrophenyl}sulfonyl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indol-4-yloxy)benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indazol-4-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide;

2-(1H-benzimidazol-4-yloxy)-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-indazol-4-yloxy)benzamide;

4-(4-{[2-(4-chlorophenyl)-4,4-dimethylcyclohex-1-en-1-yl]methyl}piperazin-1-yl)-N-({[6-[(4-fluorotetrahydro-2H- pyran-4-yl)methoxy]-5-(trifluoromethyl)pyridin-3-yl]sulfonyl}-2-(1H-indazol-4-yloxy)benzamide;

4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]-2-(1H-indazol-4-yloxy)benzamide;

4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-indazol-4-yloxy)benzamide;

N-[(5-chloro-6-{[(4-fluorotetrahydro-2H-pyran-4-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

Trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(2,2-difluoroethyl)morpholin-2-yl]methyl}amino)-3-nitrophenyl]sulfonyl}benzamide;

4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-indazol-4-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-N-{[5-chloro-6-(tetrahydrofuran-3-ylmethoxy)pyridin-3-yl]sulfonyl}-2-(1H-indazol-4-yloxy)benzamide;

Trans-N-({5-chloro-6-[(4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

N-[(5-chloro-6-{[(3R)-1-(2,2-difluoroethyl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-(indazol-4-yloxy)benzamide;

2-(1H-benzimidazol-4-yloxy)-N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)benzamide;

2-(1H-benzimidazol-4-yloxy)-N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)benzamide;

N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-indazol-4-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(cyanomethyl)pyrrolidin-3-yl]amino}-3-nitrophenyl)sulfonyl]benzamide;

2-(1H-benzimidazol-4-yloxy)-4-(4-{[2-(4-chlorophenyl)-4,4-dimethylcyclohex-1-en-1-yl]methyl}piperazin-1-yl)-N-{[4-({(3R)-1-[2-(2-methoxyethoxy)ethyl]pyrrolidin-3-yl}amino)-3-nitrophenyl]sulfonyl}benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(N,N-dimethylglycyl)pyrrolidin-3-yl]amino}-3-nitrophenyl)sulfonyl]benzamide;

2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(cyanomethyl)morpholin-2-yl]methyl}amino)-3-nitrophenyl]sulfonyl}benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(3-nitro-4-{[(4-oxetan-3-ylmorpholin-2-yl)methyl]amino}phenyl)sulfonyl]benzamide;

N-{[5-chloro-6-({(3R)-1-[2-fluoro-1-(fluoromethyl)ethyl]pyrrolidin-3-yl}oxy)pyridin-3-yl]sulfonyl}-4-(4-{[2-(4-chlorophenyl)-4,4-dimethylcyclohex-1-en-1-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-indazol-4-yloxy)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(1H-indazol-4-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-{[4-({[(2R)-4-(N,N-dimethylglycyl)morpholin-2-yl]methyl}amino)-3-nitrophenyl]sulfonyl}benzamide;

2-(1H-benzimidazol-4-yloxy)-4-(4-{[2-(4-chlorophenyl)-4,4-dimethylcyclohex-1-en-1-yl]methyl}piperazin-1-yl)-N-{[4-({[(2S)-4-(N,N-dimethylglycyl)morpholin-2-yl]methyl}amino)-3-nitrophenyl]sulfonyl}benzamide;

2-(1H-benzimidazol-4-yloxy)-4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)benzamide;

Trans-2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]benzamide;

2-(1H-benzimidazol-4-yloxy)-4-(4-{[2-(4-chlorophenyl)-4,4-dimethylcyclohex-1-en-1-yl]methyl}piperazin-1-yl)-N-

({5-fluoro-6-[(4-fluorotetrahydro-2H-pyran-4-yl)methoxy]pyridin-3-yl}sulfonyl)benzamide;

2-(1H-benzimidazol-4-yloxy)-N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)benzamide;

N-{[5-chloro-6-({(3R)-1-[2-fluoro-1-(fluoromethyl)ethyl]pyrrolidin-3-yl}methoxy)pyridin-3-yl]sulfonyl}-4-(4-{[2-(4-chlorophenyl)-4,4-dimethylcyclohex-1-en-1-yl]methyl}piperazin-1-yl)-2-(1H-indazol-4-yloxy)benzamide;

N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

Trans-4-(4-{[2-(4-chlorophenyl)-4,4-dimethylcyclohex-1-en-1-yl]methyl}piperazin-1-yl)-2-(1H-indazol-4-yloxy)-N-[(4-{[(4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indazol-4-yloxy)benzamide;

N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

2-(1H-benzimidazol-4-yloxy)-N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)benzamide;

Trans-2-(1H-benzimidazol-4-yloxy)-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]benzamide;

2-(1H-benzimidazol-4-yloxy)-4-(4-{[2-(4-chlorophenyl)-4,4-dimethylcyclohex-1-en-1-yl]methyl}piperazin-1-yl)-N-({4-[({(2R)-4-[2-(2-methoxyethoxy)ethyl]morpholin-2-yl}methyl)amino]-3-nitrophenyl}sulfonyl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]benzamide;

N-[(4-{[(4-acetylmorpholin-2-yl)methyl]amino}-3-nitrophenyl)sulfonyl]-2-(1H-benzimidazol-4-yloxy)-4-(4-{[2-(4-chlorophenyl)-4,4-dimethylcyclohex-1-en-1-yl]methyl}piperazin-1-yl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(methylsulfonyl)morpholin-2-yl]methyl}amino)-3-nitrophenyl]sulfonyl}benzamide;

4-(4-{[2-(4-chlorophenyl)-4,4-dimethylcyclohex-1-en-1-yl]methyl}piperazin-1-yl)-N-{[6-({4-fluoro-1-[2-fluoro-1-(fluoromethyl)ethyl]piperidin-4-yl}methoxy)-5-(trifluoromethyl)pyridin-3-yl]sulfonyl}-2-(1H-indazol-4-yloxy)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-phenoxybenzamide;

4-(4-{[2-(4-chlorophenyl)-4,4-dimethylcyclohex-1-en-1-yl]methyl}piperazin-1-yl)-N-{[5-chloro-6-(2-tetrahydrofuran-2-ylethoxy)pyridin-3-yl]sulfonyl}-2-(1H-indazol-4-yloxy)benzamide;

Trans-2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide;

2-(1H-benzimidazol-4-yloxy)-N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)benzamide;

N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

N-({5-chloro-6-[(4-fluorotetrahydro-2H-pyran-4-yl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-N-{[5-cyano-6-(2-tetrahydro-2H-pyran-4-ylethoxy)pyridin-3-yl]sulfonyl}-2-(1H-indazol-4-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(1R,5S)-8-methyl-8-azabicyclo[3.2.1]oct-3-yl]amino}-3-nitrophenyl)sulfonyl]benzamide;

N-({3-nitro-4-[(tetrahydro-2H-pyran-4-ylmethyl)amino]phenyl}sulfonyl)-2-phenoxy-4-(4-{(3-phenylpropanoyl)[(1S,2S,3S,5R)-2,6,6-trimethylbicyclo[3.1.1]hept-3-yl]amino}piperidin-1-yl)benzamide;

N-({4-[(3-morpholin-4-ylpropyl)amino]-3-nitrophenyl}sulfonyl)-2-phenoxy-4-(4-{(3-phenylpropanoyl)[(1S,2S,3S,5R)-2,6,6-trimethylbicyclo[3.1.1]hept-3-yl]amino}piperidin-1-yl)benzamide;

N-({3-nitro-4-[(tetrahydro-2H-pyran-4-ylmethyl)amino]phenyl}sulfonyl)-2-phenoxy-4-(4-{(3-phenylpropyl)[(1S,2S,3S,5R)-2,6,6-trimethylbicyclo[3.1.1]hept-3-yl]amino}piperidin-1-yl)benzamide;

N-({4-[(3-morpholin-4-ylpropyl)amino]-3-nitrophenyl}sulfonyl)-2-phenoxy-4-(4-{(3-phenylpropyl)[(1S,2S,3S,5R)-2,6,6-trimethylbicyclo[3.1.1]hept-3-yl]amino}piperidin-1-yl)benzamide;

4-[4-(2-{[(1R,5S)-8-methyl-8-azabicyclo[3.2.1]oct-3-yl]amino}benzyl)piperazin-1-yl]-N-({4-[(3-morpholin-4-ylpropyl)amino]-3-nitrophenyl}sulfonyl)-2-phenoxybenzamide;

4-[4-(2-{[(1R,5S)-8-methyl-8-azabicyclo[3.2.1]oct-3-yl]amino}benzyl)piperazin-1-yl]-N-({3-nitro-4-[(tetrahydro-2H-pyran-4-ylmethyl)amino]phenyl}sulfonyl)-2-phenoxybenzamide;

4-{4-[2-(3-azabicyclo[3.2.2]non-3-yl)benzyl]piperazin-1-yl}-N-({3-nitro-4-[(tetrahydro-2H-pyran-4-ylmethyl)amino]phenyl}sulfonyl)-2-phenoxybenzamide;

4-{4-[2-(3-azabicyclo[3.2.2]non-3-yl)benzyl]piperazin-1-yl}-2-phenoxy-N-({4-[(tetrahydro-2H-pyran-4-ylmethyl)amino]-3-[(trifluoromethyl)sulfonyl]phenyl}sulfonyl)benzamide;

4-{4-[2-(3-azabicyclo[3.2.2]non-3-yl)benzyl]piperazin-1-yl}-2-phenoxy-N-({4-[(tetrahydro-2H-pyran-4-ylmethyl)amino]phenyl}sulfonyl)benzamide;

4-{4-[2-(3-azabicyclo[3.2.2]non-3-yl)benzyl]piperazin-1-yl}-N-({4-[(3-morpholin-4-ylpropyl)amino]-3-nitrophenyl}sulfonyl)-2-phenoxybenzamide;

4-(4-{2-[(4R,7S)-2,3,3a,4,7,7a-hexahydro-1H-4,7-methanoinden-5-yl]benzyl}piperazin-1-yl)-N-({3-nitro-4-[(tetrahydro-2H-pyran-4-ylmethyl)amino]phenyl}sulfonyl)-2-phenoxybenzamide;

4-[4-(2-{5-[(1R,5S)-8-azabicyclo[3.2.1]oct-8-ylmethyl]thien-2-yl}benzyl)piperazin-1-yl]-N-({3-nitro-4-[(tetrahydro-2H-pyran-4-ylmethyl)amino]phenyl}sulfonyl)-2-phenoxybenzamide;

4-[4-(2-{5-[(1R,5S)-8-azabicyclo[3.2.1]oct-8-ylmethyl]thien-2-yl}benzylidene)piperidin-1-yl]-N-({3-nitro-4-[(tetrahydro-2H-pyran-4-ylmethyl)amino]phenyl}sulfonyl)-2-phenoxybenzamide;

4-[4-(3-{5-[(1R,5S)-8-azabicyclo[3.2.1]oct-8-ylmethyl]thien-2-yl}benzyl)piperazin-1-yl]-N-({3-nitro-4-[(tetrahydro-2H-pyran-4-ylmethyl)amino]phenyl}sulfonyl)-2-phenoxybenzamide;

and therapeutically acceptable salts, prodrugs, salts of prodrugs and metabolites thereof.

Another embodiment pertains to a composition for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said composition comprising an excipient and a therapeutically effective amount of the compound of Formula (I).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient a therapeutically effective amount of Formula (I).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient therapeutically effective amount of the compound of Formula (I) and a therapeutically effective amount of one additional therapeutic agent or more than one additional therapeutic agent.

DETAILED DESCRIPTION OF THE INVENTION

Variable moieties herein are represented by identifiers (capital letters with numerical and/or alphabetical superscripts) and may be specifically embodied.

It is meant to be understood that proper valences are maintained for all moieties and combinations thereof, that monovalent moieties having more than one atom are drawn from left to right and are attached through their left ends, and that divalent moieties are also drawn from left to right.

It is also meant to be understood that a specific embodiment of a variable moiety herein may be the same or different as another specific embodiment having the same identifier.

The term "alkenyl" as used herein, means a straight or branched hydrocarbon chain containing from 2 to 10 carbons and containing at least one carbon-carbon double bond. The term "$C_x$-$C_y$ alkyl" means a straight or branched hydrocarbon chain containing at least one carbon-carbon double bond containing x to y carbon atoms. The term "$C_3$-$C_6$ alkenyl" means an alkenyl group containing 3-6 carbon atoms. Representative examples of alkenyl include, but are not limited to, buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double bond. The term "$C_x$-$C_y$ alkylene" means a divalent group derived from a straight or branched hydrocarbon chain containing at least one carbon-carbon double bond and containing x to y carbon atoms. Representative examples of alkenylene include, but are not limited to, —CH═CH— and —CH$_2$CH═CH—.

The term "alkyl" as used herein, means a straight or branched, saturated hydrocarbon chain containing from 1 to 10 carbon atoms. The term "$C_x$-$C_y$ alkyl" means a straight or branched chain, saturated hydrocarbon containing x to y carbon atoms. For example "$C_1$-$C_6$ alkyl" means a straight or branched chain, saturated hydrocarbon containing 2 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched, saturated hydrocarbon chain of 1 to 10 carbon atoms, for example, of 1 to 4 carbon atoms. The term "$C_x$-$C_y$ alkylene" means a divalent group derived from a straight or branched chain, saturated hydrocarbon containing x to y carbon atoms. For example "$C_2$-$C_6$ alkylene" means a straight or branched chain, saturated hydrocarbon containing 2 to 6 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_x$-$C_y$ alkynyl" means a straight or branched chain hydrocarbon group containing from x to y carbon atoms. For example "$C_3$-$C_6$ alkynyl" means a straight or branched chain hydrocarbon group containing from 3 to 6 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "alkynylene," as used herein, means a divalent radical derived from a straight or branched chain hydrocarbon group containing from 2 to 10 carbon atoms and containing at least one carbon-carbon triple bond.

The term "aryl" as used herein, means phenyl.

The term "cyclic moiety," as used herein, means benzene, phenyl, phenylene, cycloalkane, cycloalkyl, cycloalkylene, cycloalkene, cycloalkenyl, cycloalkenylene, cycloalkyne, cycloalkynyl, cycloalkynylene, heteroarene, heteroaryl, heterocycloalkane, heterocycloalkyl, heterocycloalkene, heterocycloalkenyl and spiroalkyl.

The term "cycloalkylene" or cycloalkyl" or "cycloalkane" as used herein, means a monocyclic or bridged hydrocarbon ring system. The monocyclic cycloalkyl is a carbocyclic ring system containing three to ten carbon atoms, zero heteroatoms and zero double bonds.

Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Representative examples of such bridged cycloalkyl ring systems include, but are not limited to, bicyclo[3.1.1]heptane, bicyclo[2.2.1]heptane, bicyclo[2.2.2]octane, bicyclo[3.2.1]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic and bridged cycloalkyl can be attached to the parent molecular moiety through any substitutable atom contained within the ring system.

The term "cycloalkenylene," or "cycloalkenyl" or "cycloalkene" as used herein, means a monocyclic or a bridged hydrocarbon ring system. The monocyclic cycloalkenyl has four to ten carbon atoms and zero heteroatoms. The four-membered ring systems have one double bond, the five- or six-membered ring systems have one or two double bonds, the seven- or eight-membered ring systems have one, two, or three double bonds, and the nine- or ten-membered rings have one, two, three, or four double bonds. Representative examples of monocyclic cycloalkenyl groups include, but are not limited to, cyclobutenyl, cyclopentenyl, cyclohexenyl, cycloheptenyl, and cyclooctenyl. The monocyclic cycloalkenyl ring may contain one or two alkylene bridges, each consisting of one, two, or three carbon atoms, each linking two non-adjacent carbon atoms of the ring system. Representative examples of the bridged cycloalkenyl groups include, but are not limited to, bicyclo[2.2.1]hept-2-ene, 4,5,6,7-tetrahydro-3aH-indene, octahydronaphthalenyl, and 1,6-dihydro-pentalene. The monocyclic and bridged cycloalkenyl can be attached to the parent molecular moiety through any substitutable atom contained within the ring systems.

The term "cycloalkyne," or "cycloalkynyl," or "cycloalkynylene," as used herein, means a monocyclic or a bridged hydrocarbon ring system. The monocyclic cycloalkynyl has eight or more carbon atoms, zero heteroatoms, and one or more triple bonds. The monocyclic cycloalkynyl ring may contain one or two alkylene bridges, each consisting of one, two, or three carbon atoms, each linking two non-adjacent carbon atoms of the ring system. The monocyclic and bridged cycloalkynyl can be attached to the parent molecular moiety through any substitutable atom contained within the ring systems.

The term "heteroarene," or "heteroaryl," or "heteroarylene," as used herein, means a five-membered or six-membered aromatic ring having at least one carbon atom and one or more than one independently selected nitrogen, oxygen or sulfur atom. The heteroarenes of this invention are connected through any adjacent atoms in the ring, provided that proper valences are maintained. Representative examples of heteroaryl include, but are not limited to, furanyl (including, but not limited thereto, furan-2-yl), imidazolyl (including, but not limited thereto, 1H-imidazol-1-yl), isoxazolyl, isothiazolyl, oxadiazolyl, 1,3-oxazolyl, pyridinyl (e.g. pyridin-4-yl, pyridin-2-yl, pyridin-3-yl), pyridazinyl, pyrimidinyl, pyrazinyl, pyrazolyl, pyrrolyl, tetrazolyl, thiadiazolyl, 1,3-thiazolyl, thienyl (including, but not limited thereto, thien-2-yl, thien-3-yl), triazolyl, and triazinyl.

The term "heterocycloalkane," or "heterocycloalkyl," or "heterocycloalkylene," as used herein, means monocyclic or bridged three-, four-, five-, six-, seven-, or eight-membered ring containing at least one heteroatom independently selected from the group consisting of O, N, and S and zero double bonds. The monocyclic and bridged heterocycloalkane are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized. Representative examples of heterocycloalkane groups include, but are not limited to, 8-azabicyclo[3.2.1]octane, 3-azabicyclo[3.2.2]nonane, morpholinyl, tetrahydropyranyl, pyrrolidinyl, piperidinyl, dioxolanyl, tetrahydrofuranyl, thiomorpholinyl, 1,4-dioxanyl, tetrahydrothienyl, tetrahydrothiopyranyl, oxetanyl, piperazinyl, imidazolidinyl, azetidine, azepanyl, aziridinyl, diazepanyl, dithiolanyl, dithianyl, isoxazolidinyl, isothiazolidinyl, oxadiazolidinyl, oxazolidinyl, pyrazolidinyl, tetrahydrothienyl, thiadiazolidinyl, thiazolidinyl, thiomorpholinyl, trithianyl, and trithianyl.

The term "heterocycloalkene," or "heterocycloalkenyl," or "heterocycloalkenylene," as used herein, means monocyclic or bridged three-, four-, five-, six-, seven-, or eight-membered ring containing at least one heteroatom independently selected from the group consisting of O, N, and S and one or more double bonds. The monocyclic and bridged heterocycloalkene are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized. Representative examples of heterocycloalkene groups include, but are not limited to, 1,4,5,6-tetrahydropyridazinyl, 1,2,3,6-tetrahydropyridinyl, dihydropyranyl, imidazolinyl, isothiazolinyl, oxadiazolinyl, isoxazolinyl, oxazolinyl, pyranyl, pyrazolinyl, pyrrolinyl, thiadiazolinyl, thiazolinyl, and thiopyranyl.

The term "phenylene," as used herein, means a divalent radical formed by removal of a hydrogen atom from phenyl.

The term "spiroalkyl," as used herein, means alkylene, both ends of which are attached to the same carbon atom and is exemplified by $C_2$-spiroalkyl, $C_3$-spiroalkyl, $C_4$-spiroalkyl, $C_5$-spiroalkyl, $C_6$-spiroalkyl, $C_7$-spiroalkyl, $C_8$-spiroalkyl, $C_9$-spiroalkyl and the like.

The term "spiroheteroalkyl," as used herein, means spiroalkyl having one or two $CH_2$ moieties replaced with independently selected O, C(O), CNOH, CNOCH$_3$, S, S(O), $SO_2$ or NH and one or two CH moieties unreplaced or replaced with N.

The term "spiroheteroalkenyl," as used herein, means spiroalkenyl having one or two $CH_2$ moieties replaced with independently selected O, C(O), CNOH, CNOCH$_3$, S, S(O), $SO_2$ or NH and one or two CH moieties unreplaced or replaced with N and also means spiroalkenyl having one or two $CH_2$ moieties unreplaced or replaced with independently selected O, C(O), CNOH, CNOCH$_3$, S, S(O), $SO_2$ or NH and one or two CH moieties replaced with N.

The term, "spirocyclo," as used herein, means two substituents on the same carbon atom, that, together with the carbon atom to which they are attached, form a cycloalkane, heterocycloalkane, cycloalkene, or heterocycloalkene ring.

The term "$C_2$-$C_5$-spiroalkyl," as used herein, means $C_2$-spiroalkyl, $C_3$-spiroalkyl, $C_4$-spiroalkyl, and $C_5$-spiroalkyl.

The term "$C_2$-spiroalkyl," as used herein, means eth-1,2-ylene, both ends of which replace hydrogen atoms of the same $CH_2$ moiety.

The term "$C_3$-spiroalkyl," as used herein, means prop-1,3-ylene, both ends of which replace hydrogen atoms of the same $CH_2$ moiety.

The term "$C_4$-spiroalkyl," as used herein, means but-1,4-ylene, both ends of which replace hydrogen atoms of the same $CH_2$ moiety.

The term "$C_5$-spiroalkyl," as used herein, means pent-1,5-ylene, both ends of which replace hydrogen atoms of the same $CH_2$ moiety.

The term "$C_6$-spiroalkyl," as used herein, means hex-1,6-ylene, both ends of which replace hydrogen atoms of the same $CH_2$ moiety.

The term "NH protecting group," as used herein, means trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyl-oxycarbonyl, 4-(phenylazo)benzyloxycarbonyl, 2-furfuryl-oxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthyl-methylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclohexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group," as used herein, means methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl 2-tetrahydrofuranyl, 2,2,2-trichloroethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group," as used herein, means benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble *J. Org. Chem.* 1998, 63, 2758-2760 and E. L. Eliel, and S. H. Wilen. (1994) *Stereochemistry of Organic Compounds*. New York, N.Y.: John Wiley & Sons, Inc.

Compounds of this invention contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Compounds of this invention containing NH, C(O)OH, OH or SH moieties may have attached thereto prodrug-forming moieties. The prodrug-forming moieties are removed by metabolic processes and release the compounds having the freed hydroxyl, amino or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of Bcl-2 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999).

In addition, non-radio active isotope containing drugs, such as deuterated drugs called "heavy drugs," can be used for the treatment of diseases and conditions related to Bcl-2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-isotopic compound.

Amides, Esters and Prodrugs

Prodrugs are derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property.

Prodrugs are usually prepared by: a) formation of ester, hemi esters, carbonate esters, nitrate esters, amides, hydroxamic acids, carbamates, imines, Mannich bases, phosphates, phosphate esters, and enamines of the active drug, b) functionalizing the drug with azo, glycoside, peptide, and ether functional groups, c) use of aminals, hemi-aminals, polymers, salts, complexes, phosphoramides, acetals, hemiacetals, and ketal forms of the drug. For example, see Andrejus Korolkovas's, "Essentials of Medicinal Chemistry", John Wiley-Interscience Publications, John Wiley and Sons, New York (1988), pp. 97-118, which is incorporated in its entirety by reference herein Esters can be prepared from substrates of formula (I) containing either a hydroxyl group or a carboxy group by general methods known to persons skilled in the art. The typical reactions of these compounds are substitutions replacing one of the heteroatoms by another atom, for example:

Scheme 1

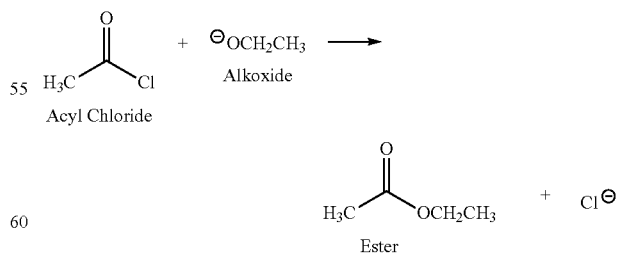

Amides can be prepared from substrates of formula (I) containing either an amino group or a carboxy group in similar fashion. Esters can also react with amines or ammonia to form amides.

Scheme 2

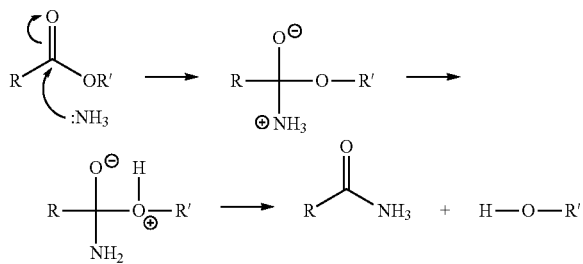

Another way to make amides from compounds of formula (I) is to heat carboxylic acids and amines together.

Scheme 3

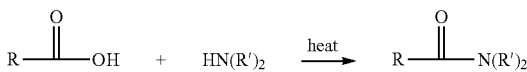

In Schemes 2 and 3 above, R and R' are independently substrates of formula (I), alkyl or hydrogen.

Suitable groups for $A^1$, $B^1$, $D^1$, $E^1$, $Y^1$, and $Z^1$ in compounds of Formula (I) are independently selected. The described embodiments of the present invention may be combined. Such combination is contemplated and within the scope of the present invention. For example, it is contemplated that embodiments for any of $A^1$, $B^1$, $D^1$, $E^1$, $Y^1$, and $Z^1$ can be combined with embodiments defined for any other of $A^1$, $B^1$, $D^1$, $E^1$, $Y^1$, and Z.

One embodiment of this invention, therefore, pertains to compounds or therapeutically acceptable salts, prodrugs or salts of prodrugs thereof, which are useful as selective inhibitors one or more than one anti-apoptotic protein family member, the compounds having formula (I)

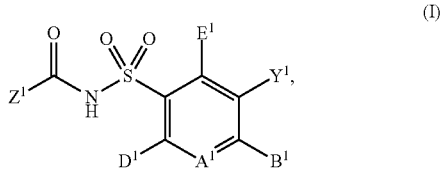

(I)

wherein $A^1$ is N or $C(A^2)$;

one or two or three or each of $A^2$, $B^1$, $D^1$ and $E^1$ are independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NR^1C(O)NHR^1$, $NR^1C(O)N(R^1)_2$, $SO_2NHR^1$, $SO_2N(R^1)_2$, $NHSO_2R^1$, $NHSO_2NHR^1$ or $N(CH_3)SO_2N(CH_3)R^1$, and the remainder are independently selected H, F, Cl, Br, I, CN, $CF_3$, C(O)OH, $C(O)NH_2$ or $C(O)OR^{1A}$; and $Y^1$ is H, CN, $NO_2$, C(O)OH, F, Cl, Br, I, $CF_3$, $OCF_3$, $CF_2CF_3$, $OCF_2CF_3$, $R^{17}$, $OR^{17}$, $C(O)R^{17}$, $C(O)OR^{17}$, $SR^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, $NHS(O)R^7$ or $NHSO_2R^{17}$; or $B^1$ and $Y^1$, together with the atoms to which they are attached, are imidazole or triazole; and one or two or each of $A^2$, $D^1$ and $E^1$ are independently selected $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NHC(O)OR^1$, $NHC(O)NHR^1$, $N(CH_3)C(O)N(CH_3)R^1$, $SO_2NHR^1$, $SO_2N(R^1)_2$, $NHSO_2R^1$, $NHSO_2NHR^1$ or $N(CH_3)SO_2N(CH_3)R^1$, and the remainder are independently selected H, F, Cl, Br, I, $CF_3$, C(O)OH, $C(O)NH_2$ or $C(O)OR^{1A}$;

$R^1$ is $R^2$, $R^3$, $R^4$ or $R^5$;

$R^{1A}$ is $C_1$-$C_6$-alkyl, $C_3$-$C_6$-alkenyl or $C_3$-$C_6$-alkynyl;

$R^2$ is phenyl which is unfused or fused with arene, heteroarene or $R^{2A}$; $R^{2A}$ is cycloalkane or heterocycloalkane;

$R^3$ is heteroaryl which is unfused or fused with benzene, heteroarene or $R^{3A}$; $R^{3A}$ is cycloalkane or heterocycloalkane;

$R^4$ is cycloalkyl, cycloalkenyl, heterocycloalkyl or heterocycloalkenyl, each of which is unfused or fused with arene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three independently selected $R^6$, $NC(R^{6A})(R^{6B})$ $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $NHC(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, OH, (O), C(O)OH, (O), $N_3$, CN, $NH_2$, $CF_3$, $CF_2CF_3$, F, Cl, Br or I substituents;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or $R^{11}$;

$R^8$ is phenyl which is unfused or fused with arene, heteroarene or $R^{8A}$;

$R^{8A}$ is cycloalkane, cycloalkene, heterocycloalkane or heterocycloalkene;

$R^9$ is heteroaryl which is unfused or fused with arene, heteroarene or $R^{9A}$; $R^{9A}$ is cycloalkane, cycloalkene, heterocycloalkane or heterocycloalkene;

$R^{10}$ is $C_3$-$C_{10}$-cycloalkyl or $C_4$-$C_{10}$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three independently selected $R^1$, $OR^{12}$, $NHR^{12}$, $N(R^{12})_2$, $C(O)NH_2$, $C(O)NHR^{12}$, $C(O)N(R^{12})_2$, OH, (O), C(O)OH, $N_3$, CN, $NH_2$, $CF_3$, $CF_2CF_3$, F, Cl, Br or I substituents;

$R^{12}$ is $R^{13}$, $R^{14}$, $R^{15}$ or $R^{16}$;

$R^{13}$ is phenyl which is unfused or fused with arene, heteroarene or $R^{13A}$; $R^{13A}$ is cycloalkane, cycloalkene, heterocycloalkane or heterocycloalkene;

$R^{14}$ is heteroaryl, each of which is unfused or fused with arene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with arene, heteroarene or $R^{15A}$; $R^{15A}$ is cycloalkane, cycloalkene, heterocycloalkane or heterocycloalkene;

$R^{16}$ is alkyl, alkenyl or alkynyl;

$R^{17}$ is $R^{18}$, $R^{19}$, $R^{20}$ or $R^{21}$;

R$^{18}$ is phenyl which is unfused or fused with arene, heteroarene or R$^{18A}$; R$^{18A}$ is cycloalkane, cycloalkene, herocycloalkane or heterocycloalkene;

R$^{19}$ is heteroaryl which is unfused or fused with arene, heteroarene or R$^{19A}$; R$^{19A}$ is cycloalkane, cycloalkene, herocycloalkane or heterocycloalkene;

R$^{20}$ is C$_3$-C$_{10}$-cycloalkyl or C$_4$-C$_{10}$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or R$^{20A}$; R$^{20A}$ is cycloalkane, cycloalkene, heterocycloalkane or heterocycloalkene;

R$^{21}$ is alkyl, alkenyl or alkynyl, each of which is unsubstituted or substituted with one or two or three independently selected R$^{22}$, OR$^{11}$, NHR$^{22}$, N(R$^{22}$)$_2$, C(O)NH$_2$, C(O)NHR$^{22}$, C(O)N(R$^{22}$)$_2$, OH, (O), C(O)OH, N$_3$, CN, NH$_2$, CF$_3$, CF$_2$CF$_3$, F, Cl, Br or I substituents;

R$^{22}$ is R$^{23}$, R$^{24}$ or R$^{25}$;

R$^{23}$ is phenyl which is unfused or fused with arene, heteroarene or R$^{23A}$; R$^{23A}$ is cycloalkane, cycloalkene, heterocycloalkane or heterocycloalkene;

R$^{24}$ is heteroarene which is unfused or fused with arene, heteroarene or R$^{24A}$; R$^{24A}$ is cycloalkane, cycloalkene, herocycloalkane or heterocycloalkene;

R$^{25}$ is C$_3$-C$_6$-cycloalkyl or C$_4$-C$_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or R$^{25A}$; R$^{25A}$ is cycloalkane, cycloalkene, heterocycloalkane or heterocycloalkene;

Z$^1$ is R$^{26}$ or R$^{27}$, each of which is substituted with R$^{28}$, R$^{29}$ or R$^{30}$, each of which is substituted with F, Cl, Br, I, CH$_2$R$^{37}$, CH(R$^{31}$)(R$^{37}$), C(R$^{31}$)(R$^{31A}$)(R$^{37}$), C(O)R$^{37}$, OR$^{37}$, SR$^{37}$, S(O)R$^{37}$, SO$_2$R$^{37}$, NHR$^{37}$ or N(R$^{32}$)R$^{37}$;

R$^{26}$ is phenyl which is unfused or fused with arene or heteroarene;

R$^{27}$ is heteroarene which is unfused or fused with arene or heteroarene;

R$^{28}$ is phenyl which is unfused or fused with arene, heteroarene or R$^{28A}$; R$^{28A}$ is cycloalkane, cycloalkene, heterocycloalkane or heterocycloalkene R$^{29}$ is heteroaryl or R$^{29A}$; R$^{29A}$ is cycloalkane, cycloalkene, heterocycloalkane or heterocycloalkene;

R$^{30}$ is cycloalkyl or cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or R$^{30A}$; R$^{30A}$ is cycloalkane, cycloalkene, heterocycloalkane or heterocycloalkene;

R$^{31}$ and R$^{31A}$ are independently F, Cl, Br or alkyl or are taken together and are C$_2$-C$_5$-spiroalkyl;

R$^{32}$ is R$^{33}$, C(O)R$^{33}$ or C(O)OR$^{33}$;

R$^{33}$ is R$^{34}$ or R$^{35}$;

R$^{34}$ is phenyl which is unfused or fused with aryl, heteroaryl or R$^{34A}$; R$^{34A}$ is cycloalkane, cycloalkene, heterocycloalkane or heterocycloalkene;

R$^{35}$ is alkyl which is unsubstituted or substituted with R$^{36}$;

R$^{36}$ is phenyl which is unfused or fused with arene, heteroarene or R$^{36A}$; R$^{36A}$ is cycloalkane, cycloalkene, heterocycloalkane or heterocycloalkene;

R$^{37}$ is R$^{38}$, R$^{39}$ or R$^{40}$, each of which is substituted with F, Cl, Br, I, R$^{41}$, OR$^{41}$, NHR$^{41}$, N(R$^{41}$)$_2$, NHC(O)OR$^{41}$, SR$^{41}$, S(O)R$^{41}$ or SO$_2$R$^{41}$;

R$^{38}$ is phenyl which is unfused or fused with arene, heteroarene or R$^{38A}$; R$^{38A}$ is cycloalkane, cycloalkene, heterocycloalkane or heterocycloalkene;

R$^{39}$ is heteroaryl which is unfused or fused with arene, heteroarene or R$^{39A}$; R$^{39A}$ is cycloalkane, cycloalkene, herocycloalkane or heterocycloalkene;

R$^{40}$ is C$_3$-C$_5$-cycloalkyl or C$_4$-C$_8$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or R$^{40A}$; R$^{40A}$ cycloalkane, cycloalkene, heterocycloalkane or heterocycloalkene;

R$^{41}$ is R$^{42}$, R$^{43}$, R$^{44}$ or R$^{45}$;

R$^{42}$ is phenyl which is unfused or fused with arene, heteroarene or R$^{42A}$; R$^{42A}$ is cycloalkane, cycloalkene, heterocycloalkane or heterocycloalkene;

R$^{43}$ is heteroaryl which is unfused or fused with arene, heteroarene or R$^{43A}$; R$^{43A}$ is cycloalkane, cycloalkene, herocycloalkane or heterocycloalkene;

R$^{44}$ is C$_3$-C$_9$-cycloalkyl or C$_4$-C$_7$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or R$^{44A}$; R$^{44}$ is cycloalkane, cycloalkene, heterocycloalkane or heterocycloalkene;

R$^{45}$ is alkyl, alkenyl or alkynyl, each of which is unsubstituted or substituted with one or two independently selected R$^{46}$, OR$^{46}$, NHR$^{46}$, N(R$^{46}$)$_2$, C(O)NH$_2$, C(O)NHR$^{46}$, C(O)N(R$^{46}$)$_2$, OH, (O), C(O)OH, N$_3$, CN, NH$_2$, CF$_3$, CF$_2$CF$_3$, F, Cl, Br or I substituents;

R$^{46}$ is R$^{47}$, R$^{48}$ or R$^{49}$;

R$^{47}$ is phenyl which is unfused or fused with arene, heteroarene or R$^{47A}$; R$^{47A}$ is cycloalkane, cycloalkene, heterocycloalkane or heterocycloalkene;

R$^{48}$ is heteroaryl or R$^{48A}$; R$^{48A}$ is cycloalkane, cycloalkene, heterocycloalkane or heterocycloalkene;

R$^{49}$ is C$_3$-C$_6$-cycloalkyl or C$_4$-C$_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or R$^{49A}$; R$^{49A}$ is cycloalkane, cycloalkene, heterocycloalkane or heterocycloalkene;

wherein the moieties represented by R$^{16}$ and R$^{27}$ are further substituted by one or two or three of independently selected R$^{50A}$, OR$^{50A}$, SR$^{50A}$, S(O)R$^{50A}$ SO$_2$R$^{50A}$ or NHR$^{50A}$, R$^{50A}$ is R$^{51A}$, R$^{52A}$, R$^{53A}$ or R$^{54A}$;

R$^{51A}$ is phenyl which is unfused or fused with benzene, heteroarene or R$^{51AA}$;

wherein R$^{51AA}$ is cycloalkane, cycloalkene or heterocloalkane heterocycloalkene, R$^{52A}$ is heteroaryl;

R$^{53A}$ is C$_3$-C$_6$-cycloalkyl or C$_4$-C$_6$-cycloalkenyl; each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or R$^{53AA}$;

wherein R$^{53AA}$ is cycloalkane, cycloalkene, heterocycloalkane or heterocycloalkene;

R$^{54A}$ is alkyl, alkenyl or alkynyl, each of which is unsubstituted or substituted with one or two or three of independently selected R$^{55AA}$, OR$^{55AA}$, SR$^{55AA}$, S(O)R$^{55AA}$, SO$_2$R$^{55AA}$, NHR$^{55AA}$, N(R$^{55AA}$), C(O)R$^{55AA}$, C(O)NH$_2$, C(O)NHR$^{55AA}$, NHC(O)R$^{55AA}$, NHSO$_2$R$^{55AA}$, NHC(O)

OR$^{55AA}$, SO$_2$NH$_2$, SO$_2$NHR$^{55AA}$, SO$_2$N(R$^{55AA}$)$_2$, NHC(O)NH$_2$, NHC(O)NHR$^{55AA}$, OH, (O), C(O)OH, (O), N$_3$, CN, NH$_2$, CF$_3$, OCF$_3$, CF$_2$CF$_3$, OCF$_2$CF$_3$, F, Cl, Br or I substituents;

R$^{55AA}$ is alkyl, alkenyl, alkynyl, phenyl or heteroaryl, or R$^{56A}$;

R$^{56A}$ is C$_3$-C$_6$-cycloalkyl or C$_4$-C$_6$-cycloalkyl, each having one or two CH$_2$ moieties unreplaced or replaced with independently selected O, C(O), CNOH, CNOCH$_3$, S, S(O), SO$_2$ or NH and one or two CH moieties unreplaced or replaced with N;

wherein moieties represented by R$^2$, R$^3$R$^4$, R$^6$, R$^{6C}$, R$^8$, R$^{8A}$R$^9$, R$^{10}$, R$^{13}$, R$^{14}$, R$^{15}$, R$^{18}$, R$^{19}$, R$^{20}$, R$^{23}$, R$^{24}$, R$^{25}$, R$^{26}$, R$^{27}$, R$^{28}$, R$^{29}$, R$^{30}$, R$^{34}$, R$^{36}$, R$^{38}$, R$^{39}$, R$^{40}$, R$^{42}$, R$^{43}$, R$^{44}$, R$^{47}$, R$^{48}$, and R$^{49}$ are independently unsubstituted, further unsubstituted, substituted or further substituted with one or two or three or four or five independently selected R$^{50}$, OR$^{50}$, SR$^{50}$, S(O)R$^{50}$, SO$_2$R$^{50}$, C(O)R$^{50}$, CO(O)R$^{50}$, OC(O)R$^{50}$, OC(O)OR$^{50}$, NH$_1$, NHR$^{50}$, N(R$^{50}$)$_2$, C(O)NH$_2$, C(O)NHR$^{50}$, C(O)N(R$^{50}$)$_2$, C(O)NHOH, C(O)NHOR$^{50}$, C(O)NHSO$_2$R$^{50}$, C(O)NR$^{55}$SO$_2$R$^{50}$, SO$_2$NH$_2$, SO$_2$NHR$^{50}$, SO$_2$N(R$^{50}$)$_2$, CF$_3$, CF$_2$CF$_3$, C(O)H, C(O)OH, C(N)NH$_2$, C(N)NHR$^{50}$, C(N)N(R$^{50}$)$_2$, OH, (O), CN, N$_3$, NO$_2$, CF$_3$, CF$_2$CF$_3$, OCF$_3$, OCF$_2$CF$_3$, F, Cl, Br or I substituents;

R$^{50}$ is R$^{51}$, R$^{52}$, R$^{53}$ or R$^{54}$,

R$^{51}$ is phenyl which is unfused or fused with arene, heteroarene or R$^{51B}$; R$^{51B}$ is cycloalkane, cycloalkene, heterocycloalkane or heterocycloalkene;

R$^{52}$ is heteroaryl;

R$^{53}$ is C$_3$-C$_6$-cycloalkyl or C$_4$-C$_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or R$^{53B}$;

wherein R$^{53B}$ is cycloalkane, cycloalkene, heterocycloalkane or heterocycloalkene;

R$^{54}$ is alkyl, alkenyl or alkynyl, each of which is unsubstituted or substituted with one or two or three independently selected R$^{55}$, OR$^{55}$, SR$^{55}$, S(O)R$^{55}$, SO$_2$R$^{55}$, NHR$^{55}$, N(R$^{55}$)$_2$, C(O)R$^{55}$, C(O)NH$_2$, C(O)NHR$^{55}$, NHC(O)R$^{55}$, NHSO$_2$R$^{55}$, NHC(O)OR$^{55}$, SO$_2$NH$_2$, SO$_2$NHR$^{55}$, SO$_2$N(R$^{55}$)$_2$, NHC(O)NH$_2$, NHC(O)NHR$^{55}$, OH, (O), C(O)OH, (O), N$_3$, CN, NH$_2$, CF$_3$, OCF$_3$, CF$_2$CF$_3$, OCF$_2$CF$_3$, F, Cl, Br or I substituents;

R$^{55}$ is alkyl, alkenyl, alkynyl, phenyl, heteroaryl or R$^{56}$; and wherein the alkyl, alkenyl, alkynyl are unsubstituted or substituted with OCH$_3$; and R$^{56}$ is C$_3$-C$_5$-cycloalkyl or C$_4$-C$_6$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N.

Another embodiment of this invention pertains to compounds of Formula (I), wherein wherein A$^1$ is N or C(A$^2$);

one or two or three or each of A$^2$, B$^1$, D$^1$ and E$^1$ are independently selected R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NHC(O)OR$^1$, NR$^1$C(O)NHR$^1$, NR$^1$C(O)N(R$^1$)$_2$, SO$_2$NHR$^1$, SO$_2$N(R$^1$)$_2$, NHSO$_2$R$^1$, NHSO$_2$NHR$^1$ or N(CH$_3$)SO$_2$N(CH$_3$)R$^1$, and the remainder are independently selected H, F, Cl, Br, I, CN, CF$_3$, C(O)OH, C(O)NH$_2$ or C(O)OR$^{14}$; and Y$^1$ is H, CN, NO$_2$, C(O)OH, F, Cl, Br, I, CF$_3$, OCF$_3$, CF$_2$CF$_3$, OCF$_2$CF$_3$, R$^{17}$, OR$^{17}$, C(O)R$^{17}$, C(O)OR$^{17}$, SR$^{17}$, NH$_2$, NHR$^{17}$, N(R$^{17}$)$_2$, NHC(O)R$^{17}$, C(O)NH$_2$, C(O)NHR$^{17}$, C(O)N(R$^{17}$)$_2$, NHS(O)R$^{17}$ or NHSO$_2$R$^{17}$;

or

B$^1$ and Y$^1$, together with the atoms to which they are attached, are imidazole or triazole; and one or two or each of A$^2$, D$^1$ and E$^1$ are independently selected R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NHC(O)OR$^1$, NHC(O)NHR$^1$, N(CH$_3$)C(O)N(CH$_3$)R$^1$, SO$_2$NHR$^1$, SO$_2$N(R$^1$)$_2$, NHSO$_2$R$^1$, NHSO$_2$NHR$^1$ or N(CH$_3$)SO$_2$N(CH$_3$)R$^1$, and the remainder are independently selected H, F, Cl, Br, I, CF$_3$, C(O)OH, C(O)NH$_2$ or C(O)OR$^{14}$;

R$^1$ is R$^2$, R$^3$, R$^4$ or R$^5$;

R$^{14}$ is C$_1$-C$_6$-alkyl, C$_3$-C$_6$-alkenyl or C$_3$-C$_6$-alkynyl;

R$^2$ is phenyl which is unfused or fused with arene, heteroarene or R$^{2A}$; R$^{2A}$ is cycloalkane or heterocycloalkane;

R$^3$ is heteroaryl which is unfused or fused with benzene, heteroarene or R$^{3A}$; R$^{3A}$ is cycloalkane or heterocycloalkane;

R$^4$ is cycloalkyl, cycloalkenyl, heterocycloalkyl or heterocycloalkenyl, each of which is unfused or fused with arene, heteroarene or R$^{4A}$; R$^{4A}$ is cycloalkane, cycloalkene, heterocycloalkane or heterocycloalkene;

R$^5$ is alkyl, alkenyl or alkynyl, each of which is unsubstituted or substituted with one or two or three independently selected R$^6$, NC(R$^{6A}$)(R$^{6B}$), R$^7$, OR$^7$, SR$^7$, S(O)R$^7$, SO$_2$R$^7$, NHR$^7$, N(R$^7$)$_2$, C(O)R$^7$, C(O)NH$_2$, C(O)NHR$^7$, NHC(O)R$^7$, NHSO$_2$R$^7$, NHC(O)OR$^7$, SO$_2$NH$_2$, SO$_2$NHR$^7$, SO$_2$N(R$^7$)$_2$, NHC(O)NH$_2$, NHC(O)NHR$^7$, NHC(O)CH(CH$_3$)NHC(O)CH(CH$_3$)NH$_2$, NHC(O)CH(CH$_3$)NHC(O)CH(CH$_3$)NHR$^7$, OH, (O), C(O)OH, (O), N$_3$, CN, NH$_2$, CF$_3$, CF$_2$CF$_3$, F, Cl, Br or I substituents;

R$^6$ is C$_2$-C$_5$-spiroalkyl, each of which is unsubstituted or substituted with OH, (O), N$_3$, CN, CF$_3$, CF$_2$CF$_3$, F, Cl, Br, I, NH$_2$, NH(CH$_3$) or N(CH$_3$)$_2$;

R$^{6A}$ and R$^{6B}$ are independently selected alkyl or, together with the N to which they are attached, R$^{6C}$;

R$^{6C}$ is aziridin-1-yl, azetidin-1-yl, pyrrolidin-1-yl or piperidin-1-yl, each having one CH$_2$ moiety unreplaced or replaced with O, C(O), CNOH, CNOCH$_3$, S, S(O), SO$_2$, nor NH;

R$^7$ is R$^8$, R$^9$, R$^{10}$ or R$^{11}$;

R$^8$ is phenyl which is unfused or fused with arene, heteroarene or R$^{8A}$;

R$^{8A}$ is cycloalkane, cycloalkene, heterocycloalkane or heterocycloalkene;

R$^9$ is heteroaryl which is unfused or fused with arene, heteroarene or R$^{9A}$; R$^{9A}$ is cycloalkane, cycloalkene, heterocycloalkane or heterocycloalkene;

R$^{10}$ is C$_3$-C$_{10}$-cycloalkyl or C$_4$-C$_{10}$-cycloalkenyl, each having one or two CH$_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or R$^{10A}$; R$^{10A}$ is cycloalkane, cycloalkene, heterocycloalkane or heterocycloalkene;

R$^{11}$ is alkyl, alkenyl or alkynyl, each of which is unsubstituted or substituted with one or two or three independently selected R$^{12}$, OR$^{12}$, NHR$^{12}$, N(R$^{12}$)$_2$, C(O)NH$_2$, C(O)NHR$^{12}$, C(O)N(R$^{12}$)$_2$, OH, (O), C(O)OH, N$_3$, CN, NH$_2$, CF$_3$, CF$_2$CF$_3$, F, Cl, Br or I substituents;

R$^{12}$ is R$^{13}$, R$^{14}$, R$^{15}$ or R$^{16}$;

R$^{13}$ is phenyl which is unfused or fused with arene, heteroarene or R$^{13A}$; R$^{13A}$ is cycloalkane, cycloalkene, heterocycloalkane or heterocycloalkene;

R$^{14}$ is heteroaryl, each of which is unfused or fused with arene, heteroarene or R$^{14A}$;

$R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with arene, heteroarene or $R^{15A}$; $R^{15A}$ is cycloalkane, cycloalkene, heterocycloalkane or heterocycloalkene;

$R^{16}$ is alkyl, alkenyl or alkynyl;

$R^{17}$ is $R^{18}$, $R^{19}$, $R^{20}$ or $R^{21}$, $R^{18}$ is phenyl which is unfused or fused with arene, heteroarene or $R^{18A}$; $R^{18A}$ is cycloalkane, cycloalkene, heterocycloalkane or heterocycloalkene;

$R^{19}$ is heteroaryl which is unfused or fused with arene, heteroarene or $R^{19A}$; $R^{19A}$ is cycloalkane, cycloalkene, heterocycloalkane or heterocycloalkene;

$R^{20}$ is $C_3$-$C_{10}$-cycloalkyl or $C_4$-$C_{10}$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{20A}$; $R^{20A}$ is cycloalkane, cycloalkene, heterocycloalkane or heterocycloalkene;

$R^{21}$ is alkyl, alkenyl or alkynyl, each of which is unsubstituted or substituted with one or two or three independently selected $R^{22}$, $OR^{22}$, $NHR^{22}$, $N(R^{22})_2$, $C(O)NH_2$, $C(O)NHR^{22}$, $C(O)N(R^{22})_2$, OH, (O), C(O)OH, $N_3$, CN, $NH_2$, $CF_3$, $CF_2CF_3$, F, Cl, Br or I substituents;

$R^{22}$ is $R^{23}$, $R^{24}$ or $R^{25}$;

$R^{23}$ is phenyl which is unfused or fused with arene, heteroarene or $R^{23A}$; $R^{23A}$ is cycloalkane, cycloalkene, heterocycloalkane or heterocycloalkene;

$R^{24}$ is heteroarene which is unfused or fused with arene, heteroarene or $R^{24A}$; $R^{24A}$ is cycloalkane, cycloalkene, heterocycloalkane or heterocycloalkene;

$R^{25}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{25A}$; $R^{25A}$ is cycloalkane, cycloalkene, heterocycloalkane or heterocycloalkene;

$Z^1$ is $R^{26}$ or $R^{27}$, each of which is substituted with $R^{28}$, $R^{29}$ or $R^{30}$, each of which is substituted with F, Cl, Br, I, $CH_2R^{37}$, $CH(R^{31})(R^{37})$, $C(R^{31})(R^{31A})(R^{37})$, $C(O)R^{37}$, $OR^{37}$, $SR^{37}$, $S(O)R^{37}$, $SO_2R^{37}$, $NHR^{37}$ or $N(R^{32})R^{37}$;

$R^{26}$ is phenyl which is unfused or fused with arene or heteroarene;

$R^{27}$ is heteroarene which is unfused or fused with arene or heteroarene;

$R^{28}$ is phenyl which is unfused or fused with arene, heteroarene or $R^{28A}$; $R^{28A}$ is cycloalkane, cycloalkene, heterocycloalkane or heterocycloalkene $R^{29}$ is heteroaryl or $R^{29A}$; $R^{29A}$ is cycloalkane, cycloalkene, heterocycloalkane or heterocycloalkene;

$R^{30}$ is cycloalkyl or cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{30A}$; $R^{30A}$ is cycloalkane, cycloalkene, heterocycloalkane or heterocycloalkene;

$R^{31}$ and $R^{31A}$ are independently F, Cl, Br or alkyl or are taken together and are $C_2$-$C_5$-spiroalkyl;

$R^{32}$ is $R^{33}$, $C(O)R^{33}$ or $C(O)OR^{33}$;

$R^{33}$ is $R^{34}$ or $R^{35}$;

$R^{34}$ is phenyl which is unfused or fused with aryl, heteroaryl or $R^{34A}$; $R^{34A}$ is cycloalkane, cycloalkene, heterocycloalkane or heterocycloalkene;

$R^{35}$ is alkyl which is unsubstituted or substituted with $R^{36}$;

$R^{36}$ is phenyl which is unfused or fused with arene, heteroarene or $R^{36A}$; $R^{36A}$ is cycloalkane, cycloalkene, heterocycloalkane or heterocycloalkene;

$R^{37}$ is $R^{38}$, $R^{39}$ or $R^{40}$, each of which is substituted with F, Cl, Br, I, $R^{41}$, $OR^{41}$, $NHR^{41}$, $N(R^{41})_2$, $NHC(O)OR^{41}$, $SR^{41}$, $S(O)R^{41}$ or $SO_2R^{41}$;

$R^{38}$ is phenyl which is unfused or fused with arene, heteroarene or $R^{38A}$; $R^{38A}$ is cycloalkane, cycloalkene, heterocycloalkane or heterocycloalkene;

$R^{39}$ is heteroaryl which is unfused or fused with arene, heteroarene or $R^{39A}$; $R^{39A}$ is cycloalkane, cycloalkene, heterocycloalkane or heterocycloalkene;

$R^{40}$ is $C_3$-$C_5$-cycloalkyl or $C_4$-$C_8$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{40A}$; $R^{40A}$ cycloalkane, cycloalkene, heterocycloalkane or heterocycloalkene;

$R^{41}$ is $R^{42}$, $R^{43}$, $R^{44}$ or $R^{45}$;

$R^{42}$ is phenyl which is unfused or fused with arene, heteroarene or $R^{42A}$; $R^{42A}$ is cycloalkane, cycloalkene, heterocycloalkane or heterocycloalkene;

$R^{43}$ is heteroaryl which is unfused or fused with arene, heteroarene or $R^{43A}$; $R^{43A}$ is cycloalkane, cycloalkene, heterocycloalkane or heterocycloalkene;

$R^{44}$ is $C_3$-$C_9$-cycloalkyl or $C_4$-$C_7$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two independently selected $R^{46}$, $OR^{46}$, $NHR^{46}$, $N(R^{46})_2$, $C(O)NH_2$, $C(O)NHR^{46}$, $C(O)N(R^{46})_2$, OH, (O), C(O)OH, $N_3$, CN, $NH_2$, $CF_3$, $CF_2CF_3$, F, Cl, Br or I substituents;

$R^{46}$ is $R^{47}$, $R^{48}$ or $R^{49}$;

$R^{47}$ is phenyl which is unfused or fused with arene, heteroarene or $R^{47A}$; $R^{47A}$ is cycloalkane, cycloalkene, heterocycloalkane or heterocycloalkene;

$R^{48}$ is heteroaryl or $R^{48A}$; $R^{48A}$ is cycloalkane, cycloalkene, heterocycloalkane or heterocycloalkene;

$R^{49}$ is $C_3$-$C_6$-cycloalkyl or $C_4$-$C_6$-cycloalkenyl, each having one or two $CH_2$ moieties unreplaced or replaced with independently selected O, C(O), CNOH, CNOCH$_3$, S, S(O), SO$_2$ or NH and one or two CH moieties unreplaced or replaced with N, and each of which is unfused or fused with arene, heteroarene or $R^{49A}$; $R^{49A}$ is cycloalkane, cycloalkene, heterocycloalkane or heterocycloalkene;

wherein the moieties represented by $R^{26}$ and $R^{27}$ are further substituted with $OR^{50A}$, $R^{50A}$ is $R^{51A}$;

$R^{51A}$ is phenyl which is fused with heteroarene;

wherein moieties represented by $R^2R^3R^4$, $R^6$, $R^{6C}$, $R^8$, $R^{8A}R^9$, $R^{10}$, $R^{13}$, $R^{14}$, $R^{15}$, $R^{18}$, $R^{19}$, $R^{20}$, $R^{23}$, $R^{24}$, $R^{25}$, $R^{26}$, $R^{27}$, $R^{28}$, $R^{29}$, $R^{30}$, $R^{34}$, $R^{36}$, $R^{38}$, $R^{39}$, $R^{40}$, $R^{42}$, $R^{43}$, $R^{44}$, $R^{47}$, $R^{48}$, and $R^{49}$ are independently unsubstituted, further unsubstituted, substituted or further substituted with one or two or three or four or five independently selected $R^{50}$, $OR^{50}$, $SR^{50}$, $S(O)R^{50}$, $SO_2R^{50}$, $C(O)R^{50}$, $CO(O)R^{50}$, $OC(O)R^{50}$, $OC(O)OR^{50}$, $NH_2$, $NHR^{50}$, $N(R^{50})_2$, $C(O)NH_2$, $C(O)NHR^{50}$, $C(O)N(R^{50})_2$, C(O)NHOH, C(O)NHOR$^{50}$, C(O)NHSO$_2$R$^{50}$, C(O)NR$^{55}$SO$_2$R$^{50}$, SO$_2$NH$_2$, SO$_2$NHR$^{50}$, SO$_2$N(R$^{50}$)$_2$, CF$_3$, CF$_2$CF$_3$, C(O)H, C(O)OH, C(N)NH$_2$, C(N)NHR$^{50}$, C(N)N $(R^{50})_2$, OH, (O), CN, $N_3$, $NO_2$, $CF_3$, $CF_2CF_3$, $OCF_3$, $OCF_2CF_3$, F, Cl, Br or I substituents;

$R^{50}$ is $R^{51}$, $R^{52}$, $R^{53}$ or $R^{54}$;

$R^{51}$ is phenyl which is unfused or fused with arene, heteroarene or $R^{51B}$; $R^{51B}$ is cycloalkane, cycloalkene, heterocycloalkane or heterocycloalkene;

$R^{52}$ is heteroaryl;

$R^{53}$ is $C_3$-$C_6$-cycloalkyl or $C_4$-$C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N, and each of which is unfused or fused with arene, heteroarene or $R^{53B}$;

wherein $R^{53B}$ is cycloalkane, cycloalkene, heterocycloalkane or heterocycloalkene;

$R^{54}$ is alkyl, alkenyl or alkynyl, each of which is unsubstituted or substituted with one or two or three independently selected $R^{55}$, $OR^{55}$, $SR^{55}$, $S(O)R^{55}$, $SO_2R^{55}$, $NHR^{55}$, $N(R^{55})_2$, $C(O)R^{55}$, $C(O)NH_2$, $C(O)NHR^{55}$, $NHC(O)R^{55}$, $NHSO_2R^{55}$, $NHC(O)OR^{55}$, $SO_2NH_2$, $SO_2NHR^{55}$, $SO_2N(R^{55})_2$, $NHC(O)NH_2$, $NHC(O)NHR^{55}$, OH, (O), C(O)OH, (O), $N_3$, CN, $NH_2$, $CF_3$, $OCF_3$, $CF_2CF_3$, $OCF_2CF_3$, F, Cl, Br or I substituents;

$R^{55}$ is alkyl, alkenyl, alkynyl, phenyl, heteroaryl or $R^{56}$; and wherein the alkyl, alkenyl, alkynyl are unsubstituted or substituted with $OCH_3$; and $R^{56}$ is $C_3$-$C_8$-cycloalkyl or $C_4$-$C_6$-cycloalkenyl, each having one or two $CH_2$ moieties unreplaced or replaced with independently selected O, C(O), CNOH, $CNOCH_3$, S, S(O), $SO_2$ or NH and one or two CH moieties unreplaced or replaced with N.

In one embodiment of Formula (I), A is N or $C(A^2)$;

one or two or three or each of $A^2$, $B^1$, $D^1$ and $E^1$ are independently selected $R^1$, $OR^1$, $SR^1$, $SO_2R^1$, $NHR^1$, $N(R^1)_2$, or $C(O)NHR^1$, and the remainder are independently selected H, F, Cl, Br, or I;

$Y^1$ is H, CN, $NO_2$, F, Cl, Br, I, $CF_3$, $R^{17}$, $NHC(O)R^{17}$, or $C(O)NH_2$;

$R^1$ is $R^2$, $R^3$, $R^4$ or $R^5$;

$R^2$ is phenyl;

$R^3$ is heteroaryl;

$R^4$ is cycloalkyl, heterocycloalkyl or heterocycloalkenyl, each of which is unfused or fused with $R^{4A}$; $R^{4A}$ is cycloalkane;

$R^5$ is alkyl, or alkynyl, each of which is unsubstituted or substituted with one or two or three independently selected $R^6$, $R^7$, $OR^7$, $SR^7$, $SO_2R^7$, $N(R^7)_2$, OH, CN, $CF_3$, F, Cl, Br or I substituents;

$R^6$ is $C_2$-$C_5$-spiroalkyl;

$R^7$ is $R^8$, $R^9$, $R^{10}$ or $R^{11}$;

$R^8$ is phenyl which is unfused or fused with $R^{8A}$;

$R^{8A}$ is heterocycloalkane;

$R^9$ is heteroaryl;

$R^{10}$ is $C_3$-$C_{10}$-cycloalkyl, each having one or two $CH_2$ moieties unreplaced or replaced with independently selected O, S(O), $SO_2$ or NH and one or two CH moieties unreplaced or replaced with N;

$R^{11}$ is alkyl, each of which is unsubstituted or substituted with one or two or three independently selected $OR^{12}$, F, Cl, Br or I substituents;

$R^{12}$ is $R^{16}$;

$R^{16}$ is alkyl;

$R^{17}$ is $R^{19}$ or $R^{21}$;

$R^{19}$ is heteroaryl which is unfused or fused with arene, heteroarene or $R^{19A}$; $R^{19A}$ is cycloalkane, cycloalkene, heterocycloalkane or heterocycloalkene;

$R^{21}$ is alkynyl;

$Z^1$ is $R^{26}$, each of which is substituted with $R^{30}$, each of which is substituted with F, Cl, Br, I, $CH_2R^{37}$, or $CH(R^{31})(R^{37})$;

$R^{26}$ is phenyl;

$R^{30}$ is cycloalkyl, each having two $CH_2$ moieties unreplaced or replaced with NH;

$R^{31}$ and $R^{31A}$ are independently alkyl;

$R^{37}$ is $R^{38}$, $R^{39}$ or $R^{40}$, each of which is substituted with F, Cl, Br, I, $NHR^{41}$, or $R^{41}$;

$R^{38}$ is phenyl;

$R^{39}$ is heteroaryl;

$R^{40}$ is $C_3$-$C_8$-cycloalkyl or $C_4$-$C_8$-cycloalkenyl, each having one or two $CH_2$ moieties unreplaced or replaced with independently selected O, C(O), CNOH, $CNOCH_3$, S, S(O), $SO_2$ or NH;

$R^{41}$ is $R^{42}$, $R^{43}$, or $R^{44}$;

$R^{42}$ is phenyl;

$R^{43}$ is heteroaryl;

$R^{44}$ is $C_3$-$C_9$-cycloalkyl or $C_4$-$C_7$-cycloalkenyl, each having one or two $CH_2$ moieties unreplaced or replaced with independently selected NH and one or two CH moieties unreplaced or replaced with N, and each of which is unfused or fused with $R^{44A}$; $R^{44A}$ is cycloalkane;

wherein the moiety represented by $R^{26}$ is further substituted by one or two or three of independently selected $R^{50A}$, $OR^{50A}$, $SR^{50A}$, $S(O)R^{50A}$, $SO_2R^{50A}$ or $NHR^{50A}$;

$R^{50A}$ is $R^{51A}$, $R^{52A}$ or $R^{54A}$;

$R^{51A}$ is phenyl which is unfused or fused with benzene, heteroarene or $R^{51AA}$; wherein $R^{51AA}$ is heterocycloalkane;

$R^{152A}$ is heteroaryl;

$R^{54A}$ is alkyl, each of which is unsubstituted or substituted with one or two or three of independently selected $R^{55AA}$, or $OR^{55AA}$;

$R^{55AA}$ is phenyl;

wherein moieties represented by $R^2R^3R^4$, $R^6$, $R^{6C}$, $R^8$, $R^{8A}R^9$, $R^{10}$, $R^{13}$, $R^4$, $R^{15}$, $R^{18}$, $R^{19}$, $R^{20}$, $R^{23}$, $R^{24}$, $R^{25}$, $R^{26}$, $R^{27}$, $R^{28}$, $R^{29}$, $R^{30}$, $R^{34}$, $R^{36}$, $R^{38}$, $R^{39}$, $R^{40}$, $R^{42}$, $R^{43}$, $R^{44}$, $R^{47}$, $R^{48}$, and $R^{49}$ are independently unsubstituted, further unsubstituted, substituted or further substituted with one or two or three or four or five independently selected $R^{50}$, $OR^{50}$, $SR^{50}$, $S(O)R^{50}$, $SO_2R^{50}$, $C(O)R^{50}$, $CO(O)R^{50}$, $NH_2$, $NHR^{50}$, $SO_2NH_2$, OH, (O), CN, $CF_3$, $OCF_3$, F, Cl, Br or I substituents;

$R^{50}$ is $R^{51}$, $R^{52}$, or $R^{54}$;

$R^{51}$ is phenyl which is unfused or fused with arene, heteroarene or $R^{51B}$; $R^{51B}$ is heterocycloalkane;

$R^{52}$ is heteroaryl;

$R^{53}$ is $C_3$-$C_6$-cycloalkyl, each having one or two $CH_2$ moieties unreplaced or replaced with independently selected O, and one or two CH moieties unreplaced or replaced with N;

$R^{54}$ is alkyl, each of which is unsubstituted or substituted with one or two or three independently selected $R^{55}$, $OR^{55}$, $N(R^{55})_2$, OH, CN, F, Cl, Br or I substituents; and $R^{55}$ is alkyl or phenyl;

wherein the alkyl is unsubstituted or substituted with $OCH_3$; and $R^{56}$ is $C_3$-$C_8$-cycloalkyl, each having one or two $CH_2$ moieties unreplaced or replaced with independently selected NH and one or two CH moieties unreplaced or replaced with N.

In one embodiment of Formula (I), $A^1$ is N. In another embodiment of Formula (I), $A^1$ is $C(A^2)$. In another embodiment of Formula (I), $A^1$ is $C(A^2)$, and $A^2$ is H.

In one embodiment of Formula (I), $B^1$ is $R^1$, $OR^1$, $SR^1$, $SO_2R^1$, $NHR^1$, $N(R^1)_2$, or $C(O)NHR^1$. In another embodiment of Formula (I), $B^1$ is $NHR^1$. In another embodiment of Formula (I), $B^1$ is $NHR^1$, and $A^1$ is $C(A^2)$, and $A^2$ is H. In another embodiment of Formula (I), $B^1$ is $OR^1$. In another embodiment of Formula (I), $B^1$ is $OR^1$, and $A^1$ is $C(A^2)$, and $A^2$ is H.

In one embodiment of Formula (I), $D^1$ and $E^1$ are H. In another embodiment of Formula (I), $B^1$ is $NHR^1$, and $A^1$ is $C(A^2)$, $A^2$ is H, and $D^1$ and $E^1$ are H. In another embodiment of Formula (I), $B^1$ is $OR^1$, and $A^1$ is $C(A^2)$, $A^2$ is H, and $D^1$ and $E^1$ are H.

In one embodiment of Formula (I), $Y^1$ is H, CN, $NO_2$, F, Cl, Br, I, $CF_3$, $R^7$, $NHC(O)R^{17}$, or $C(O)NH_2$. In another embodiment of Formula (I), $Y^1$ is $NO_2$. In another embodiment of Formula (I), $Y^1$ is Cl. In another embodiment of Formula (I), $B^1$ is $NHR^1$, and $A^1$ is $C(A^2)$, $A^2$ is H, $D^1$ and $E^1$ are H, and $Y^1$ is $NO_2$. In another embodiment of Formula (I), $B^1$ is $OR^1$, and $A^1$ is $C(A^2)$, $A^2$ is H, $D^1$ and $E^1$ are H, and yl is Cl.

In one embodiment of Formula (I), $R^1$ is $R^2$, $R^3$, $R^4$ or $R^5$. In another embodiment of Formula (I), $R^1$ is $R^2$, and $R^2$ is phenyl.

In one embodiment of Formula (I), $R^1$ is $R^3$, and $R^3$ is heteroaryl. In another embodiment of Formula (I), $R^3$ is triazolyl.

In one embodiment of Formula (I), $R^1$ is $R^4$. In another embodiment of Formula (I), $R^1$ is $R^4$, and $R^4$ is cycloalkyl. In another embodiment of Formula (I), $R^1$ is $R^4$, and $R^4$ is cyclohexyl. In another embodiment of Formula (I), $R^1$ is $R^4$, and $R^4$ is heterocycloalkyl. In another embodiment of Formula (I), $R^1$ is $R^4$, and $R^4$ is 8-azabicyclo[3.2.1]octane, azetidinyl, piperidinyl, piperazinyl, pyrrolidinyl, morpholinyl, tetrahydropyranyl, or tetrahydrothiophenyl. In another embodiment of Formula (I), $R^1$ is $R^4$, and $R^4$ is heterocycloalkenyl. In another embodiment of Formula (I), $R^1$ is $R^4$, and $R^4$ is tetrahydropyridazinyl.

In one embodiment of Formula (I), $R^1$ is $R^5$. In another embodiment of Formula (I), $R^1$ is $R^5$ and $R^5$ is alkyl or alkynyl. In another embodiment of Formula (I), $R^1$ is $R^5$ and $R^5$ is alkyl which is unsubstituted. In another embodiment of Formula (I), $R^1$ is $R^5$ and $R^5$ is alkyl which is substituted with one or two or three independently selected $R^6$, $R^7$, $OR^7$, $SR^7$, $SO_2R^7$, $N(R^7)_2$, OH, CN, $CF_3$, F, Cl, Br or I substituents. In another embodiment of Formula (I), $R^1$ is $R^5$ and $R^5$ is alkyl which is substituted with $R^7$.

In one embodiment of Formula (I), $R^7$ is $R^8$, $R^9$, $R^{10}$ or $R^{11}$. In another embodiment of Formula (I), $R^7$ is $R^8$, and $R^8$ is phenyl which is unfused or fused with $R^{8,4}$, and $R^{8,4}$ is heterocycloalkane. In another embodiment of Formula (I), $R^7$ is $R^8$, and $R^8$ is phenyl which is unfused. In another embodiment of Formula (I), $R^7$ is $R^9$, and $R^9$ is heteroaryl. In another embodiment of Formula (I), $R^7$ is $R^9$, and $R^9$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl or 1,2,3-triazolyl. In another embodiment of Formula (I), $R^7$ is $R^9$, and $R^9$ is pyridinyl, thiazolyl, imidazoyl, and 1,2,3-triazolyl. In another embodiment of Formula (I), $R^7$ is $R^{10}$, and $R^{10}$ is $C_3$-$C_{10}$-cycloalkyl. In another embodiment of Formula (I), $R^7$ is $R^{10}$, and $R^{10}$ is $C_6$ or $C_{10}$-cycloalkyl. In another embodiment of Formula (I), $R^7$ is $R^{10}$, and $R^{10}$ is cyclohexyl or adamantanyl. In another embodiment of Formula (I), $R^7$ is $R^{10}$, and $R^{10}$ is morpholinyl, piperazinyl, piperidinyl, tetrahydro-2H-pyranyl, 1,2-dihydropyridinyl, pyranyl, pyridin-1(H)-yl, pyrrolidinyl, oxetanyl, thiomorpholinyl, imidazolidinyl, tetrahydrothiophenyl, dioxolanyl, tetrahydrothiopyranyl, dioxanyl, or tetrahydrofuranyl. In another embodiment of Formula (I), $R^7$ is $R^{10}$, and $R^{10}$ is morpholinyl, piperazinyl, piperidinyl, tetrahydro-2H-pyranyl, 1,2-dihydropyridinyl, pyrrolidinyl, oxetanyl, thiomorpholinyl, imidazolidinyl, tetrahydrothiophenyl, dioxolanyl, tetrahydrothiopyranyl, dioxanyl, or tetrahydrofuranyl. In another embodiment of Formula (I), $R^7$ is $R^{11}$, and $R^{11}$ is alkyl which is unsubstituted or substituted. In another embodiment of Formula (I), $R^7$ is $R^{11}$, and $R^{11}$ is alkyl which is unsubstituted. In another embodiment of Formula (I), $R^7$ is $R^{11}$, and $R^{11}$ is alkyl which is substituted. In another embodiment of Formula (I), $R^7$ is $R^{11}$, and $R^{11}$ is alkyl which is substituted with one or two or three independently selected $OR^{12}$, F, Cl, Br or I substituents.

In another embodiment of Formula (I), $R^7$ is $R^{11}$, $R^{11}$ is alkyl which is substituted with $OR^2$, $R^{12}$ is $R^{16}$, and $R^{16}$ is alkyl.

In one embodiment of Formula (I), $R^{17}$ is $R^{19}$ or $R^{21}$. In another embodiment of Formula (I), $R^{17}$ is $R^{19}$, and $R^{19}$ is heteroaryl. In another embodiment of Formula (I), $R^{17}$ is $R^{19}$, and $R^{19}$ is thiazolyl. In another embodiment of Formula (I), $R^{17}$ is $R^1$, and $R^2$ is alkynyl. In another embodiment of Formula (I), $R^{17}$ is $R^{21}$, and $R^{21}$ is ethynyl.

Still another embodiment pertains to compounds having Formula I which are 4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;

4-(4-((4'-chloro-1,1'-biphenyl-2-yl)methyl)piperazin-1-yl)-2-phenoxy-N-((4-((tetrahydro-2H-pyran-4-ylmethyl)amino)phenyl)sulfonyl)benzamide;

2-(benzyloxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(2-phenylethoxy)benzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(phenylthio)benzamide;

4-(4-((4'-chloro-1,1'-biphenyl-2-yl)methyl)piperazin-1-yl)-2-(phenylthio)-N-((4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(phenylthio)benzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(phenylsulfonyl)benzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(phenylsulfinyl)benzamide;

2-benzyl-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

2-benzyl-4-(4-((4'-chloro-1,1'-biphenyl-2-yl)methyl)piperazin-1-yl)-N-((4-((tetrahydro-2H-pyran-4-ylmethyl)amino)phenyl)sulfonyl)benzamide;

2-benzyl-4-(4-((4'-chloro-1,1'-biphenyl-2-yl)methyl)piperazin-1-yl)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-5-(2-phenylethyl)benzamide;

2-(benzylamino)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

2-anilino-4-(4-((4'-chloro-1,1'-biphenyl-2-yl)methyl)piperazin-1-yl)-N-((34-nitro-4-((tetrahydro-2H-pyran-4-ylmethyl)amino)phenyl)sulfonyl)benzamide;

2-anilino-4-(4-((4'-chloro-1'-biphenyl-2-yl)methyl)piper-
azin-1-yl)N-((4-((tetrahydro-2H-pyran-4-ylmethyl)
amino)phenyl)sulfonyl)benzamide;

4-(4-((4'-chloro-1,1'-biphenyl-2-yl)methyl)piperazin-1-yl)-
2-methoxy-N-((3-nitro-4-((tetrahydro-2H-pyran-4-ylm-
ethyl)amino)phenyl)sulfonyl)benzamide;

4-(4-((2-(4-chlorophenyl)-4,54-dimethylcyclohex-1-en-1-
yl)methyl)piperazin-1-yl)-N-((4-((3-morpholin-4-ylpro-
pyl)amino)-3-nitrophenyl)sulfonyl)-2-phenoxybenza-
mide;

4-(4-((2-(4-chlorophenyl)-5,4-dimethylcyclohex-1-en-1-yl)
methyl)piperazin-1-yl)-2-(1H-indazol-5-yloxy)-N-((4-
((3-morpholin-4-ylpropyl)amino)-3-nitrophenyl)sulfo-
nyl)-2-phenoxybenzamide;

4-(4-((2-(4-chlorophenyl)-4,4-dimethylcyclohex-1-en-1-yl)
methyl)piperazin-1-yl)-2-(1H-indazol-5-yloxy)-N-((4-
((3-morpholin-4-ylpropyl)amino)-3-nitrophenyl)sulfo-
nyl)benzamide;

4-(4-((2-(4-chlorophenyl)-4,4-dimethylcyclohex-1-en-1-yl)
methyl)piperazin-1-yl)-2-((4-(morpholin-4-ylpropyl)
amino)-3-nitrophenyl)sulfonyl)-2-(1,2,3,4-tetrahydro-
quinolin-6-yloxy)benzamide;

4-(4-((2-(4-chlorophenyl)-4,4-dimethylcyclohex-1-en-1-yl)
methyl)piperazin-1-yl)-N-((4-((1-methylpiperidin-4-yl)
amino)-3-nitrophenyl)sulfonyl)-2-(1,2,3,4-tetrahydro-
quinolin-6-yloxy)benzamide;

4-(4-((4'-chloro-4-(pyrrolidin-1-ylmethyl)-1,1'-biphenyl-2-
yl)methyl)piperazin-1-yl)-2-(1H-indol-4-yloxy)-N-((3-
nitro-4-((tetrahydro-2H-pyran-4-ylmethyl)amino)phenyl)
sulfonyl)benzamide;

4-(4-((4'-chloro-4-(2-pyrrolidin-1-ylethyl)-1,1'-biphenyl-2-
yl)methyl)piperazin-1-yl)-2-(1H-indol-4-yloxy)-N-((3-
nitro-4-((tetrahydro-2H-pyran-4-ylmethyl)amino)phenyl)
sulfonyl)benzamide;

4-(4-((2-(4-chlorophenyl)-4,4-dimethylcyclohex-1-en-1-yl)
methyl)piperazin-1-yl)-N-((4-((1-cyclopentylpiperidin-4-
yl)amino)-3-nitrophenyl)sulfonyl)-2-(1H-indol-5-yloxy)
benzamide 4-(4-((4'-chloro-1,1'-biphenyl-2-yl)methyl)-3-isobutylpiper-
azin-1-yl)-N-((3-nitro-4-((tetrahydro-2H-pyran-4-ylm-
ethyl)amino)phenyl)sulfonyl)-2-phenoxybenzamide;

4-(4-((4'-chloro-1,1'-biphenyl-2-yl)methyl)piperazin-1-yl)-
N-((4-(2,4-dioxo-3-azabicyclo(3.2.0)hept-3-yl)phenyl)
sulfonyl)-2-phenoxybenzamide;

4-(4-((4'-chloro-1,1'-biphenyl-2-yl)methyl)piperazin-1-yl)-
N-((4-(4-methyl-6-oxo-1,4,5,6-tetrahydropyridazin-3-yl)
phenyl)sulfonyl)-2-phenoxybenzamide;

4-(4-((4'-chloro-1,1'-biphenyl-2-yl)methyl)piperazin-1-yl)-
N-((4-(3,3-dimethyl-2-oxoazetidin-1-yl)phenyl)sulfo-
nyl)-2-phenoxybenzamide;

4-(4-((4'-chloro-1,1-biphenyl-2-yl)methyl)piperazin-1-yl)-
N-((4-(4-nitro-2H-1,2,3-triazol-2-yl)phenyl)sulfonyl)-2-
phenoxybenzamide;

4-(4-((4'-chloro-1,1'-biphenyl-2-yl)methyl)piperazin-1-yl)-
2-phenoxy-N-((2-(2-piperidin-1-ylethoxy)phenyl)sulfo-
nyl)benzamide;

4-(4-((4'-chloro-1,1'-biphenyl-2-yl)methyl)piperazin-1-yl)-
N-((3-((((1-ethylpyrrolidin-2-yl)methyl)amino)carbo-
nyl)-4-methoxyphenyl)sulfonyl)-2-phenoxybenzamide;

4-(4-((4'-chloro-1,1'-biphenyl-2-yl)methyl)piperazin-1-yl)-
2-(1-naphthyloxy)-N-((3-nitro-4-((tetrahydro-2H-pyran-
4-ylmethyl)amino)phenyl)sulfonyl)benzamide;

4-(4-((4'-chloro-1,1'-biphenyl-2-yl)methyl)piperazin-1-yl)-
2-(2-naphthyloxy)-N-((3-nitro-4-((tetrahydro-2H-pyran-
4-ylmethyl)amino)phenyl)sulfonyl)benzamide;

4-(4-((4'-chloro-1,1'-biphenyl-2-yl)methyl)piperazin-1-yl)-
N-((4-((3-morpholin-4-ylpropyl)amino)-3-nitrophenyl)
sulfonyl)-2-(2-naphthyloxy)benzamide;

4-(4-((4'-chloro-1,1'-biphenyl-2-yl)methyl)piperazin-1-yl)-
2-(2-naphthyloxy)-N-((4-((tetrahydro-2H-pyran-4-ylm-
ethyl)amino)-3-((trifluoromethyl)sulfonyl)phenyl)sulfo-
nyl)benzamide;

4-(4-((4'-chloro-1'-biphenyl-2-yl)methyl)piperazin-1-yl)-N-
((3-nitro-4-((tetrahydro-2H-pyran-4-ylmethyl)amino)
phenyl)sulfonyl)-2-(quinolin-7-yloxy)benzamide;

4-(4-((4'-chloro-1,1'-biphenyl-2-yl)methyl)piperazin-1-yl)-
N-((3-nitro-4-((tetrahydro-2H-pyran-4-ylmethyl)amino)
phenyl)sulfonyl)-2-(quinolin-6-yloxy)benzamide;

4-(4-((4'-chloro-1'-biphenyl-2-yl)methyl)piperazin-1-yl)-2-
(1H-indol-5-yloxy)-N-((3-nitro-4-((tetrahydro-2H-pyran-
4-ylmethyl)amino)phenyl)sulfonyl)benzamide;

4-(4-((4'-chloro-1,1'-biphenyl-2-yl)methyl)piperazin-1-yl)-
2-(isoquinolin-5-yloxy)-N-((3-nitro-4-((tetrahydro-2H-
pyran-4-ylmethyl)amino)phenyl)sulfonyl)benzamide;

4-(4-((4'-chloro-1,1'-biphenyl-2-yl)methyl)piperazin-1-yl)-
N-((4-((3-(dimethylamino)propyl)amino)-3-nitrophenyl)
sulfonyl)-2-(isoquinolin-5-yloxy)benzamide;

4-(4-((4'-chloro-1,1'-biphenyl-2-yl)methyl)piperazin-1-yl)-
N-((4-((3-(dimethylamino)propyl)amino)-3-nitrophenyl)
sulfonyl)-2-(quinolin-6-yloxy)benzamide;

4-(4-((4'-chloro-1,1'-biphenyl-2-yl)methyl)piperazin-1-yl)-
N-((4-((3-(dimethylamino)propyl)amino)-3-nitrophenyl)
sulfonyl)-2-(1H-indol-5-yloxy)benzamide;

4-(4-((4'-chloro-1,1'-biphenyl-2-yl)methyl)piperazin-1-yl)-
2-(1H-indol-4-yloxy)-N-((3-nitro-4-((tetrahydro-2H-py-
ran-4-ylmethyl)amino)phenyl)sulfonyl)benzamide;

4-(4-((4'-chloro-1,1'-biphenyl-2-yl)methyl)piperazin-1-yl)-
N-((4-((3-(dimethylamino)propyl)amino) 3 nitrophenyl)
sulfonyl)-2-(1H-indol-4-yloxy)benzamide;

4-(4-((4'-chloro-1,1'-biphenyl-2-yl)methyl)piperazin-1-yl)-
N-((4-((3-(dimethylamino)propyl)amino)-3-nitrophenyl)
sulfonyl)-2-(1H-indol-6-yloxy)benzamide;

4-(4-((4'-chloro-1,1'-biphenyl-2-yl)methyl)piperazin-1-yl)-
2-(isoquinolin-7-yloxy)-N-((4-((3-morpholin-4-ylpropyl)
amino)-3-nitrophenyl)sulfonyl)benzamide;

4-(4-((4'-chloro-1,1'-biphenyl-2-yl)methyl)piperazin-1-yl)-
N-((4-((3-(dimethylamino)propyl)amino)-3-nitrophenyl)
sulfonyl)-2-(isoquinolin-7-yloxy)benzamide;

4-(4-((2-(4-chlorophenyl)-5,5-dimethylcyclohex-1-en-1-yl)
methyl)piperazin-1-yl)-2-(1H-indol-5-yloxy)-N-((4-((3-
morpholin-4-ylpropyl)amino)-3-nitrophenyl)sulfonyl)
benzamide;

4-(4-((2-(4-chlorophenyl)-5,5-dimethylcyclohex-1-en-1-yl)
methyl)piperazin-1-yl)-N-((4-((3-(dimethylamino)pro-
pyl)amino)-3-nitrophenyl)sulfonyl)-2-(1H-indol-5-
yloxy)benzamide;

4-(4-((2-(4-chlorophenyl)-4,4-dimethylcyclohex-1-en-1-yl)
methyl)piperazin-1-yl)-2-(1H-indol-5-yloxy)-N-((4-((3-
morpholin-4-ylpropyl)amino)-3-nitrophenyl)sulfonyl)
benzamide;

4-(4-((2-(4-chlorophenyl)-4,4-dimethylcyclohex-1-en-1-yl)
methyl)piperazin-1-yl)-N-((4-((3-(dimethylamino)pro-
pyl)amino)-3-nitrophenyl)sulfonyl)-2-(H-indol-5-yloxy)
benzamide;

4-(4-((2-(4-chlorophenyl)-5,5-dimethylcyclohex-1-en-1-yl)
methyl)piperazin-1-yl)-2-(1H-indol-4-yloxy)-N-((4-((3-
morpholin-4-ylpropyl)amino)-3-nitrophenyl)sulfonyl)
benzamide;

4-(4-((2-(4-chlorophenyl)-4,4-dimethylcyclohex-1-en-1-yl)
methyl)piperazin-1-yl)-2-(1H-indol-4-yloxy)-N-((4-((3-
morpholin-4-ylpropyl)amino)-3-nitrophenyl)sulfonyl)
benzamide;

4-(4-((2-(4-chlorophenyl)-5,5-dimethylcyclohex-1-en-1-yl)methyl)piperazin-1-yl)-N-((4-((3-(dimethylamino)propyl)amino)-3-nitrophenyl)sulfonyl)-2-(1H-indol-4-yloxy)benzamide;

4-(4-((2-(4-chlorophenyl)-4,4-dimethylcyclohex-1-en-1-yl)methyl)piperazin-1-yl)-N-((4-((3-(dimethylamino)propyl)amino)-3-nitrophenyl)sulfonyl)-2-(1H-indol-4-yloxy)benzamide;

4-(4-((4'-chloro-1,1'-biphenyl-2-yl)methyl)piperazin-1-yl)-2-(1H-indol-4-yloxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(1H-indol-5-yloxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-N-((4-methoxyphenyl)sulfonyl)-2-phenoxybenzamide;

4-(4-((4'-chloro-1,1'-biphenyl-2-yl)methyl)piperazin-1-yl)-N-((4-methylphenyl)sulfonyl)-2-phenoxybenzamide;

4-(4-((4'-chloro-1,1'-biphenyl-2-yl)methyl)piperazin-1-yl)-2-(1H-indol-5-yloxy)-N-((4-((tetrahydro-2H-pyran-4-ylmethyl)amino)-3-((trifluoromethyl)sulfonyl)phenyl)sulfonyl)benzamide;

4-(4-((4'-chloro-1,1'-biphenyl-2-yl)methyl)piperazin-1-yl)-2-(1H-indol-4-yloxy)-N-((4-((tetrahydro-2H-pyran-4-ylmethyl)amino)-3-((trifluoromethyl)sulfonyl)phenyl)sulfonyl)benzamide;

4-(4-((4'-chloro-1,1'-biphenyl-2-yl)methyl)piperazin-1-yl)-N-((4-((3-(dimethylamino)propyl)amino)-3-((trifluoromethyl)sulfonyl)phenyl)sulfonyl)-2-(1H-indol-5-yloxy)benzamide;

4-(4-((4'-chloro-1,1'-biphenyl-2-yl)methyl)piperazin-1-yl)-2-(1H-indol-4-yloxy)-N-((4-((3-morpholin-4-ylpropyl)amino)-3-((trifluoromethyl)sulfonyl)phenyl)sulfonyl)benzamide;

N-((3-((chloro(difluoro)methyl)sulfonyl)-4-((3-(dimethylamino)propyl)amino)phenyl)sulfonyl)-4-(4-((2-(4-chlorophenyl)-4,4-dimethylcyclohex-1-en-1-yl)methyl)piperazin-1-yl)-2-(1H-indol-5-yloxy)benzamide;

2-(1H-indol-4-yloxy)-4-(4-((2-(4-methoxyphenyl)-4,4-dimethylcyclohex-1-en-1-yl)methyl)piperazin-1-yl)-N-((3-nitro-4-((3-pyrrolidin-1-ylpropyl)amino)phenyl)sulfonyl)benzamide;

4-(4-((4,4-dimethyl-2-(4-(trifluoromethyl)phenyl)cyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((4,4-dimethyl-2-(4-(trifluoromethoxy)phenyl)cyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((4,4-dimethyl-2-(3-(trifluoromethyl)phenyl)cyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(3-fluorophenyl)-4,4-dimethylcyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-fluorophenyl)-4,4-dimethylcyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

N-((3-((chloro(difluoro)methyl)sulfonyl)-4-((1-methylpiperidin-4-yl)amino)phenyl)sulfonyl)-4-(4-((2-(4-chlorophenyl)-4,4-dimethylcyclohex-1-en-1-yl)methyl)piperazin-1-yl)-2-(1H-indol-5-yloxy)benzamide;

4-(4-((2-(4-chlorophenyl)cyclohex-1-en-1-yl)methyl)piperazin-1-yl)-2-(1-indol-5-yloxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-5-yloxy)-N-((4-((1-methylpiperidin-4-yl)amino)-3-((trifluoromethyl)sulfonyl)phenyl)sulfonyl)benzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(phenoxymethyl)benzamide;

4-(4-((4'-chloro-1,1'-biphenyl-2-yl)methyl)piperazin-1-yl)-N-((4-((3-morpholin-4-ylpropyl)amino)phenyl)sulfonyl)-2-phenoxybenzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(pyridin-3-yloxy)benzamide;

4-(4-((4-chloro-1,1'-biphenyl-2-yl)methyl)piperazin-1-yl)-2-(pyridin-3-yloxy)-N-((4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-(((1R)-3-(dimethylamino)-1-((phenylthio)methyl)propyl)amino)-3-nitrophenyl)sulfonyl)-2-phenoxybenzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(pyridin-4-yloxy)benzamide;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(pyridin-3-yloxy)benzamide;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(pyridin-4-yloxy)benzamide;

4-(4-((4'-chloro-1,1'-biphenyl-2-yl)methyl)piperazin-1-yl)-N-((4-((2-(4-methylpiperazin-1-yl)ethyl)amino)-3-nitrophenyl)sulfonyl)-2-phenoxybenzamide;

4-(4-((4'-chloro-1,1'-biphenyl-2-yl)methyl)piperazin-1-yl)-N-((4-((3-(4-methylpiperazin-1-yl)propyl)amino)-3-nitrophenyl)sulfonyl)-2-phenoxybenzamide;

4-(4-((4'-chloro-1,1'-biphenyl-2-yl)methyl)piperazin-1-yl)-N-((4-((3-(dimethylamino)propyl)(methyl)amino)-3-nitrophenyl)sulfonyl)-2-phenoxybenzamide;

4-(4-((4'-chloro-1,1'-biphenyl-2-yl)methyl)piperazin-1-yl)-N-((4-(((1-methylpiperidin-4-yl)methyl)amino)-3-nitrophenyl)sulfonyl)-2-phenoxybenzamide;

4-(4-((4'-chloro-1,1'-biphenyl-2-yl)methyl)piperazin-1-yl)-N-((4-((1-methylpiperidin-4-yl)amino)-3-nitrophenyl)sulfonyl)-2-phenoxybenzamide;

4-(4-((4'-chloro-1,1'-biphenyl-2-yl)methyl)piperazin-1-yl)-N-((3-cyano-4-((3-(dimethylamino)propyl)amino)phenyl)sulfonyl)-2-phenoxybenzamide;

4-(4-((4'-chloro-1,1'-biphenyl-2-yl)methyl)piperazin-1-yl)-N-((3-nitro-4-((3-pyrrolidin-1-ylpropyl)amino)phenyl)sulfonyl)-2-phenoxybenzamide;

4-(4-((4'-chloro-1,1'-biphenyl-2-yl)methyl)piperazin-1-yl)-N-((4-((3-(dimethylamino)propyl)amino)-3-(trifluoromethyl)phenyl)sulfonyl)-2-phenoxybenzamide;

4-(4-((4'-chloro-1,1'-biphenyl-2-yl)methyl)piperazin-1-yl)-N-((4-((3-(isopropyl(methyl)amino)propyl)amino)-3-nitrophenyl)sulfonyl)-2-phenoxybenzamide;

4-(4-((4'-chloro-1,1'-biphenyl-2-yl)methyl)piperazin-1-yl)-N-((4-(3-(dimethylamino)propoxy)-3-nitrophenyl)sulfonyl)-2-phenoxybenzamide;

4-(4-((2-(4-chlorophenyl)-4,4-dimethylcyclohex-1-en-1-yl)methyl)piperazin-1-yl)-2-(1H-indol-5-yloxy)-N-((4-((2-(4-methylpiperazin-1-yl)ethyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-5-yloxy)-N-((4-((3-(4-methylpiperazin-1-yl)propyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-5-yloxy)-N-((3-nitro-4-((3-pyrrolidin-1-ylpropyl)amino)phenyl)sulfonyl)benzamide 4-(4-((2-(4-chlorophenyl)-4,4-dimethylcyclohex-1-en-1-yl)methyl)piperazin-1-yl)-2-(1H-indol-5-yloxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((4-((3-(4-methylpiperazin-1-yl)propyl)amino)-3-nitrophenyl)sulfonyl)benzamide;

4-(4-((2-(4-chlorophenyl)-4,4-dimethylcyclohex-1-en-1-yl)methyl)piperazin-1-yl)-N-((4-(3-(dimethylamino)propoxy)-3-nitrophenyl)sulfonyl)-2-(1H-indol-5-yloxy)benzamide;

4-(4-((2-(4-chlorophenyl)-4,4-dimethylcyclohex-1-en-1-yl)methyl)piperazin-1-yl)-2-(1H-indol-4-yloxy)-N-((4-((2-(4-methylpiperazin-1-yl)ethyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-5-yloxy)-N-((4-(((1-methylpiperidin-4-yl)methyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((4-(((1-methylpiperidin-4-yl)methyl)amino)-3-nitrophenyl)sulfonyl)benzamide;

4-(4-((2-(4-chlorophenyl)-4,4-dimethylcyclohex-1-en-1-yl)methyl)piperazin-1-yl)-N-((4-(3-(dimethylamino)propoxy)-3-nitrophenyl)sulfonyl)-2-(1H-indol-4-yloxy)benzamide;

4-(4 ((2-(4-chlorophenyl)-4,4-dimethylcyclohex-1-en-1-yl)methyl)piperazin-1-yl)-2-(1H-indol-5-yloxy)-N-((4-(4-methylpiperazin-1-yl)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((3-nitro-4-((1-(2,2,2-trifluoroethyl)piperidin-4-yl)amino)phenyl)sulfonyl)benzamide;

4-(4-((2-(4-chlorophenyl)-4,4-dimethylcyclohex-1-en-1-yl)methyl)piperazin-1-yl)-N-((4-(((4-(dimethylamino)-1-methylpiperidin-4-yl)methyl)amino)-3-nitrophenyl)sulfonyl)-2-(1H-indol-5-yloxy)benzamide;

4-(4-((4'-chloro-1,1'-biphenyl-2-yl)methyl)piperazin-1-yl)-2-(2,3-dihydro-1,4-benzodioxin-5-yloxy)-N-((3-nitro-4-((tetrahydro-2H-pyran-4-ylmethyl)amino)phenyl)sulfonyl)benzamide;

5-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-1,1'-biphenyl-2-carboxamide;

5-(4-((4'-chloro-1,1'-biphenyl-2-yl)methyl)piperazin-1-yl)-N-((4-((3-(dimethylamino)propyl)amino)-3-nitrophenyl)sulfonyl)-1,1'-biphenyl-2-carboxamide;

4-(4-((4'-chloro-4-(2-(dimethylamino)ethoxy)-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;

4-(4-((4'-chloro-4-(3-piperidin-1-ylpropoxy)-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;

4-(4-((4'-chloro-4-(2-morpholin-4-ylethoxy)-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;

4-(4-((4'-chloro-4-(3-(dimethylamino)propoxy)-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;

4-(4-((4'-chloro-4-(2-morpholin-4-ylethoxy)-1,1'-biphenyl-2-yl)methyl)piperazin-1-yl)-2-phenoxy-N-((4-((tetrahydro-2H-pyran-4-ylmethyl)amino)-3-((trifluoromethyl)sulfonyl)phenyl)sulfonyl)benzamide;

4-(4-((4'-chloro-4-(3-piperidin-1-ylpropoxy)-1,1'-biphenyl-2-yl)methyl)piperazin-1-yl)-2-phenoxy-N-((4-((tetrahydro-2H-pyran-4-ylmethyl)amino)-3-((trifluoromethyl)sulfonyl)phenyl)sulfonyl)benzamide;

4-(4-((4'-chloro-4-(3-(dimethylamino)propoxy)-1,1'-biphenyl-2-yl)methyl)piperazin-1-yl)-2-phenoxy-N-((4-((tetrahydro-2H-pyran-4-ylmethyl)amino)-3-((trifluoromethyl)sulfonyl)phenyl)sulfonyl)benzamide;

4-(4-((4'-chloro-4-(2-(dimethylamino)ethoxy)-1,1'-biphenyl-2-yl)methyl)piperazin-1-yl)-2-phenoxy-N-((4-((tetrahydro-2H-pyran-4-ylmethyl)amino)-3-((trifluoromethyl)sulfonyl)phenyl)sulfonyl)benzamide;

4-(4-((4'-chloro-4-(2-(dimethylamino)ethoxy)-1,1'-biphenyl-2-yl)methyl)piperazin-1-yl)-N-((3-nitro-4-((3-pyrrolidin-1-ylpropyl)amino)phenyl)sulfonyl)-2-phenoxybenzamide;

4-(4-((4'-chloro-3-(2-(dimethylamino)ethoxy)-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;

4-(4-((4'-chloro-3-(2-(dimethylamino)ethoxy)-1,1'-biphenyl-2-yl)methyl)piperazin-1-yl)-N-((3-nitro-4-((3-pyrrolidin-1-ylpropyl)amino)phenyl)sulfonyl)-2-phenoxybenzamide;

4-(4-((4'-chloro-3-(2-(dimethylamino)ethoxy)-1,1'-biphenyl-2-yl)methyl)piperazin-1-yl)-2-phenoxy-N-((4-((tetrahydro-2H-pyran-4-ylmethyl)amino)-3-((trifluoromethyl)sulfonyl)phenyl)sulfonyl)benzamide;

4-(4-((4'-chloro-4-(2-(dimethylamino)ethoxy)-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((4'-chloro-4-(2-(dimethylamino)ethoxy)-1,1'-biphenyl-2-yl)methyl)piperazin-1-yl)-2-(1H-indol-5-yloxy)-N-((3-nitro-4-((tetrahydro-2H-pyran-4-ylmethyl)amino)phenyl)sulfonyl)benzamide;

4-(4-((4'-chloro-4-(2-morpholin-4-ylethoxy)-1,1'-biphenyl-2-yl)methyl)piperazin-1-yl)-2-(1H-indol-5-yloxy)-N-((3-nitro-4-((tetrahydro-2H-pyran-4-ylmethyl)amino)phenyl)sulfonyl)benzamide;

4-(4-((4'-chloro-3-(2-(dimethylamino)ethoxy)-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((4'-chloro-3-(2-(dimethylamino)ethoxy)-1,1'-biphenyl-2-yl)methyl)piperazin-1-yl)-2-(1H-indol-5-yloxy)-N-((3-nitro-4-((tetrahydro-2H-pyran-4-ylmethyl)amino)phenyl)sulfonyl)benzamide;

4-(4-((4'-chloro-4-(2-morpholin-4-ylethoxy)-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((4'-chloro-3-(2-morpholin-4-ylethoxy)-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((4'-chloro-3-(2-morpholin-4-ylethoxy)-1,1'-biphenyl-2-yl)methyl)piperazin-1-yl)-2-(1H-indol-5-yloxy)-N-((3-nitro-4-((tetrahydro-2H-pyran-4-ylmethyl)amino)phenyl)sulfonyl)benzamide;

4-(4-((4'-chloro-4-(2-(dimethylamino)ethoxy)-1,1'-biphenyl-2-yl)methyl)piperazin-1-yl)-N-((4-((1-methylpiperidin-4-yl)amino)-3-nitrophenyl)sulfonyl)-2-phenoxybenzamide;

4-(4-((4'-chloro-3-(2-(dimethylamino)ethoxy)-1,1'-biphenyl-2-yl)methyl)piperazin-1-yl)-2-(1H-indol-5-yloxy)-N-((3-nitro-4-((3-pyrrolidin-1-ylpropyl)amino)phenyl)sulfonyl)benzamide;

4-(4-((4'-chloro-4-(2-(dimethylamino)ethoxy)-1,1'-biphenyl-2-yl)methyl)piperazin-1-yl)-2-(1H-indol-5-yloxy)-N-((3-nitro-4-((3-pyrrolidin-1-ylpropyl)amino)phenyl)sulfonyl)benzamide;

4-(4-((4'-chloro-4-(2-morpholin-4-ylethoxy)-1,1'-biphenyl-2-yl)methyl)piperazin-1-yl)-2-(1H-indol-5-yloxy)-N-((3-nitro-4-((3-pyrrolidin-1-ylpropyl)amino)phenyl)sulfonyl)benzamide;

4-(4-((4'-chloro-4-(2-(dimethylamino)ethoxy)-1,1'-biphenyl-2-yl)methyl)piperazin-1-yl)-N-((3-nitro-4-((1-(2,2,2-trifluoroethyl)piperidin-4-yl)amino)phenyl)sulfonyl)-2-phenoxybenzamide;

4-(4-((4'-chloro-4-(2-pyrrolidin-1-ylethoxy)-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;

4-(4-((4'-chloro-4-(2-(diisopropylamino)ethoxy)-1,1'-biphenyl-2-yl)methyl)piperazin-1-yl)-N-((3-nitro-4-((tetrahydro-2H-pyran-4-ylmethyl)amino)phenyl)sulfonyl)-2-phenoxybenzamide;

4-(4-((4'-chloro-1,1'-biphenyl-2-yl)methyl)piperazin-1-yl)-2-(2,3-dihydro-1H-indol-5-yloxy)-N-((3-nitro-4-((tetrahydro-2H-pyran-4-ylmethyl)amino)phenyl)sulfonyl)benzamide;

4-(4-((2-(4-chlorophenyl)cyclohept-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-chlorophenyl)cyclooct-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-chlorophenyl)cyclopent-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-chlorophenyl)-4,4-dimethylcyclopent-1-en-1-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((4-(4-chlorophenyl)-6,6-dimethyl-5,6-dihydro-2H-pyran-3-yl)methyl) piperazin-1-yl)-2-(1H-indol-4-yloxy)-N-((4-((1-methylpiperidin-4-yl)amino)-3-nitrophenyl)sulfonyl)benzamide;

4-(4-((2-(4-chlorophenyl)clooct-1-en-1-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((2-(4-chlorophenyl)cyclohept-1-en-1-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((2-(4-chlorophenyl)cyclopent-1-en-1-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((2-(4-chlorophenyl)cyclohex-1-en-1-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((4-(4-chlorophenyl)-6,6-dimethyl-5,6-dihydro-2H-pyran-3-yl)methyl)piperazin-1-yl)-2-(1H-indol-5-yloxy)-N-((4-((1-methylpiperidin-4-yl)amino)-3-nitrophenyl)sulfonyl)benzamide;

4-(4-((2-(4-chlorophenyl)cyclohept-1-en-1-yl)methyl)piperazin-1-yl)-2-(1H-indol-5-yloxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)-2-phenoxybenzamide;

4-(4-((4'-chloro-1,1'-biphenyl-2-yl)methyl)piperazin-1-yl)-N-((4-((2-(dimethylamino)ethyl)amino)-3-nitrophenyl)sulfonyl)-2-phenoxybenzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-phenoxybenzamide;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-phenoxybenzamide;

4-(4-((4'-chloro-1,1'-biphenyl-2-yl)methyl)piperazin-1-yl)-N-((4-((4-(dimethylamino)butyl)amino)-3-nitrophenyl)sulfonyl)-2-phenoxybenzamide;

4-(4-((4'-chloro-1,1'-biphenyl-2-yl)methyl)piperazin-1-yl)-N-((3-nitro-4-((1-(phenylsulfonyl)piperidin-4-yl)amino)phenyl)sulfonyl)-2-phenoxybenzamide;

4-(4-((4'-chloro-1,1'-biphenyl-2-yl)methyl)piperazin-1-yl)-N-((3-nitro-4-((1-(quinolin-8-ylsulfonyl)piperidin-4-yl)amino)phenyl)sulfonyl)-2-phenoxybenzamide;

4-(4-((4'-chloro-1,1'-biphenyl-2-yl)methyl)piperazin-1-yl)-2-phenoxy-N-((4-((1-(phenylsulfonyl)piperidin-4-yl)amino)-3-((trifluoromethyl)sulfonyl)phenyl)sulfonyl)benzamide;

4-(4-((4'-chloro-1,1'-biphenyl-2-yl)methyl)piperazin-1-yl)-2-phenoxy-N-(4-((1-(quinolin-8-ylsulfonyl)piperidin-4-yl)amino)-3-((trifluoromethyl)sulfonyl)phenyl)sulfonyl)benzamide;

4-(4-((4'-chloro-1,1'-biphenyl-2-yl)methyl)piperazin-1-yl)-N-((4-(((1S)-3-(dimethylamino)-1-thien-2-ylpropyl)amino)-3-nitrophenyl)sulfonyl)-2-phenoxybenzamide;

4-(4-((4'-chloro-1,1'-biphenyl-2-yl)methyl)piperazin-1-yl)-N-((3-nitro-4-((thien-2-ylmethyl)amino)phenyl)sulfonyl)-2-phenoxybenzamide;

4-(4-((4'-chloro-1,1'-biphenyl-2-yl)methyl)piperazin-1-yl)-2-phenoxy-N-((4-((tetrahydro-2H-pyran-4-ylmethyl)amino)-3-((trifluoromethyl)sulfonyl)phenyl)sulfonyl)benzamide;

4-(4-((4'-chloro-1,1'-biphenyl-2-yl)methyl)piperazin-1-yl)-N-((3-nitro-4-((2-(1H-1,2,3-triazol-1-yl)ethyl)amino)phenyl)sulfonyl)-2-phenoxybenzamide;

4-(4-((4'-chloro-1,1'-biphenyl-2-yl)methyl)piperazin-1-yl)-N-((3-nitro-4-((2-(2H-1,2,3-triazol-2-yl)ethyl)amino)phenyl)sulfonyl)-2-phenoxybenzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(2-naphthyloxy)benzamide;

4-(4-((4'-chloro-1,1'-biphenyl-2-yl)methyl)piperazin-1-yl)-N-((3-nitro-4-((2-(2-oxopyridin-1(2H)-yl)ethyl)amino) phenyl)sulfonyl)-2-phenoxybenzamide;

4-(4-((4'-chloro-1,1'-biphenyl-2-yl)methyl)piperazin-1-yl)-N-((3-nitro-4-((2-(pyridin-2-yloxy)ethyl)amino)phenyl) sulfonyl)-2-phenoxybenzamide;

4-(4-((4'-chloro-1,1'-biphenyl-2-yl)methyl)piperazin-1-yl)-N-((3-nitro-4-((2-pyridin-4-ylethyl)amino)phenyl)sulfonyl)-2-phenoxybenzamide;

4-(4-((2-(4-chlorophenyl)-4,4-dimethylcyclohex-1-en-1-yl) methyl)piperazin-1-yl)-N-((4-((3-(dimethylamino)propyl)amino)-3-((trifluoromethyl)sulfonyl)phenyl)sulfonyl)-2-(1H-indol-5-yloxy)benzamide;

4-(4-((2-(4-chlorophenyl)-4,4-dimethylcyclohex-1-en-1-yl) methyl)piperazin-1-yl)-N-((4-((3-(dimethylamino)propyl)amino)-3-(trifluoromethyl)phenyl)sulfonyl)-2-(1H-indol-5-yloxy)benzamide;

4-(4-((2-(4-chlorophenyl)-4,4-dimethylcyclohex-1-en-1-yl) methyl)piperazin-1-yl)-N-((3-cyano-4-((3-(dimethylamino)propyl)amino)phenyl)sulfonyl)-2-(1H-indol-5-yloxy)benzamide;

4-(4-((2-(4-chlorophenyl)-4,4-dimethylcyclohex-1-en-1-yl) methyl)piperazin-1-yl)-2-(1H-indol-5-yl oxy)-N-((3-nitro-4-((1-tetrahydro-2H-pyran-4-ylpiperidin-4-yl)amino) phenyl)sulfonyl)benzamide;

4-(4-((2-(4-chlorophenyl)-4,4-dimethylcyclohex-1-en-1-yl) methyl)piperazin-1-yl)-2-(1H-indol-5-yloxy)-N-((4-((4-methylpiperazin-1-yl)amino)-3-nitrophenyl)sulfonyl) benzamide;

4-(4-(1-(4'-chloro-1,1'-biphenyl-2-yl)ethyl)piperazin-1-yl)-2-(1H-indol-4-yloxy)-N-((3-nitro-4-((tetrahydro-2H-pyran-4-ylmethyl)amino)phenyl)sulfonyl)benzamide;

N-((4-(((4-aminotetrahydro-2H-pyran-4-yl)methyl)amino)-3-nitrophenyl)sulfonyl)-4-(4-((2-(4-chlorophenyl)-4,4-dimethylcyclohex-1-en-1-yl)methyl)piperazin-1-yl)-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-ylmethyl)amino] phenyl}sulfonyl)benzamide;

Trans-4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylcyclohexyl)amino]-3-nitrophenyl}sulfonyl)benzamide;

4-(4-{[2-(4-chlorophenyl)-4,4-dimethylcyclohex-1-en-1-yl]methyl-piperazin-1-yl)-2-(1H-indol-5-yloxy)-N-({4-[(2-methoxyethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3S)-tetrahydro-2H-pyran-3-ylmethyl] amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3R)-tetrahydro-2H-pyran-3-ylmethyl] amino}phenyl)sulfonyl]benzamide;

4-(4-{[4-(4-chlorophenyl)-6,6-dimethyl-5,6-dihydro-2H-pyran-3-yl]methyl}piperazin-1-yl)-2-(1H-indol-5-yloxy)-N-({3-nitro-4-[(tetrahydro-2H-pyran-4-ylmethyl) amino]phenyl}sulfonyl)benzamide;

4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-3-fluoro-2-(1H-indol-5-yloxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-3-fluoro-2-(1H-indol-5-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]-2-(1H-indol-4-yloxy)benzamide;

N-[(4-{[(3S,4R)-1-benzyl-3-hydroxypiperidin-4-yl] amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide;

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1 1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[1-(2-methoxyethyl)piperidin-4-yl]amino}-3-nitrophenyl) sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-({4-[(4-methylpiperazin-1-yl)amino]-3-nitrophenyl}sulfonyl) benzamide;

4-(4-{[2-(4-chlorophenyl)-4,4-dimethylcyclohex-1-en-1-yl]methyl}piperazin-1-yl)-N-[(4-{[1-(2-hydroxyethyl)piperidin-4-yl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[1-(2-methoxyethyl)piperidin-4-yl]amino}-3-nitrophenyl) sulfonyl]benzamide;

4-(4-{[2-(4-chlorophenyl)-4,4-dimethylcyclohex-1-en-1-yl]methyl}piperazin-1-yl)-N-[(4-{[1-(3-hydroxypropyl)piperidin-4-yl]amino}-3-nitrophenyl)sulfonyl]-2-(1H-indol-4-yloxy)benzamide;

4-[4-({4'-chloro-3-[3-(dimethylamino)propyl]-1,1'-biphenyl-2-yl}methyl)piperazin-1-yl]-2-(1H-indol-4-yloxy)-N-({3-nitro-4-[(tetrahydro-2H-pyran-4-ylmethyl)amino] phenyl}sulfonyl)benzamide;

4-(4-{[2-(4-chlorophenyl)-4,4-dimethylcyclohex-1-en-1-yl]methyl}piperazin-1-yl)-N-[(4-{[1-(3-hydroxypropyl)piperidin-4-yl]amino}-3-nitrophenyl)sulfonyl]-2-(1H-indol-5-yloxy)benzamide;

4-{4-[(4'-chloro-4-morpholin-4-yl-1,1'-biphenyl-2-yl)methyl]piperazin-1-yl}-2-(1H-indol-4-yloxy)-N-({3-nitro-4-[(tetrahydro-2H-pyran-4-ylmethyl)amino] phenyl}sulfonyl)benzamide;

4-[4-({4'-chloro-3-[2-(dimethylamino)ethoxy]-1,1'-biphenyl-2-yl}methyl)piperazin-1-yl]-2-(1H-indol-4-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[4-(dimethylamino)cyclohexyl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(4-morpholin-4-ylcyclohexyl)amino]-3-nitrophenyl}sulfonyl)benzamide;

4-[4-({4'-chloro-3-[2-(dimethylamino)ethoxy]-1,1'-biphenyl-2-yl}methyl)piperazin-1-yl]-2-(1H-indol-4-yloxy)-N-({4-[(1-methylpiperidin-4-yl)amino]-3-nitrophenyl}sulfonyl)benzamide;

4-{4-[1-(4'-chloro-1,1'-biphenyl-2-yl)ethyl]piperazin-1-yl}-2-(1H-indol-4-yloxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-{[4-({[4-(dimethylamino)tetrahydro-2H-pyran-4-yl]methyl}amino)-3-nitrophenyl]sulfonyl}-2-(1H-indol-5-yloxy)benzamide;

N-({4-[(2-aminocyclohexyl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide;

4-[4-({4'-chloro-4-[3-(dimethylamino)prop-1-ynyl]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[1-(4,4,4-trifluorobutyl)piperidin-4-yl]amino}phenyl)sulfonyl]benzamide;

4-(4-{[2-(4-chlorophenyl)-4,4-dimethylcyclohex-1-en-1-yl]methyl}piperazin-1-yl)-N-[(4-{[2-(4-hydroxy-1-methylpiperidin-4-yl)ethyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-2-yl)piperidin-4-yl]amino}phenyl)sulfonyl]benzamide;

4-(4-{[4'-chloro-4-(2-hydroxyethoxy)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(4-methylpiperazin-1-yl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(4,4,4-trifluorobutyl)piperidin-4-yl]amino}phenyl)sulfonyl]benzamide;

4-{4-[1-(4'-chloro-1,1'-biphenyl-2-yl)ethyl]piperazin-1-yl}-2-(1H-indol-4-yloxy)-N-({4-[(4-methylpiperazin-1-yl)amino]-3-nitrophenyl}sulfonyl)benzamide;

4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({4-[(1-methylpiperidin-4-yl)amino]-3-nitrophenyl}sulfonyl)benzamide;

4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(4-methylpiperazin-1-yl)amino]-3-[(trifluoromethyl)sulfonyl]phenyl}sulfonyl)benzamide;

4-(4-{[4'-chloro-4-(2-hydroxyethoxy)-1,1'-biphenyl-2-yl]methyl}piperazin-1-yl)-2-(1H-indol-4-yloxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[3-(3-oxopiperazin-1-yl)propyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[3-(3-oxopiperazin-1-yl)propyl]amino}phenyl)sulfonyl]benzamide;

4-(4-{[2-(4-chlorophenyl)-5-hydroxycyclohex-1-en-1-yl]methyl}piperazin-1-yl)-2-(1H-indol-5-yloxy)-N-({4-[(1-methylpiperidin-4-yl)amino]-3-nitrophenyl}sulfonyl)benzamide;

4-(4-{[2-(4-chlorophenyl)-5-hydroxycyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-5-hydroxycyclohex-1-en-1-yl]methyl}piperazin-1-yl)-2-(1H-indol-5-yloxy)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[1-(2,3-dihydro-1H-inden-2-yl)piperidin-4-yl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-N-[(4-{[1-(2,3-dihydro-1H-inden-2-yl)piperidin-4-yl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(1-morpholin-4-ylcyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-2-ylmethyl)piperidin-4-yl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-4-ylmethyl)piperidin-4-yl]amino}phenyl)sulfonyl]benzamide;

4-(4-{[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[4-(2-hydroxyethyl)piperazin-1-yl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(3S)-1-methylpyrrolidin-3-yl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-[(4-{[1-(3-fluoropropyl)piperidin-4-yl]amino}-3-nitrophenyl)sulfonyl]-2-(1H-indol-5-yloxy)benzamide;

4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({3-nitro-4-[(tetrahydro-2H-pyran-4-ylmethyl)amino]phenyl}sulfonyl)benzamide;

N-[(4-{[(4-aminotetrahydro-2H-pyran-4-yl)methyl]amino}-3-nitrophenyl)sulfonyl]-4-[4-{[2-(4-chlorophenyl)-4,4- dimethylcyclohex-1-en-1-yl]methyl}-3-(hydroxymethyl)piperazin-1-yl]-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[(1-hydroxycyclohexyl)methyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(2-methoxyethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[4-(hydroxymethyl)tetrahydro-2H-pyran-4-yl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[4-(hydroxymethyl)tetrahydro-2H-pyran-4-yl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-N-({4-[(2-hydroxy-1-tetrahydro-2H-pyran-4-ylethyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[3-nitro-4-({1-[2-(1H-pyrazol-1-yl)ethyl]piperidin-4-yl}amino)phenyl]sulfonyl}benzamide;

4-(4-{[2-(4-chlorophenyl)-4,4-dimethylcyclohex-1-en-1-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-{[4-(methylamino)-3-nitrophenyl]sulfonyl}benzamide;

4-(4-{[2-(4-chlorophenyl)-4,4-dimethylcyclohex-1-en-1-yl]methyl}piperazin-1-yl)-2-(1H-indol-4-yloxy)-N-{[4-(methylamino)-3-nitrophenyl]sulfonyl}benzamide;

4-{4-[1-(4'-chloro-1,1'-biphenyl-2-yl)ethyl]piperazin-1-yl}-2-(1H-indol-4-yloxy)-N-({4-[(3-morpholin-4-ylpropyl)amino]-3-nitrophenyl}sulfonyl)benzamide;

4-(4-{[2-(4-chlorophenyl)-5-hydroxycyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-5-morpholin-4-ylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

N-[(4-{[(1-aminocyclohexyl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(2-oxopyrrolidin-1-yl)ethyl]amino}phenyl)sulfonyl]benzamide;

4-{4-[1-(4'-chloro-1,1'-biphenyl-2-yl)ethyl]piperazin-1-yl}-2-(1H-indol-5-yloxy)-N-({3-nitro-4-[(tetrahydro-2H-pyran-4-ylmethyl)amino]phenyl}sulfonyl)benzamide;

4-(4-{1-[2-(4-chlorophenyl)-4,4-dimethylcyclohex-1-en-1-yl]ethyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{1-[2-(4-chlorophenyl)-4,4-dimethylcyclohex-1-en-1-yl]ethyl}piperazin-1-yl)-2-(H-indol-5-yloxy)-N-({4-[(4-methylpiperazin-1-yl)amino]-3-nitrophenyl}sulfonyl)benzamide;

4-{4-[(1R)-1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide;

4-{4-[(1S)-1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide;

4-(4-{1-[2-(4-chlorophenyl)-4,4-dimethylcyclohex-1-en-1-yl]ethyl}piperazin-1-yl)-2-(1H-indol-5-yloxy)-N-({4-[(3-morpholin-4-ylpropyl)amino]-3-nitrophenyl}sulfonyl)benzamide;

4-(4-{1-[2-(4-chlorophenyl)-4,4-dimethylcyclohex-1-en-1-yl]ethyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-N-({4-[(cyclohexylmethyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[4-(morpholin-4-ylamino)-3-nitrophenyl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-3-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-{[4-(morpholin-4-ylamino)-3-nitrophenyl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(tetrahydro-2H-pyran-4-ylamino)phenyl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(3-methyloxetan-3-yl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-({4-[(4-methoxycyclohexyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[3-(1,1-dioxidothiomorpholin-4-yl)propyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(2-oxopiperidin-1-yl)ethyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(2-oxoimidazolidin-1-yl)ethyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2-pyridin-4-ylethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(4-morpholin-4-yl-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-{[4-(4-methoxypiperidin-1-yl)-3-nitrophenyl]sulfonyl}benzamide;

4-(4-{[2-(4-chlorophenyl)-5-pyrrolidin-1-ylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(3-oxopiperazin-1-yl)ethyl]amino}phenyl)sulfonyl]benzamide;

4-[4-({4'-chloro-4-[2-(dimethylamino)ethoxy]-1,1'-biphenyl-2-yl}methyl)piperazin-1-yl]-2-(1H-indol-4-yloxy)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[(1,1-dioxidotetrahydrothien-3-yl)methyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-N-({4-[(1,1-dioxidotetrahydrothien-3-yl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[4-[(tetrahydro-2H-pyran-4-ylmethyl)amino]-3-(trifluoromethyl)phenyl]sulfonyl}benzamide;

4-(4-{[2-(4-chlorophenyl)-4,4-dimethylcyclohex-1-en-1-yl]methyl}piperazin-1-yl)-N-({4-[2-(1,3-dioxolan-2-yl)ethyl]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(tetrahydro-2H-pyran-4-ylmethoxy)phenyl]sulfonyl}benzamide;

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[2-(3-oxopiperazin-1-yl)ethyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-({4-[(1-methyl-5-oxopyrrolidin-3-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(1-methyl-6-oxopiperidin-3-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-{[3-nitro-4-(piperidin-1-ylamino)phenyl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(piperidin-1-ylamino)phenyl]sulfonyl}benzamide;

4-(4-{[4-(4-chlorophenyl)-1-methyl-1H-pyrazol-5-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(3-methyloxetan-3-yl)methoxy]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(1-oxidotetrahydro-2H-thiopyran-4-yl)methyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1,3-thiazol-5-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-{[3-nitro-4-(tetrahydro-2H-pyran-4-ylmethoxy)phenyl]sulfonyl}benzamide;

4-(4-{[2-(4-chlorophenyl)-5,5-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2-tetrahydro-2H-pyran-4-ylethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[2-(trifluoromethoxy)ethyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[2-(2-methoxyethoxy)ethyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[3-(methylsulfonyl)propyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-[(4-{[3-(1,1-dioxidothiomorpholin-4-yl)propyl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(2-tetrahydro-2H-pyran-4-ylethyl)phenyl]sulfonyl}benzamide;

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[2-(2-methoxyethoxy)ethyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-({4-[(1,1-dioxidotetrahydrothien-3-yl)amino]-3-nitrophenyl}sulfonyl)-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(trifluoromethoxy)ethyl]amino}phenyl)sulfonyl]benzamide;

4-(4-{[2-(4-chlorophenyl)-4,4-dimethylcyclohex-1-en-1-yl]methyl}piperazin-1-yl)-N-[(4-{[(1,1-dioxidotetrahydro-2H-thiopyran-4-yl)methyl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-N-({4-[(2,2-difluoroethyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(tetrahydro-2H-pyran-4-ylmethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(tetrahydro-2H-pyran-4-ylmethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-N-({4-[(4,4-difluorocyclohexyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-indol-4-yloxy)benzamide;

4-(4-{[4-(4-chlorophenyl)-1-isopropyl-6-oxo-1,6-dihydropyridin-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(tetrahydro-2H-pyran-4-ylmethyl)amino]carbonyl}phenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-({4-[(2-methoxyethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-{[3-nitro-4-(2-tetrahydro-2H-pyran-4-ylethoxy)phenyl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-({4-[(2-methoxyethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-({4-[3-(methylsulfonyl)propoxy]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(3-methoxypropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(H-indol-4-yloxy)-N-({4-[(3-methoxypropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-indol-4-yloxy)benzamide;

4-(4-{[2-(4-chlorophenyl)-4,4-dimethylcyclohex-1-en-1-yl]methyl}piperazin-1-yl)-N-{[4-({[(3R)-4-hydroxy-1-adamantyl]methyl}amino)-3-nitrophenyl]sulfonyl}-2-(1H-indol-5-yloxy)benzamide;

4-(4-{[2-(4-chlorophenyl)-4,4-dimethylcyclohex-1-en-1-yl]methyl}piperazin-1-yl)-N-{[4-({[Cis-4-hydroxy-1-adamantyl]methyl}amino)-3-nitrophenyl]sulfonyl}-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({3-nitro-4-[(3,3,3-trifluoropropyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(3,3,3-trifluoropropyl)amino]phenyl}sulfonyl)benzamide;

N-({5-bromo-6-[(tetrahydro-2H-pyran-4-ylmethyl)amino]pyridin-3-yl}sulfonyl)-4-(4-{[2-(4-chlorophenyl)-4,4-dimethylcyclohex-1-en-1-yl]methyl}piperazin-1-yl)-2-(1H-indol-4-yloxy)benzamide;

4-(4-{[2-(4-chlorophenyl)-4,4-dimethylcyclohex-1-en-1-yl]methyl}piperazin-1-yl)-N-[(4-{[(1,1-dioxidotetrahydrothien-3-yl)methyl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({4-(methylamino)-3-[(trifluoromethyl)sulfonyl]phenyl}sulfonyl)benzamide;

N-{[5-bromo-6-(tetrahydro-2H-pyran-4-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-indol-5-yloxy)benzamide;

4-(4-{[4-(4-chlorophenyl)-6-isopropoxypyridin-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1 1H-indol-5-yloxy)-N-{[6-(tetrahydro-2H-pyran-4-ylmethoxy)-5-(1,3-thiazol-2-yl)pyridin-3-yl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(2-methoxyethyl)amino]carbonyl}phenyl)sulfonyl]benzamide;

4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-indol-5-yloxy)benzamide;

N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[1-(methylsulfonyl)piperidin-4-yl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-(1H-indol-5-yloxy)benzamide;

N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[1-(methylsulfonyl)piperidin-4-yl]amino}-3-nitrophenyl)sulfonyl]benzamide;

4-(4-{[4'-chloro-5-(trifluoromethyl)-1,1'-biphenyl-2-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[4'-chloro-5-(trifluoromethyl)-1,1'-biphenyl-2-yl]methyl}piperazin-1-yl)-2-(1H-indol-5-yloxy)-N-{[3-nitro-4-(tetrahydro-2H-pyran-4-ylmethoxy)phenyl]sulfonyl}benzamide;

4-{4-[(5-tert-butyl-4'-chloro-1,1'-biphenyl-2-yl)methyl]piperazin-1-yl}-2-(1H-indol-5-yloxy)-N-({3-nitro-4-[(tetrahydro-2H-pyran-4-ylmethyl)amino]phenyl}sulfonyl)benzamide;

4-{4-[(5-tert-butyl-4'-chloro-1,1'-biphenyl-2-yl)methyl]piperazin-1-yl}-2-(1H-indol-5-yloxy)-N-{[3-nitro-4-(tetrahydro-2H-pyran-4-ylmethoxy)phenyl]sulfonyl}benzamide;

4-(4-{[2-(4-chlorophenyl)-4,4-dimethylcyclohex-1-en-1-yl]methyl}piperazin-1-yl)-2-(1H-indol-4-yloxy)-N-({3-nitro-4-[(2,2,2-trifluoroethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2,2,2-trifluoroethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-{[(tetrahydro-2H-pyran-4-ylmethyl)amino]carbonyl}phenyl)sulfonyl]benzamide;

4-(4-{[2-(4-chlorophenyl)-4,4-dimethylcyclohex-1-en-1-yl]methyl}piperazin-1-yl)-N-({4-[(2R)-1,4-dioxan-2-ylmethoxy]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-N-({4-[(2S)-1,4-dioxan-2-ylmethoxy]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(3-morpholin-4-ylpropyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(3-morpholin-4-ylpropyl)amino]-3-[(trifluoromethyl)sulfonyl]phenyl}sulfonyl)benzamide;

N-({5-bromo-6-[(tetrahydro-2H-pyran-4-ylmethyl)amino]pyridin-3-yl}sulfonyl)-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-2-(H-indol-5-yloxy)-N-({4-[(2-morpholin-4-ylethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-N-({5-cyano-6-[(tetrahydro-2H-pyran-4-ylmethyl)amino]pyridin-3-yl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)oxy]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)methoxy]-3-nitrophenyl}sulfonyl)benzamide;

4-(4-{[4-(4-chlorophenyl)-1-(3-hydroxypropyl)-1,2,5,6-tetrahydropyridin-3-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide;

benzyl 4-({[4-({[4-(4-{[2-(4-chlorophenyl)-4,4-dimethylcyclohex-1-en-1-yl]methyl}piperazin-1-yl)-2-(1H-indol-5-yloxy)benzoyl]amino}sulfonyl)-2-nitrophenyl]amino}methyl)piperidine-1-carboxylate;

N-{[3-(aminocarbonyl)-4-(tetrahydro-2H-pyran-4-ylmethoxy)phenyl]sulfonyl}-4-(4-{[2-(4-chlorophenyl)-4,4-dimethylcyclohex-1-en-1-yl]methyl}piperazin-1-yl)-2-(1H-indol-5-yloxy)benzamide;

4-(4-{[4'-chloro-5-(trifluoromethyl)-1,1'-biphenyl-2-yl]methyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide;

4-{4-[(5-tert-butyl-4'-chloro-1,1'-biphenyl-2-yl)methyl]piperazin-1-yl}-2-(1H-indol-5-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(1-methyl-1H-imidazol-5-yl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-{[4-(morpholin-4-ylsulfonyl)phenyl]sulfonyl}benzamide;

4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylcyclohexyl)amino]-3-nitrophenyl}sulfonyl)benzamide;

N-{[5-bromo-6-(tetrahydro-2H-pyran-4-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-{[6-[(tetrahydro-2H-pyran-4-ylmethyl)amino]-5-(1,3-thiazol-2-yl)pyridin-3-yl]sulfonyl}benzamide;

4-(4-{[2-(4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-indol-4-yloxy)benzamide;

4-(4-{[2-(4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-N-({4-[(3,3-dimethylbutyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[(S)-1-(hydroxymethyl)-3-methylbutyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(2R)-tetrahydrofuran-2-ylmethyl]amino}phenyl)sulfonyl]benzamide;

4-(4-{[2-(4-chlorophenyl)-4,4-dimethylcyclohex-1-en-1-yl]methyl}piperazin-1-yl)-N-[(4-{[(1R)-1-(hydroxymethyl)-2-methylpropyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(4-methoxyphenyl)amino]-3-nitrophenyl}sulfonyl)benzamide;

N-[(4-{[2-(1,3-benzodioxol-5-yl)ethyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[3-(2-oxopyrrolidin-1-yl)propyl]amino}phenyl)sulfonyl]benzamide;

4-(4-{[2-(4-chlorophenyl)-4,4-dimethylcyclohex-1-en-1-yl]methyl}piperazin-1-yl)-N-({4-[(4-hydroxyphenyl)amino]-3-nitrophenyl}sulfonyl)-2-(1H-indol-5-yloxy)benzamide;

N-{[4-({2-[4-(aminosulfonyl)phenyl]ethyl}amino)-3-nitrophenyl]sulfonyl}-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[3-(1H-imidazol-1-yl)propyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(1S)-1-phenylethyl]amino}phenyl)sulfonyl]benzamide;

N-({2-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[2-(2-methoxyethoxy)ethyl]thio}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[2-(2-methoxyethoxy)ethyl]thio}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-{[4-(methylsulfonyl)phenyl]sulfonyl}benzamide;

4-(4-{[2-(4-chlorophenyl)-4,4-dimethylcyclohex-1-en-1-yl]methyl}piperazin-1-yl)-2-(1H-indol-4-yloxy)-N-{[4-(methylsulfonyl)phenyl]sulfonyl}benzamide;

4-(4-{[2-(4-chlorophenyl)-4,4-dimethylcyclohex-1-en-1-yl]methyl}piperazin-1-yl)-N-({4-[(2,2-dimethyltetrahydro-2H-pyran-4-yl)methoxy]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-indol-4-yloxy)benzamide;

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-indol-4-yloxy)benzamide;

4-(4-{[2-(4-chlorophenyl)-4,4-dimethylcyclohex-1-en-1-yl]methyl}piperazin-1-yl)-N-{5-cyano-6-(2-morpholin-4-ylethoxy)pyridin-3-yl]sulfonyl}-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)oxy]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylbut-2-ynyl)oxy]-3-nitrophenyl}sulfonyl)benzamide;

4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-(1H-indol-4-yloxy)benzamide;

4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-indol-4-yloxy)benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-4-yloxy)benzamide;

4-(4-{[2-(4-chlorophenyl)-4,4-dimethylcyclohex-1-en-1-yl]methyl}piperazin-1-yl)-N-({4-[(3-hydroxy-4-methoxyphenyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(2,3-dihydro-1H-indol-4-yloxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(pyridin-3-ylamino)benzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(pyridin-3-ylamino)benzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(pyridin-3-yloxy)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1,2,3,4-tetrahydroisoquinolin-5-yloxy)benzamide;

4-(4-{[2-(4-chlorophenyl)-4,4-dimethylcyclohex-1-en-1-yl]methyl}piperazin-1-yl)-2-(1H-indazol-4-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indazol-4-yloxy)-N-({3-nitro-4-[(1-tetrahydro-2H-pyran-4-ylpiperidin-4-yl)amino]phenyl}sulfonyl)benzamide;

Trans-4-(4-{[2-(4-chlorophenyl)-4,4-dimethylcyclohex-1-en-1-yl]methyl}piperazin-1-yl)-2-(1H-indazol-4-yloxy)-N-({4-[(4-morpholin-4-ylcyclohexyl)amino]-3-nitrophenyl}sulfonyl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

N-({5-chloro-6-[(4-fluorotetrahydro-2H-pyran-4-yl)methoxy]pyridin-3-yl}sulfonyl)-4-(4-{[2-(4-chlorophenyl)-4, 4-dimethylcyclohex-1-en-1-yl]methyl}piperazin-1-yl)-2-(1H-indazol-4-yloxy)benzamide;

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indol-4-yloxy)benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indazol-4-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide;

2-(1H-benzimidazol-4-yloxy)-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-indazol-4-yloxy)benzamide;

4-(4-{[2-(4-chlorophenyl)-4,4-dimethylcyclohex-1-en-1-yl]methyl}piperazin-1-yl)-N-{6-[(4-fluorotetrahydro-2H-pyran-4-yl)methoxy]-5-(trifluoromethyl)pyridin-3-yl]sulfonyl}-2-(1H-indazol-4-yloxy)benzamide;

4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]-2-(1H-indazol-4-yloxy)benzamide;

4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-indazol-4-yloxy)benzamide;

N-[(5-chloro-6-{[(4-fluorotetrahydro-2H-pyran-4-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

Trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(2,2-difluoroethyl)morpholin-2-yl]methyl}amino)-3-nitrophenyl]sulfonyl}benzamide;

4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-indazol-4-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-N-{5-chloro-6-(tetrahydrofuran-3-ylmethoxy)pyridin-3-yl]sulfonyl}-2-(1H-indazol-4-yloxy)benzamide;

Trans-N-({5-chloro-6-[(4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

N-[(5-chloro-6-{[(3R)-1-(2,2-difluoroethyl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

2-(1H-benzimidazol-4-yloxy)-N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)benzamide;

2-(1H-benzimidazol-4-yloxy)-N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)benzamide;

N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-indazol-4-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(cyanomethyl)pyrrolidin-3-yl]amino}-3-nitrophenyl)sulfonyl]benzamide;

2-(1H-benzimidazol-4-yloxy)-4-(4-{[2-(4-chlorophenyl)-4,4-dimethylcyclohex-1-en-1-yl]methyl}piperazin-1-yl)-N-{[4-({(3R)-1-[2-(2-methoxyethoxy)ethyl]pyrrolidin-3-yl}amino)-3-nitrophenyl]sulfonyl}benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(N,N-dimethylglycyl)pyrrolidin-3-yl]amino}-3-nitrophenyl)sulfonyl]benzamide;

2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(cyanomethyl)morpholin-2-yl]methyl}amino)-3-nitrophenyl]sulfonyl}benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(3-nitro-4-{[(4-oxetan-3-ylmorpholin-2-yl)methyl]amino}phenyl)sulfonyl]benzamide;

N-{[5-chloro-6-({(3R)-1-[2-fluoro-1-(fluoromethyl)ethyl]pyrrolidin-3-yl}oxy)pyridin-3-yl]sulfonyl}-4-(4-{[2-(4-chlorophenyl)-4,4-dimethylcyclohex-1-en-1-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-indazol-4-yloxy)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(1H-indazol-4-yloxy)benzamide;

2-(1H-benzimidazol-4-yloxy)-4-(4-{[2-(4-chlorophenyl)-4,4-dimethylcyclohex-1-en-1-yl]methyl}piperazin-1-yl)-N-{[4-({[(2R)-4-(N,N-dimethylglycyl)morpholin-2-yl]methyl}amino)-3-nitrophenyl]sulfonyl}benzamide;

2-(1H-benzimidazol-4-yloxy)-4-(4-{[2-(4-chlorophenyl)-4,4-dimethylcyclohex-1-en-1-yl]methyl}piperazin-1-yl)-N-{[4-({[(2S)-4-(N,N-dimethylglycyl)morpholin-2-yl]methyl}amino)-3-nitrophenyl]sulfonyl}benzamide;

2-(1H-benzimidazol-4-yloxy)-4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)benzamide;

Trans-2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]benzamide;

2-(1H-benzimidazol-4-yloxy)-4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)benzamide;

2-(1H-benzimidazol-4-yloxy)-N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)benzamide;

N-{[5-chloro-6-({(3R)-1-[2-fluoro-1-(fluoromethyl)ethyl]pyrrolidin-3-yl}methoxy)pyridin-3-yl]sulfonyl}-4-(4-{[2-(4-chlorophenyl)-4,4-dimethylcyclohex-1-en-1-yl]methyl}piperazin-1-yl)-2-(1H-indazol-4-yloxy)benzamide;

N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

Trans-4-(4-{[2-(4-chlorophenyl)-4,4-dimethylcyclohex-1-en-1-yl]methyl}piperazin-1-yl)-2-(1H-indazol-4-yloxy)-N-[(4-{[(4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indazol-4-yloxy)benzamide;

N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

2-(1H-benzimidazol-4-yloxy)-N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)benzamide;

Trans-2-(1H-benzimidazol-4-yloxy)-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]benzamide;

2-(1H-benzimidazol-4-yloxy)-4-(4-{[2-(4-chlorophenyl)-4,4-dimethylcyclohex-1-en-1-yl]methyl}piperazin-1-yl)-N-({4-[({(2R)-4-[2-(2-methoxyethoxy)ethyl]morpholin-2-yl}methyl)amino]-3-nitrophenyl}sulfonyl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]benzamide;

N-[(4-{[(4-acetylmorpholin-2-yl)methyl]amino}-3-nitrophenyl)sulfonyl]-2-(1H-benzimidazol-4-yloxy)-4-(4-{[2-(4-chlorophenyl)-4,4-dimethylcyclohex-1-en-1-yl]methyl}piperazin-1-yl)benzamide;

2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(methylsulfonyl)morpholin-2-yl]methyl}amino)-3-nitrophenyl]sulfonyl}benzamide;

4-(4-{[2-(4-chlorophenyl)-4,4-dimethylcyclohex-1-en-1-yl]methyl}piperazin-1-yl)-N-{[6-({4-fluoro-1-[2-fluoro-1-(fluoromethyl)ethyl]piperidin-4-yl}methoxy)-5-(trifluoromethyl)pyridin-3-yl]sulfonyl}-2-(1H-indazol-4-yloxy)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-phenoxybenzamide;

4-(4-{[2-(4-chlorophenyl)-4,4-dimethylcyclohex-1-en-1-yl]methyl}piperazin-1-yl)-N-{[5-chloro-6-(2-tetrahydrofuran-2-ylethoxy)pyridin-3-yl]sulfonyl}-2-(1H-indazol-4-yloxy)benzamide;

Trans-2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide;

2-(1H-benzimidazol-4-yloxy)-N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)benzamide;

N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

N-({5-chloro-6-[(4-fluorotetrahydro-2H-pyran-4-yl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-N-{[5-cyano-6-(2-tetrahydro-2H-pyran-4-ylethoxy)pyridin-3-yl]sulfonyl}-2-(H-indazol-4-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(1R,5S)-8-methyl-8-azabicyclo[3.2.1]oct-3-yl]amino}-3-nitrophenyl)sulfonyl]benzamide;

N-({3-nitro-4-[(tetrahydro-2H-pyran-4-ylmethyl)amino]phenyl}sulfonyl)-2-phenoxy-4-(4-{(3-phenylpropanoyl)[(1S,2S,3S,5R)-2,6,6-trimethylbicyclo[3.1.1]hept-3-yl]amino}piperidin-1-yl)benzamide;

N-({4-[(3-morpholin-4-ylpropyl)amino]-3-nitrophenyl}sulfonyl)-2-phenoxy-4-(4-{(3-phenylpropanoyl) [(1S,2S,3S,5R)-2,6,6-trimethylbicyclo[3.1.1]hept-3-yl]amino}piperidin-1-yl)benzamide;

N-({3-nitro-4-[(tetrahydro-2H-pyran-4-ylmethyl)amino]phenyl}sulfonyl)-2-phenoxy-4-(4-{(3-phenylpropyl)[(1S,2S,3S,5R)-2,6,6-trimethylbicyclo[3.1.1]hept-3-yl]amino}piperidin-1-yl)benzamide;

N-({4-[(3-morpholin-4-ylpropyl)amino]-3-nitrophenyl}sulfonyl)-2-phenoxy-4-(4-{(3-phenylpropyl)[(1S,2S,3S,5R)-2,6,6-trimethylbicyclo[3.1.1]hept-3-yl]amino}piperidin-1-yl)benzamide;

4-[4-(2-{[(1R,5S)-8-methyl-8-azabicyclo[3.2.1]oct-3-yl]amino}benzyl)piperazin-1-yl]-N-({4-[(3-morpholin-4-ylpropyl)amino]-3-nitrophenyl}sulfonyl)-2-phenoxybenzamide;

4-[4-(2-({[(1R,5S)-8-methyl-8-azabicyclo[3.2.1]oct-3-yl]amino}benzyl)piperazin-1-yl]-N-({3-nitro-4-[(tetrahydro-2H-pyran-4-ylmethyl)amino]phenyl}sulfonyl)-2-phenoxybenzamide;

4-{4-[2-(3-azabicyclo[3.2.2]non-3-yl)benzyl]piperazin-1-yl}-N-({3-nitro-4-[(tetrahydro-2H-pyran-4-ylmethyl)amino]phenyl}sulfonyl)-2-phenoxybenzamide;

4-{4-[2-(3-azabicyclo[3.2.2]non-3-yl)benzyl]piperazin-1-yl}-2-phenoxy-N-({4-[(tetrahydro-2H-pyran-4-ylmethyl)amino]-3-[(trifluoromethyl)sulfonyl]phenyl}sulfonyl)benzamide;

4-{4-[2-(3-azabicyclo[3.2.2]non-3-yl)benzyl]piperazin-1-yl}-2-phenoxy-N-({4-[(tetrahydro-2H-pyran-4-ylmethyl)amino]phenyl}sulfonyl)benzamide;

4-{4-[2-(3-azabicyclo[3.2.2]non-3-yl)benzyl]piperazin-1-yl}-N-({4-[(3-morpholin-4-ylpropyl)amino]-3-nitrophenyl}sulfonyl)-2-phenoxybenzamide;

4-(4-{2-[(4R,7S)-2,3,3a,4,7,7a-hexahydro-1H-4,7-methanoinden-5-yl]benzyl}piperazin-1-yl)-N-({3-nitro-4-[(tetrahydro-2H-pyran-4-ylmethyl)amino]phenyl}sulfonyl)-2-phenoxybenzamide;

4-[4-(2-{5-[(1R,5S)-8-azabicyclo[3.2.1]oct-8-ylmethyl]thien-2-yl}benzyl)piperazin-1-yl]-N-({3-nitro-4-[(tetrahydro-2H-pyran-4-ylmethyl)amino]phenyl}sulfonyl)-2-phenoxybenzamide;

4-[4-(2-{5-[(1R,5S)-8-azabicyclo[3.2.1]oct-8-ylmethyl]thien-2-yl}benzylidene)piperidin-1-yl]-N-({3-nitro-4-[(tetrahydro-2H-pyran-4-ylmethyl)amino]phenyl}sulfonyl)-2-phenoxybenzamide;

4-[4-(3-{5-[(1R,5S)-8-azabicyclo[3.2.1]oct-8-ylmethyl]thien-2-yl}benzyl)piperazin-1-yl]-N-({3-nitro-4-[(tetrahydro-2H-pyran-4-ylmethyl)amino]phenyl}sulfonyl)-2-phenoxybenzamide;

and therapeutically acceptable salts, prodrugs, salts of prodrugs and metabolites thereof.

In another aspect, the present invention provides compounds of Formula (II)

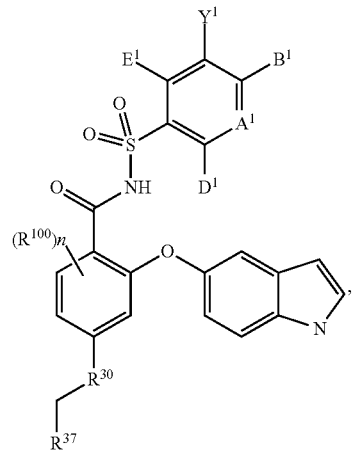

and therapeutically acceptable salts, prodrugs, salts of prodrugs and metabolites thereof, wherein $A^1$, $B^1$, $D^1$, $E^1$, $Y^1$, $R^{30}$, and $R^{37}$ are as described herein for Formula (I), n is 0, 1, 2, or 3; describing the number of substituents on $R^{26}$, and $R^{100}$ is as described for substituents on $R^{26}$.

In one embodiment of Formula (II), $A^1$ is N. In another embodiment of Formula (II), $A^1$ is $C(A^2)$. In another embodiment of Formula (II), $A^1$ is $C(A^2)$, and $A^2$ is H.

In one embodiment of Formula (II), $B^1$ is $R^1$, $OR^1$, $SR^1$, $SO_2R^1$, $NHR^1$, $N(R^1)_2$, or $C(O)NHR^1$. In another embodiment of Formula (II), $B^1$ is $NHR^1$. In another embodiment of Formula (II), $B^1$ is $NHR^1$, and $A^1$ is $C(A^2)$, and $A^2$ is H. In another embodiment of Formula (II), $B^1$ is $OR^1$. In another embodiment of Formula (II), $B^1$ is $OR^1$, and $A^1$ is $C(A^2)$, and $A^2$ is H.

In one embodiment of Formula (II), $D^1$ and $E^1$ are H. In another embodiment of Formula (II), $B^1$ is $NHR^1$, and $A^1$ is $C(A^2)$, $A^2$ is H, and $D^1$ and $E^1$ are H. In another embodiment of Formula (II), $B^1$ is $OR^1$, and $A^1$ is $C(A^2)$, $A^2$ is H, and $D^1$ and $E^1$ are H.

In one embodiment of Formula (II), $Y^1$ is H, CN, $NO_2$, F, Cl, Br, I, $CF_3$, $R^{17}$, $NHC(O)R^{17}$, or $C(O)NH_2$. In another embodiment of Formula (II), $Y^1$ is $NO_2$. In another embodiment of Formula (I), $B^1$ is $NHR^1$, and $A^1$ is $C(A^2)$, $A^2$ is H, $D^1$ and $E^1$ are H, and $Y^1$ is $NO_2$. In another embodiment of Formula (II), $Y^1$ is Cl. In another embodiment of Formula (II), $B^1$ is $OR^1$, and $A^1$ is $C(A^2)$, $A^2$ is H, $D^1$ and $E^1$ are H, and $Y^1$ is Cl.

In one embodiment of Formula (II), $R^1$ is $R^2$, $R^3$, $R^4$ or $R^5$. In another embodiment of Formula (II), $R^1$ is $R^2$, and $R^2$ is phenyl.

In one embodiment of Formula (II), $R^1$ is $R^3$, and $R^3$ is heteroaryl. In another embodiment of Formula (II), $R^3$ is triazolyl.

In one embodiment of Formula (II), $R^1$ is $R^4$. In another embodiment of Formula (II), $R^1$ is $R^4$, and $R^4$ is cycloalkyl. In another embodiment of Formula (II), $R^1$ is $R^4$, and $R^4$ is cyclohexyl. In another embodiment of Formula (II), $R^1$ is $R^4$, and $R^4$ is heterocycloalkyl. In another embodiment of Formula (II), $R^1$ is $R^4$, and $R^4$ is 8-azabicyclo[3.2.1]octane, azetidinyl, piperidinyl, piperazinyl, pyrrolidinyl, morpholinyl, tetrahydropyranyl, or tetrahydrothiophenyl. In another embodiment of Formula (II), $R^1$ is $R^4$, and $R^4$ is heterocycloalkenyl. In another embodiment of Formula (II), $R^1$ is $R^4$, and $R^4$ is tetrahydropyridazinyl.

In one embodiment of Formula (II), $R^1$ is $R^5$. In another embodiment of Formula (II), $R^1$ is $R^5$ and $R^5$ is alkyl or alkynyl. In another embodiment of Formula (II), $R^1$ is $R^5$ and $R^5$ is alkyl which is unsubstituted. In another embodiment of Formula (II), $R^1$ is $R^5$ and $R^5$ is alkyl which is substituted with one or two or three independently selected $R^6$, $R^7$, $OR^7$, $SR^7$, $SO_2R^7$, $N(R^7)_2$, OH, CN, $CF_3$, F, Cl, Br or I substituents. In another embodiment of Formula (II), $R^1$ is $R^5$ and $R^5$ is alkyl which is substituted with $R^7$.

In one embodiment of Formula (II), $R^7$ is $R^8$, $R^9$, $R^{10}$ or $R^{11}$. In another embodiment of Formula (II), $R^7$ is $R^8$, and $R^8$ is phenyl which is unfused or fused with $R^{8A}$, and $R^{8A}$ is heterocycloalkane. In another embodiment of Formula (II), $R^7$ is $R^8$, and $R^8$ is phenyl which is unfused. In another embodiment of Formula (II), $R^7$ is $R^9$, and $R^9$ is heteroaryl. In another embodiment of Formula (II), $R^7$ is $R^9$, and $R^9$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl or 1,2,3-triazolyl. In another embodiment of Formula (II), $R^1$ is $R^9$, and $R^9$ is pyridinyl, thiazolyl, imidazoyl, and 1,2,3-triazolyl. In another embodiment of Formula (II), $R^7$ is $R^{10}$, and $R^{10}$ is $C_3$-$C_{10}$-cycloalkyl. In another embodiment of Formula (II), $R^7$ is $R^{10}$, and $R^{10}$ is $C_6$ or $C_{10}$-cycloalkyl. In another embodiment of Formula (II), $R^7$ is $R^{10}$, and $R^{10}$ is cyclohexyl or adamantanyl. In another embodiment of Formula (II), $R^7$ is $R^{10}$, and $R^{10}$ is morpholinyl, piperazinyl, piperidinyl, tetrahydro-2H-pyranyl, 1,2-dihydropyridinyl, pyranyl, pyridin-1(H)-yl, pyrrolidinyl, oxetanyl, thiomorpholinyl, imidazolidinyl, tetrahydrothiophenyl, dioxolanyl, tetrahydrothiopyranyl, dioxanyl, or tetrahydrofuranyl. In another embodiment of Formula (II), $R^7$ is $R^{10}$, and $R^{10}$ is morpholinyl, piperazinyl, piperidinyl, tetrahydro-2H-pyranyl, 1,2-dihydropyridinyl, pyrrolidinyl, oxetanyl, thiomorpholinyl, imidazolidinyl, tetrahydrothiophenyl, dioxolanyl, tetrahydrothiopyranyl, dioxanyl, or tetrahydrofuranyl. In another embodiment of Formula (II), $R^7$ is $R^{11}$, and $R^{11}$ is alkyl which is unsubstituted or substituted. In another embodiment of Formula (II), $R^7$ is $R^1$, and $R^{11}$ is alkyl which is unsubstituted. In another embodiment of Formula (II), $R^7$ is $R^{11}$, and $R^{11}$ is alkyl which is substituted. In another embodiment of Formula (II), $R^7$ is $R^{11}$, and $R^{11}$ is alkyl which is substituted with one or two or three independently selected $OR^{12}$, F, Cl, Br or I substituents. In another embodiment of Formula (II), $R^7$ is $R^{11}$, $R^{11}$ is alkyl which is substituted with $OR^{12}$, $R^1$ is $R^{16}$, and $R^{16}$ is alkyl.

In one embodiment of Formula (II), $R^{17}$ is $R^{19}$ or $R^{21}$. In another embodiment of Formula (II), $R^{17}$ is $R^{19}$, and $R^{19}$ is heteroaryl. In another embodiment of Formula (II), $R^{17}$ is $R^{19}$, and $R^{19}$ is thiazolyl. In another embodiment of Formula (II), $R^{17}$ is $R^{21}$, and $R^{21}$ is alkynyl. In another embodiment of Formula (II), $R^{17}$ is $R^{21}$, and $R^{21}$ is ethynyl.

Still another embodiment pertains to compounds having Formula II which are 4-(4-((2-(4-chlorophenyl)-4,4-dimethylcyclohex-1-en-1-yl)methyl)piperazin-1-yl)-N-((4-((1-cyclopentylpiperidin-4-yl)amino)-3-nitrophenyl)sulfonyl)-2-(1H-indol-5-yloxy)benzamide 4-(4-((4'-chloro-1,1'-biphenyl-2-yl)methyl)piperazin-1-yl)-2-(1H-indol-5-yloxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(1H-indol-5-yloxy)benzamide;

4-(4-((2-(4-chlorophenyl)-5,5-dimethylcyclohex-1-en-1-yl)methyl)piperazin-1-yl)-2-(1H-indol-5-yloxy)-N-((4-((3-morpholin-4-ylpropyl)amino)-3-nitrophenyl)sulfonyl)benzamide;

4-(4-((2-(4-chlorophenyl)-5,5-dimethylcyclohex-1-en-1-yl)methyl)piperazin-1-yl)-N-((4-((3-(dimethylamino)propyl)amino)-3-nitrophenyl)sulfonyl)-2-(1H-indol-5-yloxy)benzamide;

4-(4-((2-(4-chlorophenyl)-4,4-dimethylcyclohex-1-en-1-yl)methyl)piperazin-1-yl)-2-(1H-indol-5-yloxy)-N-((4-((3-morpholin-4-ylpropyl)amino)-3-nitrophenyl)sulfonyl)benzamide;

4-(4-((2-(4-chlorophenyl)-4,4-dimethylcyclohex-1-en-1-yl)methyl)piperazin-1-yl)-N-((4-((3-(dimethylamino)propyl)amino)-3-nitrophenyl)sulfonyl)-2-(1H-indol-5-yloxy)benzamide;

4-(4-((4'-chloro-1,1'-biphenyl-2-yl)methyl)piperazin-1-yl)-2-(1H-indol-5-yloxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(1H-indol-5-yloxy)-N-((4-((tetrahydro-2H-pyran-4-ylmethyl)amino)-3-((trifluoromethyl)sulfonyl)phenyl)sulfonyl)benzamide;

4-(4-((4'-chloro-1,1'-biphenyl-2-yl)methyl)piperazin-1-yl)-N-((4-((3-(dimethylamino)propyl)amino)-3-((trifluoromethyl)sulfonyl)phenyl)sulfonyl)-2-(1H-indol-5-yloxy)benzamide;

N-((3-((chloro(difluoro)methyl)sulfonyl)-4-((3-(dimethylamino)propyl)amino)phenyl)sulfonyl)-4-(4-((2-(4-chlorophenyl)-4,4-dimethylcyclohex-1-en-1-yl)methyl)piperazin-1-yl)-2-(1H-indol-5-yloxy)benzamide;

N-((3-((chloro(difluoro)methyl)sulfonyl)-4-((1-methylpiperidin-4-yl)amino)phenyl)sulfonyl)-4-(4-((2-(4-chlorophenyl)-4,4-dimethylcyclohex-1-en-1-yl)methyl)piperazin-1-yl)-2-(1H-indol-5-yloxy)benzamide;

4-(4-((2-(4-chlorophenyl)cyclohex-1-en-1-yl)methyl)piperazin-1-yl)-2-(1H-indol-5-yloxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-5-yloxy)-N-((4-((1-methylpiperidin-4-yl)amino)-3-((trifluoromethyl)sulfonyl)phenyl)sulfonyl)benzamide;

4-(4-((2-(4-chlorophenyl)-4,4-dimethylcyclohex-1-en-1-yl)methyl)piperazin-1-yl)-2-(1H-indol-5-yloxy)-N-((4-((2-(4-methylpiperazin-1-yl)ethyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-5-yloxy)-N-((4-((3-(4-methylpiperazin-1-yl)propyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-5-yloxy)-N-((3-nitro-4-((3-pyrrolidin-1-ylpropyl)amino)phenyl)sulfonyl)benzamide 4-(4-((2-(4-chlorophenyl)-4,4-dimethylcyclohex-1-en-1-yl)methyl)piperazin-1-yl)-2-(1H-indol-5-yloxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-N-((4-(3-(dimethylamino)propoxy)-3-nitrophenyl)sulfonyl)-2-(1H-indol-5-yloxy)benzamide;

4-(4-((2-(4-chlorophenyl)-4,4-dimethylcyclohex-1-en-1-yl)methyl)piperazin-1-yl)-2 (1H-indol-5-yloxy)-N-((4-(((1-methylpiperidin-4-yl)methyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-5-yloxy)-N-((4-(4-methylpiperazin-1-yl)-3-nitrophenyl)sulfonyl)benzamide;

4-(4-((2-(4-chlorophenyl)-4,4-dimethylcyclohex-1-en-1-yl)methyl)piperazin-1-yl)-N-((4-(((4-(dimethylamino)-1-methylpiperidin-4-yl)methyl)amino)-3-nitrophenyl)sulfonyl)-2-(1H-indol-5-yloxy)benzamide;

4-(4-((4'-chloro-4-(2-(dimethylamino)ethoxy)-1,1'-biphenyl-2-yl)methyl)piperazin-1-yl)-2-(1H-indol-5-yloxy)-N-((3-nitro-4-((tetrahydro-2H-pyran-4-ylmethyl)amino)phenyl)sulfonyl)benzamide;

4-(4-((4'-chloro-4-(2-morpholin-4-ylethoxy)-1,1'-biphenyl-2-yl)methyl)piperazin-1-yl)-2-(1H-indol-5-yloxy)-N-((3-nitro-4-((tetrahydro-2H-pyran-4-ylmethyl)amino)phenyl)sulfonyl)benzamide;

4-(4-((4'-chloro-3-(2-(dimethylamino)ethoxy)-1,1'-biphenyl-2-yl)methyl)piperazin-1-yl)-2-(1H-indol-5-yloxy)-N-((3-nitro-4-((tetrahydro-2H-pyran-4-ylmethyl)amino)phenyl)sulfonyl)benzamide;

4-(4-((4'-chloro-3-(2-morpholin-4-ylethoxy)-1,1'-biphenyl-2-yl)methyl)piperazin-1-yl)-2-(1H-indol-5-yloxy)-N-((3-nitro-4-((tetrahydro-2H-pyran-4-ylmethyl)amino)phenyl)sulfonyl)benzamide;

4-(4-((4'-chloro-3-(2-(dimethylamino)ethoxy)-1,1'-biphenyl-2-yl)methyl)piperazin-1-yl)-2-(1H-indol-5-yloxy)-N-((3-nitro-4-((3-pyrrolidin-1-ylpropyl)amino)phenyl)sulfonyl)benzamide;

4-(4-((4'-chloro-4-(2-(dimethylamino)ethoxy)-1,1'-biphenyl-2-yl)methyl)piperazin-1-yl)-2-(1H-indol-5-yloxy)-N-((3-nitro-4-((3-pyrrolidin-1-ylpropyl)amino)phenyl)sulfonyl)benzamide;

4-(4-((4'-chloro-4-(2-morpholin-4-ylethoxy)-1,1'-biphenyl-2-yl)methyl)piperazin-1-yl)-2-(1H-indol-5-yloxy)-N-((3-nitro-4-((3-pyrrolidin-1-ylpropyl)amino)phenyl)sulfonyl)benzamide;

4-(4-((4'-chloro-1,1'-biphenyl-2-yl)methyl)piperazin-1-yl)-2-(2,3-dihydro-1H-indol-5-yloxy)-N-((3-nitro-4-((tetrahydro-2H-pyran-4-ylmethyl)amino)phenyl)sulfonyl)benzamide;

4-(4-((4-(4-chlorophenyl)-6,6-dimethyl-5,6-dihydro-2H-pyran-3-yl)methyl)piperazin-1-yl)-2-(1H-indol-5-yloxy)-N-((4-((1-methylpiperidin-4-yl)amino)-3-nitrophenyl)sulfonyl)benzamide;

4-(4-((2-(4-chlorophenyl)cyclohept-1-en-1-yl)methyl)piperazin-1-yl)-2-(H-indol-5-yloxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-N-((4-((3-(dimethylamino)propyl)amino)-3-((trifluoromethyl)sulfonyl)phenyl)sulfonyl)-2-(1H-indol-5-yloxy)benzamide;

4-(4-((2-(4-chlorophenyl)-4,4-dimethylcyclohex-1-en-1-yl)methyl)piperazin-1-yl)-N-((4-((3-(dimethylamino)propyl)amino)-3-(trifluoromethyl)phenyl)sulfonyl)-2-(1H-indol-5-yloxy)benzamide;

4-(4-((2-(4-chlorophenyl)-4,4-dimethylcyclohex-1-en-1-yl)methyl)piperazin-1-yl)-N-((3-cyano-4-((3-(dimethylamino)propyl)amino)phenyl)sulfonyl)-2-(1H-indol-5-yloxy)benzamide;

4-(4-((2-(4-chlorophenyl)-4,4-dimethylcyclohex-1-en-1-yl)methyl)piperazin-1-yl)-2-(1H-indol-5-yloxy)-N-((3-nitro-4-((1-tetrahydro-2H-pyran-4-ylpiperidin-4-yl)amino)phenyl)sulfonyl)benzamide;

4-(4-((2-(4-chlorophenyl)-4,4-dimethylcyclohex-1-en-1-yl)methyl)piperazin-1-yl)-2-(1H-indol-5-yloxy)-N-((4-((4-methylpiperazin-1-yl)amino)-3-nitrophenyl)sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

Trans-4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylcyclohexyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(2-methoxyethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3S)-tetrahydro-2H-pyran-3-ylmethyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3R)-tetrahydro-2H-pyran-3-ylmethyl]amino}phenyl)sulfonyl]benzamide;

4-(4-{[4-(4-chlorophenyl)-6,6-dimethyl-5,6-dihydro-2H-pyran-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-3-fluoro-2-(1H-indol-5-yloxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-3-fluoro-2-(1H-indol-5-yloxy)-N-({3-nitro-4-[(1-tetrahydro-2H-pyran-4-ylpiperidin-4-yl)amino]phenyl}sulfonyl)benzamide;

N-[(4-{[(3S,4R)-1-benzyl-3-hydroxypiperidin-4-yl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide;

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[1-(2-methoxyethyl)piperidin-4-yl]amino}-3-nitrophenyl)sulfonyl]benzamide;

4-(4-{[2-(4-chlorophenyl)-4,4-dimethylcyclohex-1-en-1-yl]methyl}piperazin-1-yl)-5-fluoro-2-(1H-indol-5-yloxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-5-fluoro-2-(1H-indol-5-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-N-[(4-{[1-(3-hydroxypropyl)piperidin-4-yl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-N-{4-({[4-(dimethylamino)tetrahydro-2H-pyran-4-yl]methyl}amino)-3-nitrophenyl]sulfonyl}-2-(1H-indol-5-yloxy)benzamide;

N-({4-[(2-aminocyclohexyl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[2-(4-hydroxy-1-methylpiperidin-4-yl)ethyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-2-yl)piperidin-4-yl]amino}phenyl)sulfonyl]benzamide;

4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(4,4,4-trifluorobutyl)piperidin-4-yl]amino}phenyl)sulfonyl]benzamide;

4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({4-[(1-methylpiperidin-4-yl)amino]-3-nitrophenyl}sulfonyl)benzamide;

4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(4-methylpiperazin-1-yl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[3-(3-oxopiperazin-1-yl)propyl]amino}phenyl)sulfonyl]benzamide;

4-(4-{[2-(4-chlorophenyl)-5-hydroxycyclohex-1-en-1-yl]methyl}piperazin-1-yl)-2-(1H-indol-5-yloxy)-N-({4-[(1-methylpiperidin-4-yl)amino]-3-nitrophenyl}sulfonyl)benzamide;

4-(4-{[2-(4-chlorophenyl)-5-hydroxycyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-5-hydroxycyclohex-1-en-1-yl]methyl}piperazin-1-yl)-2-(1H-indol-5-yloxy)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[1-(2,3-dihydro-1H-inden-2-yl)piperidin-4-yl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(1-morpholin-4-ylcyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-2-ylmethyl)piperidin-4-yl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-4-ylmethyl)piperidin-4-yl]amino}phenyl)sulfonyl]benzamide;

4-(4-{[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[4-(2-hydroxyethyl)piperazin-1-yl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(3S)-1-methylpyrrolidin-3-yl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-[(4-{[1-(3-fluoropropyl)piperidin-4-yl]amino}-3-nitrophenyl)sulfonyl]-2-(1H-indol-5-yloxy)benzamide;

4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({3-nitro-4-[(tetrahydro-2H-pyran-4-ylmethyl)amino]phenyl}sulfonyl)benzamide;

N-[(4-{[(4-aminotetrahydro-2H-pyran-4-yl)methyl]amino}-3-nitrophenyl)sulfonyl]-4-[4-{[2-(4-chlorophenyl)-4,4-dimethylcyclohex-1-en-1-yl]methyl}-3-(hydroxymethyl)piperazin-1-yl]-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[(1-hydroxycyclohexyl)methyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-N-[(4-{[4-(hydroxymethyl)tetrahydro-2H-pyran-4-yl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-N-({4-[(2-hydroxy-1-tetrahydro-2H-pyran-4-ylethyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[3-nitro-4-({1-[2-(1H-pyrazol-1-yl)ethyl]piperidin-4-yl}amino)phenyl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-{[4-(methylamino)-3-nitrophenyl]sulfonyl}benzamide;

4-(4-{[2-(4-chlorophenyl)-5-hydroxycyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-5-morpholin-4-ylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

N-[(4-{[(1-aminocyclohexyl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(2-oxopyrrolidin-1-yl)ethyl]amino}phenyl)sulfonyl]benzamide;

4-{4-[1-(4'-chloro-1,1'-biphenyl-2-yl)ethyl]piperazin-1-yl}-2-(1H-indol-5-yloxy)-N-({3-nitro-4-[(tetrahydro-2H-pyran-4-ylmethyl)amino]phenyl}sulfonyl)benzamide;

4-(4-{1-[2-(4-chlorophenyl)-4,4-dimethylcyclohex-1-en-1-yl]ethyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{1-[2-(4-chlorophenyl)-4,4-dimethylcyclohex-1-en-1-yl]ethyl}piperazin-1-yl)-2-(1H-indol-5-yloxy)-N-({4-[(4-methylpiperazin-1-yl)amino]-3-nitrophenyl}sulfonyl)benzamide;

4-(4-{1-[2-(4-chlorophenyl)-4,4-dimethylcyclohex-1-en-1-yl]ethyl}piperazin-1-yl)-2-(1H-indol-5-yloxy)-N-({4-[(3-morpholin-4-ylpropyl)amino]-3-nitrophenyl}sulfonyl)benzamide;

4-(4-{1-[2-(4-chlorophenyl)-4,4-dimethylcyclohex-1-en-1-yl]ethyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-N-({4-[(cyclohexylmethyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[4-(morpholin-4-ylamino)-3-nitrophenyl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-3-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(tetrahydro-2H-pyran-4-ylamino)phenyl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(3-methyloxetan-3-yl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-({4-[(4-methoxycyclohexyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[3-(1,1-dioxidothiomorpholin-4-yl)propyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(2-oxopiperidin-1-yl)ethyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(2-oxoimidazolidin-1-yl)ethyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2-pyridin-4-ylethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(4-morpholin-4-yl-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-{[4-(4-methoxypiperidin-1-yl)-3-nitrophenyl]sulfonyl}benzamide;

4-(4-{[2-(4-chlorophenyl)-5-pyrrolidin-1-ylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(3-oxopiperazin-1-yl)ethyl]amino}phenyl)sulfonyl]benzamide;

4-(4-{[2-(4-chlorophenyl)-4,4-dimethylcyclohex-1-en-1-yl]methyl}piperazin-1-yl)-N-[(4-{[(1,1-dioxidotetrahydrothien-3-yl)methyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-N-({4-[(1,1-dioxidotetrahydrothien-3-yl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[4-[(tetrahydro-2H-pyran-4-ylmethyl)amino]-3-(trifluoromethyl)phenyl]sulfonyl}benzamide;

4-(4-{[2-(4-chlorophenyl)-4,4-dimethylcyclohex-1-en-1-yl]methyl}piperazin-1-yl)-N-({4-[2-(1,3-dioxolan-2-yl)ethyl]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(tetrahydro-2H-pyran-4-ylmethoxy)phenyl]sulfonyl}benzamide;

4-(4-{[2-(4-chlorophenyl)-4,4-dimethylcyclohex-1-en-1-yl]methyl}piperazin-1-yl)-2-(1 1H-indol-5-yloxy)-N-({4-[(1-methyl-5-oxopyrrolidin-3-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(1-methyl-6-oxopiperidin-3-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(piperidin-1-ylamino)phenyl]sulfonyl}benzamide;

4-(4-{[4-(4-chlorophenyl)-1-methyl-1H-pyrazol-5-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(3-methyloxetan-3-yl)methoxy]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(1-oxidotetrahydro-2H-thiopyran-4-yl)methyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1,3-thiazol-5-ylmethyl)amino]phenyl}sulfonyl)benzamide;

4-(4-{[2-(4-chlorophenyl)-5,5-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2-tetrahydro-2H-pyran-4-ylethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(2-tetrahydro-2H-pyran-4-ylethyl)phenyl]sulfonyl}benzamide;

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[2-(2-methoxyethoxy)ethyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(trifluoromethoxy)ethyl]amino}phenyl)sulfonyl]benzamide;

4-(4-{[2-(4-chlorophenyl)-4,4-dimethylcyclohex-1-en-1-yl]methyl}piperazin-1-yl)-N-({4-[(2,2-difluoroethyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(tetrahydro-2H-pyran-4-ylmethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-N-({4-[(4,4-difluorocyclohexyl)amino]-3-nitrophenyl}sulfonyl)-2-(1H-indol-5-yloxy)benzamide;

4-(4-{[4-(4-chlorophenyl)-1-isopropyl-6-oxo-1,6-dihydropyridin-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(tetrahydro-2H-pyran-4-ylmethyl)amino]carbonyl}phenyl)sulfonyl]benzamide;

4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[(4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-5-yloxy)-N-({4-[(2-methoxyethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-({4-[(3-methoxypropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-N-{[4-({[(3R)-4-hydroxy-1-adamantyl]methyl}amino)-3-nitrophenyl]sulfonyl}-2-(1H-indol-5-yloxy)benzamide;

4-(4-{[2-(4-chlorophenyl)-4,4-dimethylcyclohex-1-en-1-yl]methyl}piperazin-1-yl)-N-{[4-({[(3R)-4-hydroxy-1-adamantyl]methyl}amino)-3-nitrophenyl]sulfonyl}-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(3,3,3-trifluoropropyl)amino]phenyl}sulfonyl)benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-({4-(methylamino)-3-[(trifluoromethyl)sulfonyl]phenyl}sulfonyl)benzamide;

N-{[5-bromo-6-(tetrahydro-2H-pyran-4-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-indol-5-yloxy)benzamide;

4-(4-{[4-(4-chlorophenyl)-6-isopropoxypyridin-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-{[6-(tetrahydro-2H-pyran-4-ylmethoxy)-5-(1,3-thiazol-2-yl)pyridin-3-yl]sulfonyl}benzamide;

4-(4-{[2-(4-chlorophenyl)-4,4-dimethylcyclohex-1-en-1-yl]methyl}piperazin-1-yl)-2-(H-indol-5-yloxy)-N-[(4-{[(2-methoxyethyl)amino]carbonyl}phenyl)sulfonyl]benzamide;

4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-indol-5-yloxy)benzamide;

N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide;

4-(4-{[2-(4-chlorophenyl)-4,4-dimethylcyclohex-1-en-1-yl]methyl}piperazin-1-yl)-2-(1H-indol-5-yloxy)-N-[(4-{[1-(methylsulfonyl)piperidin-4-yl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-(1H-indol-5-yloxy)benzamide;

4-(4-{[4'-chloro-5-(trifluoromethyl)-1,1'-biphenyl-2-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide;

4-(4-{[4'-chloro-5-(trifluoromethyl)-1,1'-biphenyl-2-yl]methyl}piperazin-1-yl)-2-(1 1H-indol-5-yloxy)-N-{[3-nitro-4-(tetrahydro-2H-pyran-4-ylmethoxy)phenyl]sulfonyl}benzamide;

4-{4-[(5-tert-butyl-4'-chloro-1,1'-biphenyl-2-yl)methyl]piperazin-1-yl}-2-(1H-indol-5-yloxy)-N-({3-nitro-4-[(tetrahydro-2H-pyran-4-ylmethyl)amino]phenyl}sulfonyl)benzamide;

4-{4-[(5-tert-butyl-4'-chloro-1,1'-biphenyl-2-yl)methyl]piperazin-1-yl}-2-(1H-indol-5-yloxy)-N-{[3-nitro-4-(tetrahydro-2H-pyran-4-ylmethoxy)phenyl]sulfonyl}benzamide;

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2,2,2-trifluoroethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-5-yloxy)-N-[(3-{[(tetrahydro-2H-pyran-4-ylmethyl)amino]carbonyl}phenyl)sulfonyl]benzamide;

4-(4-{[2-(4-chlorophenyl)-4,4-dimethylcyclohex-1-en-1-yl]methyl}piperazin-1-yl)-N-({4-[(2R)-1,4-dioxan-2-ylmethoxy]-3-nitrophenyl}sulfonyl)-2-(1H-indol-5-yloxy)benzamide;

4-(4-{[2-(4-chlorophenyl)-4,4-dimethylcyclohex-1-en-1-yl]
methyl}piperazin-1-yl)-N-({4-[(2S)-1,4-dioxan-2-yl-
methoxy]-3-nitrophenyl}sulfonyl)-2-(1H-indol-5-yloxy)
benzamide;

4-(4-{[2-(4-chlorophenyl)-4,4-dimethylcyclohex-1-en-1-yl]
methyl}piperazin-1-yl)-2-(1H-indol-5-yloxy)-N-({4-[(3-
morpholin-4-ylpropyl)amino]-3-[(trifluoromethyl)sulfo-
nyl]phenyl}sulfonyl)benzamide;

N-({5-bromo-6-[(tetrahydro-2H-pyran-4-ylmethyl)amino]
pyridin-3-yl}sulfonyl)-4-(4-{[2-(4-chlorophenyl)-4,4-
dimethylcyclohex-1-en-1-yl]methyl}piperazin-1-yl)-2-
(1H-indol-5-yloxy)benzamide;

4-(4-{[2-(4-chlorophenyl)-4,4-dimethylcyclohex-1-en-1-yl]
methyl}piperazin-1-yl)-2-(1H-indol-5-yloxy)-N-({4-[(2-
morpholin-4-ylethyl)amino]-3-[(trifluoromethyl)sulfo-
nyl]phenyl}sulfonyl)benzamide;

4-(4-{[2-(4-chlorophenyl)-4,4-dimethylcyclohex-1-en-1-yl]
methyl}piperazin-1-yl)-N-({5-cyano-6-[(tetrahydro-2H-
pyran-4-ylmethyl)amino]pyridin-3-yl}sulfonyl)-2-(1H-
indol-5-yloxy)benzamide;

4-(4-{[2-(4-chlorophenyl)-4,4-dimethylcyclohex-1-en-1-yl]
methyl}piperazin-1-yl)-2-(1H-indol-5-yloxy)-N-({4-[(1-
methylpiperidin-4-yl)oxy]-3-nitrophenyl}sulfonyl)benza-
mide;

4-(4-{[2-(4-chlorophenyl)-4,4-dimethylcyclohex-1-en-1-yl]
methyl}piperazin-1-yl)-2-(1H-indol-5-yloxy)-N-({4-[(1-
methylpiperidin-4-yl)methoxy]-3-nitrophenyl}sulfonyl)
benzamide;

benzyl 4-({[4-({[4-(4-{[2-(4-chlorophenyl)-4,4-dimethylcy-
clohex-1-en-1-yl]methyl}piperazin-1-yl)-2-(1H-indol-5-
yloxy)benzoyl]amino}sulfonyl)-2-nitrophenyl]
amino}methyl)piperidine-1-carboxylate;

N-{[3-(aminocarbonyl)-4-(tetrahydro-2H-pyran-4-yl-
methoxy)phenyl]sulfonyl}-4-(4-{[2-(4-chlorophenyl)-4,
4-dimethylcyclohex-1-en-1-yl]methyl}piperazin-1-yl)-2-
(1H-indol-5-yloxy)benzamide;

4-(4-{[4'-chloro-5-(trifluoromethyl)-1,1'-biphenyl-2-yl]
methyl}piperazin-1-yl)-2-(1H-indol-5-yloxy)-N-({3-ni-
tro-4-[(1-tetrahydro-2H-pyran-4-ylpiperidin-4-yl)amino]
phenyl}sulfonyl)benzamide;

4-{4-[(5-tert-butyl-4'-chloro-1,1'-biphenyl-2-yl)methyl]pip-
erazin-1-yl}-2-(1H-indol-5-yloxy)-N-({3-nitro-4-[(1-tet-
rahydro-2H-pyran-4-ylpiperidin-4-yl)amino]
phenyl}sulfonyl)benzamide;

4-(4-{[2-(4-chlorophenyl)-4,4-dimethylcyclohex-1-en-1-yl]
methyl}piperazin-1-yl)-2-(1H-indol-5-yloxy)-N-[(4-{[(1-
methyl-1H-imidazol-5-yl)methyl]amino}-3-nitrophenyl)
sulfonyl]benzamide;

4-(4-{[2-(4-chlorophenyl)-4,4-dimethylcyclohex-1-en-1-yl]
methyl}piperazin-1-yl)-2-(1H-indol-5-yloxy)-N-{[4-
(morpholin-4-ylsulfonyl)phenyl]sulfonyl}benzamide;

4-(4-{[2-(4-chlorophenyl)-4,4-dimethylcyclohex-1-en-1-yl]
methyl}piperazin-1-yl)-N-({4-[(1,1-dioxidothiomorpho-
lin-4-yl)amino]-3-nitrophenyl}sulfonyl)-2-(1H-indol-5-
yloxy)benzamide;

4-(4-{[2-(4-chlorophenyl)-4,4-dimethylcyclohex-1-en-1-yl]
methyl}piperazin-1-yl)-2-(1H-indol-5-yloxy)-N-({4-[(4-
morpholin-4-ylcyclohexyl)amino]-3-
nitrophenyl}sulfonyl)benzamide;

4-(4-{[2-(4-chlorophenyl)-4,4-dimethylcyclohex-1-en-1-yl]
methyl}piperazin-1-yl)-N-({3-cyano-4-[(tetrahydro-2H-
pyran-4-ylmethyl)amino]phenyl}sulfonyl)-2-(1H-indol-
5-yloxy)benzamide;

4-(4-{[2-(4-chlorophenyl)-4,4-dimethylcyclohex-1-en-1-yl]
methyl}piperazin-1-yl)-N-({4-[(3,3-dimethylbutyl)
amino]-3-nitrophenyl}sulfonyl)-2-(1H-indol-5-yloxy)
benzamide;

4-(4-{[2-(4-chlorophenyl)-4,4-dimethylcyclohex-1-en-1-yl]
methyl}piperazin-1-yl)-N-[(4-{[(1S)-1-(hydroxymethyl)-
3-methylbutyl]amino}-3-nitrophenyl)sulfonyl]-2-(1H-in-
dol-5-yloxy)benzamide;

4-(4-{[2-(4-chlorophenyl)-4,4-dimethylcyclohex-1-en-1-yl]
methyl}piperazin-1-yl)-2-(1H-indol-5-yloxy)-N-[(3-ni-
tro-4-{[(2R)-tetrahydrofuran-2-ylmethyl]amino}phenyl)
sulfonyl]benzamide;

4-(4-{[2-(4-chlorophenyl)-4,4-dimethylcyclohex-1-en-1-yl]
methyl}piperazin-1-yl)-N-[(4-{[(1R)-1-(hydroxym-
ethyl)-2-methylpropyl]amino}-3-nitrophenyl)sulfonyl]-
2-(1H-indol-5-yloxy)benzamide;

4-(4-{[2-(4-chlorophenyl)-4,4-dimethylcyclohex-1-en-1-yl]
methyl}piperazin-1-yl)-2-(1H-indol-5-yloxy)-N-({4-[(4-
methoxyphenyl)amino]-3-nitrophenyl}sulfonyl)benza-
mide;

N-[(4-{[2-(1,3-benzodioxol-5-yl)ethyl]amino}-3-nitrophe-
nyl)sulfonyl]-4-(4-{[2-(4-chlorophenyl)-4,4-dimethylcy-
clohex-1-en-1-yl]methyl}piperazin-1-yl)-2-(1H-indol-5-
yloxy)benzamide;

4-(4-{[2-(4-chlorophenyl)-4,4-dimethylcyclohex-1-en-1-yl]
methyl}piperazin-1-yl)-2-(1H-indol-5-yloxy)-N-[(3-ni-
tro-4-{[3-(2-oxopyrrolidin-1-yl)propyl]amino}phenyl)
sulfonyl]benzamide;

4-(4-{[2-(4-chlorophenyl)-4,4-dimethylcyclohex-1-en-1-yl]
methyl}piperazin-1-yl)-N-({4-[(4-hydroxyphenyl)
amino]-3-nitrophenyl}sulfonyl)-2-(1H-indol-5-yloxy)
benzamide;

N-{[4-({2-[4-(aminosulfonyl)phenyl]ethyl}amino)-3-nitro-
phenyl]sulfonyl}-4-(4-{[2-(4-chlorophenyl)-4,4-dimeth-
ylcyclohex-1-en-1-yl]methyl}piperazin-1-yl)-2-(1H-in-
dol-5-yloxy)benzamide;

4-(4-{[2-(4-chlorophenyl)-4,4-dimethylcyclohex-1-en-1-yl]
methyl}piperazin-1-yl)-N-[(4-{[3-(1H-imidazol-1-yl)
propyl]amino}-3-nitrophenyl)sulfonyl]-2-(1H-indol-5-
yloxy)benzamide;

4-(4-{[2-(4-chlorophenyl)-4,4-dimethylcyclohex-1-en-1-yl]
methyl}piperazin-1-yl)-2-(1H-indol-5-yloxy)-N-[(3-ni-
tro-4-{[(1S)-1-phenylethyl]amino}phenyl)sulfonyl]ben-
zamide;

N-({2-chloro-5-fluoro-4-[(tetrahydro-2H-pyran-4-ylmethyl)
amino]phenyl}sulfonyl)-4-(4-{[2-(4-chlorophenyl)-4,4-
dimethylcyclohex-1-en-1-yl]methyl}piperazin-1-yl)-2-
(1H-indol-5-yloxy)benzamide;

4-(4-{[2-(4-chlorophenyl)-4,4-dimethylcyclohex-1-en-1-yl]
methyl}piperazin-1-yl)-2-(1H-indol-5-yloxy)-N-[(4-{[2-
(2-methoxyethoxy)ethyl]thio}-3-nitrophenyl)sulfonyl]
benzamide;

4-(4-{[2-(4-chlorophenyl)-4,4-dimethylcyclohex-1-en-1-yl]
methyl}piperazin-1-yl)-2-(1H-indol-5-yloxy)-N-{[4-
(methylsulfonyl)phenyl]sulfonyl}benzamide;

4-(4-{[2-(4-chlorophenyl)-4,4-dimethylcyclohex-1-en-1-yl]
methyl}piperazin-1-yl)-N-({4-[(2,2-dimethyltetrahydro-
2H-pyran-4-yl)methoxy]-3-nitrophenyl}sulfonyl)-2-(1H-
indol-5-yloxy)benzamide;

4-(4-{[2-(4-chlorophenyl)-4,4-dimethylcyclohex-1-en-1-yl]
methyl}piperazin-1-yl)-N-({5-cyano-6-[(4-fluorotetrahy-
dro-2H-pyran-4-yl)methoxy]pyridin-3-yl}sulfonyl)-2-
(1H-indol-5-yloxy)benzamide;

4-(4-{[2-(4-chlorophenyl)-4,4-dimethylcyclohex-1-en-1-yl]
methyl}piperazin-1-yl)-N-{[5-cyano-6-(2-morpholin-4-
ylethoxy)pyridin-3-yl]sulfonyl}-2-(1H-indol-5-yloxy)
benzamide;

4-(4-{[2-(4-chlorophenyl)-4,4-dimethylcyclohex-1-en-1-yl]
methyl}piperazin-1-yl)-2-(1H-indol-5-yloxy)-N-({3-ni-
tro-4-[(1-tetrahydro-2H-pyran-4-ylpiperidin-4-yl)oxy]
phenyl}sulfonyl)benzamide;

4-(4-{[2-(4-chlorophenyl)-4,4-dimethylcyclohex-1-en-1-yl]
methyl}piperazin-1-yl)-2-(1H-indol-5-yloxy)-N-({4-[(4-
morpholin-4-ylbut-2-ynyl)oxy]-3-nitrophenyl}sulfonyl)
benzamide;

4-(4-{[2-(4-chlorophenyl)-4,4-dimethylcyclohex-1-en-1-yl]
methyl}piperazin-1-yl)-N-({4-[(3-hydroxy-4-methox-
yphenyl)amino]-3-nitrophenyl}sulfonyl)-2-(1H-indol-5-
yloxy)benzamide;

4-(4-{[2-(4-chlorophenyl)-4,4-dimethylcyclohex-1-en-1-yl]
methyl}piperazin-1-yl)-2-(1H-indol-5-yloxy)-N-[(4-
{[(1R,5S)-8-methyl-8-azabicyclo[3.2.1]oct-3-yl]amino}-
3-nitrophenyl)sulfonyl]benzamide;

and therapeutically acceptable salts, prodrugs, salts of prodrugs and metabolites thereof.

In another aspect, the present invention provides compounds of Formula (III)

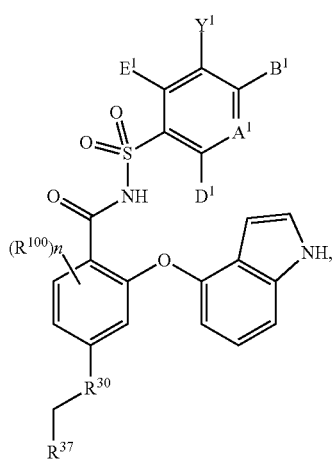

(III)

and therapeutically acceptable salts, prodrugs, salts of prodrugs and metabolites thereof, wherein $A^1$, $B^1$, $D^1$, $E^1$, $Y^1$, $R^{30}$, and $R^{37}$ are as described herein for Formula (I), n is 0, 1, 2, or 3; describing the number of substituents on $R^{26}$, and $R^{100}$ is as described for substituents on $R^{26}$.

In one embodiment of Formula (III), $A^1$ is N. In another embodiment of Formula (III), $A^1$ is $C(A^2)$. In another embodiment of Formula (III), $A^1$ is $C(A^2)$, and $A^2$ is H.

In one embodiment of Formula (III), $B^1$ is $R^1$, $OR^1$, $SR^1$, $SO_2R^1$, $NHR^1$, $N(R^1)_2$, or $C(O)NHR^1$. In another embodiment of Formula (III), $B^1$ is $NHR^1$. In another embodiment of Formula (I), $B^1$ is $NHR^1$, and $A^1$ is $C(A^2)$, and $A^2$ is H. In another embodiment of Formula (III), $B^1$ is $OR^1$. In another embodiment of Formula (III), $B^1$ is $OR^1$, and $A^1$ is $C(A^2)$, and $A^2$ is H.

In one embodiment of Formula (III), $D^1$ and $E^1$ are H. In another embodiment of Formula (III), $B^1$ is $NHR^1$, and $A^1$ is $C(A^2)$, $A^2$ is H, and $D^1$ and $E^1$ are H. In another embodiment of Formula (III), $B^1$ is $OR^1$, and $A^1$ is $C(A^2)$, $A^2$ is H, and $D^1$ and $E^1$ are H.

In one embodiment of Formula (III), Y is H, CN, $NO_2$, F, Cl, Br, I, $CF_3$, $R^{17}$, $NHC(O)R^{17}$, or $C(O)NH_2$. In another embodiment of Formula (III), $Y^1$ is $NO_2$. In another embodiment of Formula (III), $B^1$ is $NHR^1$, and $A^1$ is $C(A^2)$, $A^2$ is H, $D^1$ and $E^1$ are H, and $Y^1$ is $NO_2$. In another embodiment of Formula (III), YL is Cl. In another embodiment of Formula (III), $B^1$ is $OR^1$, and $A^1$ is $C(A^2)$, $A^2$ is H, $D^1$ and $E^1$ are H, and $Y^1$ is Cl.

In one embodiment of Formula (III), $R^1$ is $R^2$, $R^3$, $R^4$ or $R^5$. In another embodiment of Formula (III), $R^1$ is $R^2$, and $R^2$ is phenyl.

In one embodiment of Formula (III), $R^1$ is $R^3$, and $R^3$ is heteroaryl. In another embodiment of Formula (III), $R^3$ is triazolyl.

In one embodiment of Formula (III), $R^1$ is $R^4$. In another embodiment of Formula (III), $R^1$ is $R^4$, and $R^4$ is cycloalkyl. In another embodiment of Formula (III), $R^1$ is $R^4$, and $R^4$ is cyclohexyl. In another embodiment of Formula (III), $R^1$ is $R^4$, and $R^4$ is heterocycloalkyl.

In another embodiment of Formula (III), $R^1$ is $R^4$, and $R^4$ is 8-azabicyclo[3.2.1]octane, azetidinyl, piperidinyl, piperazinyl, pyrrolidinyl, morpholinyl, tetrahydropyranyl, or tetrahydrothiophenyl. In another embodiment of Formula (III), $R^1$ is $R^4$, and $R^4$ is heterocycloalkenyl. In another embodiment of Formula (III), $R^1$ is $R^4$, and $R^4$ is tetrahydropyridazinyl.

In one embodiment of Formula (III), $R^1$ is $R^5$. In another embodiment of Formula (III), $R^1$ is $R^5$ and $R^5$ is alkyl or alkynyl. In another embodiment of Formula (III), $R^1$ is $R^5$ and $R^5$ is alkyl which is unsubstituted. In another embodiment of Formula (III), $R^1$ is $R^5$ and $R^5$ is alkyl which is substituted with one or two or three independently selected $R^6$, $R^7$, $OR^7$, $SR^7$, $SO_2R^7$, $N(R^7)_2$, OH, CN, $CF_3$, F, Cl, Br or I substituents. In another embodiment of Formula (III), $R^1$ is $R^5$ and $R^5$ is alkyl which is substituted with $R^7$.

In one embodiment of Formula (III), $R^7$ is $R^8$, $R^9$, $R^{10}$ or $R^{11}$. In another embodiment of Formula (III), $R^7$ is $R^8$, and $R^8$ is phenyl which is unfused or fused with $R^{8A}$, and $R^{8A}$ is heterocycloalkane. In another embodiment of Formula (III), $R^7$ is $R^8$, and $R^8$ is phenyl which is unfused. In another embodiment of Formula (III), $R^7$ is $R^9$, and $R^9$ is heteroaryl. In another embodiment of Formula (III), $R^7$ is $R^9$, and $R^9$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl or 1,2,3-triazolyl.

In another embodiment of Formula (III), $R^7$ is $R^9$, and $R^9$ is pyridinyl, thiazolyl, imidazoyl, and 1,2,3-triazolyl. In another embodiment of Formula (III), $R^7$ is $R^{10}$, and $R^{10}$ is $C_3$-$C_{10}$-cycloalkyl. In another embodiment of Formula (III), $R^7$ is $R^{10}$, and $R^{10}$ is $C_6$ or $C_{10}$-cycloalkyl. In another embodiment of Formula (III), $R^7$ is $R^{10}$, and $R^{10}$ is cyclohexyl or adamantanyl. In another embodiment of Formula (III), $R^7$ is $R^{10}$, and $R^{10}$ is morpholinyl, piperazinyl, piperidinyl, tetrahydro-2H-pyranyl, 1,2-dihydropyridinyl, pyranyl, pyridin-1(H)-yl, pyrrolidinyl, oxetanyl, thiomorpholinyl, imidazolidinyl, tetrahydrothiophenyl, dioxolanyl, tetrahydrothiopyranyl, dioxanyl, or tetrahydrofuranyl. In another embodiment of Formula (III), $R^7$ is $R^{10}$, and $R^{10}$ is morpholinyl, piperazinyl, piperidinyl, tetrahydro-2H-pyranyl, 1,2-dihydropyridinyl, pyrrolidinyl, oxetanyl, thiomorpholinyl, imidazolidinyl, tetrahydrothiophenyl, dioxolanyl, tetrahydrothiopyranyl, dioxanyl, or tetrahydrofuranyl. In another embodiment of Formula (III), $R^7$ is $R^{11}$, and $R^{11}$ is alkyl which is unsubstituted or substituted. In another embodiment of Formula (III), $R^7$ is $R^{11}$, and $R^{11}$ is alkyl which is unsubstituted. In another embodiment of Formula (III), $R^7$ is $R^{11}$, and $R^{11}$ is alkyl which is substituted. In another embodiment of Formula (III), $R^7$ is $R^{11}$, and $R^{11}$ is alkyl which is substituted with one or two or three independently selected $OR^{12}$, F, Cl, Br or I substituents. In another embodiment of Formula (III), $R^7$ is $R^{11}$, $R^{11}$ is alkyl which is substituted with $OR^1$, $R^{12}$ is $R^{16}$, and $R^{16}$ is alkyl.

In one embodiment of Formula (III), $R^{17}$ is $R^{19}$ or $R^{21}$. In another embodiment of Formula (III), $R^{17}$ is $R^{19}$, and $R^{19}$ is heteroaryl. In another embodiment of Formula (III), $R^{17}$ is $R^{19}$, and $R^{19}$ is thiazolyl. In another embodiment of Formula (III), $R^{17}$ is $R^{21}$, and $R^{21}$ is alkynyl. In another embodiment of Formula (III), $R^{17}$ is $R^{21}$, and $R^{21}$ is ethynyl.

Still another embodiment pertains to compounds having Formula (III) which are 4-(4-((4'-chloro-4-(pyrrolidin-1-ylmethyl)-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((4'-chloro-4-(2-pyrrolidin-1-ylethyl)-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(1H-indol-4-yloxy)benzamide;

4-(4-((2-(4-chlorophenyl)-5,5-dimethylcyclohex-1-en-1-yl)methyl)piperazin-1-yl)-2-(1H-indol-4-yloxy)-N-((4-((3-morpholin-4-ylpropyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((4-((3-morpholin-4-ylpropyl)amino)-3-nitrophenyl)sulfonyl)benzamide;

4-(4-((2-(4-chlorophenyl)-5,5-dimethylcyclohex-1-en-1-yl)methyl)piperazin-1-yl)-N-((4-((3-(dimethylamino)propyl)amino)-3-nitrophenyl)sulfonyl)-2-(1H-indol-4-yloxy)benzamide;

4-(4-((2-(4-chlorophenyl)-4,4-dimethylcyclohex-1-en-1-yl)methyl)piperazin-1-yl)-N-((4-((3-(dimethylamino)propyl)amino)-3-nitrophenyl)sulfonyl)-2-(1H-indol-4-yloxy)benzamide;

4-(4-((4'-chloro-1,1'-biphenyl-2-yl)methyl)piperazin-1-yl)-2-(1H-indol-4-yloxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(1H-indol-4-yloxy)-N-((4-((tetrahydro-2H-pyran-4-ylmethyl)amino)-3-((trifluoromethyl)sulfonyl)phenyl)sulfonyl)benzamide;

4-(4-((4'-chloro-1,1'-biphenyl-2-yl)methyl)piperazin-1-yl)-2-(1H-indol-4-yloxy)-N-((4-((3-morpholin-4-ylpropyl)amino)-3-((trifluoromethyl)sulfonyl)phenyl)sulfonyl)benzamide;

2-(1H-indol-4-yloxy)-4-(4-((2-(4-methoxyphenyl)-4,4-dimethylcyclohex-1-en-1-yl)methyl)piperazin-1-yl)-N-((3-nitro-4-((3-pyrrolidin-1-ylpropyl)amino)phenyl)sulfonyl)benzamide;

4-(4-((4,4-dimethyl-2-(4-(trifluoromethyl)phenyl)cyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((4,4-dimethyl-2-(4-(trifluoromethoxy)phenyl)cyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((4,4-dimethyl-2-(3-(trifluoromethyl)phenyl)cyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(3-fluorophenyl)-4,4-dimethylcyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-fluorophenyl)-4,4-dimethylcyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((4-((3-(4-methylpiperazin-1-yl)propyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((4-((2-(4-methylpiperazin-1-yl)ethyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(1H-indol-4-yloxy)-N-((4-(((1-methylpiperidin-4-yl)methyl)amino)-3-nitrophenyl)sulfonyl)benzamide;

4-(4-((2-(4-chlorophenyl)-4,4-dimethylcyclohex-1-en-1-yl)methyl)piperazin-1-yl)-N-((4-(3-(dimethylamino)propoxy)-3-nitrophenyl)sulfonyl)-2-(1H-indol-4-yloxy)benzamide;

4-(4-((2-(4-chlorophenyl)-4,4-dimethylcyclohex-1-en-1-yl)methyl)piperazin-1-yl)-2-(1H-indol-4-yloxy)-N-((3-nitro-4-((1-(2,2,2-trifluoroethyl)piperidin-4-yl)amino)phenyl)sulfonyl)benzamide;

4-(4-((4'-chloro-4-(2-(dimethylamino)ethoxy)-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((4'-chloro-3-(2-(dimethylamino)ethoxy)-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((4'-chloro-4-(2-morpholin-4-ylethoxy)-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((4'-chloro-3-(2-morpholin-4-ylethoxy)-1,1'-biphenyl-2-yl)methyl)piperazin-1-yl)-2-(1H-indol-4-yloxy)-N-((3-nitro-4-((tetrahydro-2H-pyran-4-ylmethyl)amino)phenyl)sulfonyl)benzamide;

4-(4-((2-(4-chlorophenyl)cyclohept-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-chlorophenyl)cyclooct-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-chlorophenyl)cyclopent-1-en-1-yl)methyl)piperazin-1-yl)-2-(1H-indol-4-yloxy)-N-((3-nitro-4-((3-pyrrolidin-1-ylpropyl)amino)phenyl)sulfonyl)benzamide;

4-(4-((2-(4-chlorophenyl)-4,4-dimethylcyclopent-1-en-1-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((4-(4-chlorophenyl)-6,6-dimethyl-5,6-dihydro-2H-pyran-3-yl)methyl)piperazin-1-yl)-2-(1H-indol-4-yloxy)-N-((4-((1-methylpiperidin-4-yl)amino)-3-nitrophenyl)sulfonyl)benzamide;

4-(4-((2-(4-chlorophenyl)cyclooct-1-en-1-yl)methyl)piperazin-1-yl)-2-(1H-indol-4-yloxy)-N-((4-(((1-methylpiperidin-4-yl)amino)-3-nitrophenyl)sulfonyl)benzamide;

4-(4-((2-(4-chlorophenyl)cyclohept-1-en-1-yl)methyl)piperazin-1-yl)-2-(1H-indol-4-yloxy)-N-((4-(((1-methylpiperidin-4-yl)amino)-3-nitrophenyl)sulfonyl)benzamide;

4-(4-((2-(4-chlorophenyl)cyclopent-1-en-1-yl)methyl)piperazin-1-yl)-2-(1H-indol-4-yloxy)-N-((4-(((1-methylpiperidin-4-yl)amino)-3-nitrophenyl)sulfonyl)benzamide;

4-(4-((2-(4-chlorophenyl)cyclohex-1-en-1-yl)methyl)piperazin-1-yl)-2-(1H-indol-4-yloxy)-N-((4-(((1-methylpiperidin-4-yl)amino)-3-nitrophenyl)sulfonyl)benzamide;

4-(4-(1-(4'-chloro-1,1'-biphenyl-2-yl)ethyl)piperazin-1-yl)-2-(1H-indol-4-yloxy)-N-((3-nitro-4-((tetrahydro-2H-pyran-4-ylmethyl)amino)phenyl)sulfonyl)benzamide;

N-((4-(((4-aminotetrahydro-2H-pyran-4-yl)methyl)amino)-3-nitrophenyl)sulfonyl)-4-(4-((2-(4-chlorophenyl)-4,4-dimethylcyclohex-1-en-1-yl)methyl)piperazin-1-yl)-2-(1H-indol-4-yloxy)benzamide;

4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[1-(2-hydroxyethyl)piperidin-4-yl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[1-(2-methoxyethyl)piperidin-4-yl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-[(4-{[1-(3-hydroxypropyl)piperidin-4-yl]amino}-3-nitrophenyl)sulfonyl]-2-(1H-indol-4-yloxy)benzamide;

4-[4-({4'-chloro-3-[3-(dimethylamino)propyl]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide;

4-{4-[(4'-chloro-4-morpholin-4-yl-1,1'-biphenyl-2-yl)methyl]piperazin-1-yl}-2-(1H-indol-4-yloxy)-N-({3-nitro-4-[(tetrahydro-2H-pyran-4-ylmethyl)amino]phenyl}sulfonyl)benzamide;

4-[4-({4'-chloro-3-[2-(dimethylamino)ethoxy]-1,1'-biphenyl-2-yl}methyl)piperazin-1-yl]-2-(1H-indol-4-yloxy)-N-({3-nitro-4-[(1-tetrahydro-2H-pyran-4-ylpiperidin-4-yl)amino]phenyl}sulfonyl)benzamide;

4-{4-[1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-[(4-{[4-(dimethylamino)cyclohexyl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(4-morpholin-4-ylcyclohexyl)amino]-3-nitrophenyl}sulfonyl)benzamide;

4-[4-({4'-chloro-3-[2-(dimethylamino)ethoxy]-1,1'-biphenyl-2-yl}methyl)piperazin-1-yl]-2-(1H-indol-4-yloxy)-N-({4-[(1-methylpiperidin-4-yl)amino]-3-nitrophenyl}sulfonyl)benzamide;

4-{4-[1-(4'-chloro-1,1'-biphenyl-2-yl)ethyl]piperazin-1-yl}-2-(1H-indol-4-yloxy)-N-({4-[(1-methylpiperidin-4-yl)amino]-3-nitrophenyl}sulfonyl)benzamide;

4-[4-({4'-chloro-4-[3-(dimethylamino)prop-1-ynyl]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[1-(4,4,4-trifluorobutyl)piperidin-4-yl]amino}phenyl)sulfonyl]benzamide;

4-(4-{[4'-chloro-4-(2-hydroxyethoxy)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(4-methylpiperazin-1-yl)amino]-3-[(trifluoromethyl)sulfonyl]phenyl}sulfonyl)benzamide;

4-{4-[1-(4'-chloro-1,1'-biphenyl-2-yl)ethyl]piperazin-1-yl}-2-(1H-indol-4-yloxy)-N-({4-[(4-methylpiperazin-1-yl)amino]-3-nitrophenyl}sulfonyl)benzamide;

4-(4-{[4'-chloro-4-(2-hydroxyethoxy)-1,1'-biphenyl-2-yl]methyl}piperazin-1-yl)-2-(1H-indol-4-yloxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[3-(3-oxopiperazin-1-yl)propyl]amino}phenyl)sulfonyl]benzamide;

4-(4-{[2-(4-chlorophenyl)-4,4-dimethylcyclohex-1-en-1-yl]methyl}piperazin-1-yl)-N-[(4-{[1-(2,3-dihydro-1H-inden-2-yl)piperidin-4-yl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(2-methoxyethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[4-(hydroxymethyl)tetrahydro-2H-pyran-4-yl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-{[4-(methylamino)-3-nitrophenyl]sulfonyl}benzamide;

4-{4-[1-(4'-chloro-1,1'-biphenyl-2-yl)ethyl]piperazin-1-yl}-2-(1H-indol-4-yloxy)-N-({4-[(3-morpholin-4-ylpropyl)amino]-3-nitrophenyl}sulfonyl)benzamide;

4-{4-[(1R)-1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide;

4-{4-[(1S)-1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-{[4-(morpholin-4-ylamino)-3-nitrophenyl]sulfonyl}benzamide;

4-[4-({4'-chloro-4-[2-(dimethylamino)ethoxy]-1,1'-biphenyl-2-yl}methyl)piperazin-1-yl]-2-(1H-indol-4-yloxy)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[2-(3-oxopiperazin-1-yl)ethyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-{[3-nitro-4-(piperidin-1-ylamino)phenyl]sulfonyl}benzamide;

4-(4-{[2-(4-chlorophenyl)-4,4-dimethylcyclohex-1-en-1-yl]methyl}piperazin-1-yl)-2-(1H-indol-4-yloxy)-N-{[3-nitro-4-(tetrahydro-2H-pyran-4-ylmethoxy)phenyl]sulfonyl}benzamide;

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[2-(trifluoromethoxy)ethyl]amino}phenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[2-(2-methoxyethoxy)ethyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[3-(methylsulfonyl)propyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-[(4-{[3-(1,1-dioxidothiomorpholin-4-yl)propyl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-N-({4-[(1,1-dioxidotetrahydrothien-3-yl)amino]-3-nitrophenyl}sulfonyl)-2-(1H-indol-4-yloxy)benzamide;

4-(4-{[2-(4-chlorophenyl)-4,4-dimethylcyclohex-1-en-1-yl]methyl}piperazin-1-yl)-N-[(4-{[(1,1-dioxidotetrahydro-2H-thiopyran-4-yl)methyl]amino}-3-nitrophenyl)sulfonyl]-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(tetrahydro-2H-pyran-4-ylmethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(2-methoxyethyl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-{[3-nitro-4-(2-tetrahydro-2H-pyran-4-ylethoxy)phenyl]sulfonyl}benzamide;

4-(4-{[2-(4-chlorophenyl)-4,4-dimethylcyclohex-1-en-1-yl]methyl}piperazin-1-yl)-2-(1H-indol-4-yl oxy)-N-({4-[3-(methylsulfonyl)propoxy]-3-nitrophenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(3-methoxypropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-({3-nitro-4-[(3,3,3-trifluoropropyl)amino]phenyl}sulfonyl)benzamide;

N-({5-bromo-6-[(tetrahydro-2H-pyran-4-ylmethyl)amino]pyridin-3-yl}sulfonyl)-4-(4-{[2-(4-chlorophenyl)-4,4-dimethylcyclohex-1-en-1-yl]methyl}piperazin-1-yl)-2-(1H-indol-4-yloxy)benzamide;

4-(4-{[2-(4-chlorophenyl)-4,4-dimethylcyclohex-1-en-1-yl]methyl}piperazin-1-yl)-N-[(4-{[(1,1-dioxidotetrahydrothien-3-yl)methyl]amino}-3-nitrophenyl)sulfonyl]-2-(1H-indol-4-yloxy)benzamide;

N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[1-(methylsulfonyl)piperidin-4-yl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-({3-nitro-4-[(2,2,2-trifluoroethyl)amino]phenyl}sulfonyl)benzamide;

4-(4-{[2-(4-chlorophenyl)-4,4-dimethylcyclohex-1-en-1-yl]methyl}piperazin-1-yl)-2-(1H-indol-4-yloxy)-N-({4-[(3-morpholin-4-ylpropyl)amino]-3-[(trifluoromethyl)sulfonyl]phenyl}sulfonyl)benzamide;

4-(4-{[4-(4-chlorophenyl)-1-(3-hydroxypropyl)-1,2,5,6-tetrahydropyridin-3-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide;

N-{[5-bromo-6-(tetrahydro-2H-pyran-4-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-{[6-[(tetrahydro-2H-pyran-4-ylmethyl)amino]-5-(1,3-thiazol-2-yl)pyridin-3-yl]sulfonyl}benzamide;

4-(4-{[2-(4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-indol-4-yloxy)benzamide;

4-(4-{[2-(4-chlorophenyl)-4,4-dimethylcyclohex-1-en-1-yl]methyl}piperazin-1-yl)-2-(1H-indol-4-yloxy)-N-[(4-{[2-(2-methoxyethoxy)ethyl]thio}-3-nitrophenyl)sulfonyl]benzamide;

4-(4-{[2-(4-chlorophenyl)-4,4-dimethylcyclohex-1-en-1-yl]methyl}piperazin-1-yl)-2-(1H-indol-4-yloxy)-N-{[4-(methylsulfonyl)phenyl]sulfonyl}benzamide;

4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-indol-4-yloxy)benzamide;

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-indol-4-yloxy)benzamide;

4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-(1H-indol-4-yloxy)benzamide;

4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-indol-4-yloxy)benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-4-yloxy)benzamide;

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indol-4-yloxy)benzamide;

and therapeutically acceptable salts, prodrugs, salts of prodrugs and metabolites thereof.

In another aspect, the present invention provides compounds of Formula (IV)

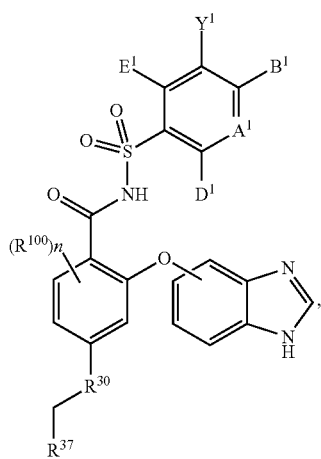

(IV)

and therapeutically acceptable salts, prodrugs, salts of prodrugs and metabolites thereof, wherein $A^1$, $B^1$, $D^1$, $E^1$, $Y^1$, $R^{30}$, and $R^{37}$ are as described herein for Formula (I), n is 0, 1, 2, or 3; describing the number of substituents on $R^{26}$, and $R^{100}$ is as described for substituents on $R^6$.

In one embodiment of Formula (IV), $A^1$ is N. In another embodiment of Formula (IV), $A^1$ is $C(A^2)$. In another embodiment of Formula (IV), $A^1$ is $C(A^2)$, and $A^2$ is H.

In one embodiment of Formula (IV), $B^1$ is $R^1$, $OR^1$, $SR^1$, $SO_2R^1$, $NHR^1$, $N(R^1)_2$, or $C(O)NHR^1$. In another embodiment of Formula (IV), $B^1$ is $NHR^1$. In another embodiment of Formula (IV), $B^1$ is $NHR^1$, and $A^1$ is $C(A^2)$, and $A^2$ is H. In another embodiment of Formula (IV), $B^1$ is $OR^1$. In another embodiment of Formula (IV), $B^1$ is $OR^1$, and $A^1$ is $C(A^2)$, and $A^2$ is H.

In one embodiment of Formula (IV), $D^1$ and $E^1$ are H. In another embodiment of Formula (IV), $B^1$ is $NHR^1$, and $A^1$ is $C(A^2)$, $A^2$ is H, and $D^1$ and E are H. In another embodiment of Formula (IV), $B^1$ is $OR^1$, and $A^1$ is $C(A^2)$, $A^2$ is H, and $D^1$ and $E^1$ are H.

In one embodiment of Formula (IV), $Y^1$ is H, CN, $NO_2$, F, Cl, Br, I, $CF_3$, $R^{17}$, $NHC(O)R^{17}$, or $C(O)NH_2$. In another embodiment of Formula (IV), $Y^1$ is $NO_2$. In another embodiment of Formula (IV), $B^1$ is $NHR^1$, and $A^1$ is $C(A^2)$, $A^2$ is H, $D^1$ and $E^1$ are H, and $Y^1$ is $NO_2$. In another embodiment of Formula (IV), $Y^1$ is Cl. In another embodiment of Formula (I), $B^1$ is $OR^1$, and $A^1$ is $C(A^2)$, $A^2$ is H, $D^1$ and $E^1$ are H, and $Y^1$ is Cl.

In one embodiment of Formula (IV), $R^1$ is $R^2$, $R^3$, $R^4$ or $R^5$. In another embodiment of Formula (IV), $R^1$ is $R^2$, and $R^2$ is phenyl.

In one embodiment of Formula (IV), $R^1$ is $R^3$, and $R^3$ is heteroaryl. In another embodiment of Formula (IV), $R^3$ is triazolyl.

In one embodiment of Formula (IV), $R^1$ is $R^4$. In another embodiment of Formula (IV), $R^1$ is $R^4$, and $R^4$ is cycloalkyl. In another embodiment of Formula (IV), $R^1$ is $R^4$, and $R^4$ is cyclohexyl. In another embodiment of Formula (IV), $R^1$ is $R^4$, and $R^4$ is heterocycloalkyl. In another embodiment of Formula (IV), $R^1$ is $R^4$, and 4 is 8-azabicyclo[3.2.1]octane, azetidinyl, piperidinyl, piperazinyl, pyrrolidinyl, morpholinyl, tetrahydropyranyl, or tetrahydrothiophenyl. In another embodiment of Formula (IV), $R^1$ is $R^4$, and $R^4$ is heterocycloalkenyl. In another embodiment of Formula (IV), $R^1$ is $R^4$, and $R^4$ is tetrahydropyridazinyl.

In one embodiment of Formula (IV), $R^1$ is $R^5$. In another embodiment of Formula (IV), $R^1$ is $R^5$ and $R^5$ is alkyl or alkynyl. In another embodiment of Formula (IV), $R^1$ is $R^5$ and $R^5$ is alkyl which is unsubstituted. In another embodiment of Formula (IV), $R^1$ is $R^5$ and $R^5$ is alkyl which is substituted with one or two or three independently selected $R^6$, $R^7$, $OR^7$, $SR^7$, $SO_2R^7$, $N(R^7)_2$, OH, CN, $CF_3$, F, Cl, Br or I substituents. In another embodiment of Formula (IV), $R^1$ is $R^5$ and $R^5$ is alkyl which is substituted with $R^7$.

In one embodiment of Formula (IV), $R^7$ is $R^8$, $R^9$, $R^{10}$ or $R^{11}$. In another embodiment of Formula (IV), $R^7$ is $R^8$, and $R^8$ is phenyl which is unfused or fused with $R^{8A}$, and $R^{8A}$ is heterocycloalkane. In another embodiment of Formula (IV), $R^7$ is $R^8$, and $R^8$ is phenyl which is unfused. In another embodiment of Formula (IV), $R^7$ is $R^9$, and $R^9$ is heteroaryl. In another embodiment of Formula (IV), $R^7$ is $R^9$, and $R^9$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl or 1,2,3-triazolyl. In another embodiment of Formula (IV), $R^7$ is $R^9$, and $R^9$ is pyridinyl, thiazolyl, imidazoyl, and 1,2,3-triazolyl. In another embodiment of Formula (IV), $R^7$ is $R^{10}$, and $R^{10}$ is $C_3$-$C_{10}$-cycloalkyl. In another embodiment of Formula (IV), $R^7$ is $R^{10}$, and $R^{10}$ is $C_6$ or $C_{10}$-cycloalkyl. In another embodiment of Formula (IV), $R^7$ is $R^{10}$, and $R^{10}$ is cyclohexyl or adamantanyl. In another embodiment of Formula (IV), $R^7$ is $R^{10}$, and $R^{10}$ is morpholinyl, piperazinyl, piperidinyl, tetrahydro-2H-pyranyl, 1,2-dihydropyridinyl, pyranyl, pyridin-1(H)-yl, pyrrolidinyl, oxetanyl, thiomorpholinyl, imidazolidinyl, tetrahydrothiophenyl, dioxolanyl, tetrahydrothiopyranyl, dioxanyl, or tetrahydrofuranyl. In another embodiment of Formula (IV), $R^7$ is $R^{10}$, and $R^{10}$ is morpholinyl, piperazinyl, piperidinyl, tetrahydro-2H-pyranyl, 1,2-dihydropyridinyl, pyrrolidinyl, oxetanyl, thiomorpholinyl, imidazolidinyl, tetrahydrothiophenyl, dioxolanyl, tetrahydrothiopyranyl, dioxanyl, or tetrahydrofuranyl. In another embodiment of Formula (IV), $R^7$ is $R^{11}$, and $R^{11}$ is alkyl which is unsubstituted or substituted. In another embodiment of Formula (IV), $R^7$ is $R^{11}$, and $R^{11}$ is alkyl which is unsubstituted. In another embodiment of Formula (IV), $R^7$ is $R^{11}$, and $R^{11}$ is alkyl which is substituted. In another embodiment of Formula (IV), $R^7$ is $R^{11}$, and $R^{11}$ is alkyl which is substituted within one or two or three independently selected $OR^{12}$, F, $C_1$, Br or substituents. In another embodiment of Formula (IV), $R^7$ is $R^{11}$, $R^{11}$ is alkyl which is substituted with $OR^{12}$, $R^{12}$ is $R^{16}$, and $R^{16}$ is alkyl.

In one embodiment of Formula (IV), $R^{17}$ is $R^{19}$ or $R^{21}$. In another embodiment of Formula (IV), $R^{17}$ is $R^{19}$, and $R^{19}$ is heteroaryl. In another embodiment of Formula (IV), $R^{17}$ is R¹⁹, and R¹⁹ is thiazolyl. In another embodiment of Formula (IV), R¹⁷ is R²¹, and R²¹ is alkynyl. In another embodiment of Formula (IV), R¹⁷ is R²¹, and R²¹ is ethynyl.

Still another embodiment pertains to compounds having Formula (IV) which are 2-(1H-benzimidazol-4-yloxy)-4-(4-{[2-(4-chlorophenyl)-4, 4-dimethylcyclohex-1-en-1-yl]methyl}piperazin-1-yl)-N-({3-nitro-4-[(tetrahydro-2H-pyran-4-ylmethyl)amino] phenyl}sulfonyl)benzamide;

2-(1H-benzimidazol-4-yloxy)-4-(4-{[2-(4-chlorophenyl)-4, 4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide;

2-(1H-benzimidazol-4-yloxy)-4-(4-{[2-(4-chlorophenyl)-4, 4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)benzamide;

2-(1H-benzimidazol-4-yloxy)-4-(4-{[2-(4-chlorophenyl)-4, 4-dimethylcyclohex-1-en-1-yl]methyl}piperazin-1-yl)-N-{[4-({[4-(2,2-difluoroethyl)morpholin-2-yl] methyl}amino)-3-nitrophenyl]sulfonyl}benzamide;

2-(1H-benzimidazol-4-yloxy)-4-(4-{[2-(4-chlorophenyl)-4, 4-dimethylcyclohex-1-en-1-yl]methyl}piperazin-1-yl)-N-({3-nitro-4-[(1-tetrahydro-2H-pyran-4-ylpiperidin-4-yl) amino]phenyl}sulfonyl)benzamide;

2-(1H-benzimidazol-4-yloxy)-4-(4-{[2-(4-chlorophenyl)-4, 4-dimethylcyclohex-1-en-1-yl]methyl}piperazin-1-yl)-N-({4-[(1-methylpiperidin-4-yl)amino]-3-nitrophenyl}sulfonyl)benzamide;

2-(1H-benzimidazol-4-yloxy)-N-[(5-chloro-6-{[(2S)-4-(N,N-dimethylglycyl)morpholin-2-yl]methoxy}pyridin-3-yl) sulfonyl]-4-(4-{[2-(4-chlorophenyl)-4,4-dimethylcyclohex-1-en-1-yl]methyl}piperazin-1-yl)benzamide;

2-(1H-benzimidazol-4-yloxy)-N-[(5-chloro-6-{[(2R)-4-(N,N-dimethylglycyl)morpholin-2-yl]methoxy}pyridin-3-yl) sulfonyl]-4-(4-{[2-(4-chlorophenyl)-4,4-dimethylcyclohex-1-en-1-yl]methyl}piperazin-1-yl)benzamide;

2-(1H-benzimidazol-4-yloxy)-4-(4-{[2-(4-chlorophenyl)-4, 4-dimethylcyclohex-1-en-1-yl]methyl}piperazin-1-yl)-N-[(4-{[(3R)-1-(cyanomethyl)pyrrolidin-3-yl]amino}-3-nitrophenyl)sulfonyl]benzamide;

2-(1H-benzimidazol-4-yloxy)-4-(4-{[2-(4-chlorophenyl)-4, 4-dimethylcyclohex-1-en-1-yl]methyl}piperazin-1-yl)-N-{[4-({(3R)-1-[2-(2-methoxyethoxy)ethyl]pyrrolidin-3-yl}amino)-3-nitrophenyl]sulfonyl}benzamide;

2-(1H-benzimidazol-4-yloxy)-4-(4-{[2-(4-chlorophenyl)-4, 4-dimethylcyclohex-1-en-1-yl]methyl}piperazin-1-yl)-N-[(4-{[(3R)-1-(N,N-dimethylglycyl)pyrrolidin-3-yl] amino}-3-nitrophenyl)sulfonyl]benzamide;

2-(1H-benzimidazol-4-yloxy)-4-(4-{[2-(4-chlorophenyl)-4, 4-dimethylcyclohex-1-en-1-yl]methyl}piperazin-1-yl)-N-{[4-({[4-(cyanomethyl)morpholin-2-yl]methyl}amino)-3-nitrophenyl]sulfonyl}benzamide;

2-(1H-benzimidazol-4-yloxy)-4-(4-{[2-(4-chlorophenyl)-4, 4-dimethylcyclohex-1-en-1-yl]methyl}piperazin-1-yl)-N-[(4-{[(4-cyclopropylmorpholin-2-yl)methyl]amino}-3-nitrophenyl)sulfonyl]benzamide;

2-(1H-benzimidazol-4-yloxy)-4-(4-{[2-(4-chlorophenyl)-4, 4-dimethylcyclohex-1-en-1-yl]methyl}piperazin-1-yl)-N-[(3-nitro-4-{[(4-oxetan-3-ylmorpholin-2-yl)methyl] amino}phenyl)sulfonyl]benzamide;

2-(1H-benzimidazol-4-yloxy)-4-(4-{[2-(4-chlorophenyl)-4, 4-dimethylcyclohex-1-en-1-yl]methyl}piperazin-1-yl)-N-{[4-({[(2R)-4-(N,N-dimethylglycyl)morpholin-2-yl] methyl}amino)-3-nitrophenyl]sulfonyl}benzamide;

2-(1H-benzimidazol-4-yloxy)-4-(4-{[2-(4-chlorophenyl)-4, 4-dimethylcyclohex-1-en-1-yl]methyl}piperazin-1-yl)-N-{[4-({[(2S)-4-(N,N-dimethylglycyl)morpholin-2-yl] methyl}amino)-3-nitrophenyl]sulfonyl}benzamide;

2-(1H-benzimidazol-4-yloxy)-4-(4-{[2-(4-chlorophenyl)-4, 4-dimethylcyclohex-1-en-1-yl]methyl}piperazin-1-yl)-N-({3-nitro-4-[(tetrahydrofuran-3-ylmethyl)amino] phenyl}sulfonyl)benzamide;

Trans-2-(1 1H-benzimidazol-4-yloxy)-4-(4-{[2-(4-chlorophenyl)-4,4-dimethylcyclohex-1-en-1-yl] methyl}piperazin-1-yl)-N-[(4-{[(4-methoxycyclohexyl) methyl]amino}-3-nitrophenyl)sulfonyl]benzamide;

2-(1H-benzimidazol-4-yloxy)-4-(4-{[2-(4-chlorophenyl)-4, 4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]benzamide;

2-(1H-benzimidazol-4-yloxy)-4-(4-{[2-(4-chlorophenyl)-4, 4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)benzamide;

2-(1H-benzimidazol-4-yloxy)-N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)benzamide;

2-(1H-benzimidazol-4-yloxy)-N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl] methyl}piperazin-1-yl)benzamide;

2-(1H-benzimidazol-4-yloxy)-4-(4-{[2-(4-chlorophenyl)-4, 4-dimethylcyclohex-1-en-1-yl]methyl}piperazin-1-yl)-N-({4-[(1,4-dioxan-2-ylmethyl)amino]-3-nitrophenyl}sulfonyl)benzamide;

2-(1H-benzimidazol-4-yloxy)-4-(4-{[2-(4-chlorophenyl)-4, 4-dimethylcyclohex-1-en-1-yl]methyl}piperazin-1-yl)-N-({4-[(1-cyclopropylpiperidin-4-yl)amino]-3-nitrophenyl}sulfonyl)benzamide;

Trans-2-(1H-benzimidazol-4-yloxy)-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide;

2-(1H-benzimidazol-4-yloxy)-4-(4-{[2-(4-chlorophenyl)-4, 4-dimethylcyclohex-1-en-1-yl]methyl}piperazin-1-yl)-N-({4-[(4-methylpiperazin-1-yl)amino]-3-nitrophenyl}sulfonyl)benzamide;

2-(1H-benzimidazol-4-yloxy)-4-(4-{[2-(4-chlorophenyl)-4, 4-dimethylcyclohex-1-en-1-yl]methyl}piperazin-1-yl)-N-[(4-{[(1-methylpiperidin-4-yl)methyl]amino}-3-nitrophenyl)sulfonyl]benzamide;

2-(1H-benzimidazol-4-yloxy)-4-(4-{[2-(4-chlorophenyl)-4, 4-dimethylcyclohex-1-en-1-yl]methyl}piperazin-1-yl)-N-({4-[({(2R)-4-[2-(2-methoxyethoxy)ethyl]morpholin-2-yl}methyl)amino]-3-nitrophenyl}sulfonyl)benzamide;

2-(1H-benzimidazol-4-yloxy)-4-(4-{[2-(4-chlorophenyl)-4, 4-dimethylcyclohex-1-en-1-yl]methyl}piperazin-1-yl)-N-[(4-{[(4,4-difluorocyclohexyl)methyl]amino}-3-nitrophenyl)sulfonyl]benzamide;

N-[(4-{[(4-acetylmorpholin-2-yl)methyl]amino}-3-nitrophenyl)sulfonyl]-2-(1H-benzimidazol-4-yloxy)-4-(4-{[2-(4-chlorophenyl)-4,4-dimethylcyclohex-1-en-1-yl] methyl}piperazin-1-yl)benzamide;

2-(1H-benzimidazol-4-yloxy)-4-(4-{[2-(4-chlorophenyl)-4, 4-dimethylcyclohex-1-en-1-yl]methyl}piperazin-1-yl)-N-{[4-({[4-(methylsulfonyl)morpholin-2-yl] methyl}amino)-3-nitrophenyl]sulfonyl}benzamide;

Trans-2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide;

2-(1H-benzimidazol-4-yloxy)-N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)benzamide;

and therapeutically acceptable salts, prodrugs, salts of prodrugs and metabolites thereof.

In another aspect, the present invention provides compounds of Formula (V)

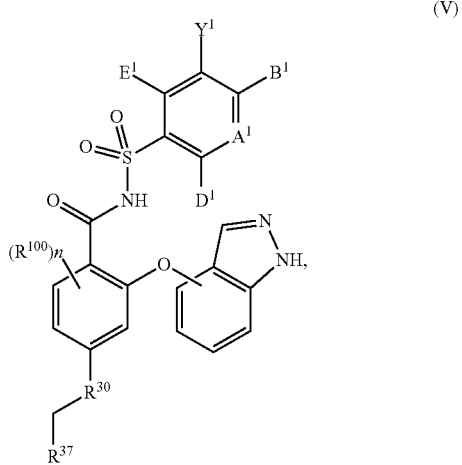

(V)

and therapeutically acceptable salts, prodrugs, salts of prodrugs and metabolites thereof, wherein $A^1$, $B^1$, $D^1$, $E^1$, Y, $R^{30}$, and $R^{37}$ are as described herein for Formula (I), n is 0, 1, 2, or 3; describing the number of substituents on $R^{26}$, and $R^{100}$ is as described for substituents on $R^{26}$.

In one embodiment of Formula (V), $A^1$ is N. In another embodiment of Formula (V), $A^1$ is $C(A^2)$. In another embodiment of Formula (V), $A^1$ is $C(A^2)$, and $A^2$ is H.

In one embodiment of Formula (V), $B^1$ is $R^1$, $OR^1$, $SR^1$, $SO_2R^1$, $NHR^1$, $N(R^1)_2$, or $C(O)NHR^1$. In another embodiment of Formula (V), $B^1$ is $NHR^1$. In another embodiment of Formula (V), $B^1$ is $NHR^1$, and $A^1$ is $C(A^2)$, and $A^2$ is H. In another embodiment of Formula (V), $B^1$ is $OR^1$. In another embodiment of Formula (V), $B^1$ is $OR^1$, and $A^1$ is $C(A^2)$, and $A^2$ is H.

In one embodiment of Formula (V), $D^1$ and $E^1$ are H. In another embodiment of Formula (V), $B^1$ is $NHR^1$, and $A^1$ is $C(A^2)$, $A^2$ is H, and $D^1$ and $E^1$ are H. In another embodiment of Formula (V), $B^1$ is $OR^1$, and $A^1$ is $C(A^2)$, $A^2$ is H, and $D^1$ and $E^1$ are H.

In one embodiment of Formula (V), $Y^1$ is H, CN, $NO_2$, F, Cl, Br, I, $CF_3$, $R^{17}$, $NHC(O)R^{17}$, or $C(O)NH_2$. In another embodiment of Formula (V), $Y^1$ is $NO_2$. In another embodiment of Formula (V), $B^1$ is $NHR^1$, and $A^1$ is $C(A^2)$, $A^2$ is H, $D^1$ and $E^1$ are H, and $Y^1$ is $NO_2$. In another embodiment of Formula (V), $Y^1$ is Cl. In another embodiment of Formula (I), $B^1$ is $OR^1$, and $A^1$ is $C(A^2)$, $A^2$ is H, $D^1$ and $E^1$ are H, and $Y^1$ is Cl.

In one embodiment of Formula (V), $R^1$ is $R^2$, $R^3$, $R^4$ or $R^5$. In another embodiment of Formula (V), $R^1$ is $R^2$, and $R^2$ is phenyl.

In one embodiment of Formula (V), $R^1$ is $R^3$, and $R^3$ is heteroaryl. In another embodiment of Formula (V), $R^3$ is triazolyl.

In one embodiment of Formula (V), $R^1$ is $R^4$. In another embodiment of Formula (V), $R^1$ is $R^4$, and $R^4$ is cycloalkyl. In another embodiment of Formula (V), $R^1$ is $R^4$, and $R^4$ is cyclohexyl. In another embodiment of Formula (V), $R^1$ is $R^4$, and $R^4$ is heterocycloalkyl. In another embodiment of Formula (V), $R^1$ is $R^4$, and $R^4$ is 8-azabicyclo[3.2.1]octane, azetidinyl, piperidinyl, piperazinyl, pyrrolidinyl, morpholinyl, tetrahydropyranyl, or tetrahydrothiophenyl. In another embodiment of Formula (V), $R^1$ is $R^4$, and $R^4$ is heterocycloalkenyl. In another embodiment of Formula (V), $R^1$ is $R^4$, and $R^4$ is tetrahydropyridazinyl.

In one embodiment of Formula (V), $R^1$ is $R^5$. In another embodiment of Formula (V), $R^1$ is $R^5$ and $R^5$ is alkyl or alkynyl. In another embodiment of Formula (V), $R^1$ is $R^5$ and $R^5$ is alkyl which is unsubstituted. In another embodiment of Formula (V), $R^1$ is $R^5$ and $R^5$ is alkyl which is substituted with one or two or three independently selected $R^6$, $R^7$, $OR^7$, $SR^7$, $SO_2R^7$, $N(R^7)_2$, OH, CN, $CF_3$, F, Cl, Br or I substituents. In another embodiment of Formula (V), $R^1$ is $R^5$ and $R^5$ is alkyl which is substituted with $R^7$.

In one embodiment of Formula (V), $R^7$ is $R^8$, $R^9$, $R^{10}$ or $R^{11}$. In another embodiment of Formula (V), $R^7$ is $R^8$, and $R^8$ is phenyl which is unfused or fused with $R^{8A}$, and $R^{8A}$ is heterocycloalkane. In another embodiment of Formula (V), $R^7$ is $R^8$, and $R^8$ is phenyl which is unfused. In another embodiment of Formula (V), $R^7$ is $R^9$, and $R^9$ is heteroaryl. In another embodiment of Formula (V), $R^7$ is $R^9$, and $R^9$ is furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl or 1,2,3-triazolyl. In another embodiment of Formula (V), $R^7$ is $R^9$, and $R^9$ is pyridinyl, thiazolyl, imidazoyl, and 1,2,3-triazolyl. In another embodiment of Formula (V), $R^7$ is $R^{10}$, and $R^{10}$ is $C_3$-$C_{10}$-cycloalkyl. In another embodiment of Formula (V), $R^7$ is $R^{10}$, and $R^{10}$ is $C_6$ or $C_{10}$-cycloalkyl. In another embodiment of Formula (V), $R^7$ is $R^{10}$, and $R^{10}$ is cyclohexyl or adamantanyl. In another embodiment of Formula (V), $R^7$ is $R^{10}$, and $R^{10}$ is morpholinyl, piperazinyl, piperidinyl, tetrahydro-2H-pyranyl, 1,2-dihydropyridinyl, pyranyl, pyridin-1(H)-yl, pyrrolidinyl, oxetanyl, thiomorpholinyl, imidazolidinyl, tetrahydrothiophenyl, dioxolanyl, tetrahydrothiopyranyl, dioxanyl, or tetrahydrofuranyl. In another embodiment of Formula (V), $R^7$ is $R^{10}$, and $R^{10}$ is morpholinyl, piperazinyl, piperidinyl, tetrahydro-2H-pyranyl, 1,2-dihydropyridinyl, pyrrolidinyl, oxetanyl, thiomorpholinyl, imidazolidinyl, tetrahydrothiophenyl, dioxolanyl, tetrahydrothiopyranyl, dioxanyl, or tetrahydrofuranyl. In another embodiment of Formula (V), $R^7$ is $R^{11}$, and $R^{11}$ is alkyl which is unsubstituted or substituted. In another embodiment of Formula (V), $R^7$ is $R^{11}$, and $R^{11}$ is alkyl which is unsubstituted. In another embodiment of Formula (V), $R^7$ is $R^{11}$, and $R^{11}$ is alkyl which is substituted. In another embodiment of Formula (V), $R^7$ is $R^{11}$, and $R^{11}$ is alkyl which is substituted with one or two or three independently selected $OR^{12}$, F, Cl, Br or I substituents.

In another embodiment of Formula (V), $R^7$ is $R^{11}$, $R^1$ is alkyl which is substituted with $OR^{12}$, $R^{12}$ is $R^{16}$, and $R^{16}$ is alkyl.

In another embodiment of Formula (V), $R^{17}$ is $R^{19}$ or $R^{21}$. In another embodiment of Formula (V), $R^{17}$ is $R^{19}$, and $R^{19}$ is heteroaryl. In another embodiment of Formula (V), $R^{17}$ is $R^{19}$, and $R^{19}$ is thiazolyl. In another embodiment of Formula (V), $R^{17}$ is $R^{21}$, and $R^{21}$ is alkynyl. In another embodiment of Formula (V), $R^{17}$ is $R^{21}$, and $R^{21}$ is ethynyl.

Still another embodiment pertains to compounds having Formula (V) which are

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indazol-4-yloxy)benzamide;

4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-indazol-4-yloxy)benzamide;

4-(4-{[2-(4-chlorophenyl)-4,4-dimethylcyclohex-1-en-1-yl]methyl}piperazin-1-yl)-N-{[6-[(4-fluorotetrahydro-2H-pyran-4-yl)methoxy]-5-(trifluoromethyl)pyridin-3-yl]sulfonyl}-2-(1H-indazol-4-yloxy)benzamide;

4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]-2-(1H-indazol-4-yloxy)benzamide;

4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-indazol-4-yloxy)benzamide;

N-[(5-chloro-6-{[(4-fluorotetrahydro-2H-pyran-4-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

Trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

4-(4-({[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-indazol-4-yloxy)benzamide;

N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-N-{[5-chloro-6-(tetrahydrofuran-3-ylmethoxy)pyridin-3-yl]sulfonyl}-2-(1H-indazol-4-yloxy)benzamide;

Trans-N-({5-chloro-6-[(4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

N-[(5-chloro-6-{[(3R)-1-(2,2-difluoroethyl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-indazol-4-yloxy)benzamide;

N-{[5-chloro-6-({(3R)-1-[2-fluoro-1-(fluoromethyl)ethyl]pyrrolidin-3-yl}oxy)pyridin-3-yl]sulfonyl}-4-(4-{[2-(4-chlorophenyl)-4,4-dimethylcyclohex-1-en-1-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-indazol-4-yloxy)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(1H-indazol-4-yloxy)benzamide;

N-{[5-chloro-6-({(3R)-1-[2-fluoro-1-(fluoromethyl)ethyl]pyrrolidin-3-yl}methoxy)pyridin-3-yl]sulfonyl}-4-(4-{[2-(4-chlorophenyl)-4,4-dimethylcyclohex-1-en-1-yl]methyl}piperazin-1-yl)-2-(1H-indazol-4-yloxy)benzamide;

N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide;

Trans-4-(4-{[2-(4-chlorophenyl)-4,4-dimethylcyclohex-1-en-1-yl]methyl}piperazin-1-yl)-2-(1H-indazol-4-yloxy)-N-[(4-{[(4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indazol-4-yloxy)benzamide;

N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

2-(1H-benzimidazol-4-yloxy)-N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)benzamide;

4-(4-{[2-(4-chlorophenyl)-4,4-dimethylcyclohex-1-en-1-yl]methyl}piperazin-1-yl)-N-{[6-({4-fluoro-1-[2-fluoro-1-(fluoromethyl)ethyl]piperidin-4-yl}methoxy)-5-(trifluoromethyl)pyridin-3-yl]sulfonyl}-2-(1H-indazol-4-yloxy)benzamide;

4-(4-{[2-(4-chlorophenyl)-4,4-dimethylcyclohex-1-en-1-yl]methyl}piperazin-1-yl)-N-{[5-chloro-6-(2-tetrahydrofuran-2-ylethoxy)pyridin-3-yl]sulfonyl}-2-(1H-indazol-4-yloxy)benzamide;

N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide;

N-({5-chloro-6-[(4-fluorotetrahydro-2H-pyran-4-yl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)-2-(1H-indazol-4-yloxy)benzamide;

4-(4-{[2-(4-chlorophenyl)-4,4-dimethylcyclohex-1-en-1-yl]methyl}piperazin-1-yl)-N-{[5-cyano-6-(2-tetrahydro-2H-pyran-4-ylethoxy)pyridin-3-yl]sulfonyl}-2-(1H-indazol-4-yloxy)benzamide;

and therapeutically acceptable salts, prodrugs, salts of prodrugs and metabolites thereof.

Pharmaceutical Compositions, Combination Therapies, Methods of Treatment, and Administration Another embodiment comprises pharmaceutical compositions comprising a compound having Formula (I) and an excipient.

Still another embodiment comprises methods of treating cancer in a mammal comprising administering thereto a therapeutically acceptable amount of a compound having Formula (I).

Still another embodiment comprises methods of treating autoimmune disease in a mammal comprising administering thereto a therapeutically acceptable amount of a compound having Formula (I).

Still another embodiment pertains to compositions for treating diseases during which anti-apoptotic Bcl-2 proteins are expressed, said compositions comprising an excipient and a therapeutically effective amount of the compound having Formula (I).

Still another embodiment pertains to methods of treating disease in a patient during which anti-apoptotic Bcl-2 proteins are expressed, said methods comprising administering to the patient a therapeutically effective amount of a compound having Formula (I).

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of the compound having Formula (I).

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer in a patient, said methods comprising administering to the patient a therapeutically effective amount of a compound having Formula (I).

Still another embodiment pertains to compositions for treating diseases during which are expressed anti-apoptotic Bcl-2 proteins, said compositions comprising an excipient and a therapeutically effective amount of the compound having Formula (I) and a therapeutically effective amount of one additional therapeutic agent or more than one additional therapeutic agent.

Still another embodiment pertains to methods of treating disease in a patient during which are expressed anti-apoptotic Bcl-2 proteins, said methods comprising administering to the patient a therapeutically effective amount of a compound having Formula (I) and a therapeutically effective amount of one additional therapeutic agent or more than one additional therapeutic agent.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said compositions comprising an excipient and a therapeutically effective amount of the compound having Formula (I) and a therapeutically effective amount of one additional therapeutic agent or more than one additional therapeutic agent.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said methods comprising administering to the patient a therapeutically effective amount of the compound having Formula (I) and a therapeutically effective amount of one additional therapeutic agent or more than one additional therapeutic agent.

Metabolites of compounds having Formula I, produced by in vitro or in vivo metabolic processes, may also have utility for treating diseases associated with anti-apoptotic Bcl-2 protein.

Certain precursor compounds which may be metabolized in vitro or in vivo to form compounds having Formula I may also have utility for treating diseases associated with expression of anti-apoptotic Bcl-2 protein.

Compounds having Formula I may exist as acid addition salts, basic addition salts or zwitterions. Salts of the compounds are prepared during isolation or following purification of the compounds. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsufonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds and prodrugs thereof are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds having Formula I may be administered, for example, bucally, ophthalmically, orally, osmotically, parenterally (intramuscularly, intraperitoneally intrasternally, intravenously, subcutaneously), rectally, topically, transdermally, or vaginally.

Therapeutically effective amounts of compounds having Formula I depend on the recipient of the treatment, the disorder being treated and the severity thereof, the composition containing the compound, the time of administration, the route of administration, the duration of treatment, the compound potency, its rate of clearance and whether or not another drug is co-administered. The amount of a compound of this invention having Formula I used to make a composition to be administered daily to a patient in a single dose or in divided doses is from about 0.03 to about 200 mg/kg body weight. Single dose compositions contain these amounts or a combination of submultiples thereof.

Compounds having Formula I may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having Formula I to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention having Formula I to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention having Formula I to be administered osmotically include, for example, chlorofluorohydrocarbons, ethanol, water and mixtures thereof. Excipients for preparation of compositions comprising a compound of this invention having Formula I to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention having Formula I to be administered rectally or vaginally include, for example, cocoa butter, polyethylene glycol, wax and mixtures thereof.

Compounds having Formula (I) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxy-nucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide) or ABT-737 (i.e., N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al, *Cancer Research* 2008, 68(9), 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054. VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY[43]-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT) (buserelin), TRELSTAR® (luteinizing hormone releasing hormone (LHRH)), VANTAS® (Histrelin implant), VETORYL® (trilostane or modrastane), ZOLADEX®(fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents.

Interferons include interferon alpha, interferon alpha-2a, interferon alpha-2b, interferon beta, interferon gamma-1a, ACTIMMUNE® (interferon gamma-1 b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE®(sipuleucel-T), sargaramostim, sizofilan, teceleukin, THERACYS® (*Bacillus Calmette-Guerin*), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE3 8QQR (cintredekin besudotox), IL-13-*pseudomonas* exotoxin, interferon-α, interferon-7, JUNOVAN™ or MEPACT™ (mifamurtide), lonafarnib, 5,10-methylenetetrahydrofolate, miltefosine (hexadecylphosphocholine), NEOVASTAT®(AE-941), NEUTREXIN® (trimetrexate glucuronate), NIPENT® (pentostatin), ONCONASE (a ribonuclease enzyme), ONCOPHAGE® (melanoma vaccine treatment), ONCOVAX (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from *ginseng* comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID®(lenalidomide), RSR13 (efaproxiral), SOMATULINE® LA (lanreotide), SORIATANE® (acitretin), staurosporine (*Streptomyces* staurospores), talabostat (PT100), TARGRETIN® (bexarotene), TAXOPREXIN (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Data

Determination of the utility of compounds having Formula I as binders to and inhibitors of anti-apoptotic Bcl-2 and Bcl-xL proteins was performed using the Time Resolved-Fluorescence Resonance Energy Transfer (TR-FRET) Assay. Tb-anti-GST antibody was purchased from Invitrogen (Catalog No. PV4216).

Probe Synthesis

All reagents were used as obtained from the vendor unless otherwise specified. Peptide synthesis reagents including diisopropylethylamine (DIEA), dichloromethane (DCM), N-methylpyrrolidone (NMP), 2-(1H-benzotriazole-1-yl)-1,1,3,3-tetramethyluronium hexafluorophosphate (HBTU), N-hydroxybenzotriazole (HOBt) and piperidine were obtained from Applied Biosystems, Inc. (ABI), Foster City, Calif. or American Bioanalytical, Natick, Mass. Preloaded 9-Fluorenylmethyloxycarbonyl (Fmoc) amino acid cartridges (Fmoc-Ala-OH, Fmoc-Cys(Trt)-OH, Fmoc-Asp(tBu)-OH, Fmoc-Glu(tBu)-OH, Fmoc-Phe-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Asn(Trt)-OH, Fmoc-Pro-OH, Fmor-Gln(Trt)-OH, Fmoc-Arg(Pbf)-OH, Fmoc-Ser(tBu)-OH, Fmoc-Thr(tBu)-OH, Fmoc-Val-OH, Fmoc-Trp(Boc)-OH, Fmoc-Tyr(tBu)-OH) were obtained from ABI or Anaspec, San Jose, Calif. The peptide synthesis resin (Fmoc-Rink amide MBHA resin) and Fmoc-Lys(Mtt)-OH were obtained from Novabiochem, San Diego, Calif. Single-isomer 6-carboxyfluorescein succinimidyl ester (6-FAM-NHS) was obtained from Anaspec. Trifluoroacetic acid (TFA) was obtained from Oakwood Products, West Columbia, S.C. Thioanisole, phenol, triisopropylsilane (TIS), 3,6-dioxa-1,8-octanedithiol (DODT) and isopropanol were obtained from Aldrich Chemical Co., Milwaukee, Wis. Matrix-assisted laser desorption ionization mass-spectra (MALDI-MS) were recorded on an Applied Biosystems Voyager DE-PRO MS). Electrospray mass-spectra (ESI-MS) were recorded on Finnigan SSQ7000 (Finnigan Corp., San Jose, Calif.) in both positive and negative ion mode.

General Procedure for Solid-Phase Peptide Synthesis (SPPS)

Peptides were synthesized with, at most, 250 μmol preloaded Wang resin/vessel on an ABI 433A peptide synthesizer using 250 μmol scale Fastmoc™ coupling cycles. Preloaded cartridges containing 1 mmol standard Fmoc-amino acids, except for the position of attachment of the fluorophore, where 1 mmol Fmoc-Lys(Mtt)-OH was placed in the cartridge, were used with conductivity feedback monitoring. N-terminal acetylation was accomplished by using 1 mmol acetic acid in a cartridge under standard coupling conditions.

Removal of 4-Methyltrityl (Mtt) from Lysine

The resin from the synthesizer was washed thrice with dichloromethane and kept wet. 150 mL of 95:4:1 dichloromethane:triisopropylsilane:trifluoroacetic acid was flowed through the resin bed over 30 minutes. The mixture turned deep yellow then faded to pale yellow. 100 mL of DMF was flowed through the bed over 15 minutes. The resin was then washed thrice with DMF and filtered. Ninhydrin tests showed a strong signal for primary amine.

Resin Labeling with 6-Carboxyiluorescein-NHS (6-FAM-NHS)

The resin was treated with 2 equivalents 6-FAM-NHS in 1% DIEA/DMF and stirred or shaken at ambient temperature overnight. When complete, the resin was drained, washed thrice with DMF, thrice with (1% DCM and 1% methanol) and dried to provide an orange resin that was negative by ninhydrin test.

General Procedure for Cleavage and Deprotection of Resin-Bound Peptide

Peptides were cleaved from the resin by shaking for 3 hours at ambient temperature in a cleavage cocktail consisting of 80% TFA, 5% water, 5% thioanisole, 5% phenol, 2.5% TIS, and 2.5% EDT (1 mL/0.1 g resin). The resin was removed by filtration and rinsing twice with TFA. The TFA was evaporated from the filtrates, and product was precipitated with ether (10 mL/0.1 g resin), recovered by centrifugation, washed twice with ether (10 mL/0.1 g resin) and dried to give the crude peptide.

General Procedure for Purification of Peptides

The crude peptides were purified on a Gilson preparative HPLC system running Unipoint® analysis software (Gilson, Inc., Middleton, Wis.) on a radial compression column containing two 25×100 mm segments packed with Delta-Pak™ C18 15 μm particles with 100 Å pore size and eluted with one of the gradient methods listed below. One to two milliliters of crude peptide solution (10 mg/mL in 90% DMSO/water) was purified per injection. The peaks containing the product(s) from each run were pooled and lyophilized. All preparative runs were run at 20 mL/min with eluents as buffer A: 0.1% TFA-water and buffer B: acetonitrile.

General Procedure for Analytical HPLC

Analytical HPLC was performed on a Hewlett-Packard 1200 series system with a diode-array detector and a Hewlett-Packard 1046A fluorescence detector running HPLC 3D ChemStation software version A.03.04 (Hewlett-Packard. Palo Alto, Calif.) on a 4.6×250 mm YMC column packed with ODS-AQ 5 µm particles with a 120 Å pore size and eluted with one of the gradient methods listed below after preequilibrating at the starting conditions for 7 minutes. Eluents were buffer A: 0.1% TFA-water and buffer B: acetonitrile. The flow rate for all gradients was 1 mL/min.
F-Bak: Peptide Probe: Acetyl-(SEQ ID NO: 1)GQVGRQLAIIGDK(6-FAM)-(SEQ ID NO: 2) INR-NH$_2$ Fmoc-Rink amide MBHA resin was extended using the general peptide synthesis procedure to provide the protected resin-bound peptide (1.020 g). The Mtt group was removed, labeled with 6-FAM-NHS and cleaved and deprotected as described hereinabove to provide the crude product as an orange solid (0.37 g). This product was purified by RP-HPLC. Fractions across the main peak were tested by analytical RP-HPLC, and the pure fractions were isolated and lyophilized, with the major peak providing the title compound (0.0802 g) as a yellow solid; MALDI-MS m/z=2137.1 ((M+H)⁻).

Alternative Synthesis of Peptide Probe F-Bak:
Acetyl-(SEQ ID NO: 1)GQVGRQLAIIGDK(6-FAM)-1-(SEQ ID NO: 2)INR-NH$_2$ The protected peptide was assembled on 0.25 mmol Fmoc-Rink amide MBHA resin (Novabiochem) on an Applied Biosystems 433A automated peptide synthesizer running Fastmoc™ coupling cycles using pre-loaded 1 mmol amino acid cartridges, except for the fluorescein (6-FAM)-labeled lysine, where 1 mmol Fmoc-Lys(4-methyltrityl) was weighed into the cartridge. The N-terminal acetyl group was incorporated by putting 1 mmol acetic acid in a cartridge and coupling as described hereinabove. Selective removal of the 4-methyltrityl group was accomplished with a solution of 95:4:1 DCM:TIS:TFA (v/v/v) flowed through the resin over 15 minutes, followed by quenching with a flow of dimethylformamide. Single-isomer 6-carboxyfluorescein-NHS was reacted with the lysine side-chain in 1% DIEA in DMF and confirmed complete by ninhydrin testing. The peptide was cleaved from the resin and side-chains deprotected by treating with 80:5:5:5:2.5:2.5 TFA:water:phenol:thioanisole:triisopropylsilane:3,6-dioxa-1,8-octanedithiol (v/v/v/v/v/v), and the crude peptide was recovered by precipitation with diethyl ether. The crude peptide was purified by reverse-phase high-performance liquid chromatography, and its purity and identity were confirmed by analytical reverse-phase high-performance liquid chromatography and matrix-assisted laser-desorption mass-spectrometry (m/z=2137.1 ((M+H)+)).

Time Resolved-Fluorescence Resonance Energy Transfer (TR-FRET) Assay

Representative compounds were serially diluted in dimethyl sulfoxide (DMSO) starting at 50 µM (2× starting concentration; 10% DMSO) and 10 µL were transferred into a 384-well plate. Then 10 µL of a protein/probe/antibody mix was added to each well at final concentrations listed in TABLE 1.

TABLE 1

Protein, Probe And Antibody Used For TR-FRET Assays

| Protein | Probe | Protein (nM) | Probe (nM) | Antibody | Antibody (nM) |
|---|---|---|---|---|---|
| GST-Bcl-2 | F-Bak(SEQ. ID. No. 1) (GQVGRQLAIIGDK(6-FAM) (SEQ ID No.2)INR-amide) | 1 | 100 | Tb-anti-GST | 1 |
| GST-Bcl-X$_L$ | F-Bak(SEQ. ID. No. 1) (GQVGRQLAIIGDK(6-FAM) (SEQ ID No.2)INR-amide) | 1 | 100 | Tb-anti-GST | 1 |

6-FAM = 6-carboxyfluorescein.; Tb = terbium; GST = glutathione S-transferase

The samples were then mixed on a shaker for 1 minute and incubated for an additional 3 hours at room temperature. For each assay, the probe/antibody and protein/probe/antibody were included on each assay plate as negative and positive controls, respectively. Fluorescence was measured on the Envision (Perkin Elmer) using a 340/35 nm excitation filter and 520/525 (F-Bak peptide) and 495/510 nm (Tb-labeled anti-Histidine antibody) emission filters.

Inhibition constants ($K_i$) for compounds according to the invention and ABT-737, and the binding selectivity ratio (Bcl-X$_L$ $K_i$:Bcl-2 $K_i$) for each are shown in TABLE 2 below. The inhibition constant ($K_i$) is the dissociation constant of an enzyme-inhibitor complex or a protein/small molecule complex, wherein the small molecule is inhibiting binding of one protein to another protein or peptide. Where the $K_i$ for a compound is represented as ">" (greater than) a certain numerical value, it is intended to mean that the binding affinity value (e.g., for Bcl-X$_L$) is greater than the limits of detection of the assay used. Where the binding selectivity ratio for a compound is represented as ">" (greater than) a certain numerical value, it is intended to mean that the selectivity of a particular compound for Bcl-2 over Bcl-X$_L$ is at least as great as the number indicated. Where the $K_i$ for a compound is represented as "<" (less than) a certain numerical value, it is intended to mean that the binding affinity value (e.g., for Bcl-2) is lower than the limit of detection of the assay used. Inhibition constants were determined using Wang's equation (Wang Z-X., An Exact Mathematical Expression For Describing Competitive Binding Of Two Different Ligands To A Protein Molecule. *FEBS Lett.* 1995, 360:111-4).

TABLE 2

TR-FRET Binding Affinity

| Example | Bcl-2 $K_i$ (µM) | Bcl-X$_L$ $K_i$ (µM) | Binding selectivity ratio (Bcl-X$_L$ $K_i$/Bcl-2 $K_i$) |
|---|---|---|---|
| ABT-737 | 0.000088 | 0.00008 | 0.9 |
| 1 | 0.006773 | 0.57833 | 85.4 |
| 18 | 0.000238 | 0.008131 | 34.2 |
| 19 | 0.000847 | 0.020027 | 23.6 |
| 20 | 0.002365 | 0.077593 | 32.8 |
| 21 | 0.005428 | 0.19038 | 35.1 |
| 22 | 0.006218 | 0.1253 | 20.2 |
| 23 | 0.006639 | 0.16782 | 25.3 |
| 24 | 0.000194 | >0.66 | >3402.1 |
| 25 | 0.00005 | 0.20519 | 4103.8 |
| 26 | 0.00014 | >0.66 | >4714.3 |
| 28 | 0.033705 | >0.66 | >19.6 |
| 29 | 0.011911 | >0.66 | >55.4 |
| 30 | 0.10292 | >0.66 | >6.4 |
| 31 | 0.036614 | >0.66 | >18.0 |

TABLE 2-continued

TR-FRET Binding Affinity

| Example | Bcl-2 $K_i$, (µM) | Bcl-$X_L$ $K_i$ (µM) | Binding selectivity ratio (Bcl-$X_L$ $K_i$/Bcl-2 $K_i$) |
|---|---|---|---|
| 32 | 0.061123 | >0.66 | >10.8 |
| 33 | 0.006684 | 0.33339 | 49.9 |
| 34 | 0.001986 | 0.088007 | 44.3 |
| 36 | 0.000796 | 0.008995 | 11.3 |
| 37 | 0.000464 | 0.044422 | 95.7 |
| 40 | 0.000534 | >0.66 | >1236.0 |
| 42 | 0.000048 | 0.003841 | 80 |
| 45 | 0.000828 | >0.66 | >797.1 |
| 46 | 0.000159 | 0.018958 | 119.2 |
| 47 | 0.00663 | 0.10428 | 15.7 |
| 50 | 0.000471 | 0.090073 | 191.2 |
| 51 | 0.000252 | 0.015646 | 62.1 |
| 52 | 0.000239 | 0.079805 | 333.9 |
| 53 | 0.000081 | 0.004845 | 59.8 |
| 54 | 0.000757 | 0.082015 | 108.3 |
| 55 | 0.000196 | 0.02488 | 126.9 |
| 56 | 0.000268 | 0.012924 | 48.2 |
| 57 | 0.000068 | 0.004674 | 68.7 |
| 58 | 0.001085 | 0.28807 | 265.5 |
| 59 | 0.000672 | 1.255 | 1867.6 |
| 60 | 0.01893 | >0.66 | >34.9 |
| 61 | 0.05221 | >0.66 | >12.6 |
| 62 | 0.003516 | 0.5711 | 162.4 |
| 64 | 0.000523 | 0.040334 | 77.1 |
| 65 | 0.004558 | 0.021805 | 4.8 |
| 67 | 0.28867 | >0.66 | >2.3 |
| 68 | 0.001227 | 0.013969 | 11.4 |
| 69 | 0.001245 | 0.092074 | 74 |
| 70 | 0.001192 | 0.074407 | 62.4 |
| 71 | 0.006233 | >0.66 | >105.9 |
| 72 | 0.003022 | 0.052359 | 17.3 |
| 73 | 0.001697 | 0.016885 | 9.9 |
| 74 | 0.00002 | 0.025249 | 1262.5 |
| 75 | 0.000125 | 0.10653 | 852.2 |
| 76 | 0.000051 | 0.003288 | 64.5 |
| 78 | 0.11251 | >0.66 | >5.9 |
| 79 | 0.00205 | 0.0972 | 47.4 |
| 85 | 0.000236 | 0.011521 | 48.8 |
| 86 | 0.000212 | 0.010522 | 49.6 |
| 87 | 0.000762 | 0.40679 | 533.8 |
| 88 | 0.000069 | 0.004642 | 67.3 |
| 89 | 0.000129 | 0.007453 | 57.8 |
| 90 | 0.002134 | 0.28384 | 133 |
| 91 | 0.000193 | 0.010191 | 52.8 |
| 92 | 0.004375 | 0.34857 | 79.7 |
| 93 | 0.000231 | 0.013861 | 60 |
| 94 | 0.00007 | 0.002317 | 33.1 |
| 95 | 0.00006 | 0.015699 | 261.7 |
| 96 | 0.000047 | 0.008781 | 186.8 |
| 97 | 0.000027 | 0.002611 | 96.7 |
| 98 | 0.000013 | >0.66 | >50769.2 |
| 99 | 0.00004 | 0.00553 | 138.3 |
| 100 | 0.000116 | 0.008288 | 71.4 |
| 101 | 0.000092 | 0.011152 | 121.2 |
| 102 | 0.000035 | 0.002242 | 64.1 |
| 103 | 0.000056 | 0.11738 | 2096.1 |
| 104 | 0.000077 | 0.049106 | 637.7 |
| 105 | 0.00008 | 0.005016 | 62.7 |
| 107 | 0.002087 | 0.13041 | 62.5 |
| 108 | 0.002342 | 0.059639 | 25.5 |
| 109 | 0.000161 | >0.66 | >4099.4 |
| 114 | 0.000096 | 0.014325 | 149.2 |
| 115 | 0.000176 | 0.027527 | 156.4 |
| 116 | 0.000036 | 0.008305 | 230.7 |
| 117 | 0.002299 | >0.66 | >287.1 |
| 118 | 0.000769 | >0.66 | >858.3 |
| 119 | 0.000622 | 0.23029 | 370.2 |
| 120 | 0.000443 | 0.099593 | 224.8 |
| 121 | 0.000001 | 0.000388 | 388 |
| 122 | 0.000058 | 0.012144 | 209.4 |
| 123 | 0.000015 | 0.001372 | 91.5 |
| 124 | 0.000335 | 0.073725 | 220.1 |
| 125 | 0.000003 | 0.011637 | 3879 |
| 126 | 0.000012 | 0.1629 | 13575 |
| 127 | 0.000459 | >0.66 | >1437.9 |
| 128 | 0.000051 | 0.363 | 7117.6 |
| 129 | 0.000056 | >0.66 | >11785.7 |
| 130 | 0.00014 | >0.66 | >4714.3 |
| 131 | 0.000106 | 0.24297 | 2292.2 |
| 132 | 0.000553 | 0.31529 | 570.1 |
| 133 | 0.000009 | 0.000281 | 31.2 |
| 134 | 0.000052 | 0.01805 | 347.1 |
| 135 | 0.000008 | 0.006239 | 779.9 |
| 136 | 0.000259 | 0.061863 | 238.9 |
| 137 | 0.000305 | 0.015977 | 52.4 |
| 138 | 0.000009 | 0.005174 | 574.9 |
| 139 | 0.000101 | 0.010416 | 103.1 |
| 140 | 0.004726 | >0.66 | >139.7 |
| 141 | 0.000673 | 0.028642 | 42.6 |
| 142 | 0.003664 | 0.10184 | 27.8 |
| 143 | 0.002232 | 0.075383 | 33.8 |
| 144 | 0.053902 | >0.66 | >12.2 |
| 145 | 0.00003 | 0.012029 | 401 |
| 146 | 0.044184 | >0.66 | >14.9 |
| 147 | 0.000514 | >0.66 | >1284.0 |
| 148 | 0.00289 | >0.66 | >228.4 |
| 149 | 0.000265 | >0.66 | >2490.6 |
| 150 | 0.000014 | 0.009338 | 667 |
| 151 | 0.000162 | >0.66 | >4074.1 |
| 152 | 0.000026 | 0.000412 | 15.8 |
| 153 | 0.000265 | 0.093006 | 351 |
| 154 | 0.000133 | 0.005375 | 40.4 |
| 155 | 0.000484 | 0.037667 | 77.8 |
| 156 | 0.000116 | 0.006155 | 53.1 |
| 157 | 0.004454 | >0.66 | >148.2 |
| 158 | 0.06478 | >0.66 | >10.2 |
| 161 | 0.00171 | >0.66 | >386.0 |
| 162 | 0.001348 | 0.16692 | 123.8 |
| 163 | 0.005616 | >0.66 | >117.5 |
| 164 | 0.000963 | 0.13795 | 143.3 |
| 165 | 0.000823 | 0.036585 | 44.5 |
| 166 | 0.000459 | 0.00327 | 7.1 |
| 169 | 0.00097 | 0.088637 | 91.4 |
| 170 | 0.000126 | 0.003802 | 30.2 |
| 171 | 0.002942 | 0.052053 | 17.7 |
| 172 | 0.002048 | 0.06569 | 32.1 |
| 173 | 0.000108 | 0.022102 | 204.6 |
| 174 | 0.000105 | 0.062087 | 591.3 |
| 175 | 0.0001 | >0.660 | >6600 |
| 176 | 0.00018 | 0.032 | 177.8 |
| 177 | 0.000165 | 0.132 | 799.7 |
| 178 | 0.000226 | >0.660 | >2915.8 |
| 179 | 0.000181 | >0.660 | >3642.4 |
| 180 | 0.000192 | >0.660 | >3438.6 |
| 181 | 0.000291 | >0.660 | >2271.9 |
| 182 | 0.000087 | >0.660 | >7595.8 |
| 183 | 0.000039 | 0.009428 | 240.5 |
| 184 | 0.000281 | >0.660 | >2345.3 |
| 185 | 0.000228 | 0.082582 | 361.5 |
| 186 | 0.00001 | 0.011199 | 1069.2 |
| 187 | 0.000329 | >0.660 | >2003.9 |
| 188 | 0.000102 | 0.11529 | 1135.4 |
| 189 | 0.000144 | 0.051724 | 358.6 |
| 190 | 0.000512 | 0.097064 | 189.6 |
| 191 | 0.000073 | 0.009162 | 125.2 |
| 194 | 0.000151 | 0.032029 | 212.4 |
| 195 | 0.000039 | 0.00671 | 170.2 |
| 196 | 0.000032 | >0.660 | >20552.4 |
| 197 | 0.000025 | 0.004837 | 193 |
| 198 | 0.003966 | >0.660 | >166.4 |
| 199 | 0.000014 | 0.005231 | 369.8 |
| 200 | 0.0001 | >0.660 | >6588.8 |
| 201 | 0.000125 | 0.024585 | 196.6 |
| 202 | 0.000052 | 0.005073 | 97.1 |

TABLE 2-continued

TR-FRET Binding Affinity

| Example | Bcl-2 $K_i$ (µM) | Bcl-$X_L$ $K_i$ (µM) | Binding selectivity ratio (Bcl-$X_L$ $K_i$/Bcl-2 $K_i$) |
|---|---|---|---|
| 203 | 0.000031 | 0.004305 | 139.5 |
| 204 | 0.000145 | 0.042341 | 291.3 |
| 205 | 0.000005 | 0.003573 | 658.6 |
| 206 | 0.000083 | >0.660 | >7916.4 |
| 207 | 0.000218 | >0.660 | >3021.3 |
| 208 | 0.000589 | >0.660 | >1120.6 |
| 209 | 0.000267 | >0.660 | >2476.0 |
| 210 | 0.000624 | >0.660 | >1057.6 |
| 211 | 0.000009 | 0.005612 | 651.1 |
| 212 | 0.000737 | >0.660 | >895.1 |
| 213 | <0.00001 | >0.660 | >66000 |
| 214 | 0.000082 | 0.064044 | 776.6 |
| 215 | 0.000503 | 0.060768 | 120.8 |
| 216 | 0.000615 | >0.660 | >1073.2 |
| 217 | 0.000262 | 0.044761 | 171.1 |
| 218 | 0.000131 | 0.096873 | 738.2 |
| 219 | 0.000236 | 0.029861 | 126.8 |
| 220 | 0.000192 | 0.031387 | 163.7 |
| 221 | 0.000057 | 0.1701 | 3005.2 |
| 222 | 0.000107 | 0.13661 | 1275.3 |
| 223 | 0.000169 | 0.097266 | 574.1 |
| 224 | <0.00001 | 0.000999 | >99.9 |
| 225 | 0.00001 | 0.003482 | >348.2 |
| 226 | 0.000017 | 0.009928 | 577.7 |
| 227 | 0.006831 | >0.660 | >96.6 |
| 228 | 0.004669 | >0.660 | >141.4 |
| 229 | 0.049413 | >0.660 | >13.4 |
| 230 | 0.008819 | >0.660 | >74.8 |
| 231 | 0.000918 | >0.660 | >718.8 |
| 232 | 0.00046 | 0.19749 | 429.1 |
| 233 | 0.000243 | >0.660 | >2714.3 |
| 234 | 0.000369 | 0.024503 | 66.3 |
| 235 | 0.000252 | 0.058196 | 231.4 |
| 236 | 0.000369 | >0.660 | >1787.6 |
| 237 | 0.000401 | 0.268 | 668.3 |
| 238 | 0.00043 | >0.660 | >1534.3 |
| 239 | 0.000252 | 0.10842 | 430.9 |
| 240 | 0.00083 | >0.660 | >795.4 |
| 241 | 0.006091 | >0.660 | >108.3 |
| 242 | 0.001796 | >0.660 | >367.6 |
| 243 | 0.00028 | >0.660 | >2357.6 |
| 244 | 0.00016 | >0.660 | >4136.9 |
| 245 | 0.001617 | >0.660 | >408.2 |
| 246 | 0.000783 | 0.38418 | 490.9 |
| 247 | 0.000188 | 0.027265 | 145.3 |
| 248 | 0.000013 | 0.15503 | 12079.4 |
| 249 | 0.00009 | >0.660 | >7302.0 |
| 250 | 0.000266 | 0.21547 | 811 |
| 251 | 0.000328 | 0.47166 | 1438.5 |
| 252 | 0.000077 | >0.660 | >8570.3 |
| 253 | 0.000142 | >0.660 | >4663.3 |
| 254 | 0.000126 | 0.053315 | 421.7 |
| 255 | 0.007834 | >0.660 | >84.2 |
| 256 | 0.00012 | >0.660 | >5519.8 |
| 257 | 0.000171 | 0.017126 | 100.2 |
| 258 | 0.000048 | 0.004085 | 86 |
| 259 | 0.001995 | >0.660 | >330.9 |
| 260 | 0.001087 | >0.660 | >607.2 |
| 261 | 0.000088 | >0.660 | >7530.1 |
| 262 | 0.003001 | >0.660 | 219.9 |
| 263 | 0.000316 | >0.660 | >2090.0 |
| 264 | 0.000235 | >0.660 | >2808.4 |
| 265 | 0.001698 | >0.660 | >388.8 |
| 266 | 0.000183 | >0.660 | >3607.7 |
| 267 | 0.000454 | >0.660 | >1453.3 |
| 268 | 0.000092 | 0.14465 | 1563.9 |
| 269 | nd | nd | nd |
| 270 | 0.003314 | >0.660 | >199.1 |
| 271 | 0.006156 | >0.660 | >107.2 |
| 272 | 0.000011 | >0.660 | >58011.8 |
| 273 | 0.000076 | 0.18104 | 2396.1 |
| 274 | 0.000135 | 0.032908 | 244.6 |
| 275 | 0.000097 | >0.660 | >6832.4 |
| 276 | 0.000144 | 0.38147 | 2650.8 |
| 277 | 0.029684 | >0.660 | >22.2 |
| 278 | 0.00071 | >0.660 | >929.4 |
| 279 | 0.000095 | >0.660 | >6923.2 |
| 280 | 0.000178 | 0.19477 | 1097.2 |
| 281 | 0.000076 | 0.11925 | 1558.9 |
| 282 | 0.000164 | 0.56153 | 3434.4 |
| 283 | 0.047464 | >0.660 | >13.9 |
| 284 | 0.001552 | >0.660 | >425.2 |
| 285 | 0.006994 | >0.660 | >94.4 |
| 286 | 0.000567 | >0.660 | >1165.0 |
| 287 | nd | nd | nd |
| 288 | 0.000177 | >0.660 | >3730.9 |
| 289 | 0.000112 | >0.660 | >5917.7 |
| 290 | 0.000365 | >0.660 | >1808.5 |
| 291 | 0.00056 | >0.660 | >1179.1 |
| 292 | 0.000598 | >0.660 | >1104.2 |
| 293 | 0.000516 | 0.2604 | 505.1 |
| 294 | 0.000258 | 0.065126 | 252 |
| 295 | 0.000183 | 0.10971 | 599.4 |
| 296 | 0.000651 | >0.660 | >1014.4 |
| 297 | 0.000128 | 0.28281 | 2209.5 |
| 298 | 0.000315 | 0.44593 | 1415.7 |
| 299 | 0.000425 | 0.24551 | 577.7 |
| 300 | nd | >0.660 | nd |
| 301 | 0.000291 | >0.660 | >2268.0 |
| 302 | 0.000504 | >0.660 | >1309.5 |
| 303 | 0.00148 | >0.660 | >445.9 |
| 304 | 0.000678 | >0.660 | >973.5 |
| 305 | 0.003684 | >0.660 | >179.2 |
| 306 | 0.000077 | 0.047895 | 622 |
| 307 | 0.003727 | >0.660 | >177.1 |
| 308 | 0.057376 | >0.660 | >11.5 |
| 309 | 0.004417 | >0.660 | >149.4 |
| 310 | 0.000049 | >0.660 | >13469.4 |
| 311 | 0.00026 | >0.660 | >2538.5 |
| 312 | 0.00034 | >0.660 | >1941.2 |
| 313 | 0.000044 | 0.066 | 1500 |
| 314 | 0.003066 | >0.660 | >215.3 |
| 315 | 0.003461 | >0.660 | >190.7 |
| 316 | 0.000149 | 0.079528 | 533.7 |
| 317 | 0.002798 | >0.660 | >235.9 |
| 318 | 0.001468 | 0.15067 | 102.6 |
| 319 | 0.000413 | 0.20791 | 503.4 |
| 320 | 0.001243 | 0.12873 | 103.6 |
| 321 | 0.000689 | >0.660 | >957.9 |
| 322 | 0.000184 | >0.660 | >3591.4 |
| 323 | 0.000949 | >0.660 | >695.2 |
| 324 | 0.001481 | >0.660 | >445.7 |
| 325 | 0.002331 | >0.660 | >283.1 |
| 326 | 0.000116 | >0.660 | >5708.8 |
| 327 | 0.000031 | 0.095575 | 3035.4 |
| 328 | 0.001859 | >0.660 | >355.0 |
| 329 | 0.000285 | >0.660 | >2319.5 |
| 330 | 0.074915 | >0.660 | >8.8 |
| 331 | 0.008266 | >0.660 | >79.8 |
| 332 | 0.012582 | >0.660 | >52.5 |
| 333 | 0.000089 | >0.660 | >7415.7 |
| 334 | 0.000179 | >0.660 | >3697.5 |
| 335 | 0.000438 | >0.660 | >1508.2 |
| 336 | 0.000105 | 0.24152 | 2301.3 |
| 337 | 0.000535 | >0.660 | >1233.3 |
| 338 | 0.000403 | >0.660 | >1637.7 |
| 339 | 0.014136 | >0.660 | >46.7 |
| 340 | 0.007593 | >0.660 | >86.9 |
| 341 | 0.012998 | >0.660 | >50.8 |
| 342 | 0.025752 | >0.660 | >25.6 |
| 343 | 0.000576 | >0.660 | >1145.9 |
| 344 | 0.000284 | 0.44708 | 1576.9 |
| 345 | 0.001146 | >0.660 | >575.9 |
| 346 | 0.000018 | 0.20364 | 11405.2 |

TABLE 2-continued

TR-FRET Binding Affinity

| Example | Bcl-2 $K_i$, (μM) | Bcl-X$_L$ $K_i$ (μM) | Binding selectivity ratio (Bcl-X$_L$ $K_i$/Bcl-2 $K_i$) |
|---|---|---|---|
| 347 | 0.000243 | 0.30556 | 1256.7 |
| 348 | 0.000302 | 0.029266 | 97.1 |
| 349 | 0.000467 | 0.024235 | 51.9 |
| 350 | 0.00597 | >0.660 | >110.6 |
| 351 | 0.001576 | >0.660 | >418.7 |
| 352 | 0.006825 | >0.660 | >96.7 |
| 353 | 0.000292 | >0.660 | >2260.0 |
| 354 | 0.000036 | 0.00541 | 148.8 |
| 355 | 0.00012 | >0.660 | >5489.5 |
| 356 | 0.005015 | >0.660 | >131.6 |
| 357 | 0.001336 | >0.660 | >493.9 |
| 358 | 0.005417 | >0.660 | >121.8 |
| 359 | 0.013481 | >0.660 | >49.0 |
| 360 | 0.000228 | 0.14423 | 633.9 |
| 361 | 0.007128 | >0.660 | >92.6 |
| 362 | 0.000082 | 0.290995 | 3548.2 |
| 363 | 0.00018 | >0.660 | >3670.5 |
| 364 | 0.000006 | 0.073182 | 12197.3 |
| 365 | 0.001077 | >0.660 | >612.9 |
| 366 | 0.005457 | >0.660 | >121.0 |
| 367 | 0.004608 | >0.660 | >143.2 |
| 368 | >1.195 | >0.660 | — |
| 369 | 0.8382 | >0.660 | >0.8 |
| 370 | 0.000904 | >0.660 | >729.9 |
| 371 | 0.008376 | >0.660 | >78.8 |
| 372 | >1.195 | >0.660 | — |
| 374 | 0.002266 | >0.660 | >291.2 |
| 375 | 0.011254 | >0.660 | >58.6 |
| 376 | 0.022405 | >0.660 | >29.5 |
| 377 | 0.00014 | 0.32457 | 2317.4 |
| 378 | 0.063003 | >0.660 | >10.5 |
| 379 | 0.25595 | >0.660 | >2.6 |
| 380 | 0.000083 | 0.17491 | 2107.3 |
| 381 | 0.000054 | 0.024207 | 448.3 |
| 382 | 0.00115 | >0.660 | >573.9 |
| 383 | 0.00217 | >0.660 | >304.1 |
| 384 | 0.000076 | >0.660 | >8684.2 |
| 385 | 0.000062 | 0.12998 | 2096.5 |
| 386 | 0.000239 | 0.11818 | 494.5 |
| 387 | 0.000162 | 0.27983 | 1723.4 |
| 388 | 0.000188 | 0.034845 | 185.1 |
| 389 | 0.000098 | 0.067181 | 685.5 |
| 390 | 0.000341 | 0.11581 | 339.6 |
| 391 | 0.00354 | >0.660 | >186.4 |
| 392 | 0.00038 | 0.121691 | 320.2394737 |
| 393 | 0.000083 | 0.0921 | 1109.638554 |
| 394 | 0.002507 | >660 | >263262.863980854 |
| 395 | 0.000798 | 0.018843 | 23.62136616 |
| 396 | 0.11567 | >660 | >5705.88743840235 |
| 397 | 0.022972 | >660 | >28730.6285913286 |
| 398 | 0.001233 | 0.083449 | 67.68513261 |
| 399 | 0.002923 | >660 | >225764.520763495 |
| 400 | <0.00001 | 0.036438 | 3643.8 |
| 401 | <0.00001 | 0.0016214 | 162.14 |
| 402 | 0.00003 | 0.004123 | 137.4441318 |
| 403 | 0.000003 | 0.024348 | 250.567777 |
| 404 | 0.000012 | 0.005082 | 423.47572 |
| 405 | 0.000040 | 0.055325 | 1394.84167 |
| 406 | 0.000035 | 0.044558 | 1263.771487 |
| 407 | 0.000015 | 0.074554 | 4930.626281 |
| 408 | 0.000002 | 0.028113 | 14701.71935 |
| 409 | <0.000010 | 0.017485 | 1748.5 |
| 410 | 0.000055 | 0.101630 | 1838.625057 |
| 411 | 0.000003 | 0.007453 | 2352.34518 |
| 412 | 0.000021 | 0.135216 | 6545.480951 |
| 413 | 0.000120 | 0.096802 | 803.8030391 |
| 414 | 0.000007 | 0.095649 | 13930.52218 |
| 415 | 0.000002 | 0.026907 | 13826.89211 |
| 416 | 0.000023 | 0.059112 | 2568.970013 |
| 417 | 0.000046 | 0.003986 | 87.05823249 |
| 418 | 0.000004 | 0.001566 | 404.6578954 |
| 419 | 0.000197 | 0.211240 | 1070.762368 |
| 420 | 0.000063 | 0.072108 | 1153.285139 |
| 421 | 0.000026 | 0.054039 | 2089.513572 |
| 422 | 0.000071 | 0.289500 | 4073.448713 |
| 423 | <0.000010 | 0.007566 | 756.62 |
| 424 | <0.000010 | 0.007825 | 782.52 |
| 425 | 0.000003 | 0.003995 | 1282.243051 |
| 426 | 0.000007 | 0.004311 | 604.2384997 |
| 427 | 0.000002 | 0.085636 | 34408.55031 |
| 428 | 0.000003 | 0.015643 | 5832.15271 |
| 429 | <0.000010 | 0.001407 | 140.65 |
| 430 | <0.000010 | 0.000998 | 99.767 |
| 431 | <0.000010 | 0.006774 | 677.36 |
| 432 | 0.000023 | 0.009298 | 408.8250813 |
| 433 | <0.000010 | 0.002286 | 228.55 |
| 434 | 0.000052 | 0.075474 | 1459.393611 |
| 435 | 0.000017 | 0.032896 | 1935.058824 |
| 436 | 0.000011 | 0.006500 | 590.9090909 |
| 437 | <0.000010 | 0.000514 | 51.4 |
| 438 | <0.000010 | 0.000345 | 34.5 |
| 439 | <0.000010 | 0.014968 | 1496.8 |
| 440 | <0.000010 | 0.045491 | 4549.1 |
| 441 | <0.000010 | 0.024219 | 2421.9 |
| 442 | <0.000010 | 0.033589 | 3358.9 |
| 443 | <0.000010 | 0.019357 | 1935.7 |
| 444 | 0.000112 | 0.081494 | 727.625 |
| 445 | 0.000028 | 0.013557 | 484.1785714 |
| 446 | 0.000038 | 0.019318 | 508.3684211 |
| 447 | 0.000028 | 0.065838 | 2373.053633 |
| 448 | 0.000005 | 0.014610 | 3119.262138 |
| 449 | 0.000240 | 0.017841 | 74.40260228 |
| 450 | 0.000299 | 0.032065 | 107.2874494 |
| 451 | <0.000010 | 0.003599 | 359.92 |
| 452 | <0.000010 | 0.006004 | 600.39 |
| 453 | <0.000010 | 0.003630 | 363.04 |
| 454 | 0.000026 | 0.018906 | 735.2415027 |
| 455 | 0.000004 | 0.000619 | 139.3622053 |
| 456 | <0.000010 | 0.000540 | 53.991 |
| 457 | 0.000045 | 0.330930 | 7413.638604 |
| 458 | <0.000010 | 0.002372 | 237.24 |
| 459 | <0.000010 | 0.005416 | 541.58 |
| 460 | 0.000049 | 0.028982 | 586.5495537 |
| 461 | 0.000093 | 0.003650 | 39.43935939 |
| 462 | 0.000026 | 0.018425 | 710.8410494 |
| 463 | 0.000007 | 0.043884 | 6042.880159 |
| 464 | 0.000081 | 0.521110 | 6431.789289 |
| 465 | 0.000025 | 0.037216 | 1472.443126 |
| 467 | 0.000080 | 0.13291 | 1653.027213 |
| 473 | 0.079276 | 0.19124 | 2.412331601 | nd = not determined

TABLE 2 shows the utility of compounds having Formula I to functionally inhibit anti-apoptotic Bcl-2 protein. It also surprisingly demonstrates these compounds having comparatively less affinity for anti-apoptotic Bcl-xL protein, which in turn gives rise to high binding selectivity ratios (Bcl-xL $K_i$/Bcl-2 $K_i$) ranging from >2 to >263,263. This selectivity for Bcl-2 protein is significantly greater than compounds previously disclosed in PCT US 2004/36770 and PCT US 2004/367911, as exemplified by ABT-737 in TABLE 2.

For some compounds (e.g., 192 and 193), the assay did not detect any activity against either Bcl-2 or Bcl-XL under the conditions stated above in the experimental description for the FRET assay. As those skilled in the art will appreciate, the upper and lower limits of detection in an assay are influenced by the assay conditions, and for the FRET assay specifically, by the concentration of the probe that is used. Since compounds represented by Examples 192 and 193 show $K_i$ values that are greater than the limits of detection in the assay format used, it can be stated that their affinity for Bcl-2 and Bcl-XL is less than the upper limit of detection of the assays. However, they may still have affinity for one or both proteins, and the inventors expect that they also have selectivity for Bcl-2.

Platelet Cell Viability Assay

Platelet-rich plasma (PRP) (prepared in-house according to conventional techniques) was incubated with ABT-737 (4-(4-((4'-chloro-1,1'-biphenyl-2-yl)methyl)piperazin-1-yl)-N-((4-(((1R)-3-(dimethylamino)-1-((phenylthio)methyl)propyl)amino)-3-nitrophenyl)sulfonyl)benzamide) or compounds of the invention at various concentrations for five hours at 37° C. After the incubation, platelets were equilibrated to room temperature for 20 minutes and then an equal volume of Cell Titer Glo reagent (Promega Corporation) was added. Samples were mixed for two minutes and then allowed to equilibrate for an additional 10 minutes at room temperature. The luminescence generated from the samples was quantitated using an LJL Analyst plate reader. $IC_{50}$ values are concentrations of compound needed for 50% inhibition of cellular viability.

FL5.12/Bcl-2 Cell Viability Assay

FL5.12 is an IL-3 dependent prolymphocytic murine cell line that undergoes apoptosis upon IL-3 withdrawal as a result of the upregulation of pro-apoptotic Bcl-2 proteins such as Bim and Puma. Stable overexpression of anti-apoptotic Bcl-2 protein (FL5.12/Bcl-2) protects against apoptosis induced by IL-3 withdrawal by sequestration of Bim and Puma. [Refs. Harada, et. al. *PNAS* 101, 15313 (2004); Certo, et. al. *Cancer Cell* 9, 351 (2006).] The ability of compounds to kill FL5.12/Bcl-2 cells upon IL-3 withdrawal is a direct measure of the compounds' ability to inhibit anti-apoptotic Bcl-2 protein function.

Wild type FL5.12/Bcl-2 overexpressing stable transfectants were cultured in RPMI-1640 supplemented with 2 mM L-glutamine, 10% FBS, 1 mM sodium pyruvate, 2 mM HEPES, 1% penicillin/streptomycin (Invitrogen), 57 µM (3-ME, and 10% WEHI-3B conditioned medium (source of IL-3) and maintained at 37° C. containing 5% $CO_2$. $1 \times 10^6$ cells/ml were washed 1×PBS and resuspended in medium not supplemented with 10% WEHI-3B for 48 hrs prior to cytotoxicity assays. Cells were then treated for an additional 24 hrs in the presence of various concentrations of the indicated compounds. Cell viability was assessed by CellTitre Glo assay (Promega Corp.) according to the manufacturer's recommendations.

Data analysis was performed using GraphPad Prism 4.0 and results are shown in TABLE 3 below.

TABLE 3

| | Cellular Activity | | |
|---|---|---|---|
| | FL5.12/Bcl-2 $EC_{50}$ (µM) | Canine platelets $EC_{50}$ (µM) | Selectivity Ratio (Platelet $EC_{50}$/ FL5.12/Bcl-2 $EC_{50}$) |
| ABT-737 | 0.025 | 0.282 | 11 |
| 18 | 0.123 | 29.69 | 241 |
| 21 | 1.01 | >50 | >49 |
| 22 | 0.825 | >50 | >61 |
| 23 | 1.44 | >50 | >35 |
| 24 | 0.055 | >50 | >906 |

TABLE 3-continued

| | Cellular Activity | | |
|---|---|---|---|
| | FL5.12/Bcl-2 $EC_{50}$ (µM) | Canine platelets $EC_{50}$ (µM) | Selectivity Ratio (Platelet $EC_{50}$/ FL5.12/Bcl-2 $EC_{50}$) |
| 25 | 0.049 | >50 | >1020 |
| 26 | 0.035 | >50 | >1429 |
| 40 | 0.165 | >50 | >303 |
| 45 | 0.139 | >50 | >360 |
| 46 | 0.041 | 30 | 725 |
| 52 | 0.016 | >50 | >3164 |
| 53 | 0.011 | 18.325 | 1697 |
| 54 | 0.064 | >50 | >785 |
| 55 | 0.022 | 36 | 1614 |
| 56 | 0.049 | 27 | 554 |
| 57 | 0.016 | 16.8 | 1077 |
| 68 | 0.044 | >50 | >1144 |
| 69 | 0.075 | >50 | >666 |
| 70 | 0.111 | >50 | >450 |
| 71 | 0.46 | >50 | >107 |
| 72 | 0.154 | >50 | >325 |
| 73 | 0.14 | 23.22 | 166 |
| 74 | 0.008 | 16.71 | 1989 |
| 75 | 0.022 | 17.73 | 821 |
| 76 | 0.039 | 8.66 | 221 |
| 86 | 0.074 | 36.27 | 489 |
| 88 | 0.032 | 19.87 | 613 |
| 89 | 0.065 | 31.95 | 495 |
| 94 | 0.04 | 23.85 | 590 |
| 96 | 0.011 | 22.27 | 2043 |
| 97 | 0.013 | 14.1 | 1052 |
| 98 | 0.004 | 17.94 | 4849 |
| 99 | 0.009 | 21.72 | 2440 |
| 100 | 0.015 | 31.25 | 2029 |
| 102 | 0.02 | 20.21 | 996 |
| 103 | 0.014 | 31.35 | 2305 |
| 104 | 0.021 | >50 | >2392 |
| 105 | 0.013 | 30.31 | 2262 |
| 106 | 0.009 | 15.24 | 1657 |
| 109 | 0.036 | >50 | >1404 |
| 120 | 0.319 | >50 | >157 |
| 121 | 0.038 | 0.309 | 8 |
| 122 | 0.04 | >50 | >1259 |
| 123 | 0.087 | 2.81 | 32 |
| 125 | 0.01 | 44.83 | 4719 |
| 126 | 0.031 | >50 | >1618 |
| 128 | 0.025 | >50 | >2000 |
| 129 | 0.021 | >50 | >2415 |
| 130 | 0.197 | >50 | >254 |
| 131 | 0.031 | >50 | >1597 |
| 132 | 0.042 | >50 | >1196 |
| 133 | 0.02 | 0.095 | 5 |
| 134 | 0.048 | 4.72 | 98 |
| 135 | 0.042 | 4.55 | 108 |
| 136 | 0.19 | >50 | >263 |
| 137 | 0.281 | >50 | >178 |
| 138 | 0.029 | 17.75 | 616 |
| 139 | 0.046 | 38.5 | 841 |
| 140 | 2.13 | >50 | >23 |
| 141 | 0.076 | >50 | >661 |
| 142 | 0.27 | >50 | >185 |
| 143 | 0.199 | >50 | >251 |
| 144 | 0.046 | 40.02 | 864 |
| 145 | 0.004 | 3.21 | 730 |
| 146 | 0.152 | 21.97 | 145 |
| 147 | 0.009 | 17.62 | 1895 |
| 148 | 0.071 | 19.77 | 278 |
| 149 | 0.013 | 16.74 | 1298 |
| 150 | 0.006 | 2.9 | 509 |
| 151 | 0.049 | 31.4 | 642 |
| 152 | 0.009 | 2.66 | 283 |
| 154 | 0.085 | 29 | 343 |
| 155 | 0.421 | >50 | >119 |
| 166 | 0.153 | >50 | >327 |
| 170 | 0.015 | 7.35 | 507 |
| 171 | 0.276 | >50 | >181 |
| 172 | 0.194 | >50 | >257 |

TABLE 3-continued

| | Cellular Activity | | |
|---|---|---|---|
| | FL5.12/Bcl-2 EC$_{50}$ (µM) | Canine platelets EC$_{50}$ (µM) | Selectivity Ratio (Platelet EC$_{50}$/FL5.12/Bcl-2 EC$_{50}$) |
| 173 | 0.011 | >50 | >4587 |
| 174 | 0.011 | 19.5 | 1857 |
| 175 | 0.0062 | nd | nd |
| 176 | 0.0585 | nd | nd |
| 177 | 0.01966 | nd | nd |
| 178 | 0.0186 | nd | nd |
| 179 | 0.02346 | nd | nd |
| 180 | 0.02047 | nd | nd |
| 181 | 0.03353 | nd | nd |
| 182 | 0.01242 | nd | nd |
| 183 | 0.03077 | nd | nd |
| 184 | 0.02698 | nd | nd |
| 185 | 0.06335 | nd | nd |
| 186 | 0.02036 | nd | nd |
| 187 | 0.34128 | nd | nd |
| 188 | 0.02466 | nd | nd |
| 189 | 0.01489 | nd | nd |
| 190 | 0.02421 | nd | nd |
| 191 | 0.01172 | nd | nd |
| 192 | >0.5 | nd | nd |
| 193 | >0.5 | nd | nd |
| 194 | 0.02697 | nd | nd |
| 195 | 0.01124 | nd | nd |
| 196 | 0.01236 | nd | nd |
| 197 | 0.00618 | nd | nd |
| 198 | nd | nd | nd |
| 199 | 0.02854 | nd | nd |
| 200 | 0.00629 | nd | nd |
| 201 | 0.0174 | nd | nd |
| 202 | 0.01383 | nd | nd |
| 203 | 0.0223 | nd | nd |
| 204 | 0.02738 | nd | nd |
| 205 | 0.03753 | nd | nd |
| 206 | 0.00501 | nd | nd |
| 207 | 0.1199 | nd | nd |
| 208 | 0.26403 | nd | nd |
| 209 | 0.13896 | nd | nd |
| 210 | 0.25691 | nd | nd |
| 211 | 0.01713 | nd | nd |
| 212 | >0.5 | nd | nd |
| 213 | 0.43216 | nd | nd |
| 214 | 0.01569 | nd | nd |
| 215 | 0.11576 | nd | nd |
| 216 | 0.03985 | nd | nd |
| 217 | 0.02083 | nd | nd |
| 218 | 0.033 | nd | nd |
| 219 | 0.02296 | nd | nd |
| 220 | 0.02403 | nd | nd |
| 221 | 0.14872 | nd | nd |
| 222 | 0.02366 | nd | nd |
| 223 | 0.03713 | nd | nd |
| 224 | 0.02116 | nd | nd |
| 225 | 0.02989 | nd | nd |
| 226 | 0.02301 | nd | nd |
| 227 | >0.5 | nd | nd |
| 228 | >0.5 | nd | nd |
| 229 | >0.5 | nd | nd |
| 230 | 0.17755 | nd | nd |
| 231 | 0.0509 | nd | nd |
| 232 | 0.01228 | nd | nd |
| 233 | nd | nd | nd |
| 234 | nd | nd | nd |
| 235 | nd | nd | nd |
| 236 | nd | nd | nd |
| 237 | nd | nd | nd |
| 238 | 0.05896 | nd | nd |
| 239 | 0.01764 | nd | nd |
| 240 | 0.20943 | nd | nd |
| 241 | nd | nd | nd |
| 242 | 0.16457 | nd | nd |
| 243 | 0.028 | nd | nd |
| 244 | 0.02025 | nd | nd |
| 245 | 0.07244 | nd | nd |
| 246 | 0.048 | nd | nd |
| 247 | 0.01607 | nd | nd |
| 248 | 0.04981 | nd | nd |
| 249 | 0.0412 | nd | nd |
| 250 | 0.07951 | nd | nd |
| 251 | 0.07812 | nd | nd |
| 252 | 0.00662 | nd | nd |
| 253 | 0.00758 | nd | nd |
| 254 | 0.01693 | nd | nd |
| 255 | >0.5 | nd | nd |
| 256 | 0.00889 | nd | nd |
| 257 | 0.00934 | nd | nd |
| 258 | 0.00911 | nd | nd |
| 259 | >0.5 | nd | nd |
| 260 | 0.05944 | nd | nd |
| 261 | 0.01701 | nd | nd |
| 262 | 0.17622 | nd | nd |
| 263 | 0.02835 | nd | nd |
| 264 | 0.02571 | nd | nd |
| 265 | 0.24417 | nd | nd |
| 266 | 0.01148 | nd | nd |
| 267 | 0.05643 | nd | nd |
| 268 | 0.06822 | nd | nd |
| 269 | nd | nd | nd |
| 270 | 0.42893 | nd | nd |
| 271 | >0.5 | nd | nd |
| 272 | 0.19406 | nd | nd |
| 273 | 0.07001 | nd | nd |
| 274 | 0.15519 | nd | nd |
| 275 | 0.03801 | nd | nd |
| 276 | 0.06218 | nd | nd |
| 277 | >0.5 | nd | nd |
| 278 | 0.15272 | nd | nd |
| 279 | 0.01623 | nd | nd |
| 280 | 0.24715 | nd | nd |
| 281 | 0.06022 | nd | nd |
| 282 | 0.09216 | nd | nd |
| 283 | >0.5 | nd | nd |
| 284 | >0.5 | nd | nd |
| 285 | >0.5 | nd | nd |
| 286 | 0.27896 | nd | nd |
| 287 | nd | nd | nd |
| 288 | 0.06432 | nd | nd |
| 289 | 0.02736 | nd | nd |
| 290 | 0.04468 | nd | nd |
| 291 | 0.05801 | nd | nd |
| 292 | 0.06916 | nd | nd |
| 293 | 0.06806 | nd | nd |
| 294 | 0.05981 | nd | nd |
| 295 | 0.04634 | nd | nd |
| 296 | 0.18237 | nd | nd |
| 297 | 0.01321 | nd | nd |
| 298 | 0.01948 | nd | nd |
| 299 | 0.07725 | nd | nd |
| 300 | 0.06215 | nd | nd |
| 301 | 0.05945 | nd | nd |
| 302 | 0.03238 | nd | nd |
| 303 | >0.5 | nd | nd |
| 304 | 0.41529 | nd | nd |
| 305 | >0.5 | nd | nd |
| 306 | 0.00716 | nd | nd |
| 307 | >0.5 | nd | nd |
| 308 | >0.5 | nd | nd |
| 309 | >0.5 | nd | nd |
| 310 | 0.00451 | nd | nd |
| 311 | 0.0334 | nd | nd |
| 312 | 0.01924 | nd | nd |
| 313 | 0.08289 | nd | nd |
| 314 | 0.24014 | nd | nd |
| 315 | >0.5 | nd | nd |
| 316 | 0.06749 | nd | nd |

TABLE 3-continued

Cellular Activity

| | FL5.12/<br>Bcl-2<br>EC$_{50}$ (μM) | Canine<br>platelets<br>EC$_{50}$<br>(μM) | Selectivity<br>Ratio<br>(Platelet EC$_{50}$/<br>FL5.12/Bcl-2<br>EC$_{50}$) |
|---|---|---|---|
| 317 | 0.08309 | nd | nd |
| 318 | 0.07695 | nd | nd |
| 319 | 0.03141 | nd | nd |
| 320 | 0.04158 | nd | nd |
| 321 | 0.02909 | nd | nd |
| 322 | 0.04445 | nd | nd |
| 323 | 0.09208 | nd | nd |
| 324 | 0.13417 | nd | nd |
| 325 | 0.25639 | nd | nd |
| 326 | 0.03509 | nd | nd |
| 327 | 0.00657 | nd | nd |
| 328 | >0.5 | nd | nd |
| 329 | 0.12652 | nd | nd |
| 330 | >0.5 | nd | nd |
| 331 | >0.5 | nd | nd |
| 332 | >0.5 | nd | nd |
| 333 | 0.10932 | nd | nd |
| 334 | 0.06592 | nd | nd |
| 335 | 0.03897 | nd | nd |
| 336 | 0.00749 | nd | nd |
| 337 | 0.12389 | nd | nd |
| 338 | 0.07113 | nd | nd |
| 339 | >0.5 | nd | nd |
| 340 | >0.5 | nd | nd |
| 341 | >0.5 | nd | nd |
| 342 | >0.5 | nd | nd |
| 343 | 0.05489 | nd | nd |
| 344 | 0.07147 | nd | nd |
| 345 | >0.5 | nd | nd |
| 346 | 0.01747 | nd | nd |
| 347 | 0.04681 | nd | nd |
| 348 | 0.0872 | nd | nd |
| 349 | 0.14571 | nd | nd |
| 350 | 0.31119 | nd | nd |
| 351 | 0.34452 | nd | nd |
| 352 | 0.15632 | nd | nd |
| 353 | 0.05828 | nd | nd |
| 354 | 0.0056 | nd | nd |
| 355 | >0.5 | nd | nd |
| 356 | >0.5 | nd | nd |
| 357 | >0.5 | nd | nd |
| 358 | >0.5 | nd | nd |
| 359 | >0.5 | nd | nd |
| 360 | 0.10622 | nd | nd |
| 361 | >0.5 | nd | nd |
| 362 | 0.17126 | nd | nd |
| 363 | 0.08692 | nd | nd |
| 364 | 0.18474 | nd | nd |
| 365 | >0.5 | nd | nd |
| 366 | >0.5 | nd | nd |
| 367 | >0.5 | nd | nd |
| 368 | >0.5 | nd | nd |
| 369 | >0.5 | nd | nd |
| 370 | 0.26334 | nd | nd |
| 371 | >0.5 | nd | nd |
| 372 | >0.5 | nd | nd |
| 374 | >0.5 | nd | nd |
| 375 | >0.5 | nd | nd |
| 376 | >0.5 | nd | nd |
| 377 | 0.08573 | nd | nd |
| 378 | >0.5 | nd | nd |
| 379 | >0.5 | nd | nd |
| 380 | 0.06849 | nd | nd |
| 381 | 0.07185 | nd | nd |
| 382 | >0.5 | nd | nd |
| 383 | >0.5 | nd | nd |
| 384 | 0.10121 | nd | nd |
| 385 | 0.05636 | nd | nd |
| 386 | 0.15353 | nd | nd |
| 387 | 0.08652 | nd | nd |
| 388 | 0.08288 | nd | nd |
| 389 | 0.02812 | nd | nd |
| 390 | 0.04118 | nd | nd |
| 391 | >0.5 | nd | nd |
| 392 | nd | nd | nd |
| 393 | nd | nd | nd |
| 394 | nd | nd | nd |
| 395 | nd | nd | nd |
| 396 | >0.5 | nd | nd |
| 397 | nd | nd | nd |
| 398 | 0.33382 | nd | nd |
| 399 | >0.5 | nd | nd |
| 400 | 0.00847 | nd | nd |
| 401 | 0.00538 | nd | nd |
| 402 | 0.01336 | nd | nd |
| 403 | 0.00292 | nd | nd |
| 404 | 0.00234 | nd | nd |
| 405 | 0.01162 | nd | nd |
| 406 | 0.02046 | nd | nd |
| 407 | 0.0081 | nd | nd |
| 408 | 0.00239 | nd | nd |
| 409 | 0.0012 | nd | nd |
| 410 | 0.01386 | nd | nd |
| 411 | 0.01145 | nd | nd |
| 412 | 0.00948 | nd | nd | nd = not determined

TABLE 3 shows the utility of compounds having Formula I to functionally inhibit anti-apoptotic Bcl-2 protein in a cellular context. FL5.12 is an IL-3 dependent prolymphocytic murine cell line that undergoes apoptosis upon IL-3 withdrawal as a result of the upregulation of pro-apoptotic Bcl-2 family proteins such as Bim and Puma. Stable overexpression of anti-apoptotic Bcl-2 protein (FL5.12/Bcl-2) protects against apoptosis induced by IL-3 withdrawal by sequestration of Bim and Puma. (Refs. Harada, et. al. *PNAS* 2004, 101, 15313; Certo, et. al. *Cancer Cell* 2006, 9, 351.) The ability of compounds to kill FL5.12/Bcl-2 cells upon IL-3 withdrawal is a direct measure of the compounds ability to inhibit anti-apoptotic Bcl-2 protein function. Compounds of Formula I are very effective in killing FL5.12/Bcl-2 cells under IL-3 withdrawal as demonstrated by low EC$_{50}$ values.

Compounds of this invention bind to anti-apoptotic Bcl-2 proteins with high affinity and potently inhibit the function of anti-apoptotic Bcl-2 protein in a cellular context and are therefore expected to have utility in treatment of diseases during which anti-apoptotic Bcl-2 protein is expressed.

The anti-apoptotic Bcl-xL protein has been disclosed elsewhere (Cell Mar. 23, 2007, 128, 1173-1176.) to be the major regulator of the survival of circulating platelets in animals. Genetic mutations to Bcl-xL protein that decrease Bcl-xL protein stability and half-life causes a decrease in platelet survival and life-span in mice bearing these mutations. A potent pharmacologic inhibitor of Bcl-xL, ABT-737, causes a rapid, concentration dependant decrease in circulating platelets following injection into C57BL/6 mice or in beagle canines (*Cell* Mar. 23, 2007, 128, 1173-1176.; *Cell Death Differ*. May 2007; 14(5), 943-51). Thus, without being limited by theory, compounds of this invention that have reduced affinity for Bcl-xL can be expected to show lower levels of platelet apoptosis than previously reported compounds with higher Bcl-xL affinity.

The effect of compounds on platelet survival can be directly evaluated ex vivo by examining the viability of isolated canine platelets in the presence of various concentrations of compound. The data in Table 3 shows that compounds of Formula I have significantly less to no effect on the viability of isolated canine platelets ex vivo (higher $EC_{50}$ values) compared to compounds previously disclosed in PCT US 2004/36770 and PCT US 2004/367911, as exemplified by ABT-737. Furthermore, the functional selectivity ratio (canine platelet $EC_{50}$: FL5.12/Bcl-2 $EC_{50}$) for compounds of Formula I ranges from 32 to 4849, which is significantly higher than that for compounds previously disclosed in PCT US 2004/36770 and PCT US 2004/367911, as exemplified by ABT-737.

Because compounds having Formula I bind to anti-apoptotic Bcl-2 protein with comparatively lower binding to anti-apoptotic Bcl-$X_L$ protein, the compounds would have utility as medicaments for the treatment of cancer and autoimmune and immune diseases with reduction of the side effect of thrombocytopenia (i.e., they would be circulating platelet-sparing). Involvement of Bcl-$X_L$ in thrombocytopenia is disclosed in *Cell* Mar. 23, 2007, 128, 1173-1176. As described herein and elsewhere, a potent inhibitor of Bcl-$X_L$, ABT-737, causes a dose-dependent decrease in circulating platelets following injection into C57BL/6 mice or in canines (*Cell Death Differ*. May 2007; 14(5), 943-51). Compounds with reduced Bcl-$X_L$ affinity exhibit substantially less to no decrease in circulating platelets. Thus, without being limited by theory, compounds of this invention that have reduced affinity for Bcl-$X_1$, can be expected to show lower levels of platelet apoptosis than previously reported compounds with higher Bcl-$X_L$ affinity. The $EC_{50}$ data in TABLE 2 show the effects of administration of compounds of this invention, compared to ABT-737, on canine platelets.

Involvement of Bcl-2 protein in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, chronic lymphocytic leukemia, myeloma, prostate cancer spleen cancer, and the like is described in commonly-owned PCT US 2004/36770, published as WO 2005/049593, and PCT US 2004/37911, published as WO 2005/024636.

Involvement of Bcl-2 proteins in immune and autoimmune diseases is described in *Current Allergy and Asthma Reports* 2003, 3, 378-384; *British Journal of Haematology* 2000, 110(3), 584-90; *Blood* 2000, 95(4), 1283-92; and *New England Journal of Medicine* 2004, 351(14), 1409-1418.

Involvement of Bcl-2 protein in arthritis is disclosed in commonly-owned U.S. Provisional Patent Application Ser. No. 60/988,479.

Involvement of Bcl-2 protein in bone marrow transplant rejection is disclosed in commonly-owned U.S. patent application Ser. No. 11/941,196 (now U.S. Published Application 20080182845A1).

Overexpression of Bcl-2 protein correlates with resistance to chemotherapy, clinical outcome, disease progression, overall prognosis or a combination thereof in various cancers and disorders of the immune system. Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophoblastic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

It is also expected that compounds having Formula I would inhibit growth of cells expressing Bcl-2 protein derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal tumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Autoimmune disorders include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, dermatitis scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multi-system disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, *mycobacterium avium intracellulare, mycobacterium tuberculosis*, myelodyplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjigren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, sporadic, polyglandular deficiency type I sporadic, polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, yersinia and salmonella-associated arthropathy and the like.

Schemes and Experimentals

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

The following abbreviations have the meanings indicated. ADDP means 1,1'-(azodicarbonyl)dipiperidine; AD-mix-3 means a mixture of $(DHQD)_2PHAL$, $K_3Fe(CN)_6$, $K_2CO_3$, and $K_2SO_4$); 9-BBN means 9-borabicyclo(3.3.1)nonane; Boc means tert-butoxycarbonyl; $(DHQD)_2PHAL$ means hydroquinidine 1,4-phthalazinediyl diethyl ether; DBU means 1,8-diazabicyclo(5.4.0)undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means DMSO; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; $MP-BH_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

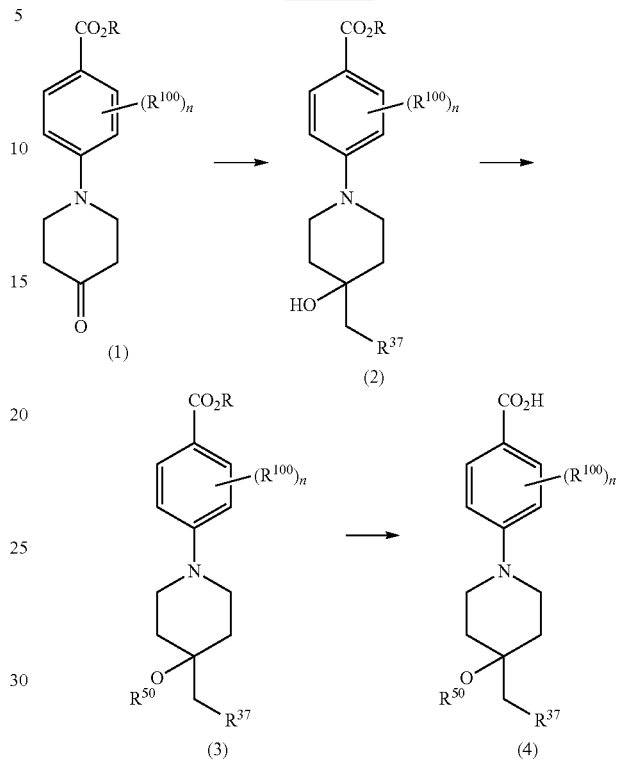

Compounds of Formula (4) can be prepared as shown in SCHEME 1, and can be used as described in SCHEME 7 to prepare compounds of Formula (I), which are representative of the compounds of the present invention. Compounds of Formula (I) wherein R is alkyl, $R^{100}$ is as described for substituents on $R^{26}$, and n is 1, 2, or 3; can be converted to compounds of Formula (2) using $R^{37}CH^2MgX^1$, wherein $X^1$ is a halide, in a solvent such as but not limited to ether or tetrahydrofuran. Compounds of Formula (3) can be prepared from compounds of Formula (2) using a strong base such as NaH and $R^{50}OX^2$, wherein $X^2$ is a halide and $R^{50a}$ is as described herein. Compounds of Formula (3), when treated with aqueous NaOH or LiOH, will provide compounds of Formula (4).

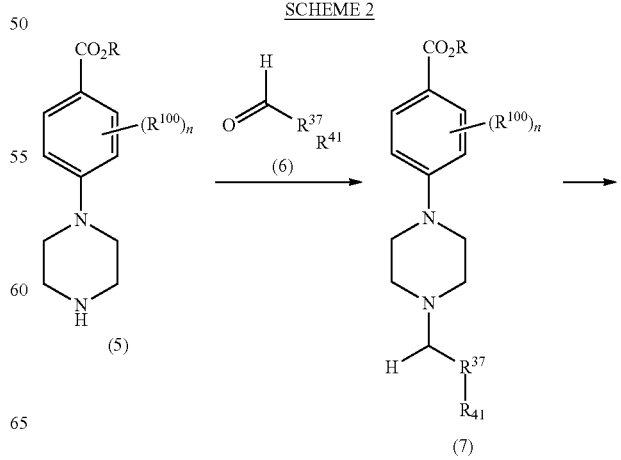

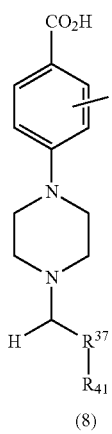

(8)

As shown in SCHEME 2, compounds of Formula (5) can be reacted with compounds of Formula (6) and a reducing agent to provide compounds of Formula (7). Examples of reducing agents include sodium borohydride, sodium cyanoborohydride, sodium triacetoxyborohydride, polymer supported cyanoborohydride, and the like. The reaction is typically performed in a solvent such as but not limited to methanol, tetrahydrofuran, and dichloromethane or mixtures thereof. Compounds of Formula (8) can be prepared from compounds of Formula (7) as described in SCHEME 1, and can be used as described in SCHEME 7 to prepare compounds of Formula (I).

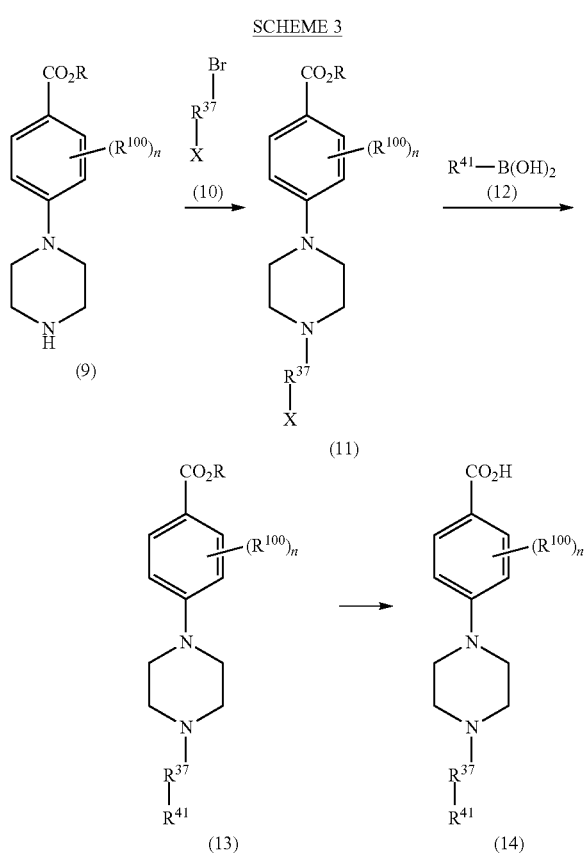

SCHEME 3

Compounds of Formula (9), when reacted with a compound a Formula (10) wherein X is a halide or triflate, and a base will provide a compound of Formula (11). Bases useful in the reaction include triethylamine, diisopropylethylamine and the like. Compounds of Formula (13), wherein $R^{41}$ is as described herein for substituents on $R^{37}$, can be prepared from compounds of Formula (11) and compounds of Formula (12) using Suzuki coupling conditions known to those skilled in the art and readily available in the literature. Compounds of Formula (14) can be prepared from compounds of Formula (13) as described in SCHEME 1, and can be used as described in SCHEME 7 to prepare compounds of Formula (I).

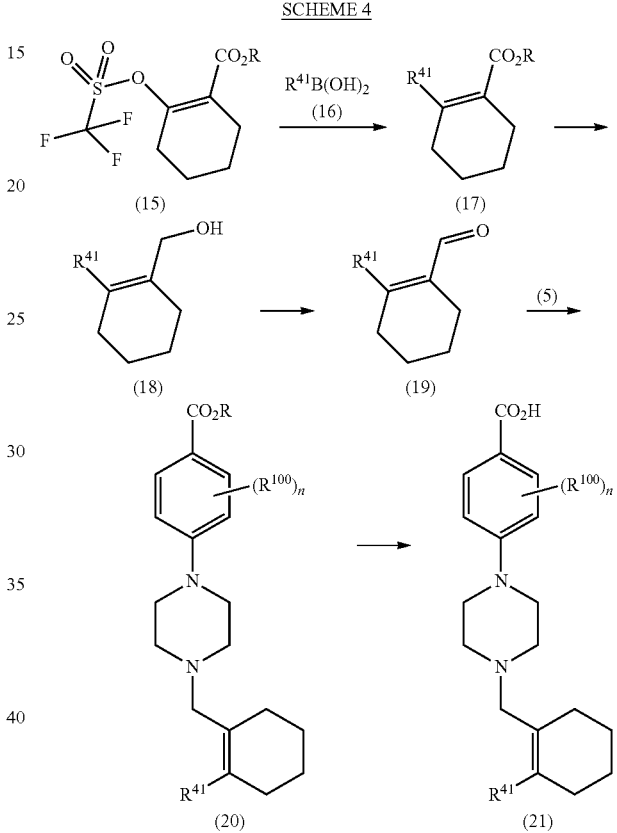

SCHEME 4

As shown in SCHEME 4, compounds of Formula (17) can be prepared from compounds of Formula (15) and compounds of Formula (16), wherein R is alkyl and $R^{41}$ is as described herein, using Suzuki coupling conditions known to those skilled in the art and readily available in the literature. Compounds of Formula (17) can be reduced to compounds of Formula (18) using a reducing agent such as $LiAlH_4$ in a solvent such as but not limited to diethyl ether or THF. Compounds of Formula (19) can be prepared from compounds of Formula (18) using Dess-Martin periodinane or Swern oxidation conditions known to those skilled in the art and readily available in the literature. Compounds of Formula (19) can be reacted with a compound of Formula (5) and a reducing agent to provide compounds of Formula (20). Examples of reducing agents include sodium borohydride, sodium cyanoborohydride, sodium triacetoxyborohydride, polymer supported cyanoborohydride, and the like. The reaction is typically performed in a solvent such as but not limited to methanol, tetrahydrofuran, 1,2-dichloroethane, and dichloromethane or mixtures thereof. Compounds of Formula (21) can be prepared from compounds of Formula (20) as described in SCHEME 1, and can be used as described in SCHEME 7 to prepare compounds of Formula (I).

SCHEME 5

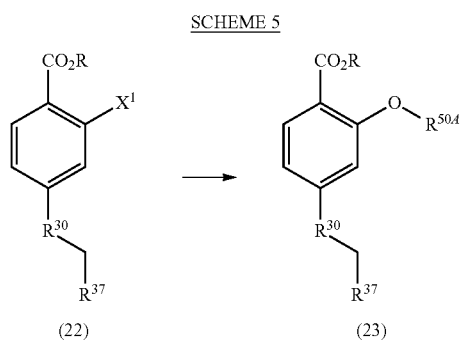

(22) → (23)

As shown in SCHEME 5, compounds of Formula (22), wherein R is alkyl, may be converted to compounds of Formula (23) by reacting the former, wherein $X^1$ is Cl, Br, I, or $CF_3SO_3$—, and compounds of Formula $R^{50A}$—OH and a catalyst, with or without a first base. Examples of catalysts include copper(I) trifluoromethanesulfonate toluene complex, $PdCl_2$, $Pd(OAc)_2$, and $Pd_2(dba)_3$. Examples of first bases include triethylamine, N,N-diisopropylethylamine, $Cs_2CO_3$, $Na_2CO_3$, $K_3PO_4$, and mixtures thereof.

Compounds of Formula (22) may also be converted to compounds of Formula (23) by reacting the former, when $X^1$ is Cl, F, or $NO_2$, and compounds of Formula $R^{50A}$—OH with a first base. Examples of first bases include triethylamine, N,N-diisopropylethylamine, $Cs_2CO_3$, $Na_2CO_3$, $K_3PO_4$, and mixtures thereof.

SCHEME 6

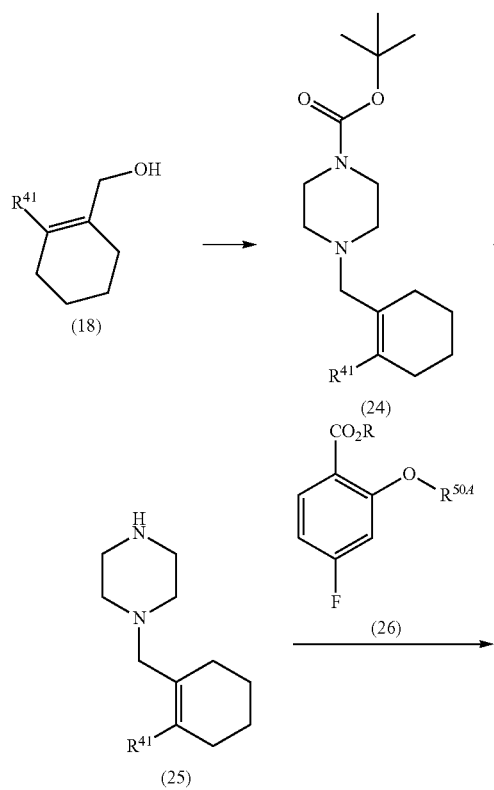

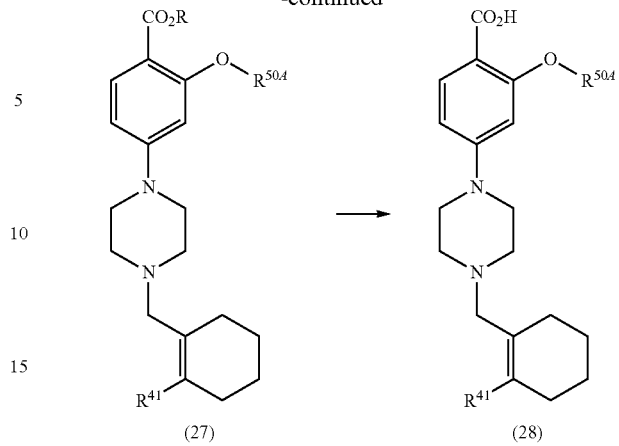

(27) → (28)

Compounds of Formula (18) can be reacted with mesyl chloride and a base such as but not limited to triethylamine, followed by N-t-butoxycarbonylpiperazine, to provide compounds of Formula (24). Compounds of Formula (25) can be prepared by reacting compounds of Formula (24) with triethylsilane and trifluoroacetic acid. Compounds of Formula (25) can be reacted with compounds of Formula (26) and $HK_2PO_4$ to provide compounds of Formula (27) in a solvent such as but not limited to dimethylsulfoxide. Compounds of Formula (28) can be prepared from compounds of Formula (27) as described in SCHEME 1, and can be used as described in SCHEME 7 to prepare compounds of Formula (I).

SCHEME 7

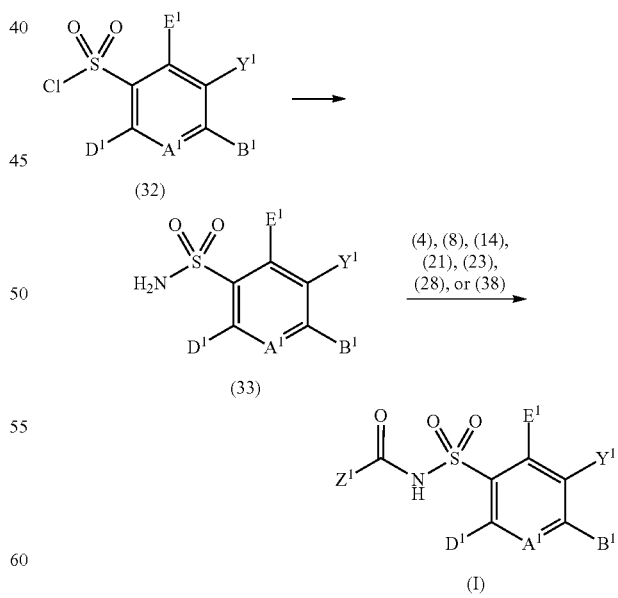

As shown in SCHEME 7, compounds of Formula (32), which can be prepared as described herein, may be converted to compounds of Formula (33) by reacting the former with ammonia. Compounds of Formula (33) may be converted to compounds of Formula (I) by reacting the former and compounds of Formula (4), (8), (14), (21), (23), (28), or (38) and a coupling agent, with or without a first base. Examples of coupling agents include 1-ethyl-3-[3-(dimethylamino)propyl]-carbodiimide hydrochloride, 1,1'-carbonyldiimidazole, and benzotriazol-1-yl-oxytripyrrolidinophosphonium hexafluorophosphate. Examples of first bases include triethylamine, N,N-diisopropylethylamine, 4-(dimethylamino)pyridine, and mixtures thereof.

SCHEME 8

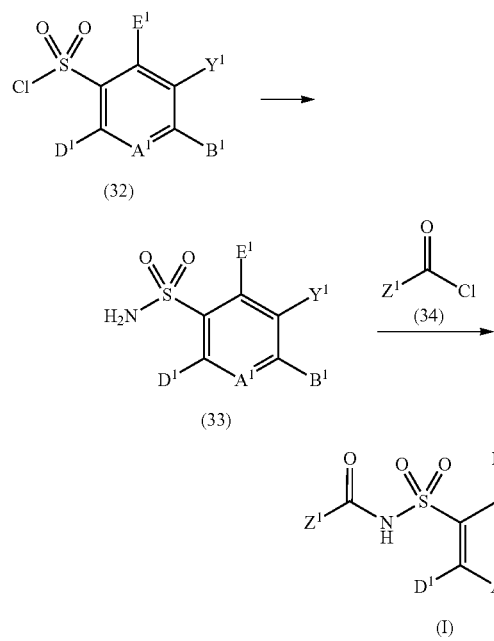

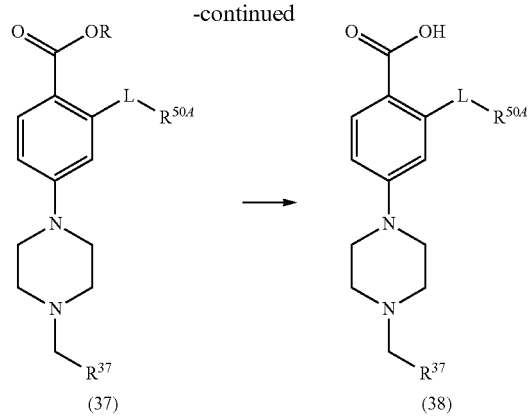

As shown in SCHEME 9, compounds of Formula (35), wherein L is a bond, alkyl, O, S, S(O), S(O)$_2$, NH, etc., can be reacted with compounds of Formula (36), to provide compounds of Formula (37). The reaction is typically performed at elevated temperatures in a solvent such as but not limited to dimethylsulfoxide, and may require the use of a base such as but not limited to potassium phosphate, potassium carbonate, and the like. Compounds of Formula (38) can be prepared from compounds of Formula (37) as described in SCHEME 1, and can be used as described in SCHEME 7 to prepare compounds of Formula (I).

SCHEME 10

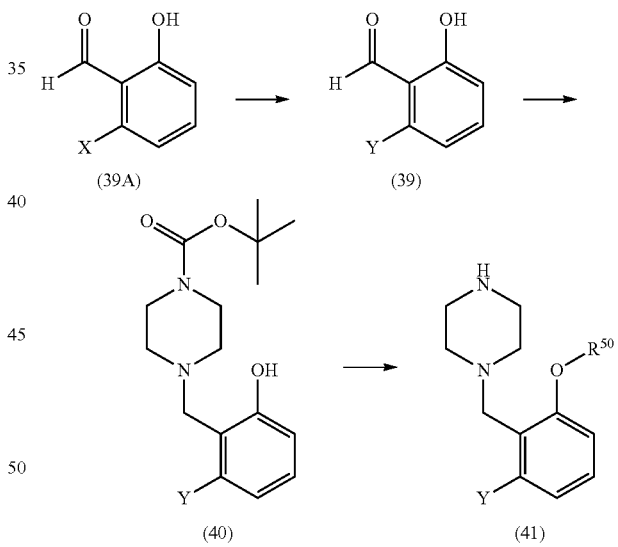

Compounds of Formula (33), prepared as described in SCHEME 7, can also be converted to compounds of Formula (I) by reacting the former and compounds of Formula (34) and a first base. Examples of first bases include but are not limited to sodium hydride, triethylamine, N,N-diisopropylethylamine, 4-(dimethylamino)pyridine, and mixtures thereof.

SCHEME 9

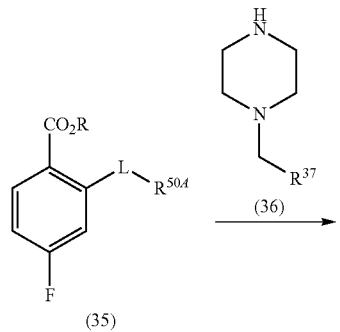

Compounds of Formula (39), wherein Y is as described herein for substituents on R$^{37}$, can be prepared from compounds of Formula (39A) wherein X is a halide or triflate, and Y—B(OH)$_2$ using Suzuki coupling conditions known to those skilled in the art and readily available in the literature. Compounds of Formula (39) can be reacted with tert-butyl piperazine-1-carboxylate and a reducing agent such as sodium triacetoxyborohydride to provide compounds of Formula (40). The reaction is typically performed in a solvent such as but not limited to methylene chloride. Compounds of Formula (41) can be prepared from compounds of Formula (40) by reacting the latter with R$^{50}$X, wherein X is a halide, and NaH in a solvent such as N,N-dimethylformamide, and

Example 1B 1-((4'-chlorobiphenyl-2-yl)methyl)piperazine

EXAMPLE 1A (3.0 g) and triethylsilane (1 mL) were stirred in CH$_2$Cl$_2$ (30 mL) and trifluoroacetic acid (30 mL) for 2 hours, and the reaction was concentrated, and then taken up in ether and concentrated again. The product was used without further purification.

Example 1C methyl 4-fluoro-2-phenoxybenzoate

Methyl 2-bromo-4-fluorobenzoate (1 g), phenol (0.565 g), cesium carbonate (1.96 g), copper(I) triflate toluene complex (0.087 g), and ethyl acetate (0.034 mL) in toluene (12 mL) was stirred at 110° C. for 24 hours. The reaction was cooled and chromatographed on silica gel with 5% ethyl acetate/hexanes.

Example 1D methyl 4-(4-((4'-chlorobiphenyl-2-yl)methyl)piperazin-1-yl)-2-phenoxybenzoate EXAMPLE 1C (630 mg), EXAMPLE 1B, and K$_2$CO$_3$ (707 mg) were stirred in dimethylsulfoxide at 125° C. for 5 hours. The reaction was cooled and chromatographed on silica gel with 10% ethyl acetate/hexanes.

Example 1E 4-(4-((4'-chlorobiphenyl-2-yl)methyl)piperazin-1-yl)-2-phenoxybenzoic acid EXAMPLE 1D (600 mg) was stirred in 25 mL 2:1 dioxane/1M NaOH at 60° C. for 24 hours. The solution was cooled and adjusted to pH 4 with NaH$_2$PO$_4$ solution and concentrated HCl, and extracted with ethyl acetate. The extract was washed with brine and dried (Na$_2$SO$_4$), filtered and concentrated.

Example 1F 3-nitro-4-((tetrahydro-2H-pyran-4-yl)methylamino)benzenesulfonamide 4-Fluoro-3-nitrobenzenesulfonamide (2.18 g), (tetrahydropyran-4-yl)methylamine (1.14 g), and triethylamine (1 g) were stirred in tetrahydrofuran (30 mL) for 24 hours. The solution was diluted with ethyl acetate, washed with NaH$_2$PO$_4$ solution and brine, and dried (Na$_2$SO$_4$), filtered and concentrated. The product was triturated from ethyl acetate.

Example 1G

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-phenoxybenzamide EXAMPLE 1E (90 mg), EXAMPLE 1F (45 mg), 1-ethyl-3-[3-(dimethylamino)propyl]-carbodiimide hydrochloride (65 mg), and 4-dimethylaminopyridine (22 mg) were stirred in CH$_2$Cl$_2$ (4 mL) for 24 hours. The reaction was cooled and chromatographed on silica gel with 20-100% ethyl acetate/hexanes. $^1$H NMR (300 MHz, dimethylsulfoxide-d$_6$) δ 11.55

--- then the resulting material can be treated with triethylsilane and trifluoroacetic acid in dichloromethane. Compounds of Formula (41) can be used as described in Scheme 9 wherein CH$_2$R$^{37}$ is as shown in Formula (41).

SCHEME 11

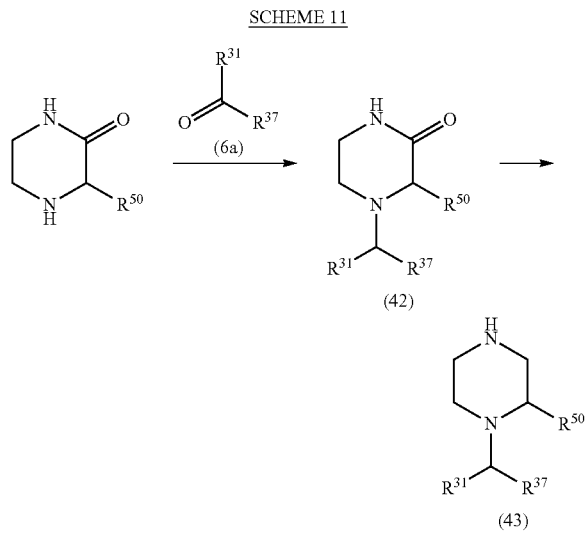

As shown in SCHEME 11, substituted piperazin-2-ones wherein R$^{50}$ is alkyl, can be reacted with compounds of Formula (6a) and a reducing agent such as sodium triacetoxyborohydride in dichloromethane to provide compounds of Formula (42). Compounds of Formula (42) can be reduced to compounds of Formula (43) using a reducing agent such as but not limited to lithium aluminum hydride in a solvent such as but not limited to tetrahydrofuran. Compounds of Formula (43) can be used as described in Scheme 9 wherein CH$_2$R$^{37}$ is as shown in Formula (43).

The following examples are presented to provide what is believed to be the most useful and readily understood description of procedures and conceptual aspects of this invention. The exemplified compounds were named using ACD/ChemSketch Version 5.06 (5 Jun. 2001, Advanced Chemistry Development Inc., Toronto, Ontario), or ChemDraw® Ver. 9.0.5 (CambridgeSoft, Cambridge, Mass.). Intermediates were named using ChemDraw® Ver. 9.0.5 (CambridgeSoft, Cambridge, Mass.).

Example 1

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-phenoxybenzamide

Example 1A tert-butyl 4-((4'-chlorobiphenyl-2-yl)methyl)piperazine-1-carboxylate 4'-Chlorobiphenyl-2-carbaldehyde (EXAMPLE 27C) (4.1 g), tert-butyl piperazine-1-carboxylate (4.23 g), and sodium triacetoxyborohydride (5.61 g) in CH$_2$Cl$_2$ (60 mL) were combined stirred for 24 hours. The reaction was quenched with methanol and poured into ether. The solution was washed with water and brine, concentrated, and chromatographed on silica gel with 2-25% ethyl acetate/hexanes.

(brs, 1H), 8.63 (t, 1H), 8.47 (d, 1H), 7.75 (d, 1H), 7.46 (m, 6H), 7.35 (m, 2H), 7.24 (m, 3H), 7.15 (d, 1H), 6.99 (dd, 1H), 6.82 (d, 2H), 6.75 (d, 1H), 6.38 (d, 1H), 3.86 (br d, 2H), 3.49 (m, 2H), 3.37 (br s, 2H), 3.15 (br s, 4H), 2.34 (br s, 4H), 1.91 (hr s, 4H), 1.64 (hr d, 2H) 1.29 (m, 3H).

Example 2

4-{4-[(4'-chloro-1,1'-biphenyl-2-yl)methyl]piperazin-1-yl}-2-phenoxy-N-({4-[(tetrahydro-2H-pyran-4-ylmethyl)amino]phenyl}sulfonyl)benzamide

Example 2A 4-((tetrahydro-2H-pyran-4-yl)methylamino)benzenesulfonamide

4-Aminobenzenesulfonamide (6.80 g), tetrahydropyran-4-carboxaldehyde (4.96 g), and sodium triacetoxyborohydride (16.74 g) in tetrahydrofuran (300 mL) and acetic acid (15 mL) were stirred in for 24 hours. The reaction was concentrated and taken up in ethyl acetate. The resulting solution was washed with water and brine, concentrated, and chromatographed on silica gel with 50% ethyl acetate/hexanes.

Example 2B

4-{4-[(4'-chloro-1,1'-biphenyl-2-yl)methyl]piperazin-1-yl}-2-phenoxy-N-({4-[(tetrahydro-2H-pyran-4-ylmethyl)amino]phenyl}sulfonyl)benzamide This example was prepared by substituting EXAMPLE 2A for EXAMPLE 1F in EXAMPLE 1G. $^1$H NMR (500 MHz, dimethylsulfoxide-ddD$_2$O) δ 7.54 (d, 1H), 7.46 (m, 8H), 7.36 (m, 4H), 7.24 (d, 1H), 7.13 (dd, 1H), 6.93 (d, 2H), 6.75 (d, 1H), 6.55 (d, 2H), 6.30 (d, 1H), 3.86 (dd, 2H), 3.36 (s, 2H), 3.28 (t, 2H), 3.10 (br s, 4H), 2.96 (d, 2H), 2.32 (br s, 4H), 1.76 (m, 1H), 1.64 (d, 2H), 1.20 (m, 2H).

Example 3

2-(benzyloxy)-4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)benzamide

Example 3A methyl 2-(benzyloxy)-4-fluorobenzoate

Methyl 4-fluoro-2-hydroxybenzoate (2.00 g), benzyl bromide (1.54 mL), and cesium carbonate (4.60 g) in N,N-dimethylformamide (50 mL) were stirred for 24 hours. The reaction was taken up in ether and washed with 3×1M NaOH solution, and brine, then concentrated to give the pure product.

Example 3B methyl 2-(benzyloxy)-4-(4-((4'-chlorobiphenyl-2-yl)methyl)piperazin-1-yl)benzoate This example was prepared by substituting EXAMPLE 3A for EXAMPLE 1C in EXAMPLE 1D.

Example 3C 2-(benzyloxy)-4-(4-((4'-chlorobiphenyl-2-yl)methyl)piperazin-1-yl)benzoic acid This example was prepared by substituting EXAMPLE 3B for EXAMPLE 1D in EXAMPLE 1E.

Example 3D 2-(benzyloxy)-4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)benzamide This example was prepared by substituting EXAMPLE 3C for EXAMPLE 1E in EXAMPLE 1G. $^1$H NMR (300 MHz, dimethylsulfoxide-d$_6$) δ 10.90 (br s, 1H), 8.66 (m, 1H), 8.59 (s, 1H), 7.82 (d, 1H), 7.33-7.55 (m, 12H), 7.18-7.27 (m, 3H), 6.61 (s, 1H), 6.56 (d, 1H), 5.22 (s, 2H), 3.86 (br d, 2H), 3.40 (m, 2H), 3.31 (m, 8H), 2.34 (br s, 4H), 1.91 (br s, 2H), 1.64 (br d, 2H), 1.29 (m, 3H).

Example 4

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(2-phenylethoxy)benzamide

Example 4A methyl 4-fluoro-2-phenethoxybenzoate

Methyl 4-fluoro-2-hydroxybenzoate (1.00 g) and phenethyl alcohol (0.64 mL) were added to triphenylphosphine (1.54 g) and diisopropylazodicarboxylate (1.04 mL) in tetrahydrofuran (20 mL) at 0° C., and the reaction was stirred at room temperature for 24 hours. The mixture was chromatographed on silica gel with 5% ethyl acetate/hexanes.

Example 4B methyl 4-(4-((4'-chlorobiphenyl-2-yl)methyl)piperazin-1-yl)-2-phenethoxybenzoate This example was prepared by substituting EXAMPLE 4A for EXAMPLE 1C in EXAMPLE 1D.

Example 4C 4-(4-((4'-chlorobiphenyl-2-yl)methyl)piperazin-1-yl)-2-phenethoxybenzoic acid This example was prepared by substituting EXAMPLE 4B for EXAMPLE 1D in EXAMPLE 1E.

Example 4D

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(2-phenylethoxy)benzamide This example was prepared by substituting EXAMPLE 4C for EXAMPLE 1E in EXAMPLE 1G. $^1$H NMR (300 MHz, dimethylsulfoxide-d$_6$) δ 10.75 (br s, 1H), 8.66 (m, 2H), 7.91

(d, 1H), 7.47 (m, 6H), 7.20-7.40 (m, 8H), 6.53 (d, 1H), 6.47 (s, 1H), 4.35 (t, 2H), 4.03 (m, 1H), 3.85 (br d, 2H), 3.38 (s, 2H), 3.25 (m, 8H), 3.13 (t, 2H), 2.36 (br s, 4H), 2.21 (br s, 2H), 1.62 (br d, 2H), 1.20 (m, 2H), 1.17 (m, 1H).

Example 5

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(phenylthio)benzamide

Example 5A methyl 4-fluoro-2-(phenylthio)benzoate

5-Fluoro-2-(methoxycarbonyl)phenylboronic acid (1.00 g), 2-(phenylthio)isoindoline-1,3-dione (0.86 g), and (2-hydroxy-3,5-diisopropylbenzoyloxy)copper (0.29 g) were stirred in dioxane (15 mL) at 50° C. for 24 hours.

The reaction mixture was chromatographed on silica gel with 5% ethyl acetate/hexanes.

Example 5B methyl 4-(4-((4'-chlorobiphenyl-2-yl)methyl)piperazin-1-yl)-2-(phenylthio)benzoate This example was prepared by substituting EXAMPLE 5A for EXAMPLE 1C in EXAMPLE 1D.

Example 5C 4-(4-((4'-chlorobiphenyl-2-yl)methyl)piperazin-1-yl)-2-(phenylthio)benzoic acid This example was prepared by substituting EXAMPLE 5B for EXAMPLE 1D in EXAMPLE 1E.

Example 5D

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(phenylthio)benzamide This example was prepared by substituting EXAMPLE 5C for EXAMPLE 1E in EXAMPLE 1G. $^1$H NMR (300 MHz, dimethylsulfoxide-$d_6$) δ 11.95 (br s, 1H), 8.59 (m, 2H), 7.93 (d, 1H), 7.63 (d, 1H), 7.15-7.50 (m, 14H), 6.73 (d, 1H), 6.18 (s, 1H), 3.82 (dd, 2H), 3.36 (m, 4H), 3.32 (m, 2H), 2.94 (br s, 4H), 2.30 (br s, 4H), 1.64 (m, 1H), 1.61 (m, 2H), 1.25 (m, 2H).

Example 6

4-{4-[(4'-chloro-1,1'-biphenyl-2-yl)methyl]piperazin-1-yl}-2-(phenylthio)-N-({4-[(tetrahydro-2H-pyran-4-ylmethyl)amino]phenyl}sulfonyl)benzamide This example was prepared by substituting EXAMPLE 5C for EXAMPLE 1E and EXAMPLE 2A for EXAMPLE 1F in EXAMPLE 1G. $^1$H NMR (500 MHz, dimethylsulfoxide-$d_6$/D$_2$O) δ 7.65 (d, 2H), 7.55 (d, 1H), 7.33-7.48 (m, 12H), 7.24 (m, 2H), 6.73 (d, 1H), 6.66 (d, 2H), 6.17 (d, 1H), 3.85 (dd, 2H), 3.34 (s, 2H), 3.26 (t, 2H), 2.98 (d, 2H), 2.92 (br s, 4H), 2.25 (br s, 4H), 1.78 (m, 1H), 1.63 (d, 2H), 1.20 (m, 2H).

Example 7

4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(phenylthio)benzamide

Example 7A 4-(3-morpholinopropylamino)-3-nitrobenzenesulfonamide

This example was prepared by substituting 3-(N-morpholinyl)-1-propylamine for (tetrahydropyran-4-yl)methylamine in EXAMPLE 1F.

Example 7B

4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(phenylthio)benzamide This example was prepared by substituting EXAMPLE 5C for EXAMPLE 1E and EXAMPLE 7A for EXAMPLE 1F in EXAMPLE 1G. $^1$H NMR (300 MHz, dimethylsulfoxide-$d_6$) δ 10.20 (br s, 1H), 8.69 (m, 1H), 8.57 (d, 1H), 7.95 (dd, 2H), 7.71 (m, 1H), 7.31-7.51 (m, 10H), 7.12-7.26 (m, 3H), 6.68 (dd, 1H), 6.07 (m, 1H), 4.06 (s, 2H), 3.68 (m, 4H), 3.50 (m, 2H), 3.32 (m, 6H), 2.88 (m, 4H), 2.27 (m, 4H), 1.91 (m, 2H).

Example 8

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(phenylsulfonyl)benzamide

Example 8A methyl 4-fluoro-2-(phenylsulfonyl)benzoate

EXAMPLE 5A (0.30 g) and KMnO$_4$ (1.80 g) were stirred in acetic acid (40 mL) at 60° C. for 24 hours. The reaction mixture was filtered through a plug of silica gel, concentrated, and chromatographed on silica gel with 50% ethyl acetate/hexanes.

Example 8B methyl 4-(4-((4'-chlorobiphenyl-2-yl)methyl)piperazin-1-yl)-2-(phenylsulfonyl)benzoate This example was prepared by substituting EXAMPLE 8A for EXAMPLE 1C in EXAMPLE 1D.

Example 8C 4-(4-((4'-chlorobiphenyl-2-yl)methyl)piperazin-1-yl)-2-(phenylsulfonyl)benzoic acid This example was prepared by substituting EXAMPLE 8B for EXAMPLE 1D in EXAMPLE 1E.

Example 8D

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(phenylsulfonyl)benzamide This example was prepared by substituting EXAMPLE 8C for EXAMPLE 1E in EXAMPLE 1G. $^1$H NMR (500 MHz, dimethylsulfoxide-d$_6$) δ 11.95 (br s, 1H), 8.54 (s, 1H), 8.41 (dd, 1H), 7.90 (m, 2H), 7.82 (d, 1H), 7.76 (d, 1H), 7.66 (m, 1H), 7.46 (m, 5H), 7.40 (m, 4H), 7.11 (m, 2H), 6.67 (dd, 1H), 6.62 (m, 1H), 4.36 (m, 1H), 3.82 (dd, 2H), 3.39 (m, 6H), 3.19 (m, 6H), 2.37 (br s, 4H), 1.91 (m, 1H), 1.63 (m, 2H), 1.26 (m, 2H).

Example 9

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(phenylsulfinyl)benzamide

Example 9A methyl 4-fluoro-2-(phenylsulfinyl)benzoate

OXONE® (Dupont) (5.60 g) was added portionwise over 1 hour to EXAMPLE 5A (1.00 g) in a mixture of acetic acid (30 mL), water (30 mL) and CH$_2$Cl$_2$ (20 mL), and the reaction was stirred for an additional 1 hour. The reaction mixture was taken up in ethyl acetate, washed with Na$_2$S$_2$O$_3$ solution, water, and brine, concentrated, and chromatographed on silica gel with 5-25% ethyl acetate/hexanes.

Example 9B methyl 4-(4-((4'-chlorobiphenyl-2-yl)methyl)piperazin-1-yl)-2-(phenylsulfinyl)benzoate This example was prepared by substituting EXAMPLE 9A for EXAMPLE 1C in EXAMPLE 1D.

Example 9C 4-(4-((4'-chlorobiphenyl-2-yl)methyl)piperazin-1-yl)-2-(phenylsulfinyl)benzoic acid This example was prepared by substituting EXAMPLE 9B for EXAMPLE 1D in EXAMPLE 1E.

Example 9D

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(phenylsulfinyl)benzamide This example was prepared by substituting EXAMPLE 9C for EXAMPLE 1E in EXAMPLE 1G. $^1$H NMR (500 MHz, dimethylsulfoxide-dd/D$_2$O) δ 8.51 (s, 1H), 7.85 (dd, 2H), 7.64 (d, 2H), 7.48 (m, 8H), 7.32 (m, 1H), 7.23 (m, 1H), 7.14 (m, 4H), 6.97 (d, 1H), 3.85 (dd, 2H), 3.35 (d, 2H), 3.34 (m, 6H), 3.27 (t, 2H), 2.74 (br s, 4H), 1.93 (m, 1H), 1.64 (d, 2H), 1.28 (m, 2H).

Example 10

2-benzyl-4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)benzamide

Example 10A methyl 2-benzyl-4-fluorobenzoate

5-Fluoro-2-(methoxycarbonyl)phenylboronic acid (1.00 g), benzyl bromide (0.50 mL), K$_2$CO$_3$ (1.75 g), and [1,1'-bis(diphenylphosphino)ferrocene]dichloropalladium(II) (PdCl$_2$(dppf)) (0.17 g) were stirred in tetrahydrofuran (20 mL) at 60° C. for 24 hours. The reaction mixture was chromatographed on silica gel with 2% ethyl acetate/hexanes.

Example 10B methyl 2-benzyl-4-(4-((4'-chlorobiphenyl-2-yl)methyl)piperazin-1-yl)benzoate This example was prepared by substituting EXAMPLE 10A for EXAMPLE 1C in EXAMPLE 1D.

Example 10C 2-benzyl-4-(4-((4'-chlorobiphenyl-2-yl)methyl)piperazin-1-yl)benzoic acid This example was prepared by substituting EXAMPLE 10B for EXAMPLE 1D in EXAMPLE 1E.

Example 10D 2-benzyl-4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)benzamide This example was prepared by substituting EXAMPLE 10C for EXAMPLE 1E in EXAMPLE 1G. $^1$H NMR (500 MHz, dimethylsulfoxide-d/D$_2$O) δ 8.55 (d, 1H), 7.90 (d, 1H), 7.38-7.56 (m, 10H), 7.25 (m, 2H), 6.96 (d, 2H), 6.83 (s, 2H), 6.75 (d, 1H), 4.06 (s, 2H), 3.85 (dd, 2H), 3.48 (s, 2H), 3.37 (d, 2H), 3.25 (t, 2H), 3.20 (br s, 4H), 2.44 (br s, 4H), 1.91 (m, 1H), 1.63 (d, 2H), 1.29 (m, 2H).

Example 11

2-benzyl-4-{4-[(4'-chloro-1,1'-biphenyl-2-yl)methyl]piperazin-1-yl}-N-({4-[(tetrahydro-2H-pyran-4-ylmethyl)amino]phenyl}sulfonyl)benzamide This example was prepared by substituting EXAMPLE 10C for EXAMPLE 1E and EXAMPLE 2A for EXAMPLE 1F in EXAMPLE 1G. $^1$H NMR (300 MHz, dimethylsulfoxide-d$_6$) δ 11.70 (br s, 1H), 7.48 (m, 6H), 6.88 (m, 6H), 6.62 (m, 6H), 6.42 (dd, 2H), 3.83 (dd, 4H), 3.24 (m, 6H), 2.96 (m, 4H), 1.82 (m, 2H), 1.63 (m, 3H), 1.18 (m, 4H).

Example 12

2-benzyl-4-{4-[(4'-chloro-1,1'-biphenyl-2-yl)methyl]piperazin-1-yl}-N-({4-[(3-morpholin-4-ylpropyl)amino]-3-nitrophenyl}sulfonyl)benzamide This example was prepared by substituting EXAMPLE 10C for EXAMPLE 1E and EXAMPLE 7A for EXAMPLE 1F in EXAMPLE 1G. $^1$H NMR (300 MHz, dimethylsulfoxide-$d_6$) δ 11.90 (br s, 1H), 8.80 (m, 1H), 8.54 (d, 1H), 7.91 (dd, 1H), 7.48 (m, 7H), 7.40 (d, 2H), 7.26 (d, 2H), 6.97 (dd, 2H), 6.86 (m, 2H), 6.76 (d, 1H), 4.04 (m, 5H), 3.72 (m, 4H), 3.56 (m, 2H), 3.40 (m, 8H), 3.21 (m, 4H), 2.34 (m, 2H), 1.98 (m, 2H).

Example 13

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(2-phenylethyl)benzamide

Example 13A methyl 4-fluoro-2-phenethylbenzoate

Methyl 2-bromo-4-fluorobenzoate (1.00 g), (E)-styrylboronic acid (0.89 g), tetrakis(triphenylphosphine)palladium (O) (0.50 g), and $K_3PO_4$ (2.28 g) were stirred in dioxane (17 mL) at 90° C. for 24 hours. The reaction mixture chromatographed on silica gel with 1-5% ethyl acetate/hexanes. The product in methanol (10 ml) was added to 20 wt % of fresh dry 5% Pd—C and stirred 4 days with $H_2$ in a pressure bottle. The mixture was filtered through a nylon membrane and concentrated.

Example 13B methyl 4-(4-((4'-chlorobiphenyl-2-yl)methyl)piperazin-1-yl)-2-phenethylbenzoate This example was prepared by substituting EXAMPLE 13A for EXAMPLE 1C in EXAMPLE 1D.

Example 13C 4-(4-((4'-chlorobiphenyl-2-yl)methyl)piperazin-1-yl)-2-phenethylbenzoic acid This example was prepared by substituting EXAMPLE 13B for EXAMPLE 1D in EXAMPLE 1E.

Example 13D 4-(4-((4'-chlorobiphenyl-2-yl)methyl)piperazin-1-yl)-N-(3-nitro-4-((tetrahydro-2H-pyran-4-yl)methylamino)phenylsulfonyl)-2-phenethylbenzamide This example was prepared by substituting EXAMPLE 13C for EXAMPLE 1E in EXAMPLE 1G. $^1$H NMR (500 MHz, dimethylsulfoxide-dd$D_2$O) δ 8.62 (d, 1H), 7.95 (d, 1H), 7.91 (m, 1H), 7.35-7.52 (m, 6H), 7.19 (m, 2H), 7.13 (m, 2H), 6.99 (m, 4H), 6.83 (d, 1H), 6.70 (d, 1H), 6.65 (s, 1H), 3.80 (m, 2H), 3.24 (m, 2H), 3.18 (t, 2H), 3.11 (br s, 4H), 2.91 (t, 2H), 2.48 (m, 2H), 2.38 (br s, 4H), 1.81 (m, 1H), 1.54 (d, 2H), 1.23 (m, 2H).

Example 14

2-(benzylamino)-4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)benzamide

Example 14A methyl 2-(benzylamino)-4-fluorobenzoate

Methyl 2-amino-4-fluorobenzoate (0.90 g), benzaldehyde (0.54 mL), sodium triacetoxyborohydride (1.58 g) and acetic acid (0.3 mL) in $CH_2Cl_2$ (20 mL) were stirred for 3 hours. The reaction was quenched with methanol, concentrated, and chromatographed on silica gel with 5% ethyl acetate/hexanes.

Example 14B methyl 2-(benzylamino)-4-(4-((4'-chlorobiphenyl-2-yl)methyl)piperazin-1-yl)benzoate This example was prepared by substituting EXAMPLE 14A for EXAMPLE 1C in EXAMPLE 1D.

Example 14C 2-(benzylamino)-4-(4-((4'-chlorobiphenyl-2-yl)methyl)piperazin-1-yl)benzoic acid This example was prepared by substituting EXAMPLE 14B for EXAMPLE 1D in EXAMPLE 1E.

Example 14D 2-(benzylamino)-4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)benzamide This example was prepared by substituting EXAMPLE 14C for EXAMPLE 1E in EXAMPLE 1G. $^1$H NMR (500 MHz, dimethylsulfoxide-$d_6$/$D_2$O) δ 8.58 (d, 1H), 7.92 (d, 1H), 7.87 (m, 1H), 7.59 (d, 2H), 7.48 (m, 2H), 7.43 (m, 4H), 7.20-7.29 (m, 8H), 6.15 (d, 1H), 4.32 (s, 2H), 3.85 (m, 2H), 3.49 (m, 2H), 3.33 (m, 2H), 3.26 (t, 2H), 3.12 (br s, 4H), 2.39 (br s, 4H), 1.90 (m, 1H), 1.62 (d, 2H), 1.27 (m, 2H).

Example 15

2-anilino-4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)benzamide

Example 15A methyl 4-fluoro-2-(phenylamino)benzoate

Methyl 2-bromo-4-fluorobenzoate (1.00 g), aniline (0.47 mL), palladium(II) acetate (0.048 g), 2,2'-bis(diphenylphosphino)-1,1'-binaphthyl (0.214 g) and $Cs_2CO_3$ (2.08 g) in toluene (12 mL) were stirred at 90° C. for 24 hours. The reaction was concentrated and chromatographed on silica gel with 5-50% ethyl acetate/hexanes.

Example 15B methyl 4-(4-((4'-chlorobiphenyl-2-yl)methyl)piperazin-1-yl)-2-(phenylamino)benzoate This example was prepared by substituting EXAMPLE 15A for EXAMPLE 1C in EXAMPLE 1D.

Example 15C 4-(4-((4'-chlorobiphenyl-2-yl)methyl)piperazin-1-yl)-2-(phenylamino)benzoic acid This example was prepared by substituting EXAMPLE 15B for EXAMPLE 1D in EXAMPLE 1E.

Example 15D 2-anilino-4-{4-[(4'-chloro-1,1'-biphenyl-2-yl)methyl] piperazin-1-yl}-N-({3-nitro-4-[(tetrahydro-2H-pyran-4-ylmethyl)amino]phenyl}sulfonyl)benzamide This example was prepared by substituting EXAMPLE 15C for EXAMPLE 1E in EXAMPLE 1G. $^1$H NMR (300 MHz, dimethylsulfoxide-d$_6$) δ 11.55 (br s, 1H), 8.56 (m, 2H), 7.92 (d, 1H), 7.72 (d, 1H), 7.47 (m, 6H), 7.25 (m, 4H), 7.12 (d, 2H), 6.95 (m, 2H), 6.53 (s, 1H), 6.38 (dd, 1H), 3.81 (dd, 2H), 3.37 (br s, 4H), 3.12 (br s, 4H), 2.41 (br s, 4H), 1.91 (m, 1H), 1.61 (br d, 2H), 1.23 (m, 4H).

Example 16

2-anilino-4-{4-[(4'-chloro-1,1'-biphenyl-2-yl)methyl] piperazin-1-yl}-N-({4-[(tetrahydro-2H-pyran-4-ylmethyl)amino]phenyl}sulfonyl)benzamide This example was prepared by substituting EXAMPLE 15C for EXAMPLE 1E and EXAMPLE 2A for EXAMPLE 1F in EXAMPLE 1G. $^1$H NMR (500 MHz, dimethylsulfoxide-d$_6$/D$_2$O) δ 7.78 (d, 1H), 7.52 (d, 2H), 7.47 (m, 6H), 7.36 (m, 3H), 7.27 (m, 3H), 7.11 (m, 2H), 6.90 (m, 1H), 6.61 (s, 1H), 6.53 (d, 1H), 6.31 (d, 1H), 4.46 (s, 1H), 3.82 (m, 2H), 3.37 (s, 2H), 3.26 (t, 2H), 3.05 (br s, 4H), 2.93 (d, 2H), 2.37 (br s, 4H), 1.77 (m, 1H), 1.63 (d, 2H), 1.20 (m, 2H).

Example 17

4-{4-[(4'-chloro-1,1'-biphenyl-2-yl)methyl]piperazin-1-yl}-2-methoxy-N-({3-nitro-4-[(tetrahydro-2H-pyran-4-ylmethyl)amino]phenyl}sulfonyl)benzamide

Example 17A methyl 4-(4-((4'-chlorobiphenyl-2-yl)methyl)piperazin-1-yl)-2-methoxybenzoate Methyl 4-bromo-2-methoxybenzoic acid (700 mg), EXAMPLE 1B (983 mg), K$_3$PO$_4$ (909 mg), tris(dibenzylideneacetone)dipalladium(O) (78 mg), and 2-(di-t-butylphosphino)biphenyl (102 mg) were stirred in 1,2-dimethoxyethane (10 mL) at 80° C. for 24 hours. The reaction mixture was chromatographed on silica gel with 20-50% ethyl acetate/hexanes.

Example 17B 4-(4-((4'-chlorobiphenyl-2-yl)methyl)piperazin-1-yl)-2-methoxybenzoic acid This example was prepared by substituting EXAMPLE 17A for EXAMPLE 1D in EXAMPLE 1E.

Example 17C

4-{4-[(4'-chloro-1,1'-biphenyl-2-yl)methyl]piperazin-1-yl}-2-methoxy-N-({3-nitro-4-[(tetrahydro-2H-pyran-4-ylmethyl)amino]phenyl}sulfonyl)benzamide This example was prepared by substituting EXAMPLE 17B for EXAMPLE 1E in EXAMPLE 1G. $^1$H NMR (300 MHz, dimethylsulfoxide-d$_6$) δ 10.81 (br s, 1H), 8.64 (m, 2H), 7.96 (d, 1H), 7.20-7.54 (m, 10 OH), 6.52 (d, 1H), 6.46 (s, 1H), 3.90 (s, 3H), 3.40 (m, 4H), 3.27 (br s, 4H), 2.39 (br s, 4H), 1.91 (m, 1H), 1.62 (br d, 2H), 1.27 (m, 4H).

Example 18

4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)-2-phenoxybenzamide

Example 18A methyl 4,4-dimethyl-2-(trifluoromethylsulfonyloxy) cyclohex-1-enecarboxylate To a suspension of hexane washed NaH (17 g) in dichloromethane (700 mL), 5,5-dimethyl-2-methoxycarbonylcyclohexanone (38.5 g) was added dropwise at 0° C. After stirring for 30 minutes, the mixture was cooled to −78° C. and trifluoromethanesulfonic anhydride (40 mL) was added. The reaction mixture was warmed to room temperature and stirred for 24 hours. The organic layer was washed with brine, dried, and concentrated to give the product.

Example 18B methyl 2-(4-chlorophenyl)-4,4-dimethylcyclohex-1-enecarboxylate

Example 18A (62.15 g), 4-chlorophenylboronic acid (32.24 g), CsF (64 g and tetrakis(triphenylphosphine)palladium(O) (2 g) in 2:1 1,2-dimethoxyethane/methanol (600 mL) were heated to 70° C. for 24 hours. The mixture was concentrated. Ether (4×200 mL) was added and the mixture was filtered. The combined ether solution was concentrated to give the product.

Example 18C (2-(4-chlorophenyl)-4,4-dimethylcyclohex-1-enyl) methanol

To a mixture of LiBH$_4$ (13 g), EXAMPLE 18B (53.8 g) and ether (400 mL), methanol (25 mL) was added slowly by syringe. The mixture was stirred at room temperature for 24 hours. The reaction was quenched with 1N HCl with ice-cooling. The mixture was diluted with water and extracted by ether (3×100 mL). The extracts were dried, and concentrated. The crude product was chromatographed on silica gel with 0-30% ethyl acetate/hexanes.

Example 18D methyl 2-bromo-4-(piperazin-1-yl)benzoate

This example was prepared by substituting piperazine for EXAMPLE 1B and methyl 2-bromo-4-fluorobenzoate for EXAMPLE 1C in EXAMPLE 1D.

Example 18E methyl 2-bromo-4-(4-((2-(4-chlorophenyl)-4,4-dimethylcyclohex-1-enyl)methyl)piperazin-1-yl)benzoate MsCl (7.5 mL) was added via syringe to EXAMPLE 18C (29.3 g) and triethylamine (30 mL) in CH$_2$Cl$_2$ (500 mL) at 0°

C., and the mixture was stirred for 1 minute. EXAMPLE 18D (25 g) was added and the reaction was stirred at room temperature for 24 hours. The suspension was washed with brine, dried, and concentrated. The crude product was chromatographed on silica gel with 10-20% ethyl acetate/hexanes.

Example 18F methyl 4-(4-((2-(4-chlorophenyl)-4,4-dimethylcyclohex-1-enyl)methyl)piperazin-1-yl)-2-phenoxybenzoate EXAMPLE 18E (500 mg), phenol (195 mg), $Cs_2CO_3$ (674 mg), 1-naphthoic acid (356 mg), copper (I) triflate-toluene complex (45 mg), ethyl acetate (0.016 mL), and 4A sieves (50 mg) in toluene (2 mL) was stirred at 105° C. for 24 hours. The reaction was cooled and taken up in ethyl acetate (100 mL) and water (40 mL). The layers were separated and the organic layer was washed with 2×$Na_2CO_3$ solution and brine, dried, and concentrated. The crude product was chromatographed on silica gel with 20% ethyl acetate/hexanes.

Example 18G 4-(4-((2-(4-chlorophenyl)-4,4-dimethylcyclohex-1-enyl)methyl)piperazin-1-yl)-2-phenoxybenzoic acid This example was prepared by substituting EXAMPLE 18F for EXAMPLE 1D in EXAMPLE 1E.

Example 18H 4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)-2-phenoxybenzamide This example was prepared by substituting EXAMPLE 18G for EXAMPLE 1E and EXAMPLE 7A for EXAMPLE 1F in EXAMPLE 1G. $^1$H NMR (300 MHz, dimethylsulfoxide-$d_6$) δ 11.10 (br s, 1H), 8.76 (m, 1H), 8.46 (d, 1H), 7.76 (dd, 1H), 7.50 (d, 1H), 7.35 (d, 2H), 7.23 (d, 2H), 7.06 (dd, 2H), 6.99 (dd, 1H), 6.81 (d, 2H), 6.74 (d, 1H), 6.34 (s, 1H), 3.62 (m, 4H), 3.46 (m, 2H), 3.13 (m, 4H), 2.76 (m, 2H), 2.48 (m, 2H), 2.22 (m, 6H), 1.97 (m, 2H), 1.82 (m, 2H), 1.40 (t, 2H), 1.06 (m, 7H), 0.94 (s, 3H).

Example 19

4-(4-{[2-(4-chlorophenyl)-5,5-dimethylcyclohex-1-en-1-yl]methyl}piperazin-1-yl)-N-({4-[(3-morpholin-4-ylpropyl)amino]-3-nitrophenyl}sulfonyl)-2-phenoxybenzamide Example 19A methyl 5,5-dimethyl-2-(trifluoromethylsulfonyloxy)cyclohex-1-enecarboxylate This example was prepared by substituting 4,4-dimethyl-2-methoxycarbonylcyclohexanone for 5,5-dimethyl-2-methoxycarbonylcyclohexanone in EXAMPLE 18A.

Example 19B methyl 2-(4-chlorophenyl)-5,5-dimethylcyclohex-1-enecarboxylate

This example was prepared by substituting EXAMPLE 19A for EXAMPLE 18A in EXAMPLE 18B.

Example 19C (2-(4-chlorophenyl)-5,5-dimethylcyclohex-1-enyl)methanol

This example was prepared by substituting EXAMPLE 19B for EXAMPLE 18B in EXAMPLE 18C.

Example 19D methyl 2-bromo-4-(4-((2-(4-chlorophenyl)-5,5-dimethylcyclohex-1-enyl)methyl)piperazin-1-yl)benzoate This example was prepared by substituting EXAMPLE 19C for EXAMPLE 18C in EXAMPLE 18E.

Example 19E methyl 4-(4-((2-(4-chlorophenyl)-5,5-dimethylcyclohex-1-enyl)methyl)piperazin-1-yl)-2-phenoxybenzoate This example was prepared by substituting EXAMPLE 19D for EXAMPLE 18E in EXAMPLE 18F.

Example 19F 4-(4-((2-(4-chlorophenyl)-5,5-dimethylcyclohex-1-enyl)methyl)piperazin-1-yl)-2-phenoxybenzoic acid This example was prepared by substituting EXAMPLE 19E for EXAMPLE 1D in EXAMPLE 1E.

Example 19G 4-(4-{[2-(4-chlorophenyl)-5,5-dimethylcyclohex-1-en-1-yl]methyl}piperazin-1-yl)-N-({4-[(3-morpholin-4-ylpropyl)amino]-3-nitrophenyl}sulfonyl)-2-phenoxybenzamide This example was prepared by substituting EXAMPLE 19F for EXAMPLE 1E and EXAMPLE 7A for EXAMPLE 1F in EXAMPLE 1G. $^1$H NMR (300 MHz, dimethylsulfoxide-$d_6$) δ 11.10 (br s, 1H), 8.71 (m, 1H), 8.42 (d, 1H), 7.73 (dd, 1H), 7.53 (d, 1H), 7.34 (d, 2H), 7.21 (dd, 2H), 7.10 (d, 2H), 6.96 (dd, 1H), 6.78 (d, 2H), 6.70 (d, 1H), 6.32 (s, 1H), 3.61 (m, 4H), 3.44 (m, 2H), 3.09 (m, 4H), 2.71 (m, 2H), 2.44 (m, 4H), 2.21 (m, 4H), 1.96 (m, 2H), 1.79 (m, 2H), 1.47 (t, 2H), 1.17 (m, 3H), 1.08 (m, 4H), 0.95 (s, 3H).

Example 20

4-(4-{[2-(4-chlorophenyl)-4,4-dimethylcyclohex-1-en-1-yl]methyl}piperazin-1-yl)-2-(1H-indazol-5-yloxy)-N-({4-[(3-morpholin-4-ylpropyl)amino]-3-nitrophenyl}sulfonyl)benzamide Example 20A ethyl 2-(1H-indazol-5-yloxy)-4-fluorobenzoate Ethyl 2,4-difluorobenzoate (1.14 g), $K_3PO_4$ (1.30 g) and 5-hydroxyindazole (0.90 g) were stirred at 110° C. in diglyme (12 mL) for 24 hours. The reaction was cooled and poured into ether. The solution was washed three times with 1M NaOH solution, and brine, and dried. The solution was then concentrated, and the crude product was chromatographed on silica gel with 20% ethyl acetate/hexanes.

Example 20B tert-butyl 4-((2-(4-chlorophenyl)-4,4-dimethylcyclohex-1-enyl)methyl)piperazine-1-carboxylate This example was prepared by substituting N-t-butoxycarbonylpiperazine for EXAMPLE 18D in EXAMPLE 18E.

Example 20C 1-((2-(4-chlorophenyl)-4,4-dimethylcyclohex-1-enyl)methyl)piperazine This EXAMPLE was prepared by substituting EXAMPLE 20B for EXAMPLE 1A in EXAMPLE 1B.

Example 20D ethyl 2-(1H-indazol-5-yloxy)-4-(4-((2-(4-chlorophenyl)-4,4-dimethylcyclohex-1-enyl)methyl)piperazin-1-yl)benzoate Example 20A 330 mg), EXAMPLE 20C (335 mg), and $HK_2PO_4$ (191 mg were stirred in dimethylsulfoxide (5 mL) at 140° C. for 24 hours. The reaction was diluted with ethyl acetate, washed three times with water, washed with brine, dried, and concentrated. The crude product was chromatographed on silica gel with 30% ethyl acetate/hexanes.

Example 20E 2-(1H-indazol-5-yloxy)-4-(4-((2-(4-chlorophenyl)-4,4-dimethylcyclohex-1-enyl)methyl)piperazin-1-yl)benzoic acid This example was prepared by substituting EXAMPLE 20D for EXAMPLE 1D in EXAMPLE 1E.

Example 20F 4-(4-{[2-(4-chlorophenyl)-4,4-dimethylcyclohex-1-en-1-yl]methyl}piperazin-1-yl)-2-(1H-indazol-5-yloxy)-N-({4-[(3-morpholin-4-ylpropyl)amino]-3-nitrophenyl}sulfonyl)benzamide This example was prepared by substituting EXAMPLE 20E for EXAMPLE 1E and EXAMPLE 7A for EXAMPLE 1F in EXAMPLE 1G. $^1$H NMR (300 MHz, dimethylsulfoxide-$d_6$) δ 13.03 (br s, 1H), 11.25 (br s, 1H), 8.70 (m, 1H), 8.48 (d, 1H), 7.94 (dd, 1H), 7.68 (dd, 1H), 7.52 (m, 2H), 7.34 (d, 2H), 7.06 (m, 4H), 6.96 (dd, 1H), 6.88 (d, 1H), 6.23 (s, 1H), 3.61 (m, 4H), 3.44 (m, 2H), 3.05 (m, 4H), 2.73 (m, 2H), 2.42 (m, 4H), 2.18 (m, 4H), 1.99 (m, 2H), 1.91 (d, 2H), 1.78 (m, 2H), 1.39 (t, 2H), 1.17 (m, 2H), 0.93 (s, 6H).

Example 21

4-(4-{[2-(4-chlorophenyl)-4,4-dimethylcyclohex-1-en-1-yl]methyl}piperazin-1-yl)-2-(1H-indazol-5-yloxy)-N-({4-[(1-methylpiperidin-4-yl)amino]-3-nitrophenyl}sulfonyl)benzamide Example 21A 4-(1-methylpiperidin-4-ylamino)-3-nitrobenzenesulfonamide This example was prepared by substituting 4-amino-N-methylpiperidine for (tetrahydropyran-4-yl)methylamine in EXAMPLE 1F.

Example 21B 4-(4-{[2-(4-chlorophenyl)-4,4-dimethylcyclohex-1-en-1-yl]methyl}piperazin-1-yl)-2-(1H-indazol-5-yloxy)-N-({4-[(1-methylpiperidin-4-yl)amino]-3-nitrophenyl}sulfonyl)benzamide This example was prepared by substituting EXAMPLE 20E for EXAMPLE 1E and EXAMPLE 21A for EXAMPLE 1F in EXAMPLE 1G. $^1$H NMR (300 MHz, dimethylsulfoxide-$d_6$) δ 12.80 (br s, 1H), 10.70 (br s, 1H), 8.34 (s, 1H), 8.02 (d, 1H), 7.87 (d, 1H), 7.70 (dd, 1H), 7.55 (m, 2H), 7.36 (d, 2H), 7.06 (m, 2H), 6.95 (m, 1H), 6.72 (d, 1H), 6.62 (d, 1H), 6.24 (s, 1H), 3.35 (m, 4H), 3.18 (m, 2H), 3.00 (m, 2H), 2.80 (m, 4H), 2.73 (m, 2H), 2.20 (m, 4H), 1.99 (m, 2H), 1.91 (s, 3H), 1.54 (m, 1H), 1.41 (t, 2H), 1.22 (m, 2H), 1.09 (s, 6H).

Example 22

4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)-2-(1,2,3,4-tetrahydroquinolin-6-yloxy)benzamide Example 22A ethyl 4-fluoro-2-(1,2,3,4-tetrahydroquinolin-6-yloxy)benzoate This example was prepared by substituting 5-hydroxy-1,2,3,4-tetrahydroquinoline for 5-hydroxyindazole in EXAMPLE 20A.

Example 22B ethyl 4-(4-((2-(4-chlorophenyl)-4,4-dimethylcyclohex-1-enyl)methyl)piperazin-1-yl)-2-(1,2,3,4-tetrahydroquinolin-6-yloxy)benzoate This example was prepared by substituting EXAMPLE 22A for EXAMPLE 20A in EXAMPLE 20D.

Example 22C 4-(4-((2-(4-chlorophenyl)-4,4-dimethylcyclohex-1-enyl)methyl)piperazin-1-yl)-2-(1,2,3,4-tetrahydroquinolin-6-yloxy)benzoic acid This example was prepared by substituting EXAMPLE 22B for EXAMPLE 1D in EXAMPLE 1E.

Example 22D 4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)-2-(1,2,3,4-tetrahydroquinolin-6-yloxy)benzamide This example was prepared by substituting EXAMPLE 22C for EXAMPLE 1E and EXAMPLE 7A for EXAMPLE 1F in EXAMPLE 1G. $^1$H NMR (300 MHz, dimethylsulfoxide-$d_6$) δ 10.95 (br s, 1H), 8.83 (m, 1H), 8.60 (d, 1H), 7.90 (dd, 1H), 7.46 (d, 1H), 7.35 (d, 2H), 7.21 (dd, 2H), 7.06 (d, 2H), 6.62 (m, 2H), 6.42 (d, 1H), 6.11 (d, 1H), 5.61 (br s, 1H), 4.02 (m, 1H), 3.61 (m, 4H), 3.48 (m, 2H), 3.17 (m, 2H), 3.07 (m, 4H), 2.74 (m, 2H), 2.63 (m, 2H), 2.44 (m, 4H), 2.19 (m, 4H), 1.97 (m, 4H), 1.79 (m, 4H), 1.41 (t, 2H), 1.17 (m, 4H), 0.94 (s, 6H).

Example 23

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(1,2,3,4-tetrahydroquinolin-6-yloxy)benzamide This example was prepared by substituting EXAMPLE 22C for EXAMPLE 1E and EXAMPLE 21A for EXAMPLE 1F in EXAMPLE 1G. $^1$H NMR (300 MHz, dimethylsulfoxide-$d_6$) δ 11.10 (br s, 1H), 8.71 (m, 1H), 8.42 (d, 1H), 7.73 (dd, 1H), 7.53 (d, 1H), 7.34 (d, 2H), 7.21 (dd, 2H), 7.10 (d, 2H), 6.96 (dd, 1H), 6.78 (d, 2H), 6.70 (d, 1H), 6.32 (s, 1H), 3.61 (m, 4H), 3.44 (m, 2H), 3.09 (m, 4H), 2.71 (m, 2H), 2.44 (m, 4H), 2.21 (m, 4H), 1.96 (m, 2H), 1.79 (m, 2H), 1.47 (t, 2H), 1.17 (m, 3H), 1.08 (m, 4H), 0.95 (s, 3H).

Example 24

4-(4-{[4'-chloro-4-(pyrrolidin-1-ylmethyl)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide

Example 24A methyl 5-formyl-2-(trifluoromethylsulfonyloxy)benzoate

Triflic anhydride (7.74 mL) was added to methyl 5-formyl-2-hydroxybenzoate (7.5 g) in 150 mL CH$_2$Cl$_2$ at 0° C., and the reaction was stirred and allowed to warm to room temperature over 3 hours. The reaction was diluted with CH$_2$Cl$_2$ (150 mL), washed with 3× brine, dried over Na$_2$SO$_4$, and concentrated. The product was used without further purification.

Example 24B methyl 4'-chloro-4-formylbiphenyl-2-carboxylate

EXAMPLE 24A (14.5 g), 4-chlorophenylboronic acid (6.88 g) CsF (12.2 g), and tetrakis(triphenylphosphine)palladium(O) were stirred at 70° C. for 24 hours. The reaction was cooled, filtered, and concentrated. The crude product was taken up in ethyl acetate (250 mL), washed with 3×1M NaOH, and brine, concentrated, and chromatographed on silica gel with 10% ethyl acetate/hexanes.

Example 24C methyl 4'-chloro-4-(pyrrolidin-1-ylmethyl)biphenyl-2-carboxylate This example was prepared by substituting EXAMPLE 24B for 4'-chlorobiphenyl-2-carboxaldehyde and pyrrolidine for tert-butyl piperazine-1-carboxylate in EXAMPLE 1A.

Example 24D (4'-chloro-4-(pyrrolidin-1-ylmethyl)biphenyl-2-yl)methanol

DIBAL in hexanes (1M, 5.9 mL) was added to EXAMPLE 24C (650 mg) in CH$_2$Cl$_2$ (30 mL) at 0° C., and the reaction was stirred for 20 minutes. The reaction was quenched by the slow addition of methanol (2 mL), and 1M NaOH (10 mL), and the resulting solution was extracted twice with ethyl acetate. The extracts were washed with brine, dried over Na$_2$SO$_4$, and concentrated. The product was used without further purification.

Example 24E

4'-chloro-4-(pyrrolidin-1-ylmethyl)biphenyl-2-carbaldehyde

Dess-Martin periodinane (1.30 g) was added to EXAMPLE 24D (770 mg) in CH$_2$Cl$_2$ (30 mL) at room temperature and the reaction was stirred for 24 hours. The reaction mixture was concentrated and chromatographed on silica gel with 1% triethylamine in 25% ethyl acetate/hexanes.

Example 24F methyl 2-(1H-indol-4-yloxy)-4-fluorobenzoate

This example was prepared by substituting 4-hydroxyindole for 5-hydroxyindazole and methyl 2,4-difluorobenzoate for ethyl 2,4-difluorobenzoate in EXAMPLE 20A.

Example 24G tert-butyl 4-(3-(1H-indol-4-yloxy)-4-(methoxycarbonyl)phenyl)piperazine-1-carboxylate This example was prepared by substituting EXAMPLE 24F for EXAMPLE 20A and tert-butyl piperazine-1-carboxylate for EXAMPLE 20C in EXAMPLE 20D.

Example 24H methyl 2-(1H-indol-4-yloxy)-4-(piperazin-1-yl)benzoate

This example was prepared by substituting EXAMPLE 24G for EXAMPLE 1A in EXAMPLE 1B.

Example 24I methyl 2-(1H-indol-4-yloxy)-4-(4-((4'-chloro-4-(pyrrolidin-1-ylmethyl)biphenyl-2-yl)methyl)piperazin-1-yl)benzoate This example was prepared by substituting EXAMPLE 24E for 4'-chlorobiphenyl-2 carboxaldehyde and EXAMPLE 24H for tert-butyl piperazine-1-carboxylate in EXAMPLE 1A.

Example 24J 2-(1H-indol-4-yloxy)-4-(4-((4'-chloro-4-(pyrrolidin 1-ylmethyl)biphenyl-2-yl)methyl)piperazin-1-yl)benzoic acid This example was prepared by substituting EXAMPLE 24I for EXAMPLE 1D in EXAMPLE 1E.

Example 24K 4-(4-{[4'-chloro-4-(pyrrolidin-1-ylmethyl)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide This example was prepared by substituting EXAMPLE 24J for EXAMPLE 1E in EXAMPLE 1G. $^1$H NMR (300 MHz, dimethylsulfoxide-$d_6$) δ 11.52 (br s, 1H), 11.26 (s, 1H), 10.68 (br s, 1H), 8.61 (dd, 1H), 8.49 (s, 1H), 8.19 (br s, 1H), 7.66 (d, 2H), 7.54 (m, 3H), 7.36 (m, 2H), 7.28 (s, 1H), 7.24 (d, 1H), 7.05 (d, 1H), 6.95 (dd, 1H), 6.75 (d, 1H), 6.35 (m, 2H), 6.26 (s, 1H), 4.38 (m, 3H), 3.85 (dd, 2H), 3.61 (m, 4H), 3.24 (m, 4H), 3.09 (m, 4H), 2.85 (m, 2H), 2.35 (m, 2H), 2.02 (m, 2H), 1.87 (m, 4H), 1.60 (m, 2H), 1.25 (m, 2H).

Example 25

4-(4-{[4'-chloro-4-(2-pyrrolidin-1-ylethyl)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide

Example 25A methyl 4'-chloro-4-(2-oxoethyl)biphenyl-2-carboxylate

To a solution of (methoxymethyl)diphenylphosphine oxide (1.62 g) in 40 mL tetrahydrofuran at −78° C., was added lithium diisopropylamide (2M, 3.3 mL), and after stirring 3 minutes, EXAMPLE 24B (1.57 g) was added, and the solution was warmed to room temperature. NaH (230 mg), and 40 mL N,N-dimethylformamide were added, and the mixture was heated to 60° C. for 1 hours. The reaction was cooled and poured into NaH$_2$PO$_4$ solution. The resulting solution was extracted twice with ether, and the combined extracts were washed twice with water, and brine, and concentrated. The crude mixture of enol ethers was taken up in 1M HCl (50 mL) and dioxane (50 mL), and stirred at 60° C. for 3 hours. The reaction was cooled and poured into NaHCO$_3$ solution. The resulting solution was extracted twice with ether, and the combined extracts were washed with water, and brine, and concentrated. The product was used without further purification.

Example 25B methyl 4'-chloro-4-(2-(pyrrolidin-1-yl)ethyl)biphenyl-2-carboxylate This example was prepared by substituting EXAMPLE 25A for 4'-chlorobiphenyl-2-carboxaldehyde and pyrrolidine for tert-butyl piperazine-1-carboxylate in EXAMPLE 1A.

Example 25C (4'-chloro-4-(2-(pyrrolidin-1-yl)ethyl)biphenyl-2-yl)methanol

This example was prepared by substituting EXAMPLE 25B for EXAMPLE 24C in EXAMPLE 24D.

Example 25D

4'-chloro-4-(2-(pyrrolidin-1-yl)ethyl)biphenyl-2-carbaldehyde

This example was prepared by substituting EXAMPLE 25C for EXAMPLE 24D in EXAMPLE 24E.

Example 25E methyl 2-(1H-indol-4-yloxy)-4-(4-((4'-chloro-4-(2-(pyrrolidin-1-yl)ethyl)biphenyl-2-yl)methyl)piperazin-1-yl)benzoate This example was prepared by substituting EXAMPLE 25D for 4'-chlorobiphenyl-2 carboxaldehyde and EXAMPLE 24H for tert-butyl piperazine-1-carboxylate in EXAMPLE 1A.

Example 25F 2-(1H-indol-4-yloxy)-4-(4-((4'-chloro-4-(2-(pyrrolidin 1-yl)ethyl)biphenyl-2-yl)methyl)piperazin-1-yl)benzoic acid This example was prepared by substituting EXAMPLE 25E for EXAMPLE 1D in EXAMPLE 1E.

Example 25G 4-(4-{[4'-chloro-4-(2-pyrrolidin-1-ylethyl)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide This example was prepared by substituting EXAMPLE 25F for EXAMPLE 1E in EXAMPLE 1G. $^1$H NMR (300 MHz, dimethylsulfoxide-$d_6$) δ 11.15 (s, 1H), 8.47 (t, 1H), 8.42 (s, 1H), 7.68 (dd, 1H), 7.58 (d, 1H), 7.44 (m, 4H), 7.22 (m, 3H), 7.10 (d, 1H), 6.92 (m, 2H), 6.68 (d, 1H), 6.34 (d, 1H), 6.26 (s, 2H), 3.87 (dd, 2H), 3.61 (m, 4H), 3.10-3.24 (m, 11H), 2.97 (m, 4H), 2.31 (m, 4H), 1.89 (m, 4H), 1.61 (m, 2H), 1.26 (m, 2H).

Example 26

4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)-2-(1H-indol-5-yloxy)benzamide

Example 26A ethyl 2-(1H-indol-5-yloxy)-4-fluorobenzoate

This example was prepared by substituting 5-hydroxyindole for 5-hydroxyindazole in EXAMPLE 20A.

Example 26B ethyl 2-(1H-indol-5-yloxy)-4-(4-((2-(4-chlorophenyl)-4,4-dimethylcyclohex-1-enyl)methyl)piperazin-1-yl)benzoate This example was prepared by substituting EXAMPLE 26A for EXAMPLE 20A in EXAMPLE 20D.

Example 26C 2-(1H-indol-5-yloxy)-4-(4-((2-(4-chlorophenyl)-4,4-dimethylcyclohex-1-enyl)methyl)piperazin-1-yl)benzoic acid This example was prepared by substituting EXAMPLE 26B for EXAMPLE 1D in EXAMPLE 1E.

Example 26D 4-(1-cyclopentylpiperidin-4-ylamino)-3-nitrobenzenesulfonamide

This example was prepared by substituting 1-cyclopentylpiperidin-4-amine for (tetrahydropyran-4-yl)methylamine in EXAMPLE 1F.

Example 26E 4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)-2-(1H-indol-5-yloxy)benzamide This example was prepared by substituting EXAMPLE 26C for EXAMPLE 1E and EXAMPLE 26D for EXAMPLE 1F in EXAMPLE 1G. $^1$H NMR (300 MHz, dimethylsulfoxide-$d_6$) δ 11.13 (br s, 1H), 8.52 (s, 1H), 8.14 (d, 1H), 7.80 (d, 1H), 7.52 (d, 1H), 7.35 (m, 4H), 7.04 (m, 4H), 6.80 (d, 1H), 6.61 (d, 1H), 6.36 (s, 1H), 6.14 (s, 1H), 5.76 (s, 1H), 3.84 (m, 2H), 3.24 (m, 4H), 2.99 (m, 4H), 2.85 (m, 2H), 2.71 (m, 2H), 2.16 (m, 6H), 1.95 (m, 4H), 1.50-1.70 (m, 6H), 1.38 (m, 2H), 1.17 (m, 2H), 0.93 (s, 6H).

Example 27

4-{4-[(4'-chloro-1,1'-biphenyl-2-yl)methyl]-3-isobutylpiperazin-1-yl}-N-({3-nitro-4-[(tetrahydro-2H-pyran-4-ylmethyl)amino]phenyl}sulfonyl)-2-phenoxybenzamide

Example 27A methyl 2-bromo-4-methylpentanoate

To concentrated HBr (48%) (20 mL) in water (214 mL), was added KBr (17.6 g, cooled to 0° C., then sodium nitrite (5.2 g) all at once, then DL-leucine (5.2 g) in a few portions. The reaction was mechanically stirred at 0° C. for 1.5 hours, then extracted with 2×200 mL ethyl acetate. The combined organic layers were washed with brine and dried over $Na_2SO_4$. After filtration and concentration, the resultant oil was dissolved in $CH_2Cl_2$/methanol and treated with 2.0M (TMS)$CHN_2$ in ether (30 mL) at room temperature for 10 minutes. The reaction was concentrated and then purified by flash chromatography using 97.5/2.5 hexane/ethyl acetate.

Example 27B 3-isobutylpiperazin-2-one

EXAMPLE 27A (2.2 g) in ethanol (15 mL) was added dropwise over a period of 2.5 hours to a stirred refluxing solution of ethane-1,2-diamine (13.2 mL) in ethanol (60 mL). Heating was continued for another 2.5 hours, then NaOEt in ethanol was added (21% by wt, 4.0 mL) and heated for another 90 minutes. The reaction was then cooled and concentrated. After trituration with ether, the title compound was used without purification.

Example 27C

4'-chlorobiphenyl-2-carbaldehyde

To 2-bromobenzaldehyde (2.3 ml) and tetrakis(triphenylphosphine)palladium(O) (0.35 g) in toluene (50 mL), was added 4-chlorophenylboronic acid (4.0 g) and 2M $Na_2CO_3$ (70 ml). The mixture was heated under reflux for one hour. The reaction was cooled, diluted with water and extracted with ethyl acetate. The organic layer was washed with brine and the combined aqueous layers back-extracted with ethyl acetate. The combined organic layers were dried over $Na_2SO_4$. The crude material was purified by flash chromatography using 97.5/2.5 hexane/ethyl acetate.

Example 27D 4-((4'-chlorobiphenyl-2-yl)methyl)-3-isobutylpiperazin-2-one

This example was prepared by substituting EXAMPLE 27B for tert-butyl piperazine-1-carboxylate in EXAMPLE 1A.

Example 27E 1-((4'-chlorobiphenyl-2-yl)methyl)-2-isobutylpiperazine

To a solution of EXAMPLE 27D in tetrahydrofuran (3.6 mL) was added borane-methyl sulfide complex (10M in tetrahydrofuran) (0.24 mL). The reaction was heated under reflux for 16 hours, then cooled in an ice/water bath. Methanol (5 mL) was added carefully, and the mixture was stirred cold for 75 minutes. Then 4N HCl in dioxane (0.65 mL) was added and the reaction heated under reflux for 60 minutes. After cooling to room temperature, 1N $NH_4OH$ (2.6 mL) was added and the reaction was stirred for 15 minutes. Then the reaction was concentrated, redissolved in methanol, concentrated, redissolved in toluene and concentrated. The crude solids were slurried in $CHCl_3$/methanol, the solids were filtered off, and the filtrate concentrated to afford the title compound.

Example 27F methyl 4-(4-((4'-chlorobiphenyl-2-yl)methyl)-3-isobutylpiperazin-1-yl)-2-phenoxybenzoate This example was prepared by substituting EXAMPLE 27E for EXAMPLE 1B in EXAMPLE 1D.

Example 27G 4-(4-((4'-chlorobiphenyl-2-yl)methyl)-3-isobutylpiperazin-1-yl)-2-phenoxybenzoic acid This example was prepared by substituting EXAMPLE 27F for EXAMPLE 1D in EXAMPLE 1E.

Example 27H

4-{4-[(4'-chloro-1,1'-biphenyl-2-yl)methyl]-3-isobutylpiperazin-1-yl}-N-({3-nitro-4-[(tetrahydro-2H-pyran-4-ylmethyl)amino]phenyl}sulfonyl)-2-phenoxybenzamide EXAMPLE 27G (13 mg), EXAMPLE 1F (7 mg), 1-ethyl-3-[3-(dimethylamino)propyl]-carbodiimide hydrochloride (8 mg), and 4-dimethylaminopyridine (5 mg) were stirred in $CH_2Cl_2$ (1 mL) for 24 hours. The product was purified by preparative HPLC using a C18 column, 250×50 mm, 10μ, and eluting with a gradient of 20-100% CHCN vs. 0.1% trifluoroacetic acid in water, giving the product as a trifluoroacetate salt. $^1$H NMR (300 MHz, dimethylsulfoxide-$d_6$) δ 11.62 (br s, 1H), 9.10 (br s, 1H), 8.65 (t, 1H), 8.47 (d, 1H), 7.77 (dd, 1H), 7.70 (br s, 1H), 7.50 (m, 5H), 7.39 (m, 3H), 7.25 (m, 2H), 7.18 (d, 1H), 7.01 (dd, 1H), 6.83 (m, 2H), 6.76 (m, 1H), 6.40 (br s, 1H), 4.70 and 4.15 (both v br s, total 1H), 3.85 (dd, 2H), 3.60 (v br s, 1H), 3.32, 3.27, 3.24, 3.06 (all m, total 11H), 1.90 (m, 1H), 1.62 (m, 3H), 1.30 (m, 4H), 0.70 (br m, 6H).

Example 28

4-{4-[(4'-chloro-1,1'-biphenyl-2-yl)methyl]piperazin-1-yl}-N-{[4-(2,4-dioxo-3-azabicyclo[3.2.0]hept-3-yl)phenyl]sulfonyl}-2-phenoxybenzamide This example was prepared by substituting EXAMPLE 1E for EXAMPLE 27G and 4-(2,4-dioxo-3-azabicyclo[3.2.0]heptan-3-yl)bezenesulfonamide for EXAMPLE 1F in EXAMPLE 27H. $^1$H NMR (300 MHz, dimethylsulfoxide-$d_6$) δ 11.87 (br s, 1H), 9.58 (br s, 1H), 7.93 (d, 2H), 7.71 (br s, 1H), 7.54 (m, 7H), 7.35 (m, 5H), 7.10 (dd, 1H), 6.89 (d, 2H), 6.78 (dd, 1H), 6.42 (s, 1H), 4.37 (br s, 1H), 3.78 (br s, 1H), 3.43 (m, 4H), 3.22, 3.00, 2.85 (all v br s, total 6H), 2.62 (m, 2H), 2.18 (m, 2H).

Example 29

4-{4-[(4'-chloro-1,1'-biphenyl-2-yl)methyl]piperazin-1-yl}-N-{[4-(4-methyl-6-oxo-1,4,5,6-tetrahydropyridazin-3-yl)phenyl]sulfonyl}-2-phenoxybenzamide This example was prepared by substituting EXAMPLE 1E for EXAMPLE 27G and 4-(4-methyl-6-oxo-1,4,5,6-tetrahydropyridazin-3-yl)bezenesulfonamide for EXAMPLE 1F in EXAMPLE 27H. $^1$H NMR (300 MHz, dimethylsulfoxide-$d_6$) δ 11.87 (br s, 1H), 11.20 (s, 1H), 9.58 (br s, 1H), 7.90 (d, 2H), 7.83 (d, 2H), 7.50 (m, 5H), 7.32 (m, 5H), 7.08 (dd, 1H), 6.85 (d, 2H), 6.76 (dd, 1H), 6.43 (s, 1H), 4.38 (br s, 1H), 3.80 (br s, 1H), 3.60 (m, 2H), 3.40 (m, 2H), 3.21, 3.00, 2.84 (all br s, total 6H), 2.75 (dd, 1H), 2.28 (d, 1H), 1.08 (d, 3H).

Example 30

4-{4-[(4'-chloro-1,1'-biphenyl-2-yl)methyl]piperazin-1-yl}-N-{[4-(3,3-dimethyl-2-oxoazetidin-1-yl)phenyl]sulfonyl}-2-phenoxybenzamide This example was prepared by substituting EXAMPLE 1E for EXAMPLE 27G and 4-(3,3-dimethyl-2-oxoazetidin-1-yl)bezenesulfonamide for EXAMPLE 1F in EXAMPLE 27H. $^1$H NMR (300 MHz, dimethylsulfoxide-$d_6$) δ 11.62 (br s, 1H), 9.58 (br s, 1H), 7.80 (d, 2H), 7.72 (br s, 1H), 7.50 (m, 5H), 7.40 (m, 4H), 7.33 (m, 3H), 7.08 (dd, 1H), 6.85 (d, 2H), 6.76 (dd, 1H), 6.41 (s, 1H), 4.38 (br s, 1H), 3.77 (br s, 1H), 3.58 (s, 2H), 3.45 (m, 2H), 3.21, 3.00, 2.84 (all br s, total 6H), 1.32 (s, 6H).

Example 31

4-{4-[(4'-chloro-1,1'-biphenyl-2-yl)methyl]piperazin-1-yl}-N-{[4-(4-nitro-2H-1,2,3-triazol-2-yl)phenyl]sulfonyl}-2-phenoxybenzamide This example was prepared by substituting EXAMPLE 1E for EXAMPLE 27G and 4-(4-nitro-2H-1,2,3-triazol-2-yl)bezenesulfonamide for EXAMPLE 1F in EXAMPLE 27H. $^1$H NMR (300 MHz, dimethylsulfoxide-$d_6$) δ 11.98 (br s, 1H), 9.58 (br s, 1H), 9.11 (s, 1H), 8.21 (d, 2H), 8.05 (d, 2H), 7.70 (br s, 1H), 7.50 (m, 5H), 7.39 (m, 2H), 7.30 (m, 1H), 7.24 (m, 2H), 7.00 (dd, 1H), 6.82 (d, 2H), 6.78 (dd, 1H), 6.43 (s, 1H), 4.38 (br s, 1H), 3.77 (br s, 1H), 3.45 (m, 2H), 3.21, 3.00, 2.84 (all br s, total 6H).

Example 32

4-{4-[(4'-chloro-1,1'-biphenyl-2-yl)methyl]piperazin-1-yl}-2-phenoxy-N-{[2-(2-piperidin-1-ylethoxy)phenyl]sulfonyl}benzamide This example was prepared by substituting EXAMPLE 1E for EXAMPLE 27G and 2-(2-(piperidin-1-yl)ethoxy)bezenesulfonamide for EXAMPLE 1F in EXAMPLE 27H. $^1$H NMR (300 MHz, dimethylsulfoxide-$d_6$) δ 11.65 (br s, 1H), 9.77 (br s, 1H), 8.95 (br s, 1H), 7.80 (dd, 1H), 7.70 (br s, 1H), 7.68 (m, 1H), 7.50 (m, 5H), 7.36 (m, 5H), 7.23 (d, 1H), 7.15 (m, 2H), 6.90 (d, 2H), 6.78 (dd, 1H), 6.42 (s, 1H), 4.40 (m, 3H), 3.80 (br s, 1H), 3.40, 3.20 3.00, 2.90 (all v br m, total 13H), 1.63 (m, 5H), 1.27 (v br s, 1H).

Example 33

4-{4-[(4'-chloro-1,1'-biphenyl-2-yl)methyl]piperazin-1-yl}-N-{[3-({[(1-ethylpyrrolidin-2-yl)methyl]amino}carbonyl)-4-methoxyphenyl]sulfonyl}-2-phenoxybenzamide This example was prepared by substituting EXAMPLE 1E for EXAMPLE 27G and N-((1-ethylpyrrolidin-2-yl)methyl)-2-methoxy-5-sulfamoylbenzamide for EXAMPLE 1F in EXAMPLE 27H. $^1$H NMR (300 MHz, dimethylsulfoxide-$d_6$) δ 11.75 (br s, 1H), 9.70 (br s, 1H), 9.25 (br s, 1H), 8.62 (t, 1H), 8.25 (d, 1H), 7.90 (dd, 1H), 7.70 (br s, 1H), 7.50 (m, 5H), 7.40 (m, 2H), 7.10 (m, 5H), 7.09 (dd, 1H), 6.85 (d, 2H), 6.76 (dd, 1H), 6.40 (s, 1H), 4.39 (br s, 1H), 3.96 (s, 3H), 3.77 (br s, 1H), 3.60 (m, 4H), 3.55-2.80 (envelope, 10H), 2.12 (m, 1H), 2.00 (m, 1H), 1.85 (m, 2H), 1.23 (t, 3H).

Example 34

4-{4-[(4'-chloro-1,1'-biphenyl-2-yl)methyl]piperazin-1-yl}-2-(1-naphthyloxy)-N-({3-nitro-4-[(tetrahydro-2H-pyran-4-ylmethyl)amino]phenyl}sulfonyl)benzamide

Example 34A methyl 2-bromo-4-(4-((4'-chlorobiphenyl-2-yl)methyl)piperazin-1-yl)benzoate This example was prepared by substituting methyl 2-bromo-4-fluorobenzoate for EXAMPLE 1C in EXAMPLE 1D.

Example 34B methyl 4-(4-((4'-chlorobiphenyl-2-yl)methyl)piperazin-1-yl)-2-(naphthalen-1-yloxy)benzoate This example was prepared by substituting EXAMPLE 34A for EXAMPLE 18E and 1-naphthol for phenol in EXAMPLE 18F.

Example 34C 4-(4-((4'-chlorobiphenyl-2-yl)methyl)piperazin-1-yl)-2-(naphthalen-1-yloxy)benzoic acid This example was prepared by substituting EXAMPLE 34B for EXAMPLE 1D in EXAMPLE 1E.

Example 34D

4-{4-[(4'-chloro-1,1'-biphenyl-2-yl)methyl]piperazin-1-yl}-2-(1-naphthyloxy)-N-({3-nitro-4-[(tetrahydro-2H-pyran-4-ylmethyl)amino]phenyl}sulfonyl)benzamide This example was prepared by substituting EXAMPLE 34C for EXAMPLE 27G in EXAMPLE 27H. $^1$H NMR (300 MHz, dimethylsulfoxide-$d_6$) δ 11.82 (br s, 1H), 9.50 (br s, 1H), 8.58 (t, 1H), 8.29 (d, 1H), 8.18 (d, 1H), 7.85 (d, 1H), 7.70 (br s, 1H), 7.50 (m, 8H), 7.38 (m, 4H), 7.20 (dd, 1H), 6.82 (m, 2H), 6.55 (s, 1H), 6.45 (d, 1H), 4.38 (br s, 1H), 3.85 (dd, 2H), 3.78 (br s, 1H), 3.27 (m, 6H), 3.22, 3.02, 2.85 (all br s, total 6H), 1.84 (m, 1H), 1.60 (m, 2H), 1.29 (m, 2H).

Example 35

4-{4-[(4'-chloro-1,1'-biphenyl-2-yl)methyl]piperazin-1-yl}-2-(2-naphthyloxy)-N-({3-nitro-4-[(tetrahydro-2H-pyran-4-ylmethyl)amino]phenyl}sulfonyl)benzamide

Example 35A 1-(difluoromethylsulfonyl)-2-fluorobenzene

This example was prepared by substituting EXAMPLE 34A for EXAMPLE 18E and 2-naphthol for phenol in EXAMPLE 18F.

Example 35B 4-(4-((4'-chlorobiphenyl-2-yl)methyl)piperazin-1-yl)-2-(naphthalen-2-yloxy)benzoic acid This example was prepared by substituting EXAMPLE 35A for EXAMPLE 1D in EXAMPLE 1E.

Example 35C

4-{4-[(4'-chloro-1,1'-biphenyl-2-yl)methyl]piperazin-1-yl}-2-(2-naphthyloxy)-N-({3-nitro-4-[(tetrahydro-2H-pyran-4-ylmethyl)amino]phenyl}sulfonyl)benzamide This example was prepared by substituting EXAMPLE 35B for EXAMPLE 27G in EXAMPLE 27H. $^1$H NMR (300 MHz, dimethylsulfoxide-$d_6$) δ 11.80 (br s, 1H), 9.55 (br s, 1H), 8.50 (t, 1H), 8.39 (d, 1H), 7.83 (m, 2H), 7.69 (br s, 1H), 7.64 (d, 1H), 7.50 (m, 6H), 7.37 (m, 5H), 7.18 (dd, 1H), 7.00 (d, 1H), 6.81 (dd, 1H), 6.77 (d, 1H), 6.56 (d, 1H), 4.38 (br s, 1H), 3.85 (dd, 2H), 3.78 (br s, 1H), 3.27 (m, 6H), 3.22, 3.02, 2.85 (all br s, total 6H), 1.84 (m, 1H), 1.60 (m, 2H), 1.29 (m, 2H).

Example 36

4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(2-naphthyloxy)benzamide This example was prepared by substituting EXAMPLE 35B for EXAMPLE 27G and EXAMPLE 7A for EXAMPLE 1F in EXAMPLE 27H. $^1$H NMR (300 MHz, dimethylsulfoxide-$d_6$) δ 11.80 (br s, 1H), 9.61 (br s, 2H), 8.57 (t, 1H), 8.40 (d, 1H), 7.83 (m, 2H), 7.66 (m, 2H), 7.50 (m, 6H), 7.40 (m, 5H), 7.18 (dd, 1H), 7.02 (d, 1H), 6.81 (d, 1H), 6.57 (s, 1H), 4.38 (br s, 1H), 4.00 (m, 2H), 3.80 (br s, 1H), 3.40 (m, 8H), 3.30-2.80 (envelope, 10H), 1.92 (m, 2H).

Example 37

4-{4-[(4'-chloro-1,1'-biphenyl-2-yl)methyl]piperazin-1-yl}-2-(2-naphthyloxy)-N-({(4-[(tetrahydro-2H-pyran-4-ylmethyl)amino]-3-[(trifluoromethyl)sulfonyl]phenyl}sulfonyl)benzamide This example was prepared by substituting EXAMPLE 35B for EXAMPLE 27G and EXAMPLE 163A for EXAMPLE 1F in EXAMPLE 27H. $^1$H NMR (300 MHz, dimethylsulfoxide-$d_6$) δ 11.82 (br s, 1H), 9.58 (br s, 1H), 8.03 (d, 1H), 7.90 (m, 2H), 7.70 (d, 1H), 7.69 (br s, 1H), 7.65 (dd, 1H), 7.50 (m, 7H), 7.36 (m, 3H), 7.18 (m, 2H), 7.05 (d, 1H), 6.81 (dd, 1H), 6.75 (d, 1H), 6.56 (d, 1H), 4.38 (br s, 1H), 3.83 (dd, 2H), 3.78 (br s, 1H), 3.23 (m, 4H), 3.22, 3.02, 2.85 (all br s, total 6H), 3.15 (m, 2H), 1.80 (m, 1H), 1.55 (m, 2H), 1.22 (m, 2H).

Example 38

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(quinolin-7-yloxy)benzamide

Example 38A methyl 4-(4-((4'-chlorobiphenyl-2-yl)methyl)piperazin-1-yl)-2-(quinolin-7-yloxy)benzoate This example was prepared by substituting EXAMPLE 34A for EXAMPLE 18E and quinolin-7-ol for phenol in EXAMPLE 18F.

Example 38B 4-(4-((4'-chlorobiphenyl-2-yl)methyl)piperazin-1-yl)-2-(quinolin-7-yloxy)benzoic acid This example was prepared by substituting EXAMPLE 38A for EXAMPLE 1D in EXAMPLE 1E.

Example 38C

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(quinolin-7-yloxy)benzamide This example was prepared by substituting EXAMPLE 38B for EXAMPLE 27G in EXAMPLE 27H. $^1$H NMR (300 MHz, dimethylsulfoxide-$d_6$) δ 8.80 (d, 1H), 8.48 (t, 1H), 8.35 (d, 1H), 8.32 (d, 1H), 7.90 (d, 1H), 7.74 (m, 1H), 7.59 (m, 2H), 7.50 (m, 4H), 7.45 (dd, 1H), 7.38 (d, 2H), 7.30 (m, 2H), 6.95 (d, 1H), 6.86 (dd, 1H), 6.83 (d, 1H), 6.71 (d, 1H), 4.38 (br s, 1H), 3.85 (dd, 2H), 3.78 (br s, 1H), 3.30-2.80 (envelope, 12H), 1.84 (m, 1H), 1.60 (m, 2H), 1.25 (m, 2H).

Example 39

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(quinolin-6-yloxy)benzamide

Example 39A methyl 4-(4-((4'-chlorobiphenyl-2-yl)methyl)piperazin-1-yl)-2-(quinolin-6-yloxy)benzoate This example was prepared by substituting EXAMPLE 34A for EXAMPLE 18E and quinolin-6-ol for phenol in EXAMPLE 18F.

Example 39B 4-(4-((4'-chlorobiphenyl-2-yl)methyl)piperazin-1-yl)-2-(quinolin-6-yloxy)benzoic acid This example was prepared by substituting EXAMPLE 39A for EXAMPLE 1D in EXAMPLE 1E.

Example 39C

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(quinolin-6-yloxy)benzamide This example was prepared by substituting EXAMPLE 39B for EXAMPLE 27G in EXAMPLE 27H. $^1$H NMR (300 MHz, dimethylsulfoxide-$d_6$) 11.90 (br s, 1H), 9.65 (br s, 1H), 8.80 (d, 1H), 8.46 (t, 1H), 8.35 (d, 1H), 7.90 (d, 1H), 7.72 (m, 1H), 7.50 (m, 6H), 7.45 (dd, 1H), 7.37 (m, 4H), 7.02 (d, 1H), 6.83 (dd, 1H), 6.79 (d, 1H), 6.63 (d, 1H), 4.38 (br s, 1H), 3.85 (dd, 2H), 3.78 (br s, 1H), 3.40-2.80 (envelope 12H), 1.87 (m, 1H), 1.62 (m, 2H), 1.26 (m, 2H).

Example 40

4-{4-[(4'-chloro-1,1'-biphenyl-2-yl)methyl]piperazin-1-yl}-2-(1H-indol-5-yloxy)-N-({3-nitro-4-[(tetrahydro-2H-pyran-4-ylmethyl)amino]phenyl}sulfonyl)benzamide

Example 40A 1-(triisopropylsilyl)-1H-indol-5-ol

5-Benzyloxy-indole (1.0 g) was treated with NaH (135 mg) and triisopropylsilyl chloride (1.0 g) in tetrahydrofuran for 1 hour, purified by flash chromatography (98/2 ethyl acetate/hexanes), then debenzylated in ethanol (35 mL) using Pearlman's catalyst (0.19 g) and a hydrogen balloon.

Example 40B methyl 2-(1H-indol-5-yloxy)-4-(4-((4'-chlorobiphenyl-2-yl)methyl)piperazin-1-yl)benzoate This example was prepared by substituting EXAMPLE 34A for EXAMPLE 18E and EXAMPLE 40A for phenol in EXAMPLE 18F. In this example, the crude material from the ether formation was desilylated using tetrabutyl ammonium fluoride in tetrahydrofuran/water 95/5 prior to purification.

Example 40C 2-(1H-indol-5-yloxy)-4-(4-((4'-chlorobiphenyl-2-yl)methyl)piperazin-1-yl)benzoic acid This example was prepared by substituting EXAMPLE 40B for EXAMPLE 1D in EXAMPLE 1E.

Example 40D

4-{4-[(4'-chloro-1,1'-biphenyl-2-yl)methyl]piperazin-1-yl}-2-(1H-indol-5-yloxy)-N-({3-nitro-4-[(tetrahydro-2H-pyran-4-ylmethyl)amino]phenyl}sulfonyl)benzamide This example was prepared by substituting EXAMPLE 40C for EXAMPLE 27G in EXAMPLE 27H. $^1$H NMR (300 MHz, dimethylsulfoxide-$d_6$) δ 11.40 (br s, 1H), 11.17 (s, 1H), 9.50 (v br s, 1H), 8.61 (t, 1H), 8.57 (d, 1H), 7.77 (dd, 1H), 7.70 (br s, 1H), 7.50 (m, 5H), 7.36 (m, 5H), 7.10 (s, 1H), 7.08 (d, 1H), 6.83 (dd, 1H), 6.69 (dd, 1H), 6.37 (m, 1H), 6.21 (d, 1H), 4.30 (br s, 1H), 3.84 (dd, 2H), 3.70 (br s, 1H), 3.30 (m, 6H), 3.20, 2.95, 2.80 (all br s, total 6H), 1.86 (m, 1H), 1.60 (m, 2H), 1.25 (m, 2H).

Example 41

4-{4-[(4'-chloro-1,1'-biphenyl-2-yl)methyl]piperazin-1-yl}-2-(isoquinolin-5-yloxy)-N-({3-nitro-4-[(tetrahydro-2H-pyran-4-ylmethyl)amino]phenyl}sulfonyl)benzamide

Example 41A methyl 4-(4-((4'-chlorobiphenyl-2-yl)methyl)piperazin-1-yl)-2-(isoquinolin-5-yloxy)benzoate This example was prepared by substituting EXAMPLE 34A for EXAMPLE 18E and isoquinolin-5-ol for phenol in EXAMPLE 18F.

Example 41B 4-(4-((4'-chlorobiphenyl-2-yl)methyl)piperazin-1-yl)-2-(isoquinolin-5-yloxy)benzoic acid This example was prepared by substituting EXAMPLE 41A for EXAMPLE 1D in EXAMPLE 1E.

Example 41C

4-{4-[(4'-chloro-1,1'-biphenyl-2-yl)methyl]piperazin-1-yl}-2-(isoquinolin-5-yloxy)-N-({3-nitro-4-[(tetrahydro-2H-pyran-4-ylmethyl)amino]phenyl}sulfonyl)benzamide This example was prepared by substituting EXAMPLE 41B for EXAMPLE 27G in EXAMPLE 27H. $^1$H NMR (300 MHz, dimethylsulfoxide-$d_6$) δ 11.90 (br s, 1H), 9.55 (v br s, 1H), 9.26 (s, 1H), 8.47 (m, 2H), 8.14 (d, 1H), 7.99 (d, 1H), 7.65 (br s, 1H), 7.60 (d, 1H), 7.45 (m, 6H), 7.29 (m, 4H), 6.80 (m, 2H), 6.60 (m, 2H), 4.38 (br s, 1H), 3.85 (dd, 2H), 3.78 (br s, 1H), 3.24 (m, 6H), 3.22, 3.00, 2.85 (all br s, total 6H), 1.87 (m, 1H), 1.62 (m, 2H), 1.26 (m, 2H).

Example 42

4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(isoquinolin-5-yloxy)benzamide This example was prepared by substituting EXAMPLE 41B for EXAMPLE 27G and EXAMPLE 154A for EXAMPLE 1F in EXAMPLE 27H. $^1$H NMR (300 MHz, dimethylsulfoxide-$d_6$) δ 11.90 (br s, 1H), 9.38 (v br s, 1H), 9.22 (s, 1H), 8.54 (t, 1H), 8.45 (d, 1H), 8.16 (d, 1H), 7.96 (d, 1H), 7.62 (br s, 1H), 7.56 (d, 1H), 7.50 (d, 1H), 7.45 (m, 5H), 7.29 (m, 4H), 6.80 (m, 2H), 6.60 (m, 2H), 4.23 (br s, 1H), 3.78 (br s, 1H), 3.40 (m, 2H), 3.35-2.80 (envelope, 8H), 3.08 (m, 2H), 2.72, 2.70 (both s, total 6H), 1.87 (m, 2H).

Example 43

4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(quinolin-6-yloxy)benzamide This example was prepared by substituting EXAMPLE 39B for EXAMPLE 27G and EXAMPLE 154A for EXAMPLE 1F in EXAMPLE 27H. $^1$H NMR (300 MHz, dimethylsulfoxide-$d_6$) δ 11.96 (br s, 1H), 9.38 (v br s, 1H), 8.77 (dd, 1H), 8.51 (t, 1H), 8.35 (d, 1H), 8.05 (d, 1H), 7.90 (d, 1H), 7.70 (br s, 1H), 7.50 (m, 6H), 7.38 (m, 5H), 6.98 (d, 1H), 6.83 (dd, 1H), 6.79 (d, 1H), 6.63 (d, 1H), 4.38 (br s, 1H), 3.78 (br s, 1H), 3.42 (m, 2H), 3.35-2.80 (envelope, 8H), 3.15 (m, 2H), 2.81, 2.79 (both s, total 6H), 1.93 (m, 2H).

Example 44

4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(1H-indol-5-yloxy)benzamide This example was prepared by substituting EXAMPLE 40C for EXAMPLE 27G and EXAMPLE 154A for EXAMPLE 1F in EXAMPLE 27H. $^1$H NMR (300 MHz, dimethylsulfoxide-$d_6$) δ 11.40 (br s, 1H), 11.18 (s, 1H), 9.30 (v br s, 1H), 8.66 (t, 1H), 8.60 (d, 1H), 7.85 (dd, 1H), 7.52 (d, 1H), 7.50 (m, 5H), 7.40 (m, 4H), 7.30 (br s, 1H), 7.14 (s, 1H), 7.10 (d, 1H), 6.84 (dd, 1H), 6.67 (dd, 1H), 6.39 (m, 1H), 6.20 (s, 1H), 4.35 (br s, 1H), 3.78 (br s, 1H), 3.40 (m, 2H), 3.35-2.80 (envelope, 8H), 3.10 (m, 2H), 2.78, 2.76 (both s, total 6H), 1.95 (m, 2H).

Example 45

4-{4-[(4'-chloro-1,1'-biphenyl-2-yl)methyl]piperazin-1-yl}-2-(1H-indol-4-yloxy)-N-({3-nitro-4-[(tetrahydro-2H-pyran-4-ylmethyl)amino]phenyl}sulfonyl)benzamide

Example 45A 1-(triisopropylsilyl)-1H-indol-4-ol

4-Benzyloxy-indole (1.0 g) was treated with NaH (135 mg) and triisopropylsilyl chloride (1.0 g) in tetrahydrofuran for 1 hour, purified by flash chromatography (98/2 ethyl acetate/hexanes), then debenzylated in ethanol (35 mL) using Pearlman's catalyst (0.19 g) and a hydrogen balloon.

Example 45B methyl 2-(1H-indol-4-yloxy)-4-(4-((4'-chlorobiphenyl-2-yl)methyl)piperazin-1-yl)benzoate This example was prepared by substituting EXAMPLE 34A for EXAMPLE 18E and EXAMPLE 45A for phenol in EXAMPLE 18F. Here the crude material from the ether formation was desilated using tetra-n-butylammonium fluoride in tetrahydrofuran/water 95/5 prior to purification.

Example 45C 2-(1H-indol-4-yloxy)-4-(4-((4'-chlorobiphenyl-2-yl)methyl)piperazin-1-yl)benzoic acid This example was prepared by substituting EXAMPLE 45B for EXAMPLE 1D in EXAMPLE 1E.

Example 45D

4-{4-[(4'-chloro-1,1'-biphenyl-2-yl)methyl]piperazin-1-yl}-2-(1H-indol-4-yloxy)-N-({3-nitro-4-[(tetrahydro-2H-pyran-4-ylmethyl)amino]phenyl}sulfonyl)benzamide This example was prepared by substituting EXAMPLE 45C for EXAMPLE 27G in EXAMPLE 27H. $^1$H NMR (300 MHz, dimethylsulfoxide-$d_6$) δ 11.50 (br s, 1H), 11.24 (s, 1H), 9.50 (v br s, 1H), 8.61 (t, 1H), 8.47 (d, 1H), 7.70 (br s, 1H), 7.64 (dd, 1H), 7.50 (m, 5H), 7.30 (m, 4H), 7.15 (d, 2H), 7.04 (d, 2H), 6.92 (dd, 1H), 6.75 (dd, 1H), 6.33 (m, 2H), 6.23 (s, 1H), 4.30 (br s, 1H), 3.84 (dd, 2H), 3.70 (br s, 1H), 3.30 (m, 6H), 3.20, 2.95, 2.80 (all br s, total 6H), 1.86 (m, 1H), 1.60 (m, 2H), 1.25 (m, 2H).

Example 46

4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(1H-indol-4-yloxy)benzamide This example was prepared by substituting EXAMPLE 45C for EXAMPLE 27G and EXAMPLE 154A for EXAMPLE 1F in EXAMPLE 27H. $^1$H NMR (300 MHz, dimethylsulfoxide-$d_6$) δ 11.50 (v br s, 1H), 11.24 (s, 1H), 9.30 (br s, 1H), 8.66 (t, 1H), 8.53 (d, 1H), 7.85 (dd, 1H), 7.55 (d, 1H), 7.50 (m, 5H), 7.39 (m, 2H), 7.30 (m, 2H), 7.148 (d, 1H), 7.10 (d, 1H), 6.96 (dd, 1H), 6.72 (dd, 1H), 6.41 (d, 1H), 6.32 (s, 1H), 6.23 (s, 1H), 4.35 (br s, 1H), 3.78 (br s, 1H), 3.40 (m, 2H), 3.35-2.80 (envelope, 8H), 3.10 (m, 2H), 2.78, 2.76 (both s, total 6H), 1.95 (m, 2H).

Example 47

4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(1H-indol-6-yloxy)benzamide

Example 47A 1-(triisopropylsilyl)-1H-indol-6-ol

6-Benzyloxy-indole (1.0 g) was treated with NaH (135 mg) and triisopropylsilyl chloride (1.0 g) in tetrahydrofuran for 1 hour, purified by flash chromatography (98/2 ethyl acetate/hexanes), then debenzylated in ethanol (35 mL) using Pearlman's catalyst (0.19 g) and a hydrogen balloon.

Example 47B methyl 2-(1H-indol-6-yloxy)-4-(4-((4'-chlorobiphenyl-2-yl)methyl)piperazin-1-yl)benzoate This example was prepared by substituting EXAMPLE 34A for EXAMPLE 18E and EXAMPLE 47A for phenol in EXAMPLE 18F. In this example, the crude material from the ether formation was desilated using tetrabutyl ammonium fluoride in tetrahydrofuran/water 95/5 prior to purification.

Example 47C 2-(1H-indol-6-yloxy)-4-(4-((4'-chlorobiphenyl-2-yl)methyl)piperazin-1-yl)benzoic acid This example was prepared by substituting EXAMPLE 47B for EXAMPLE 1D in EXAMPLE 1E.

Example 47D

4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(1H-indol-6-yloxy)benzamide This example was prepared by substituting EXAMPLE 47C for EXAMPLE 27G and EXAMPLE 154A for EXAMPLE 1F in EXAMPLE 27H. $^1$H NMR (300 MHz, dimethylsulfoxide-$d_6$) δ 11.50 (v br s, 1H), 11.00 (s, 1H), 9.38 (br s, 1H), 8.64 (t, 1H), 8.58 (d, 1H), 7.75 (dd, 1H), 7.65 (br s, 1H), 7.55 (d, 1H), 7.50 (m, 5H), 7.39 (m, 2H), 7.30 (m, 2H), 7.00 (d, 1H), 6.90 (s, 1H), 6.70 (m, 2H), 6.42 (m, 1H), 6.30 (s, 1H), 4.35 (br s, 1H), 3.78 (br s, 1H), 3.40 (m, 2H), 3.35-2.80 (envelope, 8H), 3.10 (m, 2H), 2.78, 2.76 (both s, total 6H), 1.95 (m, 2H).

Example 48

4-{4-[(4'-chloro-1,1'-biphenyl-2-yl)methyl]piperazin-1-yl}-2-(isoquinolin-7-yloxy)-N-({4-[(3-morpholin-4-ylpropyl)amino]-3-nitrophenyl}sulfonyl)benzamide

Example 48A

This EXAMPLE was prepared by substituting EXAMPLE 34A for EXAMPLE 18E and isoquinolin-7-ol for phenol in EXAMPLE 18F.

Example 48B 4-(4-((4'-chlorobiphenyl-2-yl)methyl)piperazin-1-yl)-2-(isoquinolin-7-yloxy)benzoic acid This EXAMPLE was prepared by substituting EXAMPLE 48A for EXAMPLE 1D in EXAMPLE 1E.

Example 48C

4-{4-[(4'-chloro-1,1'-biphenyl-2-yl)methyl]piperazin-1-yl}-2-(isoquinolin-7-yloxy)-N-({4-[(3-morpholin-4-ylpropyl)amino]-3-nitrophenyl}sulfonyl)benzamide This EXAMPLE was prepared by substituting EXAMPLE 48B for EXAMPLE 27G and EXAMPLE 7A for EXAMPLE 1F in EXAMPLE 27H. $^1$H NMR (300 MHz, dimethylsulfoxide-$d_6$) δ 11.98 (v br s, 1H), 9.70 (v br s, 2H), 9.10 (s, 1H), 8.56 (t, 1H), 8.42 (d, 1H), 8.13 (d, 1H), 7.93 (d, 1H), 7.81 (d, 1H), 7.70 (br s, 1H), 7.60 (m, 2H), 7.50 (m, 5H), 7.40 (d, 2H), 7.35 (m, 1H), 7.14 (d, 1H), 6.84 (m, 2H), 6.70 (d, 1H), 4.38 (br s, 1H), 4.00 (m, 2H), 3.80 (br s, 1H), 3.40 (m, 4H), 3.30-2.80 (envelope, 10H), 3.20 (m, 4H), 1.92 (m, 2H).

Example 49

4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(isoquinolin-7-yloxy)benzamide This example was prepared by substituting EXAMPLE 48B for EXAMPLE 27G and EXAMPLE 154A for EXAMPLE 1F in EXAMPLE 27H. $^1$H NMR (300 MHz, dimethylsulfoxide-$d_6$) δ 11.98 (v br s, 1H), 9.40 (br s, 2H), 9.10 (s, 1H), 8.56 (t, 1H), 8.40 (d, 1H), 8.13 (d, 1H), 7.93 (d, 1H), 7.81 (d, 1H), 7.70 (br s, 1H), 7.60 (m, 2H), 7.50 (m, 5H), 7.40 (d, 2H), 7.35 (m, 1H), 7.14 (d, 1H), 6.84 (m, 2H), 6.70 (d, 1H), 4.38 (br s, 1H), 3.78 (br s, 1H), 3.42 (m, 2H), 3.35-2.80 (envelope, 8H), 3.15 (m, 2H), 2.81, 2.79 (both s, total 6H), 1.93 (m, 2H).

Example 50

4-(4-{[2-(4-chlorophenyl)-5,5-dimethylcyclohex-1-en-1-yl]methyl}piperazin-1-yl)-2-(1H-indol-5-yloxy)-N-({4-[(3-morpholin-4-ylpropyl)amino]-3-nitrophenyl}sulfonyl)benzamide Example 50A methyl 2-(1H-indol-5-yloxy)-4-(4-((2-(4-chlorophenyl)-5,5-dimethylcyclohex-1-enyl)methyl)piperazin-1-yl)benzoate This example was prepared by substituting EXAMPLE 19D for EXAMPLE 34A in EXAMPLE 40B.

Example 50B 2-(1H-indol-5-yloxy)-4-(4-((2-(4-chlorophenyl)-5,5-dimethylcyclohex-1-enyl)methyl)piperazin-1-yl)benzoic acid This example was prepared by substituting EXAMPLE 50A for EXAMPLE 1D in EXAMPLE 1E.

Example 50C 4-(4-{[2-(4-chlorophenyl)-5,5-dimethylcyclohex-1-en-1-yl]methyl}piperazin-1-yl)-2-(1H-indol-5-yloxy)-N-({4-[(3-morpholin-4-ylpropyl)amino]-3-nitrophenyl}sulfonyl)benzamide This example was prepared by substituting EXAMPLE 50B for EXAMPLE 27G and EXAMPLE 7A for EXAMPLE 1F in EXAMPLE 27H. $^1$H NMR (300 MHz, dimethylsulfoxide-$d_6$) δ 11.98 (br s, 1H), 11.20 (s, 1H), 9.70 (v br s, 1H), 9.35 (v br s, 1H), 8.71 (t, 1H), 8.62 (d, 1H), 7.86 (dd, 1H), 7.54 (d, 1H), 7.40 (m, 4H), 7.12 (m, 4H), 6.87 (dd, 1H), 6.70 (dd, 1H), 6.40 (m, 1H), 6.20 (d, 1H), 3.98 (m, 2H), 3.50, 3.40, 3.30 (all m, total 12H), 3.19 (m, 2H), 3.00 (m, 4H), 2.75 (br s, 2H), 2.23 (br m, 2H), 1.97 (br m, 2H), 1.43 (br t, 2H), 0.98 (s, 6H).

Example 51

4-(4-{[2-(4-chlorophenyl)-5,5-dimethylcyclohex-1-en-1-yl]methyl}piperazin-1-yl)-N-[(4-{[3-(dimethylamino)propyl]amino}-3-nitrophenyl)sulfonyl]-2-(1H-indol-5-yloxy)benzamide This example was prepared by substituting EXAMPLE 50B for EXAMPLE 27G and EXAMPLE 154A for EXAMPLE 1F in EXAMPLE 27H. $^1$H NMR (300 MHz, dimethylsulfoxide-$d_6$) δ 11.42 (br s, 1H), 11.20 (s, 1H), 9.40 (v br s, 1H), 9.30 (v br s, 1H), 8.66 (t, 1H), 8.61 (d, 1H), 7.86 (dd, 1H), 7.54 (d, 1H), 7.40 (m, 4H), 7.18 (d, 1H), 7.12 (m, 3H), 6.87 (dd, 1H), 6.70 (dd, 1H), 6.40 (s, 1H), 6.20 (s, 1H), 3.60 (br s, 2H), 3.50 (m, 4H), 3.35 (br s, 2H), 3.13 (m, 3H), 3.00 (br m, 2H), 2.78, 2.77 (both s, total 6H), 2.70 (br s, 1H), 2.12 (br m, 2H), 1.97 (m, 4H), 1.42 (br t, 2H), 0.97 (s, 6H).

Example 52

4-(4-{[2-(4-chlorophenyl)-4,4-dimethylcyclohex-1-en-1-yl]methyl}piperazin-1-yl)-2-(1H-indol-5-yloxy)-N-({4-[(3-morpholin-4-ylpropyl)amino]-3-nitrophenyl}sulfonyl)benzamide This example was prepared by substituting EXAMPLE 26C for EXAMPLE 27G and EXAMPLE 7A for EXAMPLE 1F in EXAMPLE 27H. $^1$H NMR (300 MHz, dimethylsulfoxide-$d_6$) δ 11.40 (br s, 1H), 11.20 (s, 1H), 9.60 (v br s, 1H), 9.25 (v br s, 1H), 8.70 (t, 1H), 8.62 (d, 1H), 7.86 (dd, 1H), 7.54 (d, 1H), 7.40 (m, 4H), 7.18 (d, 1H), 7.09 (d, 2H), 6.87 (dd, 1H), 6.70 (dd, 1H), 6.40 (m, 1H), 6.20 (s, 1H), 3.98 (m, 2H), 3.50, 3.40, 3.30 (all m, total 12H), 3.19 (m, 2H), 3.00 (m, 4H), 2.75 (br s, 2H), 2.18 (br m, 2H), 2.00 (br m, 4H), 1.43 (br t, 2H), 0.96 (s, 6H).

Example 53

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(H-indol-5-yloxy)benzamide This example was prepared by substituting EXAMPLE 55B for EXAMPLE 27G and EXAMPLE 154A for EXAMPLE 1F in EXAMPLE 27H. $^1$H NMR (300 MHz, dimethylsulfoxide-$d_6$) δ 11.41 (br s, 1H), 11.20 (s, 1H), 9.35 (v br s, 2H), 8.66 (t, 1H), 8.62 (d, 1H), 7.86 (dd, 1H), 7.54 (d, 1H), 7.40 (m, 4H), 7.18 (d, 1H), 7.13 (d, 1H), 7.09 (d, 2H), 6.87 (dd, 1H), 6.70 (dd, 1H), 6.40 (m, 1H), 6.20 (s, 1H), 3.50 (m, 4H), 3.35 (br s, 2H), 3.13 (m, 3H), 3.00 (br m, 2H), 2.78, 2.77 (both s, total 6H), 2.70 (br s, 1H), 2.20 (br m, 2H), 2.00 (m, 2H), 1.93 (m, 2H), 1.42 (br t, 2H), 0.97 (s, 6H).

Example 54

4-(4-{[2-(4-chlorophenyl)-5,5-dimethylcyclohex-1-en-1-yl]methyl}piperazin-1-yl)-2-(1H-indol-4-yloxy)-N-({4-[(3-morpholin-4-ylpropyl)amino]-3-nitrophenyl}sulfonyl)benzamide Example 54A methyl 2-(1H-indol-4-yloxy)-4-(4-((2-(4-chlorophenyl)-5,5-dimethylcyclohex-1-enyl)methyl)piperazin-1-yl)benzoate This example was prepared by substituting EXAMPLE 19D for EXAMPLE 34A in EXAMPLE 45B.

Example 54B 2-(1H-indol-4-yloxy)-4-(4-((2-(4-chlorophenyl)-5,5-dimethylcyclohex-1-enyl)methyl)piperazin-1-yl)benzoic acid This example was prepared by substituting EXAMPLE 54A for EXAMPLE 1D in EXAMPLE 1E.

Example 54C 4-(4-{[2-(4-chlorophenyl)-5,5-dimethylcyclohex-1-en-1-yl]methyl}piperazin-1-yl)-2-(1H-indol-4-yloxy)-N-({4-[(3-morpholin-4-ylpropyl)amino]-3-nitrophenyl}sulfonyl)benzamide This example was prepared by substituting EXAMPLE 54B for EXAMPLE 27G and EXAMPLE 7A for EXAMPLE 1F in EXAMPLE 27H. $^1$H NMR (300 MHz, dimethylsulfoxide-$d_6$) δ 11.50 (br s, 1H), 11.27 (s, 1H), 9.60 (v br s, 1H), 9.20 (v br s, 1H), 8.65 (t, 1H), 8.55 (d, 1H), 7.80 (dd, 1H), 7.57 (d, 1H), 7.40 (d, 2H), 7.30 (dd, 1H), 7.12 (d, 2H), 7.10 (d, 2H), 7.00 (dd, 1H), 6.73 (dd, 1H), 6.46 (d, 1H), 6.30 (s, 1H), 6.23 (m, 1H), 3.98 (m, 2H), 3.60, 3.50, 3.40 (all m, total 12H), 3.19 (m, 2H), 3.00 (m, 4H), 2.75 (br s, 2H), 2.23 (br m, 2H), 1.97 (br m, 4H), 1.43 (br t, 2H), 0.98 (s, 6H).

Example 55

4-(4-{[2-(4-chlorophenyl)-4,4-dimethylcyclohex-1-en-1-yl]methyl}piperazin-1-yl)-2-(1H-indol-4-yloxy)-N-({4-[(3-morpholin-4-ylpropyl)amino]-3-nitrophenyl}sulfonyl)benzamide

Example 55A methyl 2-(1H-indol-4-yloxy)-4-(4-((2-(4-chlorophenyl)-4,4-dimethylcyclohex-1-enyl)methyl)piperazin-1-yl)benzoate This example was prepared by substituting EXAMPLE 45A for phenol in EXAMPLE 18F. Here the crude material from the ether formation was desilated using tetrabutyl ammonium fluoride in tetrahydrofuran/water 95/5 prior to purification.

Example 55B 2-(1H-indol-4-yloxy)-4-(4-((2-(4-chlorophenyl)-4,4-dimethylcyclohex-1-enyl)methyl)piperazin-1-yl)benzoic acid This example was prepared by substituting EXAMPLE 55A for EXAMPLE 1D in EXAMPLE 1E.

Example 55C 4-(4-{[2-(4-chlorophenyl)-4,4-dimethylcyclohex-1-en-1-yl]methyl}piperazin-1-yl)-2-(1H-indol-4-yloxy)-N-({4-[(3-morpholin-4-ylpropyl)amino]-3-nitrophenyl}sulfonyl)benzamide This example was prepared by substituting EXAMPLE 55B for EXAMPLE 27G and EXAMPLE 7A for EXAMPLE 1F in EXAMPLE 27H. $^1$H NMR (300 MHz, dimethylsulfoxide-$d_6$) δ 11.50 (br s, 1H), 11.25 (s, 1H), 9.60 (v br s, 1H), 9.20 (v br s, 1H), 8.65 (t, 1H), 8.55 (d, 1H), 7.80 (dd, 1H), 7.57 (d, 1H), 7.40 (d, 2H), 7.30 (dd, 1H), 7.20 (d, 1H), 7.10 (m, 3H), 7.00 (dd, 1H), 6.73 (dd, 1H), 6.46 (d, 1H), 6.30 (s, 1H), 6.23 (m, 1H), 3.98 (m, 2H), 3.60, 3.50, 3.40 (all m, total 12H), 3.19 (m, 2H), 3.00 (m, 4H), 2.75 (br s, 2H), 2.20 (br m, 2H), 2.00 (br m, 4H), 1.43 (br t, 2H), 0.98 (s, 6H).

Example 56

4-(4-{[2-(4-chlorophenyl)-5,5-dimethylcyclohex-1-en-1-yl]methyl}piperazin-1-yl)-N-[(4-{[3-(dimethylamino)propyl]amino}-3-nitrophenyl)sulfonyl]-2-(1H-indol-4-yloxy)benzamide This example was prepared by substituting EXAMPLE 54B for EXAMPLE 27G and EXAMPLE 154A for EXAMPLE 1F in EXAMPLE 27H. $^1$H NMR (300 MHz, dimethylsulfoxide-$d_6$) δ 11.55 (br s, 1H), 11.27 (s, 1H), 9.40 (v br s, 1H), 9.35 (v br s, 1H), 8.65 (t, 1H), 8.55 (d, 1H), 7.79 (dd, 1H), 7.57 (d, 1H), 7.40 (d, 2H), 7.30 (dd, 1H), 7.20 (d, 1H), 7.10 (m, 3H), 7.00 (dd, 1H), 6.73 (dd, 1H), 6.46 (d, 1H), 6.30 (s, 1H), 6.23 (m, 1H), 3.50 (m, 4H), 3.35 (br s, 2H), 3.13 (m, 3H), 3.00 (br m, 2H), 2.78, 2.77 (both s, total 6H), 2.70 (br s, 1H), 2.22 (br m, 2H), 1.97 (m, 2H), 1.93 (m, 2H), 1.42 (br t, 2H), 0.97 (s, 6H).

Example 57

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(1H-indol-4-yloxy)benzamide This example was prepared by substituting EXAMPLE 55B for EXAMPLE 27G and EXAMPLE 154A for EXAMPLE 1F in EXAMPLE 27H. $^1$H NMR (300 MHz, dimethylsulfoxide-$d_6$) δ 11.50 (br s, 1H), 11.25 (s, 1H), 9.60 (v br s, 1H), 9.20 (v br s, 1H), 8.65 (t, 1H), 8.55 (d, 1H), 7.79 (dd, 1H), 7.57 (d, 1H), 7.40 (d, 2H), 7.30 (dd, 1H), 7.20 (d, 1H), 7.10 (m, 3H), 7.00 (dd, 1H), 6.73 (dd, 1H), 6.46 (d, 1H), 6.30 (s, 1H), 6.23 (m, 1H), 3.50 (m, 4H), 3.35 (br s, 2H), 3.13 (m, 3H), 3.00 (br m, 2H), 2.78, 2.77 (both s, total 6H), 2.70 (br s, 1H), 2.20 (br m, 2H), 2.00 (m, 2H), 1.93 (m, 2H), 1.42 (br t, 2H), 0.97 (s, 6H).

Example 58

4-{4-[(4'-chloro-1,1'-biphenyl-2-yl)methyl]piperazin-1-yl}-2-(1H-indol-4-yloxy)-N-({4-[(3-morpholin-4-ylpropyl)amino]-3-nitrophenyl}sulfonyl)benzamide This example was prepared by substituting EXAMPLE 45C for EXAMPLE 27G and EXAMPLE 7A for EXAMPLE 1F in EXAMPLE 27H. $^1$H NMR (300 MHz, dimethylsulfoxide-$d_6$) δ 11.50 (br s, 1H), 11.24 (s, 1H), 9.50 (v br s, 1H), 8.67 (t, 1H), 8.52 (d, 1H), 7.78 (dd, 1H), 7.70 (br s, 1H), 7.55 (d, 1H), 7.50 (m, 4H), 7.38 (d, 2H), 7.30 (dd, 2H), 7.18 (d, 1H), 7.08 (d, 1H), 6.96 (dd, 1H), 6.75 (dd, 1H), 6.40 (d, 1H), 6.33 (s, 1H), 6.23 (s, 1H), 4.38 (br s, 1H), 4.00 (m, 2H), 3.80 (br s, 1H), 3.40 (m, 4H), 3.30-2.80 (envelope, 10H), 3.20 (m, 4H), 1.95 (m, 2H).

Example 59

4-{4-[(4'-chloro-1,1'-biphenyl-2-yl)methyl]piperazin-1-yl}-2-(1H-indol-5-yloxy)-N-({4-[(3-morpholin-4-ylpropyl)amino]-3-nitrophenyl}sulfonyl)benzamide This example was prepared by substituting EXAMPLE 40C for EXAMPLE 27G and EXAMPLE 7A for EXAMPLE 1F in EXAMPLE 27H. $^1$H NMR (300 MHz, dimethylsulfoxide-d$_6$) δ 11.40 (br s, 1H), 11.19 (s, 1H), 9.60 (v br s, 1H), 8.69 (t, 1H), 8.60 (d, 1H), 7.83 (dd, 1H), 7.65 (br s, 1H), 7.50 (m, 5H), 7.38 (m, 5H), 7.12 (m, 2H), 6.83 (dd, 1H), 6.69 (dd, 1H), 6.39 (m, 1H), 6.20 (d, 1H), 4.38 (br s, 1H), 4.00 (m, 2H), 3.80 (br s, 1H), 3.40 (m, 4H), 3.30-2.80 (envelope, 10H), 3.20 (m, 4H), 1.96 (m, 2H).

Example 60

4-{4-[(4'-chloro-1,1'-biphenyl-2-yl)methyl]piperazin-1-yl}-N-[(4-methoxyphenyl)sulfonyl]-2-phenoxybenzamide This example was prepared by substituting EXAMPLE 1E for EXAMPLE 27G and 4-methoxybenzenesulfonamide for EXAMPLE 1F in EXAMPLE 27H. $^1$H NMR (500 MHz, dimethylsulfoxide-d$_6$) δ 11.57 (s, 1H), 7.74 (d, 2H), 7.50 (m, 5H), 7.35 (m, 6H), 7.10 (t, 1H), 7.02 (m, 2H), 6.87 (d, 2H), 6.75 (dd, 1H), 6.41 (s, 1H), 4.36 (m, 2H), 3.83 (s, 3H), 3.76 (m, 2H), 3.23 (m, 2H), 3.01 (m, 2H), 2.84 (m, 2H).

Example 61

4-{4-[(4'-chloro-1,1'-biphenyl-2-yl)methyl]piperazin-1-yl}-N-[(4-methylphenyl)sulfonyl]-2-phenoxybenzamide This example was prepared by substituting EXAMPLE 1E for EXAMPLE 27G and 4-methylbenzenesulfonamide for EXAMPLE 1F in EXAMPLE 27H. $^1$H NMR (500 MHz, dimethylsulfoxide-d$_6$) δ 11.64 (s, 1H), 7.68 (d, 2H), 7.50 (m, 5H), 7.38 (m, 2H), 7.32 (m, 6H), 7.11 (t, 1H), 6.87 (d, 2H), 6.75 (dd, 1H), 6.41 (s, 1H), 4.36 (m, 2H), 3.76 (m, 2H), 3.23 (m, 2H), 3.01 (m, 2H), 2.84 (m, 2H), 2.37 (s, 3H).

Example 62

4-{4-[(4'-chloro-1,1'-biphenyl-2-yl)methyl]piperazin-1-yl}-2-(1H-indol-5-yloxy)-N-({4-[(tetrahydro-2H-pyran-4-ylmethyl)amino]-3-[(trifluoromethyl)sulfonyl]phenyl}sulfonyl)benzamide This example was prepared by substituting EXAMPLE 40C for EXAMPLE 27G and EXAMPLE 163A for EXAMPLE 1F in EXAMPLE 27H. $^1$H NMR (300 MHz, dimethylsulfoxide-d$_6$) δ 11.46 (s, 1H), 11.16 (s, 1H), 8.17 (d, 1H), 7.88 (dd, 1H), 7.68 (br s, 1H), 7.50 (m, 5H), 7.36 (m, 6H), 7.13 (s, 1H), 7.03 (d, 1H), 6.84 (dd, 1H), 6.68 (dd, 1H), 6.39 (m, 1H), 6.21 (br s, 1H), 4.32 (s, 2H), 3.84 (dd, 2H), 3.25 (m, 7H), 2.93 (m, 4H), 1.84 (m, 2H), 1.54 (m, 2H), 1.24 (m, 2H).

Example 63

4-{4-[(4'-chloro-1,1'-biphenyl-2-yl)methyl]piperazin-1-yl}-2-(1H-indol-4-yloxy)-N-({4-[(tetrahydro-2H-pyran-4-ylmethyl)amino]-3-[(trifluoromethyl)sulfonyl]phenyl}sulfonyl)benzamide This example was prepared by substituting EXAMPLE 45C for EXAMPLE 27G and EXAMPLE 163A for EXAMPLE 1F in EXAMPLE 27H. $^1$H NMR (300 MHz, dimethylsulfoxide-d$_6$) δ 11.58 (s, 1H), 11.27 (s, 1H), 8.12 (d, 1H), 7.71 (m, 2H), 7.52 (m, 5H), 7.32 (m, 5H), 7.18 (d, 1H), 6.96 (m, 2H), 6.74 (dd, 1H), 6.36 (m, 2H), 6.26 (m, 1H), 4.32 (s, 2H), 3.84 (dd, 2H), 3.25 (m, 7H), 2.93 (m, 4H), 1.84 (m, 2H), 1.54 (m, 2H), 1.24 (m, 2H).

Example 64

4-{4-[(4'-chloro-1,1'-biphenyl-2-yl)methyl]piperazin-1-yl}-N-({4-{[3-(dimethylamino)propyl]amino}-3-[(trifluoromethyl)sulfonyl]phenyl}sulfonyl)-2-(1H-indol-5-yloxy)benzamide This example was prepared by substituting EXAMPLE 40C and EXAMPLE 170A for EXAMPLE 27G and EXAMPLE 1F respectively, in EXAMPLE 27H. $^1$H NMR (300 MHz, dimethylsulfoxide-d$_6$) δ 11.46 (br s, 1H), 11.18 (s, 1H), 8.21 (d, 1H), 7.98 (dd, 1H), 7.50 (m, 6H), 7.41 (m, 5H), 7.29 (br s, 1H), 7.17 (s, 1H), 7.08 (d, 1H), 6.84 (dd, 1H), 6.68 (dd, 1H), 6.40 (m, 1H), 6.18 (br s, 1H), 4.32 (br s, 2H), 3.59 (m, 4H), 3.25 (m, 2H), 3.05 (m, 4H), 2.90 (m, 2H), 2.77 (d, 6H), 1.88 (m, 2H).

Example 65

4-{4-[(4'-chloro-1,1'-biphenyl-2-yl)methyl]piperazin-1-yl}-2-(1H-indol-4-yloxy)-N-({4-[(3-morpholin-4-ylpropyl)amino]-3-[(trifluoromethyl)sulfonyl]phenyl}sulfonyl)benzamide

Example 65A 4-(3-morpholinopropylamino)-3-(trifluoromethylsulfonyl)benzenesulfonamide This example was prepared by substituting EXAMPLE 159C and 3-morpholinopropan-1-amine for 4-fluoro-3-nitrobenzenesulfonamide and (tetrahydropyran-4-yl)methylamine respectively, in EXAMPLE 1F.

Example 65B

4-{4-[(4'-chloro-1,1'-biphenyl-2-yl)methyl]piperazin-1-yl}-2-(1H-indol-4-yloxy)-N-({4-[(3-morpholin-4-ylpropyl)amino]-3-[(trifluoromethyl)sulfonyl]phenyl}sulfonyl)benzamide This example was prepared by substituting EXAMPLE 40C and EXAMPLE 65A for EXAMPLE 27G and EXAMPLE 1F respectively, in EXAMPLE 27H. $^1$H NMR (300 MHz, dimethylsulfoxide-d$_6$) δ 11.46 (br s, 1H), 11.18 (s, 1H), 8.18 (d, 1H), 7.91 (m, 1H), 7.50 (m, 6H), 7.41 (m, 5H), 7.30 (m, 1H), 7.19 (d, 1H), 7.08 (m, 1H), 6.99 (m, 1H), 6.72 (dd, 1H), 6.48 (br s, 1H), 6.25 (m, 1H), 4.29 (br s, 2H), 4.01 (m; 2H) 3.59 (m, 2H), 3.41 (m, 4H), 3.05 (m, 10H), 2.58 (m, 2H), 1.91 (m, 2H).

Example 66

N-[(3-{[chloro(difluoro)methyl]sulfonyl}-4-{[3-(dimethylamino)propyl]amino}phenyl)sulfonyl]-4-(4-{[2-(4-chlorophenyl)-4,4-dimethylcyclohex-1-en-1-yl]methyl}piperazin-1-yl)-2-(1H-indol-4-yloxy)benzamide

Example 66A (difluoromethyl)(2-fluorophenyl)sulfane

Powdered NaOH (31.2 g), tris(2-(2-methoxyethoxy)ethyl)amine (5 mL) and 2-fluorobenzene thiol (33.6 mL) in benzene (400 mL) was saturated with chlorodifluoromethane, stirred at 80° C. for 30 minutes and filtered through diatomaceous earth (Celite®). The filtrate was washed with saturated NaHCO₃ and the water layer was extracted with diethyl ether. The extracts were combined and dried (MgSO₄), filtered and concentrated.

Example 66B 1-(difluoromethylsulfonyl)-2-fluorobenzene

EXAMPLE 66A (46 g) in 1:1:2 CCl₄/CH₃CN/water (1.2 L) at 25° C. was treated with NaIO₄ (164.6 g) and RuCl₃.xH₂O (534 mg), stirred for 18 hours, diluted with dichloromethane and filtered through diatomaceous earth (Celite®). The filtrate was washed with saturated NaHCO₃ and dried (Na₂SO₄), filtered and concentrated. The concentrate was filtered through silica gel.

Example 66C 1-(chlorodifluoromethylsulfonyl)-2-fluorobenzene

EXAMPLE 66B (25 g) and N-chlorosuccinimide (17.55 g) in tetrahydrofuran (690 mL) at −78° C. was treated with lithium hexamethyldisilazide (178.5 mL) over 1 hour, stirred for 1 hour and quenched with ammonium chloride. The mixture was extracted with ethyl acetate, and the extract was washed with brine and dried (MgSO₄), filtered and concentrated. The concentrate was chromatographed on silica gel with 0-5% ethyl acetate/hexanes.

Example 66D 3-(chlorodifluoromethylsulfonyl)-4-fluorobenzene-1-sulfonyl chloride EXAMPLE 66C (44 g) in chlorosulfonic acid (36.7 mL) at 120° C. was stirred for 18 hours, cooled to 25° C., pipetted onto crushed ice and extracted with ethyl acetate. The extract was washed with water and brine and dried (MgSO₄), filtered and concentrated.

Example 66E 3-(chlorodifluoromethylsulfonyl)-4-fluorobenzene-sulfonamide

EXAMPLE 66D (22 g) in isopropanol (690 mL) at −78° C. was treated with aqueous ammonia (90 mL) over 1 hour, stirred for another hour, quenched with 6M HCl (300 mL), warmed to 25° C. and concentrated. The concentrate was mixed with water and extracted with ethyl acetate. The extract was dried (MgSO₄), filtered and concentrated. The concentrate was recrystallized from hexanes/ethyl acetate.

Example 66F 3-(chlorodifluoromethylsulfonyl)-4-(3-(dimethylamino)propylamino)benzenesulfonamide This example was prepared by substituting EXAMPLE 66E and N,N-dimethylpropane-1,3-diamine for 4-fluoro-3-nitrobenzenesulfonamide and (tetrahydropyran-4-yl)methylamine respectively, in EXAMPLE 1F.

Example 66G

N-[(3-{[chloro(difluoro)methyl]sulfonyl}-4-{[3-(dimethylamino)propyl]amino}phenyl)sulfonyl]-4-(4-{[2-(4-chlorophenyl)-4,4-dimethylcyclohex-1-en-1-yl]methyl}piperazin-1-yl)-2-(1H-indol-4-yloxy)benzamide This example was prepared by substituting EXAMPLE 54B and EXAMPLE 66F for EXAMPLE 27G and EXAMPLE 1F respectively, in EXAMPLE 27H. ¹H NMR (300 MHz, dimethylsulfoxide-d₆) δ 11.20 (s, 1H), 8.28 (m, 1H), 7.99 (m, 1H), 7.55 (m, 2H), 7.38 (m, 2H), 7.21 (m, 3H), 7.09 (d, 2H), 6.98 (m, 1H), 6.71 (m, 1H), 6.41 (m, 2H), 6.21 (m, 1H), 3.57 (m, 2H), 3.28 (m, 4H), 2.84 (m, 6H), 2.67 (m, 5H), 2.19 (m, 2H), 2.02 (m, 2H), 1.77 (br s, 2H), 1.61 (m, 2H), 1.46 (m, 2H), 0.94 (s, 6H).

Example 67

N-[(3-{[chloro(difluoro)methyl]sulfonyl}-4-{[3-(dimethylamino)propyl]amino}phenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide This example was prepared by substituting EXAMPLE 26C and EXAMPLE 66F for EXAMPLE 27G and EXAMPLE 1F respectively, in EXAMPLE 27H. ¹H NMR (300 MHz, dimethylsulfoxide-d₆) δ 11.20 (s, 1H), 8.28 (m, 1H), 8.05 (m, 1H), 7.99 (m, 1H), 7.55 (m, 2H), 7.38 (m, 2H), 7.21 (m, 3H), 7.09 (d, 2H), 6.98 (m, 1H), 6.71 (m, 1H), 6.41 (m, 2H), 6.21 (m, 1H), 3.57 (m, 2H), 3.28 (m, 4H), 3.05 (m, 2H), 2.96 (m, 2H), 2.88 (s, 3H), 2.78 (m, 2H), 2.68 (m, 3H), 2.19 (m, 2H), 2.01 (br s, 2H), 1.72 (m, 2H), 1.45 (m, 2H), 0.93 (s, 6H).

Example 68

2-(1H-indol-4-yloxy)-4-(4-{[2-(4-methoxyphenyl)-4,4-dimethylcyclohex-1-en-1-yl]methyl}piperazin-1-yl)-N-({3-nitro-4-[(3-pyrrolidin-1-ylpropyl)amino]phenyl}sulfonyl)benzamide Example 68A (2-bromo-4,4-dimethylcyclohex-1-enyl)methanol N,N-dimethylformamide (18.41 ml) was taken up in chloroform (64 ml) and the resulting solution was cooled in an ice bath. Phosphorus tribromide (20.18 ml) was added dropwise over 15 minutes. The resulting suspension was then heated to 70° C. for 30 minutes. A solution of 3,3-dimethylcyclohexanone (10 g) in chloroform (21 ml) was added dropwise over 30 minutes. The mixture was stirred at 70° C. for another 2 hours. The mixture was then allowed to cool to room temperature. The solution was cautiously poured over ice. Solid sodium bicarbonate was added to neutralize acid. The mixture was extracted three times with ether, and the extracts were washed with water and brine and dried (MgSO₄). The solvent was removed under vacuum, and the crude material was flushed through a silica plug with ether as the eluent. After concentration, the crude material was dissolved in methanol. Sodium borohydride (1.757 g) was added cautiously. The resulting mixture was stirred at room temperature overnight, and diluted with ethyl acetate. The mixture was washed with water and brine and dried (MgSO₄). The solvent was removed under vacuum, and the residue was purified by flash chromatography eluting with 20% ethyl acetate in hexanes to 100% ethyl acetate.

Example 68B methyl 2-(1H-indol-4-yloxy)-4-(piperazin-1-yl)benzoate

This example was prepared by substituting EXAMPLE 24F and piperazine for EXAMPLE 1C and EXAMPLE 1B respectively, in EXAMPLE 1D.

Example 68C methyl 2-(1H-indol-4-yloxy)-4-(4-((2-bromo-4,4-dimethylcyclohex-1-enyl)methyl)piperazin-1-yl) benzoate This example was prepared by substituting EXAMPLE 68A and EXAMPLE 68B for EXAMPLE 18C and EXAMPLE 18D respectively, in EXAMPLE 18E.

Example 68D methyl 2-(1H-indol-4-yloxy)-4-(4-((2-(4-methoxyphenyl)-4,4-dimethylcyclohex 1-enyl)methyl)piperazin-1-yl)benzoate EXAMPLE 68C (142 mg), 4-methoxyphenylboronic acid (45.6 mg), bis(triphenylphosphine)palladium(II) dichloride (8.7 mg), and cesium fluoride (114 mg) were combined in dimethoxyethane (0.9 mL) and methanol (0.4 mL) and heated to 90° C. for 2 hours. The reaction mixture was diluted with ethyl acetate and poured into water. The organic layer was washed with water and with brine, dried ($MgSO_4$), filtered, and concentrated. The resulting solid was triturated with methanol, and filtered.

Example 68E 2-(1H-indol-4-yloxy)-4-(4-((2-(4-methoxyphenyl)-4,4-dimethylcyclohex-1-enyl)methyl)piperazin-1-yl) benzoic acid This example was prepared by substituting EXAMPLE 68D for EXAMPLE 1D in EXAMPLE 1E.

Example 68F 3-nitro-4-(3-(pyrrolidin-1-yl)propylamino)benzenesulfonamide

This example was prepared by substituting 3-(pyrrolidin-1-yl)propan-1-amine for (tetrahydropyran-4-yl)methylamine in EXAMPLE 1F.

Example 68G 2-(1H-indol-4-yloxy)-4-(4-{[2-(4-methoxyphenyl)-4,4-dimethylcyclohex-1-en-1-yl]methyl}piperazin-1-yl)-N-({3-nitro-4-[(3-pyrrolidin-1-ylpropyl)amino]phenyl}sulfonyl)benzamide This example was prepared by substituting EXAMPLE 68E and EXAMPLE 68F for EXAMPLE 27G and EXAMPLE 1F respectively, in EXAMPLE 27H. $^1$H NMR (300 MHz, dimethylsulfoxide-$d_6$) δ 11.56 (brs, 1H), 11.26 (s, 1H), 8.66 (t, 1H), 8.53 (d, 1H), 7.78 (dd, 1H), 7.56 (d, 1H), 7.29 (t, 1H), 7.19 (d, 1H), 7.10 (d, 1H), 6.98 (m, 3H), 6.88 (m, 2H), 6.74 (m, 1H), 6.43 (d, 1H), 6.36 (br s, 1H), 6.23 (m, 1H), 3.73 (s, 3H), 3.62 (m, 2H), 3.52 (m, 4H), 3.22 (m, 4H), 2.99 (m, 4H), 2.18 (m, 2H), 1.99 (m, 6H), 1.84 (m, 2H), 1.45 (m, 2H), 1.23 (m, 2H), 0.94 (s, 6H).

Example 69

4-[4-({4,4-dimethyl-2-[4-(trifluoromethyl)phenyl] cyclohex-1-en-1-yl}methyl)piperazin-1-yl]-2-(1H-indol-4-yloxy)-N-({3-nitro-4-[(3-pyrrolidin-1-ylpropyl)amino]phenyl}sulfonyl)benzamide

Example 69A methyl 2-(1H-indol-4-yloxy)-4-(4-((4,4-dimethyl-2-(4-(trifluoromethyl)phenyl)cyclohex-1-enyl)methyl) piperazin-1-yl)benzoate This example was prepared by substituting 4-(trifluoromethyl)phenylboronic acid for 4-methoxyphenylboronic acid in EXAMPLE 68D.

Example 69B 2-(1H-indol-4-yloxy)-4-(4-((4,4-dimethyl-2-(4-(trifluoromethyl)phenyl)cyclohex-1-enyl)methyl)piperazin-1-yl)benzoic acid This example was prepared by substituting EXAMPLE 69A for EXAMPLE 1D in EXAMPLE 1E.

Example 69C

4-[4-({4,4-dimethyl-2-[4-(trifluoromethyl)phenyl] cyclohex-1-en-1-yl}methyl)piperazin-1-yl]-2-(1H-indol-4-yloxy)-N-({3-nitro-4-[(3-pyrrolidin-1-ylpropyl)amino]phenyl}sulfonyl)benzamide This example was prepared by substituting EXAMPLE 69B and EXAMPLE 68F for EXAMPLE 27G and EXAMPLE 1F respectively, in EXAMPLE 27H. $^1$H NMR (300 MHz, dimethylsulfoxide-$d_6$) δ 11.55 (br s, 1H), 11.26 (s, 1H). 8.66 (t. 1H), 8.53 (d_1H) 778 (m, 1H), 7.67 (m, 2H), 7.56 (m, 1H), 7.29 (m, 3H), 7.19 (d, 1H), 7.10 (d, 1H), 6.98 (m, 1H), 6.72 (m, 1H), 6.46 (m, 1H), 6.36 (br s, 1H), 6.23 (m, 1H), 3.62 (m, 4H), 3.52 (m, 4H), 3.18 (m, 4H), 3.02 (m, 4H), 2.19 (m, 2H), 2.02 (m, 6H), 1.82 (m, 2H), 1.47 (m, 2H), 0.94 (s, 6H).

Example 70

4-[4-({4,4-dimethyl-2-[4-(trifluoromethoxy)phenyl] cyclohex-1-en-1-yl}methyl)piperazin-1-yl]-2-(1H-indol-4-yloxy)-N-({3-nitro-4-[(3-pyrrolidin-1-ylpropyl)amino]phenyl}sulfonyl)benzamide

Example 70A methyl 2-(1H-indol-4-yloxy)-4-(4-((4,4-dimethyl-2-(4-(trifluoromethoxy)phenyl)cyclohex-1-enyl)methyl)piperazin-1-yl)benzoate This example was prepared by substituting 4-(trifluoromethoxy)phenylboronic acid for 4-methoxyphenylboronic acid in EXAMPLE 68D.

Example 70B 2-(1H-indol-4-yloxy)-4-(4-((4,4-dimethyl-2-(4-(trifluoromethoxy)phenyl)cyclohex-1-enyl)methyl)piperazin-1-yl)benzoic acid This example was prepared by substituting EXAMPLE 70A for EXAMPLE 1D in EXAMPLE 1E.

Example 70C

4-[4-({4,4-dimethyl-2-[4-(trifluoromethoxy)phenyl]cyclohex-1-en-1-yl}methyl)piperazin-1-yl]-2-(1H-indol-4-yloxy)-N-({3-nitro-4-[(3-pyrrolidin-1-ylpropyl)amino]phenyl}sulfonyl)benzamide This example was prepared by substituting EXAMPLE 70B and EXAMPLE 68F for EXAMPLE 27G and EXAMPLE 1F respectively, in EXAMPLE 27H. $^1$H NMR (300 MHz, dimethylsulfoxide-$d_6$) δ 11.56 (br s, 1H), 11.26 (s, 1H), 8.66 (t, 1H), 8.54 (d, 1H), 7.80 (m, 1H), 7.63 (m, 2H), 7.56 (m, 3H), 7.29 (m, 2H), 7.19 (m, 2H), 6.98 (m, 1H), 6.72 (m, 1H), 6.46 (m, 1H), 6.23 (m, 1H), 3.62 (m, 4H), 3.52 (m, 4H), 3.18 (m, 4H), 3.02 (m, 4H), 2.19 (m, 2H), 2.02 (m, 6H), 1.82 (m, 2H), 1.47 (m, 2H), 0.94 (s, 6H).

Example 71

4-[4-({4,4-dimethyl-2-[3-(trifluoromethyl)phenyl]cyclohex-1-en-1-yl}methyl)piperazin-1-yl]-2-(1H-indol-4-yloxy)-N-({3-nitro-4-[(3-pyrrolidin-1-ylpropyl)amino]phenyl}sulfonyl)benzamide

Example 71A methyl 2-(1H-indol-4-yloxy)-4-(4-((4,4-dimethyl-2-(3-(trifluoromethyl)phenyl)cyclohex-1-enyl)methyl)piperazin-1-yl)benzoate This example was prepared by substituting 3-(trifluoromethyl)phenylboronic acid for 4-methoxyphenylboronic acid in EXAMPLE 68D.

Example 71B 2-(1H-indol-4-yloxy)-4-(4-((4,4-dimethyl-2-(3-(trifluoromethyl)phenyl)cyclohex-1-enyl)methyl)piperazin-1-yl)benzoic acid This example was prepared by substituting EXAMPLE 71A for EXAMPLE 1D in EXAMPLE 1E.

Example 71C

4-[4-({4,4-dimethyl-2-[3-(trifluoromethyl)phenyl]cyclohex-1-en-1-yl}methyl)piperazin-1-yl]-2-(1H-indol-4-yloxy)-N-({3-nitro-4-[(3-pyrrolidin-1-ylpropyl)amino]phenyl}sulfonyl)benzamide This example was prepared by substituting EXAMPLE 71B and EXAMPLE 68F for EXAMPLE 27G and EXAMPLE 1F respectively, in EXAMPLE 27H. $^1$H NMR (300 MHz, dimethylsulfoxide-$d_6$) δ 11.55 (br s, 1H), 11.26 (s, 1H), 8.65 (t, 1H), 8.54 (d, 1H), 7.80 (dd, 1H), 7.63 (m, 2H), 7.56 (m, 3H), 7.38 (m, 2H), 7.29 (t, 1H), 7.19 (d, 1H), 7.11 (d, 1H), 6.98 (t, 1H), 6.72 (m, 1H), 6.46 (m, 1H), 6.31 (m, 1H), 6.23 (m, 1H), 3.58 (m, 7H), 3.18 (m, 4H), 3.02 (m, 4H), 2.19 (m, 3H), 2.02 (m, 6H), 1.82 (m, 2H), 1.47 (m, 2H), 0.96 (s, 6H).

Example 72

4-(4-{[2-(3-fluorophenyl)-4,4-dimethylcyclohex-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide

Example 72A methyl 2-(1H-indol-4-yloxy)-4-(4-((2-(3-fluorophenyl)-4,4-dimethylcyclohex-1-enyl)methyl)piperazin-1-yl)benzoate This example was prepared by substituting 3-fluorophenylboronic acid for 4-methoxyphenylboronic acid in EXAMPLE 68D.

Example 72B 2-(1H-indol-4-yloxy)-4-(4-((2-(3-fluorophenyl)-4,4-dimethylcyclohex-1-enyl)methyl)piperazin-1-yl)benzoic acid This example was prepared by substituting EXAMPLE 72A for EXAMPLE 1D in EXAMPLE 1E.

Example 72C 4-(4-{[2-(3-fluorophenyl)-4,4-dimethylcyclohex-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide This example was prepared by substituting EXAMPLE 72B and EXAMPLE 68F for EXAMPLE 27G and EXAMPLE 1F respectively, in EXAMPLE 27H. $^1$H NMR (300 MHz, dimethylsulfoxide-$d_6$) δ 11.55 (br s, 1H), 11.26 (s, 1H), 8.65 (t, 1H), 8.54 (d, 1H), 7.80 (m, 1H), 7.63 (m, 2H), 7.56 (m, 3H), 7.38 (m, 2H), 7.29 (t, 1H), 7.19 (d, 1H), 7.11 (d, 1H), 6.98 (m, 1H), 6.72 (m, 1H), 6.46 (m, 1H), 6.31 (m, 1H), 6.23 (m, 1H), 3.58 (m, 7H), 3.18 (m, 4H), 3.02 (m, 4H), 2.19 (m, 3H), 2.02 (m, 6H), 1.82 (m, 2H), 1.47 (m, 2H), 0.96 (s, 6H).

Example 73

4-(4-{[2-(4-fluorophenyl)-4,4-dimethylcyclohex-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide

Example 73A methyl 2-(1H-indol-4-yloxy)-4-(4-((2-(4-fluorophenyl)-4,4-dimethylcyclohex-1-enyl)methyl)piperazin-1-yl)benzoate This example was prepared by substituting 4-fluorophenylboronic acid for 4-methoxyphenylboronic acid in EXAMPLE 68D.

Example 73B 2-(1H-indol-4-yloxy)-4-(4-((2-(4-fluorophenyl)-4,4-dimethylcyclohex-1-enyl)methyl)piperazin-1-yl)benzoic acid This example was prepared by substituting EXAMPLE 73A for EXAMPLE 1D in EXAMPLE 1E.

Example 73C 4-(4-{[2-(4-fluorophenyl)-4,4-dimethylcyclohex-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide This example was prepared by substituting EXAMPLE 73B and EXAMPLE 68F for EXAMPLE 27G and EXAMPLE 1F respectively, in EXAMPLE 27H. $^1$H NMR (300 MHz, dimethylsulfoxide-$d_6$) δ 11.56 (br s, 1H), 11.26 (s, 1H), 8.66 (t, 1H), 8.54 (d, 1H), 7.80 (m, 1H), 7.63 (m, 2H), 7.56 (m, 3H), 7.29 (m, 2H), 7.19 (m, 2H), 6.98 (m, 1H), 6.72 (m, 1H), 6.46 (m, 1H), 6.23 (m, 1H), 3.62 (m, 4H), 3.52 (m, 4H), 3.18 (m, 4H), 3.02 (m, 4H), 2.19 (m, 2H), 2.02 (m, 6H), 1.82 (m, 2H), 1.47 (m, 2H), 0.94 (s, 6H).

Example 74

N-({3-{[chloro(difluoro)methyl]sulfonyl}-4-[(1-methylpiperidin-4-yl)amino]phenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide

Example 74A 3-(chlorodifluoromethylsulfonyl)-4-(1-methylpiperidin-4-ylamino)benzenesulfonamide This example was prepared by substituting EXAMPLE 66E and 1-methylpiperidin-4-amine for 4-fluoro-3-nitrobenzenesulfonamide and (tetrahydropyran-4-yl)methylamine respectively, in EXAMPLE 1F.

Example 74B

N-({3-{[chloro(difluoro)methyl]sulfonyl}-4-[(1-methylpiperidin-4-yl)amino]phenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide This example was prepared by substituting EXAMPLE 26C and EXAMPLE 74A for EXAMPLE 1E and EXAMPLE 1F respectively, in EXAMPLE 1G. $^1$H NMR (300 MHz, dimethylsulfoxide-$d_6$) δ 11.07 (s, 1H), 8.11 (d, 1H), 7.89 (dd, 1H), 7.50 (d, 1H), 7.34 (m, 4H), 7.05 (m, 3H), 6.96 (d, 1H), 6.78 (dd, 1H), 6.60 (m, 2H), 6.36 (s, 1H), 6.13 (d, 1H), 3.67 (m, 1H), 2.97 (m, 6H), 2.71 (s, 2H), 2.59 (m, 2H), 2.46 (s, 3H), 2.16 (m, 6H), 1.98 (m, 4H), 1.55 (m, 2H), 1.38 (t, 2H), 0.92 (s, 6H).

Example 75

4-(4-{[2-(4-chlorophenyl)cyclohex-1-en-1-yl]methyl}piperazin-1-yl)-2-(1H-indol-5-yloxy)-N-({4-[(1-methylpiperidin-4-yl)amino]-3-nitrophenyl}sulfonyl)benzamide

Example 75A methyl 2-(1H-indol-5-yloxy)-4-(4-((2-(4-chlorophenyl)cyclohex-1-enyl)methyl)piperazin-1-yl)benzoate This example was prepared by substituting EXAMPLE 149D and EXAMPLE 150A for 4'-chlorobiphenyl-2-carboxaldehyde and tert-butylpiperazine-1-carboxylate respectively, in EXAMPLE 1A.

Example 75B 2-(1H-indol-5-yloxy)-4-(4-((2-(4-chlorophenyl)cyclohex-1-enyl)methyl)piperazin-1-yl)benzoic acid This example was prepared by substituting EXAMPLE 75A for EXAMPLE 1D in EXAMPLE 1E.

Example 75C 4-(4-{[2-(4-chlorophenyl)cyclohex-1-en-1-yl]methyl}piperazin-1-yl)-2-(1H-indol-5-yloxy)-N-({4-[(1-methylpiperidin-4-yl)amino]-3-nitrophenyl}sulfonyl)benzamide This example was prepared by substituting EXAMPLE 75B and EXAMPLE 21A for EXAMPLE 1E and EXAMPLE 1F respectively, in EXAMPLE 1G. $^1$H NMR (300 MHz, dimethylsulfoxide-$d_6$) δ 11.07 (s, 1H), 8.52 (d, 1H), 8.12 (d, 1H), 7.79 (dd, 1H), 7.52 (d, 1H), 7.34 (m, 4H), 7.05 (m, 4H), 6.79 (dd, 1H), 6.59 (dd, 1H), 6.36 (s, 1H), 6.13 (d, 1H), 3.72 (m, 1H), 2.97 (m., 6H), 2.69 (s, 2H) 2.59 (m, 2H), 2.46 (s 3H), 2.16 (m, 6H), 2.11 (m, 2H), 1.98 (m, 2H), 1.70 (m, 2H), 1.62 (m, 4H).

Example 76

4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)amino]-3-[(trifluoromethyl)sulfonyl]phenyl}sulfonyl)benzamide

Example 76A 4-(1-methylpiperidin-4-ylamino)-3-(trifluoromethylsulfonyl)benzenesulfonamide This example was prepared by substituting EXAMPLE 159C and 1-methylpiperidin-4-amine for 4-fluoro-3-nitrobenzenesulfonamide and (tetrahydropyran-4-yl)methylamine respectively, in EXAMPLE 1F.

Example 76B 4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)amino]-3-[(trifluoromethyl)sulfonyl]phenyl}sulfonyl)benzamide This example was prepared by substituting EXAMPLE 26C and EXAMPLE 76A for EXAMPLE 1E and EXAMPLE 1F respectively, in EXAMPLE 1G. $^1$H NMR (300 MHz, dimethylsulfoxide-$d_6$) δ 11.08 (s, 1H), 8.11 (d, 1H), 7.89 (dd, 1H), 7.50 (d, 1H), 7.34 (m, 4H), 7.05 (m, 3H), 6.98 (d, 1H), 6.78 (dd, 1H), 6.60 (m, 2H), 6.36 (t, 1H), 6.13 (d, 1H), 3.67 (br s, 1H), 2.97 (m, 6H), 2.71 (s, 3H), 2.63 (m, 1H), 2.47 (s, 3H), 2.17 (m, 6H), 1.98 (m, 4H), 1.60 (m, 2H), 1.38 (t, 2H), 0.92 (s, 6H).

Example 77

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(phenoxymethyl)benzamide Example 77A 5-(4-((4'-chlorobiphenyl-2-yl)methyl)piperazin-1-yl)isobenzofuran-1(3H)-one 5-bromoisobenzofuran-1(3H)-one (400 mg), EXAMPLE 1B (646 mg), and potassium phosphate tribasic (558 mg) were added to 1,2-dimethoxyethane (10 mL). The solution was degassed under vacuum and flushed with nitrogen three times.
Tris(dibenzylideneacetone)dipalladium(O) (51.6 mg) and 2-(di-tert-butylphosphino)biphenyl (67.2 mg) were added and the solution was heated to 80° C. for 16 hours. The solution was cooled, filtered, concentrated, and purified by flash column chromatography on silica gel with 30% ethyl acetate in hexanes.

Example 77B 4-(4-((4'-chlorobiphenyl-2-yl)methyl)piperazin-1-yl)-2-(hydroxymethyl)benzoic acid EXAMPLE 77A (256 mg) and lithium hydroxide monohydrate (154 mg) were added to 1,4-dioxane (4 mL) and water (1 mL). The solution was heated to 65° C. for 16 hours, cooled, concentrated under vacuum, and purified by flash column chromatography on silica gel with ethyl acetate. The solution was subsequently dried with anhydrous sodium sulfate to afford crude product of sufficient purity for subsequent use.

Example 77C methyl 4-(4-((4'-chlorobiphenyl-2-yl)methyl)piperazin-1-yl)-2-(hydroxymethyl)benzoate Trimethylsilyldiazomethane (2M solution in diethyl ether, 0.214 mL) was added to EXAMPLE 77B (170 mg) dissolved in ethyl acetate (2 mL) and methanol (2 mL). The solution was mixed for 5 minutes after which the solvent was removed under vacuum to afford crude product of sufficient purity for subsequent use.

Example 77D methyl 4-(4-((4'-chlorobiphenyl-2-yl)methyl)piperazin-1-yl)-2-(phenoxymethyl)benzoate Triphenylphosphine (93 mg) was added to tetrahydrofuran (3 mL) and cooled to 0° C. Diethylazodicarboxylate (40% solution, 0.161 mL) was added, and the solution was stirred at 0° C. for 15 minutes. Phenol (33.3 mg) and EXAMPLE 77C (145 mg) were added, and the solution was allowed to warm to room temperature and mix for 16 hours. The solution was concentrated on vacuum and purified by flash column chromatography on silica gel with 30% ethyl acetate (hexanes) increasing to 50% ethyl acetate (hexanes).

Example 77E 4-(4-((4'-chlorobiphenyl-2-yl)methyl)piperazin-1-yl)-2-(phenoxymethyl)benzoic acid This example was prepared by substituting EXAMPLE 77D for EXAMPLE 77A in EXAMPLE 77B.

Example 77F

This example was prepared by substituting EXAMPLE 77E for EXAMPLE 1E in EXAMPLE 1G. $^1$H NMR (300 MHz, dimethylsulfoxide-$d_6$) δ 8.52 (m, 2H), 7.88 (dd, 1H), 7.84 (d, 1H), 7.50 (m, 2H), 7.48 (s, 3H), 7.37 (m, 2H), 7.26-7.10 (m, 4H), 7.01 (s, 1H), 6.87 (t, 1H), 6.83-6.75 (m, 3H), 5.22 (broad s, 2H), 3.84 (dd, 2H), 3.41-3.10 (m, 10H), 2.39 (broad s, 4H), 1.89 (m, 1H), 1.60 (m, 2H), 1.32-1.18 (m, 2H).

Example 78

4-{4-[(4'-chloro-1,1'-biphenyl-2-yl)methyl]piperazin-1-yl}-N-({4-[(3-morpholin-4-ylpropyl)amino]phenyl}sulfonyl)-2-phenoxybenzamide Example 78A N-(4-sulfamoylphenyl)acrylamide 4-aminobenzenesulfonamide (1.00 g) and pyridine (1.41 mL) were added to 1,4-dioxane (30 mL). Acryloyl chloride (0.49 mL) was added dropwise and the solution was stirred for 3 hours at room temperature. 1M HCl was added, and the solution extracted with ethyl acetate. The extracts were dried using brine and anhydrous sodium sulfate and the solvent was removed to afford crude product of sufficient purity for subsequent use.

Example 78B 3-morpholino-N-(4-sulfamoylphenyl)propanamide

EXAMPLE 78A (359 mg) and morpholine (1.38 mL) were added to acetonitrile (10 mL) and N,N-dimethylformamide (1 mL) and mixed at room temperature for 16 hours.
The solution was concentrated on vacuum, and purified by flash column chromatography on silica gel with 5% methanol in dichloromethane.

Example 78C 4-(3-morpholinopropylamino)benzenesulfonamide

EXAMPLE 78B (268 mg) was added to tetrahydrofuran (4 mL). Borane (1M in tetrahydrofuran, 4.28 mL) was added slowly, and the solution was mixed at room temperature for 16 hours. The reaction was quenched slowly with methanol. N,N-diisopropylethylamine resin (3.42 mmol amine) was added and the solution was mixed at room temperature for 15 minutes. The solution was filtered, concentrated on vacuum, and purified by flash column chromatography on silica gel with 10% methanol in ethyl acetate.

Example 78D

4-{4-[(4'-chloro-1,1'-biphenyl-2-yl)methyl]piperazin-1-yl}-N-({4-[(3-morpholin-4-ylpropyl)amino]phenyl}sulfonyl)-2-phenoxybenzamide This example was prepared by substituting EXAMPLE 78C for EXAMPLE 1F in EXAMPLE 1G. $^1$H NMR (300 MHz, dimethylsulfoxide-$d_6$) δ 10.98 (broad s, 1H), 7.51-7.44 (m, 9H), 7.40-7.31 (m, 3H), 7.26-7.21 (m, 1H), 7.13 (tt, 1H), 6.94 (dd, 2H), 6.75 (dd, 1H), 6.66 (t, 1H), 6.54 (d, 2H), 6.32 (d, 1H), 3.57 (t, 4H), 3.35 (m, 2H), 3.16-3.04 (m, 6H), 2.35 (m, 10H), 1.60 (m, 2H).

Example 79

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(pyridin-3-yloxy)benzamide

Example 79A methyl 4-bromo-2-fluorobenzoate

4-Bromo-2-fluorobenzoic acid (5.00 g) was added to ethyl acetate (35 mL) and methanol (35 mL). Trimethylsilyldiazomethane (2M solution in diethyl ether, 12.56 mL) was added slowly and the solution was mixed at room temperature for 30 minutes. The solvent was removed under vacuum, and the crude material was dissolved in ethyl acetate. The solution was extracted with 0.5M sodium hydroxide and dried with brine then anhydrous sodium sulfate. After filtration, the solvent was removed under vacuum to afford crude product of sufficient purity for subsequent use.

Example 79B methyl 4-bromo-2-(pyridin-3-yloxy)benzoate

EXAMPLE 79A (500 mg), pyridine-3-ol (204 mg), and potassium carbonate (385 mg) were added to N,N-dimethylacetamide (18 mL) and the mixture was heated to 145° C. for 2 hours and then at 130° C. for 16 hours. The solution was cooled, added to water (100 mL), extracted with 70% ethyl acetate in hexanes, and dried with anhydrous sodium sulfate. After filtration, the solution was concentrated under vacuum and purified by flash column chromatography on silica gel with 50-70% ethyl acetate in hexanes.

Example 79C methyl 4-(4-((4'-chlorobiphenyl-2-yl)methyl)piperazin-1-yl)-2-(pyridin-3-yloxy)benzoate EXAMPLE 79B (367 mg), EXAMPLE 1B (410 mg), and potassium phosphate tribasic (379 mg) were added to 1,2-dimethoxyethane (6 mL). The solution was degassed under vacuum and flushed with nitrogen three times.
Tris(dibenzylideneacetone)dipalladium(O) (32.7 mg) and 2-(di-tert-butylphosphino)biphenyl (42.6 mg) were added and the solution was heated to 80° C. for 16 hours. The solution was cooled, filtered, concentrated, and purified by flash column chromatography on silica gel with 50-70% ethyl acetate in hexanes.

Example 79D 4-(4-((4'-chlorobiphenyl-2-yl)methyl)piperazin-1-yl)-2-(pyridin-3-yloxy)benzoic acid This example was prepared by substituting EXAMPLE 79C for EXAMPLE 1D in EXAMPLE 1E.

Example 79E

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(pyridin-3-yloxy)benzamide This example was prepared by substituting EXAMPLE 79D for EXAMPLE 1E in EXAMPLE 1G. $^1$H NMR (300 MHz, dimethylsulfoxide-$d_6$) δ 11.72 (broad s, 1H), 8.64 (t, 1H), 8.46 (d, 1H), 8.15 (t, 2H), 7.75 (dd, 1H), 7.52-7.44 (m, 6H), 7.37 (m, 2H), 7.26-7.10 (m, 4H), 6.79 (dd, 1H), 6.50 (d, 1H), 3.87 (dd, 2H), 3.40 (s, 2H), 3.38-3.24 (m, 4H), 3.19 (broad s, 4H), 2.37 (broad s, 4H), 1.92 (m, 1H), 1.65 (d, 2H), 1.28 (m, 2H).

Example 80

4-{4-[(4'-chloro-1,1'-biphenyl-2-yl)methyl]piperazin-1-yl}-2-(pyridin-3-yloxy)-N-({4-[(tetrahydro-2H-pyran-4-ylmethyl)amino]phenyl}sulfonyl)benzamide This example was prepared by substituting EXAMPLE 79D for EXAMPLE 1E and EXAMPLE 2A for EXAMPLE 1F in EXAMPLE 1G. $^1$H NMR (300 MHz, dimethylsulfoxide-$d_6$) δ 11.34 (s, 1H), 8.27 (dd, 2H), 7.51-7.44 (m, 8H), 7.41-7.29 (m, 3H), 7.27-7.19 (m, 2H), 6.78 (dd, 1H), 6.72 (t, 1H), 6.56 (d, 2H), 6.44 (d, 1H), 3.86 (dd, 2H), 3.36 (s, 2H), 3.29-3.22 (m, 2H), 3.16 (m, 4H), 2.96 (t, 2H), 2.34 (m, 4H), 1.77 (m, 1H), 1.66 (d, 2H), 1.21 (m, 2H).

Example 81

4-{4-[(4'-chloro-1,1'-biphenyl-2-yl)methyl]piperazin-1-yl}-N-{[4-({(1R)-3-(dimethylamino)-1-[(phenylthio)methyl]propyl}amino)-3-nitrophenyl]sulfonyl}-2-phenoxybenzamide

Example 81A (R)-tert-butyl 3-(((9H-fluoren-9-yl)methoxy)carbonylamino)-4-hydroxybutanoate Fmoc-D-Asp(OtBu)-OH (9.0 g) and N,N-diisopropylethylamine (4.6 mL) were added to tetrahydrofuran (100 mL) and cooled to −40° C. Isobutyl chloroformate (3.1 mL) was added, and the solution was gradually warmed to 0° C. over 30 minutes. The solution was cooled to −20° C., and to it was carefully added sodium borohydride (1.64 g, 43.6 mmol) and methanol (10 mL). The solution was gradually warmed to room temperature over two hours, diluted with ethyl acetate (200 mL), washed with water (100 mL) and brine (50 mL), dried with anhydrous magnesium sulfate, filtered, and concentrated to afford crude product of sufficient purity for subsequent use.

Example 81B (R)-tert-butyl 3-(((9H-fluoren-9-yl)methoxy)carbonylamino)-4-(phenylthio)butanoate Tri-n-butylphosphine (90 µL) and 1,1'-(azodicarbonyl)dipiperidine (91 mg) were added to tetrahydrofuran (4 mL), treated with EXAMPLE 81A (90 mg) and thiophenol (21 mg), and stirred at room temperature for 18 hours. The solution was concentrated and purified by flash column chromatography on silica gel with 50% ethyl acetate in hexanes.

Example 81C (R)-tert-butyl 3-(2-nitro-4-sulfamoylphenylamino)-4-(phenylthio)butanoate EXAMPLE 81B (600 mg), 4-fluoro-3-nitrobenzenesulfonamide (298 mg), and N,N-diisopropylethylamine (3 mL) were added to N,N-dimethylformamide (3 mL) and stirred at 60° C. for 12 hours. The reaction mixture was diluted with ethyl acetate (100 mL), washed with water (45 mL) and brine (10 mL), dried with anhydrous magnesium sulfate, filtered, and concentrated. The residue was purified by flash column chromatography on silica gel with 30% ethyl acetate in dichloromethane.

Example 81D (R)-3-(2-nitro-4-sulfamoylphenylamino)-4-(phenylthio)butanoic acid EXAMPLE 81C (468 mg) and 4 M HCl in 1,4-dioxane (10 mL) were stirred at 50° C. for 5 hours. The solution was concentrated to give the crude product of sufficient purity for subsequent use.

Example 81E (R)—N,N-dimethyl-3-(2-nitro-4-sulfamoylphenylamino)-4-(phenylthio)butanamide This example was prepared by substituting EXAMPLE 81D for EXAMPLE 1E and dimethylamine (2M in tetrahydrofuran) for EXAMPLE 1F in EXAMPLE 1G.

Example 81F (R)-4-(4-(dimethylamino)-1-(phenylthio)butan-2-ylamino)-3-nitrobenzenesulfonamide To EXAMPLE 81E (4.06 g) was added borane (1 M in tetrahydrofuran, 20.0 mL). The solution was stirred at room temperature for 16 hours. The reaction was quenched slowly with methanol (5.0 mL) and concentrated aqueous HCl (2.0 mL) was added. The solution was stirred at 80° C. for three hours, cooled to room temperature, carefully basified with 4 M sodium carbonate, diluted with ethyl acetate (150 mL), washed with water (50 mL) and brine (10 mL), dried with anhydrous magnesium sulfate, and filtered. The solution was concentrated and purified by flash column chromatography on silica gel with 20% methanol in dichloromethane.

Example 81G

4-{4-[(4'-chloro-1,1'-biphenyl-2-yl)methyl]piperazin-1-yl}-N-{[4-({(1R)-3-(dimethylamino)-1-[(phenylthio)methyl]propyl}amino)-3-nitrophenyl]sulfonyl}-2-phenoxybenzamide This example was prepared by substituting EXAMPLE 81F for EXAMPLE 1F in EXAMPLE 1G. $^1$H NMR (300 MHz, dimethylsulfoxide-$d_6$) δ 8.33 (d, 1H), 8.28 (d, 1H), 7.61 (dd, 2H), 7.50-7.43 (m, 4H), 7.37-7.14 (m, 11H), 6.90 (t, 1H), 6.84 (d, 1H), 6.71 (d, 2H), 6.70 (dd, 1H), 6.32 (d, 1H), 4.06 (m, 1H), 3.36 (s, 2H), 3.33-3.30 (m, 2H), 3.08 (t, 4H), 2.86 (m, 2H), 2.53 (s, 6H), 2.35 (t, 4H), 2.04 (m, 2H).

Example 82

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(pyridin-4-yloxy)benzamide

Example 82A methyl 4-bromo-2-(pyridin-4-yloxy)benzoate

EXAMPLE 79A (800 mg), pyridine-4-ol (359 mg), and potassium carbonate (617 mg) were added to N,N-dimethylacetamide (20 mL) and the mixture was heated to 125° C. for 16 hours. The solution was concentrated on vacuum at 48° C. and purified by flash column chromatography on silica gel with 20% methanol in dichloromethane.

Example 82B methyl 4-(4-((4'-chlorobiphenyl-2-yl)methyl)piperazin-1-yl)-2-(pyridin-4-yloxy)benzoate This example was prepared by substituting EXAMPLE 82A for EXAMPLE 79B in EXAMPLE 79C.

Example 82C 4-(4-((4'-chlorobiphenyl-2-yl)methyl)piperazin-1-yl)-2-(pyridin-4-yloxy)benzoic acid This example was prepared by substituting EXAMPLE 82B for EXAMPLE 1D in EXAMPLE 1E.

Example 82D

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(pyridin-4-yloxy)benzamide This example was prepared by substituting EXAMPLE 82C for EXAMPLE 1E in EXAMPLE 1G. $^1$H NMR (300 MHz, dimethylsulfoxide-$d_6$) δ 8.40 (t, 1H), 8.37 (d, 1H), 7.76 (dd, 1H), 7.65 (d, 1H), 7.54-7.48 (m, 1H), 7.47 (s, 3H), 7.42-7.35 (m, 5H), 7.27-7.23 (m, 1H), 7.06 (dd, 1H), 6.92 (dd, 1H), 6.88 (d, 1H), 5.91 (d, 2H), 3.85 (dd, 2H), 3.39 (s, 2H), 3.34-3.25 (m, 4H), 3.19 (broad, s, 4H), 2.39 (broad s, 4H), 1.92 (m, 1H), 1.65 (d, 2H), 1.27 (m, 2H).

Example 83

4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(pyridin-3-yloxy)benzamide This example was prepared by substituting EXAMPLE 79D for EXAMPLE 1E and EXAMPLE 7A for EXAMPLE 1F in EXAMPLE 1G. $^1$H NMR (300 MHz, dimethylsulfoxide-$d_6$) δ 8.73 (t, 1H), 8.43 (d, 1H), 8.12 (t, 2H), 7.73 (dd, 1H), 7.55 (d, 1H), 7.51-7.44 (m, 4H), 7.37 (m, 2H), 7.25-7.17 (m, 3H), 7.07 (d, 2H), 6.78 (dd, 1H), 6.47 (d, 1H), 3.65 (t, 4H), 3.47 (q, 2H), 3.38 (s, 2H), 3.28 (m, 2H), 3.17 (br s, 4H), 2.57 (br s, 4H), 2.36 (br s, 4H), 1.84 (m, 2H).

Example 84

4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(pyridin-4-yloxy)benzamide This example was prepared by substituting EXAMPLE 82C for EXAMPLE 1E and EXAMPLE 7A for EXAMPLE 1F in EXAMPLE 1G. $^1$H NMR (300 MHz, dimethylsulfoxide-$d_6$) δ 8.55 (t, 1H), 8.37 (d, 1H), 7.77 (dd, 1H), 7.65 (d, 1H), 7.54-7.43 (m, 5H), 7.42-7.32 (m, 4H), 7.26-7.22 (m, 1H), 7.01 (d, 1H), 6.91 (dd, 1H), 6.66 (d, 1H), 5.90 (d, 2H), 3.60 (t, 4H), 3.43 (q, 2H), 3.39 (s, 2H), 3.18 (br s, 4H), 2.38 (m, 10H), 1.80 (t, 2H).

Example 85

4-{4-[(4'-chloro-1,1'-biphenyl-2-yl)methyl]piperazin-1-yl}-N-[(4-{[2-(4-methylpiperazin-1-yl)ethyl]amino}-3-nitrophenyl)sulfonyl]-2-phenoxybenzamide Example 85A 4-(2-(4-methylpiperazin-1-yl)ethylamino)-3-nitrobenzenesulfonamide This example was prepared by substituting 2-(4-methylpiperazin-1-yl)ethanamine for (tetrahydropyran-4-yl)methylamine in EXAMPLE 1F.

Example 85B

4-{4-[(4'-chloro-1,1'-biphenyl-2-yl)methyl]piperazin-1-yl}-N-[(4-{[2-(4-methylpiperazin-1-yl)ethyl]amino}-3-nitrophenyl)sulfonyl]-2-phenoxybenzamide This example was prepared by substituting EXAMPLE 85A for EXAMPLE 1F in EXAMPLE 1G. $^1$H NMR (300 MHz, dimethylsulfoxide-$d_6$) δ 8.61 (t, 1H), 8.40 (d, 1H), 7.72 (dd, 1H), 7.57 (d, 1H), 7.51-7.44 (m, 5H), 7.36 (m, 2H), 7.26-7.15 (m, 3H), 6.95 (t, 1H), 6.75 (dd, 2H), 6.71 (dd, 1H), 6.34 (d, 1H), 3.45 (q, 2H), 3.36 (s, 2H), 3.34 (m, 2H), 3.10 (t, 4H), 2.79 (broad s, 4H), 2.68 (t, 2H), 2.60 (broad s, 2H), 2.49 (s, 3H), 2.35 (t, 4H).

Example 86

4-{4-[(4'-chloro-1,1'-biphenyl-2-yl)methyl]piperazin-1-yl}-N-[(4-{[3-(4-methylpiperazin-1-yl)propyl]amino}-3-nitrophenyl)sulfonyl]-2-phenoxybenzamide Example 86A 4-(3-(4-methylpiperazin-1-yl)propylamino)-3-nitrobenzenesulfonamide This example was prepared by substituting 3-(4-methylpiperazin-1-yl)propan-1-amine for (tetrahydropyran-4-yl)methylamine in EXAMPLE 1F.

Example 86B

4-{4-[(4'-chloro-1,1'-biphenyl-2-yl)methyl]piperazin-1-yl}-N-[(4-{[3-(4-methylpiperazin-1-yl)propyl]amino}-3-nitrophenyl)sulfonyl]-2-phenoxybenzamide This example was prepared by substituting EXAMPLE 86A for EXAMPLE 1F in EXAMPLE 1G. $^1$H NMR (300 MHz, dimethylsulfoxide-$d_6$) δ 8.57 (t, 1H), 8.38 (d, 1H), 7.71 (dd, 1H), 7.59 (d, 1H), 7.50-7.44 (m, 5H), 7.36 (m, 2H), 7.27-7.15 (m, 3H), 6.98 (d, 2H), 6.91 (t, 1H), 6.73 (dd, 2H), 6.70 (dd, 2H), 6.33 (d, 1H), 3.43 (q, 2H), 3.36 (s, 2H), 3.34 (m, 2H), 3.09 (t, 4H), 2.82 (broad s, 4H), 2.56 (broad s, 2H), 2.49 (s, 3H), 2.35 (t, 4H), 1.79 (t, 2H).

Example 87

4-{4-[(4'-chloro-1,1'-biphenyl-2-yl)methyl]piperazin-1-yl}-N-({4-[[3-(dimethylamino)propyl](methyl)amino]-3-nitrophenyl}sulfonyl)-2-phenoxybenzamide Example 87A 4-((3-(dimethylamino)propyl)(methyl)amino)-3-nitrobenzenesulfonamide This example was prepared by substituting $N^1,N,N^3$-trimethylpropane-1,3-diamine for 3-(pyrrolidin-1-yl)propan-1-amine in EXAMPLE 68F.

Example 87B

4-{4-[(4'-chloro-1,1'-biphenyl-2-yl)methyl]piperazin-1-yl}-N-({4-[[3-(dimethylamino)propyl](methyl)amino]-3-nitrophenyl}sulfonyl)-2-phenoxybenzamide This example was prepared by substituting EXAMPLE 87A for EXAMPLE 1F in EXAMPLE 1G. $^1$H NMR (300 MHz, dimethylsulfoxide-$d_6$) δ 8.01 (d, 1H), 7.68 (dd, 1H), 7.63 (d, 1H), 7.51-7.44 (m, 5H), 7.36 (m, 2H), 7.26-7.13 (m, 3H), 6.93 (t, 1H), 6.83 (m, 1H), 6.74 (dd, 2H), 6.69 (dd, 1H), 6.32 (d, 1H), 3.46 (q, 2H), 3.36 (s, 2H), 3.08 (t, 4H), 2.83 (t, 2H), 2.77 (s, 3H), 2.60 (s, 6H), 2.36 (t, 4H), 1.86 (m, 2H).

Example 88

4-{4-[(4'-chloro-1,1'-biphenyl-2-yl)methyl]piperazin-1-yl}-N-[(4-{[(1-methylpiperidin-4-yl)methyl]amino}-3-nitrophenyl)sulfonyl]-2-phenoxybenzamide

Example 88A 4-((1-methylpiperidin-4-yl)methylamino)-3-nitrobenzenesulfonamide This example was prepared by substituting (1-methylpiperidin-4-yl)methanamine for 3-(pyrrolidin-1-yl)propan-1-amine in EXAMPLE 68F.

Example 88B

4-{4-[(4'-chloro-1,1'-biphenyl-2-yl)methyl]piperazin-1-yl}-N-[(4-{[(1-methylpiperidin-4-yl)methyl]amino}-3-nitrophenyl)sulfonyl]-2-phenoxybenzamide This example was prepared by substituting EXAMPLE 88A for EXAMPLE 1F in EXAMPLE 1G. $^1$H NMR (300 MHz, dimethylsulfoxide-$d_6$) δ 8.44 (t, 1H), 8.35 (d, 1H), 7.79 (dd, 1H), 7.62 (d, 1H), 7.51-7.45 (m, 5H), 7.36 (m, 2H), 7.25-7.14 (m, 3H), 6.99 (d, 1H), 6.89 (t, 1H), 6.71 (d, 2H), 6.68 (dd, 1H), 6.31 (d, 1H), 3.36 (s, 2H), 3.34 (m, 4H), 3.07 (t, 4H), 2.73 (m, 2H), 2.62 (s, 3H), 2.36 (t, 4H), 1.90-1.82 (m, 3H), 1.47-1.31 (m, 2H).

Example 89

4-{4-[(4'-chloro-1,1'-biphenyl-2-yl)methyl]piperazin-1-yl}-N-({4-[(1-methylpiperidin-4-yl)amino]-3-nitrophenyl}sulfonyl)-2-phenoxybenzamide This example was prepared by substituting EXAMPLE 21A for EXAMPLE 1F in EXAMPLE 1G. $^1$H NMR (300 MHz, dimethylsulfoxide-$d_6$) δ 8.38 (t, 1H), 8.09 (d, 1H), 7.73 (m, 1H), 7.59 (d, 1H), 7.52-7.44 (m, 5H), 7.36 (m, 2H), 7.26-7.22 (m, 1H), 7.17 (t, 1H), 7.05 (d, 1H), 6.90 (t, 1H), 6.83 (m, 1H), 6.72 (d, 2H), 6.70 (dd, 1H), 6.33 (d, 1H), 3.36 (q, 2H), 3.36 (s, 2H), 3.24-3.12 (m, 2H), 3.09 (t, 4H), 2.80 (m, 1H), 2.59 (s, 3H), 2.36 (t, 4H), 2.08 (m, 2H), 1.77 (m, 2H).

Example 90

4-{4-[(4'-chloro-1,1'-biphenyl-2-yl)methyl]piperazin-1-yl}-N-[(3-cyano-4-{[3-(dimethylamino)propyl]amino}phenyl)sulfonyl]-2-phenoxybenzamide

Example 90A 3-cyano-4-fluorobenzenesulfonamide

Concentrated ammonium hydroxide (28% solution in water, 3.17 mL) was cooled to 0° C. and 3-cyano-4-fluorobenzene-1-sulfonyl chloride (1.00 g) was added. The solution was mixed at 0° C. for four minutes. 4M HCl (10 mL) was added slowly and the solution was extracted with ethyl acetate. The extract was dried on brine and anhydrous sodium sulfate and the solvent removed under vacuum.

Example 90B 3-cyano-4-(3-(dimethylamino)propylamino)benzenesulfonamide

This example was prepared by substituting EXAMPLE 90A for 4-chloro-3-nitrobenzenesulfonamide and $N^1,N^1$-dimethylpropane-1,3-diamine for 3-(pyrrolidin-1-yl)propan-1-amine in EXAMPLE 68F.

Example 90C

4-{4-[(4'-chloro-1,1'-biphenyl-2-yl)methyl]piperazin-1-yl}-N-[(3-cyano-4-{[3-(dimethylamino)propyl]amino}phenyl)sulfonyl]-2-phenoxybenzamide This example was prepared by substituting EXAMPLE 90B for EXAMPLE 1F in EXAMPLE 1G. $^1$H NMR (300 MHz, dimethylsulfoxide-$d_6$) δ 7.67 (s, 1H), 7.66 (dd, 1H), 7.59 (d, 1H), 7.51-7.44 (m, 5H), 7.36 (m, 2H), 7.28-7.20 (m, 3H), 6.98 (t, 2H), 6.77 (dd, 2H), 6.70 (d, 2H), 6.33 (d, 1H), 3.36 (s, 2H), 3.27 (q, 2H), 3.09 (t, 4H), 2.82 (t, 2H), 2.54 (s, 6H), 2.35 (t, 4H), 1.82 (m, 2H).

Example 91

4-{4-[(4'-chloro-1,1'-biphenyl-2-yl)methyl]piperazin-1-yl}-N-({3-nitro-4-[(3-pyrrolidin-1-ylpropyl)amino]phenyl}sulfonyl)-2-phenoxybenzamide This example was prepared by substituting EXAMPLE 68F for EXAMPLE 1F in EXAMPLE 1G. $^1$H NMR (300 MHz, dimethylsulfoxide-$d_6$) δ 8.49 (t, 1H), 8.37 (d, 1H), 7.72 (dd, 1H), 7.62 (d, 1H), 7.50-7.43 (m, 5H), 7.35 (m, 2H), 7.26-7.14 (m, 3H), 6.97 (d, 1H), 6.90 (t, 1H), 6.72 (d, 2H), 6.69 (dd, 1H), 6.31 (d, 1H), 3.47 (q, 2H), 3.36 (s, 2H), 3.20 (m, 2H), 3.07 (broad s, 8H), 2.35 (broad s, 4H), 1.95-1.83 (m, 6H).

Example 92

4-{4-[(4'-chloro-1,1'-biphenyl-2-yl)methyl]piperazin-1-yl}-N-{[4-{[3-(dimethylamino)propyl]amino}-3-(trifluoromethyl)phenyl]sulfonyl}-2-phenoxybenzamide

Example 92A 4-fluoro-3-(trifluoromethyl)benzenesulfonamide

This example was prepared by substituting 4-fluoro-3-(trifluoromethyl)benzene-1-sulfonyl chloride for 3-cyano-4-fluorobenzene-1-sulfonyl chloride in EXAMPLE 90A.

Example 92B 4-(3-(dimethylamino)propylamino)-3-(trifluoromethyl)benzenesulfonamide This example was prepared by substituting EXAMPLE 92A for 4-fluoro-3-nitrobenzenesulfonamide and $N^1,N^1$-dimethylpropane-1,3-diamine for tetrahydropyran-4-yl)methylamine in EXAMPLE 1F

Example 92C

4-{4-[(4'-chloro-1,1'-biphenyl-2-yl)methyl]piperazin-1-yl}-N-{[4-{[3-(dimethylamino)propyl]amino}-3-(trifluoromethyl)phenyl]sulfonyl}-2-phenoxybenzamide This example was prepared by substituting EXAMPLE 92B for EXAMPLE 1F in EXAMPLE 1G. $^1$H NMR (300 MHz, dimethylsulfoxide-$d_6$) δ 7.77 (s, 1H), 7.68 (dd, 1H), 7.57 (d, 1H), 7.51-7.45 (m, 5H), 7.36 (m, 2H), 7.29-7.21 (m, 3H), 6.99 (t, 1H), 6.82-6.68 (m, 5H), 6.32 (d, 1H), 3.36 (s, 2H), 3.28 (q, 2H), 3.09 (t, 4H), 2.73 (m, 2H), 2.48 (s, 6H), 2.35 (t, 4H), 1.79 (m, 2H).

Example 93

4-{4-[(4'-chloro-1,1'-biphenyl-2-yl)methyl]piperazin-1-yl}-N-{[4-({3-[isopropyl(methyl)amino]propyl}amino)-3-nitrophenyl]sulfonyl}-2-phenoxybenzamide

Example 93A tert-butyl methyl(3-(2-nitro-4-sulfamoylphenylamino)propyl)carbamate This example was prepared by substituting tert-butyl 3-aminopropyl(methyl)carbamate for 3-(pyrrolidin-1-yl)propan-1-amine in EXAMPLE 68F.

Example 93B tert-butyl 3-(4-(N-(4-(4-((4'-chlorobiphenyl-2-yl)methyl)piperazin-1-yl)-2-phenoxybenzoyl)sulfamoyl)-2-nitrophenylamino)propyl(methyl)carbamate This example was prepared by substituting EXAMPLE 93A for EXAMPLE 1F in EXAMPLE 1G.

Example 93C 4-(4-((4'-chlorobiphenyl-2-yl)methyl)piperazin-1-yl)-N-(4-(3-(methylamino)propylamino)-3-nitrophenylsulfonyl)-2-phenoxybenzamide EXAMPLE 93B (112 mg) and triethylsilane (0.082 mL) were added to dichloromethane (2 mL). Trifluoroacetic acid (0.198 mL) was added, the solution stirred at room temperature for one hour, and the solvent removed under vacuum.

Example 93D

4-{4-[(4'-chloro-1,1'-biphenyl-2-yl)methyl]piperazin-1-yl}-N-{[4-({3-[isopropyl(methyl)amino]propyl}amino)-3-nitrophenyl]sulfonyl}-2-phenoxybenzamide EXAMPLE 93C (128 mg), acetone (0.014 mL), and sodium cyanoborohydride resin (2.15 mmol/g, 66 mg) were added to tetrahydrofuran (0.9 mL) and acetic acid (0.3 mL), and the solution was stirred at room temperature for 16 hours. More acetone (0.014 mL), and sodium cyanoborohydride resin (66 mg) were added, and the solution was stirred for 24 hours. The solution was purified by flash column chromatography on silica gel with 1% acetic acid and 10% methanol in dichloromethane. $^1$H NMR (300 MHz, dimethylsulfoxide-$d_6$) δ 11.93 (broad s, 3H), 8.53 (broad s, 1H), 8.40 (d. 1H), 7.75 (dd, 1H), 7.60 (d, 1H), 7.51-7.45 (m, 5H), 7.36 (m, 2H), 7.25-7.16 (m, 3H), 7.02 (d, 1H), 6.92 (t, 1H), 6.74 (d, 2H), 6.70 (dd, 1H), 6.32 (d, 1H), 3.47 (m, 4H), 3.36 (s, 2H), 3.09 (t, 4H), 3.01 (broad s, 2H), 2.58 (s, 3H), 2.35 (t, 4H), 1.94 (m, 1H), 1.18-1.14 (m, 6H).

Example 94

4-{4-[(4'-chloro-1,1'-biphenyl-2-yl)methyl]piperazin-1-yl}-N-({4-[3-(dimethylamino)propoxy]-3-nitrophenyl}sulfonyl)-2-phenoxybenzamide

Example 94A 4-(3-(dimethylamino)propoxy)-3-nitrobenzenesulfonamide

Triphenylphosphine (1.398 g) was added to tetrahydrofuran (20 mL) and cooled to 0° C. Diethylazodicarboxylate (40% solution, 2.428 mL) was added, and the solution was stirred for at 0° C. for 15 minutes. 4-Hydroxy-3-nitrobenzenesulfonamide (1.163 g) and 3-(dimethylamine)propan-1-ol (0.567 mL) were added, and the solution was allowed to warm to room temperature and stir for 16 hours. Solvent was removed under vacuum and the material recrystallized using 20% methanol (dichloromethane). The recrystallized solid was washed with dichloromethane, dissolved in methanol/dichloromethane, treated with triethylamine (0.13 mL, 0.924 mmol), and purified by flash column chromatography on silica gel with 10-20% methanol in dichloromethane.

Example 94B

4-{4-[(4'-chloro-1,1'-biphenyl-2-yl)methyl]piperazin-1-yl}-N-({4-[3-(dimethylamino)propoxy]-3-nitrophenyl}sulfonyl)-2-phenoxybenzamide This example was prepared by substituting EXAMPLE 94A for EXAMPLE 1F in EXAMPLE 1G. $^1$H NMR (300 MHz, dimethylsulfoxide-$d_6$) δ 8.06 (d, 1H), 7.84 (dd, 1H), 7.65 (d, 1H), 7.52-7.45 (m, 5H), 7.36 (m, 2H), 7.26-7.22 (m, 2H), 7.18 (td, 2H), 6.89 (t, 1H), 6.69 (d, 1H), 6.68 (d, 2H), 6.32 (d, 1H), 4.25 (t, 2H), 3.36 (s, 2H), 3.13 (t, 2H), 3.08 (t, 4H), 2.75 (s, 6H), 2.36 (t, 4H), 2.11 (m, 2H).

Example 95

4-(4-{[2-(4-chlorophenyl)-4,4-dimethylcyclohex-1-en-1-yl]methyl}piperazin-1-yl)-2-(1H-indol-5-yloxy)-N-[(4-{[2-(4-methylpiperazin-1-yl)ethyl]amino}-3-nitrophenyl)sulfonyl]benzamide This example was prepared by substituting EXAMPLE 26C for EXAMPLE 1E and EXAMPLE 85A for EXAMPLE 1F in EXAMPLE 1G. $^1$H NMR (300 MHz, dimethylsulfoxide-$d_6$) δ 11.10 (s, 1H), 8.67 (t, 1H), 8.53 (d, 1H), 7.78 (dd, 1H), 7.52 (d, 1H), 7.39-7.31 (m, 4H), 7.08-7.02 (m, 3H), 6.94 (d, 1H), 6.80 (dd, 1H), 6.61 (dd, 1H), 6.36 (t, 1H), 6.14 (d, 1H), 3.42 (q, 2H), 2.99 (t, 4H), 2.71 (s, 2H), 2.70-2.48 (m, 10H), 2.39 (s, 3H), 2.16 (m, 6H), 1.95 (s, 2H), 1.38 (t, 2H), 0.92 (s, 6H).

Example 96

4-(4-{[2-(4-chlorophenyl)-4,4-dimethylcyclohex-1-en-1-yl]methyl}piperazin-1-yl)-2-(1H-indol-5-yloxy)-N-[(4-{[3-(4-methylpiperazin-1-yl)propyl]amino}-3-nitrophenyl)sulfonyl]benzamide This example was prepared by substituting EXAMPLE 26C for EXAMPLE 1E and EXAMPLE 86A for EXAMPLE 1F in EXAMPLE 1G. $^1$H NMR (300 MHz, dimethylsulfoxide-$d_6$) δ 11.09 (s, 1H), 8.62 (t, 1H), 8.51 (d, 1H), 7.76 (dd, 1H), 7.53 (d, 1H), 7.38-7.31 (m, 4H), 7.05 (s, 1H), 7.02 (d, 2H), 6.96 (d, 1H), 6.79 (dd, 1H), 6.60 (dd, 1H), 6.35 (t, 1H), 6.14 (d, 1H), 3.40 (q, 2H), 2.98 (t, 4H), 2.71 (s, 2H), 2.67 (broad s, 4H), 2.55-2.40 (m, 6H), 2.39 (s, 3H), 2.16 (m, 6H), 1.95 (s, 2H), 1.77 (m, 2H), 1.38 (t, 2H), 0.92 (s, 6H).

Example 97

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(3-pyrrolidin-1-ylpropyl)amino]phenyl}sulfonyl)benzamide This example was prepared by substituting EXAMPLE 26C for EXAMPLE 1E and EXAMPLE 68F for EXAMPLE 1F in EXAMPLE 1G. $^1$H NMR (300 MHz, dimethylsulfoxide-$d_6$) δ 11.06 (s, 1H), 8.58 (t, 1H), 8.49 (d, 1H), 7.77 (dd, 1H), 7.54 (d, 1H), 7.36-7.31 (m, 4H), 7.06-7.01 (m, 3H), 6.95 (d, 1H), 6.76 (dd, 1H), 6.57 (dd, 1H), 6.35 (t, 1H), 6.14 (d, 1H), 3.44 (q, 2H), 2.97 (broad s, 10H), 2.71 (s, 2H), 2.16 (m, 6H), 1.95 (s, 2H), 1.90-1.80 (m, 6H), 1.38 (t, 2H), 0.92 (s, 6H).

Example 98

4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)amino]-3-nitrophenyl}sulfonyl)benzamide This example was prepared by substituting EXAMPLE 26C for EXAMPLE 1E and EXAMPLE 21A for EXAMPLE 1F in EXAMPLE 1G. $^1$H NMR (300 MHz, dimethylsulfoxide-$d_6$) δ 11.08 (s, 1H), 8.51 (d, 1H), 8.13 (d, 1H), 7.78 (dd, 1H), 7.52 (d, 1H), 7.37-7.31 (m, 4H), 7.06-7.00 (m, 4H), 6.79 (dd, 1H), 6.59 (dd, 1H), 6.35 (t, 1H), 6.14 (d, 1H), 3.73 (m, 1H), 3.05-2.95 (m, 6H), 2.71 (s, 2H), 2.60 (m, 2H), 2.48 (s, 3H), 2.16 (m, 6H), 2.01 (m, 2H), 1.95 (s, 2H), 1.70 (m, 2H), 1.38 (t, 2H), 0.92 (s, 6H).

Example 99

4-(4-{[2-(4-chlorophenyl)-4,4-dimethylcyclohex-1-en-1-yl]methyl}piperazin-1-yl)-2-(1H-indol-4-yloxy)-N-[(4-{[3-(4-methylpiperazin-1-yl)propyl]amino}-3-nitrophenyl)sulfonyl]benzamide This example was prepared by substituting EXAMPLE 55B for EXAMPLE 1E and EXAMPLE 86A for EXAMPLE 1F in EXAMPLE 1G. $^1$H NMR (300 MHz, dimethylsulfoxide-$d_6$) δ 11.16 (s, 1H), 8.59 (t, 1H), 8.45 (d, 1H), 7.72 (dd, 1H), 7.55 (d, 1H), 7.34 (d, 2H), 7.23 (t, 1H), 7.12 (d, 1H), 7.02 (d, 2H), 6.95 (d, 1H), 6.94 (t, 1H), 6.64 (dd, 1H), 6.35 (d, 1H), 6.23 (m, 2H), 3.41 (q, 2H), 2.98 (t, 4H), 2.71 (broad s, 6H), 2.52-2.42 (m, 6H), 2.41 (s, 3H), 2.15 (m, 6H), 1.95 (s, 2H), 1.77 (m, 2H), 1.38 (t, 2H), 0.92 (s, 6H).

Example 100

4-(4-{[2-(4-chlorophenyl)-4,4-dimethylcyclohex-1-en-1-yl]methyl}piperazin-1-yl)-N-({4-[3-(dimethylamino)propoxy]-3-nitrophenyl}sulfonyl)-2-(1H-indol-5-yloxy)benzamide This example was prepared by substituting EXAMPLE 26C for EXAMPLE 1E and EXAMPLE 94A for EXAMPLE 1F in EXAMPLE 1G. $^1$H NMR (300 MHz, dimethylsulfoxide-$d_6$) δ 11.03 (s, 1H), 8.23 (d, 1H), 7.91 (dd, 1H), 7.56 (d, 1H), 7.36-7.29 (m, 4H), 7.19 (d, 1H), 7.05 (d, 2H), 6.97 (s, 1H), 6.73 (dd, 1H), 6.57 (dd, 1H), 6.33 (t, 1H), 6.15 (d, 1H), 4.23 (t, 2H), 3.04 (m, 2H), 2.96 (t, 4H), 2.72 (s, 2H), 2.67 (s, 6H), 2.22-2.02 (m, 8H), 1.95 (s, 2H), 1.38 (t, 2H), 0.92 (s, 6H).

Example 101

4-(4-{[2-(4-chlorophenyl)-4,4-dimethylcyclohex-1-en-1-yl]methyl}piperazin-1-yl)-2-(1H-indol-4-yloxy)-N-[(4-{[2-(4-methylpiperazin-1-yl)ethyl]amino}-3-nitrophenyl)sulfonyl]benzamide This example was prepared by substituting EXAMPLE 55B for EXAMPLE 1E and EXAMPLE 85A for EXAMPLE 1F in EXAMPLE 1G. $^1$H NMR (300 MHz, dimethylsulfoxide-$d_6$) δ 11.18 (s, 1H), 8.64 (t, 1H), 8.47 (d, 1H), 7.73 (dd, 2H), 7.56 (d, 1H), 7.34 (d, 2H), 7.24 (t, 1H), 7.04 (d, 2H), 6.96 (d, 1H), 6.94 (d, 1H), 6.65 (dd, 1H), 6.37 (d, 1H), 6.23 (m, 2H), 3.43 (q, 2H), 2.99 (t, 4H), 2.71 (s, 2H), 2.65 (m, 6H), 2.56 (m, 4H), 2.42 (s, 3H), 2.15 (m, 6H), 1.95 (s, 2H), 1.38 (t, 2H), 0.92 (s, 6H).

Example 102

4-(4-{[2-(4-chlorophenyl)-4,4-dimethylcyclohex-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide This example was prepared by substituting EXAMPLE 55B for EXAMPLE 1E and EXAMPLE 68F for EXAMPLE 1F in EXAMPLE 1G. $^1$H NMR (300 MHz, dimethylsulfoxide-$d_6$) δ 11.14 (s, 1H), 8.54 (t, 1H), 8.44 (d, 1H), 7.76 (dd, 1H), 7.59 (d, 1H), 7.34 (d, 2H), 7.22 (t, 1H), 7.10 (d, 1H), 7.05 (d, 2H), 6.98-6.89 (m, 2H), 6.62 (dd, 1H), 6.33 (d, 1H), 6.23 (t, 1H), 6.21 (d, 1H), 3.44 (q, 2H), 3.10-2.91 (m, 10H), 2.71 (s, 2H), 2.16 (m, 6H), 1.95 (s, 2H), 1.92-1.79 (m, 6H), 1.38 (t, 2H), 0.92 (s, 6H).

Example 103

4-(4-{[2-(4-chlorophenyl)-4,4-dimethylcyclohex-1-en-1-yl]methyl}piperazin-1-yl)-2-(1H-indol-4-yloxy)-N-({4-[(1-methylpiperidin-4-yl)amino]-3-nitrophenyl}sulfonyl)benzamide This example was prepared by substituting EXAMPLE 55B for EXAMPLE 1E and EXAMPLE 21A for EXAMPLE 1F in EXAMPLE 1G. $^1$H NMR (300 MHz, dimethylsulfoxide-$d_6$) δ 11.14 (s, 1H), 8.44 (d, 1H), 8.11 (d, 1H), 7.75 (dd, 1H), 7.56 (d, 1H), 7.34 (d, 2H), 7.23 (t, 1H), 7.11 (d, 1H), 7.04 (d, 2H), 7.03 (d, 1H), 6.93 (t, 1H), 6.64 (dd, 1H), 6.34 (d, 1H), 6.22 (m, 2H), 3.73 (m, 1H), 3.08-2.93 (m, 6H), 2.71 (s, 2H), 2.70-2.56 (m, 2H), 2.48 (s, 3H), 2.16 (m, 6H), 2.02 (m, 2H), 1.95 (s, 2H), 1.70 (m, 2H), 1.38 (t, 2H), 0.92 (s, 6H).

Example 104

4-(4-{[2-(4-chlorophenyl)-4,4-dimethylcyclohex-1-en-1-yl]methyl}piperazin-1-yl)-2-(1H-indol-5-yloxy)-N-[(4-{[(1-methylpiperidin-4-yl)methyl]amino}-3-nitrophenyl)sulfonyl]benzamide This example was prepared by substituting EXAMPLE 26C for EXAMPLE 1E and EXAMPLE 88A for EXAMPLE 1F in EXAMPLE 1G. $^1$H NMR (300 MHz, dimethylsulfoxide-$d_6$) δ 10.99 (s, 1H), 8.39 (d, 1H), 8.32 (t, 1H), 7.65 (dd, 1H), 7.54 (d, 1H), 7.34 (d, 2H), 7.30-7.26 (m, 2H), 7.05 (d, 2H), 6.92 (d, 1H), 6.81 (d, 1H), 6.70 (dd, 1H), 6.53 (dd, 1H), 6.30 (t, 1H), 6.15 (d, 1H), 3.28-3.19 (m, 2H), 2.93 (t, 4H), 2.83 (m, 2H), 2.71 (s, 2H), 2.68-2.50 (m, 2H), 2.54 (s, 3H), 2.24-2.10 (m, 6H), 1.95 (broad s, 2H), 1.68 (d, 2H), 1.59 (m, 1H), 1.38 (t, 2H), 1.32-1.17 (m, 2H), 0.92 (s, 6H).

Example 105

4-(4-{[2-(4-chlorophenyl)-4,4-dimethylcyclohex-1-en-1-yl]methyl}piperazin-1-yl)-2-(1H-indol-4-yloxy)-N-[(4-{[(1-methylpiperidin-4-yl)methyl]amino}-3-nitrophenyl)sulfonyl]benzamide This example was prepared by substituting EXAMPLE 55B for EXAMPLE 1E and EXAMPLE 88A for EXAMPLE 1F in EXAMPLE 1G. $^1$H NMR (300 MHz, dimethylsulfoxide-$d_6$) δ 11.11 (s, 1H), 8.44 (t, 1H), 8.41 (d, 1H), 7.74 (dd, 1H), 7.59 (d, 1H), 7.34 (d, 2H), 7.21 (t, 1H), 7.11-7.02 (m, 3H), 6.98-6.90 (m, 2H), 6.61 (dd, 1H), 6.31 (d, 1H), 6.23 (t, 1H), 6.20 (d, 1H), 3.20 (m, 2H), 2.95 (t, 4H), 2.71 (s, 2H), 2.62-2.49 (m, 4H), 2.55 (s, 3H), 2.16 (m, 6H), 1.95 (s, 2H), 1.86-1.78 (m, 3H), 1.42-1.31 (m, 4H), 0.92 (s, 6H).

Example 106

4-(4-{[2-(4-chlorophenyl)-4,4-dimethylcyclohex-1-en-1-yl]methyl}piperazin-1-yl)-N-({4-[3-(dimethylamino)propoxy]-3-nitrophenyl}sulfonyl)-2-(1H-indol-4-yloxy)benzamide This example was prepared by substituting EXAMPLE 55B for EXAMPLE 1E and EXAMPLE 94A for EXAMPLE 1F in EXAMPLE 1G. $^1$H NMR (300 MHz, dimethylsulfoxide-$d_6$) δ 11.10 (s, 1H), 8.16 (d, 1H), 7.90 (dd, 1H), 7.61 (d, 1H), 7.35 (d, 2H), 7.24-7.19 (m, 2H), 7.10-7.01 (m, 3H), 6.91 (t, 1H), 6.60 (dd, 1H), 6.28 (d, 1H), 6.23 (t, 1H), 6.20 (d, 1H), 4.23 (t, 2H), 3.03 (t, 2H), 2.95 (t, 4H), 2.72 (s, 2H), 2.67 (s, 6H), 2.17 (m, 6H), 2.07 (m, 2H), 1.95 (s, 2H), 1.38 (t, 2H), 0.92 (s, 6H).

Example 107

4-(4-{[2-(4-chlorophenyl)-4,4-dimethylcyclohex-1-en-1-yl]methyl}piperazin-1-yl)-2-(1H-indol-5-yloxy)-N-{[4-(4-methylpiperazin-1-yl)-3-nitrophenyl]sulfonyl}benzamide Example 107A 4-(4-methylpiperazin-1-yl)-3-nitrobenzenesulfonamide This example was prepared by substituting 1-methylpiperazine for 3-(pyrrolidin-1-yl)propan-1-amine in EXAMPLE 68F.

Example 107B 4-(4-{[2-(4-chlorophenyl)-4,4-dimethylcyclohex-1-en-1-yl]methyl}piperazin-1-yl)-2-(1H-indol-5-yloxy)-N-{[4-(4-methylpiperazin-1-yl)-3-nitrophenyl]sulfonyl}benzamide This example was prepared by substituting EXAMPLE 26C for EXAMPLE 1E and EXAMPLE 107A for EXAMPLE 1F in EXAMPLE 1G. $^1$H NMR (300 MHz, dimethylsulfoxide-$d_6$) δ 11.21 (s, 1H), 8.18 (d, 1H), 7.77 (dd, 1H), 7.57 (d, 1H), 7.34 (d, 2H), 7.26 (t, 1H), 7.22 (d, 1H), 7.16 (d, 1H), 7.07-7.02 (m, 2H), 6.96 (t, 1H), 6.87 (dd, 1H), 6.39 (d, 1H), 6.25 (m, 2H), 3.16 (m, 4H), 3.01 (t, 4H), 2.73 (s, 2H), 2.66 (broad s, 4H), 2.39 (s, 3H), 2.18 (m, 6H), 1.95 (s, 2H), 1.38 (t, 2H), 0.92 (s, 6H).

Example 108

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[1-(2,2,2-trifluoroethyl)piperidin-4-yl]amino}phenyl)sulfonyl]benzamide Example 108A 3-nitro-4-(1-(2,2,2-trifluoroethyl)piperidin-4-ylamino)benzenesulfonamide 4-chloro-3-nitrobenzenesulfonamide (1.300 g), 1-(2,2,2-trifluoroethyl)piperidin-4-amine hydrochloride (1.201 g), and triethylamine (2.30 mL) were added to 1,4-dioxane (50 mL) and water (5 mL) and heated at 90° C. for 16 hours. The solution was concentrated on vacuum and purified by flash column chromatography on silica gel with ethyl acetate increasing to 5% methanol in ethyl acetate.

Example 108B 4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[1-(2,2,2-trifluoroethyl)piperidin-4-yl]amino}phenyl)sulfonyl]benzamide This EXAMPLE was prepared by substituting EXAMPLE 55B for EXAMPLE 1E and EXAMPLE 108A for EXAMPLE 1F in EXAMPLE 1G. $^1$H NMR (300 MHz, dimethylsulfoxide-$d_6$) δ 11.24 (s, 1H), 8.50 (d, 1H), 8.25 (d, 1H), 7.71 (dd, 1H), 7.52 (d, 1H), 7.34 (d, 2H), 7.27 (t, 1H), 7.17 (d, 1H), 7.11 (d, 1H), 7.04 (d, 2H), 6.97 (t, 1H), 6.71 (dd, 1H), 6.43 (d, 1H), 6.28 (d, 1H), 6.24 (t, 1H), 3.68 (m, 1H), 3.23 (q, 2H), 3.06 (broad s, 4H), 2.95-2.87 (m, 2H), 2.78-2.71 (m, 2H), 2.58 (t, 2H), 2.25-2.11 (m, 6H), 1.98-1.85 (m, 4H), 1.64 (m, 2H), 1.39 (t, 2H), 0.92 (s, 6H).

Example 109

4-(4-{[2-(4-chlorophenyl)-4,4-dimethylcyclohex-1-en-1-yl]methyl}piperazin-1-yl)-N-{[4-({[4-(dimethylamino)-1-methylpiperidin-4-yl]methyl}amino)-3-nitrophenyl]sulfonyl}-2-(1H-indol-5-yloxy)benzamide

Example 109A 4-((4-(dimethylamino)-1-methylpiperidin-4-yl)methylamino)-3-nitrobenzenesulfonamide This example was prepared by substituting 4-(aminomethyl)-N,N,1-trimethylpiperidin-4-amine for 1-(2,2,2-trifluoroethyl)piperidin-4-amine hydrochloride in EXAMPLE 108A.

Example 109B 4-(4-{[2-(4-chlorophenyl)-4,4-dimethylcyclohex-1-en-1-yl]methyl}piperazin-1-yl)-N-{[4-({[4-(dimethylamino)-1-methylpiperidin-4-yl]methyl}amino)-3-nitrophenyl]sulfonyl}-2-(1H-indol-5-yloxy)benzamide This example was prepared by substituting EXAMPLE 26C for EXAMPLE 1E and EXAMPLE 109A for EXAMPLE 1F in EXAMPLE 1G. $^1$H NMR (300 MHz, dimethylsulfoxide-$d_6$) δ 11.06 (s, 1H), 8.56 (broad s, 1H), 8.50 (d, 1H), 7.81 (dd, 1H), 7.54 (d, 1H), 7.36-7.31 (m, 4H), 7.08-7.02 (m, 4H), 6.77 (dd, 1H), 6.57 (dd, 1H), 6.34 (t, 1H), 6.13 (d, 1H), 3.50 (d, 2H), 3.04 (m, 2H), 2.96 (t, 4H), 2.87 (m, 2H), 2.71 (s, 2H), 2.58 (s, 3H), 2.28 (s 6H), 2.16 (m, 6H) 1.98 (m, 2H) 1.95 (s, 2H), 1.65-1.54 (m, 2H), 1.38 (t, 2H), 0.94 (s, 6H).

Example 110

4-{4-[(4'-chloro-1,1'-biphenyl-2-yl)methyl]piperazin-1-yl}-2-(2,3-dihydro-1,4-benzodioxin-5-yloxy)-N-({3-nitro-4-[(tetrahydro-2H-pyran-4-ylmethyl)amino]phenyl}sulfonyl)benzamide

Example 110A methyl 4-(4-((4'-chlorobiphenyl-2-yl)methyl)piperazin-1-yl)-2-(2,3-dihydrobenzo[b][1,4]dioxin-5-yloxy)benzoate This example was prepared by substituting EXAMPLE 34A for EXAMPLE 18E and 2,3-dihydrobenzo[b][1,4]dioxin-5-ol for phenol in EXAMPLE 18F.

Example 110B 4-(4-((4'-chlorobiphenyl-2-yl)methyl)piperazin-1-yl)-2-(2,3-dihydrobenzo[b][1,4]dioxin-5-yloxy)benzoic acid This example was prepared by substituting EXAMPLE 110A for EXAMPLE 1D in EXAMPLE 1E.

Example 110C

4-{4-[(4'-chloro-1,1'-biphenyl-2-yl)methyl]piperazin-1-yl}-2-(2,3-dihydro-1,4-benzodioxin-5-yloxy)-N-({3-nitro-4-[(tetrahydro-2H-pyran-4-ylmethyl)amino]phenyl}sulfonyl)benzamide This example was prepared by substituting EXAMPLE 110B for EXAMPLE 1E in EXAMPLE 1G. $^1$H NMR (300 MHz, dimethylsulfoxide-$d_6$) δ ppm 11.40 (s, 1H), 8.65 (t, 1H), 8.55 (d, 1H), 7.83 (dd, 1H), 7.46 (m, 6H), 7.36 (m, 2H), 7.23 (m, 2H), 6.77 (d, 1H), 6.70 (dd, 1H), 6.42 (m, 2H), 6.27 (d, 1H), 4.20 (s, 4H), 3.85 (dd, 2H), 3.37 (m, 4H), 3.25 (m, 2H), 3.13 (m, 4H), 2.35 (m, 4H), 1.90 (m, 1H), 1.62 (dd, 2H), 1.27 (m, 2H).

Example 111

5-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-1,1'-biphenyl-2-carboxamide

Example 111A methyl 5-(4-((4'-chlorobiphenyl-2-yl)methyl)piperazin-1-yl)biphenyl-2-carboxylate EXAMPLE 34A (100 mg, 0.2 mmol) in tetrahydrofuran (1.5 mL) was treated with phenylboronic acid (36.6 mg, 0.3 mmol), tris(dibenzylideneacetone)dipalladium(O) (9.2 mg, 0.01 mmol), tri-tert-butylphosphonium tetrafluoroborate (5.8 mg, 0.02 mmol) and cesium fluoride (91 mg, 0.6 mmol), flushed with nitrogen and stirred overnight at ambient temperature. The reaction mixture was diluted with ethyl acetate, washed with water and brine, dried (MgSO$_4$), filtered and concentrated. The concentrate was purified by column chromatography on silica gel eluting with a gradient of 0 to 3% methanol in CH$_2$Cl$_2$ to give the product.

Example 111B 5-(4-((4'-chlorobiphenyl-2-yl)methyl)piperazin-1-yl)biphenyl-2-carboxylic acid This example was prepared by substituting EXAMPLE 111A for EXAMPLE 1D in EXAMPLE 1E.

Example 111C

5-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-1,1'-biphenyl-2-carboxamide This example was prepared by substituting EXAMPLE 111B for EXAMPLE 27G in EXAMPLE 27H. $^1$H NMR (300 MHz, dimethylsulfoxide-$d_6$) δ ppm 12.09 (s, 1H), 8.72 (t, 1H), 8.46 (d, 1H), 7.79 (m, 2H), 7.52 (m, 4H), 7.35 (dd, 5H), 7.16 (m, 1H), 7.04 (m, 4H), 6.91 (dd, 1H), 6.78 (m, 1H), 4.39 (m, 1H), 3.88 (m, 3H), 3.42 (m, 4H), 3.27 (m, 4H), 2.96 (m, 4H), 1.95 (m, 1H), 1.67 (m, 2H), 1.31 (m, 2H).

Example 112

5-{4-[(4'-chloro-1,1'-biphenyl-2-yl)methyl]piperazin-1-yl}-N-[(4-{[3-(dimethylamino)propyl]amino}-3-nitrophenyl)sulfonyl]-1,1'-biphenyl-2-carboxamide This example was prepared by substituting EXAMPLE 111B for EXAMPLE 27G and EXAMPLE 154A for EXAMPLE 1F in EXAMPLE 27H. $^1$H NMR (300 MHz, dimethylsulfoxide-d) δ ppm 12.09 (s, 1H), 8.74 (t, 1H), 8.47 (d, 1H), 7.83 (dd, 1H), 7.70 (m, 1H), 7.40 (m, 8H), 7.27 (m, 1H), 7.20 (m, 1H), 7.07 (m, 4H), 6.91 (dd, 1H), 6.77 (m, 1H), 4.39 (m, 1H), 3.87 (m, 1H), 3.55 (m, 4H), 3.26 (m, 2H), 3.16 (m, 4H), 3.03 (m, 2H), 2.80 (m, 6H), 1.98 (m, 2H).

Example 113

4-[4-({4'-chloro-4-[2-(dimethylamino)ethoxy]-1,1'-biphenyl-2-yl}methyl)piperazin-1-yl]-N-({3-nitro-4-[(tetrahydro-2H-pyran-4-ylmethyl)amino]phenyl}sulfonyl)-2-phenoxybenzamide

Example 113A methyl 2-phenoxy-4-(piperazin-1-yl)benzoate

This example was made by substituting piperazine for EXAMPLE 1B in EXAMPLE 1D.

Example 113B methyl 4-(4-(2-bromo-5-hydroxybenzyl)piperazin-1-yl)-2-phenoxybenzoate This example was made by substituting 2-bromo-5-hydroxybenzaldehyde for 4'-chlorobiphenyl-2-carboxaldehyde and EXAMPLE 113A for tert-butyl piperazine-1-carboxylate in EXAMPLE 1A.

Example 113C methyl 4-(4-(2-bromo-5-(2-(dimethylamino)ethoxy)benzyl)piperazin-1-yl)-2-phenoxybenzoate A mixture of EXAMPLE 113B (170 mg), 2-chloro-N,N-dimethylethanamine hydrochloride salt (80 mg) and cesium carbonate (278 mg) was suspended in anhydrous N,N-dimethylformamide (3 mL). The reaction mixture was heated at 50° C. overnight. The reaction mixture was cooled to room temperature and diluted with ethyl acetate. The organic phase was washed with water and brine, and dried over anhydrous Na$_2$SO$_4$. The solvent was removed under vacuum to afford an oily residue which was used in the next step without further purification.

Example 113D methyl 4-(4-((4'-chloro-4-(2-(dimethylamino)ethoxy)biphenyl-2-yl)methyl)piperazin-1-yl)-2-phenoxybenzoate This example was made by substituting EXAMPLE 113C for EXAMPLE 68C and 4-chlorophenylboronic acid for 4-methoxyphenylboronic acid in EXAMPLE 68D.

Example 113E 4-(4-((4'-chloro-4-(2-(dimethylamino)ethoxy)biphenyl-2-yl)methyl)piperazin-1-yl)-2-phenoxybenzoic acid This example was made by substituting EXAMPLE 113D for EXAMPLE 1D in EXAMPLE 1E.

Example 113F

4-[4-({4'-chloro-4-[2-(dimethylamino)ethoxy]-1,1'-biphenyl-2-yl}methyl)piperazin-1-yl]-N-({3-nitro-4-[(tetrahydro-2H-pyran-4-ylmethyl)amino]phenyl}sulfonyl)-2-phenoxybenzamide This example was made by substituting EXAMPLE 113E for EXAMPLE 1E in EXAMPLE 27H. $^1$H NMR (400 MHz, dimethylsulfoxide-d$_6$) δ 11.69 (br s, 1H), 9.87 (br s, 1H), 8.63 (t, 1H), 8.46 (d, 1H), 7.75 (dd, 1H), 7.50 (m, 3H), 7.34-7.23 (m, 6H), 7.14 (m, 2H), 6.98 (m, 1H), 6.78 (m, 3H), 6.44 (d, 1H), 4.37 (t, 2H), 3.86 (m, 2H), 3.60-3.41 (m, 10H), 3.34 (t, 4H), 3.28 (m, 2H), 2.89 (s, 6H), 1.91 (m, 1H), 1.62 (m, 2H), 1.28 (m, 2H).

Example 114

4-(4-{[4'-chloro-4-(3-piperidin-1-ylpropoxy)-1,1'-biphenyl-2-yl]methyl}piperazin-1-yl)-N-({3-nitro-4-[(tetrahydro-2H-pyran-4-ylmethyl)amino]phenyl}sulfonyl)-2-phenoxybenzamide

Example 114A methyl 4-(4-(2-bromo-5-(3-(piperidin-1-yl)propoxy)benzyl)piperazin-1-yl)-2-phenoxybenzoate This example was made by substituting 1-(3-chloropropyl)piperidine hydrochloride salt for 2-chloro-N,N-dimethylethanamine hydrochloride salt in EXAMPLE 113C.

Example 114B methyl 4-(4-((4'-chloro-4-(3-(piperidin-1-yl)propoxy)biphenyl-2-yl)methyl)piperazin-1-yl)-2-phenoxybenzoate This example was made by substituting EXAMPLE 114A for EXAMPLE 68C and 4-chlorophenylboronic acid for 4-methoxyphenylboronic acid in EXAMPLE 68D.

Example 114C 4-(4-((4'-chloro-4-(3-(piperidin-1-yl)propoxy)biphenyl-2-yl)methyl)piperazin-1-yl)-2-phenoxybenzoic acid This example was made by substituting EXAMPLE 114B for EXAMPLE 1D in EXAMPLE 1E.

Example 114D 4-(4-{[4'-chloro-4-(3-piperidin-1-ylpropoxy)-1,1'-biphenyl-2-yl]methyl}piperazin-1-yl)-N-({3-nitro-4-[(tetrahydro-2H-pyran-4-ylmethyl)amino]phenyl}sulfonyl)-2-phenoxybenzamide This example was made by substituting EXAMPLE 114C for EXAMPLE 1E in EXAMPLE 27H. $^1$H NMR (400 MHz, dimethylsulfoxide-d$_6$) δ 11.69 (br s, 1H), 9.18 (br s, 1H), 8.63 (t, 1H), 8.46 (d, 1H), 7.75 (dd, 1H), 7.50 (m, 3H), 7.33-7.21 (m, 6H), 7.15 (d, 2H), 6.98 (m, 1H), 6.78 (m, 3H), 6.44 (d, 1H), 4.11 (t, 2H), 3.87 (dd, 2H), 3.60-3.38 (m, 10H), 3.34 (m, 4H), 3.25 (m, 4H), 2.92 (m, 2H), 2.17 (m, 2H), 1.85 (m, 3H), 1.64 (m, 6H), 1.29 (m, 2H).

Example 115

4-(4-{[4'-chloro-4-(2-morpholin-4-ylethoxy)-1,1'-biphenyl-2-yl]methyl}piperazin-1-yl)-N-({3-nitro-4-[(tetrahydro-2H-pyran-4-ylmethyl)amino]phenyl}sulfonyl)-2-phenoxybenzamide Example 115A methyl 4-(4-(2-bromo-5-(2-morpholinoethoxy)benzyl)piperazin-1-yl)-2-phenoxybenzoate This example was made by substituting 4-(2-chloroethyl) morpholine hydrochloride salt for 2-chloro-N,N-dimethylethanamine hydrochloride salt in EXAMPLE 113C.

Example 115B methyl 4-(4-((4'-chloro-4-(2-morpholinoethoxy)biphenyl-2-yl)methyl)piperazin-1-yl)-2-phenoxybenzoate This example was made by substituting EXAMPLE 115A for EXAMPLE 68C and 4-chlorophenylboronic acid for 4-methoxyphenylboronic acid in EXAMPLE 68D.

Example 115C 4-(4-((4'-chloro-4-(2-morpholinoethoxy)biphenyl-2-yl)methyl)piperazin-1-yl)-2-phenoxybenzoic acid This example was made by substituting EXAMPLE 115B for EXAMPLE 1D in EXAMPLE 1E.

Example 115D 4-(4-{[4'-chloro-4-(2-morpholin-4-ylethoxy)-1,1'-biphenyl-2-yl]methyl}piperazin-1-yl)-N-({3-nitro-4-[(tetrahydro-2H-pyran-4-ylmethyl)amino]phenyl}sulfonyl)-2-phenoxybenzamide This example was made by substituting EXAMPLE 115C for EXAMPLE 1E in EXAMPLE 27H. $^1$H NMR (400 MHz, dimethylsulfoxide-d$_6$) δ 11.66 (br s, 1H), 8.63 (t, 1H), 8.46 (d, 1H), 7.75 (dd, 1H), 7.50 (m, 3H), 7.31 (m, 4H), 7.23 (m, 2H), 7.15 (m, 2H), 6.98 (m, 1H), 6.78 (m, 3H), 6.44 (d, 1H), 4.41 (m, 2H), 3.87 (m, 6H), 3.60-3.38 (m, 12H), 3.36-3.25 (m, 8H), 1.91 (m, 1H), 1.64 (m, 2H), 1.29 (m, 2H).

Example 116

4-[4-({4'-chloro-4-[3-(dimethylamino)propoxy]-1,1'-biphenyl-2-yl}methyl)piperazin-1-yl]-N-({3-nitro-4-[(tetrahydro-2H-pyran-4-ylmethyl)amino]phenyl}sulfonyl)-2-phenoxybenzamide Example 116A methyl 4-(4-(2-bromo-5-(3-(dimethylamino)propoxy)benzyl)piperazin-1-yl)-2-phenoxybenzoate This example was made by substituting 3-chloro-N,N-dimethylpropan-1-amine hydrochloride salt for 2-chloro-N,N-dimethylethanamine hydrochloride salt in EXAMPLE 113C.

Example 116B methyl 4-(4-((4'-chloro-4-(3-(dimethylamino)propoxy)biphenyl-2-yl)methyl)piperazin-1-yl)-2-phenoxybenzoate This example was made by substituting EXAMPLE 116A for EXAMPLE 68C and 4-chlorophenylboronic acid for 4-methoxyphenylboronic acid in EXAMPLE 68D.

Example 116C 4-(4-((4'-chloro-4-(3-(dimethylamino)propoxy)biphenyl-2-yl)methyl)piperazin-1-yl)-2-phenoxybenzoic acid This example was made by substituting EXAMPLE 116B for EXAMPLE JD in EXAMPLE 1E.

Example 116D

4-[4-({4'-chloro-4-[3-(dimethylamino)propoxy]-1,1'-biphenyl-2-yl}methyl)piperazin-1-yl]-N-({3-nitro-4-[(tetrahydro-2H-pyran-4-ylmethyl)amino]phenyl}sulfonyl)-2-phenoxybenzamide This example was made by substituting EXAMPLE 116C for EXAMPLE 1E in EXAMPLE 27H. $^1$H NMR (400 MHz, dimethylsulfoxide-d$_6$) δ 11.64 (br s, 1H), 9.52 (br s, 1H), 8.63 (t, 1H), 8.47 (d, 1H), 7.75 (dd, 1H), 7.50 (m, 3H), 7.34 (m, 2H), 7.23 (m, 4H), 7.14 (d, 1H), 6.98 (m, 2H), 6.78 (m, 3H), 6.42 (s, 1H), 4.09 (t, 2H), 3.86 (m, 2H), 3.50-3.36 (m, 8H), 3.28 (m, 8H), 2.83 (s, 6H), 2.12 (m, 2H), 1.91 (m, 1H), 1.62 (m, 2H), 1.29 (m, 2H).

Example 117

4-(4-{[4'-chloro-4-(2-morpholin-4-ylethoxy)-1,1'-biphenyl-2-yl]methyl}piperazin-1-yl)-2-phenoxy-N-({4-[(tetrahydro-2H-pyran-4-ylmethyl)amino]-3-[(trifluoromethyl)sulfonyl]phenyl}sulfonyl)benzamide This example was made by substituting EXAMPLE 115C for EXAMPLE 27G and EXAMPLE 163A for EXAMPLE 1F in EXAMPLE 27H. $^1$H NMR (400 MHz, dimethylsulfoxide-d$_6$) δ 8.11 (d, 1H), 7.86 (dd, 1H), 7.49 (m, 3H), 7.36-7.26 (m, 7H), 7.10 (m, 3H), 6.84 (d, 2H), 6.77 (dd, 1H), 6.41 (s, 1H), 4.38 (m, 2H), 3.84 (m, 4H), 3.55 (m, 2H), 3.50-3.30 (m, 10H), 3.28 (m, 8H), 3.20 (m, 2H), 1.86 (m, 1H), 1.55 (m, 2H), 1.26 (m, 2H).

Example 118

4-(4-{[4'-chloro-4-(3-piperidin-1-ylpropoxy)-1,1'-biphenyl-2-yl]methyl}piperazin-1-yl)-2-phenoxy-N-({4-[(tetrahydro-2H-pyran-4-ylmethyl)amino]-3-[(trifluoromethyl)sulfonyl]phenyl}sulfonyl) benzamide This example was made by substituting EXAMPLE 114C for EXAMPLE 27G and EXAMPLE 163A for EXAMPLE 1F in EXAMPLE 27H. $^1$H NMR (400 MHz, dimethylsulfoxide-$d_6$) δ 11.65 (br s, 1H), 9.06 (br s, 1H), 8.11 (d, 1H), 7.86 (dd, 1H), 7.49 (m, 3H), 7.36-7.20 (m, 7H), 7.06 (m, 3H), 6.83 (d, 2H), 6.76 (dd, 1H), 6.41 (s, 1H), 4.10 (t, 2H), 3.85 (dd, 2H), 3.40-3.05 (m, 16H), 2.90 (m, 2H), 2.15 (m, 2H), 1.84 (m, 3H), 1.60 (m, 6H), 1.41 (m, 2H), 1.26 (m, 2H).

Example 119

4-[4-({4'-chloro-4-[3-(dimethylamino)propoxy]-1,1'-biphenyl-2-yl}methyl)piperazin-1-yl]-2-phenoxy-N-({4-[(tetrahydro-2H-pyran-4-ylmethyl)amino]-3-[(trifluoromethyl)sulfonyl]phenyl}sulfonyl) benzamide This example was made by substituting EXAMPLE 116C for EXAMPLE 27G and EXAMPLE 163A for EXAMPLE 1F in EXAMPLE 27H. $^1$H NMR (400 MHz, dimethylsulfoxide-$d_6$) δ 8.11 (d, 1H), 7.86 (dd, 1H), 7.49 (m, 3H), 7.36-7.26 (m, 7H), 7.06 (m, 3H), 6.84 (d, 2H), 6.76 (dd, 1H), 6.41 (d, 1H), 4.09 (t, 2H), 3.84 (dd, 2H), 3.50-3.24 (m, 14H), 3.10 (m, 2H), 2.83 (s, 6H), 2.12 (m, 2H), 1.86 (m, 1H), 1.55 (m, 2H), 1.26 (m, 2H).

Example 120

4-[4-({4'-chloro-4-[2-(dimethylamino)ethoxy]-1,1'-biphenyl-2-yl}methyl)piperazin-1-yl]-2-phenoxy-N-({4-[(tetrahydro-2H-pyran-4-ylmethyl)amino]-3-[(trifluoromethyl)sulfonyl]phenyl}sulfonyl) benzamide This example was made by substituting EXAMPLE 113E for EXAMPLE 27G and EXAMPLE 163A for EXAMPLE 1F in EXAMPLE 27H. $^1$H NMR (400 MHz, dimethylsulfoxide-$d_6$) δ 11.75 (br s, 1H), 9.90 (br s, 1H), 8.10 (d, 1H), 7.85 (dd, 1H), 7.49 (m, 3H), 7.38-7.25 (m, 7H), 7.11 (d, 2H), 7.03 (m, 1H), 6.82 (d, 2H), 6.77 (dd, 1H), 6.44 (s, 1H), 4.37 (t, 2H), 3.85 (m, 6H), 3.55 (m, 2H), 3.29 (m, 8H), 3.10 (m, 2H), 2.89 (s, 6H), 1.86 (m, 1H), 1.55 (m, 2H), 1.24 (m, 2H).

Example 121

4-[4-({4'-chloro-4-[2-(dimethylamino)ethoxy]-1,1'-biphenyl-2-yl}methyl)piperazin-1-yl]-N-({3-nitro-4-[(3-pyrrolidin-1-ylpropyl)amino]phenyl}sulfonyl)-2-phenoxybenzamide This example was made by substituting EXAMPLE 113E for EXAMPLE 27G and EXAMPLE 68F for EXAMPLE 1F in EXAMPLE 27H. $^1$H NMR (400 MHz, dimethylsulfoxide-$d_6$) δ 11.70 (br s, 1H), 9.95 (br s, 1H), 9.73 (br s, 1H), 8.69 (t, 1H), 8.49 (d, 1H), 7.79 (dd, 1H), 7.50 (m, 3H), 7.34 (m, 2H), 7.23 (m, 3H), 7.16 (d, 1H), 7.09 (m, 1H), 7.00 (m, 1H), 6.82 (d, 2H), 6.77 (dd, 1H), 6.42 (s, 1H), 4.37 (m, 2H), 3.70 (m, 6H), 3.54 (m, 8H), 3.21 (m, 4H), 3.19 (m, 2H), 2.88 (s, 6H), 1.97 (m, 4H), 1.85 (m, 2H).

Example 122

4-[4-({4'-chloro-3-[2-(dimethylamino)ethoxy]-1,1'-biphenyl-2-yl}methyl)piperazin-1-yl]-N-({3-nitro-4-[(tetrahydro-2H-pyran-4-ylmethyl)amino] phenyl}sulfonyl)-2-phenoxybenzamide

Example 122A methyl 4-(4-(2-bromo-6-hydroxybenzyl)piperazin-1-yl)-2-phenoxybenzoate This example was made by substituting 2-bromo-6-hydroxybenzaldehyde for 4'-chlorobiphenyl-2-carboxaldehyde and EXAMPLE 113A for tert-butyl piperazine-1-carboxylate in EXAMPLE 1A.

Example 122B methyl 4-(4-((4'-chloro-3-hydroxybiphenyl-2-yl) methyl)piperazin-1-yl)-2-phenoxybenzoate This example was made by substituting EXAMPLE 122A for EXAMPLE 68C and 4-chlorophenylboronic acid for 4-methoxyphenylboronic acid in EXAMPLE 68D.

Example 122C methyl 4-(4-((4'-chloro-3-(2-(dimethylamino) ethoxy)biphenyl-2-yl)methyl)piperazin-1-yl)-2-phenoxybenzoate EXAMPLE 122B (100 mg) and 2-chloro-N,N-dimethylethanamine hydrochloride salt (30 mg) was dissolved in mixed solvent of dichloromethane (1.5 mL) and 50% sodium hydroxide aqueous solution (0.5 mL), followed by addition of tetrabutylammonium iodide (15 mg). The reaction mixture was stirred at room temperature overnight. The reaction mixture was diluted with ethyl acetate, and washed with water and brine. The organic phase was dried over $Na_2SO_4$ and concentrated. Flash column purification was performed with 0-5% methanol/dichloromethane to afford the product.

Example 122D 4-(4-((4'-chloro-3-(2-(dimethylamino)ethoxy)biphenyl-2-yl)methyl)piperazin 1-yl)-2-phenoxybenzoic acid This example was made by substituting EXAMPLE 122C for EXAMPLE 1D in EXAMPLE 1E.

Example 122E

4-[4-({4'-chloro-3-[2-(dimethylamino)ethoxy]-1,1'-biphenyl-2-yl}methyl)piperazin-1-yl]-N-({3-nitro-4-[(tetrahydro-2H-pyran-4-ylmethyl)amino] phenyl}sulfonyl)-2-phenoxybenzamide This example was made by substituting EXAMPLE 122D for EXAMPLE 1E in EXAMPLE 27H. $^1$H NMR (400 MHz, dimethylsulfoxide-$d_6$) δ 10.20 (br s, 1H), 9.46 (br s, 1H), 8.65

(t, 1H), 8.47 (d, 1H), 7.78 (d, 1H), 7.75 (dd, 1H), 7.52 (m, 4H), 7.38 (m, 3H), 7.23 (m, 3H), 7.12 (m, 1H), 6.98 (m, 2H), 6.78 (d, 2H), 6.76 (dd, 1H), 6.43 (s, 1H), 4.43 (m, 2H), 3.87 (m, 2H), 3.62 (m, 4H), 3.35-3.15 (m, 12H), 2.90 (s, 6H), 1.90 (m, 1H), 1.62 (m, 2H), 1.27 (m, 2H).

Example 123

4-[4-({4'-chloro-3-[2-(dimethylamino)ethoxy]-1,1'-biphenyl-2-yl}methyl)piperazin-1-yl]-N-({3-nitro-4-[(3-pyrrolidin-1-ylpropyl)amino]phenyl}sulfonyl)-2-phenoxybenzamide This example was made by substituting EXAMPLE 122C for EXAMPLE 1E and EXAMPLE 68F for EXAMPLE 1F in EXAMPLE 1G. $^1$H NMR (400 MHz, dimethylsulfoxide-$d_6$) δ 10.01 (brs, 1H), 9.63 (brs, 1H), 9.32 (brs, 1H), 8.69 (t, 1H), 8.49 (d, 1H), 7.80 (dd, 1H), 7.52 (m, 4H), 7.38 (m, 2H), 7.25 (m, 3H), 7.15 (d, 1H), 7.01 (m, 1H), 6.95 (m, 1H), 6.81 (d, 2H), 6.76 (m, 1H), 6.41 (s, 1H), 4.43 (m, 4H), 3.56-3.51 (m, 8H), 3.20 (m, 4H), 3.10 (m, 6H), 2.91 (s, 6H), 1.98 (m, 4H), 1.85 (m, 2H).

Example 124

4-[4-({4'-chloro-3-[2-(dimethylamino)ethoxy]-1,1'-biphenyl-2-yl}methyl)piperazin-1-yl]-2-phenoxy-N-({4-[(tetrahydro-2H-pyran-4-ylmethyl)amino]-3-[(trifluoromethyl)sulfonyl]phenyl}sulfonyl)benzamide This example was made by substituting EXAMPLE 122C for EXAMPLE 27G and EXAMPLE 163A for EXAMPLE 1F in EXAMPLE 27H. $^1$H NMR (400 MHz, dimethylsulfoxide-$d_6$) δ 11.71 (brs, 1H), 9.89 (brs, 1H), 9.14 (brs, 1H), 8.11 (d, 1H), 7.86 (dd, 1H), 7.52 (m, 4H), 7.38 (m, 2H), 7.29 (m, 3H), 7.20 (m, 1H), 7.11 (d, 1H), 7.05 (m, 1H), 6.95 (m, 1H), 6.83 (d, 2H), 6.76 (dd, 1H), 6.40 (s, 1H), 4.41 (m, 2H), 3.85 (m, 2H), 3.59 (m, 4H), 3.44 (m, 2H), 3.28 (m, 8H), 3.06 (m, 2H), 2.91 (s, 6H), 1.84 (m, 1H), 1.55 (m, 2H), 1.26 (m, 2H).

Example 125

4-[4-({4'-chloro-4-[2-(dimethylamino)ethoxy]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide Example 125A 4'-chloro-4-hydroxybiphenyl-2-carbaldehyde This example was made by substituting 2-bromo-5-hydroxybenzaldehyde for EXAMPLE 68C and 4-chlorophenylboronic acid for 4-methoxyphenylboronic acid in EXAMPLE 68D.

Example 125B

4'-chloro-4-(2-(dimethylamino)ethoxy)biphenyl-2-carbaldehyde

This example was made by substituting EXAMPLE 125A for EXAMPLE 122B in EXAMPLE 122C.

Example 125C methyl 2-(1H-indol-4-yloxy)-4-(4-((4'-chloro-4-(2-(dimethylamino)ethoxy)biphenyl-2-yl)methyl)piperazin-1-yl)benzoate This example was made by substituting EXAMPLE 125B for 4'-chlorobiphenyl-2-carboxaldehyde and EXAMPLE 68B for tert-butyl piperazine-1-carboxylate in EXAMPLE 1A.

Example 125D 2-(1H-indol-4-yloxy)-4-(4-((4'-chloro-4-(2-(dimethylamino)ethoxy)biphenyl-2-yl)methyl)piperazin-1-yl)benzoic acid This example was made by substituting EXAMPLE 125C for EXAMPLE 1D in EXAMPLE 1E.

Example 125E

4-[4-({4'-chloro-4-[2-(dimethylamino)ethoxy]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide This example was made by substituting EXAMPLE 125D for EXAMPLE 1E in EXAMPLE 27H. $^1$H NMR (400 MHz, dimethylsulfoxide-$d_6$) δ 11.46 (br s, 1H), 11.25 (s, 1H), 9.80 (br s, 1H), 8.60 (t, 1H), 8.48 (d, 1H), 7.65 (dd, 1H), 7.55 (d, 1H), 7.46 (d, 2H), 7.28 (m, 5H), 7.15 (d, 1H), 7.10 (m, 1H), 7.04 (d, 1H), 6.94 (m, 1H), 6.73 (dd, 1H), 6.36 (m, 2H), 6.26 (m, 1H), 4.35 (t, 2H), 3.85 (m, 6H), 3.54 (m, 4H), 3.31 (m, 6H), 3.06 (m, 2H), 2.88 (s, 6H), 1.88 (m, 1H), 1.60 (m, 2H), 1.28 (m, 2H).

Example 126

4-[4-({4'-chloro-4-[2-(dimethylamino)ethoxy]-1,1'-biphenyl-2-yl}methyl)piperazin-1-yl]-2-(1H-indol-5-yloxy)-N-({3-nitro-4-[(tetrahydro-2H-pyran-4-ylmethyl)amino]phenyl}sulfonyl)benzamide Example 126A methyl 2-(1H-indol-5-yloxy)-4-(4-((4'-chloro-4-(2-(dimethylamino)ethoxy)biphenyl-2-yl)methyl)piperazin-1-yl)benzoate This example was made by substituting EXAMPLE 125B for 4'-chlorobiphenyl-2-carboxaldehyde and EXAMPLE 150A for tert-butyl piperazine-1-carboxylate in EXAMPLE 1A.

Example 126B 2-(1H-indol-5-yloxy)-4-(4-((4'-chloro-4-(2-(dimethylamino)ethoxy)biphenyl-2-yl)methyl)piperazin-1-yl)benzoic acid This example was made by substituting EXAMPLE 126A for EXAMPLE 1D in EXAMPLE 1E.

Example 126C

4-[4-({4'-chloro-4-[2-(dimethylamino)ethoxy]-1,1'-biphenyl-2-yl}methyl)piperazin-1-yl]-2-(1H-indol-5-yloxy)-N-({3-nitro-4-[(tetrahydro-2H-pyran-4-ylmethyl)amino]phenyl}sulfonyl)benzamide This example was made by substituting EXAMPLE 126B for EXAMPLE 1E in EXAMPLE 27H. $^1$H NMR (400 MHz, dimethylsulfoxide-d$_6$) δ 11.35 (br s, 1H), 11.17 (s, 1H), 9.85 (br s, 1H), 8.61 (t, 1H) 8.57 (d, 1H), 7.77 (dd, 1H), 7.54 (d, 1H), 7.46 (d, 2H), 7.38 (m, 2H), 7.30 (m, 4H), 7.09 (m, 3H), 6.84 (dd, 1H), 6.69 (dd, 1H), 6.36 (m, 1H), 6.26 (m, 1H), 4.35 (t, 2H), 3.85 (m, 6H), 3.54 (m, 4H), 3.31 (m, 6H), 3.06 (m, 2H), 2.88 (s, 6H), 1.88 (m, 1H), 1.60 (m, 2H), 1.28 (m, 2H).

Example 127

4-(4-{[4'-chloro-1,1'-biphenyl-2-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide

Example 127A

4'-chloro-4-(2-morpholinoethoxy)biphenyl-2-carbaldehyde

This example was made by substituting EXAMPLE 125A for EXAMPLE 122B in and 4-(2-chloroethyl)morpholine hydrochloride salt for 2-chloro-N,N-dimethylethanamine hydrochloride salt EXAMPLE 122C.

Example 127B methyl 2-(1H-indol-5-yloxy)-4-(4-((4'-chloro-4-(2-morpholinoethoxy)biphenyl-2-yl)methyl)piperazin-1-yl)benzoate This example was made by substituting EXAMPLE 127A for 4'-chlorobiphenyl-2-carboxaldehyde and EXAMPLE 150A for tert-butyl piperazine-1-carboxylate in EXAMPLE 1A.

Example 127C 2-(1H-indol-5-yloxy)-4-(4-((4'-chloro-4-(2-morpholinoethoxy)biphenyl-2-yl)methyl)piperazin-1-yl)benzoic acid This example was made by substituting EXAMPLE 127B for EXAMPLE 1D in EXAMPLE 1E.

Example 127D 4-(4-{[4'-chloro-4-(2-morpholin-4-ylethoxy)-1,1'-biphenyl-2-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide This example was made by substituting EXAMPLE 127C for EXAMPLE 1E in EXAMPLE 27H. $^1$H NMR (400 MHz, dimethylsulfoxide-d$_6$) δ 11.35 (br s, 1H), 11.17 (s, 1H), 8.61 (t, 1H), 8.57 (d, 1H), 7.77 (dd, 1H), 7.54 (d, 1H), 7.46 (d, 2H), 7.38 (m, 2H), 7.29 (m, 4H), 7.09 (m, 3H), 6.84 (dd, 1H), 6.69 (dd, 1H), 6.36 (m, 1H), 6.26 (d, 1H), 4.39 (t, 2H), 3.85 (m, 6H), 3.54 (m, 10H), 3.31 (m, 8H), 3.06 (m, 2H), 1.88 (m, 1H), 1.60 (m, 2H), 1.27 (m, 2H).

Example 128

4-[4-({4'-chloro-3-[2-(dimethylamino)ethoxy]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide

Example 128A

4'-chloro-3-hydroxybiphenyl-2-carb aldehyde

This example was made by substituting 2-bromo-6-hydroxybenzaldehyde for EXAMPLE 68C and 4-chlorophenylboronic acid for 4-methoxyphenylboronic acid in EXAMPLE 68D.

Example 128B

4'-chloro-3-(2-(dimethylamino)ethoxy)biphenyl-2-carbaldehyde

This example was made by substituting EXAMPLE 128A for EXAMPLE 122B in EXAMPLE 122C.

Example 128C methyl 2-(1H-indol-4-yloxy)-4-(4-((4'-chloro-3-(2-(dimethylamino)ethoxy)biphenyl-2-yl)methyl)piperazin-1-yl)benzoate This example was made by substituting EXAMPLE 128B for 4'-chlorobiphenyl-2-carboxaldehyde and EXAMPLE 68B for tert-butyl piperazine-1-carboxylate in EXAMPLE 1A.

Example 128D 2-(1H-indol-4-yloxy)-4-(4-((4'-chloro-3-(2-(dimethylamino)ethoxy)biphenyl-2-yl)methyl)piperazin-1-yl)benzoic acid This example was made by substituting EXAMPLE 128C for EXAMPLE 1D in EXAMPLE 1E.

Example 128E

4-[4-({4'-chloro-3-[2-(dimethylamino)ethoxy]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide This example was made by substituting EXAMPLE 128D for EXAMPLE 1E in EXAMPLE 27H. $^1$H NMR (400 MHz, dimethylsulfoxide-d$_6$) δ 11.15 (s, 1H), 8.47 (t, 1H) 8.45 (d, 1H), 7.68 (dd, 1H), 7.57 (d, 1H), 7.50 (d, 2H), 7.42 (d, 2H), 7.32 (m, 1H), 7.24 (m, 1H), 7.12 (d, 1H), 7.05 (d, 1H), 6.94 (m, 2H), 6.84 (d, 1H), 6.66 (dd, 1H), 6.35 (d, 1H), 6.25 (m, 2H), 4.17 (t, 2H), 3.85 (m, 2H), 3.54 (m, 10H), 3.40 (m, 6H), 3.30 (s, 6H), 3.02 (m, 2H), 2.96 (m, 4H), 2.28 (m, 4H), 1.88 (m, 1H), 1.60 (m, 2H), 1.28 (m, 2H).

Example 129

4-[4-({4'-chloro-3-[2-(dimethylamino)ethoxy]-1,1'-biphenyl-2-yl}methyl)piperazin-1-yl]-2-(1H-indol-5-yloxy)-N-({3-nitro-4-[(tetrahydro-2H-pyran-4-ylmethyl)amino]phenyl}sulfonyl)benzamide Example 129A methyl 2-(1H-indol-5-yloxy)-4-(4-((4'-chloro-3-(2-(dimethylamino)ethoxy)biphenyl-2-yl)methyl)piperazin-1-yl)benzoate This example was made by substituting EXAMPLE 128B for 4'-chlorobiphenyl-2-carboxaldehyde and EXAMPLE 150A for tert-butyl piperazine-1-carboxylate in EXAMPLE 1A.

Example 129B 2-(1H-indol-5-yloxy)-4-(4-((4'-chloro-3-(2-(dimethylamino)ethoxy)biphenyl-2-yl)methyl)piperazin-1-yl)benzoic acid This example was made by substituting EXAMPLE 129A for EXAMPLE 1D in EXAMPLE 1E.

Example 129C

4-[4-({4'-chloro-3-[2-(dimethylamino)ethoxy]-1,1'-biphenyl-2-yl}methyl)piperazin-1-yl]-2-(1H-indol-5-yloxy)-N-({3-nitro-4-[(tetrahydro-2H-pyran-4-ylmethyl)amino]phenyl}sulfonyl)benzamide This example was made by substituting EXAMPLE 129B for EXAMPLE 1E in EXAMPLE 27H. $^1$H NMR (400 MHz, dimethylsulfoxide-$d_6$) δ 11.38 (br s, 1H), 11.19 (s, 1H), 10.00 (br s, 1H), 8.61 (t, 1H) 8.58 (d, 1H), 7.79 (dd, 1H), 7.53 (m, 4H), 7.39 (m, 4H), 7.19 (m, 1H), 7.11 (m, 2H), 6.93 (d, 1H), 6.84 (dd, 1H), 6.69 (dd, 1H), 6.39 (m, 1H), 6.19 (d, 1H), 4.40 (m, 2H), 3.85 (m, 8H), 3.58 (m, 2H), 3.27 (m, 6H), 3.06 (m, 2H), 2.89 (s, 6H), 1.89 (m, 1H), 1.60 (m, 2H), 1.27 (m, 2H).

Example 130

4-(4-{[4'-chloro-4-(2-morpholin-4-ylethoxy)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide Example 130A methyl 2-(1H-indol-4-yloxy)-4-(4-((4'-chloro-4-(2-morpholinoethoxy)biphenyl-2-yl)methyl)piperazin-1-yl)benzoate This example was made by substituting EXAMPLE 127A for 4'-chlorobiphenyl-2-carboxaldehyde and EXAMPLE 68B for tert-butyl piperazine-1-carboxylate in EXAMPLE 1A.

Example 130B 2-(1H-indol-4-yloxy)-4-(4-((4'-chloro-4-(2-morpholinoethoxy)biphenyl-2-yl)methyl)piperazin-1-yl) benzoic acid This example was made by substituting EXAMPLE 130A for EXAMPLE 1D in EXAMPLE 1E.

Example 130C 4-(4-{[4'-chloro-4-(2-morpholin-4-ylethoxy)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide This example was made by substituting EXAMPLE 130B for EXAMPLE 1E in EXAMPLE 27H. $^1$H NMR (400 MHz, dimethylsulfoxide-$d_6$) δ 11.47 (br s, 1H), 11.23 (s, 1H), 8.59 (t, 1H) 8.47 (d, 1H), 7.63 (dd, 1H), 7.54 (d, 1H), 7.47 (d, 2H), 7.27 (m, 6H), 7.13 (m, 2H), 7.03 (m, 1H), 6.93 (m, 1H), 6.74 (dd, 1H), 6.35 (m, 1H), 6.24 (m, 1H), 4.39 (t, 2H), 3.85 (m, 6H), 3.54 (m, 10H), 3.26 (m, 10H), 1.88 (m, 1H), 1.59 (m, 2H), 1.27 (m, 2H).

Example 131

4-(4-{[4'-chloro-3-(2-morpholin-4-ylethoxy)-1,1'-biphenyl-2-yl]methyl}piperazin-1-yl)-2-(1H-indol-4-yloxy)-N-(({3-nitro-4-[(tetrahydro-2H-pyran-4-ylmethyl)amino]phenyl}sulfonyl)benzamide Example 131A 4'-chloro-3-(2-morpholinoethoxy)biphenyl-2-carbaldehyde This example was made by substituting EXAMPLE 128A for EXAMPLE 122B and 4-(2-chloroethyl)morpholine hydrochloride salt for 2-chloro-N,N-dimethylethanamine hydrochloride salt in EXAMPLE 122C.

Example 131B methyl 2-(1H-indol-4-yloxy)-4-(4-((4'-chloro-3-(2-morpholinoethoxy)biphenyl-2-yl)methyl)piperazin-1-yl)benzoate This example was made by substituting EXAMPLE 131A for 4'-chlorobiphenyl-2-carboxaldehyde and EXAMPLE 68B for tert-butyl piperazine-1-carboxylate in EXAMPLE 1A.

Example 131C 2-(1H-indol-4-yloxy)-4-(4-((4'-chloro-3-(2-morpholinoethoxy)biphenyl-2-yl)methyl)piperazin-1-yl) benzoic acid This example was made by substituting EXAMPLE 131B for EXAMPLE 1D in EXAMPLE 1E.

Example 131D 4-(4-{[4'-chloro-3-(2-morpholin-4-ylethoxy)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide This example was made by substituting EXAMPLE 131C for EXAMPLE 1E in EXAMPLE 27H. ¹H NMR (400 MHz, dimethylsulfoxide-d₆) δ 11.49 (br s, 1H), 11.25 (s, 1H), 8.59 (t, 1H), 8.50 (d, 1H), 7.68 (dd, 1H), 7.52 (m, 4H), 7.34 (d, 2H), 7.28 (m, 1H), 7.18 (m, 2H), 7.06 (d, 1H), 6.94 (m, 2H), 6.73 (dd, 1H), 6.40 (d, 1H), 6.33 (d, 1H), 6.24 (m, 1H), 4.43 (t, 2H), 3.85 (m, 10H), 3.61 (m, 6H), 3.27 (m, 8H), 3.02 (m, 2H), 1.88 (m, 1H), 1.60 (m, 2H), 1.28 (m, 2H).

Example 132

4-(4-{[4'-chloro-3-(2-morpholin-4-ylethoxy)-1,1'-biphenyl-2-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide

Example 132A methyl 2-(1H-indol-5-yloxy)-4-(4-((4'-chloro-3-(2-morpholinoethoxy)biphenyl-2-yl)methyl)piperazin-1-yl)benzoate This example was made by substituting EXAMPLE 131A for 4'-chlorobiphenyl-2-carboxaldehyde and EXAMPLE 150A for tert-butyl piperazine-1-carboxylate in EXAMPLE 1A.

Example 132B 2-(1H-indol-5-yloxy)-4-(4-((4'-chloro-3-(2-morpholinoethoxy)biphenyl-2-yl)methyl)piperazin-1-yl) benzoic acid This example was made by substituting EXAMPLE 132A for EXAMPLE 1D in EXAMPLE 1E.

Example 132C 4-(4-{[4'-chloro-3-(2-morpholin-4-ylethoxy)-1,1'-biphenyl-2-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide This example was made by substituting EXAMPLE 132B for EXAMPLE 1E in EXAMPLE 27H. ¹H NMR (400 MHz, dimethylsulfoxide-d₆) δ 11.34 (br s, 1H), 11.17 (s, 1H), 8.60 (t, 1H), 8.58 (d, 1H), 7.79 (dd, 1H), 7.50 (m, 4H), 7.39 (m, 4H), 7.19 (d, 1H), 7.14 (d, 1H), 7.09 (d, 1H), 6.93 (d, 1H), 6.84 (dd, 1H), 6.69 (dd, 1H), 6.39 (m, 1H), 6.19 (d, 1H), 4.40 (m, 2H), 3.85 (m, 6H), 3.48 (m, 8H), 3.27 (m, 10H), 3.06 (m, 2H), 1.89 (m, 1H), 1.60 (m, 2H), 1.27 (m, 2H).

Example 133

4-[4-({4'-chloro-4-[2-(dimethylamino)ethoxy]-1,1'-biphenyl-2-yl}methyl)piperazin-1-yl]-N-({4-[(1-methylpiperidin-4-yl)amino]-3-nitrophenyl}sulfonyl)-2-phenoxybenzamide This example was made by substituting EXAMPLE 113D for EXAMPLE 27G and EXAMPLE 21A for EXAMPLE 1F in EXAMPLE 27H. ¹H NMR (400 MHz, dimethylsulfoxide-d₆) δ 8.34 (d, 1H), 8.05 (d, 1H), 7.69 (dd, 1H), 7.59 (d, 1H), 7.42 (m, 4H), 7.14 (m, 3H), 7.09 (d, 1H), 6.98 (d, 1H), 6.92 (dd, 1H), 6.87 (m, 1H), 6.84 (m, 3H), 6.30 (d, 1H), 4.16 (t, 2H), 3.07 (m, 6H), 2.95 (m, 4H), 2.56 (m, 2H), 2.45 (s, 3H), 2.35 (m, 4H), 2.03 (m, 2H), 1.68 (m, 2H).

Example 134

4-[4-({4'-chloro-3-[2-(dimethylamino)ethoxy]-1,1'-biphenyl-2-yl}methyl)piperazin-1-yl]-2-(1H-indol-5-yloxy)-N-({3-nitro-4-[(3-pyrrolidin-1-ylpropyl)amino]phenyl}sulfonyl)benzamide This example was made by substituting EXAMPLE 129B for EXAMPLE 27G and EXAMPLE 68F for EXAMPLE 1F in EXAMPLE 27H. ¹H NMR (400 MHz, dimethylsulfoxide-d₆) δ 11.34 (br s, 1H), 11.17 (s, 1H), 9.65 (br s, 1H), 8.63 (t, 1H), 8.60 (d, 1H), 7.86 (dd, 1H), 7.53 (d, 2H), 7.41 (m, 6H), 7.15 (m, 3H), 6.92 (m, 1H), 6.84 (dd, 1H), 6.66 (dd, 1H), 6.38 (m, 1H), 6.16 (d, 1H), 4.37 (m, 2H), 3.50 (m, 12H), 3.17 (m, 4H), 2.97 (m, 4H), 2.88 (s, 6H), 1.95 (m, 4H), 1.85 (m, 2H).

Example 135

4-[4-({4'-chloro-4-[2-(dimethylamino)ethoxy]-1,1'-biphenyl-2-yl}methyl)piperazin-1-yl]-2-(1H-indol-5-yloxy)-N-({3-nitro-4-[(3-pyrrolidin-1-ylpropyl)amino]phenyl}sulfonyl)benzamide This example was made by substituting EXAMPLE 126B for EXAMPLE 27G and EXAMPLE 68F for EXAMPLE 1F in EXAMPLE 27H. ¹H NMR (400 MHz, dimethylsulfoxide-d₆) δ 11.29 (br s, 1H), 11.16 (s, 1H), 9.56 (br s, 1H), 8.63 (t, 1H), 8.60 (d, 1H), 7.85 (dd, 1H), 7.53 (d, 1H), 7.41 (m, 4H), 7.32 (m, 3H), 7.24 (m, 1H), 7.12 (m, 3H), 6.84 (dd, 1H), 6.66 (dd, 1H), 6.38 (m, 1H), 6.18 (d, 1H), 4.33 (t, 2H), 3.50 (m, 12H), 3.17 (m, 4H), 2.97 (m, 4H), 2.86 (s, 6H), 1.95 (m, 4H), 1.85 (m, 2H).

Example 136

4-(4-{[4'-chloro-4-(2-morpholin-4-ylethoxy)-1,1'-biphenyl-2-yl]methyl}piperazin-1-yl)-2-(1H-indol-5-yloxy)-N-({3-nitro-4-[(3-pyrrolidin-1-ylpropyl)amino]phenyl}sulfonyl)benzamide This example was made by substituting EXAMPLE 127C for EXAMPLE 27G and EXAMPLE 68F for EXAMPLE 1F in EXAMPLE 27H. ¹H NMR (400 MHz, dimethylsulfoxide-d₆) δ 11.29 (br s, 1H), 11.16 (s, 1H), 9.54 (br s, 1H), 8.63 (t, 1H), 8.60 (d, 1H), 7.85 (dd, 1H), 7.53 (d, 1H), 7.45 (d, 2H), 7.38 (m, 2H), 7.31 (d, 2H), 7.23 (m, 2H), 7.12 (m, 3H), 6.84 (dd, 1H), 6.66 (dd, 1H), 6.38 (m, 1H), 6.18 (d, 1H), 4.36 (t, 2H), 3.82 (m, 4H), 3.50 (m, 8H), 3.17 (m, 10H), 2.98 (m, 4H), 1.95 (m, 6H), 1.85 (m, 2H).

Example 137

4-[4-({4'-chloro-4-[2-(dimethylamino)ethoxy]-1,1'-biphenyl-2-yl}methyl)piperazin-1-yl]-N-[(3-nitro-4-{[1-(2,2,2-trifluoroethyl)piperidin-4-yl]amino}phenyl)sulfonyl]-2-phenoxybenzamide This example was made by substituting EXAMPLE 113E for EXAMPLE 27G and EXAMPLE 108A for EXAMPLE 1F in EXAMPLE 27H. ¹H NMR (400 MHz, dimethylsulfoxide-d₆) δ 11.71 (br s, 1H), 9.81 (br s, 1H), 8.46 (d, 1H), 8.29 (d, 1H), 7.75 (dd, 1H), 7.50 (m, 3H), 7.30 (m, 4H), 7.21 (m, 3H), 7.10 (m, 1H), 6.97 (m, 1H), 6.77 (m, 3H), 6.43 (s, 1H), 4.36 (t, 2H), 3.72 (m, 2H), 3.58 (m, 4H), 3.23 (m, 6H), 2.95 (m, 4H), 2.89 (s, 6H), 2.60 (m, 2H), 1.92 (m, 2H), 1.68 (m, 2H).

Example 138

4-(4-{[4'-chloro-4-(2-pyrrolidin-1-ylethoxy)-1,1'-biphenyl-2-yl]methyl}piperazin-1-yl)-N-({3-nitro-4-[(tetrahydro-2H-pyran-4-ylmethyl)amino]phenyl}sulfonyl)-2-phenoxybenzamide Example 138A methyl 4-(4-((4'-chloro-4-hydroxybiphenyl-2-yl)methyl)piperazin-1-yl)-2-phenoxybenzoate This example was made by substituting EXAMPLE 113B for EXAMPLE 68C and 4-chlorophenylboronic acid for 4-methoxyphenylboronic acid in EXAMPLE 68D.

Example 138B methyl 4-(4-((4'-chloro-4-(2-(pyrrolidin-1-yl)ethoxy)biphenyl-2-yl)methyl)piperazin-1-yl)-2-phenoxybenzoate This example was made by substituting EXAMPLE 138A for EXAMPLE 113B and 1-(2-chloroethyl)pyrrolidine HCl salt for 2-chloro-N,N-dimethylethanamine hydrochloride salt in EXAMPLE 113C.

Example 138C 4-(4-((4'-chloro-4-(2-(pyrrolidin-1-yl)ethoxy)biphenyl-2-yl)methyl)piperazin-1-yl)-2-phenoxybenzoic acid This example was made by substituting EXAMPLE 138B for EXAMPLE 1D in EXAMPLE 1E.

Example 138D 4-(4-{[4'-chloro-4-(2-pyrrolidin-1-ylethoxy)-1,1'-biphenyl-2-yl]methyl}piperazin-1-yl)-N-(3-nitro-4-{[(tetrahydro-2H-pyran-4-ylmethyl)amino]phenyl}sulfonyl)-2-phenoxybenzamide This example was made by substituting EXAMPLE 138C for EXAMPLE 1E in EXAMPLE 27H. ¹H NMR (400 MHz, dimethylsulfoxide-d₆) δ 11.64 (br s, 1H), 9.98 (br s, 1H), 8.62 (d, 1H), 8.47 (d, 1H), 7.75 (dd, 1H), 7.50 (m, 3H), 7.26 (m, 6H), 7.14 (m, 2H), 6.99 (m, 1H), 6.81 (d, 2H), 6.77 (dd, 1H), 6.43 (d, 1H), 4.36 (t, 2H), 3.86 (dd, 2H), 3.62 (m, 8H), 3.28 (m, 8H), 3.10 (m, 4H), 2.04 (m, 2H), 1.90 (m, 3H), 1.65 (m, 2H), 1.29 (m, 2H).

Example 139

4-[4-({4'-chloro-4-[2-(diisopropylamino)ethoxy]-1,1'-biphenyl-2-yl}methyl)piperazin-1-yl]-N-({3-nitro-4-[(tetrahydro-2H-pyran-4-ylmethyl)amino]phenyl}sulfonyl)-2-phenoxybenzamide Example 139A methyl 4-(4-((4'-chloro-4-(2-(diisopropylamino)ethoxy)biphenyl-2-yl)methyl)piperazin-1-yl)-2-phenoxybenzoate This example was made by substituting EXAMPLE 138A for EXAMPLE 113B and 2-diisopropylaminoethyl chloride hydrochloride salt for 2-chloro-N,N-dimethylethanamine hydrochloride salt in EXAMPLE 113C.

Example 139B 4-(4-((4'-chloro-4-(2-(diisopropylamino)ethoxy)biphenyl-2-yl)methyl)piperazin-1-yl)-2-phenoxybenzoic acid This example was made by substituting EXAMPLE 139A for EXAMPLE 1D in EXAMPLE 1E.

Example 139C

4-[4-({4'-chloro-4-[2-(diisopropylamino)ethoxy]-1,1'-biphenyl-2-yl}methyl)piperazin-1-yl]-N-({3-nitro-4-[(tetrahydro-2H-pyran-4-ylmethyl)amino]phenyl}sulfonyl)-2-phenoxybenzamide This example was made by substituting EXAMPLE 139B for EXAMPLE 1E in EXAMPLE 27H. ¹H NMR (400 MHz, dimethylsulfoxide-d₆) δ 11.65 (br s, 1H), 8.75 (br s, 1H), 8.62 (d, 1H), 8.47 (d, 1H), 7.75 (dd, 1H), 7.50 (m, 3H), 7.31 (m, 4H), 7.23 (m, 2H), 7.13 (m, 2H), 6.99 (m, 1H), 6.79 (m, 3H), 6.44 (m, 1H), 4.31 (t, 2H), 3.86 (dd, 2H), 3.62 (m, 10H), 3.28 (m, 6H), 1.91 (m, 1H), 1.62 (m, 2H), 1.32 (m, 14H).

Example 140

4-{4-[(4'-chloro-1,1'-biphenyl-2-yl)methyl]piperazin-1-yl}-2-(2,3-dihydro-1H-indol-5-yloxy)-N-({3-nitro-4-[(tetrahydro-2H-pyran-4-ylmethyl)amino]phenyl}sulfonyl)benzamide A suspension of EXAMPLE 40D (22.57 mg) and sodium cyanoborohydride (25 mg) in acetic acid (5 ml) was stirred at room temperature for 2 hours. The product was partitioned between dichloromethane and water. The organic layer was separated, dried over Na₂SO₄, and concentrated. The crude product was purified by RP HPLC (C8, 30-100 acetonitrile/water/0.1% trifluoroacetic acid). ¹H NMR (300 MHz, dimethylsulfoxide-d₆) δ 11.56 (s, 1H), 9.60 (s, 1H), 8.66 (t, 1H), 8.57 (d, 1H), 7.85 (dd, 1H), 7.71 (s, 1H), 7.46-7.60 (m, 5H), 7.29-7.42 (m, 3H), 7.25 (d, 1H), 6.95 (s, 1H), 6.82 (s, 1H), 6.73 (d, 1H), 6.36 (s, 1H), 4.32 (bs, 2H), 3.85 (dd, 4H), 3.59 (t, 4H), 3.35 (t, 2H), 3.27 (t, 2H), 3.02 (t, 4H), 1.80-1.99 (m, 1H), 1.62 (d, 2H), 1.15-1.36 (m, 2H).

Example 141

4-(4-{[2-(4-chlorophenyl)cyclohept-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide

Example 141A (Z)-methyl 2-(trifluoromethylsulfonyloxy)cyclohept-1-enecarboxylate This example was prepared by substituting methyl 2-oxocycloheptanecarboxylate for 5,5-dimethyl-2-methoxycarbonylcyclohexanone in EXAMPLE 18A.

Example 141B (Z)-methyl 2-(4-chlorophenyl)cyclohept-1-enecarboxylate

This example was prepared by substituting EXAMPLE 141A for EXAMPLE 18A in EXAMPLE 18B.

Example 141C (Z)-(2-(4-chlorophenyl)cyclohept-1-enyl)methanol

This example was prepared by substituting EXAMPLE 141B for EXAMPLE 18B in EXAMPLE 18C.

Example 141D (Z)-2-(4-chlorophenyl)cyclohept-1-enecarbaldehyde

This example was prepared by substituting EXAMPLE 141C for EXAMPLE 143C in EXAMPLE 143D.

Example 141E (Z)-ethyl 2-(1H-indol-4-yloxy)-4-(4-((2-(4-chlorophenyl)cyclohept-1-enyl)methyl)piperazin-1-yl)benzoate This example was prepared by substituting EXAMPLE 141D for 4'-chlorobiphenyl-2-carboxaldehyde and EXAMPLE 68B for tert-butyl piperazine-1-carboxylate in EXAMPLE 1A.

Example 141F (Z)-2-(1H-indol-4-yloxy)-4-(4-((2-(4-chlorophenyl)cyclohept-1-enyl)methyl)piperazin-1-yl)benzoic acid This example was prepared by substituting EXAMPLE 141E for EXAMPLE 143E in EXAMPLE 143F.

Example 141G 4-(4-{[2-(4-chlorophenyl)cyclohept-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide This example was prepared by substituting EXAMPLE 141F for EXAMPLE 1E and EXAMPLE 68F for EXAMPLE 1F in EXAMPLE 1G. $^1$H NMR (300 MHz, dimethylsulfoxide-$d_6$) δ 11.45 (m, 1H), 10.03 (m, 1H), 8.58 (m, 2H), 8.30 (m, 1H), 7.26 (m, 11H), 6.25 (m, 2H), 3.14 (m, 12H), 2.73 (m, 5H), 1.94 (m, 12H), 1.54 (m, 5H).

Example 142

4-(4-{[2-(4-chlorophenyl)cyclooct-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide

Example 142A (Z)-ethyl 2-(trifluoromethylsulfonyloxy)cyclooct-1-enecarboxylate This example was prepared by substituting ethyl 2-oxocyclooctanecarboxylate for 5,5-dimethyl-2-methoxycarbonylcyclohexanone in EXAMPLE 18A.

Example 142B (Z)-ethyl 2-(4-chlorophenyl)cyclooct-1-enecarboxylate

This example was prepared by substituting EXAMPLE 142A for EXAMPLE 18A in EXAMPLE 18B.

Example 142C (Z)-(2-(4-chlorophenyl)cyclooct-1-enyl)methanol

This example was prepared by substituting EXAMPLE 142B for EXAMPLE 18B in EXAMPLE 18C.

Example 142D (Z)-2-(4-chlorophenyl)cyclooct-1-enecarbaldehyde

This example was prepared by substituting EXAMPLE 142C for EXAMPLE 143C in EXAMPLE 143D.

Example 142E (Z)-ethyl 2-(1H-indol-4-yloxy)-4-(4-((2-(4-chlorophenyl)cyclooct-1-enyl)methyl)piperazin-1-yl)benzoate This example was prepared by substituting EXAMPLE 142D for 4'-chlorobiphenyl-2-carboxaldehyde and EXAMPLE 68B for tert-butyl piperazine-1-carboxylate in EXAMPLE 1A.

Example 142F (Z)-2-(1H-indol-4-yloxy)-4-(4-((2-(4-chlorophenyl)cyclooct-1-enyl)methyl)piperazin-1-yl)benzoic acid This example was prepared by substituting EXAMPLE 142E for EXAMPLE 143E in EXAMPLE 143F.

Example 142G 4-(4-{[2-(4-chlorophenyl)cyclooct-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide This example was prepared by substituting EXAMPLE 142F for EXAMPLE 1E and EXAMPLE 68F for EXAMPLE 1F in EXAMPLE 1G. $^1$H NMR (300 MHz, dimethylsulfoxide-d6) δ 11.51 (m, 1H), 10.01 (m, 1H), 8.58 (m, 2H), 7.26 (m, 12H), 6.35 (m, 2H), 3.14 (m, 13H), 2.73 (m, 5H), 1.88 (m, 7H), 1.45 (m, 10H).

Example 143

4-(4-{[2-(4-chlorophenyl)cyclopent-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide

Example 143A ethyl 2-(trifluoromethylsulfonyloxy)cyclopent-1-enecarboxylate

This example was prepared by substituting ethyl 2-oxocyclopentanecarboxylate for 5,5-dimethyl-2-methoxycarbonylcyclohexanone in EXAMPLE 18A.

Example 143B ethyl 2-(4-chlorophenyl)cyclopent-1-enecarboxylate

This example was prepared by substituting EXAMPLE 143A for EXAMPLE 18A in EXAMPLE 18B.

Example 143C (2-(4-chlorophenyl)cyclopent-1-enyl)methanol

This example was prepared by substituting EXAMPLE 143B for EXAMPLE 18B in EXAMPLE 18C.

Example 143D 2-(4-chlorophenyl)cyclopent-1-enecarbaldehyde

To a solution of oxalyl chloride (1.1 g) in dichloromethane (30 ml) at −78° C. was added dimethylsulfoxide (6.12 ml). The mixture was stirred at −78° C. for 30 minutes, and then a solution of EXAMPLE 143C (1.2 g) in dichloromethane (10 ml) was added. The mixture was stirred at −78° C. for 2 hours before the addition of triethylamine (10 ml). The mixture was stirred overnight and the temperature was allowed to rise to room temperature.

The mixture was diluted with ether (300 ml) and washed with water, brine and dried over $Na_2SO_4$. Evaporation of solvent and column purification (5% ethyl acetate in hexane) to give the product.

Example 143E ethyl 2-(1H-indol-4-yloxy)-4-(4-((2-(4-chlorophenyl)cyclopent-1-enyl)methyl)piperazin-1-yl)benzoate This example was prepared by substituting EXAMPLE 143D for 4'-chlorobiphenyl-2-carboxaldehyde and EXAMPLE 68B for tert-butyl piperazine-1-carboxylate in EXAMPLE 1A.

Example 143F 2-(1H-indol-4-yloxy)-4-(4-((2-(4-chlorophenyl)cyclopent-1-enyl)methyl)piperazin-1-yl)benzoic acid To a solution of EXAMPLE 143E (254 mg) in tetrahydrofuran (4 ml), methanol (2 ml) and water (2 ml) was added LiOH—$H_2O$ (126 mg). The mixture was stirred overnight. The mixture was then neutralized with 5% HCl and diluted with ethyl acetate (200 ml). After washing with brine, it was dried over $Na_2SO_4$. Evaporation of solvent gave the product.

Example 143G 4-(4-{[2-(4-chlorophenyl)cyclopent-1-en-1-yl]methyl}piperazin-1-yl)-2-(1H-indol-4-yloxy)-N-({3-nitro-4-[(3-pyrrolidin-1-ylpropyl)amino]phenyl}sulfonyl)benzamide This example was prepared by substituting EXAMPLE 143F for EXAMPLE 1E and EXAMPLE 68F for EXAMPLE 1F in EXAMPLE 1G. $^1$H NMR (300 MHz, dimethylsulfoxide-d6) δ ppm 11.41 (m, 1H), 10.19 (m, 1H), 8.58 (m, 2H), 7.26 (m, 14H), 6.33 (m, 2H), 3.80 (m, 4H), 3.13 (m, 12H), 2.69 (m, 5H), 1.95 (m, 7H).

Example 144

4-(4-{[2-(4-chlorophenyl)-4,4-dimethylcyclopent-1-en-1-yl]methyl}piperazin-1-yl)-2-(1H-indol-4-yloxy)-N-({4-[(1-methylpiperidin-4-yl)amino]-3-nitrophenyl}sulfonyl)benzamide

Example 144A methyl 4,4-dimethyl-2-oxocyclopentanecarboxylate

This compound was prepared according to WO 2006/035061 (page 53).

Example 144B methyl 4,4-dimethyl-2-(trifluoromethylsulfonyloxy)cyclopent-1-enecarboxylate This example was prepared by substituting ethyl 2-oxocyclopentanecarboxylate for 5,5-dimethyl-2-methoxycarbonylcyclohexanone in EXAMPLE 18A.

Example 144C ethyl 2-(4-chlorophenyl)-4,4-dimethylcyclopent-1-enecarboxylate This example was prepared by substituting EXAMPLE 144B for EXAMPLE 18A in EXAMPLE 18B.

Example 144D (2-(4-chlorophenyl)-4,4-dimethylcyclopent-1-enyl)methanol

This example was prepared by substituting EXAMPLE 144C for EXAMPLE 18B in EXAMPLE 18C.

Example 144E 2-(4-chlorophenyl)-4,4-dimethylcyclopent-1-enecarbaldehyde

This example was prepared by substituting EXAMPLE 144D for EXAMPLE 143C in EXAMPLE 143D.

Example 144F ethyl 2-(1H-indol-4-yloxy)-4-(4-((2-(4-chlorophenyl)-4,4-dimethylcyclopent-1-enyl)methyl)piperazin-1-yl)benzoate This example was prepared by substituting EXAMPLE 144E for 4'-chlorobiphenyl-2-carboxaldehyde and EXAMPLE 68B for tert-butyl piperazine-1-carboxylate in EXAMPLE 1A.

Example 144G 2-(1H-indol-4-yloxy)-4-(4-((2-(4-chlorophenyl)-4,4-dimethylcyclopent-1-enyl)methyl)piperazin-1-yl) benzoic acid This example was prepared by substituting EXAMPLE 144F for EXAMPLE 143E in EXAMPLE 143F.

Example 144H 4-(4-{[2-(4-chlorophenyl)-4,4-dimethylcyclopent-1-en-1-yl]methyl}piperazin-1-yl)-2-(1H-indol-4-yloxy)-N-({4-[(1-methylpiperidin-4-yl)amino]-3-nitrophenyl}sulfonyl)benzamide This example was prepared by substituting EXAMPLE 144G for EXAMPLE 1E and EXAMPLE 21A for EXAMPLE 1F in EXAMPLE 1G. $^1$H NMR (300 MHz, dimethylsulfoxide-d6) δ 11.59 (m, 1H), 11.25 (s, 1H), 9.53 (m, 1H), 8.50 (d, 1H), 8.16 (d, 1H), 8.16 (d, 1H), 7.80 (m, 1H), 7.56 (d, 1H), 7.26 (m, 7H), 6.95 (m, 1H), 6.77 (dd, 1H), 6.41 (m, 2H), 6.23 (s, 1H), 2.87 (m, 10H), 2.28 (m, 12H), 1.11 (m, 6H).

Example 145

4-(4-{[4-(4-chlorophenyl)-6,6-dimethyl-5,6-dihydro-2H-pyran-3-yl]methyl}piperazin-1-yl)-2-(1H-indol-4-yloxy)-N-({4-[(1-methylpiperidin-4-yl)amino]-3-nitrophenyl}sulfonyl)benzamide

Example 145A methyl 6,6-dimethyl-4-oxotetrahydro-2H-pyran-3-carboxylate

To a suspension of hexane-washed NaH (0.72 g, 60%) in tetrahydrofuran (30 ml) was added a solution of 2,2-dimethyldihydro-2H-pyran-4(3H)-one (2.0 g) in tetrahydrofuran (20 ml). The suspension was stirred for 30 minutes. The dimethylcarbonate (6.31 ml) was added dropwise by syringe. The mixture was heated to reflux for 4 hours. The mixture was acidified with 5% HCl and extracted with dichloromethane (3×100 ml) and washed with water, brine and dried over Na$_2$SO$_4$. After evaporation, the crude product was loaded on a column and eluted with 10% ethyl acetate in hexane to give the product.

Example 145B methyl 6,6-dimethyl-4-(trifluoromethylsulfonyloxy)-5,6-dihydro-2H-pyran-3-carboxylate This example was prepared by substituting EXAMPLE 145A for 5,5-dimethyl-2-methoxycarbonylcyclohexanone in EXAMPLE 18A.

Example 145C methyl 4-(4-chlorophenyl)-6,6-dimethyl-5,6-dihydro-2H-pyran-3-carboxylate This example was prepared by substituting EXAMPLE 145B for EXAMPLE 18A in EXAMPLE 18B.

Example 145D (4-(4-chlorophenyl)-6,6-dimethyl-5,6-dihydro-2H-pyran-3-yl)methanol This example was prepared by substituting EXAMPLE 145C for EXAMPLE 18B in EXAMPLE 18C.

Example 145E 4-(4-chlorophenyl)-6,6-dimethyl-5,6-dihydro-2H-pyran-3-carbaldehyde This example was prepared by substituting EXAMPLE 145D for EXAMPLE 143C in EXAMPLE 143D.

Example 145F ethyl 2-(1H-indol-4-yloxy)-4-(4-((4-(4-chlorophenyl)-6,6-dimethyl-5,6-dihydro-2H-pyran-3-yl)methyl)piperazin-1-yl)benzoate This example was prepared by substituting EXAMPLE 145E for 4'-chlorobiphenyl-2-carboxaldehyde and EXAMPLE 68B for tert-butyl piperazine-1-carboxylate in EXAMPLE 1A.

Example 145G 2-(1H-indol-4-yloxy)-4-(4-((4-(4-chlorophenyl)-6,6-dimethyl-5,6-dihydro-2H-pyran-3-yl)methyl)piperazin-1-yl)benzoic acid This example was prepared by substituting EXAMPLE 145F for EXAMPLE 143E in EXAMPLE 143F.

Example 145H 4-(4-{[4-(4-chlorophenyl)-6,6-dimethyl-5,6-dihydro-2H-pyran-3-yl]methyl}piperazin-1-yl)-2-(1H-indol-4-yloxy)-N-({4-[(1-methylpiperidin-4-yl)amino]-3-nitrophenyl}sulfonyl)benzamide This example was prepared by substituting EXAMPLE 145G for EXAMPLE 1E and EXAMPLE 21A for EXAMPLE 1F in EXAMPLE 1G. $^1$H NMR (300 MHz, dimethylsulfoxide-d6) δ 11.56 (m, 1H), 11.26 (s, 1H), 9.52 (m, 1H), 8.51 (m, 1H), 8.16 (d, 1H), 7.80 (dd, 1H), 7.55 (d, 1H), 7.41 (d, 2H), 7.28 (t, 1H), 7.17 (m, 4H), 6.96 (m, 2H), 6.74 (d, 1H), 6.39 (m, 2H), 6.23 (s, 1H), 4.18 (s, 2H), 3.85 (m, 3H), 2.93 (m, 10H), 2.10 (m, 7H), 1.22 (s, 6H).

Example 146

4-(4-{[2-(4-chlorophenyl)cycloact-1-en-1-yl]methyl}piperazin-1-yl)-2-(1H-indol-4-yloxy)-N-({4-[(1-methylpiperidin-4-yl)amino]-3-nitrophenyl}sulfonyl)benzamide This example was prepared by substituting EXAMPLE 142F for EXAMPLE 1E and EXAMPLE 21A for EXAMPLE 1F in EXAMPLE 1G. $^1$H NMR (300 MHz, dimethylsulfoxide-d6) 611.59 (s, 1H), 11.25 (s, 1H), 9.36 (m, 2H), 8.50 (d, 1H), 8.16 (d, 1H), 7.79 (dd, 1H), 7.55 (d, 1H), 7.40 (d, 2H), 7.28 (m, 1H), 7.14 (m, 5H), 6.96 (t, 1H), 6.74 (dd, 1H), 6.38 (m, 2H), 6.23 (s, 1H), 2.91 (m, 14H), 2.27 (m, 6H), 1.49 (m, 11H).

Example 147

4-(4-{[2-(4-chlorophenyl)cyclohept-1-en-1-yl]methyl}piperazin-1-yl)-2-(1H-indol-4-yloxy)-N-({4-[(1-methylpiperidin-4-yl)amino]-3-nitrophenyl}sulfonyl)benzamide This example was prepared by substituting EXAMPLE 141F for EXAMPLE 1E and EXAMPLE 21A for EXAMPLE 1F in EXAMPLE 1G. $^1$H NMR (300 MHz, dimethylsulfoxide-d6) δ 11.60 (s, 1H), 11.26 (s, 1H), 9.32 (m, 2H), 8.51 (m, 1H), 8.16 (d, 1H), 7.79 (m, 1H), 7.55 (d, 1H), 7.39 (d, 2H), 7.29 (t, 1H), 7.14 (m, 4H), 6.97 (t, 1H), 6.75 (dd, 1H), 6.40 (m, 2H), 6.22 (s, 1H), 2.94 (m, 17H), 2.27 (m, 4H), 1.80 (m, 4H), 1.55 (m, 5H).

Example 148

4-(4-{[2-(4-chlorophenyl)cyclopent-1-en-1-yl]methyl}piperazin-1-yl)-2-(1H-indol-4-yloxy)-N-({4-[(1-methylpiperidin-4-yl)amino]-3-nitrophenyl}sulfonyl)benzamide This example was prepared by substituting EXAMPLE 143F for EXAMPLE 1E and EXAMPLE 21A for EXAMPLE 1F in EXAMPLE 1G. $^1$H NMR (300 MHz, dimethylsulfoxide-d6) δ 11.60 (s, 1H), 11.26 (s, 1H), 9.47 (m, 2H), 8.51 (m, 1H), 8.16 (d, 1H), 7.77 (m, 1H), 7.56 (d, 1H), 7.43 (d, 2H), 7.20 (m, 6H), 6.96 (t, 1H), 6.77 (dd, 1H), 6.41 (m, 2H), 6.24 (s, 1H), 2.93 (m, 17H), 2.01 (m, 8H).

Example 149

4-(4-{[2-(4-chlorophenyl)cyclohex-1-en-1-yl]methyl}piperazin-1-yl)-2-(1H-indol-4-yloxy)-N-({4-[(1-methylpiperidin-4-yl)amino]-3-nitrophenyl}sulfonyl)benzamide

Example 149A ethyl 2-(trifluoromethylsulfonyloxy)cyclohex-1-enecarboxylate

This example was prepared by substituting ethyl 2-oxocyclohexanecarboxylate for 5,5-dimethyl-2-methoxycarbonylcyclohexanone in EXAMPLE 18A.

Example 149B ethyl 2-(4-chlorophenyl)cyclohex-1-enecarboxylate

This example was prepared by substituting EXAMPLE 149A for EXAMPLE 18A in EXAMPLE 18B.

Example 149C (2-(4-chlorophenyl)cyclohex-1-enyl)methanol

This example was prepared by substituting EXAMPLE 149B for EXAMPLE 18B in EXAMPLE 18C.

Example 149D 2-(4-chlorophenyl)cyclohex-1-enecarbaldehyde

This example was prepared by substituting EXAMPLE 149C for EXAMPLE 143C in EXAMPLE 143D.

Example 149E ethyl 2-(1H-indol-4-yloxy)-4-(4-((2-(4-chlorophenyl)cyclohex-1-enyl)methyl)piperazin-1-yl)benzoate The title compound was prepared by substituting EXAMPLE 149D for 4'-chlorobiphenyl-2-carboxaldehyde and EXAMPLE 68B for tert-butyl piperazine-1-carboxylate in EXAMPLE 1A.

Example 149F 2-(1H-indol-4-yloxy)-4-(4-((2-(4-chlorophenyl)cyclohex-1-enyl)methyl)piperazin-1-yl)benzoic acid This example was prepared by substituting EXAMPLE 149E for EXAMPLE 143E in EXAMPLE 143F.

Example 149G 4-(4-{[2-(4-chlorophenyl)cyclohex-1-en-1-yl]methyl}piperazin-1-yl)-2-(1H-indol-4-yloxy)-N-({4-[(1-methylpiperidin-4-yl)amino]-3-nitrophenyl}sulfonyl)benzamide This example was prepared by substituting EXAMPLE 149F for EXAMPLE 1E and EXAMPLE 21A for EXAMPLE 1F in EXAMPLE 1G. $^1$H NMR (300 MHz, dimethylsulfoxide-d6) δ 11.14 (s, 1H), 8.44 (d, 1H), 8.10 (d, 1H), 7.74 (dd, 1H), 7.56 (d, 1H), 7.34 (d, 2H), 7.23 (m, 1H), 7.01 (m, 5H), 6.63 (dd, 1H), 6.34 (d, 1H), 6.22 (m, 2H), 3.74 (m, 1H), 3.03 (m, 7H), 2.67 (m, 5H), 2.07 (m, 11H), 1.67 (m, 7H).

Example 150

4-(4-{[4-(4-chlorophenyl)-6,6-dimethyl-5,6-dihydro-2H-pyran-3-yl]methyl}piperazin-1-yl)-2-(1H-indol-5-yloxy)-N-({4-[(1-methylpiperidin-4-yl)amino]-3-nitrophenyl}sulfonyl)benzamide

Example 150A methyl 2-(1H-indol-5-yloxy)-4-(piperazin-1-yl)benzoate

This example was prepared by substituting EXAMPLE 26A for EXAMPLE 1C and piperazine for EXAMPLE 1B in EXAMPLE 1D.

Example 150B methyl 2-(1H-indol-5-yloxy)-4-(4-((4-(4-chlorophenyl)-6,6-dimethyl-5,6-dihydro-2H-pyran-3-yl)methyl)piperazin-1-yl)benzoate This example was prepared by substituting EXAMPLE 145E for 4'-chlorobiphenyl-2-carboxaldehyde and EXAMPLE 150A for tert-butyl piperazine-1-carboxylate in EXAMPLE 1A.

Example 150C 2-(1H-indol-5-yloxy)-4-(4-((4-(4-chlorophenyl)-6,6-dimethyl-5,6-dihydro-2H-pyran-3-yl)methyl)piperazin-1-yl)benzoic acid This example was prepared by substituting EXAMPLE 150B for EXAMPLE 143E in EXAMPLE 143F.

Example 150D 4-(4-{[4-(4-chlorophenyl)-6,6-dimethyl-5,6-dihydro-2H-pyran-3-yl]methyl}piperazin-1-yl)-2-(1H-indol-5-yloxy)-N-({4-[(1-methylpiperidin-4-yl)amino]-3-nitrophenyl}sulfonyl)benzamide This example was prepared by substituting EXAMPLE 150C for EXAMPLE 1E and EXAMPLE 21A for EXAMPLE 1F in EXAMPLE 1G. $^1$H NMR (300 MHz, dimethylsulfoxide-d6) δ 11.00 (s, 1H), 8.42 (d, 1H), 8.07 (d, 1H), 7.67 (dd, 1H), 7.52 (d, 1H), 7.37 (d, 2H), 7.29 (m, 1H), 7.14 (d, 2H), 6.93 (d, 1H), 6.86 (d, 1H), 6.72 (dd, 1H), 6.55 (dd, 1H), 6.31 (s, 1H), 6.15 (d, 1H), 5.85 (m, 3H), 4.11 (s, 2H), 3.00 (m, 8H), 2.82 (s, 2H), 2.73 (m, 3H), 2.23 (m, 8H), 1.57 (m, 2H), 1.18 (s, 6H).

Example 151

4-(4-{[2-(4-chlorophenyl)cyclohept-1-en-1-yl]methyl}piperazin-1-yl)-2-(1H-indol-5-yloxy)-N-({4-[(1-methylpiperidin-4-yl)amino]-3-nitrophenyl}sulfonyl)benzamide

Example 151A (Z)-methyl 2-(1H-indol-5-yloxy)-4-(4-((2-(4-chlorophenyl)cyclohept-1-enyl)methyl)piperazin-1-yl)benzoate This example was prepared by substituting EXAMPLE 141D for 4'-chlorobiphenyl-2-carboxaldehyde and EXAMPLE 150A for tert-butyl piperazine-1-carboxylate in EXAMPLE 1A.

Example 151B (Z)-2-(1H-indol-5-yloxy)-4-(4-((2-(4-chlorophenyl)cyclohept-1-enyl)methyl)piperazin-1-yl)benzoic acid This example was prepared by substituting EXAMPLE 151A for EXAMPLE 143E in EXAMPLE 143F.

Example 151C 4-(4-{[2-(4-chlorophenyl)cyclohept-1-en-1-yl]methyl}piperazin-1-yl)-2-(1H-indol-5-yloxy)-N-({4-[(1-methylpiperidin-4-yl)amino]-3-nitrophenyl}sulfonyl)benzamide This example was prepared by substituting EXAMPLE 151B for EXAMPLE 1E and EXAMPLE 21A for EXAMPLE 1F in EXAMPLE 1G. $^1$H NMR (300 MHz, dimethylsulfoxide-d6) δ 11.06 (s, 1H), 8.48 (d, 1H), 8.11 (d, 1H), 7.74 (dd, 1H), 7.52 (d, 1H), 7.33 (m, 4H), 7.01 (m, 4H), 6.76 (dd, 1H), 6.58 (dd, 1H), 6.34 (s, 1H), 6.14 (d, 1H), 5.75 (s, 1H), 3.69 (m, 1H), 2.96 (m, 6H), 2.71 (m, 2H), 2.36 (m, 8H), 2.21 (s, 5H), 1.98 (m, 2H), 1.63 (m, 8H).

Example 152

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-phenoxybenzamide This compound was made by substituting EXAMPLE 18G for EXAMPLE 1E and EXAMPLE 21A for EXAMPLE 1F in EXAMPLE 1G. $^1$H NMR (400 MHz, dimethylsulfoxide-d$_6$) δ 8.43 (m, 1H) 8.18 (d, 1H) 7.82 (dd, 1H) 7.52 (d, 1H) 7.40 (m, 2H) 7.22 (m, 3H) 7.11 (m, 2H) 7.01 (t, 1H) 6.79 (m, 3H) 6.45 (d, 1H) 3.06 (m, 14H) 2.20 (m, 4H) 2.04 (s, 3H) 1.85 (m, 2H) 1.47 (m, 2H) 0.96 (s, 6H).

Example 153

4-{4-[(4'-chloro-1,1'-biphenyl-2-yl)methyl]piperazin-1-yl}-N-[(4-{[2-(dimethylamino)ethyl]amino}-3-nitrophenyl)sulfonyl]-2-phenoxybenzamide

Example 153A 4-(2-(dimethylamino)ethylamino)-3-nitrobenzenesulfonamide

This example was prepared by substituting N,N-dimethylethylenediamine for (tetrahydropyran-4-yl)methylamine in EXAMPLE 1F.

Example 153B

4-{4-[(4'-chloro-1,1'-biphenyl-2-yl)methyl]piperazin-1-yl}-N-[(4-{[2-(dimethylamino)ethyl]amino}-3-nitrophenyl)sulfonyl]-2-phenoxybenzamide This example was prepared by substituting EXAMPLE 153A for EXAMPLE 1F and EXAMPLE 1E for EXAMPLE 27G in EXAMPLE 27H. $^1$H NMR (500 MHz, dimethylsulfoxide-d$_6$) δ 11.75 (br s, 1H), 9.78 (br s, 1H), 9.44 (br s, 1H), 8.66 (t, 1H), 8.49 (d, 1H), 7.83 (d, 1H), 7.70 (m, 2H), 7.51 (m, 4H), 7.38 (d, 2H), 7.33 (m, 1H), 7.24 (d, 2H), 7.18 (d, 1H), 7.02 (dd, 1H), 6.81 (d, 2H), 6.76 (d, 1H), 6.44 (s, 1H), 4.30 (m, 1H), 3.83 (m, 4H), 3.31 (m, 6H), 3.15 (m, 2H), 3.04 (m, 2H), 2.85 (s, 6H).

Example 154

4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2 phenoxybenzamide

Example 154A 4-(3-(dimethylamino)propylamino)-3-nitrobenzenesulfonamide

This example was prepared by substituting N,N-dimethyl-1,3-propanediamine for (tetrahydropyran-4-yl)methylamine in EXAMPLE 1F.

Example 154B

4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-phenoxybenzamide This example was prepared by substituting EXAMPLE 154A for EXAMPLE 1F and EXAMPLE 1E for EXAMPLE 27G in EXAMPLE 27H. $^1$H NMR (400 MHz, dimethylsulfoxide-$d_6$) δ 11.68 (br s, 1H), 9.38 (br s, 1H), 8.66 (t, 1H), 8.49 (d, 1H), 7.80 (d, 1H), 7.68 (m, 2H), 7.51 (m, 4H), 7.38 (d, 1H), 7.33 (m, 2H), 7.24 (d, 2H), 7.16 (d, 1H), 7.02 (dd, 1H), 6.81 (d, 2H), 6.76 (d, 1H), 6.43 (s, 1H), 4.25 (m, 1H), 3.50 (m, 4H), 3.30 (m, 4H), 3.12 (m, 6H), 2.78 (s, 6H), 1.95 (m, 2H).

Example 155

4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-phenoxybenzamide This example was prepared by substituting EXAMPLE 7A for EXAMPLE 1F and EXAMPLE 1E for EXAMPLE 27G in EXAMPLE 27H. $^1$H NMR (400 MHz, dimethylsulfoxide-$d_6$) δ 11.70 (br s, 1H), 9.72 (br s, 1H), 8.68 (t, 1H), 8.49 (d, 1H), 7.81 (d, 1H), 7.70 (m, 2H), 7.51 (m, 4H), 7.37 (d, 2H), 7.33 (m, 1H), 7.24 (d, 2H), 7.15 (d, 1H), 7.03 (dd, 1H), 6.81 (d, 2H), 6.76 (d, 1H), 6.44 (s, 1H), 4.24 (m, 1H), 3.97 (m, 2H), 3.63 (m, 4H), 3.28 (m, 4H), 3.18 (m, 4H), 3.06 (m, 4H), 2.88 (m, 4H), 1.99 (m, 2H).

Example 156

4-{4-[(4'-chloro-1,1'-biphenyl-2-yl)methyl]piperazin-1-yl}-N-[(4-{[4-(dimethylamino)butyl]amino}-3-nitrophenyl)sulfonyl]-2-phenoxybenzamide

Example 156A 4-(4-(dimethylamino)butylamino)-3-nitrobenzenesulfonamide

This example was prepared by substituting N,N-dimethyl-1,4-butanediamine for (tetrahydropyran-4-yl)methylamine in EXAMPLE 1F.

Example 156B

4-{4-[(4'-chloro-1,1'-biphenyl-2-yl)methyl]piperazin-1-yl}-N-[(4-{[4-(dimethylamino)butyl]amino}-3-nitrophenyl)sulfonyl]-2-phenoxybenzamide This example was prepared by substituting EXAMPLE 156A for EXAMPLE 1F and EXAMPLE 1E for EXAMPLE 27G in EXAMPLE 27H. $^1$H NMR (400 MHz, dimethylsulfoxide-$d_6$) δ 11.70 (br s, 1H), 9.34 (br s, 1H), 8.63 (t, 1H), 8.48 (d, 1H), 7.79 (d, 1H), 7.70 (m, 2H), 7.51 (m, 4H), 7.39 (d, 2H), 7.33 (m, 1H), 7.24 (d, 2H), 7.12 (d, 1H), 7.01 (dd, 1H), 6.80 (d, 2H), 6.75 (d, 1H), 6.44 (s, 1H), 4.28 (m, 1H), 3.83 (m, 4H), 3.45 (m, 10H), 3.10 (m, 4H), 2.85 (s, 6H), 1.66 (m, 4H).

Example 157

4-{4-[(4'-chloro-1,1'-biphenyl-2-yl)methyl]piperazin-1-yl}-N-[(3-nitro-4-{[1-(phenylsulfonyl)piperidin-4-yl]amino}phenyl)sulfonyl]-2-phenoxybenzamide

Example 157A tert-butyl 4-(2-nitro-4-sulfamoylphenylamino)piperidine-1-carboxylate This example was prepared by substituting 1-Boc-4-aminopiperidine for (tetrahydropyran-4-yl)methylamine in EXAMPLE 1F.

Example 157B 3-nitro-4-(piperidin-4-ylamino)benzenesulfonamide

This example was prepared by substituting EXAMPLE 157A for EXAMPLE 1A in EXAMPLE 1B.

Example 157C 3-nitro-4-(1-(phenylsulfonyl)piperidin-4-ylamino)benzenesulfonamide A mixture of EXAMPLE 157B (84 mg), benzenesulfonyl chloride (46 mg), and triethylamine (101 mg) in CH$_2$Cl$_2$ (2 mL) was stirred for 1 hours. The product was chromatographed on silica gel with 25% ethyl acetate/hexanes.

Example 157D

4-{4-[(4'-chloro-1,1'-biphenyl-2-yl)methyl]piperazin-1-yl}-N-[(3-nitro-4-{[1-(phenylsulfonyl)piperidin-4-yl]amino}phenyl)sulfonyl]-2-phenoxybenzamide This example was prepared by substituting EXAMPLE 157C for EXAMPLE 1F and EXAMPLE 1E for EXAMPLE 27G in EXAMPLE 27H. $^1$H NMR (400 MHz, dimethylsulfoxide-$d_6$) δ 11.68 (br s, 1H), 9.65 (br s, 1H), 8.42 (s, 1H), 8.19 (d, 1H), 7.78 (m, 2H), 7.70 (m, 4H), 7.51 (m, 5H), 7.37 (m, 3H), 7.19 (m, 3H), 6.94 (dd, 1H), 6.75 (m, 3H), 6.44 (s, 1H), 4.28 (m, 1H), 3.73 (m, 4H), 3.50 (m, 4H), 3.17 (m, 2H), 3.03 (m, 2H), 2.86 (m, 2H), 1.99 (m, 2H), 1.74 (m, 2H).

Example 158

4-{4-[(4'-chloro-1,1'-biphenyl-2-yl)methyl]piperazin-1-yl}-N-[(3-nitro-4-{[1-(quinolin-8-ylsulfonyl)piperidin-4-yl]amino}phenyl)sulfonyl]-2-phenoxybenzamide

Example 158A 3-nitro-4-(1-(quinolin-8-ylsulfonyl)piperidin-4-ylamino)benzenesulfonamide This example was prepared by substituting quinoline-8-sulfonyl chloride for benzenesulfonyl chloride in EXAMPLE 157C.

Example 158B

4-{4-[(4'-chloro-1,1'-biphenyl-2-yl)methyl]piperazin-1-yl}-N-[(3-nitro-4-{[1-(quinolin-8-ylsulfonyl)piperidin-4-yl]amino}phenyl)sulfonyl]-2-phenoxybenzamide This example was prepared by substituting EXAMPLE 158A for EXAMPLE 1F and EXAMPLE 1E for EXAMPLE 27G in EXAMPLE 27H. $^1$H NMR (400 MHz, dimethylsulfoxide-d6) δ 11.66 (br s, 1H), 9.10 (dd, 1H), 8.55 (s, 1H), 8.41 (m, 2H), 8.32 (d, 1H), 8.20 (d, 1H), 7.78 (dd, 2H), 7.72 (d, 2H), 7.48 (m, 4H), 7.39 (dd, 2H), 7.33 (m, 1H), 7.17 (m, 3H), 6.95 (dd, 1H), 6.76 (m, 3H), 6.42 (s, 1H), 4.35 (m, 1H), 3.90 (d, 2H), 3.77 (m, 2H), 3.34 (m, 6H), 2.99 (m, 4H), 1.97 (m, 2H), 1.65 (m, 2H).

Example 159

4-{4-[(4'-chloro-1,1'-biphenyl-2-yl)methyl]piperazin-1-yl}-2-phenoxy-N-({4-{[1-(phenylsulfonyl)piperidin-4-yl]amino}-3-[(trifluoromethyl)sulfonyl]phenyl}sulfonyl)benzamide

Example 159A (2-fluorophenyl)(trifluoromethyl)sulfane

Methyl viologen hydrochloride (1.17 g) in N,N-dimethylformamide (80 mL) at 25° C. was saturated with trifluoromethyl iodide, treated with 2-fluorobenzenethiol (9.7 mL) and triethylamine (20 mL), stirred for 24 hours, diluted with water (240 mL) and extracted with diethyl ether. The extract was washed with 1M NaOH, saturated ammonium chloride and brine and concentrated.

Example 159B 1-fluoro-2-(trifluoromethylsulfonyl)benzene

Example 159A 17.346 g) in 1:1:2 carbon tetrachloride:acetonitrile:water (800 mL at 25° C. was treated with sodium periodate (56.8 g) and ruthenium(III) chloride hydrate (183 mg), stirred for 18 hours, diluted with dichloromethane (100 mL) and filtered through diatomaceous earth (Celite®). The filtrate was washed with saturated sodium bicarbonate and extracted with dichloromethane. The extract was washed with brine and dried (MgSO$_4$), filtered and concentrated. The concentrate was filtered through silica gel.

Example 159C 4-fluoro-3-(trifluoromethylsulfonyl)benzenesulfonamide

EXAMPLE 159B (37.3 g) in chlorosulfonic acid (32.8 mL) at 120° C. was stirred for 18 hours, cooled to 25° C. and pipetted onto crushed ice. The mixture was extracted with ethyl acetate, and the extract was washed with water and brine and dried (MgSO$_4$), filtered and concentrated. The crude product was taken up in isopropanol (706 mL) at −78° C., treated with ammonium hydroxide (98 mL) over 1 hour, stirred for 1 hour, quenched with 6M HCl (353 mL), warmed to 25° C. and concentrated. The concentrate was mixed with water and extracted with ethyl acetate. The extract was dried over MgSO$_4$, filtered and concentrated. The concentrate was recrystallized from ethyl acetate/hexane.

Example 159D tert-butyl 4-(4-sulfamoyl-2-(trifluoromethylsulfonyl)phenylamino)piperidine-1-carboxylate This example was prepared by substituting 1-Boc-4-aminopiperidine for (tetrahydropyran-4-yl)methylamine and EXAMPLE 159C for 4-fluoro-3-nitrobenzenesulfonamide in EXAMPLE 1F.

Example 159E 4-(piperidin-4-ylamino)-3-(trifluoromethylsulfonyl)benzenesulfonamide This example was prepared by substituting EXAMPLE 159D for EXAMPLE 1A in EXAMPLE 1B.

Example 159F 4-(1-(phenylsulfonyl)piperidin-4-ylamino)-3-(trifluoromethylsulfonyl)benzenesulfonamide This example was prepared by substituting EXAMPLE 159E for EXAMPLE 157B in EXAMPLE 157C.

Example 159G

4-{4-[(4'-chloro-1,1'-biphenyl-2-yl)methyl]piperazin-1-yl}-2-phenoxy-N-({4-{[1-(phenylsulfonyl)piperidin-4-yl]amino}-3-[(trifluoromethyl)sulfonyl]phenyl}sulfonyl)benzamide This example was prepared by substituting EXAMPLE 159F for EXAMPLE 1F and EXAMPLE 1E for EXAMPLE 27G in EXAMPLE 27H. $^1$H NMR (400 MHz, dimethylsulfoxide-d$_6$) δ 11.72 (br s, 1H), 9.70 (br s, 1H), 8.07 (s, 1H), 7.67-7.82 (m, 7H), 7.52 (d, 2H), 7.47 (d, 2H), 7.36 (m, 3H), 7.24 (dd, 2H), 7.14 (d, 1H), 7.01 (m, 1H), 6.78 (d, 2H), 6.72 (m, 2H), 6.44 (d, 1H), 4.27 (m, 1H), 3.73 (m, 4H), 3.46 (m, 4H), 3.17 (m, 2H), 3.03 (m, 2H), 2.87 (m, 2H), 1.97 (m, 2H), 1.64 (m, 2H).

Example 160

4-{4-[(4'-chloro-1,1'-biphenyl-2-yl)methyl]piperazin-1-yl}-2-phenoxy-N-({4-{[1-(quinolin-8-ylsulfonyl)piperidin-4-yl]amino}-3-[(trifluoromethyl)sulfonyl]phenyl}sulfonyl)benzamide

Example 160A 4-(1-(quinolin-8-ylsulfonyl)piperidin-4-ylamino)-3-(trifluoromethylsulfonyl)benzenesulfonamide This example was prepared by substituting EXAMPLE 159E for EXAMPLE 157B and quinoline-8-sulfonyl chloride for benzenesulfonyl chloride in EXAMPLE 157C.

Example 160B

4-{4-[(4'-chloro-1,1'-biphenyl-2-yl)methyl]piperazin-1-yl}-2-phenoxy-N-({4-{[1-(quinolin-8-ylsulfonyl)piperidin-4-yl]amino}-3-[(trifluoromethyl)sulfonyl]phenyl}sulfonyl)benzamide This example was prepared by substituting EXAMPLE 160A for EXAMPLE 1F and EXAMPLE 1E for EXAMPLE 27G in EXAMPLE 27H. $^1$H NMR (400 MHz, dimethylsulfoxide-d$_6$) δ 11.74 (br s, 1H), 9.50 (br s, 1H), 9.08 (dd, 1H), 8.55 (s, 1H), 8.39 (d, 1H), 8.33 (d, 1H), 8.06 (s, 1H), 7.82 (dd, 2H), 7.70 (m, 1H), 7.50 (m, 3H), 7.40 (dd, 2H), 7.33 (m, 1H), 7.21 (m, 2H), 7.08 (m, 2H), 6.99 (dd, 1H), 6.95 (s, 1H), 6.78 (d, 1H), 6.73 (m, 2H), 6.42 (s, 1H), 4.35 (m, 1H), 3.75 (m, 4H), 3.34 (m, 6H), 3.05 (m, 4H), 1.93 (m, 2H), 1.55 (m, 2H.

Example 161

4-{4-[(4'-chloro-1,1'-biphenyl-2-yl)methyl]piperazin-1-yl}-N-[(4-{[(S)-3-(dimethylamino)-1-thien-2-ylpropyl]amino}-3-nitrophenyl)sulfonyl]-2-phenoxybenzamide

Example 161A (S)-3-(benzyloxycarbonylamino)-3-(thiophen-2-yl)propanoic acid (S)-3-amino-3-(thiophen-2-yl)propanoic acid (0.894 g) and benzyloxycarbonyl chloride 0.980 g) were stirred in 2M NaOH (8 mL) and dioxane (26 mL) at 0° C. for 24 hours. The reaction mixture was acidified with concentrated aqueous HCl, extracted twice with ethyl acetate, and the extracts were dried over MgSO$_4$, filtered, concentrated, and chromatographed on silica gel with 50% ethyl acetate/hexanes.

Example 161B (S)-benzyl 3-(dimethylamino)-3-oxo-1-(thiophen-2-yl)propylcarbamate This example was prepared by substituting EXAMPLE 161A for EXAMPLE 1E and dimethylamine for EXAMPLE 1F in EXAMPLE 1G.

Example 161C (S)—N$^1$,N$^1$-dimethyl-3-(thiophen-2-yl)propane-1,3-diamine

A solution of EXAMPLE 161B (400 mg) and borane in tetrahydrofuran (1M, 2.5 mL) in tetrahydrofuran (6 mL) was stirred for 24 hours. The reaction was quenched with methanol, taken up in pH 7 buffer solution, and extracted three times with ethyl acetate. The combined extracts were washed with brine and concentrated. The crude product was taken up in HBr in acetic acid (1.1 mL) and stirred for 2 hours. The reaction was poured into CH$_2$Cl$_2$ (50 mL) and washed with 1M NaOH solution. The organic layer was dried over Na$_2$SO$_4$, and concentrated.

Example 161D (S)-4-(3-(dimethylamino)-1-(thiophen-2-yl)propylamino)-3-nitrobenzenesulfonamide This example was prepared by substituting EXAMPLE 161C for (tetrahydropyran-4-yl)methylamine in EXAMPLE 1F.

Example 161E

4-{4-[(4'-chloro-1,1'-biphenyl-2-yl)methyl]piperazin-1-yl}-N-[(4-{[(1S)-3-(dimethylamino)-1-thien-2-ylpropyl]amino}-3-nitrophenyl)sulfonyl]-2-phenoxybenzamide This example was prepared by substituting EXAMPLE 161D for EXAMPLE 1F and EXAMPLE 1E for EXAMPLE 27G in EXAMPLE 27H. $^1$H NMR (400 MHz, dimethylsulfoxide-ddD$_2$O) δ 11.72 (br s, 1H), 9.51 (br s, 1H), 8.60 (d, 1H), 8.48 (s, 1H), 7.75 (d, 1H), 7.70 (m, 1H), 7.51 (m, 4H), 7.38 (d, 2H), 7.32 (m, 1H), 7.25 (d, 1H), 7.16 (m, 3H), 7.06 (d, 1H), 6.92 (m, 1H), 6.75 (d, 3H), 6.44 (d, 1H), 5.31 (m, 1H), 4.30 (m, 1H), 3.54 (m, 8H), 3.20 (m, 2H), 3.07 (m, 2H), 2.80 (s, 6H), 2.35 (m, 2H).

Example 162

4-{4-[(4'-chloro-1,1'-biphenyl-2-yl)methyl]piperazin-1-yl}-N-({3-nitro-4-[(thien-2-ylmethyl)amino]phenyl}sulfonyl)-2-phenoxybenzamide

Example 162A 3-nitro-4-(thiophen-2-ylmethylamino)benzenesulfonamide

This example was prepared by substituting 2-thiophenemethylamine for (tetrahydropyran-4-yl)methylamine in EXAMPLE 1F.

Example 162B

4-{4-[(4'-chloro-1,1'-biphenyl-2-yl)methyl]piperazin-1-yl}-N-({3-nitro-4-[(thien-2-ylmethyl)amino]phenyl}sulfonyl)-2-phenoxybenzamide This example was prepared by substituting EXAMPLE 162B for EXAMPLE 1F and EXAMPLE 1E for EXAMPLE 27G in EXAMPLE 27H. $^1$H NMR (400 MHz, dimethylsulfoxide-d$_6$/D$_2$O) δ 11.67 (br s, 1H), 9.55 (br s, 1H), 9.11 (t, 1H), 8.47 (s, 1H), 7.70 (m, 2H), 7.51 (m, 4H), 7.38 (d, 2H), 7.33 (m, 1H), 7.15 (m, 4H), 7.02 (d, 1H), 6.94 (m, 1H), 6.74 (d, 3H), 6.44 (d, 1H), 4.87 (m, 2H), 4.37 (m, 1H), 3.34 (m, 8H), 3.03 (m, 2H).

Example 163

4-{4-[(4'-chloro-1,1'-biphenyl-2-yl)methyl]piperazin-1-yl}-2-phenoxy-N-({4-[(tetrahydro-2H-pyran-4-ylmethyl)amino]-3-[(trifluoromethyl)sulfonyl]phenyl}sulfonyl)benzamide

Example 163A 4-((tetrahydro-2H-pyran-4-yl)methylamino)-3-(trifluoromethylsulfonyl)benzenesulfonamide This example was prepared by substituting EXAMPLE 159C for 4-fluoro-3-nitrobenzenesulfonamide in EXAMPLE 1F.

Example 163B

4-{4-[(4'-chloro-1,1'-biphenyl-2-yl)methyl]piperazin-1-yl}-2-phenoxy-N-({4-[(tetrahydro-2H-pyran-4-ylmethyl)amino]-3-[(trifluoromethyl)sulfonyl]phenyl}sulfonyl)benzamide This example was prepared by substituting EXAMPLE 163A for EXAMPLE 1F and EXAMPLE 1E for EXAMPLE 27G in EXAMPLE 27H. $^1$H NMR (400 MHz, dimethylsulfoxide-$d_6$) δ 11.71 (br s, 1H), 8.10 (d, 1H), 7.86 (d, 1H), 7.10 (m, 1H), 7.50 (m, 4H), 7.37 (m, 2H), 7.27 (m, 3H), 7.08 (m, 1H), 7.03 (dd, 1H), 6.95 (d, 1H), 6.82 (d, 1H), 6.76 (d, 1H), 6.43 (s, 1H), 4.35 (m, 1H), 3.84 (dd, 2H), 3.35 (m, 8H), 3.22 (m, 2H), 3.03 (m, 2H), 2.86 (m, 2H), 1.86 (m, 1H), 1.55 (m, 2H), 1.26 (m, 2H).

Example 164

4-{4-[(4'-chloro-1,1'-biphenyl-2-yl)methyl]piperazin-1-yl}-N-[(3-nitro-4-{[2-(1H-1,2,3-triazol-1-yl)ethyl]amino}phenyl)sulfonyl]-2-phenoxybenzamide

Example 164A 4-(2-hydroxyethylamino)-3-nitrobenzenesulfonamide

This example was prepared by substituting 2-aminoethanol for (tetrahydropyran-4-yl)methylamine in EXAMPLE 1F.

Example 164B 4-(2-(tert-butyldimethylsilyloxy)ethylamino)-3-nitrobenzenesulfonamide EXAMPLE 164A (131 mg), t-butyldimethylsilyl chloride (75 mg) and imidazole (68 mg) were stirred in $CH_2Cl_2$ (17 mL) for 24 hours. The reaction mixture was chromatographed on silica gel with 10% ethyl acetate/hexanes.

Example 164C

N-(4-(2-(tert-butyldimethylsilyloxy)ethylamino)-3-nitrophenylsulfonyl)-4-(4-((4'-chlorobiphenyl-2-yl)methyl)piperazin-1-yl)-2-phenoxybenzamide This example was prepared by substituting EXAMPLE 164B for EXAMPLE 1F in EXAMPLE 1G.

Example 164D 2-(4-(N-(4-(4-((4'-chlorobiphenyl-2-yl)methyl)piperazin-1-yl)-2-phenoxybenzoyl)sulfamoyl)-2-nitrophenylamino)ethyl 4-methylbenzenesulfonate EXAMPLE 164C (150 mg) and concentrated aqueous HCl (0.020 mL) were stirred in tetrahydrofuran (1 mL) and methanol (1 mL) for 1 hours. The mixture was filtered through a short silica gel column. The product was taken up in $CH_2Cl_2$ (1 mL) and to it was added triethylamine (0.074 mL) and p-toluenesulfonic anhydride (58 mg) and the reaction was stirred for 24 hours. The reaction mixture was chromatographed on silica gel with 10% ethyl acetate/hexanes.

Example 164E

4-{4-[(4'-chloro-1,1'-biphenyl-2-yl)methyl]piperazin-1-yl}-N-[(3-nitro-4-{[2-(1H-1,2,3-triazol-1-yl)ethyl]amino}phenyl)sulfonyl]-2-phenoxybenzamide Example 164D (30 mg), 1,2,3-triazole (7 mg) and cesium carbonate (55 mg were stirred in N,N-dimethylformamide (0.2 mL) for 24 hours. The reaction was quenched with ammonium chloride, and was extracted twice with ethyl acetate. The combined organic layers were dried over $MgSO_4$, filtered, and concentrated. The product was purified by preparative HPLC using a C18 column, 250×50 mm, 10, and eluting with a gradient of 20-100% $CH_3CN$ vs. 0.1% trifluoroacetic acid in water, giving the product as a trifluoroacetate salt. $^1$H NMR (500 MHz, dimethylsulfoxide-$d_6$) δ 11.75 (br s, 1H), 9.62 (br s, 1H), 8.66 (dd, 1H), 8.44 (d, 1H), 8.18 (s, 1H), 7.72 (m, 3H), 7.51 (m, 5H), 7.36 (m, 3H), 7.19 (dd, 2H), 7.06 (m, 1H), 6.93 (dd, 1H), 6.75 (d, 2H), 6.45 (s, 1H), 4.70 (t, 2H), 3.93 (dt, 2H), 3.61 (m, 4H), 3.22 (m, 2H), 3.01 (m, 2H), 2.84 (m, 2H).

Example 165

4-{4-[(4'-chloro-1,1'-biphenyl-2-yl)methyl]piperazin-1-yl}-N-[(3-nitro-4-{[2-(2H-1,2,3-triazol-2-yl)ethyl]amino}phenyl)sulfonyl]-2-phenoxybenzamide This example was prepared in the same reaction as that for EXAMPLE 164E. $^1$H NMR (500 MHz, dimethylsulfoxide-$d_6$) δ 11.75 (br s, 1H), 9.70 (br s, 1H), 8.67 (dd, 1H), 8.42 (s, 1H), 7.80 (s, 1H), 7.75 (m, 1H), 7.68 (d, 2H), 7.51 (m, 5H), 7.37 (m, 3H), 7.18 (dd, 2H), 6.97 (m, 1H), 6.92 (dd, 1H), 6.75 (d, 2H), 6.46 (s, 1H), 4.76 (t, 2H), 3.93 (dt, 2H), 3.67 (m, 4H), 3.22 (m, 2H), 3.03 (m, 2H), 2.84 (m, 2H).

Example 166

4-{4-[(4'-chloro-1,1'-biphenyl-2-yl)methyl]piperazin-1-yl}-N-[(4-{[3-(dimethylamino)propyl]amino}-3-nitrophenyl)sulfonyl]-2-(2-naphthyloxy)benzamide This example was prepared by substituting EXAMPLE 35B for EXAMPLE 27G and EXAMPLE 154A for EXAMPLE 1F in EXAMPLE 27H. $^1$H NMR (400 MHz, dimethylsulfoxide-$d_6$) δ 11.83 (br s, 1H), 9.46 (br s, 1H), 8.53 (t, 1H), 8.40 (s, 1H), 7.81 (d, 2H), 7.71 (m, 1H), 7.63 (m, 2H), 7.51 (m, 5H), 7.37 (m, 4H), 7.17 (d, 1H), 7.03 (s, 1H), 6.82 (d, 2H), 6.57 (d, 1H), 4.27 (m, 1H), 3.62 (m, 6H), 3.39 (m, 2H), 3.09 (m, 2H), 2.80-3.25 (m, 6H), 2.79 (s, 6H), 1.91 (m, 2H).

Example 167

4-{4-[(4'-chloro-1,1'-biphenyl-2-yl)methyl]piperazin-1-yl}-N-[(3-nitro-4-{[2-(2-oxopyridin-1(2H)-yl)ethyl]amino}phenyl)sulfonyl]-2-phenoxybenzamide This example was prepared by substituting pyridin-2-ol for 1,2,3-triazole in EXAMPLE 164E. $^1$H NMR (400 MHz, dimethylsulfoxide-$d_6$) δ 11.70 (br s, 1H), 9.65 (br s, 1H), 8.75 (t, 1H), 8.44 (d, 1H), 7.72 (d, 2H), 7.64 (d, 1H), 7.51 (m, 5H), 7.37 (m, 3H), 7.20 (m, 3H), 6.95 (t, 1H), 6.77 (d, 3H), 6.46 (s, 1H), 6.41 (d, 1H), 6.21 (t, 1H), 4.31 (m, 1H), 4.17 (t, 2H), 3.74 (dt, 2H), 3.60 (m, 6H), 3.20 (m, 2H), 3.03 (m, 2H), 2.87 (m, 2H).

Example 168

4-{4-[(4'-chloro-1,1'-biphenyl-2-yl)methyl]piperazin-1-yl}-N-[(3-nitro-4-{[2-(pyridin-2-yloxy)ethyl]amino}phenyl)sulfonyl]-2-phenoxybenzamide This example was prepared by substituting pyridin-2-ol for 1,2,3-triazole in EXAMPLE 164E. $^1$H NMR (400 MHz, dimethylsulfoxide-$d_6$) δ 11.71 (br s, 1H), 9.65 (br s, 1H), 8.84 (t, 1H), 8.44 (d, 1H), 8.19 (d, 1H), 7.74 (m, 3H), 7.51 (m, 5H), 7.37 (m, 3H), 7.20 (m, 3H), 7.00 (dd, 1H), 6.92 (t, 1H), 6.83 (d, 1H), 6.76 (m, 2H), 6.45 (d, 1H), 4.56 (t, 2H), 4.31 (m, 1H), 3.81 (dt, 2H), 3.71 (m, 6H), 3.23 (m, 2H), 3.04 (m, 2H), 2.89 (m, 2H).

Example 169

4-{4-[(4'-chloro-1,1'-biphenyl-2-yl)methyl]piperazin-1-yl}-N-({3-nitro-4-[(2-pyridin-4-ylethyl)amino]phenyl}sulfonyl)-2-phenoxybenzamide

Example 169A 3-nitro-4-(2-(pyridin-4-yl)ethylamino)benzenesulfonamide

This example was prepared by substituting 2-(pyridin-4-yl)ethanamine for (tetrahydropyran-4-yl)methylamine in EXAMPLE 1E.

Example 169B

4-{4-[(4'-chloro-1,1'-biphenyl-2-yl)methyl]piperazin-1-yl}-N-({3-nitro-4-[(2-pyridin-4-ylethyl)amino]phenyl}sulfonyl)-2-phenoxybenzamide This example was prepared by substituting EXAMPLE 169A for EXAMPLE 1F and EXAMPLE 1E for EXAMPLE 27G in EXAMPLE 27H. H NMR (400 MHz, dimethylsulfoxide-$d_6$) δ 11.71 (br s, 1H), 9.70 (br s, 1H), 8.69 (d, 1H), 8.61 (t, 1H), 8.46 (s, 1H), 7.79 (dd, 1H), 7.72 (d, 3H), 7.51 (m, 5H), 7.37 (d, 2H), 7.32 (d, 1H), 7.21 (m, 3H), 6.95 (t, 1H), 6.78 (d, 2H), 6.75 (d, 1H), 6.44 (d, 1H), 4.23 (m, 1H), 3.76 (dt, 2H), 3.63 (m, 4H), 3.13 (t, 2H), 2.76-3.24 (m, 6H).

Example 170

4-(4-{[2-(4-chlorophenyl)-4,4-dimethylcyclohex-1-en-1-yl]methyl}piperazin-1-yl)-N-({4-{[3-(dimethylamino)propyl]amino}-3-[(trifluoromethyl)sulfonyl]phenyl}sulfonyl)-2-(1H-indol-5-yloxy)benzamide

Example 170A 4-(3-(dimethylamino)propylamino)-3-(trifluoromethylsulfonyl)benzenesulfonamide This example was prepared by substituting N,N-dimethyl-1,3-propanediamine for (tetrahydropyran-4-yl)methylamine and EXAMPLE 159C for 4-fluoro-3-nitrobenzenesulfonamide in EXAMPLE 1F.

Example 170B 4-(4-{[2-(4-chlorophenyl)-4,4-dimethylcyclohex-1-en-1-yl]methyl}piperazin-1-yl)-N-({4-{[3-(dimethylamino)propyl]amino}-3-[(trifluoromethyl)sulfonyl]phenyl}sulfonyl)-2-(1H-indol-5-yloxy)benzamide This example was prepared by substituting EXAMPLE 170A for EXAMPLE 1F and EXAMPLE 26C for EXAMPLE 27G in EXAMPLE 27H. $^1$H NMR (400 MHz, dimethylsulfoxide-$d_6$) δ 11.42 (br s, 1H), 11.17 (s, 1H), 9.37 (br s, 1H), 8.22 (d, 1H), 7.98 (d, 1H), 7.52 (d, 1H), 7.35-7.45 (m, 4H), 7.19 (d, 1H), 7.08 (m, 3H), 6.85 (dd, 1H), 6.67 (dd, 1H), 6.40 (d, 1H), 6.19 (d, 1H), 3.55 (m, 8H), 3.04 (m, 4H), 2.77 (s, 6H), 2.72 (m, 2H), 2.17 (m, 2H), 2.00 (m, 2H), 1.88 (m, 2H), 1.44 (m, 2H), 0.93 (s, 6H).

Example 171

4-(4-{[2-(4-chlorophenyl)-4,4-dimethylcyclohex-1-en-1-yl]methyl}piperazin-1-yl)-N-{[4-{[3-(dimethylamino)propyl]amino}-3-(trifluoromethyl)phenyl]sulfonyl}-2-(1H-indol-5-yloxy)benzamide This example was prepared by substituting EXAMPLE 26C for EXAMPLE 27G and EXAMPLE 92B for EXAMPLE 1F in EXAMPLE 27H. $^1$H NMR (400 MHz, dimethylsulfoxide-$d_6$) δ 11.19 (br s, 1H), 9.33 (br s, 1H), 7.94 (d, 1H), 7.85 (d, 1H), 7.54 (d, 1H), 7.35-7.45 (m, 4H), 7.20 (d, 1H), 7.07 (d, 2H), 6.88 (dd, 2H), 6.67 (dd, 1H), 6.58 (m, 1H), 6.41 (s, 1H), 6.18 (s, 1H), 3.57 (m, 6H), 3.33 (m, 2H), 3.09 (m, 2H), 3.04 (m, 2H), 2.77 (s, 6H), 2.74 (m, 2H), 2.17 (m, 2H), 2.00 (m, 2H), 1.87 (m, 2H), 1.44 (m, 2H), 0.93 (s, 6H).

Example 172

4-(4-{[2-(4-chlorophenyl)-4,4-dimethylcyclohex 1-en-1-yl]methyl}piperazin-1-yl)-N-[(3-cyano-4-{[3-(dimethylamino)propyl]amino}phenyl)sulfonyl]-2-(1H-indol-5-yloxy)benzamide This example was prepared by substituting EXAMPLE 26C for EXAMPLE 27G and EXAMPLE 90B for EXAMPLE 1F in EXAMPLE 27H. $^1$H NMR (400 MHz, dimethylsulfoxide-$d_6$) δ 11.19 (br s, 1H), 9.38 (br s, 1H), 7.98 (s, 1H), 7.81 (d, 1H), 7.55 (d, 1H), 7.35-7.45 (m, 4H), 7.20 (s, 1H), 7.16 (t, 1H), 7.07 (d, 2H), 6.86 (dd, 2H), 6.68 (dd, 1H), 6.41 (s, 1H), 6.18 (s, 1H), 3.57 (m, 6H), 3.31 (m, 2H), 3.09 (m, 2H), 3.04 (m, 2H), 2.77 (s, 6H), 2.74 (m, 2H), 2.17 (m, 2H), 2.00 (m, 2H), 1.87 (m, 2H), 1.44 (m, 2H), 0.93 (s, 6H).

Example 173

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide Example 173A tert-butyl 1-(tetrahydro-2H-pyran-4-yl)piperidin-4-ylcarbamate A mixture of tert-butyl piperidin-4-ylcarbamate (45 g) and dihydro-2H-pyran-4(3H)-one (24.74 g) in dichloromethane (1000 mL) was treated with sodium triacetoxyborohydride (61.9 g), stirred at room temperature for 16 hours, washed with 1M sodium hydroxide and dried with anhydrous sodium sulfate, filtered and concentrated. The concentrate was flash column chromatographed on silica gel with 10-20% methanol/dichloromethane.

Example 173B 1-(tetrahydro-2H-pyran-4-yl)piperidin-4-amine

A solution of EXAMPLE 173A (52.57 g) in dichloromethane (900 mL) was treated with 4M HCl (462 mL), mixed vigorously at room temperature for 16 hours and concentrated.

Example 173C 3-nitro-4-(1-(tetrahydro-2H-pyran-4-yl)piperidin-4-ylamino)benzenesulfonamide A mixture of EXAMPLE 173B (22.12 g), water (43 mL), and triethylamine (43.6 mL) in 1,4-dioxane (300 mL) was stirred at room temperature until EXAMPLE 173B completely dissolved. The solution was then treated with 4-chloro-3-nitrobenzenesulfonamide, heated at 90° C. for 16 hours, cooled and concentrated. 10% methanol in dichloromethane was added, and the solution was stirred vigorously at room temperature until a fine suspension existed and the mixture was filtered.

Example 173D 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide A mixture of EXAMPLE 26C (3.95 g), EXAMPLE 173C (2.66 g), 1-ethyl-3-[3-(dimethylamino)propyl]-carbodiimide hydrochloride (2.66 g), and 4-dimethylaminopyridine (0.846 g) in dichloromethane (70 mL) and acetonitrile (20 mL) was stirred at 35° C. for 24 hours, cooled and chromatographed on silica gel with 0-10% methanol in ethyl acetate, then 10% methanol in 1:1 ethyl acetate/dichloromethane. The combined fractions were concentrated, dissolved in of 5% methanol/ethyl acetate (1.5 L), and the solution was washed with saturated $NaH_2PO_4$ solution and brine and dried over $Na_2SO_4$, filtered, concentrated to 300 mL, cooled, and filtered. The remaining solution was concentrated partway and filtered again to isolate more product. $^1$H NMR (300 MHz, dimethysulfoxide-$d_6$) δ 11.17 (brs, 1H), 10.70 (br s, 1H), 8.60 (d, 1H), 8.20 (br d, 1H), 7.88 (dd, 1H), 7.50 (d, 1H), 7.39 (m, 2H), 7.33 (d, 2H), 7.16 (m, 2H), 7.03 (d, 2H), 6.85 (dd, 1H), 6.65 (dd, 1H), 6.39 (s, 1H), 6.14 (s, 1H), 3.97 (m, 4H), 3.44 (m, 4H), 3.04 (m, 6H), 2.75 (m, 2H), 2.14 (m, 8H), 1.95 (m, 6H), 1.66 (m, 2H), 1.38 (t, 2H), 0.92 (s, 6H).

Example 174

4-(4-{[2-(4-chlorophenyl)-4,4-dimethylcyclohex-1-en-1-yl]methyl}piperazin-1-yl)-2-(1 1H-indol-5-yloxy)-N-({4-[(4-methylpiperazin-1-yl)amino]-3-nitrophenyl}sulfonyl)benzamide Example 174A 4-(4-methylpiperazin-1-ylamino)-3-nitrobenzenesulfonamide A mixture of 4-chloro-3-nitrobenzenesulfonamide (1 g), 4-methylpiperazin-1-amine dihydrochloride (1 g) and $N^1,N^1,N^2,N^2$-tetramethylethane-1,2-diamine (3 mL) in dioxane (10 mL) was refluxed for 12 hours, cooled to ambient temperature and filtered. The filtrate was added to a silica gel column (Analogix, SF65-200g) and purified by eluting with 1-5% methanol/dichloromethane).

Example 174B 4-(4-{[2-(4-chlorophenyl)-4,4-dimethylcyclohex-1-en-1-yl]methyl}piperazin-1-yl)-2-(1H-indol-5-yloxy)-N-({4-[(4-methylpiperazin-1-yl)amino]-3-nitrophenyl}sulfonyl)benzamide A mixture of EXAMPLE 26C (0.108 g), EXAMPLE 174A (64 mg), 1-ethyl-3-[3-(dimethylamino)propyl]-carbodiimide hydrochloride (0.08 g) and 4-dimethylaminopyridine (0.08 g) in dichloromethane (3 mL) was stirred at ambient temperature overnight and concentrated. The concentrate was added to a preparative HPLC column and eluted with 20-100% acetonitrile/water with 0.1% trifluoroacetic acid. The trifluoroacetic acid salt solution was neutralized with $NaHCO_3$ and extracted with dichloromethane. This solution was washed with saturated $NaHCO_3$, dried over $Na_2SO_4$, and filtered and concentrated. $^1$H NMR (500 MHz, dimethysulfoxide-$d_6$) δ 11.14 (s, 1H), 9.17 (s, 1H), 8.52 (s, 1H), 7.83 (m, 1H), 7.53 (m, 2H), 7.36 (m, 4H), 7.12 (s, 1H), 7.03 (d, 2H), 6.83 (m, 1H), 6.62 (m, 1H), 6.38 (s, 1H), 6.13 (m, 1H), 5.76 (s, 2H), 2.85 (m, 12H), 2.35 (m, 4H), 2.14 (m, 6H), 1.94 (m, 2H), 1.38 (m, 2H), 0.92 (s, 6H).

Example 175

4-{4-[1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide Example 175A 1-(4'-chlorobiphenyl-2-yl)ethanone A mixture of 1-(2-bromophenyl)ethanone (3.1 g, 15.57 mmol)$_4$-chlorophenylboronic acid (2.92 g), $(Ph_3P)_2PdCl_2$ (bis(triphenylphosphine)palladium(II) dichloride) (1.202 g)

and Na$_2$CO$_3$ (3.30 g) in dimethoxyethane-ethanol-water (7:2: 3, 50 mL) was heated at 100° C. for 3 hours and concentrated. The concentrate was suspended in dichloromethane (30 mL) and the insoluble material was removed by filtration. The filtrate was loaded onto a silica gel column, eluted with 0%-50% dichloromethane in hexane to provide the title compound.

Example 175B tert-butyl 4-(1-(4'-chlorobiphenyl-2-yl)ethyl)piperazine-1-carboxylate

Example 175A 1.9 g) was dissolved in dichloromethane (3 mL) and titanium(IV chloride (9.06 mL, 9.06 mmol) was added. The solution was cooled to 0° C. and tert-butyl piperazine-1-carboxylate (3.07 g) was added. The resulting mixture was stirred at ambient temperature for 3 hours and NaCNBH$_3$ (0.828 g) in methanol (5 mL) was added. The resulting mixture was stirred at room temperature overnight and neutralized by aqueous NaOH, and then concentrated. To the concentrate was added ethyl acetate and the insoluble material was filtered off. The organic layer was washed with water and concentrated. The concentrate was dissolved in a mixture of methanol-trifluoroacetic acid-dimethysulfoxide, loaded onto a reverse phase C18 column, and eluted with 0-80% acetonitrile in 0.1% trifluoroacetic acid water over 70 minutes.

Example 175C 1-(1-(4'-chlorobiphenyl-2-yl)ethyl)piperazine

To a solution of EXAMPLE 175B (650 mg) in dichloromethane (6 mL) was added trifluoroacetic acid (6 mL) at 0° C. The reaction mixture was stirred at 0° C. for 50 minutes and concentrated. The concentrate was dissolved in dichloromethane, washed with aqueous NaHCO$_3$ and the organic layer was dried over Na$_2$SO$_4$, and concentrated.

Example 175D ethyl 2-(1H-indol-4-yloxy)-4-(4-(1-(4'-chlorobiphenyl-2-yl)ethyl)piperazin-1-yl)benzoate EXAMPLE 175C (193 mg) and ethyl 2-(1H-indol-4-yloxy)-4-fluorobenzoate (211 mg) in dimethysulfoxide (15 mL) was treated with potassium hydrogen phosphate (168 mg) at 135° C. overnight and cooled. The reaction mixture was diluted with dichloromethane and washed with water. The organic layer was concentrated. The concentrate was dissolved in dichloromethane, loaded onto a silica gel column, eluted with 0%-10% 10 M ammonia methanol in dichloromethane.

Example 175E 2-(1H-indol-4-yloxy)-4-(4-(1-(4'-chlorobiphenyl-2-yl)ethyl)piperazin-1-yl)benzoic acid EXAMPLE 175D (200 mg) in tetrahydrofuran (10 mL) and methanol (10 mL) was treated with 10% NaOH (3 mL) at 50° C. overnight and neutralized with HCl. The mixture was concentrated and the concentrate was taken up in water and extracted with dichloromethane. The organic layer was dried over Na$_2$SO$_4$ and concentrated.

Example 175F 4-(4-(1-(4'-chloro-1,1'-biphenyl-2-yl)ethyl)piperazin-1-yl)-2-(1H-indol-4-yloxy)-N-((3-nitro-4-((tetrahydro-2H-pyran-4-ylmethyl)amino)phenyl)sulfonyl)benzamide To a mixture of EXAMPLE 175E (66 mg), 3-nitro-4-((tetrahydro-2H-pyran-4-yl)methylamino)benzenesulfonamide (75 mg) and 4-dimethylaminopyridine (58.4 mg) in dichloromethane (5 mL) was added 1-ethyl-3-[3-(dimethylamino)propyl]-carbodiimide hydrochloride (45.8 mg). The mixture was stirred at ambient temperature overnight and concentrated. The concentrate was purified by RP HPLC (10-70% acetonitrile in 0.1% trifluoroacetic acid water/70 minutes). The desired fractions were concentrated to remove acetonitrile and the concentrate was diluted with dichloromethane and neutralized with aqueous NaHCO$_3$. The dichloromethane layer was dried over Na$_2$SO$_4$ and concentrated to provide the title compound. $^1$H NMR (500 MHz, dimethysulfoxide-d$_6$) δ ppm 11.31 (1H, s), 11.25 (1H, s), 8.62 (1H, t), 8.50 (1H, d), 7.68 (1H, dd), 7.53 (2H, d), 7.46 (2H, d), 7.37 (1H, t), 7.24-7.31 (4H, m), 7.17 (1H, d), 7.12 (1H, dd), 7.07 (1H, d), 6.96 (1H, t), 6.69 (1H, dd), 6.42 (1H, d), 6.26 (2H, s), 3.85 (2H, dd), 3.21-3.33 (5H, m), 3.01 (4H, s), 2.29-2.39 (2H, m), 2.15-2.22 (2H, m), 1.83-1.94 (1H, m), 1.57-1.68 (2H, m), 1.22-1.31 (2H, m), 1.17 (3H, d).

Example 176

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-4-yloxy)benzamide

Example 176A 4-((4-aminotetrahydro-2H-pyran-4-yl)methylamino)-3-nitrobenzenesulfonamide A mixture of 4-chloro-3-nitrobenzenesulfonamide, 4-(aminomethyl)tetrahydro-2H-pyran-4-amine bis-hydrochloric acid salt and triethylamine in dioxane (10 mL) was heated at 110° C. overnight. After cooling, the reaction mixture was diluted with water (10 mL), and the solid was filtered to give the title compound.

Example 176B

N-((4-(((4-aminotetrahydro-2H-pyran-4-yl)methyl)amino)-3-nitrophenyl)sulfonyl)-4-(4-((2-(4-chlorophenyl)-4,4-dimethylcyclohex-1-en-1-yl)methyl)piperazin-1-yl)-2-(1H-indol-4-yloxy)benzamide This EXAMPLE was prepared by substituting EXAMPLE 55B for EXAMPLE 1F and EXAMPLE 176A (4-aminotetrahydro-2H-pyran-4-yl)methylamino)-3-nitrobenzenesulfonamide) for EXAMPLE 1G in EXAMPLE 1H. $^1$H NMR (500 MHz, dimethysulfoxide-d$_6$) δ 11.15 (s, 1H), 8.51 (s, 1H), 8.45 (d, J=2.14 Hz, 1H), 7.70 (dd, J=9.0, 1.98 Hz, 1H), 7.59 (d, J=8.85 Hz, 1H), 7.34 (d, J=8.24 Hz, 2H), 7.22 (t, J=2.59 Hz, 1H), 7.11-7.12 (m, 2H), 7.04 (d, J=8.54 Hz, 2H), 6.93 (t, J=7.78 Hz, 1H), 6.62 (dd, J=9.0, 1.98 Hz, 1H), 6.34 (d, J=7.63 Hz, 1H), 6.20-6.23 (m, 2H), 3.55-3.70 (m, 6H), 2.96 (m, 3H), 2.71 (s, 2H), 2.16 (m, 6H), 1.95 (m, 2H), 1.70-1.74 (m, 2H), 1.55-1.59 (m, 2H), 1.37-1.39 (m, 2H), 0.92 (s, 6H).

Example 177

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide A mixture of EXAMPLE 26C (2.85 g, 10 mmol), EXAMPLE 1F (1.577 g, 5 mmol), 1-ethyl-3-[3-(dimethylamino)propyl]-carbodiimide hydrochloride (1.917 g, 10 mmol), 4-(dimethylamino)pyridine (1.222 g, 10 mmol), and triethyl amine (2.8 mL, 20 mmol) was treated with $CH_2Cl_2$ (20 mL) and N,N-dimethylformamide (2 mL). The reaction mixture was stirred over night. The solvent was removed, and the residue was partitioned between water and ethyl acetate. The organic layers were washed with 1% HCl twice, then with sat $NaHCO_3$, brine, dried, filtered, and concentrated The residue was purified by reverse phase HPLC on a C18 column using a gradient of 40-60% acetonitrile/0.1% TFA in water to give the title compound as the trifluoroacetate salt. The TFA salt was dissolved in dichloromethane (6 ml) and washed with 50% aqueous $NaHCO_3$. The organic layer was dried over anhydrous $Na_2SO_4$ and concentrated to give the title compound. $^1$H NMR (300 MHz, dimethylsulfoxide-$d_6$) δ 11.18 (s, 2H), 8.59-8.64 (m, 2H), 7.80 (dd, 1H), 7.52 (d, 1H), 7.39-7.42 (m, 2H), 7.33 (d, 2H), 7.16 (d, 1H), 7.10 (d, 1H), 7.03 (d, 2H), 6.8 (dd, 1H), 6.65 (dd, 1H), 6.40)s, 1H), 6.14 (d, 1H), 3.85 (dd, 2H), 3.24-3.32 (m, 4H), 3.03 (s, 3H), 2.73 (s, 2H), 2.12-2.17 (m, 5H), 1.68-1.94 (m, 3H), 1.61 (d, 2H), 1.37 (t, 2H), 1.24-1.27 (m, 2H), 0.92 (s, 6H).

Example 178

Trans-4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylcyclohexyl)amino]-3-nitrophenyl}sulfonyl)benzamide

Example 178A

Trans-4-(4-morpholinocyclohexylamino)-3-nitrobenzenesulfonamide

This EXAMPLE was prepared by substituting 4-amino-N-morpholinylpiperidine for 1-(tetrahydropyran-4-yl)methylamine in EXAMPLE 1F.

Example 178B

Trans-4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylcyclohexyl)amino]-3-nitrophenyl}sulfonyl)benzamide The title compound was prepared as in EXAMPLE 177 by replacing EXAMPLE 1F with EXAMPLE 178A. $^1$H NMR (500 MHz, pyridine-$d_5$) δ 12.29 (s, 1H), 9.29 (d, J=2.1 Hz, 1H), 8.37 (d, J=7.6 Hz, 1H), 8.32 (dd, J=9.3, 2.3 Hz, 1H), 8.18 (d, J=8.8 Hz, 1H), 7.52-7.57 (m, 2H), 7.39-7.47 (m, 3H), 7.10 (dd, J=8.7, 2.3 Hz, 1H), 7.05-7.08 (m, 2H), 6.90 (d, J=9.5 Hz, 1H), 6.74 (dd, J=9.0, 2.3 Hz, 1H), 6.59-6.63 (m, 1H), 6.55 (d, J=2.4 Hz, 1H), 3.72-3.78 (m, 4H), 3.33-3.43 (m, 1H), 2.99-3.09 (m, 4H), 2.76 (s, 2H), 2.46-2.54 (m, 4H), 2.16-2.29 (m, 3H), 2.09-2.14 (m, 4H), 2.05 (d, J=11.9 Hz, 2H), 1.97 (d, J=1.8 Hz, 2H), 1.87 (d, J=11.6 Hz, 2H), 1.19-1.42 (m, 6H), 0.93 (s, 6H).

Example 179

4-(4-{[2-(4-chlorophenyl)-4,4-dimethylcyclohex-1-en-1-yl]methyl}piperazin-1-yl)-2-(1H-indol-5-yloxy)-N-({4-[(2-methoxyethyl)amino]-3-nitrophenyl}sulfonyl)benzamide

Example 179A 4-(2-methoxyethylamino)-3-nitrobenzenesulfonamide

This EXAMPLE was prepared by substituting 2-methoxyethylamine for 1-(tetrahydropyran-4-yl)methylamine in EXAMPLE 1F.

Example 179B 4-(4-{[2-(4-chlorophenyl)-4,4-dimethylcyclohex-1-en-1-yl]methyl}piperazin-1-yl)-2-(1H-indol-5-yloxy)-N-({4-[(2-methoxyethyl)amino]-3-nitrophenyl}sulfonyl)benzamide The title compound was prepared as in EXAMPLE 177 by replacing EXAMPLE 1F with EXAMPLE 179A. $^1$H NMR (400 MHz, DMSO-$d_6$) δ 11.20 (br. s, 1H) 11.15 (s, 1H) 8.59 (m, 2H) 7.81 (dd, 1H) 7.50 (d, 1H) 7.36 (m, 4H) 7.08 (m, 4H) 6.85 (dd, 1H) 6.65 (dd, 1H) 6.38 (m, 1H) 6.14 (m, 1H) 3.58 (m, 4H) 3.30 (s, 3H) 3.03 (m, 4H) 2.73 (s, 2H) 2.15 (m, 6H) 1.96 (s, 2H) 1.38 (t, 2H) 0.92 (s, 6H).

Example 180

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3S)-tetrahydro-2H-pyran-3-ylmethyl]amino}phenyl)sulfonyl]benzamide

Example 180A (R)-3-nitro-4-((tetrahydro-2H-pyran-3-yl)methylamino)benzenesulfonamide and (S)-3-nitro-4-((tetrahydro-2H-pyran-3-yl)methylamino)benzenesulfonamide This EXAMPLE was prepared by substituting (tetrahydro-2H-pyran-3-yl)methanamine for 1-(tetrahydropyran-4-yl)methylamine in EXAMPLE 1F.

Example 180B (S)-3-nitro-4-((tetrahydro-2H-pyran-3-yl)methylamino)benzenesulfonamide The racemic mixture of EXAMPLE 180A was resolved by chiral SFC on an AD column (21 mm i.d.×250 mm in length) using a gradient of 10-30% 0.1% diethylamine methanol in $CO_2$ over 15 min (oven temperature: 40° C.; flow rate: 40 mL/min) to provide the title compound.

Example 180C (R)-3-nitro-4-((tetrahydro-2H-pyran-3-yl)methylamino)benzenesulfonamide The racemic mixture of EXAMPLE 180A was resolved by chiral SFC on an AD column (21 mm i.d.×250 mm in length)

Example 180D 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3S)-tetrahydro-2H-pyran-3-ylmethyl]amino}phenyl)sulfonyl]benzamide The title compound was prepared as in EXAMPLE 177 by replacing EXAMPLE 1F with EXAMPLE 180B. $^1$H NMR (400 MHz, DMSO-$d_6$) δ 11.17 (s, 2H), 8.53-8.65 (m, 2H), 7.80 (d, 1H), 7.51 (d, 1H), 7.38-7.44 (m, 2H), 7.33 (d, 2H), 7.15 (s, 1H), 7.02-7.09 (m, 3H), 6.82-6.92 (m, 1H), 6.65 (d, 1H), 6.39 (s, 1H), 6.14 (s, 1H), 3.68-3.82 (m, 2H), 3.22-3.32 (m, 2H), 3.13-3.22 (m, 1H), 3.03 (s, 4H), 2.72 (s, 2H), 2.09-2.23 (m, 6H), 1.78-1.98 (m, 4H), 1.56-1.66 (m, 1H), 1.43-1.51 (m, 1H), 1.37 (t, 2H), 1.22-1.33 (m, 1H), 0.92 (s, 6H).

Example 181

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3R)-tetrahydro-2H-pyran-3-ylmethyl]amino}phenyl)sulfonyl]benzamide The title compound was prepared as in EXAMPLE 177 by replacing EXAMPLE 1F with EXAMPLE 180C. $^1$H NMR (400 MHz, DMSO-$d_6$) δ 11.17 (s, 2H), 8.53-8.65 (m, 2H), 7.80 (d, 1H), 7.51 (d, 1H), 7.38-7.44 (m, 2H), 7.33 (d, 2H), 7.15 (s, 1H), 7.02-7.09 (m, 3H), 6.82-6.92 (m, 1H), 6.65 (d, 1H), 6.39 (s, 1H), 6.14 (s, 1H), 3.68-3.82 (m, 2H), 3.22-3.32 (m, 2H), 3.13-3.22 (m, 1H), 3.03 (s, 4H), 2.72 (s, 2H), 2.09-2.23 (m, 6H), 1.78-1.98 (m, 4H), 1.56-1.66 (m, 1H), 1.43-1.51 (m, 1H), 1.37 (t, 2H), 1.22-1.33 (m, 1H), 0.92 (s, 6H).

Example 182

4-(4-{[4-(4-chlorophenyl)-6,6-dimethyl-5,6-dihydro-2H-pyran-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide The title compound was prepared as in EXAMPLE 177 by replacing EXAMPLE 26C with EXAMPLE 150C. $^1$H NMR (400 MHz, DMSO-$d_6$) δ 11.20 (br s, 1H), 11.17 (s, 1H), 8.63 (t, 1H), 8.59 (d, 1H), 7.79 (dd, 1H), 7.51 (d, 1H), 7.36 (m, 3H), 7.13 (m, 2H), 6.86 (dd, 1H), 6.66 (dd, 1H), 6.39 (s, 1H), 6.15 (d, 1H), 4.10 (s, 2H), 3.85 (m, 3H), 3.50 (m, 2H), 3.42 (m, 2H), 3.24 (m, 4H), 3.02 (m, 4H), 2.82 (m, 2H), 2.16 (m, 2H), 1.61 (m, 3H), 1.25 (m, 4H), 1.17 (s, 6H).

Example 183

4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]-2-(1H-indol-5-yloxy)benzamide

Example 183A 4-((4-hydroxy-1-methylpiperidin-4-yl)methylamino)-3-nitrobenzenesulfonamide This example was prepared by substituting 4-(aminomethyl)-1-methylpiperidin-4-ol for (tetrahydropyran-4-yl)methylamine in EXAMPLE 1F.

Example 183B 4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]-2-(1H-indol-5-yloxy)benzamide This example was prepared by substituting EXAMPLE 183A for EXAMPLE 1F in EXAMPLE 177. $^1$H NMR (500 MHz, dimethylsulfoxide-$d_6$) δ 11.04 (s, 1H), 8.46-8.48 (m, 2H), 7.92 (s, 1H), 7.74 (d, 1H), 7.54 (d, 1H), 7.32-7.34 (m, 5H), 6.97-7.05 (m, 5H), 6.74-6.76 (m, 1H), 6.55-6.57 (m, 1H), 6.33 (s, 1H), 6.13 (d, 1H), 5.10 (s, 1H), 3.14-3.17 (m, 2H), 2.95 (br, 5H), 2.71 (br, 2H), 2.14-2.17 (m, 6H), 1.95 (br s, 2H), 1.70 (br, 4H), 1.36-1.39 (m, 2H), 1.24-1.26 (m, 2H), 0.92 (s, 6H).

Example 184

4-(4-{[2-(4-chlorophenyl)-4,4-dimethylcyclohex-1-en-1-yl]methyl}piperazin-1-yl)-3-fluoro-2-(1H-indol-5-yloxy)-N-({4-[(1-methylpiperidin-4-yl)amino]-3-nitrophenyl}sulfonyl)benzamide

Example 184A ethyl 2-(1H-indol-5-yloxy)-3,4-difluorobenzoate

This example was prepared by substituting ethyl 2,3,4-trifluorobenzoate for ethyl 2,4-difluorobenzoate and 5-hydroxyindole for 5-hydroxyindazole in EXAMPLE 20A.

Example 184B ethyl 2-(1H-indol-5-yloxy)-4-(4-((2-(4-chlorophenyl)-4,4-dimethylcyclohex-1-enyl)methyl)piperazin-1-yl)-3-fluorobenzoate This example was prepared by substituting EXAMPLE 184A for EXAMPLE 20A in EXAMPLE 20D.

Example 184C 2-(1H-indol-5-yloxy)-4-(4-((2-(4-chlorophenyl)-4,4-dimethylcyclohex-1-enyl)methyl)piperazin-1-yl)-3-fluorobenzoic acid This example was prepared by substituting EXAMPLE 184B for EXAMPLE 1D in EXAMPLE 1E.

Example 184D 4-(4-{[2-(4-chlorophenyl)-4,4-dimethylcyclohex-1-en-1-yl]methyl}piperazin-1-yl)-3-fluoro-2-(1H-indol-5-yloxy)-N-({4-[(1-methylpiperidin-4-yl)amino]-3-nitrophenyl}sulfonyl)benzamide This example was prepared by substituting EXAMPLE 184C for EXAMPLE 1E and EXAMPLE 21A for EXAMPLE 1F in EXAMPLE 1G. $^1$H NMR (300 MHz, dimethylsulfoxide-$d_6$) δ 10.98 (br s, 1H), 8.35 (d, 1H), 7.98 (dd, 1H), 7.59 (dd, 1H), 7.35 (m, 3H), 7.28 (t, 1H), 7.21 (d, 1H), 7.06 (d, 2H), 6.78 (m, 2H), 6.67 (m, 2H), 6.22 (s, 1H), 3.74 (dd, 2H), 3.39 (m, 4H), 3.06 (m, 3H), 2.97 (m, 4H), 2.79 (m, 2H), 2.73 (s, 3H), 2.29 (m, 2H), 2.18 (m, 2H), 2.05 (m, 2H), 1.81 (m, 2H), 1.41 (t, 2H), 0.94 (s, 6H).

Example 185

4-(4-{[2-(4-chlorophenyl)-4,4-dimethylcyclohex-1-en-1-yl]methyl}piperazin-1-yl)-3-fluoro-2-(1H-indol-5-yloxy)-N-({3-nitro-4-[(1-tetrahydro-2H-pyran-4-ylpiperidin-4-yl)amino]phenyl}sulfonyl)benzamide This example was prepared by substituting EXAMPLE 184C for EXAMPLE 1E and EXAMPLE 173C for EXAMPLE 1F in EXAMPLE 1G. $^1$H NMR (300 MHz, dimethylsulfoxide-$d_6$) δ 10.98 (br s, 1H), 8.33 (d, 1H), 8.02 (dd, 1H), 7.50 (dd, 1H), 7.35 (m, 3H), 7.26 (t, 1H), 7.19 (d, 1H), 7.06 (d, 2H), 6.77 (dd, 2H), 6.67 (m, 2H), 6.22 (s, 1H), 3.90 (dd, 2H), 3.57 (m, 5H), 3.30 (dd, 2H), 3.06 (m, 3H), 2.94 (m, 4H), 2.78 (m, 2H), 2.27 (m, 4H), 2.18 (m, 2H), 1.98 (m, 4H), 1.80 (m, 2H), 1.55 (m, 2H), 1.41 (t, 2H), 0.94 (s, 6H).

Example 186

4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]-2-(1H-indol-4-yloxy)benzamide This example was prepared by substituting EXAMPLE 183A for EXAMPLE 1F and EXAMPLE 55B for EXAMPLE 26C in EXAMPLE 177. $^1$H NMR (500 MHz, dimethylsulfoxide-$d_6$) δ 11.12 (s, 1H), 8.49 (s, 1H), 8.42 (s, 1H), 7.73-7.75 (m, 1H), 7.58 (d, 1H), 7.34 (d, 2H), 7.22 (s, 1H), 7.09 (d, 1H), 7.01-7.05 (m, 3H), 6.92 (t, 1H), 6.61-6.62 (m, 1H), 6.31 (d, 1H), 6.23 (s, 1H), 6.20 (s, 1H), 5.16 (s, 1H), 4.05 (s, 3H), 2.95 (br s, 6H), 2.71 (br s, 2H), 2.62 (br, 3H), 2.16 (br s, 6H), 1.95 (br s, 2H), 1.72 (br, 4H), 1.37-1.39 (m, 2H), 0.92 (s, 6H).

Example 187

N-[(4-{[(3S,4R)-1-benzyl-3-hydroxypiperidin-4-yl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide

Example 187A 2-(1H-indol-5-yloxy)-N-(4-chloro-3-nitrophenylsulfonyl)-4-(4-((2-(4-chlorophenyl)-4,4-dimethylcyclohex-1-enyl)methyl)piperazin-1-yl)benzamide This example was prepared by substituting 4-chloro-3-nitrobenzenesulfonamide for EXAMPLE 1F and EXAMPLE 26C for EXAMPLE 1E in EXAMPLE 1G.

Example 187B

N-[(4-{[(3S,4R)-1-benzyl-3-hydroxypiperidin-4-yl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide A mixture of EXAMPLE 187A (0.158 g), (3S,4R)-4-amino-1-benzylpiperidin-3-ol, hydrochloric acid (0.049 g), and triethylamine (0.1 mL) in dioxane (2 mL) was heated at 100° C. overnight. The solvent was removed, and the residue was re-dissolved in 1:1 methanol:dimethylsulfoxide (3 mL). It was then purified by reverse phase Prep HPLC. The residue was purified by reverse phase HPLC on a C18 column using a gradient of 20-80% acetonitrile/0.1% TFA in water. The desired fractions were collected, and the organic solvent was partially removed under reduced pressure. The resulting mixture was treated with saturated aqueous NaHCO$_3$ mixture. It was then extracted with ethyl acetate three times. The combined organic layers were washed with brine, dried (MgSO$_4$), filtered, and concentrated to give the desired product. $^1$H NMR (500 MHz, dimethylsulfoxide-$d_6$) δ 11.14 (s, 1H), 8.69 (d, 1H), 8.14 (d, 1H), 7.77 (dd, 1H), 7.51 (d, 1H), 7.29-7.41 (m, 9H), 7.10-7.13 (m, 1H), 7.13 (d, 2H), 6.84 (dd, 1H), 6.63 (dd, 1H), 6.38 (s, 1H), 6.13 (d, 1H), 5.21-5.22 (br s, 1H), 3.82 (m, 2H), 3.62 (br s, 2H), 3.01 (br s, 4H), 2.71-2.82 (m, 4H), 2.12-2.15 (m, 7H), 1.94 (br s, 2H), 1.81 (br s, 2H), 1.36-1.39 (m, 2H), 0.92 (s, 6H).

Example 188

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide This example was prepared by substituting 4-(aminomethyl)tetrahydro-2H-pyran-4-amine for (3S,4R)-4-amino-1-benzylpiperidin-3-ol hydrochloric acid in EXAMPLE 187B. $^1$H NMR (500 MHz, dimethylsulfoxide-$d_6$) δ 11.08 (s, 1H), 8.60 (br s, 1H), 8.51 (d, 1H), 7.80 (dd, 1H), 7.54 (d, 1H), 7.32-7.36 (m, 4H), 7.12 (d, 1H), 7.03-7.05 (m, 3H), 6.77 (dd, 1H), 6.58 (dd, 1H), 6.35 (s, 1H), 6.13 (d, 1H), 3.61-3.70 (m, 4H), 3.53 (br s, 2H), 2.97 (br, 4H), 2.71 (br, 2H), 2.16 (br s, 6H), 1.94 (br s, 2H), 1.67-1.72 (m, 2H), 1.52-1.57 (m, 2H), 1.36-1.39 (m, 2H), 0.92 (s, 6H).

Example 189

4-(4-{[2-(4-chlorophenyl)-4,4-dimethylcyclohex-1-en-1-yl]methyl}piperazin-1-yl)-2-(1H-indol-5-yloxy)-N-[(4-{[1-(2-methoxyethyl)piperidin-4-yl]amino}-3-nitrophenyl)sulfonyl]benzamide

Example 189A

4-[1-(2-methoxy-ethyl)-piperidin-4-ylamino]-3-nitro-benzenesulfonamide 1-(2-Methoxy-ethyl)-piperidin-4-ylamine (2.01 g) and triethylamine (3.24 mL, 2.35 g) were added to 1,4-dioxane (60 mL). 4-Chloro-3-nitrobenzenesulfonamide (2.50 g) was added, and the mixture was heated to 90° C. for 16 hours. The mixture was cooled and the material purified by flash column chromatography on silica gel using 10% methanol in dichloromethane.

Example 189B 4-(4-{[2-(4-chlorophenyl)-4,4-dimethylcyclohex-1-en-1-yl]methyl}piperazin-1-yl)-2-(1 1H-indol-5-yloxy)-N-[(4-{[1-(2-methoxyethyl)piperidin-4-yl]amino}-3-nitrophenyl)sulfonyl]benzamide This example was prepared by substituting EXAMPLE 26C for EXAMPLE 1E and EXAMPLE 189A for EXAMPLE 1F in EXAMPLE 1G. $^1$H NMR (300 MHz, dimethylsulfoxide-$d_6$) δ 11.12 (br s, 1H), 8.52 (d, 1H), 8.18 (d, 1H), 7.76 (dd, 1H), 7.51 (d, 1H), 7.39-7.31 (m, 4H), 7.08-7.05 (m, 4H), 6.80 (dd, 1H), 6.61, (dd, 1H), 6.36 (t, 1H), 6.14 (d, 1H), 3.70 (m, 1H), 3.50 (t, 2H), 3.27 (s, 3H), 2.99 (m, 6H), 2.71 (br s, 4H), 2.16 (m, 6H), 2.02-1.90 (m, 6H), 1.65 (m, 2H), 1.37 (t, 2H), 0.92 (s, 6H).

Example 190

4-(4-{[2-(4-chlorophenyl)-4,4-dimethylcyclohex-1-en-1-yl]methyl}piperazin-1-yl)-2-(1H-indol-4-yloxy)-N-({4-[(4-methylpiperazin-1-yl)amino]-3-nitrophenyl}sulfonyl)benzamide This example was prepared by substituting EXAMPLE 174A for EXAMPLE 1F and EXAMPLE 55B for EXAMPLE 26C in EXAMPLE 177. $^1$H NMR (400 MHz, dimethylsulfoxide-d$_6$) δ 11.21 (br s, 1H), 9.14 (s, 1H), 8.45 (d, 1H), 7.71 (dd, 1H), 7.52 (m, 2H), 7.34 (m, 2H), 7.26 (m, 1H), 7.15 (d, 1H), 7.04 (m, 2H), 6.95 (t, 1H), 6.67 (m, 1H), 6.38 (d, 1H), 6.25 (m, 2H), 3.01 (m, 4H), 2.87 (m, 5H), 2.72 (m, 2H), 2.33 (m, 4H), 2.15 (m, 6H), 1.95 (s, 2H), 1.39 (m, 2H), 0.92 (s, 6H).

Example 191

4-(4-{[2-(4-chlorophenyl)-4,4-dimethylcyclohex-1-en-1-yl]methyl}piperazin-1-yl)-N-[(4-{[1-(2-hydroxyethyl)piperidin-4-yl]amino}-3-nitrophenyl)sulfonyl]-2-(1H-indol-4-yloxy)benzamide Example 191A tert-butyl 4-(4-(N-(2-(1H-indol-4-yloxy)-4-(-4-((2-(4-chlorophenyl)-4,4-dimethylcyclohex-1-enyl)methyl)piperazin-1-yl)benzoyl)sulfamoyl)-2-nitrophenylamino)piperidine-1-carboxylate This example was prepared by substituting EXAMPLE 55B for EXAMPLE 1E and EXAMPLE 157A for EXAMPLE 1F in EXAMPLE 1G, except 5-7% methanol in CH$_2$Cl$_2$ was used for the chromatography.

Example 191B 2-(1H-indol-4-yloxy)-N-(4-(1-(2-(tert-butyldimethylsilyloxy)ethyl)piperidin-4-ylamino)-3-nitrophenylsulfonyl)-4-(-4-((2-(4-chlorophenyl)-4,4-dimethylcyclohex-1-enyl)methyl)piperazin-1-yl)benzamide EXAMPLE 191A (400 mg) was dissolved in CH$_2$Cl$_2$ (2.5 mL) and 4N HCl in dioxane (2.5 mL), then stirred at room temperature for 30 minutes. The reaction was concentrated and then partitioned between CH$_2$Cl$_2$ and saturated aqueous NaHCO$_3$. The organic layer was washed with brine and dried over Na$_2$SO$_4$. After filtration and concentration the resultant crude amine was slurried in CH$_2$Cl$_2$ (2.5 mL) and (tert-butyldimethylsilyloxy)acetaldehyde (73 mg) was added. After stirring for 15 minutes, sodium triacetoxyborohydride (400 mg) was added and the reaction was stirred at room temperature overnight. The reaction was diluted with CH$_2$Cl$_2$ and washed with saturated aqueous NaHCO$_3$ The organic layer was washed with brine and dried over Na$_2$SO$_4$. The product was purified using column chromatography using 1.0-2.5% methanol in CH$_2$Cl$_2$ Example 191C 4-(4-{[2-(4-chlorophenyl)-4,4-dimethylcyclohex-1-en-1-yl]methyl}piperazin-1-yl)-N-[(4-{[1-(2-hydroxyethyl)piperidin-4-yl]amino}-3-nitrophenyl)sulfonyl]-2-(1H-indol-4-yloxy)benzamide EXAMPLE 191B (46 mg) was dissolved in tetrahydrofuran (0.8 mL), then 1.0M tetrabutyl ammonium fluoride in 95/5 tetrahydrofuran/H$_2$O (0.075 mL) was added and the reaction stirred at room temperature overnight. The reaction was concentrated and purified with column chromatography using 2-6% methanol in CH$_2$Cl$_2$. $^1$H NMR (500 MHz, dimethylsulfoxide-d$_6$) δ 11.15 (br s, 1H), 8.44 (d, 1H), 8.13 (br d, 1H), 7.74 (dd, 1H), 7.55 (d, 1H), 7.33 (d, 2H), 7.23 (s, 1H), 7.11 (d, 1H), 7.03 (m, 3H), 6.93 (dd, 1H), 6.64 (d, 1H), 6.33 (d, 1H), 6.23 (s, 1H), 6.22 (s, 1H), 3.75 (br s, 1H), 3.61 (br s, 2H), 3.40 (br s, 2H), 3.10 (br s, 2H), 2.98 br s, 4H), 2.78 (br s, 2H), 2.71 (s, 2H), 2.16 (br m, 6H), 2.00 (br d, 2H), 1.95 (s, 2H), 1.72 (br s, 2H), 1.38 (t, 2H), 0.92 (s, 6H).

Example 194

4-(4-{[2-(4-chlorophenyl)-4,4-dimethylcyclohex-1-en-1-yl]methyl}piperazin-1-yl)-2-(1H-indol-4-yloxy)-N-[(4-{[1-(2-methoxyethyl)piperidin-4-yl]amino}-3-nitrophenyl)sulfonyl]benzamide This example was prepared by substituting EXAMPLE 55B for EXAMPLE 1E and EXAMPLE 189A for EXAMPLE 1F in EXAMPLE 1G. $^1$H NMR (300 MHz, dimethylsulfoxide-d$_6$) δ 11.19 (br s, 1H), 8.46 (d, 1H), 8.17 (d, 1H), 7.72 (dd, 1H), 7.55 (d, 1H), 7.35 (d, 2H), 7.25 (t, 1H), 7.12 (d, 1H), 7.07-7.02 (m, 3H), 6.94 (t, 1H), 6.66, (dd, 1H), 6.36 (d, 1H), 6.24 (m, 2H), 3.73 (m, 1H), 3.52 (t, 2H), 3.27 (s, 3H), 3.00 (m, 6H), 2.79 (m, 2H), 2.72 (br s, 2H), 2.16 (m, 6H), 2.04-1.93 (m, 6H), 1.68 (m, 2H), 1.37 (t, 2H), 0.92 (s, 6H).

Example 195

4-(4-{[2-(4-chlorophenyl)-4,4-dimethylcyclohex-1-en-1-yl]methyl}piperazin-1-yl)-N-[(4-{[1-(3-hydroxypropyl)piperidin-4-yl]amino}-3-nitrophenyl)sulfonyl]-2-(1H-indol-4-yloxy)benzamide Example 195A 4-(1-(3-(tert-butyldimethylsilyloxy)propyl)piperidin-4-ylamino)-3-nitrobenzenesulfonamide A mixture of EXAMPLE 157B (300 mg), (3-bromopropoxy)(tert-butyl)dimethylsilane (304 mg) and cesium carbonate (967 mg) was suspended in anhydrous N,N-dimethylformamide (5 mL). The reaction mixture was heated at 70° C. overnight. The reaction mixture was cooled to room temperature and diluted with ethyl acetate. The organic phase was washed with water, brine, dried over anhydrous sodium sulfate, and concentrated.

The crude material was purified using flash column purification with 3-10% methanol/dichloromethane to afford the title compound.

Example 195B 2-(1H-indol-4-yloxy)-N-(4-(1-(3-(tert-butyldimethylsilyloxy)propyl)piperidin-4-ylamino)-3-nitrophenylsulfonyl)-4-(4-((2-(4-chlorophenyl)-4,4-dimethylcyclohex-1-enyl)methyl)piperazin-1-yl)benzamide This example was prepared by substituting EXAMPLE 55B for EXAMPLE 1E and EXAMPLE 195A for EXAMPLE 1F in EXAMPLE 1G.

Example 195C 4-(4-{[2-(4-chlorophenyl)-4,4-dimethylcyclohex-1-en-1-yl]methyl}piperazin-1-yl)-N-[(4-{[1-(3-hydroxypropyl)piperidin-4-yl]amino}-3-nitrophenyl)sulfonyl]-2-(1H-indol-4-yloxy)benzamide A mixture of EXAMPLE 195B (180 mg) in anhydrous tetrahydrofuran (1 mL) and tetrabutyl ammonium fluoride (0.5 mL 1M in tetrahydrofuran) was stirred at room temperature for 2 hours. The solvent was removed under vacuum. The residue was purified by reverse phase HPLC on a C18 column using a gradient of 40-70% acetonitrile/0.1% trifluroacetic acid in water to give the title compound as the trifluoroacetate salt. The trifluroacetic acid salt was dissolved in dichloromethane (6 ml) and washed with 50% aqueous $NaHCO_3$. The organic layer was dried over anhydrous $Na_2SO_4$, filtered, and concentrated to give the title compound. $^1$H NMR (400 MHz, dimethylsulfoxide-$d_6$) δ 11.16 (s, 1H), 8.43 (d, 1H), 8.10 (m, 1H), 7.74 (dd, 1H), 7.57 (d, 1H), 7.34 (d, 2H), 7.23 (m, 1H), 7.10 (m, 1H), 7.02 (m, 3H), 6.93 (m, 1H), 6.65 (dd, 1H), 6.34 (d, 1H), 6.22 (m, 2H), 3.74 (m, 2H), 3.47 (m, 4H), 3.14 (m, 2H), 2.97 (m, 4H), 2.74 (m, 4H), 2.60 (m, 1H), 2.17 (m, 4H), 1.97 (m, 4H), 1.69 (m, 4H), 1.40 (m, 2H), 0.93 (s, 6H).

Example 196

4-[4-({4'-chloro-3-[3-(dimethylamino)propyl]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide

Example 196A

4'-chloro-3-hydroxybiphenyl-2-carbaldehyde

The title compound was prepared as described in EXAMPLE 175A by replacing 1-(2-bromophenyl)ethanone with 2-bromo-6-hydroxybenzaldehyde.

Example 196B tert-butyl 4-((4'-chloro-3-hydroxybiphenyl-2-yl)methyl)piperazine-1-carboxylate The title compound was prepared as described in EXAMPLE 1A by replacing 4'-chlorobiphenyl-2-carboxaldehyde with EXAMPLE 196A.

Example 196C tert-butyl 4-((4'-chloro-3-(trifluoromethylsulfonyloxy)biphenyl-2-yl)methyl)piperazine-1-carboxylate To a mixture of EXAMPLE 196B (390 mg) in pyridine (5 ml) at 0° C. was added dropwise trifluoromethanesulfonic anhydride (0.326 ml). The reaction mixture was stirred in an ice bath for 1 hour and diluted with ethyl acetate. The resulting mixture was washed with brine extensively and the organic layer was dried over $Na_2SO_4$, filtered, and concentrated to provide the title compound.

Example 196D tert-butyl 4-((4'-chloro-3-(3-(dimethylamino)prop-1-ynyl)biphenyl-2-yl)methyl)piperazine-1-carboxylate To a mixture of EXAMPLE 196C (380 mg), N,N-dimethylprop-2-yn-1-amine (0.227 ml), tetrakis(triphenylphosphine)palladium(0) (123 mg) and triethylamine (0.492) in N,N-dimethylformamide (1.5 ml) was added copper(I) iodide (27.1 mg) and $^t$BuNI (394 mg). The reaction mixture was heated at 100° C. for 4 hours, cooled and diluted with ethyl acetate. The organic layer was dried over $Na_2SO_4$ and concentrated. The residue was purified by flash chromatography, eluting with a mixture of methanol, dichloromethane and triethyl amine to provide the title compound.

Example 196E tert-butyl 4-((4'-chloro-3-(3-(dimethylamino)propyl)biphenyl-2-yl)methyl)piperazine-1-carboxylate Example 196D (200 mg) in methanol (8 ml) was treated with platinum(IV) oxide (29.1 mg) under $H_2$ atmosphere overnight. The insoluble material was filtered off and the filtrate was concentrated to provide the title compound.

Example 196F 3-(4'-chloro-2-(piperazin-1-ylmethyl)biphenyl-3-yl)-N,N-dimethylpropan-1-amine The title compound was prepared as described in EXAMPLE 175C by replacing EXAMPLE 175B with EXAMPLE 196E.

Example 196G ethyl 2-(1H-indol-4-yloxy)-4-(4-((4'-chloro-3-(3-(dimethylamino)propyl)biphenyl-2-yl)methyl)piperazin-1-yl)benzoate The title compound was prepared as described in EXAMPLE 175D by replacing EXAMPLE 175C with EXAMPLE 196F.

Example 196H 2-(1H-indol-4-yloxy)-4-(4-((4'-chloro-3-(3-(dimethylamino)propyl)biphenyl-2-yl)methyl)piperazin-1-yl)benzoic acid The title compound was prepared as described in EXAMPLE 175E by replacing EXAMPLE 175D with EXAMPLE 196G.

Example 196I

4-[4-({4'-chloro-3-[3-(dimethylamino)propyl]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide The title compound was prepared as described in EXAMPLE 175F by replacing EXAMPLE 175E with EXAMPLE 196H. ¹H NMR (500 MHz, dimethylsulfoxide-d₆) δ 11.11 (s, 1H), 8.38-8.44 (m, 2H), 7.68 (dd, 1H), 7.56 (d, 1H), 7.44 (d, 2H), 7.19-7.29 (m, 5H), 7.07 (d, 1H), 6.99 (dd, 1H), 6.87-6.93 (m, 2H), 6.59 (dd, 1H), 6.26 (d, 1H), 6.23 (s, 1H), 6.19 (d, 1H), 3.84 (dd, 2H), 3.22-3.29 (m, 4H), 2.87 (s, 6H), 2.69-2.75 (m, 2H), 2.59 (s, 5H), 2.14 (s, 4H), 1.83-1.92 (m, 3H), 1.56-1.65 (m, 2H), 1.19-1.31 (m, 4H), 0.81-0.90 (m, 1H)

Example 197

4-(4-{[2-(4-chlorophenyl)-4,4-dimethylcyclohex-1-en-1-yl]methyl}piperazin-1-yl)-N-[(4-{[1-(3-hydroxypropyl)piperidin-4-yl]amino}-3-nitrophenyl)sulfonyl]-2-(1H-indol-5-yloxy)benzamide Example 197A 2-(1H-indol-5-yloxy)-N-(4-(1-(3-(tert-butyldimethylsilyloxy)propyl)piperidin-4-ylamino)-3-nitrophenylsulfonyl)-4-(4-((2-(4-chlorophenyl)-4,4-dimethylcyclohex-1-enyl)methyl)piperazin-1-yl)benzamide This example was prepared by substituting EXAMPLE 26C for EXAMPLE 1E and EXAMPLE 195A for EXAMPLE 1F in EXAMPLE 1G.

Example 197B 4-(4-{[2-(4-chlorophenyl)-4,4-dimethylcyclohex-1-en-1-yl]methyl}piperazin-1-yl)-N-[(4-{[1-(3-hydroxypropyl)piperidin-4-yl]amino}-3-nitrophenyl)sulfonyl]-2-(1H-indol-5-yloxy)benzamide This example was prepared by substituting EXAMPLE 197A for EXAMPLE 195B in EXAMPLE 195C. ¹H NMR (400 MHz, dimethylsulfoxide-d₆) δ 11.07 (bs, 1H), 8.50 (d, 1H), 8.14 (d, 1H), 7.75 (dd, 1H), 7.52 (d, 1H), 7.34 (m, 4H), 7.02 (m, 4H), 6.78 (dd, 1H), 6.59 (dd, 1H), 6.34 (m, 1H), 6.14 (d, 1H), 3.46 (m, 4H), 3.16 (m, 2H), 2.98 (m, 4H), 2.68 (m, 4H), 2.60 (m, 1H), 2.16 (m, 6H), 1.97 (m, 4H), 1.68 (m, 4H), 1.38 (t, 2H), 0.93 (s, 6H).

Example 198

4-{4-[(4'-chloro-4-morpholin-4-yl-1,1'-biphenyl-2-yl)methyl]piperazin-1-yl}-2-(1H-indol-4-yloxy)-N-({3-nitro-4-[(tetrahydro-2H-pyran-4-ylmethyl)amino]phenyl}sulfonyl)benzamide Example 198A tert-butyl 4-((4'-chloro-4-hydroxybiphenyl-2-yl)methyl)piperazine-1-carboxylate This example was prepared by substituting EXAMPLE 125A for 4'-chlorobiphenyl-2-carboxaldehyde in EXAMPLE 1A.

Example 198B tert-butyl 4-((4'-chloro-4-(trifluoromethylsulfonyloxy)biphenyl-2-yl)methyl)piperazine-1-carboxylate A mixture of EXAMPLE 198A (3.0 g), trifluoromethanesulfonic anhydride (3.14 g) in anhydrous pyridine (50 mL) mixture was stirred at room temperature overnight. The reaction mixture was diluted with ethyl acetate. The organic phase was washed with water, brine, dried over anhydrous sodium sulfate and concentrated. The residue was used in the next step without further purification.

Example 198C tert-butyl 4-((4'-chloro-4-morpholinobiphenyl-2-yl)methyl)piperazine-1-carboxylate A suspension of EXAMPLE 198B (500 mg), morpholine (80 mg), palladium (II) acetate (22 mg), biphenyl-2-yldi-tert-butylphosphine (50 mg) and cesium carbonate (427 mg) in anhydrous tetrahydrofuran (6 mL) was heated at 50° C. overnight. The reaction mixture was cooled to room temperature and diluted with ethyl acetate. The organic phase was washed with water, brine, dried over anhydrous sodium sulfate, filtered and concentrated. The crude material was purified by flash column purification with 30-50% ethyl acetate/hexane to afford the title compound.

Example 198D 4-(4'-chloro-2-(piperazin-1-ylmethyl)biphenyl-4-yl)morpholine

This example was prepared by substituting EXAMPLE 198C for EXAMPLE 1A in EXAMPLE 1B.

Example 198E methyl 2-(1H-indol-4-yloxy)-4-(4-((4'-chloro-4-morpholinobiphenyl-2-yl)methyl)piperazin-1-yl)benzoate This example was prepared by substituting EXAMPLE 24F for EXAMPLE 20A and EXAMPLE 198D for EXAMPLE 20C in EXAMPLE 20D.

Example 198F 2-(1H-indol-4-yloxy)-4-(4-((4'-chloro-4-morpholinobiphenyl-2-yl)methyl)piperazin-1-yl)benzoic acid This example was prepared by substituting EXAMPLE 198E for EXAMPLE 1D in EXAMPLE 1E.

Example 198G

4-{4-[(4'-chloro-4-morpholin-4-yl-1,1'-biphenyl-2-yl)methyl]piperazin-1-yl}-2-(1H-indol-4-yloxy)-N-({3-nitro-4-[(tetrahydro-2H-pyran-4-ylmethyl)amino]phenyl}sulfonyl)benzamide This example was prepared by substituting EXAMPLE 198F for EXAMPLE 26C in EXAMPLE 177. ¹H NMR (400 MHz, dimethylsulfoxide-d₆) δ 11.26 (bs, 1H), 8.63 (t, 1H), 8.49 (d, 1H), 7.66 (dd, 1H), 7.54 (d, 1H), 7.40 (m, 4H), 7.29 (m, 1H), 7.02 (m, 6H), 6.73 (dd, 1H), 6.39 (d, 1H), 6.30 (m, 2H), 3.85 (dd, 2H), 3.74 (m, 4H), 3.24 (m, 6H), 3.10 (m, 8H), 2.29 (m, 4H), 1.89 (m, 1H), 1.63 (m, 2H), 1.28 (m, 2H).

Example 199

4-[4-({4'-chloro-3-[2-(dimethylamino)ethoxy]-1,1'-biphenyl-2-yl}methyl)piperazin-1-yl]-2-(1H-indol-4-yloxy)-N-({3-nitro-4-[(1-tetrahydro-2H-pyran-4-ylpiperidin-4-yl)amino]phenyl}sulfonyl)benzamide

Example 199A tert-butyl 4-((4'-chloro-3-hydroxybiphenyl-2-yl)methyl)piperazine-1-carboxylate The title compound was prepared as described in EXAMPLE 1A by replacing EXAMPLE 27C with EXAMPLE 196A.

Example 199B tert-butyl 4-((4'-chloro-3-(2-(dimethylamino)ethoxy)biphenyl-2-yl)methyl)piperazine-1-carboxylate To a mixture of EXAMPLE 199A (1.5 g) in N,N-dimethylformamide (20 ml) was added 60% sodium hydride (0.596 g). The mixture was stirred at room temperature for 30 minutes and dimethylaminoethyl chloride hydrochloride salt (1.073 g) was added. After the resulting mixture was stirred overnight, additional 60% sodium hydride (0.596 g) and dimethylaminoethyl chloride hydrochloride salt (1.073 g) were added. The reaction mixture was further stirred overnight, diluted with ethyl acetate and washed with water, saturated $NaHCO_3$ and brine. The organic layer was dried over $Na_2SO_4$, filtered, and concentrated to provide the title compound.

Example 199C 2-(4'-chloro-2-(piperazin-1-ylmethyl)biphenyl-3-yloxy)-N,N-dimethylethanamine To a mixture of EXAMPLE 199B (2 g) in dichloromethane (10 ml) was added trifluroacetic acid (10 ml) at 0° C. The reaction mixture was stirred at room temperature for 30 minutes and concentrated. The residue was loaded onto a C18 column, and eluted with 0-50% 0.1% trifluroacetic acid/water in acetonitrile. The title compound was obtained as a trifluroacetic acid salt.

Example 199D ethyl 2-(1H-indol-4-yloxy)-4-(4-((4'-chloro-3-(2-(dimethylamino)ethoxy)biphenyl-2-yl)methyl)piperazin-1-yl)benzoate The title compound was prepared as described in EXAMPLE 175D by replacing EXAMPLE 175C with EXAMPLE 199C.

Example 199E 2-(1H-indol-4-yloxy)-4-(4-((4'-chloro-3-(2-(dimethylamino)ethoxy)biphenyl-2-yl)methyl)piperazin-1-yl)benzoic acid The title compound was prepared as described in EXAMPLE 175E by replacing EXAMPLE 175D with EXAMPLE 199D.

Example 199F

4-[4-({4'-chloro-3-[2-(dimethylamino)ethoxy]-1,1'-biphenyl-2-yl}methyl)piperazin-1-yl]-2-(1H-indol-4-yloxy)-N-({3-nitro-4-[(1-tetrahydro-2H-pyran-4-ylpiperidin-4-yl)amino]phenyl}sulfonyl)benzamide The title compound was prepared as described in EXAMPLE 175F by replacing EXAMPLE 175E and EXAMPLE 1F with EXAMPLE 199E and EXAMPLE 173C, respectively. $^1$H NMR (500 MHz, dimethylsulfoxide-$d_6$) δ 11.13 (s, 1H), 8.41 (d, 1H), 8.12 (d, 1H), 7.70 (dd, 1H), 7.58 (d, 1H), 7.52 (d, 2H), 7.43 (d, 2H), 7.31 (t, 1H), 7.22 (t, 1H), 7.06 (dd, 2H), 6.89-6.97 (m, 2H), 6.84 (d, 1H), 6.64 (dd, 1H), 6.30 (d, 1H), 6.24 (dd, 2H), 4.14 (t, 2H), 3.90 (dd, 2H), 3.53-3.73 (m, 2H), 3.22-3.32 (m, 4H), 2.93 (s, 6H), 2.34-2.46 (m, 7H), 2.29 (s, 5H), 1.97 (d, 2H), 1.73 (d, 2H), 1.41-1.62 (m, 4H).

Example 201

4-(4-{[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]-2-(1H-indol-5-yloxy)benzamide

Example 201A 4-(4-(diethylamino)cyclohexylamino)-3-nitrobenzenesulfonamide

This example was prepared by substituting $N^1,N^1$-diethylcyclohexane-1,4-diamine for 1-(2-methoxy-ethyl)-piperidin-4-ylamine in EXAMPLE 189A.

Example 201B 4-(4-{[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]-2-(1H-indol-5-yloxy)benzamide This example was prepared by substituting EXAMPLE 26C for EXAMPLE 1E and EXAMPLE 201A for EXAMPLE 1F in EXAMPLE 1G. $^1$H NMR (500 MHz, pyridine-$d_5$) δ ppm 12.28 (s, 1H), 9.29 (d, 1H), 8.29-8.38 (m, 2H), 8.19 (d, 1H), 7.52-7.57 (m, 2H), 7.40-7.47 (m, 3H), 7.10 (dd, 1H), 7.06 (d, 2H), 6.92 (d, 1H), 6.74 (dd, 1H), 6.61 (s, 1H), 6.55 (d, 1H), 3.31-3.42 (m, 1H), 3.00-3.08 (m, 4H), 2.76 (s, 2H), 2.54-2.61 (m, 1H), 2.51 (q, 4H), 2.21-2.28 (m, 2H), 2.08-2.15 (m, 4H), 2.04 (d, 2H), 1.97 (s, 2H), 1.81 (d, 2H), 1.38 (t, 2H), 1.29-1.36 (m, 2H), 1.17-1.28 (m, 2H), 1.05 (t, 6H), 0.93 (s, 6H).

Example 202

4-(4-{[2-(4-chlorophenyl)-4,4-dimethylcyclohex-1-en-1-yl]methyl}piperazin-1-yl)-N-[(4-{[4-(dimethylamino)cyclohexyl]amino}-3-nitrophenyl)sulfonyl]-2-(1H-indol-4-yloxy)benzamide

Example 202A 4-(4-(dimethylamino)cyclohexylamino)-3-nitrobenzenesulfonamide

This example was prepared by substituting $N^1,N^1$-dimethylcyclohexane-1,4-diamine for 1-(2-methoxy-ethyl)-piperidin-4-ylamine in EXAMPLE 189A.

Example 202B 4-(4-{[2-(4-chlorophenyl)-4,4-dimethylcyclohex-1-en-1-yl]methyl}piperazin-1-yl)-N-[(4-{[4-(dimethylamino)cyclohexyl]amino}-3-nitrophenyl)sulfonyl]-2-(1H-indol-4-yloxy)benzamide This example was prepared by substituting EXAMPLE 55B for EXAMPLE 1E and EXAMPLE 202A for EXAMPLE 1F in EXAMPLE 1G. $^1$H NMR (500 MHz, pyridine-$d_5$) δ ppm 12.45 (s, 1H), 9.21 (d, 1H), 8.33 (d, 1H), 8.27 (dd, 1H), 8.18 (d, 1H), 7.48 (t, 1H), 7.45 (d, 2H), 7.40 (d, 1H), 7.11 (t, 1H), 7.08 (d, 2H), 6.87 (d, 1H), 6.72-6.81 (m, 3H), 6.67 (d, 1H), 3.31-3.41 (m, 1H), 3.00-3.06 (m, 4H), 2.77 (s, 2H), 2.31 (s, 6H), 2.25 (t, 2H), 2.20-2.25 (m, 1H), 2.10-2.16 (m, 4H), 2.00-2.07 (d, 2H), 1.97 (s, 2H), 1.88 (d, 2H), 1.39 (t, 3H), 1.34 (d, 2H), 1.15-1.28 (m, 4H), 0.94 (s, 6H).

Example 203

4-(4-{[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]-2-(1H-indol-4-yloxy)benzamide This example was prepared by substituting EXAMPLE 55B for EXAMPLE 1E and EXAMPLE 201A for EXAMPLE 1F in EXAMPLE 1G. $^1$H NMR (500 MHz, pyridine-$d_5$) δ 12.44 (s, 1H), 9.21 (d, 1H), 8.34 (d, 1H), 8.28 (dd, 1H), 8.18 (d, 1H), 7.47-7.50 (m, 1H), 7.45 (d, 2H), 7.40 (d, 1H), 7.11 (t, 1H), 7.08 (d, 2H), 6.90 (d, 1H), 6.73-6.81 (m, 3H), 6.67 (d, 1H), 3.32-3.40 (m, 1H), 2.99-3.06 (m, 4H), 2.76 (s, 2H), 2.52-2.60 (m, 1H), 2.49 (q, 4H), 2.25 (t, 2H), 2.09-2.16 (m, 4H), 2.04 (d, 2H), 1.97 (s, 2H), 1.79 (d, 2H), 1.29-1.42 (m, 4H), 1.16-1.28 (m, 2H), 1.04 (t, 6H), 0.92-0.95 (m, 6H).

Example 204

Trans-4-(4-{[2-(4-chlorophenyl)-4,4-dimethylcyclohex-1-en-1-yl]methyl}piperazin-1-yl)-2-(1H-indol-4-yloxy)-N-({4-[(4-morpholin-4-ylcyclohexyl)amino]-3-nitrophenyl}sulfonyl)benzamide

Example 204A trans-4-(4-morpholinocyclohexylamino)-3-nitrobenzenesulfonamide This example was prepared by substituting trans-4-morpholinocyclohexanamine for 1-(2-methoxy-ethyl)-piperidin-4-ylamine in EXAMPLE 189A.

Example 204B trans-4-(4-{[2-(4-chlorophenyl)-4,4-dimethylcyclohex-1-en-1-yl]methyl}piperazin-1-yl)-2-(1H-indol-4-yloxy)-N-({4-[(4-morpholin-4-ylcyclohexyl)amino]-3-nitrophenyl}sulfonyl)benzamide This example was prepared by substituting EXAMPLE 55B for EXAMPLE 1E and EXAMPLE 204A for EXAMPLE 1F in EXAMPLE 1G. $^1$H NMR (500 MHz, pyridine-$d_5$) δ 12.45 (s, 1H), 9.21 (d, 1H), 8.36 (d, 1H), 8.26 (dd, 1H), 8.16 (d, 1H), 7.47-7.51 (m, 1H), 7.45 (d, 1H), 7.40 (d, 1H), 7.12 (t, 1H), 6.87 (d, 1H), 6.73-6.81 (m, 3H), 6.68 (d, 1H), 3.71-3.78 (m, 2H), 3.33-3.42 (m, 1H), 3.00-3.06 (m, 4H), 2.76 (s, 2H), 2.44-2.52 (m, 4H), 2.25 (t, 2H), 2.16-2.23 (m, 2H), 2.09-2.16 (m, 4H), 2.06 (d, 2H), 1.97 (s, 2H), 1.86 (s, 2H), 1.39 (t, 2H), 1.17-1.35 (m, 6H), 0.94 (s, 6H).

Example 205

4-[4-({4'-chloro-3-[2-(dimethylamino)ethoxy]-1,1'-biphenyl-2-yl}methyl)piperazin-1-yl]-2-(1H-indol-4-yloxy)-N-({4-[(1-methylpiperidin-4-yl)amino]-3-nitrophenyl}sulfonyl)benzamide The title compound was prepared as described in EXAMPLE 177 by replacing EXAMPLE 26C and EXAMPLE 1F with EXAMPLE 199E and EXAMPLE 21A, respectively. $^1$H NMR (500 MHz, dichloromethane-$d_2$) δ 8.70 (d, 1H), 8.56 (s, 1H), 8.40 (d, 1H), 7.95 (dd, 1H), 7.91 (d, 1H), 7.46 (d, 2H), 7.24-7.35 (m, 5H), 7.15 (t, 1H), 6.90 (dd, 2H), 6.83 (d, 1H), 6.75 (d, 1H), 6.60 (dd, 1H), 6.41 (d, 1H), 6.19 (d, 1H), 4.05 (t, 2H), 3.58 (s, 1H), 3.32 (s, 2H), 2.95-3.02 (m, 4H), 2.66-2.80 (m, 4H), 2.30-2.35 (m, 4H), 2.24-2.29 (m, 9H), 2.15-2.23 (m, 2H), 2.05 (d, 2H), 1.63-1.73 (m, 2H)

Example 206

4-{4-[1-(4'-chloro-1,1'-biphenyl-2-yl)ethyl]piperazin-1-yl}-2-(1H-indol-4-yloxy)-N-({4-[(1-methylpiperidin-4-yl)amino]-3-nitrophenyl}sulfonyl)benzamide The title compound was prepared as described in EXAMPLE 177 by replacing EXAMPLE 26C and EXAMPLE 1F with EXAMPLE 175E and EXAMPLE 21A, respectively. $^1$H NMR (400 MHz, dichloromethane-$d_2$) δ 8.70 (d, 1H), 8.51 (s, 1H), 8.40 (d, 1H), 7.94 (dd, 1H), 7.90 (d, 1H), 7.54 (d, 1H), 7.33 (t, 4H), 7.21-7.27 (m, 2H), 7.10-7.19 (m, 4H), 6.91 (d, 1H), 6.73 (d, 1H), 6.55-6.60 (m, 1H), 6.41 (s, 1H), 6.16 (d, 1H), 3.52-3.63 (m, 1H), 3.36 (q, 1H), 2.96-3.07 (m, 4H), 2.72-2.79 (m, 2H), 2.33-2.41 (m, 2H), 2.27 (s, 3H), 2.14-2.27 (m, 4H), 2.00-2.09 (m, 2H), 1.63-1.74 (m, 2H), 1.19 (d, 3H).

Example 207

4-(4-{[2-(4-chlorophenyl)-4,4-dimethylcyclohex-1-en-1-yl]methyl}piperazin-1-yl)-N-{[4-(({[4-(dimethylamino)tetrahydro-2H-pyran-4-yl]methyl}amino)-3-nitrophenyl]sulfonyl}-2-(1H-indol-5-yloxy)benzamide This example was prepared by substituting 4-(aminomethyl)-N,N-dimethyltetrahydro-2H-pyran-4-amine for (3S,4R)-4-amino-1-benzylpiperidin-3-ol, hydrochloric acid in EXAMPLE 187B. $^1$H NMR (500 MHz, dimethylsulfoxide-d$_6$) δ 11.17 (s, 1H), 8.84 (br s, 1H), 8.59 (d, 1H), 7.84 (dd, 1H), 7.51 (d, 1H), 7.39-7.43 (m, 2H), 7.33 (d, 2H), 7.17-7.21 (m, 2H), 7.03 (d, 2H), 6.89 (dd, Hz, 1H), 6.64 (d, 1H), 6.40 (s, 1H), 6.13 (d, 1H), 3.72-3.75 (m, 2H), 3.34-3.57 (m, 4H), 3.02 (br, 4H), 2.71 (br, 2H), 2.27 (s, 6H), 2.16 (br s, 6H), 1.94 (br s, 2H), 1.78-1.85 (m, 2H), 1.36-1.39 (m, 2H), 0.92 (s, 6H).

Example 208

N-({4-[(2-aminocyclohexyl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide

Example 208A

This example was prepared by substituting tert-butyl 2-aminocyclohexylcarbamate for (3S,4R)-4-amino-1-benzylpiperidin-3-ol, hydrochloric acid in EXAMPLE 187B.

Example 208B

N-({4-[(2-aminocyclohexyl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide EXAMPLE 208A (0.1 g) in dimethylsulfoxide (4 mL) was heated under microwave conditions (200° C., 1 hour). The residue was purified by reverse phase HPLC on a C18 column using a gradient of 30-70% acetonitrile/0.1% TFA in water. The desired fractions were collected, and the organic solvent was partially removed under reduced pressure. The resulting mixture was treated with saturated aqueous NaHCO$_3$ mixture. It was then extracted with ethyl acetate three times. The combined organic layers were washed with brine, dried (MgSO$_4$), filtered, and concentrated to give the title compound. $^1$H NMR (500 MHz, dimethylsulfoxide-d$_6$) δ 11.02 (s, 1H), 8.45 (s, 1H), 8.05 (d, 1H), 7.79-7.81 (m, 1H), 7.56 (d, 1H), 7.30-7.34 (m, 4H), 6.98-7.06 (m, 4H), 6.73 (d, 1H), 6.54 (dd, 1H), 6.33 (s, 1H), 6.11 (d, 1H), 3.64-3.70 (m, 1H), 2.93 (br, 4H), 2.71 (br, 2H), 2.14-2.16 (br s, 6H), 1.95 (br s, 2H), 1.67-1.73 (m, 2H), 1.36-1.39 (m, 2H), 0.92 (s, 6H).

Example 209

4-[4-({4'-chloro-4-[3-(dimethylamino)prop-1-ynyl]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide

Example 209A tert-butyl 4-((4'-chloro-4-(3-(dimethylamino)prop-1-ynyl)biphenyl-2-yl)methyl)piperazine-1-carboxylate A suspension of EXAMPLE 198B (800 mg), N,N-dimethylprop-2-yn-1-amine (373 mg), copper(I) iodide (57 mg), tetrakis(triphenylphosphine)palladium(O) (259 mg), triethylamine (757 mg) and tert-butyl ammonium iodide (829 mg) in anhydrous N,N-dimethylformamide (5 mL) was heated at 100° C. for 5 hours. The reaction mixture was cooled to room temperature and diluted with ethyl acetate. The organic phase was washed with water, brine, dried over anhydrous sodium sulfate, filtered, and concentrated. The crude material was purified by flash column purification with 0-3% methanol/dichloromethane to afford the title compound.

Example 209B 3-(4'-chloro-2-(piperazin-1-ylmethyl)biphenyl-4-yl)-N,N-dimethylprop-2-yn-1-amine This example was prepared by substituting EXAMPLE 209A for EXAMPLE 1A in EXAMPLE 1B.

Example 209C methyl 2-(1H-indol-4-yloxy)-4-(4-((4'-chloro-4-(3-(dimethylamino)prop-1-ynyl)biphenyl-2-yl)methyl)piperazin-1-yl)benzoate This example was prepared by substituting EXAMPLE 24F for EXAMPLE 20A and EXAMPLE 209B for EXAMPLE 20C in EXAMPLE 20D.

Example 209D 2-(1H-indol-4-yloxy)-4-(4-((4'-chloro-4-(3-(dimethylamino)prop-1-ynyl)biphenyl-2-yl)methyl)piperazin-1-yl)benzoic acid This example was prepared by substituting EXAMPLE 209C for EXAMPLE 1D in EXAMPLE 1E.

Example 209E

4-[4-({4'-chloro-4-[3-(dimethylamino)prop-1-ynyl]-1,1'-biphenyl-2-yl}methyl)piperazin-1-yl]-2-(1H-indol-4-yloxy)-N-({3-nitro-4-[(tetrahydro-2H-pyran-4-ylmethyl)amino]phenyl}sulfonyl)benzamide This example was prepared by substituting EXAMPLE 209D for EXAMPLE 26C in EXAMPLE 177. $^1$H NMR (400 MHz, dimethylsulfoxide-d$_6$) δ 11.23 (bs, 1H), 8.57 (t, 1H), 8.47 (d, 1H), 7.67 (dd, 1H), 7.54 (m, 2H), 7.43 (m, 5H), 7.24 (m, 2H), 7.14 (m, 1H), 7.03 (m, 1H), 6.94 (m, 1H), 6.71 (d, 1H), 6.38 (d, 1H), 6.27 (d, 2H), 3.85 (m, 2H), 3.60 (m, 2H), 3.23 (m, 6H), 3.04 (m, 4H), 2.35 (s, 6H), 2.28 (m, 4H), 1.88 (m, 1H), 1.58 (m, 2H), 1.24 (m, 2H).

Example 210

4-(4-({[2-(4-chlorophenyl)-4,4-dimethylcyclohex-1-en-1-yl]methyl}piperazin-1-yl)-2-(1H-indol-4-yloxy)-N-[(3-nitro-4-{[1-(4,4,4-trifluorobutyl)piperidin-4-yl]amino}phenyl)sulfonyl]benzamide

Example 210A 3-nitro-4-(1-(4,4,4-trifluorobutyl)piperidin-4-ylamino)benzenesulfonamide EXAMPLE 157B (600 mg) was combined with 1,1,1-trifluoro-4-iodobutane (595 mg) and potassium carbonate (829 mg) in acetonitrile (15 mL). The reaction was heated to 70° C. overnight. The reaction was concentrated, and then taken up in ether and concentrated again. The product was used in the next step without further purification.

Example 210B 4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[1-(4,4,4-trifluorobutyl)piperidin-4-yl]amino}phenyl)sulfonyl]benzamide This example was prepared by substituting EXAMPLE 210A for EXAMPLE 1F and EXAMPLE 55B for EXAMPLE 1E in EXAMPLE 1G. $^1$H NMR (500 MHz, dimethylsulfoxide-$d_6$) δ 11.20 (s, 1H), 8.47 (d, 1H), 8.20 (d, 1H), 7.72 (dd, 1H), 7.54 (d, 1H), 7.34 (d, 2H), 7.25 (t, 1H), 7.14 (d, 1H), 7.05 (m, 3H), 6.95 (t, 1H), 6.68 (dd, 1H), 6.38 (d, 1H), 6.25 (s, 2H), 3.71 (m, 1H), 3.01 (m, 4H), 2.92 (m, 2H), 2.72 (s, 2H), 2.40 (m, 2H), 2.30 (m, 2H), 2.16 (m, 6H), 1.95 (m, 4H), 1.68 (m, 4H), 1.38 (t, 2H), 1.24 (br s, 1H), 0.92 (s, 6H).

Example 211

4-(4-{[2-(4-chlorophenyl)-4,4-dimethylcyclohex-1-en-1-yl]methyl}piperazin-1-yl)-N-[(4-{[2-(4-hydroxy-1-methylpiperidin-4-yl)ethyl]amino}-3-nitrophenyl)sulfonyl]-2-(1H-indol-5-yloxy)benzamide This example was prepared by substituting 4-(2-aminoethyl)-1-methylpiperidin-4-ol for (3S,4R)-4-amino-1-benzylpiperidin-3-ol, hydrochloric acid in EXAMPLE 187B. 1H NMR (500 MHz, dimethylsulfoxide-$d_6$) δ 11.05 (s, 1H), 8.61 (s, 1H), 8.47 (d, 1H), 7.77 (dd, 1H), 7.54 (d, 1H), 7.32-7.34 (m, 4H), 7.04 (d, 2H), 7.01 (s, 1H), 6.90 (d, 2H), 6.76 (dd, 1H), 6.57 (dd, 1H), 6.33 (s, 1H), 6.13 (d, 1H), 4.92 (s, 1H), 3.43-3.46 (m, 2H), 2.95-3.01 (br, 8H), 2.71 (br, 2H), 2.65 (s, 3H), 2.12-2.16 (br s, 6H), 1.95 (br s, 2H), 1.77-1.80 (m, 2H), 1.67-1.71 (m, 4H), 1.36-1.39 (m, 2H), 0.92 (s, 6H).

Example 212

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-2-yl)piperidin-4-yl]amino}phenyl)sulfonyl]benzamide This example was prepared by substituting 4-(2-aminoethyl)-1-methylpiperidin-4-ol for (3S,4R)-4-amino-1-benzylpiperidin-3-ol, hydrochloric acid in EXAMPLE 187B. $^1$H NMR (500 MHz, dimethylsulfoxide-$d_6$) δ 11.16 (s, 1H), 8.58 (s, 1H), 8.28 (d, 1H), 7.82 (dd, 1H), 7.51 (d, 1H), 7.39-7.42 (m, 2H), 7.33 (d, 2H), 7.20 (d, 1H), 7.17 (d, 1H), 7.14 (d, 1H), 7.03 (d, 2H), 6.86 (d, 2H), 6.85 (d, 1H), 6.65 (dd, 1H), 6.39 (s, 1H), 6.15 (d, 1H), 3.87-3.90 (m, 2H), 3.20-3.24 (m, 2H), 3.04 (br, 4H), 2.73 (br, 2H), 2.11-2.17 (m, 5H), 1.95 (br s, 2H), 1.71-1.75 (m, 2H), 1.36-1.39 (m, 2H), 0.92 (s, 6H).

Example 213

4-(4-{[4'-chloro-4-(2-hydroxyethoxy)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide

Example 213A 4-(2-(tert-butyldimethylsilyloxy)ethoxy)-4'-chlorobiphenyl-2-carbaldehyde A mixture of EXAMPLE 125A (0.5 g), (2-bromoethoxy)(tert-butyl)dimethylsilane (0.771 g) and cesium carbonate (1.4 g) was suspended in anhydrous N,N-dimethylformamide (5 mL). The reaction mixture was heated at 70° C. overnight. The reaction mixture was cooled to room temperature and diluted with ethyl acetate. The organic phase was washed with water, brine, dried over anhydrous sodium sulfate, filtered, and concentrated. The crude material was purified by flash column purification with 0-5% ethyl acetate/hexane to afford the title compound.

Example 213B methyl 2-(1H-indol-4-yloxy)-4-(4-((4'-(2-(tert-butyldimethylsilyloxy)ethoxy)-4'-chlorobiphenyl-2-yl)methyl)piperazin-1-yl)benzoate This example was made by substituting EXAMPLE 213A for 4'-chlorobiphenyl-2-carboxaldehyde and EXAMPLE 68B for tert-butyl piperazine-1-carboxylate in EXAMPLE 1A.

Example 213C 2-(1H-indol-4-yloxy)-4-(4-((4'-(2-(tert-butyldimethylsilyloxy)ethoxy)-4'-chlorobiphenyl-2-yl)methyl)piperazin-1-yl)benzoic acid This example was prepared by substituting EXAMPLE 213B for EXAMPLE 1D in EXAMPLE 1E.

Example 213D 2-(1H-indol-4-yloxy)-4-(4-((4'-(2-(tert-butyldimethylsilyloxy)ethoxy)-4'-chlorobiphenyl-2-yl)methyl)piperazin-1-yl)-N-(3-nitro-4-((tetrahydro-2H-pyran-4-yl)methylamino)phenylsulfonyl)benzamide This example was prepared by substituting EXAMPLE 213C for EXAMPLE 1E in EXAMPLE 1G.

Example 213E 4-(4-{[4'-chloro-4-(2-hydroxyethoxy)-1,1'-biphenyl-2-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide This example was prepared by substituting EXAMPLE 213D for EXAMPLE 195B in EXAMPLE 195C. $^1$H NMR (400 MHz, dimethylsulfoxide-$d_6$) δ 11.24 (m, 1H), 8.62 (t, 1H), 8.50 (d, 1H), 7.67 (dd, 1H), 7.54 (m, 1H), 7.43 (d, 2H), 7.37 (d, 2H), 7.28 (m, 1H), 7.15 (m, 2H), 7.05 (m, 2H), 6.96 (m, 1H), 6.90 (dd, 1H), 6.73 (dd, 1H), 6.40 (d, 1H), 6.31 (m, 1H), 6.27 (m, 1H), 4.82 (t, 1H), 3.99 (t, 2H), 3.86 (m, 2H), 3.71 (m, 2H), 3.26 (m, 6H), 2.66 (m, 2H), 2.31 (m, 5H), 1.89 (m, 1H), 1.63 (m, 2H), 1.27 (m, 2H).

Example 214

4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]-2-(1H-indol-5-yloxy)benzamide

Example 214A tert-butyl 1-(cyclopropylmethyl)piperidin-4-ylcarbamate

This example was prepared by substituting cyclopropanecarbaldehyde for 4'-chlorobiphenyl-2-carboxaldehyde and tert-butyl piperidin-4-ylcarbamate for tert-butyl piperazine-1-carboxylate in EXAMPLE 1A.

Example 214B 1-(cyclopropylmethyl)piperidin-4-amine bis(2,2,2-trifluoroacetate)

This example was prepared by substituting EXAMPLE 214A for EXAMPLE 1A in EXAMPLE 1B.

Example 214C 4-(1-(cyclopropylmethyl)piperidin-4-ylamino)-3-nitrobenzenesulfonamide This example was prepared by substituting EXAMPLE 214B for 1-(2-Methoxy-ethyl)-piperidin-4-ylamine in EXAMPLE 189A.

Example 214D 4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]-2-(1H-indol-5-yloxy)benzamide This example was prepared by substituting EXAMPLE 26C for EXAMPLE 1E and EXAMPLE 214C for EXAMPLE 1F in EXAMPLE 1G. $^1$H NMR (500 MHz, pyridine-$d_5$) δ 12.28 (s, 1H), 9.30 (d, 1H), 8.49 (d, 1H), 8.34 (dd, 1H), 8.18 (d, 1H), 7.52-7.56 (m, 2H), 7.41-7.46 (m, 3H), 7.09 (dd, 1H), 7.06 (d, 2H), 6.91 (d, 1H), 6.73 (dd, 1H), 6.61 (d, 1H), 6.54 (d, 1H), 3.45-3.56 (m, 1H), 3.00-3.08 (m, 4H), 2.87 (d, 2H), 2.76 (s, 2H), 2.25 (t, 2H), 2.19 (d, 4H), 2.09-2.14 (m, 4H), 1.97 (s, 4H), 1.63-1.73 (m, 2H), 1.38 (t, 2H), 0.84-0.91 (m, 1H), 0.43-0.50 (m, 2H), 0.11 (q, H).

Example 215

4-(4-{[2-(4-chlorophenyl)-4,4-dimethylcyclohex-1-en-1-yl]methyl}piperazin-1-yl)-2-(1H-indol-4-yloxy)-N-({4-[(4-methylpiperazin-1-yl)amino]-3-[(trifluoromethyl)sulfonyl]phenyl}sulfonyl)benzamide

Example 215A 4-(4-methylpiperazin-1-ylamino)-3-(trifluoromethylsulfonyl)benzenesulfonamide This example was prepared by substituting 4-methylpiperazin-1-amine for (tetrahydropyran-4-yl)methanamine and EXAMPLE 159C for 4-fluoro-3-nitrobenzenesulfonamide in EXAMPLE 1F.

Example 215B 4-(4-{[2-(4-chlorophenyl)-4,4-dimethylcyclohex-1-en-1-yl]methyl}piperazin-1-yl)-2-(1H-indol-4-yloxy)-N-({4-[(4-methylpiperazin-1-yl)amino]-3-[(trifluoromethyl)sulfonyl]phenyl}sulfonyl)benzamide This example was prepared by substituting EXAMPLE 215A for EXAMPLE 1F and EXAMPLE 55B for EXAMPLE 26C in EXAMPLE 177. $^1$H NMR (500 MHz, dimethylsulfoxide-$d_6$) δ 11.21 (br s, 1H), 8.09 (m, 1H), 7.98 (m, 1H), 7.83 (dd, 1H), 7.53 (d, 1H), 7.45 (d, 1H), 7.34 (d, 2H), 7.26 (t, 1H), 7.16 (d, 1H), 7.04 (d, 2H), 6.97 (t, 1H), 6.66 (dd, 1H), 6.39 (d, 1H), 6.24 (m, 2H), 2.87 (m, 13H), 2.38 (s, 3H), 2.17 (m, 6H), 1.95 (s, 2H), 1.39 (t, 2H), 0.93 (s, 6H)

Example 216

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(4,4,4-trifluorobutyl)piperidin-4-yl]amino}phenyl)sulfonyl]benzamide This example was prepared by substituting EXAMPLE 26C for EXAMPLE 1E and EXAMPLE 210A for EXAMPLE 1F in EXAMPLE 1G. $^1$H NMR (300 MHz, dimethylsulfoxide-$d_6$) δ 11.13 (s, 1H), 10.89 (br s, 1H), 8.55 (d, 1H), 8.22 (d, 1H), 7.79 (dd, 1H), 7.50 (d, 1H), 7.34 (m, 4H), 7.07 (m, 4H), 6.83 (dd, 1H), 6.63 (dd, 1H), 6.37 (m, 1H), 6.15 (d, 1H), 3.71 (m, 1H), 3.01 (m, 4H), 2.92 (m, 2H), 2.72 (s, 2H), 2.40 (m, 2H), 2.30 (m, 2H), 2.16 (m, 6H), 1.95 (m, 4H), 1.68 (m, 4H), 1.38 (t, 2H), 1.24 (br s, 1H), 0.92 (s, 6H).

Example 217

4-{4-[1-(4'-chloro-1,1'-biphenyl-2-yl)ethyl]piperazin-1-yl}-2-(1H-indol-4-yloxy)-N-({4-[(4-methylpiperazin-1-yl)amino]-3-nitrophenyl}sulfonyl)benzamide The title compound was prepared as described in EXAMPLE 177 by replacing EXAMPLE 26C and EXAMPLE 1F with EXAMPLE 175E and EXAMPLE 174A, respectively. $^1$H NMR (400 MHz, dimethylsulfoxide-$d_6$) δ 11.21 (s, 1H), 9.15 (s, 1H), 8.45 (d, 1H), 7.70 (dd, 1H), 7.43-7.56 (m, 5H), 7.34-7.41 (m, 1H), 7.24-7.31 (m, 4H), 7.10-7.16 (m, 2H), 6.94 (t, 1H), 6.66 (dd, 1H), 6.37 (d, 1H), 6.24 (dd, 2H), 2.80-3.02 (m, 10H), 2.28-2.39 (m, 5H), 2.14-2.24 (m, 2H), 1.16 (d, 3H).

Example 218

4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({4-[(1-methylpiperidin-4-yl)amino]-3-nitrophenyl}sulfonyl)benzamide

Example 218A 2-(4-chlorophenyl)-4,4-dimethylcyclohex-1-enecarbaldehyde

This example was prepared by substituting EXAMPLE 18C for EXAMPLE 143C in EXAMPLE 143D.

Example 218B tert-butyl 4-((2-(4-chlorophenyl)-4,4-dimethylcyclohex-1-enyl)methyl)-3-(hydroxymethyl)piperazine-1-carboxylate This example was prepared by substituting EXAMPLE 218A for EXAMPLE 27C and tert-butyl 3-(hydroxymethyl)piperazine-1-carboxylate for tert-butyl piperazine-1-carboxylate in EXAMPLE 1A.

Example 218C (1-((2-(4-chlorophenyl)-4,4-dimethylcyclohex-1-enyl)methyl)piperazin-2-yl)methanol This example was prepared by substituting EXAMPLE 218B for EXAMPLE 1A in EXAMPLE 1B.

Example 218D ethyl 2-(1H-indol-5-yloxy)-4-(4-((2-(4-chlorophenyl)-4,4-dimethylcyclohex-1-enyl)methyl)-3-(hydroxymethyl)piperazin-1-yl)benzoate This example was prepared by substituting EXAMPLE 218C for EXAMPLE 20C and EXAMPLE 26A for EXAMPLE 20A in EXAMPLE 20D.

Example 218E 2-(1H-indol-5-yloxy)-4-(4-((2-(4-chlorophenyl)-4,4-dimethylcyclohex-1-enyl)methyl)-3-(hydroxymethyl)piperazin-1-yl)benzoic acid This example was prepared by substituting EXAMPLE 218D for EXAMPLE 1D in EXAMPLE 1E.

Example 218F

4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({4-[(1-methylpiperidin-4-yl)amino]-3-nitrophenyl}sulfonyl)benzamide This example was prepared by substituting EXAMPLE 218E for EXAMPLE 26C and EXAMPLE 21A for EXAMPLE 1F in EXAMPLE 177. $^1$H NMR (500 MHz, dimethylsulfoxide-$d_6$) δ 11.07 (s, 1H), 8.50 (d, 1H), 8.14 (d, 1H), 7.45 (d, J=9.46 Hz, 1H), 7.52 (d, 1H), 7.32-7.35 (m, 4H), 6.99-7.05 (m, 4H), 6.78 (dd, 1H), 6.58-6.59 (m, 1H), 6.34 (s, 1H), 6.14 (d, 1H), 4.42-4.44 (m, 1H), 3.72 (br s, 1H), 3.10-3.25 (m, 6H), 3.00 (br, 2H), 2.58-2.69 (m, 6H), 1.82-2.01 (m, 6H), 1.70 (br, 2H), 1.36-1.39 (m, 2H), 0.92 (s, 6H).

Example 219

4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({3-nitro-4-[(1-tetrahydro-2H-pyran-4-ylpiperidin-4-yl)amino]phenyl}sulfonyl)benzamide This example was prepared by substituting EXAMPLE 218E for EXAMPLE 26C and EXAMPLE 173C for EXAMPLE 1F in EXAMPLE 177. $^1$H NMR (500 MHz, dimethylsulfoxide-$d_6$) δ 11.11 (s, 1H), 8.52 (d, 1H), 8.20 (d, 1H), 7.77 (dd, 1H), 7.52 (d, 1H), 7.32-7.38 (m, 4H), 7.03-7.07 (m, 4H), 6.81 (dd, 1H), 6.58-6.60 (m, 1H), 6.36 (s, 1H), 6.14 (d, 1H), 4.44 (s, 1H), 3.92 (dd, 2H), 3.71 (br s, 1H), 3.41-3.43 (m, 2H), 3.02-3.06 (m, 4H), 2.55-2.72 (m, 6H), 2.18-2.24 (m, 2H), 1.91-2.00 (m, 8H), 1.76-1.80 (m, 2H), 1.63-1.65 (m, 2H), 1.49-1.51 (m, 2H), 1.35-1.38 (m, 2H), 0.92 (s, 6H).

Example 220

4-(4-{[2-(4-chlorophenyl)-4,4-dimethylcyclohex-1-en-1-yl]methyl}piperazin-1-yl)-2-(1H-indol-5-yloxy)-N-({4-[(4-methylpiperazin-1-yl)amino]-3-[(trifluoromethyl)sulfonyl]phenyl}sulfonyl)benzamide This example was prepared by substituting EXAMPLE 215A for EXAMPLE 1F in EXAMPLE 177. $^1$H NMR (500 MHz, dimethylsulfoxide-$d_6$) δ 11.14 (s, 1H), 8.15 (d, 1H), 8.04 (s, 1H), 7.95 (dd, 1H), 7.50 (t, 2H), 7.35 (m, 4H), 7.12 (d, 1H), 7.04 (d, 2H), 6.83 (dd, 1H), 6.61 (dd, 1H), 6.39 (m, 1H), 6.12 (d, 1H), 2.92 (m, 10H), 2.71 (s, 2H), 2.35 (s, 3H), 2.17 (m, 6H), 1.95 (s, 2H), 1.38 (t, 2H), 0.92 (s, 6H).

Example 221

4-(4-{[4'-chloro-4-(2-hydroxyethoxy)-1,1'-biphenyl-2-yl]methyl}piperazin-1-yl)-2-(1H-indol-4-yloxy)-N-({4-[(1-methylpiperidin-4-yl)amino]-3-nitrophenyl}sulfonyl)benzamide

Example 221A 2-(H-indol-4-yloxy)-4-((4-(2-(tert-butyldimethylsilyloxy)ethoxy)-4'-chlorobiphenyl-2-yl)methyl)piperazin-1-yl)-N-(4-(1-methylpiperidin-4-ylamino)-3-nitrophenylsulfonyl)benzamide This example was prepared by substituting EXAMPLE 213C for EXAMPLE 1E and EXAMPLE 21A for EXAMPLE 1F in EXAMPLE 1G.

Example 221B 4-(4-{[4'-chloro-4-(2-hydroxyethoxy)-1,1'-biphenyl-2-yl]methyl}piperazin-1-yl)-2-(1H-indol-4-yloxy)-N-({4-[(1-methylpiperidin-4-yl)amino]-3-nitrophenyl}sulfonyl)benzamide This example was prepared by substituting EXAMPLE 221A for EXAMPLE 195B in EXAMPLE 195. $^1$H NMR (400 MHz, dimethylsulfoxide-$d_6$) S 11.12 (s, 1H), 8.42 (d, 1H), 8.10 (d, 1H), 7.74 (dd, 1H), 7.58 (d, 1H), 7.40 (m, 4H), 7.21 (m, 1H), 7.06 (m, 4H), 6.90 (m, 2H), 6.65 (m, 1H), 6.31 (d, 1H), 6.23 (m. 2H), 4.84 (t. 1H), 4.00 (t, 2H), 3.71 (m, 3H), 3.24 (m, 4H), 3.02 (m, 6H), 2.66 (m, 2H), 2.32 (m, 5H), 2.00 (m, 2H), 1.69 (m, 2H).

Example 222

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[3-(3-oxopiperazin-1-yl)propyl]amino}phenyl)sulfonyl]benzamide

Example 222A 3-nitro-4-[3-(3-oxo-piperazin-1-yl)-propylamino]-benzenesulfonamide 4-(3-Amino-propyl)-piperazin-2-one (3.45 g) and triethylamine (5.18 mL, 3.76 g) were added to 1,4-dioxane (100 mL) and N,N-dimethylacetamide (20 mL) and mixed until dissolved. 4-Chloro-3-nitrobenzenesulfonamide (4.00 g) was added, and the mixture was heated to 90° C. for 16 hours. The

Example 222B 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[3-(3-oxopiperazin-1-yl)propyl]amino}phenyl)sulfonyl]benzamide

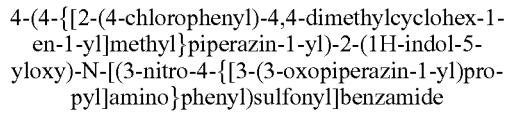

This example was prepared by substituting EXAMPLE 26C for EXAMPLE 1E and EXAMPLE 222A for EXAMPLE 1F in EXAMPLE 1G. $^1$H NMR (300 MHz, dimethylsulfoxide-$d_6$) δ 11.16 (br s, 1H), 8.85 (t, 1H), 8.58 (d, 1H), 7.79 (dd, 1H), 7.74 (br s, 1H), 7.51 (d, 1H), 7.43-7.37 (m, 2H), 7.34 (d, 2H), 7.16 (d, 1H), 7.07-7.01 (m, 3H), 6.86 (dd, 1H), 6.65, (d, 1H), 6.39 (t, 1H), 6.15 (d, 1H), 3.43 (q, 2H), 3.17 (t, 2H), 3.03 (m, 4H), 2.95 (s, 2H), 2.72 (s, 2H), 2.56 (t, 2H), 2.47 (t, 2H), 2.16 (m, 6H), 1.95 (br s, 2H), 1.79 (m, 2H), 1.38 (t, 2H), 0.92 (s, 6H).

Example 223

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[3-(3-oxopiperazin-1-yl)propyl]amino}phenyl)sulfonyl]benzamide

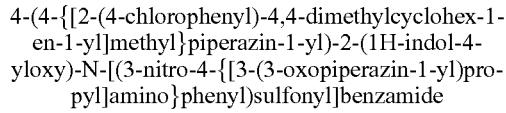

This example was prepared by substituting EXAMPLE 55B for EXAMPLE 1E and EXAMPLE 222A for EXAMPLE 1F in EXAMPLE 1G. $^1$H NMR (300 MHz, dimethylsulfoxide-$d_6$) 11.24 (br s, 1H), 8.83 (t, 1H), 8.50 (d, 1H), 7.75 (br s, 1H), 7.68 (dd, 1H), 7.53 (d, 1H), 7.34 (d, 2H), 7.28 (t, 1H), 7.18 (d, 1H), 7.04 (d, 2H), 7.02-6.94 (m, 2H), 6.71 (dd, 1H), 6.42 (d, 1H), 6.29-6.23 (m, 2H), 3.43 (q, 2H), 3.17 (m, 2H), 3.05 (m, 4H), 2.96 (s, 2H), 2.72 (s, 2H), 2.57 (t, 2H), 2.48 (t, 2H), 2.17 (m, 6H), 1.95 (br s, 2H), 1.79 (m, 2H), 1.38 (t, 2H), 0.92 (s, 6H).

Example 224

4-(4-{[2-(4-chlorophenyl)-5-hydroxycyclohex-1-en-1-yl]methyl}piperazin-1-yl)-2-(1H-indol-5-yloxy)-N-({4-[(1-methylpiperidin-4-yl)amino]-3-nitrophenyl}sulfonyl)benzamide

Example 224A 2-chloro-5-hydroxycyclohex-1-enecarbaldehyde

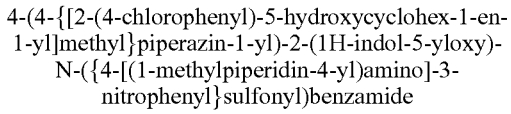

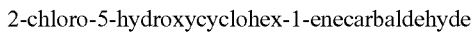

Phosphorus oxychloride (4.08 mL) was added to cooled (−10° C.) N,N-dimethylformamide (20 mL). The temperature was maintained below 0° C. Stirring was continued for another 30 minutes before the addition of 4-(tert-butyldimethylsilyloxy)cyclohexanone (10 g). The mixture was then stirred at room temperature for 2 hours before it was diluted with ethyl acetate (300 mL) and washed with water (3×), brine and dried over Na$_2$SO$_4$. After filtration and concentration, the crude product was used directly in the next reaction without further purification.

Example 224B 2-(4-chlorophenyl)-5-hydroxycyclohex-1-enecarbaldehyde

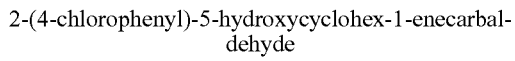

To a mixture of 4-chlorophenylboronic acid (6.88 g), EXAMPLE 224A (4.65 g), palladium(II) acetate (131 mg), K$_2$CO$_3$ (18.24 g) and tetrabutylammonium bromide (14.18 g) was added water (200 mL). The mixture was stirred at 50° C. for 4 hours, cooled, and diluted with ethyl acetate (400 mL) and washed with water (3×) and brine and dried over Na$_2$SO$_4$. After filtration and concentration, the residue was loaded on a column and eluted with 5-20% ethyl acetate in hexane to give the title compound.

Example 224C methyl 2-(1H-indol-5-yloxy)-4-(4-((2-(4-chlorophenyl)-5-hydroxycyclohex-1-enyl)methyl)piperazin-1-yl)benzoate

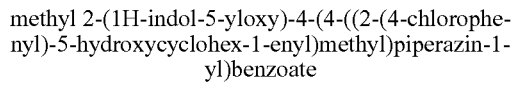

To a mixture of EXAMPLE 224B (0.8 g) and EXAMPLE 150A (1.2 g) in dichloromethane (20 mL) was added sodium triacetoxyborohydride (1.2 g). The mixture was stirred overnight. The mixture was diluted with ethyl acetate (200 mL) and washed with 2% NaOH, water and brine. After drying over Na$_2$SO$_4$, the solvent was evaporated under vacuum and the residue was loaded on a column and eluted with 5-10% methanol in dichloromethane to give the title compound.

Example 224D 2-(1H-indol-5-yloxy)-4-(4-((2-(4-chlorophenyl)-5-hydroxycyclohex-1-enyl)methyl)piperazin-1-yl)benzoic acid

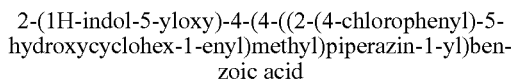

To a mixture of EXAMPLE 224C (1.78 g) in tetrahydrofuran (30 mL), methanol (10 mL) and water (10 mL) was added LiOH.H$_2$O (0.262 g). The mixture was stirred overnight. The mixture was then neutralized with 5% aqueous HCl and exacted with ethyl acetate (3×) and the combined organic layers were washed with brine and dried over Na$_2$SO$_4$. Evaporation of solvent gave the title compound.

Example 224E 4-(4-{[2-(4-chlorophenyl)-5-hydroxycyclohex-1-en-1-yl]methyl}piperazin-1-yl)-2-(1H-indol-5-yloxy)-N-({4-[(1-methylpiperidin-4-yl)amino]-3-nitrophenyl}sulfonyl)benzamide

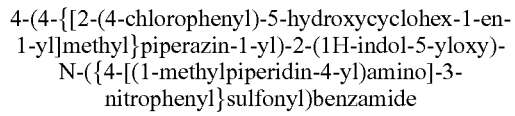

This example was prepared by substituting EXAMPLE 224D for EXAMPLE 1E and EXAMPLE 21A for EXAMPLE 1F in EXAMPLE 1G. $^1$H NMR (300 MHz, dimethylsulfoxide-$d_6$) δ 11.08 (s, 1H), 8.50 (d, 1H), 8.13 (d, 1H), 7.77 (dd, 1H), 7.52 (d, 1H), 7.34 (m, 4H), 7.04 (m, 4H), 6.78 (dd, 1H), 6.59 (dd, 1H), 6.35 (s, 1H), 6.13 (d, 1H), 4.59 (d, 1H), 3.74 (m, 2H), 3.39 (m, 1H), 3.03 (m, 7H), 2.68 (m, 3H), 2.41 (m, 4H), 2.17 (m, 7H), 2.00 (m, 3H), 1.71 (m, 3H).

Example 225

4-(4-{[2-(4-chlorophenyl)-5-hydroxycyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide

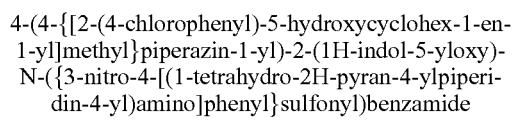

This example was prepared by substituting EXAMPLE 224D for EXAMPLE 1E and EXAMPLE 173C for EXAMPLE 1F in EXAMPLE 1G. $^1$H NMR (300 MHz, dimethylsulfoxide-$d_6$) δ 11.07 (s, 1H), 8.47 (d, 1H), 8.14 (d, 1H), 7.92 (s, 1H), 7.72 (dd, 1H), 7.52 (d, 1H), 7.46 (d, 1H), 7.33 (m, 4H), 7.07 (d, 2H), 6.98 (d, 1H), 6.77 (m, 1H), 6.58 (dd, 1H), 6.34 (s, 1H), 6.14 (d, 1H), 4.59 (m, 1H), 3.90 (dd, 2H), 3.70 (m, 1H), 3.01 (m, 8H), 2.71 (m, 6H), 2.56 (m, 8H), 2.19 (m, 4H), 1.94 (m, 3H), 1.56 (m, 3H).

Example 226

4-(4-{[2-(4-chlorophenyl)-5-hydroxycyclohex-1-en-1-yl]methyl}piperazin-1-yl)-2-(1H-indol-5-yloxy)-N-({4-[(4-methylpiperazin-1-yl)amino]-3-nitrophenyl}sulfonyl)benzamide This example was prepared by substituting EXAMPLE 224D for EXAMPLE 1E and EXAMPLE 174A for EXAMPLE 1F in EXAMPLE 1G. $^1$H NMR (300 MHz, dimethylsulfoxide-$d_6$) δ 11.13 (s, 1H), 9.13 (s, 1H), 8.52 (d, 1H), 7.83 (dd, 1H), 7.53 (t, 2H), 7.36 (m, 4H), 7.09 (m, 3H), 6.83 (dd, 1H), 6.61 (dd, 1H), 6.38 (s, 1H), 6.12 (d, 1H), 4.59 (d, 1H), 3.75 (m, 1H), 2.81 (m, 12H), 2.27 (m, 12H), 1.79 (m, 4H).

Example 227

4-(4-{[2-(4-chlorophenyl)-4,4-dimethylcyclohex-1-en-1-yl]methyl}piperazin-1-yl)-N-[(4-{[1-(2,3-dihydro-1H-inden-2-yl)piperidin-4-yl]amino}-3-nitrophenyl)sulfonyl]-2-(1H-indol-4-yloxy)benzamide Example 227A 4-(1-indan-2-yl-piperidin-4-ylamino)-3-nitro-benzenesulfonamide 2-Aminoindane (12.84 g) and triethylamine (15.04 mL, 10.92 g) were added to 1,4-dioxane (150 mL) and the mixture was stirred until the solids were dissolved. 4-Chloro-3-nitrobenzenesulfonamide (12.77 g) was added, and the mixture was heated to 90° C. for 16 hours. The mixture was cooled and the precipitate vacuum was filtered, washed with 20% methanol in dichloromethane, and washed with 100% dichloromethane.

Example 227B 4-(4-{[2-(4-chlorophenyl)-4,4-dimethylcyclohex-1-en-1-yl]methyl}piperazin-1-yl)-N-[(4-{[1-(2,3-dihydro-1H-inden-2-yl)piperidin-4-yl]amino}-3-nitrophenyl)sulfonyl]-2-(1H-indol-4-yloxy)benzamide This example was prepared by substituting EXAMPLE 55B for EXAMPLE 1E and EXAMPLE 227A for EXAMPLE 1F in EXAMPLE 1G. $^1$H NMR (300 MHz, dimethylsulfoxide-$d_6$) δ 11.20 (br s, 1H), 8.48 (d, 1H), 8.21 (d, 1H), 7.73 (dd, 1H), 7.54 (d, 1H), 7.34 (d, 2H), 7.26-7.21 (m, 3H), 7.16-7.12 (m, 2H), 7.09-7.02 (m, 3H), 6.95 (t, 2H), 6.68 (dd, 1H), 6.39 (d, 1H), 6.24 (m, 2H), 3.74 (m, 1H), 3.18-2.80 (m, 13H), 2.72 (br s, 2H), 2.16 (m, 6H), 2.03 (m, 2H), 1.95 (br s, 2H), 1.68 (m, 2H), 1.38 (t, 2H), 0.92 (s, 6H).

Example 228

4-(4-{[2-(4-chlorophenyl)-4,4-dimethylcyclohex-1-en-1-yl]methyl}piperazin-1-yl)-N-[(4-{[1-(2,3-dihydro-1H-inden-2-yl)piperidin-4-yl]amino}-3-nitrophenyl)sulfonyl]-2-(1H-indol-5-yloxy)benzamide This example was prepared by substituting EXAMPLE 26C for EXAMPLE 1E and EXAMPLE 227A for EXAMPLE 1F in EXAMPLE 1G. $^1$H NMR (300 MHz, dimethylsulfoxide-$d_6$) δ 11.12 (br s, 1H), 8.55 (d, 1H), 8.23 (d, 1H), 7.79 (dd, 1H), 7.51 (d, 1H), 7.41-7.31 (m, 4H), 7.22 (m, 2H), 7.16-7.09 (m, 3H), 7.07-7.01 (m, 3H), 6.83 (dd, 1H), 6.63 (dd, 1H), 6.37 (t, 1H), 6.15 (d, 1H), 3.73 (m, 1H), 3.16-2.82 (m, 13H), 2.71 (br s, 2H), 2.16 (m, 6H), 2.02 (m, 2H), 1.95 (br s, 2H), 1.67 (m, 2H), 1.38 (t, 2H), 0.92 (s, 6H).

Example 229

4-(4-{[2-(4-chlorophenyl)-4,4-dimethylcyclohex-1-en-1-yl]methyl}piperazin-1-yl)-2-(1H-indol-5-yloxy)-N-[(4-{[(1-morpholin-4-ylcyclohexyl)methyl]amino}-3-nitrophenyl)sulfonyl]benzamide This example was prepared by substituting (1-morpholinocyclohexyl)methanamine for (3S,4R)-4-amino-1-benzylpiperidin-3-ol, hydrochloric acid in EXAMPLE 187B. $^1$H NMR (500 MHz, dimethylsulfoxide-$d_6$) δ 11.19 (s, 1H), 9.08 (s, 1H), 8.60 (d, 1H), 7.81 (dd, 1H), 7.51 (d, 1H), 7.43 (d, 1H), 7.39 (t, 1H), 7.33 (d, 2H), 7.16-7.18 (m, 2H), 7.03 (d, 2H), 6.88 (dd, 1H), 6.65 (dd, 1H), 6.40 (s, 1H), 6.13 (d, 1H), 3.60 (s, 4H), 3.42-3.43 (m, 2H), 3.01 (br s, 4H), 2.72 (br s, 2H), 2.57 (br s, 4H), 2.12-2.16 (m, 7H), 1.94 (br s, 2H), 1.46-1.60 (m, 12H), 1.36-1.39 (m, 2H), 0.92 (s, 6H).

Example 230

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-2-ylmethyl)piperidin-4-yl]amino}phenyl)sulfonyl]benzamide Example 230A tert-butyl 1-(thiazol-2-ylmethyl)piperidin-4-ylcarbamate This example was prepared by substituting thiazole-2-carbaldehyde for EXAMPLE 27C and tert-butyl piperidin-4-ylcarbamate for tert-butyl piperazine-1-carboxylate in EXAMPLE 1A.

Example 230B 1-(thiazol-2-ylmethyl)piperidin-4-amine

This example was prepared by substituting EXAMPLE 230A for EXAMPLE 1A in EXAMPLE 1B.

Example 230C 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-2-ylmethyl)piperidin-4-yl]amino}phenyl)sulfonyl]benzamide This example was prepared by substituting EXAMPLE 230B for (3S,4R)-4-amino-1-benzylpiperidin-3-ol, hydrochloric acid in EXAMPLE 187B. 11 NMR (500 MHz, dimethylsulfoxide-$d_6$) S 11.14 (s, 1H), 8.23 (d, 1H), 7.76-7.79 (m, 2H), 7.65 (s, 1H), 7.53 (d, 1H), 7.38-7.40 (m, 2H), 7.34 (d, 2H), 7.17 (d, 1H), 7.11 (s, 1H), 7.04 (d, 2H), 6.82 (dd, 1H), 6.62 (d, 1H), 6.38 (s, 1H), 6.14 (d, 1H), 4.19 (s, 2H), 3.01 (s, 4H), 2.91-2.96 (m, 2H), 2.72 (s, 2H), 2.12-2.17 (m, 6H), 1.95-1.99 (m, 4H), 1.47-1.51 (m, 2H), 1.36-1.39 (m, 2H), 0.92 (s, 6H).

Example 231

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-4-ylmethyl)piperidin-4-yl]amino}phenyl)sulfonyl]benzamide

Example 231A tert-butyl 1-(thiazol-4-ylmethyl)piperidin-4-ylcarbamate

This example was prepared by substituting thiazole-4-carbaldehyde for EXAMPLE 27C and tert-butyl piperidin-4-ylcarbamate for tert-butyl piperazine-1-carboxylate in EXAMPLE 1A.

Example 231B 1-(thiazol-4-ylmethyl)piperidin-4-amine

This example was prepared by substituting EXAMPLE 231A for EXAMPLE 1A in EXAMPLE 1B.

Example 231C 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[1-(1,3-thiazol-4-ylmethyl)piperidin-4-yl]amino}phenyl)sulfonyl]benzamide This example was prepared by substituting EXAMPLE 231B for (3S,4R)-4-amino-1-benzylpiperidin-3-ol, hydrochloric acid in EXAMPLE 187B. $^1$H NMR (500 MHz, dimethylsulfoxide-$d_6$) δ 11.11 (s, 1H), 9.06 (s, 1H), 8.21 (d, 1H), 7.98 (s, 1H), 7.77 (dd, 1H), 7.54 (d, 1H), 7.33-7.38 (m, 4H), 7.13 (d, 2H), 7.03-7.07 (m, 3H), 6.79 (dd, 1H), 6.60 (dd, 1H), 6.37 (s, 1H), 6.14 (d, 1H), 4.23 (s, 2H), 2.99 (s, 4H), 2.89-2.94 (m, 2H), 2.71 (s, 2H), 2.12-2.17 (m, 6H), 1.95-1.99 (m, 4H), 1.47-1.51 (m, 2H), 1.36-1.39 (m, 2H), 0.92 (s, 6H).

Example 232

4-(4-{[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}-2-(1H-indol-5-yloxy)benzamide This example was prepared by substituting (4-(aminomethyl)tetrahydro-2H-pyran-4-yl)methanol for (3S,4R)-4-amino-1-benzylpiperidin-3-ol, hydrochloric acid in EXAMPLE 187B. $^1$H NMR (500 MHz, dimethylsulfoxide-$d_6$) δ 11.17 (s, 1H), 9.10 (t, 1H), 8.59 (d, 1H), 7.81 (dd, 1H), 7.51 (d, 1H), 7.42 (d, 1H), 7.39 (t, 1H), 7.16-7.18 (m, 2H), 7.03 (d, 2H), 6.87 (dd, 1H), 6.65 (d, 1H), 6.39 (s, 1H), 6.14 (d, 1H), 5.22 (t, 1H), 3.51-3.62 (m, 6H), 3.19 (d, 2H), 3.03 (s, 4H), 2.72 (s, 2H), 2.12-2.17 (m, 6H), 1.94 (s, 2H), 1.45-1.49 (m, 4H), 1.36-1.39 (m, 2H), 0.92 (s, 6H).

Example 233

4-(4-{[2-(4-chlorophenyl)-4,4-dimethylcyclohex-1-en-1-yl]methyl}piperazin-1-yl)-N-[(4-{[4-(2-hydroxyethyl)piperazin-1-yl]amino}-3-nitrophenyl)sulfonyl]-2-(1H-indol-5-yloxy)benzamide

Example 233A 4-(4-(2-hydroxyethyl)piperazin-1-ylamino)-3-nitrobenzenesulfonamide This example was prepared by substituting 2-(4-aminopiperazin-1-yl)ethanol for (tetrahydro-2H-pyran-4-yl)methanamine in EXAMPLE 1F.

Example 233B 4-(4-{[2-(4-chlorophenyl)-4,4-dimethylcyclohex-1-en-1-yl]methyl}piperazin-1-yl)-N-[(4-{[4-(2-hydroxyethyl)piperazin-1-yl]amino}-3-nitrophenyl)sulfonyl]-2-(1H-indol-5-yloxy)benzamide This example was prepared by substituting EXAMPLE 233A for EXAMPLE 1F in EXAMPLE 177. $^1$H NMR (500 MHz, dimethylsulfoxide-$d_6$) δ 11.15 (s, 1H), 9.17 (m, 1H), 8.53 (d, 1H), 7.83 (dd, 1H), 7.56 (d, 1H), 7.51 (d, 1H), 7.36 (m, 4H), 7.13 (m, 1H), 7.03 (m, 2H), 6.84 (dd, 1H), 6.62 (dd, 1H), 6.38 (m, 1H), 6.12 (m, 1H), 4.57 (m, 1H), 3.54 (m, 2H), 2.95 (m, 10H), 2.71 (s, 2H), 2.57 (m, 2H), 2.15 (m, 6H), 1.94 (s, 2H), 1.38 (t, 2H), 0.93 (s, 6H)

Example 234

4-(4-{[2-(4-chlorophenyl)-4,4-dimethylcyclohex-1-en-1-yl]methyl}piperazin-1-yl)-2-(1H-indol-5-yloxy)-N-[(4-{[(3S)-1-methylpyrrolidin-3-yl]amino}-3-nitrophenyl)sulfonyl]benzamide

Example 234A (S)-tert-butyl 1-methylpyrrolidin-3-ylcarbamate

To a mixture of (S)-tert-butyl 1-methylpyrrolidin-3-ylcarbamate (438 mg) in methanol (10 mL) was added 37% formaldehyde mixture in water (0.53 mL) and sodium borohydride (267 mg). The reaction mixture was stirred overnight at room temperature and then concentrated. The residue was dissolved in chloroform (15 mL), washed with brine and NaHCO$_3$ solution, dried over MgSO$_4$, filtered and concentrated. The title compound was used in the next step without further purification.

Example 234B (S)-1-methylpyrrolidin-3-amine

This example was prepared by substituting EXAMPLE 234A for EXAMPLE 1A in EXAMPLE 1B.

Example 234C 4-(4-{[2-(4-chlorophenyl)-4,4-dimethylcyclohex-1-en-1-yl]methyl}piperazin-1-yl)-2-(1H-indol-5-yloxy)-N-[(4-{[(3S)-1-methylpyrrolidin-3-yl]amino}-3-nitrophenyl)sulfonyl]benzamide This example was prepared by substituting EXAMPLE 234B for 1-(2-methoxy-ethyl)-piperidin-4-ylamine and EXAMPLE 310B for 4-chloro-3-nitrobenzenesulfonamide in EXAMPLE 189A. $^1$H NMR (500 MHz, dimethylsulfoxide-$d_6$) δ 10.98 (s, 1H), 8.38 (d, 1H), 8.16 (d, 1H), 7.64 (dd, 1H), 7.53 (d, 1H), 7.34 (d, 2H), 7.28 (m, 2H), 7.05 (d, 2H), 6.89 (d, 1H), 6.72 (d, 1H), 6.68 (dd, 1H), 6.53 (dd, 1H), 6.29 (t, 1H), 6.15 (d, 1H), 4.14 (br s, 1H), 2.93 (m, 4H), 2.71 (m, 4H), 2.33 (m, 2H), 2.27 (s, 3H), 2.16 (m, 6H), 1.95 (s, 2H), 1.61 (m, 1H), 1.38 (t, 2H), 1.24 (br s, 1H), 0.92 (s, 6H).

Example 235

4-(4-{[2-(4-chlorophenyl)-4,4-dimethylcyclohex-1-en-1-yl]methyl}piperazin-1-yl)-N-[(4-{[1-(3-fluoropropyl)piperidin-4-yl]amino}-3-nitrophenyl)sulfonyl]-2-(1H-indol-5-yloxy)benzamide

Example 235A 4-(1-(3-fluoropropyl)piperidin-4-ylamino)-3-nitrobenzenesulfonamide This example was prepared by substituting 1-fluoro-3-iodopropane for 1,1,1-trifluoro-4-iodobutane in EXAMPLE 210A.

Example 235B 4-(4-{[2-(4-chlorophenyl)-4,4-dimethylcyclohex-1-en-1-yl]methyl}piperazin-1-yl)-N-[(4-{[1-(3-fluoropropyl)piperidin-4-yl]amino}-3-nitrophenyl)sulfonyl]-2-(1H-indol-5-yloxy)benzamide This example was prepared by substituting EXAMPLE 235A for EXAMPLE 1F and EXAMPLE 26C for EXAMPLE 1E in EXAMPLE 1G. $^1$H NMR (300 MHz, dimethylsulfoxide-$d_6$) δ 11.12 (s, 1H), 10.89 (br s, 1H), 8.48 (d, 1H), 8.152 (d, 1H), 7.79 (dd, 1H), 7.50 (d, 1H), 7.34 (m, 4H), 7.03 (m, 4H), 6.83 (dd, 1H), 6.63 (dd, 1H), 6.37 (m, 1H), 6.15 (d, 1H), 3.71 (br s, 1H), 3.01 (m, 4H), 2.92 (m, 2H), 2.72 (m, 2H), 2.56 (m, 1H), 2.30 (m, 2H), 2.16 (m, 6H), 1.95 (m, 5H), 1.83 (m, 1H), 1.68 (m, 2H), 1.38 (m, 2H), 1.24 (br s, 1H), 0.92 (s, 6H).

Example 236

4-[4-{[2-(4-chlorophenyl)-4,4-dimethylcyclohex-1-en-1-yl]methyl}-3-(hydroxymethyl)piperazin-1-yl]-2-(1H-indol-5-yloxy)-N-({3-nitro-4-[(tetrahydro-2H-pyran-4-ylmethyl)amino]phenyl}sulfonyl)benzamide This example was prepared by substituting EXAMPLE 218E for EXAMPLE 26C in EXAMPLE 177. $^1$H NMR (500 MHz, dimethylsulfoxide-$d_6$) δ 11.17 (s, 2H), 8.62 (s, 1H), 8.58 (s, 1H), 7.78 (d, 1H), 7.52 (d, 1H), 7.39-7.42 (m, 2H), 7.33 (d, 1H), 7.14 (s, 1H), 7.09 (d, 1H), 7.04 (d, 1H), 6.86 (d, 1H), 6.62 (d, 1H), 6.39 (s, 1H), 6.14 (s, 1H), 4.46 (m, 1H), 3.85 (dd, 2H), 3.17-3.25 (m, 8H), 2.76 (br s, 2H), 2.58 (br s. 2H), 1.89-2.01 (m, 6H), 1.80 (br, 2H), 1.29-1.38 (m, 2H), 0.91 (s, 6H).

Example 237

N-[(4-{[(4-aminotetrahydro-2H-pyran-4-yl)methyl]amino}-3-nitrophenyl)sulfonyl]-4-[4-{[2-(4-chlorophenyl)-4,4-dimethylcyclohex-1-en-1-yl]methyl)}-3-(hydroxymethyl)piperazin-1-yl]-2-(1H-indol-5-yloxy)benzamide

Example 237A 4-((4-aminotetrahydro-2H-pyran-4-yl)methylamino)-3-nitrobenzenesulfonamide This example was prepared by substituting 4-(aminomethyl)tetrahydro-2H-pyran-4-amine for (tetrahydropyran-4-yl)methylamine in EXAMPLE 1F.

Example 237B

N-[(4-{[(4-aminotetrahydro-2H-pyran-4-yl)methyl]amino}-3-nitrophenyl)sulfonyl]-4-[4-{[2-(4-chlorophenyl)-4,4-dimethylcyclohex-1-en-1-yl]methyl}-3-(hydroxymethyl)piperazin-1-yl]-2-(1H-indol-5-yloxy)benzamide This example was prepared by substituting EXAMPLE 218E for EXAMPLE 26C and EXAMPLE 237A for EXAMPLE 1F in EXAMPLE 177. $^1$H NMR (500 MHz, dimethylsulfoxide-$d_6$) δ 11.46 (s, 1H), 11.19 (s, 1H), 8.16 (d, 1H), 8.51-8.55 (m, 1H), 8.11 (s, 2H), 7.88 (d, 1H), 7.53 (d, 1H), 7.32-7.43 (m, 5H), 7.15 (s, 1H), 7.09 (d, 1H), 6.85 (dd, 1H), 6.68 (s, 1H), 6.40 (s, 1H), 6.21 (s, 1H), 3.81-3.82 (m, 2H), 3.70-3.72 (m, 4H), 3.10 (br s, 2H), 2.02-2.09 (m, 2H), 1.60-1.85 (m, 2H), 1.66-1.73 (m, 2H), 1.35-1.38 (m, 2H), 0.93 (s, 6H).

Example 238

4-(4-{[2-(4-chlorophenyl)-4,4-dimethylcyclohex-1-en-1-yl]methyl}piperazin-1-yl)-N-[(4-{[(1-hydroxycyclohexyl)methyl]amino}-3-nitrophenyl)sulfonyl]-2-(1H-indol-5-yloxy)benzamide This example was prepared by substituting 1-(aminomethyl)cyclohexanol for (3S,4R)-4-amino-1-benzylpiperidin-3-ol, hydrochloric acid in EXAMPLE 187B. $^1$H NMR (500 MHz, dimethylsulfoxide-$d_6$) δ 11.17 (s, 2H), 8.69 (t, 1H), 8.60 (d, 1H), 7.80 (dd, 1H), 7.51 (d, 1H), 7.39-7.43 (m, 2H), 7.33 (d, 2H), 7.17 (d, 2H), 7.14 (d, 1H), 7.03 (d, 2H), 6.87 (dd, 1H), 6.65 (d, 1H), 6.40 (s, 1H), 6.14 (d, 1H), 4.73 (s, 1H), 3.03 (s, 4H), 2.74 (s, 2H), 2.12-2.18 (m, 6H), 1.94 (s, 2H), 1.54-1.58 (m, 4H), 1.36-1.43 (m, 7H), 0.92 (s, 6H).

Example 239

4-(4-{[2-(4-chlorophenyl)-4,4-dimethylcyclohex-1-en-1-yl]methyl}piperazin-1-yl)-2-(1H-indol-4-yloxy)-N-({4-[(2-methoxyethyl)amino]-3-nitrophenyl}sulfonyl)benzamide This example was prepared by substituting EXAMPLE 179A for EXAMPLE 1F and EXAMPLE 55B for EXAMPLE 26C in EXAMPLE 177. $^1$H NMR (500 MHz, dimethylsulfoxide-d$_6$) δ 11.25 (s, 2H), 8.57 (m, 1H), 8.50 (d, 1H), 7.70 (dd, 1H), 7.52 (d, 1H), 7.34 (d, 2H), 7.28 (t, 1H), 7.17 (d, 1H), 7.05 (m, 3H), 6.97 (t, 1H), 6.71 (dd, 1H), 6.42 (d, 1H), 6.26 (m, 2H), 3.58 (m, 4H), 3.31 (s, 3H), 3.05 (m, 4H), 2.73 (s, 2H), 2.17 (m, 6H), 1.96 (s, 2H), 1.38 (t, 2H), 0.93 (s, 6H)

Example 240

4-(4-{[2-(4-chlorophenyl)-4,4-dimethylcyclohex-1-en-1-yl]methyl}piperazin-1-yl)-N-[(4-{[4-(hydroxymethyl)tetrahydro-2H-pyran-4-yl]amino}-3-nitrophenyl)sulfonyl]-2-(1H-indol-5-yloxy)benzamide Example 240A 4-(4-(hydroxymethyl)tetrahydro-2H-pyran-4-ylamino)-3-nitrobenzenesulfonamide This example was prepared by substituting (4-aminotetrahydro-2H-pyran-4-yl)methanol for (tetrahydropyran-4-yl)methylamine and 4-fluoro-3-nitrobenzenesulfonamide for 4-chloro-3-nitrobenzenesulfonamide in EXAMPLE 1F.

Example 240B 4-(4-{[2-(4-chlorophenyl)-4,4-dimethylcyclohex-1-en-1-yl]methyl}piperazin-1-yl)-N-[(4-{[4-(hydroxymethyl)tetrahydro-2H-pyran-4-yl]amino}-3-nitrophenyl)sulfonyl]-2-(1H-indol-5-yloxy)benzamide This example was prepared by substituting EXAMPLE 240A for EXAMPLE 1F in EXAMPLE 177. $^1$H NMR (500 MHz, dimethylsulfoxide-d$_6$) δ 11.14 (s, 2H), 8.63 (d, 1H), 8.50 (s, 1H), 7.92 (s, 1H), 7.79 (dd, 1H), 7.52 (d, 1H), 7.39-7.43 (m, 2H), 7.33-7.34 (m, 3H), 7.18 (s, 1H), 7.03 (d, 2H), 6.87 (dd, 1H), 6.65 (dd, 1H), 6.40 (s, 1H), 6.13 (d, 1H), 5.04 (t, 1H), 3.67-3.72 (m, 4H), 3.56 (t, 2H), 3.02 (s, 4H), 2.72 (br, 2H), 2.12-2.16 (m, 6H), 1.94-2.01 (m, 3H), 1.81-1.85 (m, 2H), 1.36-1.39 (m, 2H), 1.24 (m, 6H), 0.92 (s, 6H).

Example 241

4-(4-({2-[2-(4-chlorophenyl)-4,4-dimethylcyclohex-1-en-1-yl]methyl}piperazin-1-yl)-N-[(4-{[4-(hydroxymethyl)tetrahydro-2H-pyran-4-yl]amino}-3-nitrophenyl)sulfonyl]-2-(1H-indol-4-yloxy)benzamide This example was prepared by substituting EXAMPLE 240A for EXAMPLE 1F and EXAMPLE 55B for EXAMPLE 26 C in EXAMPLE 177. $^1$H NMR (500 MHz, dimethylsulfoxide-d$_6$) δ 11.26 (s, 2H), 8.55 (d, J=2.14 Hz, 1H), 8.48 (s, 1H), 7.66 (dd, 1H), 7.54 (d, 1H), 7.34 (d, 2H), 7.27-7.29 (m, 2H), 7.19 (d, 2H), 7.03 (d, 2H), 6.99 (t, 1H), 6.70 (dd, 1H), 6.44 (d, 1H), 6.27 (s, 1H), 5.04 (t, 1H), 3.67-3.72 (m, 4H), 3.56 (t, 2H), 3.04 (s, 4H), 2.74 (s, 2H), 2.12-2.17 (m, 6H), 1.95-2.01 (m, 5H), 1.80-1.85 (m, 2H), 1.38 (t, 2H), 1.24 (m, 4H), 0.92 (s, 6H).

Example 242

4-(4-{[2-(4-chlorophenyl)-4,4-dimethylcyclohex-1-en-1-yl]methyl}piperazin-1-yl)-N-({4-[(2-hydroxy-1-tetrahydro-2H-pyran-4-ylethyl)amino]-3-nitrophenyl}sulfonyl)-2-(1H-indol-5-yloxy)benzamide This example was prepared by substituting 2-amino-2-(tetrahydro-2H-pyran-4-yl)ethanol for (3S,4R)-4-amino-1-benzylpiperidin-3-ol, hydrochloric acid in EXAMPLE 187B. $^1$H NMR (500 MHz, dimethylsulfoxide-d$_6$) δ 11.18 (s, 1H), 8.60 (d, 1H), 8.57 (d, 1H), 7.79 (dd, 1H), 7.52 (d, 1H), 7.43 (d, 1H), 7.40 (t, 1H), 7.33 (d, 2H), 7.23 (d, 1H), 7.19 (d, 1H), 7.03 (d, 2H), 6.88 (dd, 1H), 6.65 (dd, 1H), 6.41 (s, 1H), 6.13 (d, 1H), 5.03 (t, 1H), 3.83-3.87 (m, 2H), 3.56-3.73 (m, 4H), 3.26 (t, 2H), 3.03 (s, 4H), 2.72 (s, 2H), 2.12-2.17 (br s, 4H), 1.58-1.62 (m, 2H), 1.36-1.39 (m, 2H), 0.92 (s, 6H).

Example 243

4-(4-{[2-(4-chlorophenyl)-4,4-dimethylcyclohex-1-en-1-yl]methyl}piperazin-1-yl)-2-(H-indol-5-yloxy)-N-{[3-nitro-4-({1-[2-(1H-pyrazol-1-yl)ethyl]piperidin-4-yl}amino)phenyl]sulfonyl}benzamide Example 243A 4-(1-(2-(1H-pyrazol-1-yl)ethyl)piperidin-4-ylamino)-3-nitrobenzenesulfonamide This example was prepared by substituting 1-(2-bromoethyl)-1H-pyrazole for 1,1,1-trifluoro-4-iodobutane in EXAMPLE 210A. After concentrating the reaction mixture, the title compound was collected by filtration of the ether slurry.

Example 243B 4-(4-{[2-(4-chlorophenyl)-4,4-dimethylcyclohex-1-en-1-yl]methyl}piperazin-1-yl)-2-(1H-indol-5-yloxy)-N-{[3-nitro-4-({1-[2-(1H-pyrazol-1-yl)ethyl]piperidin-4-yl}amino)phenyl]sulfonyl}benzamide This example was prepared by substituting EXAMPLE 243A for EXAMPLE 1F and EXAMPLE 26C for EXAMPLE 1E in EXAMPLE 1G. $^1$H NMR (300 MHz, dimethylsulfoxide-d$_6$) δ 11.25 (br s, 1H), 11.14 (s, 1H), 8.55 (d, 1H), 8.22 (d, 1H), 7.74 (m, 2H), 7.50 (d, 1H), 7.40 (m, 3H), 7.33 (d, 2H), 7.10 (m, 1H), 7.03 (d, 2H), 6.83 (dd, 1H), 6.63 (dd, 1H), 6.38 (t, 1H), 6.22 (t, 1H), 6.15 (d, 1H), 4.24 (t, 2H), 3.65 (br s, 1H), 3.02 (m, 4H), 2.78 (m, 6H), 2.27 (m, 2H), 2.16 (m, 6H), 1.94 (m, 3H), 1.60 (m, 2H), 1.38 (t, 2H), 1.23 (br s, 1H), 0.92 (s, 6H).

Example 244

4-(4-{[2-(4-chlorophenyl)-4,4-dimethylcyclohex-1-en-1-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide This example was prepared by substituting EXAMPLE 55B for EXAMPLE 26 C in EXAMPLE 177. $^1$H NMR (500 MHz, dimethylsulfoxide-d$_6$) δ 11.26 (s, 2H), 8.61 (t, 1H), 8.50 (d, 1H), 7.69 (dd, 1H), 7.28 (t, 2H), 7.18 (d, 2H), 7.07 (d, 1H), 7.04 (d, 2H), 6.97 (t, 1H), 6.71 (dd, 1H), 6.43 (d, 1H), 6.28 (d, 1H), 6.26 (d, 1H), 5.04 (t, 1H), 3.85 (dd, 2H), 3.25-3.31 (m, 6H), 3.05 (s, 4H), 2.74 (s, 2H), 2.14-2.18 (m, 6H), 1.87-1.90 (m, 2H), 1.61-1.63 (m, 2H), 1.38 (t, 2H), 0.92 (s, 6H).

Example 245

4-(4-{[2-(4-chlorophenyl)-4,4-dimethylcyclohex-1-en-1-yl]methyl}piperazin-1-yl)-2-(1H-indol-5-yloxy)-N-{[4-(methylamino)-3-nitrophenyl]sulfonyl}benzamide

Example 245A 4-(methylamino)-3-nitrobenzenesulfonamide

This example was prepared by substituting methanamine for (tetrahydro-2H-pyran-4-yl)methanamine in EXAMPLE 1F.

Example 245B 4-(4-{[2-(4-chlorophenyl)-4,4-dimethylcyclohex-1-en-1-yl]methyl}piperazin-1-yl)-2-(1H-indol-5-yloxy)-N-{[4-(methylamino)-3-nitrophenyl]sulfonyl}benzamide This example was prepared by substituting EXAMPLE 245A for EXAMPLE 1F in EXAMPLE 177. $^1$H NMR (500 MHz, dimethylsulfoxide-$d_6$) δ 11.12 (m, 2H), 8.54 (m, 2H), 7.76 (m, 1H), 7.51 (d, 1H), 7.35 (m, 4H), 7.06 (m, 3H), 6.85 (m, 2H), 6.63 (d, 1H), 6.37 (m, 1H), 6.15 (d, 1H), 3.01 (m, 4H), 2.96 (d, 3H), 2.71 (s, 2H), 2.15 (m, 6H), 1.94 (s, 2H), 1.38 (t, 2H), 0.92 (s, 6H)

Example 246

4-(4-{[2-(4-chlorophenyl)-4,4-dimethylcyclohex-1-en-1-yl]methyl}piperazin-1-yl)-2-(1H-indol-4-yloxy)-N-{[4-(methylamino)-3-nitrophenyl]sulfonyl}benzamide This example was prepared by substituting EXAMPLE 245A for EXAMPLE 1F and EXAMPLE 55B for EXAMPLE 26C in EXAMPLE 177. $^1$H NMR (500 MHz, dimethylsulfoxide-$d_6$) δ 11.32 (br s, 1H), 11.20 (br s, 1H), 8.54 (br s, 1H), 8.46 (s, 1H), 7.70 (dd, 1H), 7.53 (d, 1H), 7.34 (d, 2H), 7.26 (m, 1H), 7.14 (d, 1H), 7.04 (d, 2H), 6.94 (t, 1H), 6.87 (m, 1H), 6.67 (m, 1H), 6.37 (m, 1H), 6.25 (m, 2H), 3.02 (m, 4H), 2.97 (d, 3H), 2.72 (s, 2H), 2.16 (m, 6H), 1.94 (s, 2H), 1.38 (t, 2H), 0.93 (s, 6H).

Example 247

4-{4-[1-(4'-chloro-1,1'-biphenyl-2-yl)ethyl]piperazin-1-yl}-2-(1H-indol-4-yloxy)-N-({4-[(3-morpholin-4-ylpropyl)amino]-3-nitrophenyl}sulfonyl)benzamide This example was prepared by substituting EXAMPLE 175E for EXAMPLE 1E and EXAMPLE 7A for EXAMPLE 1F in EXAMPLE 1G. $^1$H NMR (500 MHz, PYRIDINE-$d_5$) δ ppm 12.45 (s, 1H), 9.24 (d, 1H), 8.96 (t, 1H), 8.26 (dd, 1H), 8.16 (d, 1H), 7.65 (d, 1H), 7.46 (m, 5H), 7.35 (t, 1H), 7.30 (d, 2H), 7.24 (d, 1H), 7.15 (t, 1H), 6.86 (d, 1H), 6.79 (d, 1H), 6.74 (m, 2H), 6.61 (d, 1H), 3.78 (t, 4H), 3.41 (q, 1H), 3.31 (m, 2H), 2.94 (m, 4H), 2.34 (m, 6H), 2.24 (m, 2H), 2.10 (m, 2H), 1.72 (m, 2H), 1.15 (d, 3H).

Example 248

4-(4-{[2-(4-chlorophenyl)-5-hydroxycyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide This example was prepared by substituting EXAMPLE 224D for EXAMPLE 1E in EXAMPLE 1G. $^1$H NMR (300 MHz, dimethylsulfoxide-$d_6$) δ 11.17 (s, 1H), 8.60 (m, 1H), 7.80 (dd, 1H), 7.52 (d, 1H), 7.38 (m, 4H), 7.11 (m, 4H), 6.87 (dd, 1H), 6.65 (dd, 1H), 6.40 (s, 1H), 6.13 (d, 1H), 4.59 (d, 1H), 3.85 (m, 2H), 3.28 (m, 6H), 3.03 (m, 2H), 2.72 (m, 2H), 2.18 (m, 3H), 1.87 (m, 3H), 1.53 (m, 5H), 1.26 (m, 7H).

Example 249

4-(4-{[2-(4-chlorophenyl)-5-morpholin-4-ylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide

Example 249A 8-chloro-1,4-dioxaspiro[4.5]dec-7-ene-7-carbaldehyde

This example was prepared by substituting 1,4-dioxaspiro[4.5]decan-8-one for 4-(tert-butyldimethylsilyloxy)cyclohexanone in EXAMPLE 224A.

Example 249B 8-(4-chlorophenyl)-1,4-dioxaspiro[4.5]dec-7-ene-7-carbaldehyde

This example was prepared by substituting EXAMPLE 249A for EXAMPLE 224A in EXAMPLE 224B.

Example 249C methyl 2-(1H-indol-5-yloxy)-4-(4-((8-(4-chlorophenyl)-1,4-dioxaspiro[4.5]dec-7-en-7-yl)methyl)piperazin-1-yl)benzoate This example was prepared by substituting EXAMPLE 249B for EXAMPLE 224B in EXAMPLE 224C.

Example 249D 2-(1H-indol-5-yloxy)-4-(4-((8-(4-chlorophenyl)-1,4-dioxaspiro[4.5]dec-7-en-7-yl)methyl)piperazin-1-yl)benzoic acid The title compound was prepared by substituting EXAMPLE 249C for EXAMPLE 224C in EXAMPLE 224D.

Example 249E 2-(1H-indol-5-yloxy)-4-(4-((8-(4-chlorophenyl)-1,4-dioxaspiro[4.5]dec-7-en-7-yl)methyl)piperazin-1-yl)-N-(3-nitro-4-((tetrahydro-2H-pyran-4-yl)methylamino)phenylsulfonyl)benzamide This example was prepared by substituting EXAMPLE 249D for EXAMPLE 1E in EXAMPLE 1G.

Example 249F 2-(1H-indol-5-yloxy)-4-(4-((2-(4-chlorophenyl)-5-oxocyclohex-1-enyl)methyl)piperazin-1-yl)-N-(3-nitro-4-((tetrahydro-2H-pyran-4-yl)methylamino)phenylsulfonyl)benzamide A mixture of EXAMPLE 249E (20 mg) and pyridinium p-toluenesulfonate (16.8 mg) in acetone/H$_2$O (1:1, 3 mL) was heated in a microwave to 135° C. for 8 minutes.

The mixture was diluted with dichloromethane (100 mL), washed with water and brine, and dried over Na$_2$SO$_4$. Filtration and evaporation of solvent gave the product.

Example 249G 4-(4-{[2-(4-chlorophenyl)-5-morpholin-4-ylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide To a mixture of EXAMPLE 249F (120 mg) in dichloromethane (2 mL) and methanol (0.5 mL) was added morpholine (37 mg) and 2-picoline borane complex (15.04 mg). The mixture was stirred overnight. The mixture was then diluted with dichloromethane (200 mL) and washed with aqueous NaHCO$_3$, water, and brine, and dried over Na$_2$SO$_4$. The residue, after evaporation of solvent, was dissolved in dichloromethane and chromatographed with 0-10% 7N NH$_3$ in 5% methanol in dichloromethane to give the title compound. $^1$H NMR (300 MHz, dimethylsulfoxide-d$_6$) δ 11.15 (s, 1H), 8.58 (m, 2H), 7.79 (dd, 1H), 7.53 (m, 1H), 7.35 (m, 4H), 7.17 (m, 1H), 7.07 (m, 2H), 6.85 (dd, 1H), 6.64 (dd, 1H), 6.39 (s, 1H), 6.13 (d, 1H), 3.84 (m, 2H), 3.58 (m, 5H), 3.01 (m, 5H), 2.63 (m, 6H), 2.10 (m, 14H), 1.61 (m, 3H), 1.26 (m, 3H).

Example 250

N-[(4-{[(1-aminocyclohexyl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide This example was prepared by substituting 1-(aminomethyl)cyclohexanamine, 2hydrochloric acid for (3S,4R)-4-amino-1-benzylpiperidin-3-ol, hydrochloric acid in EXAMPLE 187B. $^1$H NMR (500 MHz, dimethylsulfoxide-d$_6$) δ 11.04 (s, 1H), 8.47 (d, 1H), 8.39 (s, 1H), 7.79 (dd, 1H), 7.55 (d, 1H), 7.31-7.34 (m, 4H), 6.99-7.08 (m, 4H), 6.73 (d, 1H), 6.65 (dd, 1H), 6.33 (s, 1H), 6.12 (d, 1H), 3.55 (d, 2H), 2.94 (s, 4H), 2.71 (s, 2H), 2.14-2.17 (m, 6H), 1.95 (s, 2H), 1.50-1.64 (m, 8H), 1.36-1.39 (m, 2H), 0.92 (s, 6H).

Example 251

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(2-oxopyrrolidin-1-yl)ethyl]amino})phenyl)sulfonyl]benzamide This example was prepared by substituting 1-(2-aminoethyl)pyrrolidin-2-one for (3S,4R)-4-amino-1-benzylpiperidin-3-ol, hydrochloric acid in EXAMPLE 187B. 1H NMR (500 MHz, dimethylsulfoxide-d$_6$) δ 11.17 (s, 1H), 8.58-8.60 (m, 2H), 7.84 (dd, 1H), 7.51 (d, 1H), 7.39-7.32 (m, 2H), 7.33 (d, 2H), 7.18 (d, 1H), 7.12 (d, 1H), 7.03 (d, 2H), 6.87 (dd, 1H), 6.65 (dd, 1H), 6.40 (s, 1H), 6.17 (d, 1H), 3.53-3.56 (m, 2H), 3.45 (t, 2H), 3.39 (t, 2H), 3.04 (s, 4H), 2.74 (s, 2H), 2.11-2.18 (m, 8H), 1.94 (s, 2H), 1.83-1.90 (m, 2H), 1.38 (t, 2H), 0.92 (s, 6H).

Example 252

4-{4-[1-(4'-chloro-1,1'-biphenyl-2-yl)ethyl]piperazin-1-yl}-2-(1H-indol-5-yloxy)-N-({3-nitro-4-[(tetrahydro-2H-pyran-4-ylmethyl)amino]phenyl}sulfonyl)benzamide

Example 252A methyl 2-(1H-indol-5-yloxy)-4-(4-(1-(4'-chlorobiphenyl-2-yl)ethyl)piperazin-1-yl)benzoate The title compound was prepared as described in EXAMPLE 175D by replacing ethyl 2-(1H-indol-4-yloxy)-4-fluorobenzoate with EXAMPLE 26A.

Example 252B 2-(1H-indol-5-yloxy)-4-(4-(1-(4'-chlorobiphenyl-2-yl)ethyl)piperazin-1-yl)benzoic acid The title compound was prepared as described in EXAMPLE 175E by replacing EXAMPLE 175D with v 252A.

Example 252C

4-{4-[1-(4'-chloro-1,1'-biphenyl-2-yl)ethyl]piperazin-1-yl}-2-(1H-indol-5-yloxy)-N-({3-nitro-4-[(tetrahydro-2H-pyran-4-ylmethyl)amino]phenyl}sulfonyl)benzamide The title compound was prepared as described in EXAMPLE 175F by replacing EXAMPLE 175E with EXAMPLE 252B. $^1$H NMR (500 MHz, dimethylsulfoxide-d$_6$) δ 11.20 (s, 1H), 11.16 (s, 1H), 8.62 (t, 1H), 8.58 (d, 1H), 7.79 (dd, 1H), 7.48-7.54 (m, 2H), 7.45 (d, 2H), 7.35-7.41 (m, 3H), 7.25-7.29 (m, 3H), 7.15 (d, 1H), 7.08-7.13 (m, 2H), 6.86 (dd, 1H), 6.63 (dd, 1H), 6.38 (s, 1H), 6.13 (d, 1H), 3.85 (dd, 2H), 3.22-3.32 (m, 4H), 3.00 (s, 4H), 2.33 (s, 2H), 2.18 (s, 2H), 1.84-1.95 (m, 1H), 1.56-1.66 (m, 2H), 1.21-1.31 (m, 3H), 1.16 (d, 3H).

Example 253

4-(4-{1-[2-(4-chlorophenyl)-4,4-dimethylcyclohex-1-en-1-yl]ethyl}piperazin-1-yl)-2-(1H-indol-5-yloxy)-N-({3-nitro-4-[(tetrahydro-2H-pyran-4-ylmethyl)amino]phenyl}sulfonyl)benzamide

Example 253A 1-(2-(4-chlorophenyl)-4,4-dimethylcyclohex-1-enyl)ethanol

To a mixture of EXAMPLE 218A (3.52 g) in tetrahydrofuran (30 ml) was slowly added methylmagnesium chloride (3 M in tetrahydrofuran, 7.08 ml) at −78° C. After the addition was completed, the reaction mixture was stirred at 0° C. for 30 minutes and ice-water was added. The resulting mixture was extracted with dichloromethane and the organic layer was dried over $Na_2SO_4$ and concentrated. The residue was purified by flash chromatography, eluting with 0-100% dichloromethane in hexane to provide the title compound.

Example 253B 1-(2-(4-chlorophenyl)-4,4-dimethylcyclohex-1-enyl)ethanone

To a mixture of EXAMPLE 253A (1.18 g) in dichloromethane (20 ml) was slowly added Dess-Martin Periodinane (2.457 g). The reaction mixture was stirred at room temperature for 3 hours and diluted with ether. The resulting mixture was washed with aqueous NaOH and water. The organic layer was dried over $Na_2SO_4$ and concentrated. The residue was purified by flash chromatography, eluting with 0-100% dichloromethane in hexane to provide the title compound.

Example 253C tert-butyl 4-(1-(2-(4-chlorophenyl)-4,4-dimethylcyclohex-1-enyl)ethyl)piperazine-1-carboxylate EXAMPLE 253B (2.06 g) and tert-butyl piperazine-1-carboxylate (2.92 g) was treated with titanium(IV) isopropoxide (4.59 ml) at ambient temperature for 24 hours. Sodium cyanoborohydride (0.493 g) in methanol (10 ml) was added. The reaction mixture was stirred overnight and aqueous NaOH was added. The resulting mixture was diluted with ethyl acetate (300 ml). The precipitate was filtered off and washed with ethyl acetate. The organic layer was separated and washed with brine, dried over $Na_2SO_4$, filtered, and concentrated. The residue was dissolved in dichloromethane and loaded onto a silica gel column, eluted with 0-25% ethyl acetate in dichloromethane to provide the title compound.

Example 253D 1-(1-(2-(4-chlorophenyl)-4,4-dimethylcyclohex-1-enyl)ethyl)piperazine The title compound was prepared as described in EXAMPLE 175C by replacing EXAMPLE 175B with EXAMPLE 253C.

Example 253E ethyl 2-(1H-indol-5-yloxy)-4-(4-(1-(2-(4-chlorophenyl)-4,4-dimethylcyclohex-1-enyl)ethyl)piperazin-1-yl)benzoate The title compound was prepared as described in EXAMPLE 175D by replacing ethyl 2-(1H-indol-4-yloxy)-4-fluorobenzoate and EXAMPLE 175C with EXAMPLE 26A and EXAMPLE 253D, respectively.

Example 253F 2-(1H-indol-5-yloxy)-4-(4-(1-(2-(4-chlorophenyl)-4,4-dimethylcyclohex-1-enyl)ethyl)piperazin-1-yl)benzoic acid The title compound was prepared as described in EXAMPLE 175E by replacing EXAMPLE 175D with EXAMPLE 253E.

Example 253G 4-(4-{1-[2-(4-chlorophenyl)-4,4-dimethylcyclohex-1-en-1-yl]ethyl}piperazin-1-yl)-2-(1H-indol-5-yloxy)-N-({3-nitro-4-[(tetrahydro-2H-pyran-4-ylmethyl)amino]phenyl}sulfonyl)benzamide The title compound was prepared as described in EXAMPLE 177 by replacing EXAMPLE 26C with EXAMPLE 253F. $^1$H NMR (500 MHz, dimethylsulfoxide-$d_6$) δ 11.18 (s, 2H), 8.62 (t, 1H), 8.59 (d, 1H), 7.81 (dd, 1H), 7.52 (d, 1H), 7.38-7.44 (m, 2H), 7.34 (d, 2H), 7.17 (d, 1H), 7.11 (d, 1H), 7.01 (d, 2H), 6.87 (dd, 1H), 6.65 (dd, 1H), 6.40 (t, 1H), 6.13 (d, 1H), 3.85 (dd, 2H), 3.22-3.31 (m, 4H), 3.02 (s, 4H), 2.57-2.73 (m, 1H), 2.23 (s, 4H), 1.78-2.15 (m, 5H), 1.57-1.65 (m, 2H), 1.32-1.42 (m, 2H), 1.19-1.31 (m, 2H), 1.01 (d, 3H), 0.91 (d, 6H).

Example 254

4-(4-{1-[2-(4-chlorophenyl)-4,4-dimethylcyclohex-1-en-1-yl]ethyl}piperazin-1-yl)-2-(1H-indol-5-yloxy)-N-({4-[(4-methylpiperazin-1-yl)amino]-3-nitrophenyl}sulfonyl)benzamide The title compound was prepared as described in EXAMPLE 175F by replacing EXAMPLE 175E and EXAMPLE 1F with EXAMPLE 253F and EXAMPLE 174A. $^1$H NMR (500 MHz, dimethylsulfoxide-$d_6$) δ 11.15 (s, 1H), 9.19 (s, 1H), 8.54 (d, 1H), 7.85 (dd, 1H), 7.57 (d, 1H), 7.52 (d, 1H), 7.37-7.41 (m, 2H), 7.34 (d, 2H), 7.14 (d, 1H), 7.01 (d, 2H), 6.84 (dd, 1H), 6.62 (dd, 1H), 6.39 (s, 1H), 6.12 (d, 1H), 2.81-3.04 (m, 10H), 2.58-2.67 (m, 1H), 2.29-2.45 (m, 5H), 2.15-2.28 (m, 4H), 1.92-2.13 (m, 3H), 1.82 (d, 1H), 1.29-1.41 (m, 2H), 1.00 (d, 3H), 0.91 (d, 6H).

Example 255

4-{4-[(1R)-1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide The title compound was obtained by the separation of the racemic mixture of EXAMPLE 175F on a chiral HPLC. $^1$H NMR (500 MHz, dimethysulfoxide-$d_6$) δ 11.31 (1H, s), 11.25

(1H, s), 8.62 (1H, t), 8.50 (1H, d), 7.68 (1H, dd), 7.53 (2H, d), 7.46 (2H, d), 7.37 (1H, t), 7.24-7.31 (4H, m), 7.17 (1H, d), 7.12 (1H, dd), 7.07 (1H, d), 6.96 (1H, t), 6.69 (1H, dd), 6.42 (1H, d), 6.26 (2H, s), 3.85 (2H, dd), 3.21-3.33 (5H, m), 3.01 (4H, s), 2.29-2.39 (2H, m), 2.15-2.22 (2H, m), 1.83-1.94 (1H, m), 1.57-1.68 (2H, m), 1.22-1.31 (2H, m), 1.17 (3H, d).

Example 256

4-{4-[(1S)-1-(4'-chloro-1,1'-biphenyl-2-yl)ethyl] piperazin-1-yl}-2-(1H-indol-4-yloxy)-N-({3-nitro-4-[(tetrahydro-2H-pyran-4-ylmethyl)amino] phenyl}sulfonyl)benzamide The title compound was obtained by the separation of the racemic mixture of EXAMPLE 175F on a chiral HPLC. $^1$H NMR (500 MHz, dimethysulfoxide-$d_6$) δ 11.31 (1H, s), 11.25 (1H, s), 8.62 (1H, t), 8.50 (1H, d), 7.68 (1H, dd), 7.53 (2H, d), 7.46 (2H, d), 7.37 (1H, t), 7.24-7.31 (4H, m), 7.17 (1H, d), 7.12 (1H, dd), 7.07 (1H, d), 6.96 (1H, t), 6.69 (1H, dd), 6.42 (1H, d), 6.26 (2H, s), 3.85 (2H, dd), 3.21-3.33 (5H, m), 3.01 (4H, s), 2.29-2.39 (2H, m), 2.15-2.22 (2H, m), 1.83-1.94 (1H, m), 1.57-1.68 (2H, m), 1.22-1.31 (2H, m), 1.17 (3H, d).

Example 257

4-(4-{1-[2-(4-chlorophenyl)-4,4-dimethylcyclohex-1-en-1-yl]ethyl}piperazin-1-yl)-2-(1H-indol-5-yloxy)-N-({4-[(3-morpholin-4-ylpropyl)amino]-3-nitrophenyl}sulfonyl)benzamide The title compound was prepared as described in EXAMPLE 175F by replacing EXAMPLE 175E and EXAMPLE 1F with EXAMPLE 253F and EXAMPLE 7A. $^1$H NMR (500 MHz, dimethylsulfoxide-$d_6$) δ 8.79 (t, 1H), 8.57 (d, 1H), 7.80 (dd, 1H), 7.51 (d, 1H), 7.37-7.44 (m, 2H), 7.34 (d, 2H), 7.15 (d, 1H), 7.06 (d, 1H), 7.01 (d, 2H), 6.85 (dd, 1H), 6.63 (dd, 1H), 6.39 (s, 1H), 6.13 (d, 1H), 3.60 (t, 4H), 3.43 (q, 2H), 3.01 (s, 4H), 2.63 (d, 1H), 2.33-2.47 (m, 6H), 2.22 (d, 4H), 1.94-2.15 (m, 3H), 1.75-1.86 (m, 3H), 1.32-1.40 (m, 2H), 1.00 (d, 3H), 0.91 (s, 3H), 0.90 (s, 3H).

Example 258

4-(4-{1-[2-(4-chlorophenyl)-4,4-dimethylcyclohex-1-en-1-yl]ethyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide The title compound was prepared as described in EXAMPLE 175F by replacing EXAMPLE 175E and EXAMPLE 1F with EXAMPLE 253F and EXAMPLE 173C. $^1$H NMR (500 MHz, dimethylsulfoxide-$d_6$) δ 11.12 (s, 1H), 8.53 (d, 1H), 8.19 (d, 1H), 7.79 (dd, 1H), 7.52 (d, 1H), 7.32-7.40 (m, 4H), 6.99-7.12 (m, 4H), 6.81 (dd, 1H), 6.60 (dd, 1H), 6.37 (s, 1H), 6.13 (d, 1H), 3.92 (dd, 2H), 3.72 (s, 1H), 3.26-3.31 (m, 2H), 2.98 (s, 6H), 2.77 (s, 1H), 2.54-2.66 (m, 3H), 2.15-2.30 (m, 4H), 1.94-2.14 (m, 5H), 1.73-1.87 (m, 3H), 1.57-1.68 (m, 2H), 1.44-1.54 (m, 2H), 1.31-1.40 (m, 2H), 1.00 (d, 3H), 0.91 (d, 2H).

Example 259

4-(4-{[2-(4-chlorophenyl)-4,4-dimethylcyclohex-1-en-1-yl]methyl}piperazin-1-yl)-N-({4-[(cyclohexylmethyl)amino]-3-nitrophenyl}sulfonyl)-2-(H-indol-5-yloxy)benzamide Example 259A 4-(cyclohexylmethylamino)-3-nitrobenzenesulfonamide This example was prepared by substituting cyclohexylmethylamine for (tetrahydropyran-4-yl)methylamine in EXAMPLE 1F.

Example 259B 4-(4-{[2-(4-chlorophenyl)-4,4-dimethylcyclohex-1-en-1-yl]methyl}piperazin-1-yl)-N-({4-[(cyclohexylmethyl)amino]-3-nitrophenyl}sulfonyl)-2-(1H-indol-5-yloxy)benzamide This example was prepared by substituting EXAMPLE 259A for EXAMPLE 1F in EXAMPLE 177. $^1$H NMR (500 MHz, dimethylsulfoxide-$d_6$) δ 11.10 (s, 1H), 8.53 (m, 1H), 8.52 (d, 1H), 7.72 (dd, 1H), 7.44 (d, 1H), 7.32, (d, 1H), 7.31 (dd, 1H), 7.26 (d, 2H), 7.08 (d, 1H), 6.99 (d, 1H), 6.96 (d, 2H), 6.80 (dd, 1H), 6.58 (dd, 1H), 6.32 (s, 1H), 6.07 (d, 1H), 3.18 (t, 2H), 2.96 (br m, 4H), 2.65 (d, 2H), 2.06 (br m, 6H), 1.87 (s, 2H), 1.63 (m, 4H), 1.56 (m, 2H), 1.30 (t, 2H), 1.11 (m, 2H), 0.91 (m, 3H), 0.85 (s, 6H).

Example 260

4-(4-{[2-(4-chlorophenyl)-4,4-dimethylcyclohex-1-en-1-yl]methyl}piperazin-1-yl)-2-(1H-indol-5-yloxy)-N-{[4-(morpholin-4-ylamino)-3-nitrophenyl] sulfonyl}benzamide Example 260A 4-(morpholinoamino)-3-nitrobenzenesulfonamide This example was prepared by substituting morpholin-4-amine for 1-(2-methoxy-ethyl)-piperidin-4-ylamine in EXAMPLE 189A.

Example 260B 4-(4-{[2-(4-chlorophenyl)-4,4-dimethylcyclohex-1-en-1-yl]methyl}piperazin-1-yl)-2-(1H-indol-5-yloxy)-N-{[4-(morpholin-4-ylamino)-3-nitrophenyl] sulfonyl}benzamide This example was prepared by substituting EXAMPLE 26C for EXAMPLE 1E and EXAMPLE 260A for EXAMPLE 1F in EXAMPLE 1G. $^1$H NMR (500 MHz, pyridine-$d_5$) δ 9.28 (s, 1H), 9.25 (d, 1H), 8.39 (dd, 1H), 8.18 (d, 1H), 7.66 (d, 1H), 7.52-7.56 (m, 2H), 7.40-7.46 (m, 3H), 7.09 (dd, 1H), 7.06 (d, 2H), 6.73 (dd, 1H), 6.60 (s, 1H), 6.54 (d, 1H), 3.87 (s, 2H), 3.74 (d, 2H), 3.00-3.08 (m, 4H), 2.89 (d, 4H), 2.76 (s, 2H), 2.24 (t, 2H), 2.08-2.15 (m, 4H), 1.97 (s, 2H), 1.38 (t, 2H), 0.93 (s, 6H).

Example 261

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-3-ylmethyl)amino]phenyl}sulfonyl)benzamide The title compound was prepared as described in EXAMPLE 175F by replacing EXAMPLE 175E and EXAMPLE 1F with EXAMPLE 26C and EXAMPLE 180A, respectively. $^1$H NMR (500 MHz, dimethylsulfoxide-$d_6$) δ 11.17 (s, 2H), 8.45-8.70 (m, 2H), 7.80 (dd, 1H), 7.51 (d, 1H), 7.38-7.42 (m, 2H), 7.33 (d, 2H), 7.16 (d, 1H), 7.07 (d, 1H), 7.03 (d, 2H), 6.86 (dd, 1H), 6.65 (dd, 1H), 6.39 (s, 1H), 6.14 (d, 1H), 3.79 (dd, 1H), 3.68-3.75 (m, 1H), 3.23-3.38 (m, 3H), 3.18 (dd, 1H), 3.03 (s, 4H), 2.72 (s, 2H), 2.07-2.21 (m, 6H), 1.79-1.96 (m, 4H), 1.57-1.64 (m, 1H), 1.41-1.51 (m, 1H), 1.37 (t, 2H), 1.22-1.33 (m, 1H), 0.92 (s, 6H).

Example 262

4-(4-{[2-(4-chlorophenyl)-4,4-dimethylcyclohex-1-en-1-yl]methyl}piperazin-1-yl)-2-(1H-indol-4-yloxy)-N-{[4-(morpholin-4-ylamino)-3-nitrophenyl]sulfonyl}benzamide This example was prepared by substituting EXAMPLE 55B for EXAMPLE 1E and EXAMPLE 260A for EXAMPLE 1F in EXAMPLE 1G. $^1$H NMR (500 MHz, pyridine-$d_5$) δ 12.45 (s, 1H), 9.26 (s, 1H), 9.17 (d, 1H), 8.27 (dd, 1H), 8.17 (d, 1H), 7.61 (d, 1H), 7.48 (t, 1H), 7.45 (d, 2H), 7.39 (d, 1H), 7.05-7.13 (m, 3H), 6.71-6.81 (m, 3H), 6.67 (d, J=2.1 Hz, 1H), 3.87 (s, 2H), 3.61-3.78 (m, 2H), 2.99-3.08 (m, 4H), 2.89 (d, 4H), 2.76 (s, 2H), 2.25 (t, 2H), 2.08-2.16 (m, 4H), 1.97 (s, 2H), 1.39 (t, 2H), 0.94 (s, 6H).

Example 263

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(tetrahydro-2H-pyran-4-ylamino)phenyl]sulfonyl}benzamide This example was prepared by substituting tetrahydro-2H-pyran-4-amine, hydrochloric acid for (3S,4R)-4-amino-1-benzylpiperidin-3-ol, hydrochloric acid in EXAMPLE 187B. $^1$H NMR (500 MHz, dimethylsulfoxide-$d_6$) δ 11.15 (s, 2H), 8.57 (d, 1H), 8.24 (d, 1H), 7.78 (dd, 1H), 7.49 (d, 1H), 7.37-7.40 (m, 3H), 7.32 (d, 2H), 7.12-7.16 (m, 2H), 7.22 (d, 2H), 6.84 (dd, 1H), 6.64 (dd, 1H), 6.37 (s, 1H), 6.13 (d, 1H), 3.85-3.87 (m, 2H), 3.45 (t, 2H), 3.02 (s, 4H), 2.71 (s, 2H), 2.11-2.16 (m, 7H), 1.87-1.93 (m 4H), 1.58-1.62 (m, 2H), 1.36 (t, 2H), 0.90 (s, 6H).

Example 264

4-(4-{[2-(4-chlorophenyl)-4,4-dimethylcyclohex-1-en-1-yl]methyl}piperazin-1-yl)-2-(1H-indol-5-yloxy)-N-[(4-{[(3-methyloxetan-3-yl)methyl]amino}-3-nitrophenyl)sulfonyl]benzamide This example was prepared by substituting (3-methyloxetan-3-yl)methanamine for (3S,4R)-4-amino-1-benzylpiperidin-3-ol, hydrochloric acid in EXAMPLE 187B. $^1$H NMR (500 MHz, dimethylsulfoxide-$d_6$) δ 11.14 (s, 2H), 8.67 (t, 1H), 8.58 (d, 1H), 7.81 (dd, 1H), 7.49 (d, 1H), 7.36-7.39 (m, 2H), 7.32 (d, 2H), 7.12-7.14 (m, 2H), 7.02 (d, 2H), 6.84 (dd, 1H), 6.63 (dd, 1H), 6.37 (s, 1H), 6.13 (d, 1H), 4.44 (d, 2H), 4.30 (d, 2H), 3.55 (d, 2H), 3.01 (s, 4H), 2.70 (s, 2H), 2.11-2.15 (m, 7H), 1.93 (s 3H), 1.36 (t, 2H), 0.90 (s, 6H).

Example 265

4-(4-{[2-(4-chlorophenyl)-4,4-dimethylcyclohex-1-en-1-yl]methyl}piperazin-1-yl)-2-(1H-indol-5-yloxy)-N-({4-[(4-methoxycyclohexyl)amino]-3-nitrophenyl}sulfonyl)benzamide This example was prepared by substituting 4-methoxycyclohexanamine for (3S,4R)-4-amino-1-benzylpiperidin-3-ol, hydrochloric acid in EXAMPLE 187B. $^1$H NMR (500 MHz, dimethylsulfoxide-$d_6$) δ 11.16 (s, 2H), 8.83 (d, 1H), 8.30 (d, 1H), 7.79 (dd, 1H), 7.50 (d, 1H), 7.37-7.41 (m, 2H), 7.33 (d, 2H), 7.10-7.14 (m, 2H), 7.03 (d, 2H), 6.85 (dd, 1H), 6.65 (dd, 1H), 6.39 (s, 1H), 6.14 (d, 1H), 3.24-3.25 (m, 5H), 3.03 (s, 4H), 2.72 (s, 2H), 2.14-2.17 (m, 8H), 1.92 (m 3H), 1.63-1.65 (m, 2H), 1.38 (t, 2H), 0.92 (s, 6H).

Example 266

4-(4-{[2-(4-chlorophenyl)-4,4-dimethylcyclohex-1-en-1-yl]methyl}piperazin-1-yl)-N-[(4-{[3-(1,1-dioxidothiomorpholin-4-yl)propyl]amino}-3-nitrophenyl)sulfonyl]-2-(1H-indol-5-yloxy)benzamide This example was prepared by substituting EXAMPLE 187A for 4-chloro-3-nitrobenzene sulfonamide and 4-(3-aminopropyl)thiomorpholine-1,1-dioxide for 1-(2-methoxyethyl)-piperidin-4-ylamine in EXAMPLE 189A. $^1$H NMR (400 MHz, dimethylsulfoxide-$d_6$) δ 11.16 (s, 1H), 8.86 (t, 1H), 8.58 (d, 1H), 7.82 (dd, 1H), 7.50 (t, 1H), 7.40 (m, 2H), 7.33 (d, 2H), 7.15 (m, 1H), 7.04 (m, 3H), 6.85 (dd, 1H), 6.64 (m, 1H), 6.38 (m, 1H), 6.13 (m, 1H), 3.43 (m, 2H), 3.12 (m, 4H), 3.01 (m, 4H), 2.89 (m, 4H), 2.72 (m, 2H), 2.57 (t, 2H), 2.16 (m, 6H), 1.94 (m, 2H), 1.78 (t, 2H), 1.37 (t, 2H), 0.93 (s, 6H).

Example 267

4-(4-{[2-(4-chlorophenyl)-4,4-dimethylcyclohex-1-en-1-yl]methyl}piperazin-1 yl)-2-(1H-indol-5-yloxy)-N-[(3-nitro-4-{[2-(2-oxopiperidin-1-yl)ethyl]amino}phenyl)sulfonyl]benzamide This example was prepared by substituting EXAMPLE 187A for 4-chloro-3-nitrobenzene sulfonamide and 1-(2-aminoethyl)piperidine-2-one for 1-(2-methoxy-ethyl)-piperidin-4-ylamine in EXAMPLE 189A. $^1$H NMR (400 MHz, dimethylsulfoxide-$d_6$) δ 11.12 (s, 1H), 8.61 (m, 1H), 8.52 (m, 1H), 7.78 (d, 1H), 7.51 (d, 1H), 7.37 (m, 2H), 7.33 (d, 2H), 7.10 (m, 2H), 7.04 (d, 2H), 6.81 (m, 1H), 6.61 (d, 1H), 6.37 (s, 1H), 6.13 (d, 1H), 3.52 (m, 4H), 3.28 (t, 2H), 3.00 (m, 4H), 2.71 (m, 2H), 2.17 (m, 8H), 1.94 (m, 2H), 1.63 (m, 4H), 1.38 (t, 2H), 0.92 (s, 6H).

Example 268

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(2-oxoimidazolidin-1-yl)ethyl]amino}phenyl)sulfonyl]benzamide This example was prepared by substituting EXAMPLE 187A for 4-chloro-3-nitrobenzene sulfonamide and 1-(2- aminoethyl)-2-imidazolidone for 1-(2-methoxy-ethyl)-piperidin-4-ylamine in EXAMPLE 189A. $^1$H NMR (400 MHz, dimethylsulfoxide-d$_6$) δ 11.17 (s, 1H), 8.60 (t, 1H), 8.56 (d, 1H), 7.81 (dd, 1H), 7.50 (m, 1H), 7.39 (m, 2H), 7.33 (d, 2H), 7.15 (m, 1H), 7.08 (d, 1H), 7.02 (d, 2H), 6.85 (dd, 1H), 6.65 (m, 1H), 6.39 (m, 2H), 6.15 (m, 1H), 3.51 (m, 2H), 3.39 (t, 2H), 3.30 (m, 2H), 3.21 (t, 2H), 3.03 (m, 4H), 2.72 (m, 2H), 2.14 (m, 6H), 1.93 (m, 2H), 1.37 (t, 2H), 0.92 (s, 6H).

Example 269

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2-pyridin-4-ylethyl)amino]phenyl}sulfonyl)benzamide This example was prepared by substituting 4-(2-aminoethyl)pyridine for 1-(2-methoxyethyl)-piperidin-4-ylamine and EXAMPLE 187A for 4-chloro-3-nitrobenzenesulfonamide in EXAMPLE 189A, except the material was purified by preparative HPLC on a Phenomenex Luna C8(2) 5 um 100 Å AXIA column (30 mm×75 mm). A gradient of acetonitrile and 0.1% trifluoroacetic acid in water was used, at a flow rate of 50 mL/minute (0-0.5 minutes 10% acetonitrile, 0.5-6.0 minutes linear gradient 10-100% acetonitrile, 6.0-7.0 minutes 100% acetonitrile, 7.0-8.0 minutes linear gradient 100-10% acetonitrile) to isolate the title compound as the bis trifluoroacetic acid salt. $^1$H NMR (300 MHz, dimethylsulfoxide-d$_6$) δ 11.45 (br s, 1H), 11.18 (br s, 1H), 8.77 (d, 2H), 8.61 (t, 1H), 8.60 (d, 1H), 7.86 (dd, 1H), 7.84 (d, 2H), 7.54 (d, 1H), 7.43-7.37 (m, 4H), 7.22 (d, 1H), 7.15 (d, 1H), 7.08 (d, 2H), 6.85 (dd, 1H), 6.70 (dd, 1H), 6.38 (t, 1H), 6.22 (d, 1H), 3.77 (q, 2H), 3.68-3.54 (m, 4H), 3.27 (m, 2H), 3.16 (t, 2H), 3.00 (m, 2H), 2.74 (m, 2H), 2.18 (m, 2H), 2.01 (d, 2H), 1.45 (t, 2H), 0.94 (s, 6H).

Example 270

4-(4-{[2-(4-chlorophenyl)-4,4-dimethylcyclohex-1-en-1-yl]methyl}piperazin-1-yl)-2-(1H-indol-5-yloxy)-N-[(4-morpholin-4-yl-3-nitrophenyl)sulfonyl]benzamide This example was prepared by substituting EXAMPLE 187A for 4-chloro-3-nitrobenzenesulfonamide and morpholine for 1-(2-methoxy-ethyl)-piperidin-4-ylamine in EXAMPLE 189A, except the crude material was purified by preparative HPLC using a C18 column, 250×50 mm, 10μ, and eluting with a gradient of 20-100% CH$_3$CN vs. 0.1% trifluoroacetic acid in water, giving the title compound as a trifluoroacetate salt. The salt was dissolved in dichloromethane (6 mL) and was washed with 50% aqueous NaHCO$_3$. The organic layer was dried over anhydrous Na$_2$SO$_4$, filtered, and concentrated to give the title compound. $^1$H NMR (500 MHz, dimethylsulfoxide-d$_6$) δ 11.17 (s, 1H), 8.31 (d, 1H), 7.87 (dd, 1H), 7.53 (d, 1H), 7.41 (m, 2H), 7.33 (d, 2H), 7.24 (d, 1H), 7.16 (s, 1H), 7.02 (d, 2H), 6.85 (dd, 1H), 6.64 (dd, 1H), 6.40 (s, 1H), 6.14 (s, 1H), 3.69 (t, 4H), 3.13 (t, 4H), 3.03 (br s, 4H), 2.75 (s, 2H), 2.19 (br s, 4H), 2.14 (br t, 2H), 1.95 (s, 2H), 1.38 (t, 2H), 0.92 (s, 6H).

Example 271

4-(4-{[2-(4-chlorophenyl)-4,4-dimethylcyclohex-1-en-1-yl]methyl}piperazin-1-yl)-2-(1H-indol-5-yloxy)-N-{[4-(4-methoxypiperidin-1-yl)-3-nitrophenyl]sulfonyl}benzamide This example was prepared by substituting EXAMPLE 187A for 4-chloro-3-nitrobenzenesulfonamide and 4-methoxy-piperidine for 1-(2-methoxy-ethyl)-piperidin-4-ylamine in EXAMPLE 189A, except the crude material was purified by preparative HPLC using a C18 column, 250×50 mm, 10μ, and eluting with a gradient of 20-100% CH$_3$CN vs. 0.1% trifluoroacetic acid in water, giving the product as a trifluoroacetate salt. The salt was dissolved in dichloromethane (6 mL) and washed with 50% aqueous NaHCO$_3$. The organic layer was dried over anhydrous Na$_2$SO$_4$, filtered, and concentrated to give the title compound. $^1$H NMR (500 MHz, dimethylsulfoxide-d$_6$) 611.17 (s, 1H), 8.28 (d, 1H), 7.81 (dd, 1H), 7.53 (d, 1H), 7.41 (m, 2H), 7.33 (d, 2H), 7.22 (d, 1H), 7.16 (s, 1H), 7.04 (d, 2H), 6.86 (dd, 1H), 6.64 (dd, 1H), 6.40 (s, 1H), 6.14 (s, 1H), 3.42 (m, 1H), 3.27 (s, 3H), 3.25 (m, 2H), 3.00 (m, 6H), 2.73 (s, 2H), 2.18 (br s, 4H), 2.13 (br t, 2H), 1.94 (s, 2H), 1.91 (m, 2H), 1.56 (m, 2H), 1.38 (t, 2H), 0.92 (s, 6H).

Example 272

4-(4-{[2-(4-chlorophenyl)-5-pyrrolidin-1-ylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide This example was prepared by substituting pyrrolidine for morpholine in EXAMPLE 249G. $^1$H NMR (300 MHz, dimethylsulfoxide-d$_6$) δ 11.04 (s, 1H), 8.44 (d, 1H), 8.42 (m, 1H), 7.70 (dd, 1H), 7.55 (d, 1H), 7.37 (d, 2H), 7.32 (m, 2H), 7.09 (d, 2H), 7.00 (d, 1H), 6.89 (d, 1H), 6.76 (d, 1H), 6.54 (d, 1H), 6.32 (d, 1H), 6.13 (d, 1H), 3.83 (m, 3H), 3.06 (m, 15H), 2.23 (m, 6H), 1.84 (m, 6H), 1.62 (m, 4H), 1.24 (m, 3H).

Example 273

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(3-oxopiperazin-1-yl)ethyl]amino}phenyl)sulfonyl]benzamide

Example 273A 3-nitro-4-[2-(3-oxo-piperazin-1-yl)-ethylamino]-benzenesulfonamide 4-(2-Amino-ethyl)-piperazin-2-one (5.51 g) and triethylamine (9.07 mL, 6.59 g) were added to 1,4-dioxane (100 mL), N,N-dimethylacetamide (20 mL), and water (10 mL) and mixed until dissolved. 4-Chloro-3-nitrobenzenesulfonamide (7.00 g) was added, and the mixture was heated to 90° C. for 16 hours. The mixture was cooled and the solvent was removed under vacuum. The crude material was purified by recrystallization from 20% methanol in dichloromethane with subsequent washing of the recrystallized solid with 10% methanol in dichloromethane followed by washing with 100% dichloromethane.

Example 273B 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(3-oxopiperazin-1-yl)ethyl]amino}phenyl)sulfonyl]benzamide This example was prepared by substituting EXAMPLE 26C for EXAMPLE 1E and EXAMPLE 273A for EXAMPLE 1F in EXAMPLE 1G. $^1$H NMR (300 MHz, dimethylsulfoxide-d$_6$) δ 11.15 (br s, 1H), 8.73 (t, 1H), 8.58 (d, 1H), 7.82 (dd, 1H), 7.76 (br s, 1H), 7.51 (d, 1H), 7.42-7.38 (m, 2H), 7.34 (d, 2H), 7.16 (d, 1H), 7.06-7.01 (m, 3H), 6.85 (dd, 1H), 6.65 (dd, 1H), 6.38 (t, 1H), 6.15 (d, 1H), 3.48 (q, 2H), 3.17 (m, 2H), 3.04 (m, 6H), 2.72 (br s, 2H), 2.70-2.62 (m, 2H), 2.16 (m, 8H), 1.95 (br s, 2H), 1.38 (t, 2H), 0.92 (s, 6H).

Example 274

4-[4-({4'-chloro-4-[2-(dimethylamino)ethoxy]-1,1'-biphenyl-2-yl}methyl)piperazin-1-yl]-2-(1H-indol-4-yloxy)-N-({4-[(4-methylpiperazin-1-yl)amino]-3-nitrophenyl}sulfonyl)benzamide This example was prepared by substituting EXAMPLE 125D for EXAMPLE 26C and EXAMPLE 174A for EXAMPLE 1F in EXAMPLE 177. $^1$H NMR (400 MHz, dimethylsulfoxide-d$_6$) δ 11.62 (s, 1H), 11.33 (s, 1H), 9.55 (d, 1H), 8.49 (d, 1H), 7.74 (dd, 1H), 7.55 (m, 5H), 7.35 (m, 2H), 7.30 (m, 1H), 7.19 (dd, 2H), 6.96 (m, 2H), 6.73 (dd, 1H), 6.40 (m, 1H), 6.33 (m, 1H), 6.24 (s, 1H), 4.37 (m, 2H), 3.53 (m, 8H), 3.30 (m, 8H), 3.23 (m, 4H), 2.90 (s, 6H), 2.84 (s, 3H).

Example 275

4-(4-{[2-(4-chlorophenyl)-4,4-dimethylcyclohex-1-en-1-yl]methyl}piperazin-1-yl)-N-[(4-{[(1,1-dioxidotetrahydrothien-3-yl)methyl]amino}-3-nitrophenyl)sulfonyl]-2-(1H-indol-5-yloxy)benzamide This example was prepared by substituting EXAMPLE 187A for 4-chloro-3-nitrobenzene sulfonamide and (1,1-dioxidotetrahydrothien-3-yl)methylamine hydrochloride for 1-(2-methoxy-ethyl)-piperidin-4-ylamine in EXAMPLE 189A. $^1$H NMR (400 MHz, dimethylsulfoxide-d$_6$) δ 11.17 (s, 1H), 8.72 (t, 1H), 8.59 (d, 1H), 7.82 (dd, 1H), 7.51 (d, 1H), 7.40 (m, 2H), 7.33 (d, 2H), 7.16 (m, 2H), 7.03 (d, 2H), 6.86 (dd, 1H), 6.65 (dd, 1H), 6.40 (m, 1H), 6.14 (d, 1H), 3.55 (t, 2H), 3.28 (m, 1H), 3.23 (m, 1H), 3.05 (m, 5H), 2.91 (m, 1H), 2.74 (m, 3H), 2.27 (m, 1H), 2.15 (m, 6H), 1.95 (m, 2H), 1.86 (m, 1H), 1.38 (t, 2H), 0.91 (s, 6H).

Example 276

4-(4-{[2-(4-chlorophenyl)-4,4-dimethylcyclohex-1-en-1-yl]methyl}piperazin-1-yl)-N-({4-[(1,1-dioxidotetrahydrothien-3-yl)amino]-3-nitrophenyl}sulfonyl)-2-(1H-indol-5-yloxy)benzamide This example was prepared by substituting EXAMPLE 187A for 4-chloro-3-nitrobenzene sulfonamide and 1,1-dioxidotetrahydrothiene-3ylamine for 1-(2-methoxy-ethyl)-piperidin-4-ylamine in EXAMPLE 189A. $^1$H NMR (400 MHz, dimethylsulfoxide-d$_6$) δ 11.20 (bs, 1H), 11.15 (s, 1H), 8.59 (d, 1H), 8.50 (d, 1H), 7.86 (dd, 1H), 7.50 (d, 1H), 7.39 (m, 2H), 7.33 (d, 2H), 7.19 (d, 1H), 7.14 (m, 1H), 7.03 (d, 2H), 6.85 (dd, 1H), 6.65 (dd, 1H), 6.39 (m, 1H), 6.15 (d, 1H), 4.63 (m, 1H), 3.64 (m, 1H), 3.37 (m, 2H), 3.20 (m, 1H), 3.03 (m, 4H), 2.73 (m, 2H), 2.57 (m, 1H), 2.28 (m, 1H), 2.15 (m, 6H), 1.95 (m, 2H), 1.38 (t, 2H), 0.91 (s, 6H).

Example 277

4-(4-{[2-(4-chlorophenyl)-4,4-dimethylcyclohex-1-en-1-yl]methyl}piperazin-1-yl)-2-(1H-indol-5-yloxy)-N-{[4-[(tetrahydro-2H-pyran-4-ylmethyl)amino]-3-(trifluoromethyl)phenyl]sulfonyl}benzamide Example 277A 4-((tetrahydro-2H-pyran-4-yl)methylamino)-3-(trifluoromethyl)benzenesulfonamide A mixture of 4-fluoro-3-(trifluoromethyl)benzenesulfonamide (1.056 g), (tetrahydro-2H-pyran-4-yl)methanamine (0.5 g) and N,N-diisopropylethylamine (1.68 g) in anhydrous dimethylsulfoxide (15 mL) solution was heated at 90° C. overnight. The reaction mixture was cooled to room temperature and diluted with ethyl acetate. The organic phase was washed with water, brine, dried over anhydrous sodium sulfate, filtered and concentrated to afford the title compound.

Example 277B 4-(4-{[2-(4-chlorophenyl)-4,4-dimethylcyclohex-1-en-1-yl]methyl}piperazin-1-yl)-2-(1H-indol-5-yloxy)-N-{[4-[(tetrahydro-2H-pyran-4-ylmethyl)amino]-3-(trifluoromethyl)phenyl]sulfonyl}benzamide This example was prepared by substituting EXAMPLE 277A for EXAMPLE 1F in EXAMPLE 177. $^1$H NMR (400 MHz, dimethylsulfoxide-d$_6$) δ 11.22 (s, 1H), 11.20 (s, 1H), 7.91 (d, 1H), 7.76 (dd, 1H), 7.55 (d, 1H). 7.41 (m, 4H), 7.20 (m, 1H) 7.08 (d, 2H), 6.88 (m, 2H), 6.70 (dd, 1H), 6.58 (m, 1H), 6.42 (m, 1H), 6.19 (m, 1H), 3.83 (m, 2H), 3.56 (m, 4H), 3.25 (m, 4H), 3.15 (m, 2H), 2.99 (m, 2H), 2.74 (m, 2H), 2.18 (m, 2H), 2.02 (m, 2H), 1.84 (m, 1H), 1.57 (m, 2H), 1.44 (m, 2H), 1.19 (m, 2H), 0.93 (s, 6H).

Example 278

4-(4-{[2-(4-chlorophenyl)-4,4-dimethylcyclohex-1-en-1-yl]methyl}piperazin-1-yl)-N-({4-[2-(1,3-dioxolan-2-yl)ethyl]-3-nitrophenyl}sulfonyl)-2-(1H-indol-5-yloxy)benzamide A mixture of EXAMPLE 187A (0.079 g), dicyclohexyl(2',6'-dimethoxybiphenyl-2-yl)phosphine (0.016 g), and palladium acetate (0.0045 g) in tetrahydrofuran (1 mL) was stirred at room temperature for 5 minutes. To this mixture was added (2-(1,3-dioxolan-2-yl)ethyl)zinc(II) bromide (0.6 mL). The reaction mixture was stirred overnight. The solvent was removed, and the residue was purified by reverse phase Prep HPLC. The desired fractions were combined, and the organic solvent was partially removed. The resulting mixture was treated with saturated aqueous NaHCO$_3$, extracted with ethyl acetate, dried over MgSO$_4$, filtered, and concentrated to give the title compound. $^1$H NMR (500 MHz, dimethylsulfoxide-d$_6$) δ 11.14 (s, 1H), 8.37 (s, 1H), 8.00 (s, 1H), 7.55 (br s., 1H), 7.52 (d, 1H), 7.33-7.39 (m, 4H), 7.08 (br s, 1H), 7.04 (d, 2H), 6.83 (dd, 1H), 6.62 (d, 1H), 6.38 (s, 1H), 6.15 (d, 1H), 4.85 (t, 1H), 3.87-3.89 (m, 2H), 3.76-3.79 (m, 2H), 3.04 (s, 4H), 2.91-2.94 (m, 2H), 2.11-2.15 (m, 4H), 1.88-1.91 (s, 4H), 1.39 (t, 2H), 0.92 (s, 6H).

Example 279

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(tetrahydro-2H-pyran-4-yl-methoxy)phenyl]sulfonyl}benzamide

Example 279A 3-nitro-4-((tetrahydro-2H-pyran-4-yl)methoxy)benzenesulfonamide (Tetrahydro-2H-pyran-4-yl)methanol (2.0 g) in tetrahydrofuran (20 mL) was treated with 60% NaH (1.377 g). The mixture was stirred for 20 minutes at the room temperature. To this mixture was added 4-fluoro-3-nitrobenzenesulfonamide (2.84 g) portionwise. The reaction was stirred for another 2 hours. The mixture was poured into water, neutralized with 10% HCl, and extracted with ethyl acetate three times. The combined organic layers were washed with brine, dried over MgSO$_4$, filtered, and concentrated. The residue was purified with flash column chromatography on silica gel eluting with 20%-60% ethyl acetate in hexanes.

Example 279B 4-(4-{[2-(4-chlorophenyl)-4,4-dimethylcyclohex-1-en-1-yl]methyl}piperazin-1-yl)-2-(1H-indol-5-yloxy)-N-{[3-nitro-4-(tetrahydro-2H-pyran-4-yl-methoxy)phenyl]sulfonyl}benzamide This example was prepared by substituting EXAMPLE 279A for EXAMPLE 1F in EXAMPLE 177. $^1$H NMR (500 MHz, dimethylsulfoxide-d$_6$) δ 11.16 (s, 1H), 8.38 (d, 1H), 8.05 (dd, 1H), 7.51 (d, 1H), 7.38-7.41 (m, 3H), 7.34 (d, 1H), 7.15 (d, 1H), 7.04 (d, 2H), 6.85 (dd, 1H), 6.65 (dd, 1H), 6.39 (s, 1H), 6.15 (d, 1H), 4.08 (d, 2H), 3.88 (dd, 2H), 3.04 (s, 4H), 2.77 (s, 2H), 2.12-2.22 (m, 4H), 1.95 (br s, 2H), 1.64 (dd, 2H), 1.36-1.39 (m, 2H), 0.92 (s, 6H).

Example 280

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[2-(3-oxopiperazin-1-yl)ethyl]amino}phenyl)sulfonyl]benzamide This example was prepared by substituting EXAMPLE 55B for EXAMPLE 1E and EXAMPLE 273A for EXAMPLE 1F in EXAMPLE 1G. $^1$H NMR (300 MHz, dimethylsulfoxide-d$_6$) δ 11.24 (br s, 1H), 8.72 (t, 1H), 8.51 (d, 1H), 7.76 (br s, 1H), 7.72 (dd, 1H), 7.53 (d, 1H), 7.34 (d, 2H), 7.28 (t, 1H), 7.18 (d, 1H), 7.04 (d, 2H), 6.97 (t, 2H), 6.70 (dd, 1H), 6.43 (d, 1H), 6.28-6.23 (m, 2H), 3.48 (q, 2H), 3.17 (m, 2H), 3.04 (m, 6H), 2.70 (br s, 2H), 2.68-2.63 (m, 2H), 2.16 (m, 8H), 1.95 (br s, 2H), 1.38 (t, 2H), 0.92 (s, 6H).

Example 281

4-(4-{[2-(4-chlorophenyl)-4,4-dimethylcyclohex-1-en-1-yl]methyl}piperazin-1-yl)-2-(1H-indol-5-yloxy)-N-({4-[(1-methyl-5-oxopyrrolidin-3-yl)amino]-3-nitrophenyl}sulfonyl)benzamide This example was prepared by substituting EXAMPLE 187A for 4-chloro-3-nitrobenzenesulfonamide and 4-amino-1-methylpyrrolidin-2-one hydrochloride for 1-(2-methoxyethyl)-piperidin-4-ylamine in EXAMPLE 189A, except the crude was purified by preparative HPLC using a C18 column, 250×50 mm, 10μ, and eluting with a gradient of 20-100% CH$_3$CN vs. 0.1% trifluoroacetic acid in water, giving the product as a trifluoroacetate salt. The salt was dissolved in dichloromethane (6 mL) and washed with 50% aqueous NaHCO$_3$. The organic layer was dried over anhydrous Na$_2$SO$_4$, filtered, and concentrated to give the title compound. $^1$H NMR (500 MHz, dimethylsulfoxide-d$_6$) δ 11.14 (s, 1H), 8.56 (d, 1H), 8.34 (br d, 1H), 7.82 (dd, 1H), 7.53 (d, 1H), 7.39 (m, 2H), 7.33 (d, 2H), 7.11 (s, 1H), 7.04 (m, 3H), 6.83 (dd, 1H), 6.64 (dd, 1H), 6.38 (s, 1H), 6.15 (s, 1H), 4.45 (m, 1H), 3.80 (dd, 1H), 3.35 (m, 1H), 3.02 (br s, 4H), 2.81 (dd, 1H), 2.75 (s, 3H), 2.71 (s, 2H), 2.40 (dd, 1H), 2.15 (m, 6H), 1.94 (s, 2H), 1.38 (t, 2H), 0.92 (s, 6H).

Example 282

4-(4-{[2-(4-chlorophenyl)-4,4-dimethylcyclohex-1-en-1-yl]methyl}piperazin-1-yl)-2-(1H-indol-5-yloxy)-N-({4-[(1-methyl-6-oxopiperidin-3-yl)amino]-3-nitrophenyl}sulfonyl)benzamide This example was prepared by substituting EXAMPLE 187A for 4-chloro-3-nitrobenzenesulfonamide and 5-amino-1-methylpiperidin-2-one hydrochloride for 1-(2-methoxyethyl)-piperidin-4-ylamine in EXAMPLE 189A, except the crude was purified by preparative HPLC using a C18 column, 250×50 mm, 10 t, and eluting with a gradient of 20-100% CH$_3$CN vs. 0.1% trifluoroacetic acid in water, giving the product as a trifluoroacetate salt. The salt was dissolved in dichloromethane (6 mL) and washed with 50% aqueous NaHCO$_3$. The organic layer was dried over anhydrous Na$_2$SO$_4$ and concentrated to give the title compound. $^1$H NMR (500 MHz, dimethylsulfoxide-d$_6$) δ 11.16 (s, 1H), 8.58 (d, 1H), 8.31 (br d, 1H), 7.85 (dd, 1H), 7.53 (d, 1H), 7.39 (m, 2H), 7.33 (d, 2H), 7.25 (d, 1H), 7.14 (s, 1H), 7.03 (d, 2H), 6.85 (dd, 1H), 6.64 (dd, 1H), 6.39 (s, 1H), 6.14 (s, 1H), 4.22 (m, 1H), 3.57 (dd, 1H), 3.02 (br s, 4H), 2.84 (m, 1H), 2.83 (s, 3H), 2.72 (s, 2H), 2.36 (m, 2H), 2.16 (m, 6H), 2.05 (m, 2H), 1.94 (s, 2H), 1.38 (t, 2H), 0.92 (s, 6H).

Example 283

4-(4-{[2-(4-chlorophenyl)-4,4-dimethylcyclohex-1-en-1-yl]methyl}piperazin-1-yl)-2-(1H-indol-4-yloxy)-N-{[3-nitro-4-(piperidin-1-ylamino)phenyl]sulfonyl}benzamide

Example 283A 3-nitro-4-(piperidin-1-ylamino)benzenesulfonamide

This example was prepared by substituting piperidin-1-amine for (tetrahydro-2H-pyran-4-yl)methanamine in EXAMPLE 1F.

Example 283B 4-(4-{[2-(4-chlorophenyl)-4,4-dimethylcyclohex-1-en-1-yl]methyl}piperazin-1-yl)-2-(1H-indol-4-yloxy)-N-{[3-nitro-4-(piperidin-1-ylamino)phenyl]sulfonyl}benzamide This example was prepared by substituting EXAMPLE 283A for EXAMPLE 1F and EXAMPLE 55B for EXAMPLE 26C in EXAMPLE 177. $^1$H NMR (500 MHz, dimethylsulfoxide-d$_6$) δ 11.27 (brs, 1H), 11.33 (s, 1H), 9.14 (s, 1H), 8.48 (d, 1H), 7.66 (dd, 1H), 7.52 (t, 2H), 7.34 (d, 2H), 7.29 (t, 1H), 7.19 (d, 1H), 7.04 (d, 2H), 6.97 (t, 1H), 6.71 (dd, 1H), 6.41 (d, 1H), 6.28 (m, 2H), 3.05 (m, 4H), 2.78 (m, 6H), 2.17 (m, 6H), 1.95 (s, 2H), 1.67 (m, 6H), 1.38 (t, 2H), 0.93 (s, 6H).

Example 284

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(piperidin-1-ylamino)phenyl]sulfonyl}benzamide This example was prepared by substituting EXAMPLE 283A for EXAMPLE 1F in EXAMPLE 177. $^1$H NMR (500 MHz, dimethylsulfoxide-d$_6$) δ 11.28 (s, 1H), 11.11 (s, 1H), 9.02 (s, 1H), 8.50 (s, 1H), 7.79 (dd, 1H), 7.52 (m, 2H), 7.35 (m, 4H), 7.07 (m, 3H), 6.82 (m, 1H), 6.60 (m, 1H), 6.36 (m, 1H), 6.14 (m, 1H), 2.99 (m, 4H), 2.75 (m, 6H), 2.16 (m, 6H), 1.99 (m, 2H), 1.94 (m, 2H), 1.64 (m, 4H), 1.38 (t, 2H), 0.92 (s, 6H).

Example 285

4-(4-{[4-(4-chlorophenyl)-1-methyl-1H-pyrazol-5-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide Example 285A 4-(4-chlorophenyl)-1-methyl-1H-pyrazole-5-carbaldehyde 4-Bromo-1-methyl-1H-pyrazole-5-carbaldehyde (0.500 g), 4-chlorophenylboronic acid (0.455 g), tetrabutylammonium bromide (0.853 g), potassium carbonate (0.914 g) and palladium acetate (0.030 g) were stirred together in 5 mL of water and heated to 45° C. After stirring for 2.5 hours, the reaction was diluted with ethyl acetate (75 mL) and washed with water (25 mL), brine (50 mL), dried over magnesium sulfate, filtered and concentrated to give the crude material. The solid was chromatographed over silica gel (SF40-80) eluted using a gradient of 5% to 25% ethyl acetate/hexanes over 30 minutes.

Example 285B methyl 2-(1H-indol-5-yloxy)-4-(4-((4-(4-chlorophenyl)-1-methyl-1H-pyrazol-5-yl)methyl)piperazin-1-yl)benzoate This example was prepared by substituting EXAMPLE 285A for 4'-chlorobiphenyl-2 carboxaldehyde and methyl 2-(1H-indol-5-yloxy)-4-(piperazin-1-yl)benzoate for tert-butyl piperazine-1-carboxylate in EXAMPLE 1A.

Example 285C 2-(1H-indol-5-yloxy)-4-(4-((4-(4-chlorophenyl)-1-methyl-1H-pyrazol-5-yl)methyl)piperazin-1-yl)benzoic acid This example was prepared by substituting EXAMPLE 285B for EXAMPLE 1D in EXAMPLE 1E.

Example 285D 2-(1H-indol-5-yloxy)-4-(4-((4-(4-chlorophenyl)-1-methyl-1H-pyrazol-5-yl)methyl)piperazin-1-yl)-N-(3-nitro-4-((tetrahydro-2H-pyran-4-yl)methylamino)phenylsulfonyl)benzamide This example was prepared by substituting EXAMPLE 285C for EXAMPLE 1E in EXAMPLE 1G. $^1$H NMR (300 MHz, CDCL3) δ 10.30 (s, 1H), 8.85 (d, 1H), 8.50 (s, 1H), 8.30 (s, 1H), 8.12 (dd, 1H), 7.95 (d, 1H), 7.49 (s, 1H), 7.43 (d, 1H), 7.36-7.22 (m, 6H), 6.97 (dd, 1H), 6.87 (d, 1H), 6.53 (d, 2H), 6.08 (s, 1H), 4.08-3.98 (m, 2H), 3.92 (s, 3H), 3.55 (s, 2H), 3.42 (s, 2H), 3.33-3.19 (m, 2H), 3.08 (s, 4H), 2.38 (s, 4H), 1.98 (d, 1H), 1.72 (s, 2H), 1.52-1.33 (m, 2H).

Example 286

4-(4-{[2-(4-chlorophenyl)-4,4-dimethylcyclohex-1-en-1-yl]methyl}piperazin-1-yl)-2-(1H-indol-5-yloxy)-N-({4-[(3-methyloxetan-3-yl)methoxy]-3-nitrophenyl}sulfonyl)benzamide Example 286A 4-((3-methyloxetan-3-yl)methoxy)-3-nitrobenzenesulfonamide This example was prepared by substituting (3-methyloxetan-3-yl)methanol for (tetrahydro-2H-pyran-4-yl)methanol in EXAMPLE 279A.

Example 286B 4-(4-{[2-(4-chlorophenyl)-4,4-dimethylcyclohex-1-en-1-yl]methyl}piperazin-1-yl)-2-(1H-indol-5-yloxy)-N-({4-[(3-methyloxetan-3-yl)methoxy]-3-nitrophenyl}sulfonyl)benzamide This example was prepared by substituting EXAMPLE 286A for EXAMPLE 1F in EXAMPLE 177. $^1$H NMR (400 MHz, dimethylsulfoxide-d$_6$) δ 11.08 (s, 1H), 8.26 (d, 1H), 8.18 (d, 1H), 7.92 (m, 1H), 7.53 (m, 1H), 7.34 (m, 3H), 7.25 (m, 1H), 7.04 (m, 3H), 6.91 (m, 1H), 6.76 (m, 1H), 6.59 (m, 1H), 6.35 (m, 1H), 6.15 (d, 1H), 4.47 (d, 1H), 4.29 (d, 1H), 3.40 (m, 2H), 3.13 (m, 2H), 2.98 (m, 4H), 2.72 (m, 2H), 2.16 (m, 6H), 1.94 (m, 2H), 1.36 (m, 5H), 0.93 (s, 6H).

Example 287

4-(4-{[2-(4-chlorophenyl)-4,4-dimethylcyclohex-1-en-1-yl]methyl}piperazin-1-yl)-2-(H-indol-5-yloxy)-N-[(3-nitro-4-{[(1-oxidotetrahydro-2H-thiopyran-4-yl)methyl]amino}phenyl)sulfonyl]benzamide Example 287A 3-nitro-4-((tetrahydro-2H-thiopyran-4-yl)methylamino)benzenesulfonamide This example was prepared by substituting (tetrahydro-2H-thiopyran-4-yl)methanamine, hydrochloride for (tetrahydropyran-4-yl)methylamine in EXAMPLE 1F.

Example 287B 3-nitro-4-((1-oxidotetrahydro-2H-thiopyran-4-yl)methylamino)benzenesulfonamide EXAMPLE 287A (150 mg) was suspended in methanol (5 mL). The reaction mixture was cooled to 0° C., followed by the addition of Oxone® (220 mg) in water (3 mL).

The reaction mixture was stirred at room temperature for 2 hours. The precipitate was filtered and washed with $Na_2S_2O_3$ solution and water. The solid was dried in a vacuum oven overnight, and used in the next step without further purification.

Example 287C 4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(1-oxidotetrahydro-2H-thiopyran-4-yl)methyl]amino}phenyl)sulfonyl]benzamide This example was prepared by substituting EXAMPLE 287B for EXAMPLE 1F in EXAMPLE 177. $^1$H NMR (400 MHz, dimethylsulfoxide-$d_6$) δ 11.17 (s, 1H). 8.69 (t, 1H), 8.58 (d, 1H), 7.81 (dd, 1H), 7.51 (d, 1H), 7.40 (m, 2H), 7.33 (d, 2H), 7.15 (m, 2H), 7.03 (d, 2H), 6.86 (dd, 1H), 6.65 (dd, 1H), 6.40 (m, 1H), 6.13 (m, 1H), 3.38 (m, 4H), 3.05 (m, 6H), 2.73 (m, 2H), 2.11 (m, 8H), 1.95 (m, 3H), 1.67 (m, 2H), 1.38 (t, 2H), 0.90 (s, 6H).

Example 288

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1,3-thiazol-5-ylmethyl)amino]phenyl}sulfonyl)benzamide This example was prepared by substituting thiazol-5-ylmethanamine, hydrochloric acid for (3S,4R)-4-amino-1-benzylpiperidin-3-ol, hydrochloric acid in EXAMPLE 187B. $^1$H NMR (500 MHz, dimethylsulfoxide-$d_6$) δ 11.18 (s, 2H), 9.13 (t, 1H), 8.99 (s, 1H), 8.60 (d, 1H), 7.95 (s, 1H), 7.82 (dd, 1H), 7.50 (d, 1H), 7.39-7.42 (, 2H), 7.33 (d, 2H), 7.17 (d, 1H), 7.14 (d, 1H), 7.03 (d, 2H), 6.85 (dd, 1H), 6.64 (dd, 1H), 6.40 (s, 1H), 6.13 (d, 1H), 4.91 (d, 2H), 3.03 (s, 4H), 2.73 (s, 2H), 2.12-2.18 (m, 6H), 1.94 (s, 2H), 1.38 (t, 2H), 0.92 (s, 6H).

Example 289

4-(4-{[2-(4-chlorophenyl)-4,4-dimethylcyclohex-1-en-1-yl]methyl}piperazin-1-yl)-2-(1H-indol-4-yloxy)-N-{[3-nitro-4-(tetrahydro-2H-pyran-4-ylmethoxy)phenyl]sulfonyl}benzamide This example was prepared by substituting EXAMPLE 279A for EXAMPLE 1F and EXAMPLE 55B for EXAMPLE 26C in EXAMPLE 177. $^1$H NMR (500 MHz, dimethylsulfoxide-$d_6$) δ 11.25 (s, 1H), 8.21 (d, J=2.14 Hz, 1H), 7.95 (dd, 1H), 7.54 (d, 1H), 7.33-7.38 (m, 3H), 7.28 (t, 1H), 7.17 (d, 1H), 7.04 (d, 2H), 6.97 (t, 1H), 6.70 (dd, 1H), 6.41 (d, 1H), 6.27-6.29 (m, 2H), 4.08 (d, 2H), 3.88 (dd, 2H), 3.07 (s, 4H), 2.80 (s, 2H), 2.24 (br s, 2H), 2.12-2.16 (m, 2H), 1.96 (s, 2H), 1.65 (dd, 2H), 1.37-1.40 (m, 2H), 0.92 (s, 6H).

Example 290

4-(4-{[2-(4-chlorophenyl)-5,5-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide

Example 290A 2-(4-chlorophenyl)-5,5-dimethylcyclohex-1-enecarbaldehyde

The title compound was prepared as described in EXAMPLE 253B by replacing EXAMPLE 253A with EXAMPLE 19C.

Example 290B tert-butyl 4-((2-(4-chlorophenyl)-5,5-dimethylcyclohex-1-enyl)methyl)piperazine-1-carboxylate The title compound was prepared as described in EXAMPLE 1A by replacing EXAMPLE 27C with EXAMPLE 290A.

Example 290C 1-((2-(4-chlorophenyl)-5,5-dimethylcyclohex-1-enyl)methyl)piperazine The title compound was prepared as described in EXAMPLE 1B by replacing EXAMPLE 1A with EXAMPLE 290B.

Example 290D ethyl 2-(1H-indol-5-yloxy)-4-(4-((2-(4-chlorophenyl)-5,5-dimethylcyclohex-1-enyl)methyl)piperazin-1-yl)benzoate The title compound was prepared as described in EXAMPLE 20D by replacing EXAMPLE 20A and EXAMPLE 20C with EXAMPLE 26A and EXAMPLE 290C, respectively.

Example 290E 2-(1H-indol-5-yloxy)-4-(4-((2-(4-chlorophenyl)-5,5-dimethylcyclohex-1-enyl)methyl)piperazin-1-yl)benzoic acid The title compound was prepared as described in EXAMPLE 1E by replacing EXAMPLE 1D with EXAMPLE 290D.

Example 290F 2-(1H-indol-5-yloxy)-4-(4-((2-(4-chlorophenyl)-5,5-dimethylcyclohex-1-enyl)methyl)piperazin-1-yl)-N-(3-nitro-4-((tetrahydro-2H-pyran-4-yl)methylamino)phenylsulfonyl)benzamide The title compound was prepared as described in EXAMPLE 175F by replacing EXAMPLE 175E with EXAMPLE 290E. ¹H NMR (500 MHz, dimethylsulfoxide-d₆) δ 11.17 (s, 2H), 8.62 (t, 1H), 8.58 (d, 1H), 7.80 (dd, 1H), 7.51 (d, 1H), 7.38-7.43 (m, 2H), 7.33 (d, 2H), 7.16 (d, 1H), 7.10 (d. 1H), 7.07 (d, 3H), 6.86 (dd, 1H), 6.65 (dd, 1H), 6.39 (s, 1H), 6.14 (d, 1H), 3.85 (dd, 2H), 3.23-3.31 (m, 4H), 3.02 (s, 4H), 2.68 (s, 2H), 2.17 (d, 6H), 1.85-1.95 (m, 3H), 1.61 (d, 2H), 1.39 (t, 2H), 1.20-1.30 (m, 2H), 0.92 (s, 6H).

Example 291

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2-tetrahydro-2H-pyran-4-ylethyl)amino]phenyl}sulfonyl)benzamide Example 291A 3-nitro-4-(2-(tetrahydro-2H-pyran-4-yl)ethylamino)benzenesulfonamide The title compound was prepared as described in EXAMPLE 1F by replacing (tetrahydropyran-4-yl)methylamine with 2-(tetrahydro-2H-pyran-4-yl)ethanamine.

Example 291B 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2-tetrahydro-2H-pyran-4-ylethyl)amino]phenyl}sulfonyl)benzamide The title compound was prepared as described in EXAMPLE 175F by replacing EXAMPLE 175E and EXAMPLE 1F with EXAMPLE 26C and EXAMPLE 291A, respectively. ¹H NMR (500 MHz, dimethylsulfoxide-d₆) δ 11.16 (s, 2H), 8.57 (d, 1H), 8.53 (t, 1H), 7.80 (dd, 1H), 7.51 (d, 1H), 7.37-7.42 (m, 2H), 7.33 (d, 2H), 7.14 (d, 1H), 7.01-7.05 (m, 3H), 6.85 (dd, 1H), 6.64 (dd, 1H), 6.39 (s, 1H), 6.14 (d, 1H), 3.83 (dd, 2H), 3.41 (q, 2H), 3.23-3.30 (m, 2H), 3.02 (s, 4H), 2.71 (s, 2H), 2.08-2.21 (m, 6H), 1.94 (s, 2H), 1.52-1.67 (m, 5H), 1.37 (t, 2H), 1.14-1.25 (m, 2H), 0.92 (s, 6H).

Example 292

4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[2-(trifluoromethoxy)ethyl]amino}phenyl)sulfonyl]benzamide Example 292A 3-nitro-4-(2-(trifluoromethoxy)ethylamino)benzenesulfonamide This example was prepared by substituting piperidin-1-amine for (tetrahydro-2H-pyran-4-yl)methanamine in EXAMPLE 1F.

Example 292B 4-(4-{[2-(4-chlorophenyl)-4,4-dimethylcyclohex-1-en-1-yl]methyl}piperazin-1-yl)-2-(1H-indol-4-yloxy)-N-[(3-nitro-4-{[2-(trifluoromethoxy)ethyl]amino}phenyl)sulfonyl]benzamide This example was prepared by substituting EXAMPLE 292A for EXAMPLE 1F and EXAMPLE 55B for EXAMPLE 26C in EXAMPLE 177. ¹H NMR (500 MHz, dimethylsulfoxide-d₆) δ 11.07 (s, 1H), 8.36 (m, 2H), 7.72 (dd, 1H), 7.58 (d, 1H), 7.34 (d, 2H), 7.19 (m, 1H), 7.05 (m, 3H), 6.91 (m, 2H), 6.59 (d, 1H), 6.21 (m, 3H), 4.28 (t, 2H), 3.72 (q, 2H), 2.94 (m, 4H), 2.71 (s, 2H), 2.15 (m, 6H), 1.95 (s, 2H), 1.39 (t, 2H), 0.93 (s, 6H).

Example 293

4-(4-{[2-(4-chlorophenyl)-4,4-dimethylcyclohex-1-en-1-yl]methyl}piperazin-1-yl)-2-(1H-indol-4-yloxy)-N-[(4-{[2-(2-methoxyethoxy)ethyl]amino}-3-nitrophenyl)sulfonyl]benzamide Example 293A 4-(2-(2-methoxyethoxy)ethylamino)-3-nitrobenzenesulfonamide This example was prepared by substituting 2-(2-methoxyethoxy)ethanamine for (tetrahydro-2H-pyran-4-yl)methanamine in EXAMPLE 1F.

Example 293B 4-(4-{[2-(4-chlorophenyl)-4,4-dimethylcyclohex-1-en-1-yl]methyl}piperazin-1-yl)-2-(1H-indol-4-yloxy)-N-[(4-{[2-(2-methoxyethoxy)ethyl]amino}-3-nitrophenyl)sulfonyl]benzamide This example was prepared by substituting EXAMPLE 293A for EXAMPLE 1F and EXAMPLE 55B for EXAMPLE 26C in EXAMPLE 177. ¹H NMR (500 MHz, dimethylsulfoxide-d₆) δ 11.28 (s, 1H), 11.23 (s, 1H), 8.59 (m, 1H), 8.50 (d, 1H), 7.70 (dd, 1H), 7.52 (d, 1H), 7.34 (d, 2H), 7.28 (t, 1H), 7.17 (d, 1H), 7.05 (m, 3H), 6.96 (t, 1H), 6.71 (dd, 1H), 6.42 (d, 1H), 6.26 (m, 2H), 3.67 (t, 2H), 3.56 (m, 4H), 3.45 (m, 2H), 3.22 (s, 3H), 3.04 (m, 4H), 2.74 (s, 2H), 2.16 (m, 6H), 1.95 (s, 2H), 1.38 (t, 2H), 0.93 (s, 6H).

Example 294

4-(4-{[2-(4-chlorophenyl)-4,4-dimethylcyclohex-1-en-1-yl]methyl}piperazin-1-yl)-2-(1H-indol-4-yloxy)-N-[(4-{[3-(methylsulfonyl)propyl]amino}-3-nitrophenyl)sulfonyl]benzamide Example 294A 4-(3-(methylthio)propylamino)-3-nitrobenzenesulfonamide This example was prepared by substituting 3-(methylthio)propan-1-amine for (tetrahydropyran-4-yl)methylamine in EXAMPLE 1F.

Example 294B 4-(3-(methylsulfonyl)propylamino)-3-nitrobenzenesulfonamide

EXAMPLE 294A (150 mg) was suspended in anhydrous dichloromethane (5 mL) and meta-chloroperoxybenzoic acid (848 mg) was added at 0° C. The reaction mixture was stirred at room temperature overnight. The cloudy suspension was filtered. The solid was washed with aqueous Na₂S₂O₃ solution, saturated aqueous NaHCO₃ solution and water.

The solid was dried and used in the next step without further purification.

Example 294C 4-(4-{[2-(4-chlorophenyl)-4,4-dimethylcyclohex-1-en-1-yl]methyl}piperazin-1-yl)-2-(1H-indol-4-yloxy)-N-[(4-{[3-(methylsulfonyl)propyl]amino}-3-nitrophenyl)sulfonyl]benzamide This example was prepared by substituting EXAMPLE 55B for EXAMPLE 26C and EXAMPLE 294B for EXAMPLE 1F in EXAMPLE 177. $^1$H NMR (400 MHz, dimethylsulfoxide-$d_6$) δ 11.25 (m, 1H), 8.65 (t, 1H), 8.51 (d, 1H), 7.69 (dd, 1H), 7.52 (d, 1H), 7.34 (d, 2H), 7.28 (m, 1H), 7.18 (m, 1H), 7.05 (m, 3H), 6.97 (m, 1H), 6.70 (dd, 1H), 6.42 (d, 1H), 6.26 (m, 2H), 3.55 (m, 2H), 3.23 (t, 2H), 3.05 (t, 4H), 2.98 (s, 3H), 2.76 (m, 2H), 2.18 (m, 6H), 2.02 (m, 2H), 1.96 (m, 2H), 1.38 (t, 2H), 0.93 (s, 6H).

Example 295

4-(4-{[2-(4-chlorophenyl)-4,4-dimethylcyclohex-1-en-1-yl]methyl}piperazin-1-yl)-N-[(4-{[3-(1-dioxidothiomorpholin-4-yl)propyl]amino}-3-nitrophenyl)sulfonyl]-2-(1H-indol-4-yloxy)benzamide This example was prepared by substituting EXAMPLE 337A for 4-chloro-3-nitrobenzene sulfonamide and 4-(3-aminopropyl)thiomorpholine-1,1-dioxide for 1-(2-methoxyethyl)-piperidin-4-ylamine in EXAMPLE 189A. $^1$H NMR (400 MHz, dimethylsulfoxide-$d_6$) δ 11.23 (s, 1H), 8.79 (s, 1H), 8.48 (d, 1H), 7.72 (dd, 1H), 7.54 (d, 1H), 7.34 (d, 2H), 7.26 (t, 1H), 7.15 (d, 1H), 6.99 (m, 4H), 6.67 (dd, 1H), 6.40 (d, 1H), 6.24 (m, 2H), 3.42 (q, 2H), 3.11 (m, 4H), 3.01 (m, 4H), 2.90 (m, 4H), 2.72 (m, 2H), 2.56 (t, 2H), 2.16 (m, 6H), 1.95 (m, 2H), 1.78 (m, 2H), 1.38 (t, 2H), 0.92 (s, 6H).

Example 296

4-(4-{[2-(4-chlorophenyl)-4,4-dimethylcyclohex-1-en-1-yl]methyl}piperazin-1-yl)-2-(1H-indol-5-yloxy)-N-{[3-nitro-4-(2-tetrahydro-2H-pyran-4-yl-ethyl)phenyl]sulfonyl}benzamide

Example 296A (2-(tetrahydro-2H-pyran-4-yl)ethyl)zinc(II) bromide

A 25 mL round bottom flask was dried at 120° C. for 6 hours. It was cooled by a stream of dry $N_2$. To this flask was charged with zinc (0.508 g). The flask was heated at 70° C. under high vacuum for 30 minutes. After back-filling with $N_2$, iodine (0.033 g) and N,N-dimethylacetamide (5.2 mL) were added, and the resulting mixture was stirred until the red color of iodine had faded. Then, 4-(2-bromoethyl)tetrahydro-2H-pyran (1.0 g) was added to the above mixture via a syringe. The reaction mixture was allowed to stir for 12 hours at 70° C. After cooling, the reaction mixture was used directly for next step.

Example 296B 4-(4-{[2-(4-chlorophenyl)-4,4-dimethylcyclohex-1-en-1-yl]methyl}piperazin-1-yl)-2-(1H-indol-5-yloxy)-N-{[3-nitro-4-(2-tetrahydro-2H-pyran-4-yl-ethyl)phenyl]sulfonyl}benzamide This example was prepared by substituting EXAMPLE 296A for (2-(1,3-dioxolan-2-yl)ethyl)zinc(II) bromide in EXAMPLE 278. $^1$H NMR (500 MHz, dimethylsulfoxide-$d_6$) δ 11.15 (s, 2H), 8.38 (d, 1H), 8.01 (d, 1H), 7.57 (d, 1H), 7.51 (d, 1H), 7.38-7.40 (m, 2H), 7.34 (d, 2H), 7.12 (d, 1H), 7.04 (d, 2H), 6.82 (dd, 1H), 6.64 (dd, 1H), 6.38 (s, 1H), 6.16 (d, 1H), 3.83 (dd, 2H), 3.24-3.29 (m, 4H), 3.06 (s, 4H), 2.83-2.86 (m, 3H), 2.27 (br s, 2H), 2.12-2.14 (m, 4H), 1.96 (s, 2H), 1.95 (s, 2H), 1.46-1.62 (m, 6H), 1.37-1.40 (m, 2H), 0.92 (s, 6H).

Example 297

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indol-5-yloxy)benzamide

Example 297A 4-((1,4-dioxan-2-yl)methoxy)-3-nitrobenzene-sulfonamide (1,4-Dioxan-2-yl)methanol (380 mg) in tetrahydrofuran (30 ml) was treated with sodium hydride (60%) (245 mg) at room temperature for 30 minutes. The reaction mixture was cooled in an ice bath and 4-fluoro-3-nitrobenzenesulfonamide (675 mg) was added. The resulting mixture was stirred at room temperature for 2 hours and another portion of sodium hydride (60%, 245 mg) was added. The reaction mixture was stirred overnight and quenched with ice water (3 ml). The cloudy mixture was filtered and the filtrate was concentrated. The residue was triturated with methanol to give the title compound.

Example 297B 4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indol-5-yloxy)benzamide The title compound was prepared as described in EXAMPLE 175F by replacing EXAMPLE 175E and EXAMPLE 1F with EXAMPLE 26C and EXAMPLE 297A, respectively. $^1$H NMR (500 MHz, dimethylsulfoxide-$d_6$) δ 11.16 (s, 2H), 8.39 (d, 1H), 8.06 (dd, 1H), 7.51 (d, 1H), 7.38-7.43 (m, 3H), 7.34 (d, 2H), 7.15 (d, 1H), 7.04 (d, 2H), 6.85 (dd, 1H), 6.64 (dd, 1H), 6.39 (s, 1H), 6.15 (d, 1H), 4.20-4.28 (m, 2H), 3.85-3.91 (m, 1H), 3.82 (dd, 1H), 3.74-3.78 (m, 1H), 3.59-3.69 (m, 2H), 3.40-3.51 (m, 2H), 3.05 (s, 4H), 2.78 (s, 2H), 2.23 (s, 4H), 2.14 (s, 2H), 1.95 (s, 2H), 1.38 (t, 2H), 0.92 (s, 6H).

Example 298

4-(4-{[2-(4-chlorophenyl)-4,4-dimethylcyclohex-1-en-1-yl]methyl}piperazin-1-yl)-2-(1H-indol-5-yloxy)-N-[(4-{[2-(2-methoxyethoxy)ethyl]amino}-3-nitrophenyl)sulfonyl]benzamide This example was prepared by substituting EXAMPLE 293A for EXAMPLE 1F in EXAMPLE 177. $^1$H NMR (500 MHz, dimethylsulfoxide-$d_6$) δ 11.17 (s, 1H), 11.15 (s, 1H), 8.59 (m, 2H), 7.80 (dd, 1H), 7.50 (d, 1H), 7.36 (m, 4H), 7.15 (d, 1H), 7.09 (d, 1H), 7.03 (d, 2H), 6.85 (dd, 1H), 6.65 (dd, 1H), 6.39 (m, 1H), 6.14 (d, 1H), 3.67 (t, 2H), 3.56 (m, 4H), 3.44 (m, 2H), 3.22 (s, 3H), 3.03 (m, 4H), 2.72 (s, 2H), 2.16 (m, 6H), 1.95 (s, 2H), 1.38 (t, 2H), 0.92 (s, 6H).

Example 299

4-(4-{[2-(4-chlorophenyl)-4,4-dimethylcyclohex-1-en-1-yl]methyl}piperazin-1-yl)-N-({4-[(1,1-dioxidotetrahydrothien-3-yl)amino]-3-nitrophenyl}sulfonyl)-2-(1H-indol-4-yloxy)benzamide This example was prepared by substituting EXAMPLE 337A for 4-chloro-3-nitrobenzene sulfonamide and 1,1-dioxidotetrahydrothiene-3ylamine for 1-(2-methoxy-ethyl)-piperidin-4-ylamine in EXAMPLE 189A. $^1$H NMR (400 MHz, dimethylsulfoxide-d$_6$) δ 11.35 (s, 1H), 11.23 (s, 1H), 8.49 (m, 2H), 7.78 (dd, 1H), 7.52 (d, 1H), 7.34 (d, 2H), 7.27 (m, 1H), 7.16 (m, 2H), 7.04 (d, 1H), 6.97 (m, 1H), 6.70 (dd, 1H), 6.42 (d, 1H), 6.26 (m, 2H), 4.63 (m, 1H), 3.64 (dd, 1H), 3.37 (m, 2H), 3.20 (m, 1H), 3.05 (m, 4H), 2.74 (m, 2H), 2.58 (m, 1H), 2.28 (m, 1H), 2.16 (m, 6H), 1.95 (m, 2H), 1.38 (t, 2H), 0.92 (s, 6H).

Example 300

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[2-(trifluoromethoxy)ethyl]amino}phenyl)sulfonyl]benzamide This example was prepared by substituting EXAMPLE 292A for EXAMPLE 1F in EXAMPLE 177. $^1$H NMR (500 MHz, dimethylsulfoxide-d$_6$) δ 11.17 (m, 2H), 8.64 (t, 1H), 8.59 (d, 1H), 7.84 (dd, 1H), 7.51 (d, 1H), 7.40 (m, 2H), 7.33 (d, 2H), 7.16 (m, 2H), 7.04 (d, 2H), 6.85 (dd, 1H), 6.64 (dd, 1H), 6.39 (m, 1H), 6.14 (d, 1H), 4.31 (t, 2H), 3.78 (q, 2H), 3.04 (m, 4H), 2.74 (s, 2H), 2.17 (m, 6H), 1.94 (s, 2H), 1.38 (t, 2H), 0.92 (s, 6H).

Example 301

4-(4-{[2-(4-chlorophenyl)-4,4-dimethylcyclohex-1-en-1-yl]methyl}piperazin-1-yl)-N-[(4-{[(1,1-dioxidotetrahydro-2H-thiopyran-4-yl)methyl]amino}-3-nitrophenyl)sulfonyl]-2-(1H-indol-4-yloxy)benzamide

Example 301A 3-nitro-4-((1-dioxidotetrahydro-2H-thiopyran-4-yl)methylamino)benzenesulfonamide This example was prepared by substituting EXAMPLE 287A for EXAMPLE 294A in EXAMPLE 294B.

Example 301B 4-(4-{[2-(4-chlorophenyl)-4,4-dimethylcyclohex-1-en-1-yl]methyl}piperazin-1-yl)-N-[(4-{[(1,1-dioxidotetrahydro-2H-thiopyran-4-yl)methyl]amino}-3-nitrophenyl)sulfonyl]-2-(1H-indol-4-yloxy)benzamide This example was prepared by substituting EXAMPLE 55B for EXAMPLE 26C and EXAMPLE 301A for EXAMPLE 1F in EXAMPLE 177. $^1$H NMR (400 MHz, dimethylsulfoxide-d$_6$) δ 11.26 (s, 1H), 8.68 (t, 1H), 8.51 (d, 1H), 7.73 (dd, 1H), 7.53 (d, 1H), 7.34 (d, 2H), 7.29 (m, 1H), 7.19 (d, 1H), 7.12 (d, 1H), 7.04 (d, 2H), 6.99 (m, 1H), 6.70 (dd, 1H), 6.46 (d, 1H), 6.26 (m, 2H), 3.38 (t, 2H), 3.09 (m, 8H), 2.75 (m, 2H), 2.16 (m, 6H), 2.07 (m, 2H), 1.95 (m, 3H), 1.70 (m, 2H), 1.38 (t, 2H), 0.91 (s, 6H).

Example 302

4-(4-{[2-(4-chlorophenyl)-4,4-dimethylcyclohex-1-en-1-yl]methyl}piperazin-1-yl)-N-({4-[(2,2-difluoroethyl)amino]-3-nitrophenyl}sulfonyl)-2-(H-indol-5-yloxy)benzamide

Example 302A 4-(2,2-difluoroethylamino)-3-nitrobenzenesulfonamide

This example was prepared by substituting 2,2-difluoroethanamine for (tetrahydro-2H-pyran-4-yl)methanamine in EXAMPLE 1F.

Example 302B 4-(4-{[2-(4-chlorophenyl)-4,4-dimethylcyclohex-1-en-1-yl]methyl}piperazin-1-yl)-N-({4-[(2,2-difluoroethyl)amino]-3-nitrophenyl}sulfonyl)-2-(1H-indol-5-yloxy)benzamide This example was prepared by substituting EXAMPLE 302A for EXAMPLE 1F in EXAMPLE 177. $^1$H NMR (500 MHz, dimethylsulfoxide-d$_6$) δ 11.22 (s, 1H), 11.05 (s, 1H), 8.46 (m, 2H), 7.76 (m, 1H), 7.53 (d, 1H), 7.33 (m, 4H), 7.05 (m, 4H), 6.76 (m, 1H), 6.57 (d, 1H), 6.34 (m, 1H), 6.14 (m, 1H), 3.89 (m, 2H), 2.97 (m, 4H), 2.71 (s, 2H), 2.16 (m, 6H), 1.95 (s, 2H), 1.38 (t, 2H), 0.92 (s, 6H).

Example 303

4-(4-{[2-(4-chlorophenyl)-4,4-dimethylcyclohex-1-en-1-yl]methyl}piperazin-1-yl)-2-(1H-indol-4-yloxy)-N-({4-[(tetrahydro-2H-pyran-4-ylmethyl)amino]-3-[(trifluoromethyl)sulfonyl]phenyl}sulfonyl)benzamide This example was prepared by substituting EXAMPLE 55B for EXAMPLE 26C and EXAMPLE 163A for EXAMPLE 1F in EXAMPLE 177. $^1$H NMR (400 MHz, dimethylsulfoxide-d$_6$) δ 11.28 (m, 1H), 8.13 (d, 1H), 7.78 (dd, 1H), 7.52 (d, 1H), 7.34 (d, 2H), 7.29 (m, 2H), 7.20 (d, 1H), 7.01 (m, 4H), 6.70 (dd, 1H), 6.45 (d, 1H), 6.27 (m, 2H), 3.85 (dd, 2H), 3.26 (t, 4H), 3.05 (m, 4H), 2.75 (m, 2H), 2.16 (m, 6H), 1.95 (m, 2H), 1.84 (m, 1H), 1.55 (m, 2H), 1.38 (t, 2H), 1.23 (m, 2H), 0.92 (s, 6H).

Example 304

4-(4-{[2-(4-chlorophenyl)-4,4-dimethylcyclohex-1-en-1-yl]methyl}piperazin-1-yl)-2-(1H-indol-5-yloxy)-N-({4-[(tetrahydro-2H-pyran-4-ylmethyl)amino]-3-[(trifluoromethyl)sulfonyl]phenyl}sulfonyl)benzamide This example was prepared by substituting EXAMPLE 163A for EXAMPLE 1F in EXAMPLE 177. $^1$H NMR (400 MHz, dimethylsulfoxide-d$_6$) δ 11.46 (s, 1H), 11.20 (s, 1H), 9.23 (s, 1H), 8.19 (d, 1H), 7.90 (dd, 1H), 7.53 (d, 1H), 7.41 (m, 4H), 7.33 (m, 1H), 7.17 (d, 1H), 6.86 (dd, 1H), 6.70 (dd, 1H), 6.41 (m, 1H), 6.21 (d, 1H), 3.84 (dd, 2H), 3.57 (m, 4H), 3.26

(m, 6H), 3.00 (m, 2H), 2.74 (s, 2H), 2.18 (s, 2H), 2.01 (s, 2H), 1.83 (m, 1H), 1.54 (m, 2H), 1.45 (t, 2H), 1.23 (m, 2H), 0.94 (s, 6H).

Example 305

4-(4-{[2-(4-chlorophenyl)-4,4-dimethylcyclohex-1-en-1-yl]methyl}piperazin-1-yl)-N-({4-[(4,4-difluorocyclohexyl)amino]-3-nitrophenyl}sulfonyl)-2-(1H-indol-5-yloxy)benzamide This example was prepared by substituting 4,4-difluorocyclohexanamine, hydrochloric Acid for (3S,4R)-4-amino-1-benzylpiperidin-3-ol, hydrochloric acid in EXAMPLE 187B. $^1$H NMR (500 MHz, dimethylsulfoxide-$d_6$) δ 11.16 (s, 2H), 8.59 (d, 1H), 8.25 (d, 1H), 7.84 (dd, 1H), 7.50 (d, 2H), 7.39-7.41 (m, 2H), 7.33 (d, 2H), 7.15-7.18 (m, 2H), 7.03 (d, 2H), 6.85 (dd, 1H), 6.65 (dd, 1H), 6.39 (s, 1H), 6.14 (d, 1H), 3.86 (d, 1H), 3.04 (s, 4H), 2.74 (s, 2H), 1.95-2.18 (m, 14H), 1.69-1.73 (m, 2H), 1.38 (d, 2H), 0.92 (s, 6H).

Example 306

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-indol-4-yloxy)benzamide

Example 306A 1,6-dioxaspiro[2.5]octane-2-carbonitrile

A mixture of dihydro-2H-pyran-4(3H)-one (10.0 g) and 2-chloroacetonitrile (7.55 g) in tert-butanol (10 mL) was treated with 1.0 N potassium tert-butoxide (100 mL) dropwise over 20 minutes. The reaction mixture was stirred at room temperature for 16 hours. It was diluted with water (10 mL) and 10% HCl (20 mL). The reaction mixture was concentrated to one-third of its original volume, and extracted with diethyl ether four times.

The combined organic layers were washed with brine, dried over MgSO$_4$, filtered, and concentrated. The residue was purified with flash column chromatography on silica gel eluting with 20-40% ethyl acetate in hexanes to give the title compound.

Example 306B 2-(4-fluorotetrahydro-2H-pyran-4-yl)-2-hydroxyacetonitrile

EXAMPLE 306A (11.5 g) was dissolved in dichloromethane (40 mL) in a polypropylene bottle. The bottle was cooled to 0° C. To this mixture was added 70% hydrogen fluoride-pyridine (10.31 mL) slowly. The mixture was allowed to warm to room temperature over 3 hours, and stirred for 24 hours. The reaction mixture was diluted with ethyl acetate (200 mL) and poured into saturated aqueous NaHCO$_3$. Additional solid NaHCO$_3$ was used to neutralize the mixture carefully until bubbling ceased. The organic layer was isolated, and the aqueous layer was extracted with additional ethyl acetate three times (150 mL each). The combined organic layers were washed with 1% HCl, brine, dried (MgSO$_4$), filtered and concentrated to give the desired compound which was used directly in the next reaction.

Example 306C (4-fluorotetrahydro-2H-pyran-4-yl)methanol

EXAMPLE 306B (11.78 g) in 2-propanol (150 mL) and water (37.5 mL) was cooled to 0° C. To this mixture was added sodium borohydride (4.2 g). The mixture was stirred and allowed to warm to room temperature over 3 hours. The reaction was quenched with acetone, and stirred for another 1 hour. The clear liquid was separated from solid by decanting. Additional ethyl acetate was used to wash the solid, and was decanted. The combined organic solution was concentrated. The residue was purified with flash column chromatography on silica gel eluting with 20-40% ethyl acetate in hexanes to give the title compound.

Example 306D 4-((4-fluorotetrahydro-2H-pyran-4-yl)methoxy)-3-nitrobenzenesulfonamide This example was prepared by substituting EXAMPLE 306C for (tetrahydro-2H-pyran-4-yl)methanol in EXAMPLE 279A.

Example 306E 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-indol-4-yloxy)benzamide This example was prepared by substituting EXAMPLE 306D for EXAMPLE 1F and EXAMPLE 55B for EXAMPLE 26C in EXAMPLE 177. $^1$H NMR (500 MHz, dimethylsulfoxide-$d_6$) δ 11.24 (s, 1H), 8.28 (d, 1H), 7.98 (dd, 1H), 7.54 (d, 1H), 7.42 (d, 1H), 7.34 (d, 2H), 7.28 (t, 1H), 7.17 (d, 1H), 7.04 (d, 2H), 6.97 (t, 1H), 6.70 (dd, 1H), 6.41 (d, 1H), 6.26-6.28 (m, 2H), 4.38 (d, 2H), 3.76-3.80 (m, 2H), 3.57-3.62 (m, 2H), 3.06 (s, 4H), 2.80 (s, 2H), 2.24 (br s, 2H), 2.15-2.25 (m, 2H), 1.96 (s, 2H), 1.82-1.89 (m, 4H), 1.39 (t, 2H), 0.93 (s, 6H).

Example 307

4-(4-(4-{[4-(4-chlorophenyl)-1-isopropyl-6-oxo-1,6-dihydropyridin-3-yl]methyl}piperazin-1-yl)-2-(1 1H-indol-5-yloxy)-N-({3-nitro-4-[(tetrahydro-2H-pyran-4-ylmethyl)amino]phenyl}sulfonyl)benzamide

Example 307A 4-(4-chlorophenyl)-2-fluoro-5-methylpyridine

A mixture of 2-fluoro-4-iodo-5-methylpyridine (1.9 g), 4-chlorophenylboronic acid (1.504 g), tetrakis(triphenylphosphine)palladium(O) (0.463 g), and sodium carbonate (2.55 g) in ethanol (20 mL), water (10 mL) and toluene (10 mL) was heated under reflux for 6 hours. The reaction mixture was partitioned between ethyl acetate and water. The organic layer was separated, and the aqueous layers were extracted with additional ethyl acetate three times. The combined organic layers were washed with brine, dried over MgSO$_4$, filtered, and concentrated. The residue was purified with flash column chromatography on silica gel using 5% ethyl acetate in hexanes to give the title compound.

Example 307B 5-(bromomethyl)-4-(4-chlorophenyl)-2-fluoropyridine

A mixture of EXAMPLE 307A (1.2 g), N-bromosuccinimide (1.06 g) and AIBN (azobisisobutyronitrile) (0.178 g) in CCl$_4$ (30 mL) was heated under reflux for 6 hours. After cooling, the solid was filtered off. The filtrate was concentrated and loaded onto a silica gel column eluting with 3% ethyl acetate in hexanes to give the title compound.

Example 307C tert-butyl 4-((4-(4-chlorophenyl)-6-fluoropyridin-3-yl)methyl)piperazine-1-carboxylate A mixture of EXAMPLE 307B (1.24 g), tert-butyl piperazine-1-carboxylate (0.768 g), and potassium carbonate (0.570) in N,N-dimethylformamide (20 mL) was stirred at room temperature for 2 hours. The reaction mixture was partitioned between ethyl acetate and water. The organic layer was separated, and the aqueous layer was extracted with additional ethyl acetate three times. The combined organic layers were washed with brine, dried over MgSO$_4$, filtered, and concentrated. The residue was purified with flash column chromatography on silica gel using 10% ethyl acetate in hexanes to give the title compound.

Example 307D tert-butyl 4-((4-(4-chlorophenyl)-6-oxo-1,6-dihydropyridin-3-yl)methyl)piperazine-1-carboxylate A mixture of EXAMPLE 307C (1.6 g) and 5% HCl (20 mL) in tetrahydrofuran (20 mL) was heated at 80° C. overnight. The solvent was removed to dryness. This solid was re-dissolved and added to tetrahydrofuran (50 mL). To this mixture were added BOC$_2$O (di-t-butyl-dicarbonate) (1.118 g), triethylamine (0.72 mL), and 4-dimethylamionpyridine (1.4 g).

The solvent was removed, and the residue was partitioned between water and ethyl acetate.

The reaction mixture was stirred overnight. The organic layers were dried (MgSO$_4$), filtered, and concentrated. The residue was purified by Prep HPLC eluting with 20-100% acetonitrile/water with 0.1% trifluoroacetic acid to give the title compound.

Example 307E tert-butyl 4-((4-(4-chlorophenyl)-1-isopropyl-6-oxo-1,6-dihydropyridin-3-yl)methyl)piperazine-1-carboxylate EXAMPLE 307D (0.404 g) in N,N-dimethylformamide (5 mL) was treated with 60% sodium hydride (0.24 g) at room temperature. To this mixture was added 2-iodopropane (0.204 g). The mixture was stirred overnight. The reaction mixture was partitioned between ethyl acetate and water. The organic layer was separated, and the aqueous layer was extracted with additional ethyl acetate three times. The combined organic layers were washed with brine, dried over MgSO$_4$, filtered, and concentrated. The residue was purified with flash column chromatography on silica gel using 10% ethyl acetate in hexanes to give EXAMPLE 307E and EXAMPLE 307F.

Example 307F tert-butyl 4-((4-(4-chlorophenyl)-6-isopropoxypyridin-3-yl)methyl)piperazine-1-carboxylate This compound was isolated as a by-product during the preparation of EXAMPLE 307E.

Example 307G 4-(4-chlorophenyl)-1-isopropyl-5-(piperazin-1-ylmethyl)pyridin-2(1H)-one This example was prepared by substituting EXAMPLE 307E for EXAMPLE 1A in EXAMPLE 1B.

Example 307H ethyl 2-(1H-indol-5-yloxy)-4-(4-((4-(4-chlorophenyl)-1-isopropyl-6-oxo-1,6-dihydropyridin-3-yl)methyl)piperazin-1-yl)benzoate This example was prepared by substituting EXAMPLE 307G for EXAMPLE 20C and EXAMPLE 26A for EXAMPLE 20A in EXAMPLE 20D.

Example 307I 2-(1H-indol-5-yloxy)-4-(4-((4-(4-chlorophenyl)-1-isopropyl-6-oxo-1,6-dihydropyridin-3-yl)methyl)piperazin-1-yl)benzoic acid This example was prepared by substituting EXAMPLE 307H for EXAMPLE 1D in EXAMPLE 1E.

Example 307J 4-(4-{[4-(4-chlorophenyl)-1-isopropyl-6-oxo-1,6-dihydropyridin-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide This example was prepared by substituting EXAMPLE 307I for EXAMPLE 26C in EXAMPLE 177. $^1$H NMR (500 MHz, dimethylsulfoxide-d$_6$) δ 11.07 (s, 1H), 8.62 (t, 1H), 8.59 (d, 1H), 7.79 (dd, 1H), 7.59 (s, 1H), 7.52-7.53 (m, J 3H), 7.38-7.45 (m, 4H), 7.15 (d, 1H), 7.10 (d, 1H), 6.87 (dd, 1H), 6.68 (dd, 1H), 6.39 (s, 1H), 6.22 (s, 1H), 6.17 (d, 1H), 5.01-5.06 (m, 1H), 3.85 (dd, 2H), 3.24-3.31 (m, 6H), 3.09 (s, 2H), 3.00 (s, 4H), 2.26 (m, 4H), 2.09 (m, 2H), 1.60-1.63 (m, 2H), 1.30 (d, 6H).

Example 308

4-(4-{[2-(4-chlorophenyl)-4,4-dimethylcyclohex-1-en-1-yl]methyl}piperazin-1-yl)-2-(1H-indol-5-yloxy)-N-[(4-{[(tetrahydro-2H-pyran-4-ylmethyl)amino]carbonyl}phenyl)sulfonyl]benzamide

Example 308A 4-sulfamoyl-N-((tetrahydro-2H-pyran-4-yl)methyl)benzamide

4-Sulfamoylbenzoic acid (201 mg), (tetrahydro-2H-pyran-4-yl)methanamine (144 mg), 1-hydroxybenzotriazole

329 hydrate (230 mg), and 1-ethyl-3-[3-(dimethylamino)propyl]-carbodiimide hydrochloride (288 mg) were combined in acetonitrile.

The mixture was stirred at room temperature overnight. The solids were filtered off and reaction mixture was concentrated. The crude material was purified by flash chromatography eluting with a gradient of 2% methanol/dichloromethane to 10% methanol/dichloromethane.

Example 308B 4-(4-{[2-(4-chlorophenyl)-4,4-dimethylcyclohex-1-en-1-yl]methyl}piperazin-1-yl)-2-(1H-indol-5-yloxy)-N-[(4-{[(tetrahydro-2H-pyran-4-ylmethyl)amino]carbonyl}phenyl)sulfonyl]benzamide This example was prepared by substituting EXAMPLE 308A for EXAMPLE 1F and EXAMPLE 26C for EXAMPLE 1E in EXAMPLE 1G. $^1$H NMR (500 MHz, dimethylsulfoxide-$d_6$) δ 11.19 (s, 1H), 8.57 (t, 1H), 7.94 (m, 4H), 7.48 (d, 1H), 7.43 (d, 1H), 7.40 (t, 1H), 7.33 (d, 2H), 7.21 (d, 1H), 7.03 (d, 2H), 6.88 (dd, 1H), 6.63 (dd, 1H), 6.42 (t, 1H), 6.13 (d, 1H), 3.84 (dd, 2H), 3.26 (m, 2H), 3.16 (t, 2H), 3.03 (br s, 4H), 2.74 (br s, 2H), 2.15 (m, 6H), 1.95 (s, 2H), 1.79 (m, 1H), 1.59 (d, 2H), 1.38 (t, 2H), 1.19 (m, 2H), 0.92 (s, 6H).

Example 309

4-(4-{[2-(4-chlorophenyl)-4,4-dimethylcyclohex-1-en-1-yl]methyl}piperazin-1-yl)-2-(1H-indol-4-yloxy)-N-({4-[(2-methoxyethyl)amino]-3-[(trifluoromethyl)sulfonyl]phenyl}sulfonyl)benzamide

Example 309A 4-(2-methoxyethylamino)-3-(trifluoromethylsulfonyl)benzenesulfonamide This example was prepared by substituting EXAMPLE 159C for 4-fluoro-3-nitrobenzenesulfonamide and 2-methoxyethylamine for (tetrahydropyran-4-yl)methylamine in EXAMPLE 1F.

Example 309B 4-(4-{[2-(4-chlorophenyl)-4,4-dimethylcyclohex-1-en-1-yl]methyl}piperazin-1-yl)-2-(1H-indol-4-yloxy)-N-({4-[(2-methoxyethyl)amino]-3-[(trifluoromethyl)sulfonyl]phenyl}sulfonyl)benzamide This example was prepared by substituting EXAMPLE 55B for EXAMPLE 26C and EXAMPLE 309A for EXAMPLE 1F in EXAMPLE 177. $^1$H NMR (400 MHz, dimethylsulfoxide-$d_6$) δ 11.26 (s, 1H), 8.13 (d, 1H), 7.79 (dd, 1H), 7.51 (d, 1H), 7.34 (d, 2H), 7.29 (t, 1H), 7.24 (m, 1H), 7.19 (d, 1H), 7.04 (d, 2H), 6.99 (m, 3H), 6.70 (dd, 1H), 6.44 (d, 1H), 6.27 (m, 2H), 3.52 (m, 4H), 3.28 (s, 3H), 3.05 (m, 4H), 2.75 (s, 2H), 2.17 (m, 6H), 1.95 (s, 2H), 1.38 (t, 2H), 0.92 (s, 6H).

Example 310

Trans-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]-2-(1H-indol-5-yloxy)benzamide

Example 310A 4-(aminomethyl)cyclohexanol

The title compound was prepared as described in EXAMPLE 311A by replacing (4-methoxyphenyl)methanamine with (4-hydroxyphenyl)methanamine.

Example 310B 2-(1H-indol-5-yloxy)-N-(4-chloro-3-nitrophenylsulfonyl)-4-(4-((2-(4-chlorophenyl)-4,4-dimethylcyclohex-1-en-1-yl)methyl)piperazin-1-yl)benzamide The title compound was prepared as described in EXAMPLE 1G by replacing EXAMPLE 1E and EXAMPLE 1F with EXAMPLE 26C and 4-chloro-3-nitrobenzenesulfonamide.

Example 310C

Trans-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]-2-(1H-indol-5-yloxy)benzamide A mixture of EXAMPLE 310B (100 mg), triethylamine (0.2 ml) and EXAMPLE 310A (35 mg) in dioxane (5 ml) was heated at 100° C. for 20 hours and concentrated. The residue was purified by RP-HPLC (10-70% acetonitrile in 0.1% trifluoroacetic acid water/70 minutes) to provide the title compound as a trifluroacetic acid salt. $^1$H NMR (500 MHz, dimethylsulfoxide-$d_6$) δ 11.40 (s, 1H), 11.18 (s, 1H), 9.20 (s, 1H), 8.60 (t, 1H), 8.58 (d, 1H), 7.77 (dd, 1H), 7.54 (d, 1H), 7.42 (s, 1H), 7.37-7.41 (m, 3H), 7.14 (d, 1H), 7.04-7.09 (m, 3H), 6.86 (dd, 1H), 6.69 (dd, 1H), 6.39 (s, 1H), 6.21 (s, 1H), 3.50-3.68 (m, 3H), 3.20-3.27 (m, 3H), 2.93-3.07 (m, 2H), 2.66-2.82 (m, 2H), 2.13-2.22 (m, 2H), 2.01 (s, 2H), 1.83 (d, 2H), 1.67-1.77 (m, 3H), 1.50-1.60 (m, 1H), 1.44 (s, 2H), 0.96-1.17 (m, 4H), 0.94 (s, 6H).

Example 311

Trans-4-(4-{[2-(4-chlorophenyl)-4,4-dimethylcyclohex-1-en-1-yl]methyl}piperazin-1-yl)-2-(1H-indol-5-yloxy)-N-[(4-{[(4-methoxycyclohexyl)methyl]amino}-3-nitrophenyl)sulfonyl]benzamide

Example 311A (4-methoxycyclohexyl)methanamine (4-Methoxyphenyl)methanamine (1 g) in ethanol (10 ml) was treated with 5% dry Rh—$Al_2O_3$ (0.5 g) under $H_2$ (500 psi) at 60° C. for 6 hours and then at 125° C. for 26 hours. The insoluble material was filtered off and the filtrate was concentrated to provide the title compound.

Example 311B 4-(((Trans-4-methoxycyclohexyl)methylamino)-3-nitrobenzenesulfonamide 4-fluoro-3-nitrobenzenesulfonamide (15 g) and EXAMPLE 311A (11.71 g) in tetrahydrofuran (200 ml) was treated with triethylamine (28.5 ml) overnight. The reaction was concentrated and the residue was loaded onto a C18 column, and eluted with 40-55% acetonitrile in water to provide the title compound.

Example 311C 4-(((Cis-4-methoxycyclohexyl)methylamino)-3-nitrobenzenesulfonamide This compound was made from the same procedure that also produced EXAMPLE 311B.

Example 311D

Trans-4-(4-{[2-(4-chlorophenyl)-4,4-dimethylcyclohex-1-en-1-yl]methyl}piperazin-1-yl)-2-(1H-indol-5-yloxy)-N-[(4-{[(4-methoxycyclohexyl)methyl]amino}-3-nitrophenyl)sulfonyl]benzamide The title compound was prepared as described in EXAMPLE 175F by replacing EXAMPLE 175E and EXAMPLE 1F with EXAMPLE 26C and EXAMPLE 311B, respectively. $^1$H NMR (500 MHz, dimethylsulfoxide-$d_6$) δ 11.17 (s, 2H), 8.55-8.62 (m, 2H), 7.78 (dd, 1H), 7.51 (d, 1H), 7.37-7.43 (m, 2H), 7.33 (d, 2H), 7.15 (d, 1H), 7.01-7.08 (m, 3H), 6.86 (dd, 1H), 6.65 (dd, 1H), 6.39 (s, 1H), 6.14 (d, 1H), 3.25 (t, 2H), 3.22 (s, 3H), 3.00-3.10 (m, 5H), 2.72 (s, 2H), 2.15 (d, 6H), 2.00 (d, 2H), 1.94 (s, 2H), 1.78 (d, 2H), 1.53-1.65 (m, 1H), 1.38 (t, 2H), 0.96-1.12 (m, 4H), 0.92 (s, 6H).

Example 312

Cis-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]-2-(1H-indol-5-yloxy)benzamide The title compound (trifluroacetic acid salt) was obtained during the purification of EXAMPLE 310C. $^1$H NMR (500 MHz, dimethylsulfoxide-$d_6$) δ 11.39 (s, 1H), 11.18 (s, 1H), 9.17 (s, 1H), 8.61 (t, 1H), 8.58 (d, 1H), 7.78 (dd, 1H), 7.54 (d, 1H), 7.34-7.43 (m, 5H), 7.14 (d, 1H), 7.07 (t, 3H), 6.85 (dd, 1H), 6.69 (d, 1H), 6.39 (s, 1H), 6.21 (s, 1H), 3.77 (s, 1H), 3.58 (s, 2H), 3.24-3.29 (m, 2H), 2.91-3.07 (m, 2H), 2.60-2.81 (m, 2H), 2.17 (s, 2H), 2.00 (s, 2H), 1.57-1.72 (m, 4H), 1.43 (t, 7H), 0.94 (s, 6H).

Example 313

Cis-4-(4-{[2-(4-chlorophenyl)-4,4-dimethylcyclohex-1-en-1-yl]methyl}piperazin-1-yl)-2-(1H-indol-5-yloxy)-N-[(4-{[(4-methoxycyclohexyl)methyl]amino}-3-nitrophenyl)sulfonyl]benzamide The title compound was prepared as described in EXAMPLE 175F by replacing EXAMPLE 175E and EXAMPLE 1F with EXAMPLE 26C and EXAMPLE 311C, respectively. $^1$H NMR (500 MHz, dimethylsulfoxide-$d_6$) δ 11.17 (s, 2H), 8.60 (t, 1H), 8.58 (d, 1H), 7.78 (dd, 1H), 7.51 (d, 1H), 7.37-7.44 (m, 2H), 7.33 (d, 2H), 7.16 (d, 1H), 7.07 (d, 1H), 7.03 (d, 2H), 6.86 (dd, 1H), 6.65 (dd, 1H), 6.39 (s, 1H), 6.14 (d, 1H), 3.36-3.39 (m, 1H), 3.26 (t, 2H), 3.20 (s, 3H), 3.03 (s, 4H), 2.72 (s, 2H), 2.15 (d, 6H), 1.94 (s, 2H), 1.81 (dd, 2H), 1.63-1.73 (m, 1H), 1.48 (dd, 2H), 1.23-1.41 (m, 6H), 0.92 (s, 6H).

Example 314

4-(4-{[2-(4-chlorophenyl)-4,4-dimethylcyclohex-1-en-1-yl]methyl}piperazin-1-yl)-2-(1H-indol-4-yloxy)-N-{[3-nitro-4-(2-tetrahydro-2H-pyran-4-ylethoxy)phenyl]sulfonyl}benzamide

Example 314A 3-nitro-4-(2-(tetrahydro-2H-pyran-4-yl)ethoxy)benzenesulfonamide This example was prepared by substituting 2-(tetrahydro-2H-pyran-4-yl)ethanol for (tetrahydro-2H-pyran-4-yl)methanol in EXAMPLE 279A.

Example 314B 4-(4-{[2-(4-chlorophenyl)-4,4-dimethylcyclohex-1-en-1-yl]methyl}piperazin-1-yl)-2-(1H-indol-4-yloxy)-N-{[3-nitro-4-(2-tetrahydro-2H-pyran-4-ylethoxy)phenyl]sulfonyl}benzamide This example was prepared by substituting EXAMPLE 55B for EXAMPLE 26C and EXAMPLE 314A for EXAMPLE 1F in EXAMPLE 177. $^1$H NMR (400 MHz, dimethylsulfoxide-$d_6$) δ 11.25 (s, 1H), 8.25 (d, 1H), 7.95 (dd, 1H), 7.54 (d, 1H), 7.39 (d, 1H), 7.34 (d, 2H), 7.29 (m, 1H), 7.17 (m, 1H), 7.04 (d, 2H), 6.97 (m, 1H), 6.70 (dd, 1H), 6.41 (d, 1H), 6.28 (m, 2H), 4.26 (t, 2H), 3.83 (m, 2H), 3.27 (m, 2H), 3.07 (m, 4H), 2.80 (m, 2H), 2.15 (m, 6H), 1.96 (s, 2H), 1.70 (m, 3H), 1.60 (m, 2H), 1.39 (t, 2H), 1.22 (m, 2H), 0.93 (s, 6H).

Example 315

4-(4-{[2-(4-chlorophenyl)-4,4-dimethylcyclohex-1-en-1-yl]methyl}piperazin-1-yl)-2-(1H-indol-5-yloxy)-N-({4-[(2-methoxyethyl)amino]-3-[(trifluoromethyl)sulfonyl]phenyl}sulfonyl)benzamide This example was prepared by substituting EXAMPLE 309A for EXAMPLE 1F in EXAMPLE 177. $^1$H NMR (400 MHz, dimethylsulfoxide-$d_6$) δ 11.17 (s, 1H), 8.18 (d, 1H), 7.92 (dd, 1H), 7.49 (d, 1H), 7.40 (m, 2H), 7.33 (d, 2H), 7.26 (m, 1H), 7.17 (d, 1H), 7.04 (m, 3H), 6.86 (dd, 1H), 6.65 (dd, 1H), 6.40 (m, 1H), 6.14 (d, 1H), 3.51 (m, 4H), 3.28 (s, 3H), 3.03 (s, 4H), 2.74 (m, 2H), 2.16 (m, 6H), 1.95 (s, 2H), 1.38 (t, 2H), 0.92 (s, 6H).

Example 316

4-(4-{[2-(4-chlorophenyl)-4,4-dimethylcyclohex-1-en-1-yl]methyl}piperazin-1-yl)-2-(1H-indol-4-yloxy)-N-({4-[3-(methylsulfonyl)propoxy]-3-nitrophenyl}sulfonyl)benzamide

Example 316A 4-(3-(methylthio)propoxy)-3-nitrobenzenesulfonamide

This example was prepared by substituting 3-(methylthio)propan-1-ol for (tetrahydro-2H-pyran-4-yl)methanol in EXAMPLE 279A.

Example 316B 4-(3-(methylsulfonyl)propoxy)-3-nitrobenzenesulfonamide

This example was prepared by substituting EXAMPLE 316A for EXAMPLE 294A in EXAMPLE 294B.

Example 316C 4-(4-{[2-(4-chlorophenyl)-4,4-dimethylcyclohex-1-en-1-yl]methyl}piperazin-1-yl)-2-(1H-indol-4-yloxy)-N-({4-[3-(methylsulfonyl)propoxy]-3-nitrophenyl}sulfonyl)benzamide This example was prepared by substituting EXAMPLE 55B for EXAMPLE 26C and EXAMPLE 316B for EXAMPLE 1F in EXAMPLE 177. $^1$H NMR (400 MHz, dimethylsulfoxide-$d_6$) δ 11.24 (s, 1H), 8.28 (d, 1H), 7.96 (dd, 1H), 7.54 (d, 1H), 7.35 (m, 3H), 7.29 (t, 1H), 7.17 (d, 1H), 7.04 (d, 2H), 6.96 (m, 1H), 6.71 (dd, 1H), 6.39 (d, 1H), 6.29 (m, 2H), 4.34 (t, 2H), 3.27 (m, 4H), 3.07 (m, 4H), 3.03 (s, 3H), 2.81 (s, 2H), 2.21 (m, 6H), 1.96 (s, 2H), 1.39 (t, 2H), 0.93 (s, 6H).

Example 317

4-(4-{[2-(4-chlorophenyl)-4,4-dimethylcyclohex-1-en-1-yl]methyl}piperazin-1-yl)-2-(1H-indol-5-yloxy)-N-({4-[(3-methoxypropyl)amino]-3-nitrophenyl}sulfonyl)benzamide

Example 317A 4-(3-methoxypropylamino)-3-nitrobenzenesulfonamide

This example was prepared by substituting 3-methoxypropan-1-amine for (tetrahydropyran-4-yl)methylamine in EXAMPLE 1F.

Example 317B 4-(4-{[2-(4-chlorophenyl)-4,4-dimethylcyclohex-1-en-1-yl]methyl}piperazin-1-yl)-2-(1H-indol-5-yloxy)-N-({4-[(3-methoxypropyl)amino]-3-nitrophenyl}sulfonyl)benzamide This example was prepared by substituting EXAMPLE 26C for EXAMPLE 1E and EXAMPLE 317A for EXAMPLE 1F in EXAMPLE 1G. $^1$H NMR (500 MHz, pyridine-$d_5$) δ 12.24 (s, 1H), 9.30 (d, 1H), 8.88 (t, 1H), 8.28 (dd, 1H), 8.19 (d, 1H), 7.51-7.56 (m, 2H), 7.41-7.46 (m, 3H), 7.04-7.12 (m, 3H), 6.78 (d, 1H), 6.73 (dd, 1H), 6.60 (s, 1H), 6.55 (d, 1H), 3.40 (t, 2H), 3.29-3.36 (m, 2H), 3.27 (s, 3H), 3.01-3.08 (m, 4H), 2.76 (s, 2H), 2.25 (t, 2H), 2.06-2.15 (m, 4H), 1.97 (s, 2H), 1.78-1.86 (m, 2H), 1.38 (t, 2H), 0.93 (s, 6H).

Example 318

4-(4-{[2-(4-chlorophenyl)-4,4-dimethylcyclohex-1-en-1-yl]methyl}piperazin-1-yl)-2-(1H-indol-4-yloxy)-N-({4-[(3-methoxypropyl)amino]-3-nitrophenyl}sulfonyl)benzamide This example was prepared by substituting EXAMPLE 55B for EXAMPLE 1E and EXAMPLE 317A for EXAMPLE 1F in EXAMPLE 1G. $^1$H NMR (500 MHz, pyridine-$d_5$) δ 12.39 (s, 1H), 9.21 (d, 1H), 8.86 (t, 1H), 8.15-8.24 (m, 2H), 7.42-7.50 (m, 3H), 7.38 (d, 1H), 7.04-7.13 (m, 3H), 6.73-6.81 (m, 4H), 6.67 (d, 1H), 3.39 (t, 2H), 3.32 (q, 2H), 3.27 (s, 3H), 2.96-3.07 (m, 4H), 2.76 (s, 2H), 2.25 (t, 2H), 2.07-2.16 (m, 4H), 1.97 (s, 2H), 1.77-1.87 (m, 2H), 1.39 (t, 2H), 0.94 (s, 6H).

Example 319

4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-indol-5-yloxy)benzamide

Example 319A 4-(2-cyanoethylamino)-3-nitrobenzenesulfonamide

This example was prepared by substituting 3-aminopropanenitrile for (tetrahydropyran-4-yl)methylamine in EXAMPLE 1F.

Example 319B 4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-indol-5-yloxy)benzamide This example was prepared by substituting EXAMPLE 26C for EXAMPLE 1E and EXAMPLE 319A for EXAMPLE 1F in EXAMPLE 1G. $^1$H NMR (500 MHz, pyridine-$d_5$) δ 9.26 (d, 1H), 9.06 (t, 1H), 8.34 (dd, 1H), 8.18 (d, 1H), 7.51-7.57 (m, 2H), 7.39-7.47 (m, 3H), 7.04-7.11 (m, 3H), 7.00 (d, 1H), 6.74 (dd, 1H), 6.60 (s, 1H), 6.54 (d, 1H), 3.83 (q, J=6.7 Hz, 2H), 3.01-3.08 (m, 4H), 2.98 (t, 2H), 2.76 (s, 2H), 2.25 (t, 2H), 2.07-2.15 (m, 4H), 1.97 (s, 2H), 1.38 (t, 2H), 0.93 (s, 6H).

Example 320

4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-indol-4-yloxy)benzamide This example was prepared by substituting EXAMPLE 55B for EXAMPLE 1E and EXAMPLE 319A for EXAMPLE 1F in EXAMPLE 1G. $^1$H NMR (500 MHz, pyridine-$d_5$) δ 12.41 (s, 1H), 9.16 (d, 1H), 9.05 (t, 1H), 8.31 (dd, 1H), 8.17 (d, 1H), 7.39 (d, 1H), 7.05-7.13 (m, 3H), 6.99 (d, 1H), 6.78 (dd, 1H), 6.72-6.76 (m, 2H), 6.66 (d, 1H), 3.83 (q, 2H), 3.01-3.07 (m, 4H), 2.98 (t, 2H), 2.76 (s, 2H), 2.25 (t, 2H), 2.08-2.16 (m, 4H), 1.97 (s, 2H), 1.39 (t, 2H), 0.94 (s, 6H).

Example 321

4-(4-{[2-(4-chlorophenyl)-4,4-dimethylcyclohex-1-en-1-yl]methyl}piperazin-1-yl)-N-{[4-({[(3R)-4-hydroxy-1-adamantyl]methyl}amino)-3-nitrophenyl]sulfonyl}-2-(1H-indol-5-yloxy)benzamide The title compound was prepared as described in EXAMPLE 310C by replacing EXAMPLE 310A with 5-aminomethyl-admantan-2-ol. $^1$H NMR (500 MHz, dimethylsulfoxide-$d_6$) δ 11.17 (s, 2H), 8.57 (d, 1H), 8.51 (t, 1H), 7.76 (dd, 1H), 7.50 (d, 1H), 7.38-7.42 (m, 2H), 7.33 (d, 2H), 7.11-7.16 (m, 2H), 7.03 (d, 2H), 6.86 (dd, 1H), 6.65 (dd, 1H), 6.39 (s, 1H), 6.14 (d, 1H), 4.61 (d, 1H), 3.63 (d, 1H), 3.13 (d, 2H), 3.03 (s, 4H), 2.73 (s, 2H), 2.11-2.21 (m, 6H), 2.04 (d, 2H), 1.95 (s, 2H), 1.78-1.86 (m, 3H), 1.49-1.60 (m, 6H), 1.38 (t, 2H), 1.29 (d, 2H), 0.92 (s, 6H).

Example 322

4-(4-{[2-(4-chlorophenyl)-4,4-dimethylcyclohex-1-en-1-yl]methyl}piperazin-1-yl)-N-{[4-({[Cis-4-hydroxy-1-adamantyl]methyl}amino)-3-nitrophenyl]sulfonyl}-2-(1H-indol-5-yloxy)benzamide The title compound was prepared as described in EXAMPLE 310C by replacing EXAMPLE 310A with 5-aminomethyl-admantan-2-ol. $^1$H NMR (500 MHz, dimethylsulfoxide-$d_6$) δ 11.16 (s, 2H), 8.57 (d, 1H), 8.52 (t, 1H), 7.71-7.80 (m, 1H), 7.51 (d, 1H), 7.37-7.42 (m, 2H), 7.33 (d, 2H), 7.09-7.17 (m, 2H), 7.03 (d, 2H), 6.85 (dd, 1H), 6.65 (dd, 1H), 6.39 (s, 1H), 6.14 (d, 1H), 4.61 (d, 1H), 3.61 (d, 1H), 3.08 (d, 2H), 3.03 (s, 4H), 2.72 (s, 2H), 2.09-2.21 (m, 6H), 1.82-1.96 (m, 7H), 1.55-1.69 (m, 4H), 1.49 (s, 2H), 1.38 (t, 2H), 1.19-1.27 (m, 3H), 0.92 (s, 6H).

Example 323

4-(4-{[2-(4-chlorophenyl)-4,4-dimethylcyclohex-1-en-1-yl]methyl}piperazin-1-yl)-2-(1H-indol-4-yloxy)-N-({3-nitro-4-[(3,3,3-trifluoropropyl)amino]phenyl}sulfonyl)benzamide

Example 323A 3-nitro-4-(3,3,3-trifluoropropylamino)benzenesulfonamide

This example was prepared by substituting 3,3,3-trifluoropropan-1-amine for (tetrahydro-2H-pyran-4-yl)methanamine in EXAMPLE 1F.

Example 323B 4-(4-{[2-(4-chlorophenyl)-4,4-dimethylcyclohex-1-en-1-yl]methyl}piperazin-1-yl)-2-(1H-indol-4-yloxy)-N-({3-nitro-4-[(3,3,3-trifluoropropyl)amino]phenyl}sulfonyl)benzamide This example was prepared by substituting EXAMPLE 323A for EXAMPLE 1F and EXAMPLE 55B for EXAMPLE 26C in EXAMPLE 177. $^1$H NMR (500 MHz, dimethylsulfoxide-$d_6$) δ 11.34 (s, 1H), 11.19 (s, 1H), 8.53 (m, 1H), 8.47 (s, 1H), 7.74 (dd, 1H), 7.54 (d, 1H), 7.34 (d, 2H), 7.25 (m, 1H), 7.13 (d, 1H), 6.99 (m, 4H), 6.67 (d, 1H), 6.36 (d, 1H), 6.24 (m, 2H), 3.65 (q, 2H), 3.01 (m, 4H), 2.68 (m, 4H), 2.16 (m, 6H), 1.95 (s, 2H), 1.38 (t, 2H), 0.93 (s, 6H).

Example 324

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(3,3,3-trifluoropropyl)amino]phenyl}sulfonyl)benzamide This example was prepared by substituting EXAMPLE 323A for EXAMPLE 1F in EXAMPLE 177. $^1$H NMR (500 MHz, dimethylsulfoxide-$d_6$) δ 11.06 (s, 1H), 8.44 (m, 2H), 7.75 (dd, 1H), 7.54 (d, 1H), 7.33 (m, 4H), 7.02 (m, 3H), 6.90 (d, 1H), 6.76 (dd, 1H), 6.58 (dd, 1H), 6.33 (m, 1H), 6.15 (d, 1H), 3.63 (q, 2H), 2.97 (m, 4H), 2.68 (m, 4H), 2.16 (m, 6H), 1.95 (s, 2H), 1.38 (t, 2H), 0.92 (s, 6H).

Example 325

N-({5-bromo-6-[(tetrahydro-2H-pyran-4-ylmethyl)amino]pyridin-3-yl}sulfonyl)-4-(4-{[2-(4-chlorophenyl)-4,4-dimethylcyclohex-1-en-1-yl]methyl}piperazin-1-yl)-2-(1H-indol-4-yloxy)benzamide

Example 325A 5-bromo-6-((tetrahydro-2H-pyran-4-yl)methylamino)pyridine-3-sulfonamide The mixture of EXAMPLE 329A (93 mg), (tetrahydro-2H-pyran-4-yl)methanamine (40 mg) and triethylamine (0.144 mL) in anhydrous dixoane (4 mL) was heated at 110° C. overnight. The organic solvent was removed under vacuum. The residue was suspended in dichloromethane. The solid was filtered and dried to afford the title compound.

Example 325B

N-({5-bromo-6-[(tetrahydro-2H-pyran-4-ylmethyl)amino]pyridin-3-yl}sulfonyl)-4-(4-{[2-(4-chlorophenyl)-4,4-dimethylcyclohex-1-en-1-yl]methyl}piperazin-1-yl)-2-(1H-indol-4-yloxy)benzamide This example was prepared by substituting EXAMPLE 55B for EXAMPLE 26C and EXAMPLE 325A for EXAMPLE 1F in EXAMPLE 177. $^1$H NMR (400 MHz, dimethylsulfoxide-$d_6$) δ 11.28 (s, 1H), 11.10 (s, 1H), 8.38 (d, 1H), 7.93 (d, 1H), 7.57 (d, 1H), 7.32 (m, 4H), 7.22 (d, 1H), 7.02 (m, 3H), 6.71 (dd, 1H), 6.51 (d, 1H), 6.27 (m, 2H), 3.82 (dd, 2H), 3.31 (m, 2H), 3.23 (m, 2H), 3.05 (m, 4H), 2.74 (s, 2H), 2.16 (m, 6H), 1.95 (s, 2H), 1.88 (m, 1H), 1.55 (m, 2H), 1.37 (m, 2H), 1.18 (m, 2H), 0.92 (s, 6H).

Example 326

4-(4-{[2-(4-chlorophenyl)-4,4-dimethylcyclohex-1-en-1-yl]methyl}piperazin-1-yl)-N-[(4-{[(1,1-dioxidotetrahydrothien-3-yl)methyl]amino}-3-nitrophenyl)sulfonyl]-2-(1H-indol-4-yloxy)benzamide This example was prepared by substituting EXAMPLE 337A for 4-chloro-3-nitrobenzene sulfonamide and (1,1-dioxidotetrahydrothien-3-yl)methylamine hydrochloride for 1-(2-methoxy-ethyl)-piperidin-4-ylamine in EXAMPLE 189A. $^1$H NMR (400 MHz, dimethylsulfoxide-d$_6$) δ 11.25 (s, 1H), 8.71 (m, 1H), 8.51 (d, 1H), 7.72 (dd, 1H), 7.53 (d, 1H), 7.34 (d, 2H), 7.29 (m, 1H), 7.18 (d, 1H), 7.12 (d, 1H), 7.04 (d, 2H), 6.98 (m, 1H), 6.70 (dd, 1H), 6.44 (d, 1H), 6.26 (dd, 2H), 3.55 (t, 2H), 3.27 (m, 2H), 3.04 (m, 5H), 2.91 (m, 1H), 2.74 (s, 3H), 2.28 (m, 1H), 2.16 (m, 6H), 1.95 (s, 2H), 1.85 (m, 1H), 1.38 (t, 2H), 0.92 (s, 6H).

Example 327

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-indol-5-yloxy)benzamide This example was prepared by substituting EXAMPLE 306D for EXAMPLE 1F in EXAMPLE 177. $^1$H NMR (500 MHz, dimethylsulfoxide-d$_6$) δ 11.16 (s, 2H), 8.41 (d, 1H), 8.10 (dd, 1H), 7.51 (d, 1H), 7.39-7.46 (m, 3H), 7.34 (d, 2H), 7.16 (s, 1H), 7.04 (d2H), 6.85 (dd, 1H), 6.64 (dd, 1H), 6.40 (d, 1H), 6.15 (d, 1H), 4.38 (d, 2H), 3.76-3.80 (m, 2H), 3.56-3.61 (m, 2H), 3.05 (s, 4H), 2.78 (s, 2H), 2.12-2.23 (m, 6H), 1.95 (s, 2H), 1.80-1.89 (m, 4H), 1.38 (t, 2H), 0.92 (s, 6H).

Example 328

4-(4-{[2-(4-chlorophenyl)-4,4-dimethylcyclohex-1-en-1-yl]methyl}piperazin-1-yl)-2-(1H-indol-5-yloxy)-N-({4-(methylamino)-3-[(trifluoromethyl)sulfonyl]phenyl}sulfonyl)benzamide Example 328A 4-(methylamino)-3-(trifluoromethylsulfonyl)benzenesulfonamide This example was prepared by substituting EXAMPLE 159C for 4-fluoro-3-nitrobenzenesulfonamide and methylamine for (tetrahydropyran-4-yl)methylamine in EXAMPLE 1F.

Example 328B 4-(4-{[2-(4-chlorophenyl)-4,4-dimethylcyclohex-1-en-1-yl]methyl}piperazin-1-yl)-2-(1H-indol-5-yloxy)-N-({4-(methylamino)-3-[(trifluoromethyl)sulfonyl]phenyl}sulfonyl)benzamide This example was prepared by substituting EXAMPLE 328A for EXAMPLE 1F in EXAMPLE 177. $^1$H NMR (400 MHz, dimethylsulfoxide-d$_6$) δ 11.17 (s, 1H), 8.17 (d, 1H), 7.91 (dd, 1H), 7.49 (d, 1H), 7.40 (m, 3H), 7.33 (d, 2H), 7.16 (m, 1H), 7.04 (d, 2H), 6.87 (m, 2H), 6.65 (dd, 1H), 6.40 (m, 1H), 6.14 (d, 1H), 3.03 (m, 4H), 2.91 (d, 3H), 2.73 (s, 2H), 2.15 (m, 6H), 1.95 (s, 2H), 1.38 (t, 2H), 0.92 (s, 6H).

Example 329

N-{[5-bromo-6-(tetrahydro-2H-pyran-4-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-indol-5-yloxy)benzamide Example 329A 5-bromo-6-chloropyridine-3-sulfonamide 5-Bromo-6-chloropyridine-3-sulfonyl chloride (8.2 g) in methanol (20 mL) was cooled to 0° C. To this mixture was added 7N NH$_3$ in methanol (80 mL). The reaction mixture was stirred overnight. The solvent was removed at low temperature, and the residue was partitioned between ethyl acetate and water. The aqueous layer was extracted with ethyl acetate three times. The combined organic layers were washed with brine, dried (MgSO$_4$), filtered, and concentrated. The solid was purified by flash column chromatography on silica gel using 10-50% ethyl acetate in hexanes to give the title compound.

Example 329B 5-bromo-6-((tetrahydro-2H-pyran-4-yl)methoxy)pyridine-3-sulfonamide (Tetrahydro-2H-pyran-4-yl)methanol (0.65 g) in tetrahydrofuran (20 mL) was treated with 60% sodium hydride (0.895 g). The reaction mixture was stirred for 10 minutes. To this mixture was added EXAMPLE 329A (1.519 g). The reaction mixture was stirred overnight. It was poured into water, neutralized with 10% aqueous HCl, and extracted with ethyl acetate three times. The combined organic layers were washed with brine, dried over MgSO$_4$, filtered, and concentrated. The residue was purified with flash column chromatography on silica gel eluting with 20%-60% ethyl acetate in hexanes to give the title compound.

Example 329C

N-{[5-bromo-6-(tetrahydro-2H-pyran-4-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-indol-5-yloxy)benzamide This example was prepared by substituting EXAMPLE 329B for EXAMPLE 1F in EXAMPLE 177. $^1$H NMR (500 MHz, dimethylsulfoxide-d$_6$) δ 11.15 (s, 1H), 8.60 s, 1H), 8.38 (d, 1H), 7.54 (d, 1H), 7.38-7.42 (m, 2H), 7.34 (d, 2H), 7.17 (s, 1H), 7.04 (d, 2H), 6.85 (dd, 1H), 6.64 (dd, 1H), 6.39 (s, 1H), 6.14 (d, 1H), 4.25 (d, 2H), 3.87 (dd, 2H), 3.05 (s, 4H), 2.80 (s, 2H), 2.25 (s, 4H), 2.12-2.14 (m, 4H), 1.95 (s, 2H), 1.63-1.66 (m, 2H), 1.37-1.40 (m, 2H), 0.92 (s, 6H).

Example 330

4-(4-{[4-(4-chlorophenyl)-6-isopropoxypyridin-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide Example 330A 1-((4-(4-chlorophenyl)-6-isopropoxypyridin-3-yl)methyl)piperazine This example was prepared by substituting EXAMPLE 307F for EXAMPLE 1A in EXAMPLE 1B.

Example 330B ethyl 2-(1H-indol-5-yloxy)-4-(4-((4-(4-chlorophenyl)-6-isopropoxypyridin-3-yl)methyl)piperazin-1-yl)benzoate This example was prepared by substituting EXAMPLE 330A for EXAMPLE 20C and EXAMPLE 26A for EXAMPLE 20A in EXAMPLE 20D.

Example 330C 2-(1H-indol-5-yloxy)-4-(4-((4-(4-chlorophenyl)-6-isopropoxypyridin-3-yl)methyl)piperazin-1-yl)benzoic acid This example was prepared by substituting EXAMPLE 330B for EXAMPLE 1D in EXAMPLE 1E.

Example 330D 4-(4-{[4-(4-chlorophenyl)-6-isopropoxypyridin-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide This example was prepared by substituting EXAMPLE 330C for EXAMPLE 26C in EXAMPLE 177. $^1$H NMR (500 MHz, dimethylsulfoxide-$d_6$) δ 11.21, (s, 1H), 11.17 (s, 1H), 8.63 (t, 1H), 8.59 (d, 1H), 8.08 (s, 1H), 7.79 (dd1H), 7.54-7.56 (m, 3H), 7.47 (d, 2H), 7.38-7.42 (m, 2H), 7.15 (d, 1H), 7.10 (d, 1H), 6.87 (dd, 1H), 6.68 (dd, 1H), 6.59 (s, 1H), 6.39 (s, 1H), 6.17 (d, 1H), 5.23-5.28 (m, 1H), 3.85 (dd, 2H), 3.24-3.31 (m, 4H), 3.02 (s, 4H), 2.29 (s, 4H), 1.86-1.91 (m, 1H), 1.61-1.63 (m, 2H), 1.28 (d, 6H).

Example 331

4-(4-{[2-(4-chlorophenyl)-4,4-dimethylcyclohex-1-en-1-yl]methyl}piperazin-1-yl)-2-(1H-indol-5-yloxy)-N-{6-(tetrahydro-2H-pyran-4-ylmethoxy)-5-(1,3-thiazol-2-yl)pyridin-3-yl]sulfonyl}benzamide

Example 331A 6-((tetrahydro-2H-pyran-4-yl)methoxy)-5-(thiazol-2-yl)pyridine-3-sulfonamide A mixture of EXAMPLE 329B (0.070 g), 2-(tributylstannyl)thiazole (0.090 g), and tetrakis(triphenylphosphine)palladium(O) (0.069 g) in dioxane (2 mL) was heated at 90° C. for 4 hours. After cooling, the mixture was loaded onto a silica gel column and eluting with 1:3 ethyl acetate:hexanes to give the title compound.

Example 331B 4-(4-{[2-(4-chlorophenyl)-4,4-dimethylcyclohex-1-en-1-yl]methyl}piperazin-1-yl)-2-(1H-indol-5-yloxy)-N-{6-(tetrahydro-2H-pyran-4-ylmethoxy)-5-(1,3-thiazol-2-yl)pyridin-3-yl]sulfonyl}benzamide This example was prepared by substituting EXAMPLE 331A for EXAMPLE 1F in EXAMPLE 177. $^1$H NMR (500 MHz, dimethylsulfoxide-$d_6$) δ 11.14 (s, 1H), 9.09 (s, 1H), 8.73 (s, 1H), 8.06 (d, 1H), 7.98 (d, 1H), 7.50 (d, 1H), 7.37-7.38 (m, 2H), 7.33 (d, 2H), 7.17 (d, 1H), 7.03 (d, 2H), 6.84 (dd, 1H), 6.62 (dd, 1H), 6.37 (s, 1H), 6.11 (d, 1H), 4.46 (d, 2H), 3.91 (dd, 2H), 3.36-3.39 (m, 4H), 3.02 (s, 4H), 2.76 (s, 2H), 2.12-2.20 (s, 8H), 1.94 (s, 2H), 1.45-1.47 (m, 2H), 1.37 (t, 2H), 0.91 (s, 6H).

Example 332

4-(4-{[2-(4-chlorophenyl)-4,4-dimethylcyclohex-1-en-1-yl]methyl}piperazin-1-yl)-2-(1H-indol-5-yloxy)-N-[(4-{[(2-methoxyethyl)amino]carbonyl}phenyl)sulfonyl]benzamide

Example 332A

N-(2-methoxyethyl)-4-sulfamoylbenzamide

This example was prepared by substituting 2-methoxyethanamine for (tetrahydro-2H-pyran-4-yl)methanamine in EXAMPLE 308A.

Example 332B 4-(4-{[2-(4-chlorophenyl)-4,4-dimethylcyclohex-1-en-1-yl]methyl}piperazin-1-yl)-2-(1H-indol-5-yloxy)-N-[(4-{[(2-methoxyethyl)amino]carbonyl}phenyl)sulfonyl]benzamide This example was prepared by substituting EXAMPLE 332A for EXAMPLE 1F and EXAMPLE 26C for EXAMPLE 1E in EXAMPLE 1G. $^1$H NMR (300 MHz, dimethylsulfoxide-$d_6$) t 11.28 (br s, 1H), 11.17 (s, 1H), 8.71 (m, 1H), 7.94 (m, 4H), 7.48 (d, 1H), 7.41 (m, 2H), 7.33 (d, 2H), 7.21 (d, 1H), 7.03 (d, 2H), 6.88 (dd, 1H), 6.63 (dd, 1H), 6.42 (t, 1H), 6.13 (d, 1H), 3.45 (m, 4H), 3.27 (s, 3H), 3.03 (m, 4H), 2.73 (br s, 2H), 2.16 (m, 6H), 1.95 (br s, 2H), 1.38 (m, 2H), 0.92 (s, 6H).

Example 333

4-(4-{[2-(4-chlorophenyl)-4,4-dimethylcyclohex-1-en-1-yl]methyl}piperazin-1-yl)-N-{5-cyano-6-(tetrahydro-2H-pyran-4-ylmethoxy)pyridin-3-yl]sulfonyl}-2-(1H-indol-5-yloxy)benzamide

Example 333A 5-cyano-6-((tetrahydro-2H-pyran-4-yl)methoxy)pyridine-3-sulfonamide A mixture of EXAMPLE 329B (0.702 g), dicyanozinc (0.129 g), and tetrakis(triphenylphosphine)palladium(O) (0.231 g) in N,N-dimethylformamide (2 mL) was degassed via vacuum/nitrogen cycle three times. The reaction mixture was heated at 120° C. for 3 hours. After cooling, it was poured into water and extracted with ethyl acetate three times. The combined organic layers were washed with brine, dried over MgSO$_4$, filtered, and concentrated. The residue was purified with flash column chromatography on silica gel eluting with 20%-60% ethyl acetate in hexanes to give the title compound.

Example 333B 4-(4-{[2-(4-chlorophenyl)-4,4-dimethylcyclohex-1-en-1-yl]methyl}piperazin-1-yl)-N-{5-cyano-6-(tetrahydro-2H-pyran-4-ylmethoxy)pyridin-3-yl]sulfonyl}-2-(1H-indol-5-yloxy)benzamide This example was prepared by substituting EXAMPLE 333A for EXAMPLE 1F in EXAMPLE 177. $^1$H NMR (500 MHz, dimethylsulfoxide-$d_6$) δ 11.17 (s, 1H), 8.84 (d, 1H), 8.64 (d, 1H), 7.57 (d, 1H), 7.38-7.41 (m, 4H), 7.12 (d, 1H), 7.08 (d, 2H), 6.87 (dd, 1H), 6.71 (dd, 1H), 6.38 (s, 1H), 6.23

(d, 1H), 4.31 (d, 2H), 3.88 (dd, 2H), 3.54 (br s, 2H), 3.02 (br s, 4H), 2.76 (br s, 2H), 2.18 (s, 4H), 2.01 (s, 2H), 1.63-1.66 (m, 2H), 1.49 (t, 2H), 0.94 (s, 6H).

Example 334

N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide This example was prepared by substituting 1-acetylpiperidin-4-amine for 1-(2-methoxy-ethyl)-piperidin-4-ylamine and EXAMPLE 310B for 4-chloro-3-nitrobenzenesulfonamide in EXAMPLE 189A. $^1$H NMR (300 MHz, dimethylsulfoxide-$d_6$) δ 11.16 (br s, 1H), 8.58 (d, 1H), 8.25 (d, 1H), 7.81 (dd, 1H), 7.51 (d, 1H), 7.43-7.37 (m, 2H), 7.34 (d, 2H), 7.19 (d, 1H), 7.15 (d, 1H), 7.04 (d, 2H), 6.85 (dd, 1H), 6.65 (dd, 1H), 6.39 (t, 1H), 6.15 (d, 1H), 4.32-4.23 (m, 1H), 3.96-3.77 (m, 2H), 3.21 (m, 2H), 3.03 (m, 4H), 2.80 (m, 2H), 2.73 (br s, 2H), 2.16 (m, 6H), 2.02 (s, 3H), 1.95 (br s, 2H), 1.65-1.44 (m, 2H), 1.38 (t, 2H), 0.92 (s, 6H).

Example 335

4-(4-{[2-(4-chlorophenyl)-4,4-dimethylcyclohex-1-en-1-yl]methyl}piperazin-1-yl)-2-(1H-indol-5-yloxy)-N-[(4-{[1-(methylsulfonyl)piperidin-4-yl]amino}-3-nitrophenyl)sulfonyl]benzamide This example was prepared by substituting 1-(methylsulfonyl)piperidin-4-amine for 1-(2-methoxy-ethyl)-piperidin-4-ylamine and EXAMPLE 187A for 4-chloro-3-nitrobenzenesulfonamide in EXAMPLE 189A. $^1$H NMR (300 MHz, dimethylsulfoxide-$d_6$) δ 11.15 (br s, 1H), 8.59 (d, 1H), 8.25 (d, 1H), 7.82 (dd, 1H), 7.51 (d, 1H), 7.43-7.38 (m, 2H), 7.34 (d, 2H), 7.14 (m, 2H), 7.04 (d, 2H), 6.85 (dd, 1H), 6.65 (dd, 1H), 6.39 (t, 1H), 6.15 (d, 1H), 3.80 (m, 1H), 3.57 (m, 2H), 3.04 (m, 4H), 2.95 (m, 2H), 2.92 (br s, 3H), 2.73 (m, 2H), 2.15 (m, 6H), 2.06-1.98 (m, 2H), 1.95 (br s, 2H), 1.70 (m, 2H), 1.38 (t, 2H), 0.92 (s, 6H).

Example 336

4-(4-{[2-(4-chlorophenyl)-4,4-dimethylcyclohex-1-en-1-yl]methyl}piperazin-1-yl)-N-((4-{[(1,4-dioxan-2-ylmethyl)amino]-3-nitrophenyl}sulfonyl)-2-(1H-indol-5-yloxy)benzamide

Example 336A 4-((1,4-dioxan-2-yl)methylamino)-3-nitrobenzenesulfonamide

The title compound was prepared as described in EXAMPLE 1F by replacing (tetrahydro-2H-pyran-4-yl)methanamine with (1,4-dioxan-2-yl)methanamine.

Example 336B 4-(4-{[2-(4-chlorophenyl)-4,4-dimethylcyclohex-1-en-1-yl]methyl}piperazin-1-yl)-N-((4-{[(1,4-dioxan-2-ylmethyl)amino]-3-nitrophenyl}sulfonyl)-2-(1H-indol-5-yloxy)benzamide The title compound was prepared as described in EXAMPLE 175F by replacing EXAMPLE 175E and EXAMPLE 1F with EXAMPLE 26C and EXAMPLE 336A, respectively. $^1$H NMR (500 MHz, dimethylsulfoxide-$d_6$) δ 11.16 (s, 2H), 8.54-8.63 (m, 2H), 7.82 (dd, 1H), 7.50 (d, 1H), 7.38-7.42 (m, 2H), 7.33 (d, 2H), 7.16 (d, 1H), 7.10 (d, 1H), 7.03 (d, 2H), 6.86 (dd, 1H), 6.65 (dd, 1H), 6.39 (s, 1H), 6.14 (d, 1H), 3.76-3.82 (m, 3H), 3.57-3.68 (m, 2H), 3.45-3.52 (m, 2H), 3.36-3.42 (m, 1H), 3.03 (s, 4H), 2.73 (d, 2H), 2.10-2.22 (m, 6H), 1.95 (s, 2H), 1.38 (t, 2H), 0.92 (s, 6H).

Example 337

N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-4-yloxy)benzamide

Example 337A

This example was prepared by substituting EXAMPLE 55B for EXAMPLE 1E and 4-chloro-3-nitrobenzenesulfonamide for EXAMPLE 1F in EXAMPLE 1G.

Example 337B

N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-indol-4-yloxy)benzamide This example was prepared by substituting 1-acetylpiperidin-4-amine for 1-(2-methoxy-ethyl)-piperidin-4-ylamine and EXAMPLE 337A for 4-chloro-3-nitrobenzenesulfonamide in EXAMPLE 189A. $^1$H NMR (300 MHz, dimethylsulfoxide-$d_6$) δ 11.24 (br s, 1H), 8.50 (d, 1H), 8.24 (d, 1H), 7.73 (dd, 1H), 7.52 (d, 1H), 7.34 (d, 2H), 7.27 (t, 1H), 7.19-7.13 (m, 2H), 7.04 (t, 2H), 6.97 (t, 1H), 6.70 (dd, 1H), 6.42 (d, 1H), 6.27 (dd, 1H), 6.24 (t, 1H), 4.29 (m, 1H), 3.97-3.78 (m, 2H), 3.22 (m, 2H), 3.05 (m, 4H), 2.81 (m, 2H), 2.72 (br s, 2H), 2.15 (m, 6H), 2.03 (s, 3H), 1.95 (br s, 2H), 1.66-1.44 (m, 2H), 1.38 (t, 2H), 0.92 (s, 6H).

Example 338

4-(4-{[2-(4-chlorophenyl)-4,4-dimethylcyclohex-1-en-1-yl]methyl}piperazin-1-yl)-2-(1H-indol-4-yloxy)-N-[(4-{[1-(methylsulfonyl)piperidin-4-yl]amino}-3-nitrophenyl)sulfonyl]benzamide This example was prepared by substituting 1-(methylsulfonyl)piperidin-4-amine for 1-(2-methoxy-ethyl)-piperidin-4-ylamine and EXAMPLE 337A for 4-chloro-3-nitrobenzenesulfonamide in EXAMPLE 189A. $^1$H NMR (300 MHz, dimethylsulfoxide-$d_6$) δ 11.24 (br s, 1H), 8.50 (d, 1H), 8.25 (d, 1H), 7.74 (dd, 1H), 7.52 (d, 1H), 7.34 (d, 2H), 7.27 (t, 1H), 7.17 (d, 1H), 7.12 (d, 1H), 7.04 (d, 2H), 6.97 (t, 1H), 6.70 (dd, 1H), 6.42 (d, 1H), 6.27 (d, 1H), 6.24 (t, 1H), 3.81 (m, 1H), 3.58 (m, 2H), 3.05 (m, 4H), 2.96 (m, 2H), 2.92 (s, 3H), 2.74 (m, 2H), 2.16 (m, 6H), 2.06-1.98 (m, 2H), 1.95 (br s, 2H), 1.70 (m, 2H), 1.38 (t, 2H), 0.92 (s, 6H).

Example 339

4-(4-{[4'-chloro-5-(trifluoromethyl)-1,1'-biphenyl-2-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide

Example 339A methyl 2-(1H-indol-5-yloxy)-4-(4-(2-bromo-4-(trifluoromethyl)benzyl)piperazin-1-yl)benzoate This example was prepared by substituting 4-trifluoromethyl-2-bromobenzaldehyde for EXAMPLE 27C and EXAMPLE 150A for tert-butyl piperazine-1-carboxylate in EXAMPLE 1A.

Example 339B methyl 2-(1H-indol-5-yloxy)-4-(4-((4'-chloro-5-(trifluoromethyl)biphenyl-2-yl)methyl)piperazin-1-yl)benzoate This example was prepared by substituting EXAMPLE 339A for 2-fluoro-4-iodo-5-methylpyridine in EXAMPLE 307A.

Example 339C 2-(1H-indol-5-yloxy)-4-(4-((4'-chloro-5-(trifluoromethyl)biphenyl-2-yl)methyl)piperazin-1-yl)benzoic acid This example was prepared by substituting EXAMPLE 339B for EXAMPLE 1D in EXAMPLE 1E.

Example 339D 4-(4-{[4'-chloro-5-(trifluoromethyl)-1,1'-biphenyl-2-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide This example was prepared by substituting EXAMPLE 339C for EXAMPLE 26C in EXAMPLE 177. $^1$H NMR (500 MHz, dimethylsulfoxide-$d_6$) δ 11.24, (s, 1H), 11.17 (s, 1H), 8.63 (t, 1H), 7.79 (dd, 1H), 7.72 (m, 2H), 7.38-7.53 (m, 8H), 7.15 (d, 1H), 7.10 (d, 1H), 6.87 (dd, 1H), 6.67 (dd, 1H), 6.39 (s, 1H), 6.16 (d, 1H), 3.85 (dd, 2H), 3.41 (s, 2H), 3.24-3.31 (m, 6H), 3.04 (s, 4H), 2.29 (s, 4H), 1.60-1.63 (m, 2H), 1.24-1.28 (m, 2H).

Example 340

4-(4-{[4'-chloro-5-(trifluoromethyl)-1,1'-biphenyl-2-yl]methyl}piperazin-1-yl)-2-(1H-indol-5-yloxy)-N-{[3-nitro-4-(tetrahydro-2H-pyran-4-ylmethoxy)phenyl]sulfonyl}benzamide This example was prepared by substituting EXAMPLE 339C for EXAMPLE 26C and EXAMPLE 279A for EXAMPLE 1F in EXAMPLE 177. $^1$H NMR (500 MHz, dimethylsulfoxide-$d_6$) δ 11.40, (s, 1H), 11.17 (s, 1H), 8.41 (d, 1H), 8.07 (dd, 1H), 7.70-7.74 (m, 2H), 7.38-7.53 (m, 8H), 7.16 (d, 1H), 6.87 (dd, 1H), 6.67 (dd, 1H), 6.40 (s, 1H), 6.17 (d, 1H), 4.09 (d, 2H), 3.88 (dd, 2H), 3.42 (s, 2H), 3.05 (s, 4H), 2.30 (s, 4H), 2.00-2.05 (m, 1H), 1.63-1.66 (m, 2H), 1.31-1.37 (m, 2H).

Example 341

4-{4-[(5-tert-butyl-4'-chloro-1,1'-biphenyl-2-yl)methyl]piperazin-1-yl}-2-(1H-indol-5-yloxy)-N-({3-nitro-4-[(tetrahydro-2H-pyran-4-ylmethyl)amino]phenyl}sulfonyl)benzamide

Example 341A methyl 2-(1H-indol-5-yloxy)-4-(4-(2-bromo-4-tert-butylbenzyl)piperazin-1-yl)benzoate This example was prepared by substituting 4-tert-butyl-2-bromobenzaldehyde for EXAMPLE 27C and EXAMPLE 150A for tert-butyl piperazine-1-carboxylate in EXAMPLE 1A.

Example 341B methyl 2-(1H-indol-5-yloxy)-4-(4-((5-tert-butyl-4'-chlorobiphenyl-2-yl)methyl)piperazin-1-yl)benzoate This example was prepared by substituting EXAMPLE 341A for 2-fluoro-4-iodo-5-methylpyridine in EXAMPLE 307A.

Example 341C 2-(1H-indol-5-yloxy)-4-(4-((5-tert-butyl-4'-chlorobiphenyl-2-yl)methyl)piperazin-1-yl)benzoic acid This example was prepared by substituting EXAMPLE 341B for EXAMPLE 1D in EXAMPLE 1E.

Example 341D

4-{4-[(5-tert-butyl-4'-chloro-1,1'-biphenyl-2-yl)methyl]piperazin-1-yl}-2-(1H-indol-5-yloxy)-N-({3-nitro-4-[(tetrahydro-2H-pyran-4-ylmethyl)amino]phenyl}sulfonyl)benzamide This example was prepared by substituting EXAMPLE 341C for EXAMPLE 26C in EXAMPLE 177. $^1$H NMR (500 MHz, dimethylsulfoxide-$d_6$) δ 11.22, (s, 1H), 11.16 (s, 1H), 8.62 (t, 1H), 8.58 (d, 1H), 7.79 (dd, 1H), 7.53 (d, 1H), 7.34-7.44 (m, 8H), 7.18 (s, 1H), 7.14 (d, 1H), 7.09 (d, 1H), 6.86 (dd, 1H), 6.67 (dd, 1H), 6.39 (s, 1H), 6.17 (d, 1H), 3.85 (dd, 2H), 3.24-3.30 (m, 6H), 3.04 (s, 4H), 2.29 (s, 4H), 1.86-1.91 (m, 1H), 1.60-1.63 (m, 2H), 1.28 (s, 9H).

Example 342

4-{4-[(5-tert-butyl-4'-chloro-1,1'-biphenyl-2-yl)methyl]piperazin-1-yl}-2-(1H-indol-5-yloxy)-N-{[3-nitro-4-(tetrahydro-2H-pyran-4-ylmethoxy)phenyl]sulfonyl}benzamide This example was prepared by substituting EXAMPLE 341C for EXAMPLE 26C and EXAMPLE 279A for EXAMPLE 1F in EXAMPLE 177. $^1$H NMR (500 MHz, dimethylsulfoxide-$d_6$) δ 11.25, (br s, 1H), 11.16 (s, 1H), 8.40 (d, 1H), 8.06 (dd, 1H), 7.52 (d, 1H), 7.35-7.46 (m, 8H), 7.19 (s, 1H), 7.15 (d, 1H), 6.85 (dd, 1H), 6.66 (dd, 1H), 6.39 (s, 1H), 6.17 (d, 1H), 4.08 (d, 2H), 3.88 (dd, 2H), 3.05 (s, 4H), 2.32 (s, 4H), 1.64 (dd, 2H), 1.32-1.37 (m, 2H), 1.28 (s, 9H).

Example 343

4-(4-{[2-(4-chlorophenyl)-4,4-dimethylcyclohex-1-en-1-yl]methyl}piperazin-1-yl)-2-(1H-indol-4-yloxy)-N-({3-nitro-4-[(2,2,2-trifluoroethyl)amino]phenyl}sulfonyl)benzamide Example 343A 3-nitro-4-(2,2,2-trifluoroethylamino)benzenesulfonamide This example was prepared by substituting 2,2,2-trifluoroethanamine for (tetrahydro-2H-pyran-4-yl)methanamine in EXAMPLE 1F.

Example 343B 4-(4-{[2-(4-chlorophenyl)-4,4-dimethylcyclohex-1-en-1-yl]methyl}piperazin-1-yl)-2-(1H-indol-4-yloxy)-N-({3-nitro-4-[(2,2,2-trifluoroethyl)amino]phenyl}sulfonyl)benzamide This example was prepared by substituting EXAMPLE 343A for EXAMPLE 1F and EXAMPLE 55B for EXAMPLE 26C in EXAMPLE 177. $^1$H NMR (500 MHz, dimethylsulfoxide-$d_6$) δ 10.98 (s, 1H), 8.41 (m, 2H), 7.75 (dd, 1H), 7.54 (d, 1H), 7.34 (d, 2H), 7.28 (m, 2H), 7.06 (m, 3H), 6.93 (m, 1H), 6.70 (dd, 1H), 6.53 (dd, 1H), 6.30 (m, 1H), 6.14 (d, 1H), 4.32 (m, 2H), 2.93 (m, 4H), 2.71 (s, 2H), 2.16 (m, 6H), 1.95 (s, 2H), 1.38 (t, 2H), 0.92 (s, 6H).

Example 344

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(2,2,2-trifluoroethyl)amino]phenyl}sulfonyl)benzamide This example was prepared by substituting EXAMPLE 343A for EXAMPLE 1F in EXAMPLE 177. $^1$H NMR (500 MHz, dimethylsulfoxide-$d_6$) δ 11.05 (s, 1H), 8.40 (m, 2H), 7.77 (dd, 1H), 7.60 (d, 1H), 7.34 (d, 2H), 7.18 (m, 1H), 7.12 (d, 1H), 7.04 (m, 3H), 6.88 (t, 1H), 6.58 (dd, 1H), 6.22 (m, 3H), 4.33 (m, 2H), 2.93 (m, 4H), 2.71 (s, 2H), 2.16 (m, 6H), 1.95 (s, 2H), 1.38 (t, 2H), 0.93 (s, 6H).

Example 345

4-(4-{[2-(4-chlorophenyl)-4,4-dimethylcyclohex-1-en-1-yl]methyl}piperazin-1-yl)-2-(1H-indol-5-yloxy)-N-[3-{[(tetrahydro-2H-pyran-4-ylmethyl)amino]carbonyl}phenyl)sulfonyl]benzamide Example 345A 3-sulfamoyl-N-((tetrahydro-2H-pyran-4-yl)methyl)benzamide This example was prepared by substituting 3-sulfamoylbenzoic acid for 4-sulfamoylbenzoic acid in EXAMPLE 308A.

Example 345B 4-(4-{[2-(4-chlorophenyl)-4,4-dimethylcyclohex-1-en-1-yl]methyl}piperazin-1-yl)-2-(1H-indol-5-yloxy)-N-[(3-{[(tetrahydro-2H-pyran-4-ylmethyl)amino]carbonyl}phenyl)sulfonyl]benzamide This example was prepared by substituting EXAMPLE 345A for EXAMPLE 1F and EXAMPLE 26C for EXAMPLE 1E in EXAMPLE 1G. $^1$H NMR (300 MHz, dimethylsulfoxide-$d_6$) δ 11.28 (br s, 1H), 11.18 (s, 1H), 8.75 (t, 1H), 8.41 (m, 1H), 8.10 (d, 1H), 8.01 (d, 1H), 7.60 (t, 1H), 7.48 (d, 1H), 7.41 (m, 2H), 7.33 (d, 2H), 7.23 (d, 1H), 7.03 (d, 2H), 6.88 (dd, 1H), 6.83 (dd, 1H), 6.42 (t, 1H), 6.11 (d, 1H), 3.83 (dd, 2H), 3.19 (m, 4H), 3.02 (m, 4H), 2.73 (m, 2H), 2.16 (m, 6H), 1.94 (br s, 2H), 1.80 (m, 1H), 1.58 (dd, 2H), 1.37 (t, 2H), 1.24 (m, 2H), 0.92 (s, 6H).

Example 346

4-(4-{[2-(4-chlorophenyl)-4,4-dimethylcyclohex-1-en-1-yl]methyl}piperazin-1-yl)-N-({4-[(2R)-1,4-dioxan-2-ylmethoxy]-3-nitrophenyl}sulfonyl)-2-(1H-indol-5-yloxy)benzamide Example 346A (R)-4-((1,4-dioxan-2-yl)methoxy)-3-nitrobenzenesulfonamide The racemic mixture of EXAMPLE 297A was resolved on a SFC chiral AD column to provide the title compound.

Example 346B 4-(4-{[2-(4-chlorophenyl)-4,4-dimethylcyclohex-1-en-1-yl]methyl}piperazin-1-yl)-N-({4-[(2R)-1,4-dioxan-2-ylmethoxy]-3-nitrophenyl}sulfonyl)-2-(1H-indol-5-yloxy)benzamide The title compound was prepared as described in EXAMPLE 175F by replacing EXAMPLE 175E and EXAMPLE 1F with EXAMPLE 26C and EXAMPLE 346A, respectively. $^1$H NMR (500 MHz, dimethylsulfoxide-$d_6$) δ 11.16 (s, 2H), 8.39 (d, 1H), 8.06 (dd, 1H), 7.51 (d, 1H), 7.38-7.43 (m, 3H), 7.34 (d, 2H), 7.15 (d, 1H), 7.04 (d, 2H), 6.85 (dd, 1H), 6.64 (dd, 1H), 6.39 (s, 1H), 6.15 (d, 1H), 4.20-4.28 (m, 2H), 3.85-3.91 (m, 1H), 3.82 (dd, 1H), 3.74-3.78 (m, 1H), 3.59-3.69 (m, 2H), 3.40-3.51 (m, 2H), 3.05 (s, 4H), 2.78 (s, 2H), 2.23 (s, 4H), 2.14 (s, 2H), 1.95 (s, 2H), 1.38 (t, 2H), 0.92 (s, 6H).

Example 347

4-(4-{[2-(4-chlorophenyl)-4,4-dimethylcyclohex-1-en-1-yl]methyl}piperazin-1-yl)-N-({4-[(2S)-1,4-dioxan-2-ylmethoxy]-3-nitrophenyl}sulfonyl)-2-(1H-indol-5-yloxy)benzamide Example 347A (S)-4-((1,4-dioxan-2-yl)methoxy)-3-nitrobenzenesulfonamide The racemic mixture of EXAMPLE 297A was resolved on a SFC chiral AD column to provide the title compound.

Example 347B 4-(4-{[2-(4-chlorophenyl)-4,4-dimethylcyclohex-1-en-1-yl]methyl}piperazin-1-yl)-N-({4-[(2S)-1,4-dioxan-2-ylmethoxy]-3-nitrophenyl}sulfonyl)-2-(1H-indol-5-yloxy)benzamide The title compound was prepared as described in EXAMPLE 175F by replacing EXAMPLE 175E and EXAMPLE 1F with EXAMPLE 26C and EXAMPLE 347A, respectively. $^1$H NMR (500 MHz, dimethylsulfoxide-$d_6$) δ 11.16 (s, 2H), 8.39 (d, 1H), 8.06 (dd, 1H), 7.51 (d, 1H), 7.38-7.43 (m, 3H), 7.34 (d, 2H), 7.15 (d, 1H), 7.04 (d, 2H), 6.85 (dd, 1H), 6.64 (dd, 1H), 6.39 (s, 1H), 6.15 (d, 1H), 4.20-4.28 (m, 2H), 3.85-3.91 (m, 1H), 3.82 (dd, 1H), 3.74-3.78 (m, 1H), 3.59-3.69 (m, 2H), 3.40-3.51 (m, 2H), 3.05 (s, 4H), 2.78 (s, 2H), 2.23 (s, 4H), 2.14 (s, 2H), 1.95 (s, 2H), 1.38 (t, 2H), 0.92 (s, 6H).

Example 348

4-(4-{[2-(4-chlorophenyl)-4,4-dimethylcyclohex-1-en-1-yl]methyl}piperazin-1-yl)-2-(1H-indol-5-yloxy)-N-({4-[(3-morpholin-4-ylpropyl)amino]-3-[(trifluoromethyl)sulfonyl]phenyl}sulfonyl)benzamide

Example 348A 4-(3-morpholinopropylamino)-3-(trifluoromethylsulfonyl)benzenesulfonamide This example was prepared by substituting EXAMPLE 159C for 4-fluoro-3-nitrobenzenesulfonamide and 3-morpholinopropan-1-amine for (tetrahydropyran-4-yl)methylamine in EXAMPLE 1F.

Example 348B 4-(4-{[2-(4-chlorophenyl)-4,4-dimethylcyclohex-1-en-1-yl]methyl}piperazin-1-yl)-2-(1H-indol-5-yloxy)-N-({4-[(3-morpholin-4-ylpropyl)amino]-3-[(trifluoromethyl)sulfonyl]phenyl}sulfonyl)benzamide 5-yloxy)-N-({4-(methylamino)-3-[(trifluoromethyl)sulfonyl]phenyl}sulfonyl)benzamide This example was prepared by substituting EXAMPLE 348A for EXAMPLE 1F in EXAMPLE 177. $^1$H NMR (400 MHz, dimethylsulfoxide-$d_6$) δ 11.17 (s, 1H), 8.17 (d, 1H), 7.91 (dd, 1H), 7.49 (d, 1H), 7.40 (m, 3H), 7.33 (d, 2H), 7.15 (d, 1H), 7.03 (m, 3H), 6.85 (dd, 1H), 6.64 (dd, 1H), 6.40 (s, 1H), 6.13 (d, 1H), 3.59 (m, 4H), 3.38 (m, 4H), 3.02 (m, 4H), 2.72 (s, 2H), 2.40 (m, 6H), 2.15 (m, 6H), 1.95 (s, 2H), 1.73 (m, 2H), 0.92 (s, 6H).

Example 349

4-(4-{[2-(4-chlorophenyl)-4,4-dimethylcyclohex-1-en-1-yl]methyl}piperazin-1-yl)-2-(1H-indol-4-yloxy)-N-({4-[(3-morpholin-4-ylpropyl)amino]-3-[(trifluoromethyl)sulfonyl]phenyl}sulfonyl)benzamide This example was prepared by substituting EXAMPLE 55B for EXAMPLE 26C and EXAMPLE 348A for EXAMPLE 1F in EXAMPLE 177. $^1$H NMR (400 MHz, dimethylsulfoxide-$d_6$) δ 11.25 (s, 1H), 11.08 (m, 1H), 8.12 (d, 1H), 7.81 (dd, 1H), 7.52 (d, 1H), 7.36 (m, 3H), 7.28 (m, 1H), 7.19 (d, 1H), 7.04 (d, 2H), 6.98 (m, 2H), 6.69 (dd, 1H), 6.44 (d, 1H), 6.25 (m, 2H), 3.60 (m, 4H), 3.38 (m, 2H), 3.03 (m, 4H), 2.73 (s, 2H), 2.43 (m, 6H), 2.16 (m, 6H), 1.95 (s, 2H), 1.73 (m, 2H), 1.38 (t, 2H), 0.92 (s, 6H).

Example 350

N-({5-bromo-6-[(tetrahydro-2H-pyran-4-ylmethyl)amino]pyridin-3-yl}sulfonyl)-4-(4-{[2-(4-chlorophenyl)-4,4-dimethylcyclohex-1-en-1-yl]methyl}piperazin-1-yl)-2-(1H-indol-5-yloxy)benzamide This example was prepared by substituting EXAMPLE 325A for EXAMPLE 1F in EXAMPLE 177. $^1$H NMR (400 MHz, dimethylsulfoxide-$d_6$) δ 11.19 (s, 1H), 11.02 (s, 1H), 8.47 (d, 1H), 8.07 (d, 1H), 7.55 (d, 1H), 7.39 (m, 5H), 7.25 (d, 1H), 7.03 (d, 2H), 6.89 (dd, 1H), 6.65 (dd, 1H), 6.42 (s, 1H), 6.11 (d, 1H), 3.82 (dd, 2H), 3.31 (m, 2H), 3.24 (m, 2H), 3.03 (m, 4H), 2.72 (s, 2H), 2.15 (m, 6H), 1.94 (s, 2H), 1.89 (m, 1H), 1.54 (m, 2H), 1.38 (t, 2H), 1.17 (m, 2H), 0.92 (s, 6H).

Example 351

4-(4-{[2-(4-chlorophenyl)-4,4-dimethylcyclohex-1-en-1-yl]methyl}piperazin-1-yl)-2-(1H-indol-5-yloxy)-N-({4-[(2-morpholin-4-ylethyl)amino]-3-[(trifluoromethyl)sulfonyl]phenyl}sulfonyl)benzamide

Example 351A 4-(2-morpholinoethylamino)-3-(trifluoromethylsulfonyl)benzenesulfonamide This example was prepared by substituting EXAMPLE 159C for 4-fluoro-3-nitrobenzenesulfonamide and 2-morpholinoethanamine for (tetrahydropyran-4-yl)methylamine in EXAMPLE 1F.

Example 351B 4-(4-{[2-(4-chlorophenyl)-4,4-dimethylcyclohex-1-en-1-yl]methyl}piperazin-1-yl)-2-(1H-indol-5-yloxy)-N-({4-[(2-morpholin-4-ylethyl)amino]-3-[(trifluoromethyl)sulfonyl]phenyl}sulfonyl)benzamide This example was prepared by substituting EXAMPLE 351A for EXAMPLE 1F in EXAMPLE 177. $^1$H NMR (400 MHz, dimethylsulfoxide-$d_6$) δ 11.22 (s, 1H), 11.17 (s, 1H), 8.17 (d, 1H), 7.92 (dd, 1H), 7.61 (s, 1H), 7.48 (d, 1H), 7.40 (m, 2H), 7.33 (d, 2H), 7.15 (d, 1H), 7.03 (d, 2H), 6.93 (d, 1H), 6.85 (dd, 1H), 6.64 (dd, 1H), 6.40 (s, 1H), 6.13 (m, 1H), 3.57 (m, 4H), 3.35 (m, 2H), 3.02 (m, 4H), 2.72 (s, 2H), 2.58 (t, 2H), 2.42 (m, 4H), 2.15 (m, 6H), 1.95 (s, 2H), 1.37 (m, 2H), 0.92 (s, 6H).

Example 352

4-(4-{[2-(4-chlorophenyl)-4,4-dimethylcyclohex-1-en-1-yl]methyl}piperazin-1-yl)-N-({5-cyano-6-[(tetrahydro-2H-pyran-4-ylmethyl)amino]pyridin-3-yl}sulfonyl)-2-(1H-indol-5-yloxy)benzamide

Example 352A 5-cyano-6-((tetrahydro-2H-pyran-4-yl)methylamino)pyridine-3-sulfonamide This example was prepared by substituting EXAMPLE 325A for EXAMPLE 329B in EXAMPLE 333A.

Example 352B 4-(4-{[2-(4-chlorophenyl)-4,4-dimethylcyclohex-1-en-1-yl]methyl}piperazin-1-yl)-N-({5-cyano-6-[(tetrahydro-2H-pyran-4-ylmethyl)amino]pyridin-3-yl}sulfonyl)-2-(1H-indol-5-yloxy)benzamide This example was prepared by substituting EXAMPLE 352A for EXAMPLE 1F in EXAMPLE 177. $^1$H NMR (400 MHz, dimethylsulfoxide-d$_6$) δ 11.18 (s, 1H), 8.65 (d, 1H), 8.27 (d, 1H), 8.15 (s, 1H), 7.56 (d, 1H), 7.41 (m, 2H), 7.34 (d, 2H), 7.22 (d, 1H), 7.04 (d, 2H), 6.88 (dd, 1H), 6.65 (dd, 1H), 6.41 (m, 1H), 6.12 (d, 1H), 3.82 (dd, 2H), 3.33 (m, 2H), 3.24 (t, 2H), 3.04 (m, 4H), 2.75 (s, 2H), 2.16 (m, 6H), 1.95 (s, 2H), 1.89 (m, 1H), 1.55 (m, 2H), 1.38 (t, 2H), 1.19 (m, 2H), 0.91 (s, 6H).

Example 353

4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)oxy]-3-nitrophenyl}sulfonyl)benzamide

Example 353A 4-(1-methylpiperidin-4-yloxy)-3-nitrobenzenesulfonamide

To a mixture of 1-methylpiperidin-4-ol (0.542 g) in tetrahydrofuran (10 mL) at 0° C. was added NaH (60% in mineral oil) (0.753 g). After stirring for 15 minutes, 4-fluoro-3-nitrobenzenesulfonamide (1.036 g) was added as a solution in tetrahydrofuran (10 mL). The reaction was removed from the ice bath and allowed to warm to room temperature. After 1 hour, the reaction was poured into water and the pH adjusted to ~7 with 1N aqueous HCl.

The reaction was extracted with dichloromethane (3×100 mL), washed with brine, dried over magnesium sulfate, filtered, and concentrated. The product was suspended in dichloromethane (mL), sonicated and then filtered to give the title compound.

Example 353B 4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)oxy]-3-nitrophenyl}sulfonyl)benzamide This example was prepared by substituting EXAMPLE 26C for EXAMPLE 1E and EXAMPLE 353A for EXAMPLE 1F in EXAMPLE 1G. $^1$H NMR (300 MHz, dimethylsulfoxide) δ 11.03 (s, 1H), 8.21 (d, 1H), 7.87 (dd, 1H), 7.55 (d, 1H), 7.33 (dd, 4H), 7.25 (d, 1H), 7.04 (d, 2H), 6.98 (d, 1H), 6.73 (dd, 1H), 6.56 (d, 1H), 6.33 (s, 1H), 6.14 (d, 1H), 4.79 (s, 1H), 2.96 (s, 6H), 2.72 (s, 2H), 2.57 (s, 3H), 2.18 (s, 6H), 1.94 (m, 6H), 1.39 (m, 2H), 0.92 (s, 6H).

Example 354

4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)methoxy]-3-nitrophenyl}sulfonyl)benzamide

Example 354A 4-((1-methylpiperidin-4-yl)methoxy)-3-nitrobenzenesulfonamide

This example was prepared by substituting (1-methylpiperidin-4-yl)methanol for 1-methylpiperidin-4-ol in EXAMPLE 353A.

Example 354B 4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)methoxy]-3-nitrophenyl}sulfonyl)benzamide This example was prepared by substituting EXAMPLE 26C for EXAMPLE 1E and EXAMPLE 354A for EXAMPLE 1F in EXAMPLE 1G. $^1$H NMR (300 MHz, dimethylsulfoxide) δ 11.01 (s, 1H), 8.19 (d, 1H), 7.87 (dd, 1H), 7.55 (d, 1H), 7.39-7.26 (m, 4H), 7.16 (d, 1H), 7.08-7.01 (m, 2H), 6.96 (d, 1H), 6.72 (dd, 1H), 6.54 (d, 1H), 6.32 (s, 1H), 6.14 (d, 1H), 4.05 (d, 2H), 2.95 (s, 4H), 2.89-2.59 (m, 7H), 2.17 (s, 6H), 2.00-1.78 (m, 5H), 1.53 (s, 2H), 1.37 (m, 2H), 0.92 (s, 6H).

Example 355

4-(4-{[4-(4-chlorophenyl)-1-(3-hydroxypropyl)-1,2,5,6-tetrahydropyridin-3-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide

Example 355A tert-butyl 4-chloro-3-formyl-5,6-dihydropyridine-1(2H)-carboxylate To N,N-dimethylformamide (3.87 mL) at 0° C., phosphorus oxychloride (3.73 mL) was added dropwise, maintaining the temperature below 5° C. The resulting mixture was diluted with dichloromethane (15 mL) and stirred at room temperature for 1.5 hours. The reaction was then cooled in an ice bath. tert-Butyl 4-oxopiperidine-1-carboxylate (4.98 g) was added as a solution in dichloromethane (20 mL) and the reaction was stirred at room temperature for 1 hour. The reaction mixture was poured over ice and solid sodium acetate, stirred for 15 minutes, and extracted with dichloromethane. The extracts were washed thoroughly with water and with brine, dried over MgSO$_4$, filtered, and concentrated to obtain the title compound.

Example 355B tert-butyl 4-(4-chlorophenyl)-3-formyl-5,6-dihydropyridine-1(2H)-carboxylate EXAMPLE 355A (6.14 g), 4-chlorophenylboronic acid (4.10 g) and palladium(II) acetate (0.112 g) were combined in water to give a suspension. Potassium carbonate (8.98 g) and tetrabutylammonium bromide (4.03 g) were added. The resulting mixture was stirred at 45° C. overnight, cooled, and the reaction mixture was diluted with ethyl acetate (200 mL) in order to dissolve any insoluble material, then washed thoroughly with water, dried over MgSO$_4$, filtered, and concentrated. The crude material was purified by flash chromatography eluting with a gradient of 10% ethyl acetate/hexanes to 40% ethyl acetate/hexanes.

Example 355C tert-butyl 3-((4-(3-(1H-indol-4-yloxy)-4-(methoxycarbonyl)phenyl)piperazin-1-yl)methyl)-4-(4-chlorophenyl)-5,6-dihydropyridine-(2H)-carboxylate This example was prepared by substituting EXAMPLE 355B for 4'-chlorobiphenyl-2-carboxaldehyde and EXAMPLE 68B for tert-butyl piperazine-1-carboxylate in EXAMPLE 1A.

Example 355D methyl 2-(1H-indol-4-yloxy)-4-(4-((4-(4-chlorophenyl)-1,2,5,6-tetrahydropyridin-3-yl)methyl)piperazin-1-yl)benzoate This example was prepared by substituting EXAMPLE 355C for EXAMPLE 1A in EXAMPLE 1B.

Example 355E methyl 2-(1H-indol-4-yloxy)-4-(4-((4-(4-chlorophenyl)-1-(3-hydroxypropyl)-1,2,5,6-tetrahydropyridin-3-yl)methyl)piperazin-1-yl)benzoate EXAMPLE 355D (539 mg), 3-bromopropan-1-ol (83 mg) and triethylamine (0.42 mL) were combined in acetonitrile. The mixture was heated to 60° C. overnight, concentrated and then triturated with ether and filtered to give the title compound.

Example 355F 2-(1H-indol-4-yloxy)-4-(4-((4-(4-chlorophenyl)-1-(3-hydroxypropyl)-1,2,5,6-tetrahydropyridin-3-yl)methyl)piperazin-1-yl)benzoic acid This example was prepared by substituting EXAMPLE 355E for EXAMPLE 1D in EXAMPLE 1E.

Example 355G 4-(4-{[4-(4-chlorophenyl)-1-(3-hydroxypropyl)-1,2,5,6-tetrahydropyridin-3-yl]methyl}piperazin-1-yl)-2-(1H-indol-4-yloxy)-N-({3-nitro-4-[(tetrahydro-2H-pyran-4-ylmethyl)amino]phenyl}sulfonyl)benzamide This example was prepared by substituting EXAMPLE 355F for EXAMPLE 1E in EXAMPLE 1G. $^1$H NMR (300 MHz, dimethylsulfoxide-d$_6$) δ 11.17 (s, 1H), 8.49 (br s, 1H), 8.44 (s, 1H), 7.69 (dd, 1H), 7.56 (d, 1H), 7.40 (d, 1H), 7.24 (m, 1H), 7.13 (m, 3H), 6.98 (m, 1H), 6.94 (t, 1H), 6.86 (dd, 1H), 6.36 (m, 1H), 6.24 (m, 2H), 3.84 (dd, 2H), 3.47 (t, 2H), 3.26 (m, 4H), 2.99 (br s, 4H), 2.80 (m, 3H), 2.44 (m, 2H), 2.21 (m, 4H), 1.86 (m, 1H), 1.73 (m, 2H), 1.62 (m, 2H), 1.26 (m, 5H), 1.17 (m, 2H).

Example 356 benzyl 4-({[4-({[4-(4-{[2-(4-chlorophenyl)-4,4-dimethylcyclohex-1-en-1-yl]methyl}piperazin-1-yl)-2-(1H-indol-5-yloxy)benzoyl]amino}sulfonyl)-2-nitrophenyl]amino}methyl)piperidine-1-carboxylate

Example 356A benzyl 4-((2-nitro-4-sulfamoylphenylamino)methyl)piperidine-1-carboxylate The title compound was prepared as described in EXAMPLE 1F by replacing (tetrahydro-2H-pyran-4-yl)methanamine with benzyl 4-(aminomethyl)piperidine-1-carboxylate.

Example 356B benzyl 4-({[4-({[4-(4-{[2-(4-chlorophenyl)-4,4-dimethylcyclohex-1-en-1-yl]methyl}piperazin-1-yl)-2-(1H-indol-5-yloxy)benzoyl]amino}sulfonyl)-2-nitrophenyl]amino}methyl)piperidine-1-carboxylate The title compound was prepared as described in EXAMPLE 175F by replacing EXAMPLE 175E and EXAMPLE 1F with EXAMPLE 26C and EXAMPLE 356A, respectively. $^1$H NMR (500 MHz, dimethylsulfoxide-d$_6$) δ 11.17 (s, 2H), 8.63 (t, 1H), 8.58 (d, 1H), 7.79 (dd, 1H), 7.51 (d, 1H), 7.30-7.42 (m, 8H), 7.16 (d, 1H), 7.10 (d, 1H), 7.03 (d, 2H), 6.86 (dd, 1H), 6.65 (dd, 1H), 6.39 (s, 1H), 6.14 (d, 1H), 5.07 (s, 2H), 4.02 (d, 2H), 3.29-3.34 (m, 2H), 3.03 (s, 4H), 2.70-2.88 (m, 4H), 2.08-2.23 (m, 6H), 1.94 (s, 2H), 1.81-1.89 (m, 1H), 1.71 (d, 2H), 1.37 (t, 2H), 1.07-1.16 (m, 2H), 0.92 (s, 6H).

Example 357

N-{[3-(aminocarbonyl)-4-(tetrahydro-2H-pyran-4-ylmethoxy)phenyl]sulfonyl}-4-(4-{[2-(4-chlorophenyl)-4,4-dimethylcyclohex-1-en-1-yl]methyl}piperazin-1-yl)-2-(1H-indol-5-yloxy)benzamide

Example 357A 3-cyano-4-((tetrahydro-2H-pyran-4-yl)methoxy)benzenesulfonamide To (tetrahydro-2H-pyran-4-yl)methanol (0.206 g) in tetrahydrofuran (5 mL) was added sodium hydride (0.284 g) and the reaction stirred at room temperature for 20 minutes. The reaction was cooled to 0° C. and 3-cyano-4-fluorobenzenesulfonamide (0.355 g) in tetrahydrofuran (2 mL) was added dropwise and the reaction was allowed to warm to room temperature. After 3 hours, the reaction was poured into water, made acidic (pH=1) with 1N HCl and extracted with dichloromethane (2×75 mL). The organics were combined, washed with brine (50 mL), dried over magnesium sulfate, filtered and concentrated to give the title compound.

Example 357B 5-sulfamoyl-2-((tetrahydro-2H-pyran-4-yl)methoxy) benzamide

A mixture of EXAMPLE 357A (0.455 g) in ethanol (3 mL) and tetrahydrofuran (1 mL) was added to hydrogen peroxide (30%, 2 mL) followed by NaOH (1.024 ml) and heated to 35° C. for 3 hours. The mixture was poured into dichloromethane (50 mL) and 1N aqueous HCl (25 mL), upon which a precipitate formed. The title compound was extracted into dichloromethane (3×50 mL). The organic layer contained a solid which was collected by filtration and dried to give the title compound.

Example 357C

N-{[3-(aminocarbonyl)-4-(tetrahydro-2H-pyran-4-ylmethoxy)phenyl]sulfonyl}-4-(4-{[2-(4-chlorophenyl)-4,4-dimethylcyclohex-1-en-1-yl] methyl}piperazin-1-yl)-2-(1H-indol-5-yloxy) benzamide This example was prepared by substituting EXAMPLE 26C for EXAMPLE 1E and EXAMPLE 357B for EXAMPLE 1F in EXAMPLE 1G. $^1$H NMR (300 MHz, CDCL3) δ 10.35 (s, 1H), 8.80 (d, 1H), 8.35 (dd, 2H), 7.91 (d, 1H), 7.44 (d, 2H), 7.39 (d, 1H), 7.34-7.29 (m, 1H), 7.22 (d, 2H), 7.07 (d, 1H), 6.99 (dd, 1H), 6.93-6.87 (m, 2H), 6.58 (s, 1H), 6.48 (dd, 1H), 6.06 (d, 1H), 5.80 (s, 1H), 4.05 (dd, 4H), 3.46 (dd, 2H), 3.03 (s, 4H), 2.73 (s, 2H), 2.19 (m, 7H), 1.96 (s, 2H), 1.74 (m, 2H), 1.43 (m, 4H), 0.93 (s, 6H).

Example 358

4-(4-{[4'-chloro-5-(trifluoromethyl)-,1'-biphenyl-2-yl]methyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide This example was prepared by substituting EXAMPLE 339C for EXAMPLE 26C and EXAMPLE 173C for EXAMPLE 1F in EXAMPLE 177. $^1$H NMR (500 MHz, dimethylsulfoxide-$d_6$) δ 11.11 (s, 1H), 8.54 (d, 1H), 8.19 (d, 1H), 7.78 (dd, 1H), 7.71-7.74 (m, 2H), 7.44-7.54 (m, 7H), 7.36-7.38 (m, 2H), 7.04-7.07 (m, 2H), 6.87 (dd, 1H), 6.63 (dd, J=8.7, 1.68 Hz, 1H), 6.36 (s, 1H), 6.16 (d, 1H), 3.93 (dd, 2H), 3.75 (br s, 2H), 3.41 (s, 2H), 3.01-3.07 (m, 6H), 2.66-2.68 (m, 2H), 2.30 (s, 4H), 1.77-1.80 (m, 2H), 1.47-1.53 (m, 2H).

Example 359

4-{4-[(5-tert-butyl-4'-chloro-1,1'-biphenyl-2-yl)methyl]piperazin-1-yl}-2-(1H-indol-5-yloxy)-N-({3-nitro-4-[(1-tetrahydro-2H-pyran-4-ylpiperidin-4-yl)amino]phenyl}sulfonyl)benzamide This example was prepared by substituting EXAMPLE 341C for EXAMPLE 26C and EXAMPLE 173C for EXAMPLE 1F in EXAMPLE 177. $^1$H NMR (500 MHz, dimethylsulfoxide-$d_6$) δ 11.11, (s, 1H), 8.53 (t, 1H), 8.19 (d, 1H), 7.76 (dd, 1H), 7.53 (d, 1H), 7.36-7.44 (m, 8H), 7.19 (s, 1H), 7.04-7.07 (m, 2H), 6.81 (dd, 1H), 6.63 (dd, 1H), 6.36 (s, 1H), 6.17 (d, 1H), 3.93 (dd, 2H), 3.74-3.75 (m, 2H), 3.01-3.07 (m, 6H), 2.64-2.67 (m, 2H), 2.29 (s, 4H), 1.99-2.03 (m, 4H), 1.77-1.80 (m, 2H), 1.65-1.67 (m, 2H), 1.28 (s, 9H).

Example 360

4-(4-{[2-(4-chlorophenyl)-4,4-dimethylcyclohex-1-en-1-yl]methyl}piperazin-1-yl)-2-(1H-indol-5-yloxy)-N-[(4-{[(1-methyl-1H-imidazol-5-yl)methyl]amino}-3-nitrophenyl)sulfonyl]benzamide This example was prepared by substituting (1-methyl-1H-imidazol-5-yl)methanamine for (3S,4R)-4-amino-1-benzylpiperidin-3-ol, hydrochloric acid in EXAMPLE 187B. $^1$H NMR (500 MHz, dimethylsulfoxide-$d_6$) δ 11.17 (s, 1H), 8.81 (t, 1H), 8.59 (d, 1H), 7.83 (dd, 1H), 7.64 (s, 1H), 7.50 (d, 1H), 7.39-7.42 (m, 2H), 7.33 (d, 2H), 7.16-7.17 (m, 2H), 7.03 (d, 2H), 6.98 (s, 1H), 6.85 (dd, 1H), 6.63 (dd, 1H), 6.40 (s, 1H), 6.13 (d, 1H), 4.66 (d, 2H), 3.64 (s, 3H), 3.02 (s, 4H), 2.72 (s, 2H), 2.12-2.16 (m, 6H), 1.94 (s, 2H), 1.37 (t, 2H), 0.92 (s, 6H).

Example 361

4-(4-{[2-(4-chlorophenyl)-4,4-dimethylcyclohex-1-en-1-yl]methyl}piperazin-1-yl)-2-(1H-indol-5-yloxy)-N-{[4-(morpholin-4-ylsulfonyl)phenyl]sulfonyl}benzamide

Example 361A 4-(morpholinosulfonyl)benzenesulfonamide

This example was prepared by substituting 4-(morpholinosulfonyl)benzene-1-sulfonyl chloride for EXAMPLE 66D in EXAMPLE 66E.

Example 361B 4-(4-{[2-(4-chlorophenyl)-4,4-dimethylcyclohex-1-en-1-yl]methyl}piperazin-1-yl)-2-(1H-indol-5-yloxy)-N-{[4-(morpholin-4-ylsulfonyl)phenyl]sulfonyl}benzamide This example was prepared by substituting EXAMPLE 361A for EXAMPLE 1F in EXAMPLE 177. $^1$H NMR (500 MHz, dimethylsulfoxide-$d_6$) δ 10.99 (s, 1H), 7.76 (d, 2H), 7.57 (d, 1H), 7.46 (d, 2H), 7.35 (d, 2H), 7.28 (m, 2H), 7.05 (d, 2H), 6.89 (d, 1H), 6.70 (dd, 1H), 6.57 (dd, 1H), 6.31 (m, 1H), 6.21 (m, 1H), 3.60 (m, 4H), 2.97 (m, 4H), 2.79 (m, 4H), 2.72 (s, 2H), 2.18 (m, 6H), 1.96 (s, 2H), 1.39 (t, 2H), 0.93 (s, 6H).

Example 362

4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-(1H-indol-5-yloxy) benzamide

Example 362A

4-[(1,1-dioxidothiomorpholin-4-yl)amino]-3-nitrophenyl}sulfonamide

This example was prepared by substituting 4-aminothiomorpholine-1,1-dioxide for (tetrahydropyran-4-yl)methylamine in EXAMPLE 1F.

Example 362B 4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-(1H-indol-5-yloxy)benzamide This example was prepared by substituting EXAMPLE 362A for EXAMPLE 1F in EXAMPLE 177. $^1$H NMR (400 MHz, dimethylsulfoxide-$d_6$) δ 11.19 (s, 1H), 11.17 (s, 1H), 9.64 (s, 1H), 8.55 (d, 1H), 7.86 (m, 1H), 7.78 (m, 1H), 7.51 (d, 1H), 7.40 (m, 2H), 7.33 (d, 2H), 7.16 (s, 1H), 7.03 (d, 2H), 6.86 (dd, 1H), 6.64 (dd, 1H), 6.39 (s, 1H), 6.13 (d, 1H), 3.50 (m, 4H), 3.17 (m, 4H), 3.02 (m, 4H), 2.72 (s, 2H), 2.15 (m, 6H), 1.94 (s, 2H), 1.37 (t, 2H), 0.91 (s, 6H).

Example 363

4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylcyclohexyl)amino]-3-nitrophenyl}sulfonyl)benzamide

Example 363A tert-butyl cis-4-morpholinocyclohexylcarbamate

To a mixture of morpholine (4.08 ml) and tert-butyl 4-oxocyclohexylcarbamate (10 g) stirred for 24 hours at room temperature in titanium(IV) isopropoxide (27.5 ml), methanol (10 ml) was added followed by careful addition of sodium borohydride (3.55 g). The reaction mixture was quenched with water, extracted with ether (2×100 mL), dried over magnesium sulfate, filtered and concentrated. The crude product was purified by FC (silica gel 200 g, 30%-100% acetone/hexanes) providing two products, the title compound and trans 4-morpholinocyclohexylcarbamate.

Example 363B cis-4-morpholinocyclohexanamine bis(2,2,2-trifluoroacetate)

This example was prepared by substituting EXAMPLE 363A for EXAMPLE 1A in EXAMPLE 1B.

Example 363C 4-(cis-4-morpholinocyclohexylamino)-3-nitrobenzenesulfonamide

This example was prepared by substituting EXAMPLE 363B for (tetrahydropyran-4-yl)methylamine in EXAMPLE 1F.

Example 363D 4-(4-{[2-(4-chlorophenyl)-4,4-dimethylcyclohex-1-en-1-yl]methyl}piperazin-1-yl)-2-(1H-indol-5-yloxy)-N-({4-[cis-(4-morpholin-4-ylcyclohexyl)amino]-3-nitrophenyl}sulfonyl)benzamide This example was prepared by substituting EXAMPLE 26C for EXAMPLE 1E and EXAMPLE 363C for EXAMPLE 1F in EXAMPLE 1G. $^1$H NMR (500 MHz, pyridine-$d_5$) δ 12.28 (s, 1H), 9.31 (d, 1H), 8.65 (d, 1H), 8.34 (dd, 1H), 8.17 (d, 1H), 7.53-7.57 (m, 2H), 7.40-7.47 (m, 3H), 7.03-7.12 (m, 3H), 6.89 (d, 1H), 6.72 (dd, 1H), 6.62 (s, 1H), 6.54 (d, 1H), 3.69-3.75 (m, 4H), 3.67 (s, 1H), 3.00-3.07 (m, 4H), 2.75 (s, 2H), 2.41-2.47 (m, 4H), 2.24 (t, 2H), 2.07-2.16 (m, 5H), 1.97 (s, 2H), 1.76-1.85 (m, 2H), 1.54-1.65 (m, 6H), 1.38 (t, 2H), 0.93 (s, 6H).

Example 364

N-{[5-bromo-6-(tetrahydro-2H-pyran-4-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-indol-4-yloxy)benzamide This example was prepared by substituting EXAMPLE 55B for EXAMPLE 26C and EXAMPLE 329B for EXAMPLE 1F in EXAMPLE 177. $^1$H NMR (400 MHz, dimethylsulfoxide-$d_6$) δ 11.17 (s, 1H), 8.65 (d, 1H), 8.33 (s, 1H), 7.58 (d, 1H), 7.35 (d, 2H), 7.24 (t, 1H), 7.07 (m, 3H), 6.89 (m, 1H), 6.67 (dd, 1H), 6.27 (m, 3H), 4.29 (d, 2H), 3.88 (dd, 2H), 3.35 (m, 4H), 3.09 (m, 4H), 2.88 (m, 2H), 2.34 (m, 2H), 2.17 (s, 2H), 2.06 (m, 1H), 1.98 (m, 2H), 1.65 (m, 2H), 1.36 (m, 4H), 0.93 (s, 6H).

Example 365

4-(4-{[2-(4-chlorophenyl)-4,4-dimethylcyclohex-1-en-1-yl]methyl}piperazin-1-yl)-2-(1H-indol-4-yloxy)-N-{[6-[(tetrahydro-2H-pyran-4-ylmethyl)amino]-5-(1,3-thiazol-2-yl)pyridin-3-yl]sulfonyl}benzamide This example was prepared by substituting EXAMPLE 325B for EXAMPLE 329B in EXAMPLE 331A. $^1$H NMR (400 MHz, dimethylsulfoxide-$d_6$) δ 11.22 (s, 1H), 9.76 (t, 1H), 9.12 (m, 1H), 8.50 (d, 1H), 8.26 (d, 1H), 8.02 (d, 1H), 7.87 (d, 1H), 7.58 (d, 1H), 7.38 (d, 2H), 7.23 (t, 1H), 7.15 (d, 1H), 7.08 (d, 2H), 6.96 (m, 1H), 6.74 (dd, 1H), 6.47 (d, 1H), 6.33 (s, 1H), 6.22 (s, 1H), 3.86 (dd, 2H), 3.52 (t, 6H), 3.29 (m, 4H), 2.99 (m, 2H), 2.74 (m, 2H), 2.18 (s, 2H), 2.01 (s, 2H), 1.88 (m, 1H), 1.62 (m, 2H), 1.45 (t, 2H), 1.28 (m, 2H), 0.94 (s, 6H).

Example 366

4-(4-{[2-(4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-indol-4-yloxy)benzamide

Example 366A 3-cyano-4-((tetrahydro-2H-pyran-4-yl)methylamino)benzenesulfonamide 3-Cyano-4-fluorobenzenesulfonamide (500 mg), (tetrahydropyran-4-yl)methylamine (288 mg), and N,N-diisopropylethylamine (1.3 mL) were heated at 80° C. in tetrahydrofuran (15 mL) overnight. The mixture was diluted with ethyl acetate, washed with NaHCO$_3$ solution and brine, and dried (Na$_2$SO$_4$), filtered and concentrated. The product was triturated from ethyl acetate.

Example 366B 4-(4-{[2-(4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-indol-4-yloxy)benzamide This example was prepared by substituting EXAMPLE 55B for EXAMPLE 26C and EXAMPLE 366A for EXAMPLE 1F in EXAMPLE 177. $^1$H NMR (400 MHz, dimethylsulfoxide-$d_6$) δ 11.30 (s, 1H), 11.08 (m, 1H), 7.81 (d, 1H), 7.63 (dd, 1H), 7.55 (d, 1H), 7.32 (m, 3H), 7.22 (d, 1H), 7.17 (m, 1H), 7.02 (m, 3H), 6.79 (d, 1H), 6.71 (dd, 1H), 6.47 (d, 1H), 6.28 (m, 2H), 3.84 (dd, 2H), 3.25 (t, 2H), 3.13 (t, 2H), 3.05 (m, 4H), 2.73 (s, 2H), 2.15 (m, 6H), 1.95 (s, 2H), 1.82 (m, 1H), 1.59 (m, 2H), 1.38 (t, 2H), 1.20 (m, 2H), 0.92 (s, 6H).

Example 367

4-(4-{[2-(4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-indol-5-yloxy)benzamide This example was prepared by substituting EXAMPLE 366A for EXAMPLE 1F in EXAMPLE 177. $^1$H NMR (400 MHz, dimethylsulfoxide-$d_6$) δ 11.20 (s, 1H), 10.99 (s, 1H), 7.94 (d, 1H), 7.74 (dd, 1H), 7.53 (d, 1H), 7.44 (d, 1H), 7.41 (m, 1H), 7.33 (d, 2H), 7.21 (m, 2H), 7.04 (d, 2H), 6.89 (dd, 1H), 6.82 (d, 1H), 6.66 (dd, 1H), 6.42 (s, 1H), 3.83 (dd, 2H), 3.25 (t, 2H), 3.13 (t, 2H), 3.03 (m, 4H), 2.72 (s, 2H), 2.14 (m, 6H), 1.94 (s, 2H), 1.83 (m, 1H), 1.57 (m, 2H), 1.37 (m, 2H), 1.21 (m, 2H), 0.92 (s, 6H).

Example 368

4-(4-{[2-(4-chlorophenyl)-4,4-dimethylcyclohex-1-en-1-yl]methyl}piperazin-1-yl)-N-({4-[(3,3-dimethylbutyl)amino]-3-nitrophenyl}sulfonyl)-2-(1H-indol-5-yloxy)benzamide This example was prepared by substituting 3,3-dimethylbutylamine for 1-(2-methoxy-ethyl)-piperidin-4-ylamine and EXAMPLE 187A for 4-chloro-3-nitrobenzenesulfonamide in EXAMPLE 189A.

Example 369

4-(4-{[2-(4-chlorophenyl)-4,4-dimethylcyclohex-1-en-1-yl]methyl}piperazin-1-yl)-N-[(4-{[(1S)-1-(hydroxymethyl)-3-methylbutyl]amino}-3-nitrophenyl)sulfonyl]-2-(1H-indol-5-yloxy)benzamide This example was prepared by substituting L-leucinol for 1-(2-methoxy-ethyl)-piperidin-4-ylamine and EXAMPLE 187A for 4-chloro-3-nitrobenzenesulfonamide in EXAMPLE 189A.

Example 370

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(2R)-tetrahydrofuran-2-ylmethyl]amino}phenyl)sulfonyl]benzamide This example was prepared by substituting (R)-(−)-tetrahydrofurfurylamine for 1-(2-methoxy-ethyl)-piperidin-4-ylamine and EXAMPLE 187A for 4-chloro-3-nitrobenzenesulfonamide in EXAMPLE 189A.

Example 371

4-(4-{[2-(4-chlorophenyl)-4,4-dimethylcyclohex-1-en-1-yl]methyl}piperazin-1-yl)-N-[(4-{[(1R)-1-(hydroxymethyl)-2-methylpropyl]amino}-3-nitrophenyl)sulfonyl]-2-(1H-indol-5-yloxy)benzamide This example was prepared by substituting D-valinol for 1-(2-methoxy-ethyl)-piperidin-4-ylamine and EXAMPLE 187A for 4-chloro-3-nitrobenzenesulfonamide in EXAMPLE 189A.

Example 372

4-(4-{[2-(4-chlorophenyl)-4,4-dimethylcyclohex-1-en-1-yl]methyl}piperazin-1-yl)-2-(1H-indol-5-yloxy)-N-({4-[(4-methoxyphenyl)amino]-3-nitrophenyl}sulfonyl)benzamide This example was prepared by substituting 4-anisidine for 1-(2-methoxy-ethyl)-piperidin-4-ylamine and EXAMPLE 187A for 4-chloro-3-nitrobenzenesulfonamide in EXAMPLE 189A.

Example 373

N-[(4-{[2-(1,3-benzodioxol-5-yl)ethyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-indol-5-yloxy)benzamide This example was prepared by substituting 2-benzo[1,3]dioxol-5-yl-ethylamine for 1-(2-methoxy-ethyl)-piperidin-4-ylamine and EXAMPLE 187A for 4-chloro-3-nitrobenzenesulfonamide in EXAMPLE 189A.

Example 374

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[3-(2-oxopyrrolidin-1-yl)propyl]amino}phenyl)sulfonyl]benzamide This example was prepared by substituting 1-(3-aminopropyl)-pyrrolidin-2-one for 1-(2-methoxy-ethyl)-piperidin-4-ylamine and EXAMPLE 187A for 4-chloro-3-nitrobenzenesulfonamide in EXAMPLE 189A.

Example 375

4-(4-{[2-(4-chlorophenyl)-4,4-dimethylcyclohex-1-en-1-yl]methyl}piperazin-1-yl)-N-({4-[(4-hydroxyphenyl)amino]-3-nitrophenyl}sulfonyl)-2-(1H-indol-5-yloxy)benzamide This example was prepared by substituting 4-aminophenol for 1-(2-methoxy-ethyl)-piperidin-4-ylamine and EXAMPLE 187A for 4-chloro-3-nitrobenzenesulfonamide in EXAMPLE 189A.

Example 376

N-{[4-({2-[4-(aminosulfonyl)phenyl]ethyl}amino)-3-nitrophenyl]sulfonyl}-4-(4-{[2-(4-chlorophenyl)-4,4-dimethylcyclohex-1-en-1-yl]methyl}piperazin-1-yl)-2-(1H-indol-5-yloxy)benzamide This example was prepared by substituting 4-(2-aminoethyl)benzenesulfonamide for 1-(2-methoxy-ethyl)-piperidin-4-ylamine and EXAMPLE 187A for 4-chloro-3-nitrobenzenesulfonamide in EXAMPLE 189A.

Example 377

4-(4-{[2-(4-chlorophenyl)-4,4-dimethylcyclohex-1-en-1-yl]methyl}piperazin-1-yl)-N-[(4-{[3-(1H-imidazol-1-yl)propyl]amino}-3-nitrophenyl)sulfonyl]-2-(1H-indol-5-yloxy)benzamide This example was prepared by substituting 1-(3-aminopropyl)imidazole for 1-(2-methoxy-ethyl)-piperidin-4-ylamine and EXAMPLE 187A for 4-chloro-3-nitrobenzenesulfonamide in EXAMPLE 189A.

Example 378

4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(1S)-1-phenylethyl]amino}phenyl)sulfonyl]benzamide This example was prepared by substituting (S)-(−)-1-phenylethylamine for 1-(2-methoxy-ethyl)-piperidin-4-ylamine and EXAMPLE 187A for 4-chloro-3-nitrobenzenesulfonamide in EXAMPLE 189A.

Example 379

N-({2-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide

Example 379A 2-chloro-5-fluoro-4-((tetrahydro-2H-pyran-4-yl)methylamino)benzenesulfonamide 2-Chloro-4,5-difluorobenzenesulfonamide (0.683 g), (tetrahydro-2H-pyran-4-yl)methanamine (0.346 g), N,N-diisopropylethylamine (0.681 ml) and dioxane (10 ml) were heated at 65° C. for 2.5 days. Additional (tetrahydro-2H-pyran-4-yl)methanamine (0.346 g) and N,N-diisopropylethylamine (0.681 ml) were added and heating was continued at 70° C. for 1.5 days. The reaction mixture was concentrated and column chromatographed on silica gel with 0-3% methanol in dichloromethane as eluent. The obtained solid was triturated with dichloromethane to give the title compound.

Example 379B

N-({2-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-indol-5-yloxy)benzamide This example was prepared by substituting EXAMPLE 26C for EXAMPLE 1E and EXAMPLE 379A for EXAMPLE 1F in EXAMPLE 1G. $^1$H NMR (300 MHz, dimethylsulfoxide-d$_6$) δ ppm 11.23 (s, 1H), 11.02 (s, 1H), 7.61 (m, 2H), 7.44 (m, 2H), 7.33 (d, 2H), 7.30 (m, 1H), 7.03 (d, 2H), 6.95 (m, 1H), 6.88 (m, 2H), 6.67 (dd, 1H), 6.44 (m, 1H), 6.09 (d, 1H), 3.82 (dd, 2H), 3.22 (m, 2H), 3.03 (m, 6H), 2.72 (m, 2H), 2.14 (m, 6H), 1.94 (m, 2H), 1.81 (m, 1H), 1.61 (m, 2H), 1.37 (t, 2H), 1.18 (m, 2H), 0.91 (s. 6H).

Example 380

4-(4-{[2-(4-chlorophenyl)-4,4-dimethylcyclohex-1-en-1-yl]methyl}piperazin-1-yl)-2-(1H-indol-5-yloxy)-N-[(4-{[2-(2-methoxyethoxy)ethyl]thio}-3-nitrophenyl)sulfonyl]benzamide

Example 380A 4-(2-(2-methoxyethoxy)ethylthio)-3-nitrobenzenesulfonamide

In a 100 mL round-bottomed flask was added sodium hydride (0.6 g) in tetrahydrofuran (10 ml) to give a suspension. 2-(2-Methoxyethoxy)ethanethiol (1 g) was added slowly. After the mixture stirred for 30 minutes, 4-fluoro-3-nitrobenzenesulfonamide (1.616 g) in 10 ml tetrahydrofuran was added slowly. After the mixture stirred overnight, water was added slowly, and ethyl acetate (20 ml×3) was used to extract the product. The combined organic layers were dried over Na$_2$SO$_4$. After the mixture was filtered and concentrated, the crude product was added to a silica gel column and purified eluting with 0-10% methanol in dichloromethane.

Example 380B 4-(4-{[2-(4-chlorophenyl)-4,4-dimethylcyclohex-1-en-1-yl]methyl}piperazin-1-yl)-2-(1H-indol-5-yloxy)-N-[(4-{[2-(2-methoxyethoxy)ethyl]thio}-3-nitrophenyl)sulfonyl]benzamide This example was prepared by substituting EXAMPLE 380A for EXAMPLE 1F in EXAMPLE 177. $^1$H NMR (500 MHz, dimethylsulfoxide-d$_6$) δ 10.99 (s, 1H), 8.42 (s, 1H), 7.75 (d, 1H), 7.56 (d, 1H), 7.34 (m, 5H), 7.05 (d, 2H), 6.90 (d, 1H), 6.69 (dd, 1H), 6.55 (dd, 1H), 6.30 (m, 1H), 6.17 (d, 1H), 3.67 (t, 2H), 3.54 (m, 2H), 3.43 (m, 2H), 3.21 (m, 5H), 2.95 (m, 4H), 2.71 (s, 2H), 2.17 (m, 6H), 1.95 (s, 2H), 1.38 (t, 2H), 0.92 (s, 6H).

Example 381

4-(4-{[2-(4-chlorophenyl)-4,4-dimethylcyclohex-1-en-1-yl]methyl}piperazin-1-yl)-2-(1H-indol-4-yloxy)-N-[(4-{[2-(2-methoxyethoxy)ethyl]thio}-3-nitrophenyl)sulfonyl]benzamide This example was prepared by substituting EXAMPLE 380A for EXAMPLE 1F and EXAMPLE 55B for EXAMPLE 26C in EXAMPLE 177. $^1$H NMR (500 MHz, dimethylsulfoxide-d$_6$) δ 11.06 (s, 1H), 8.37 (d, 1H), 7.80 (dd, 1H), 7.61 (d, 1H), 7.45 (d, 1H), 7.34 (d, 2H), 7.18 (t, 1H), 7.04 (m, 3H), 6.87 (t, 1H), 6.60 (dd, 1H), 6.22 (m, 3H), 3.68 (t, 2H), 3.55 (m, 2H). 3.43 (m. 2H), 3.22 (m. 5H), 2.94 (m, 4H), 2.72 (s, 2H), 2.16 (m, 6H), 1.95 (s, 2H), 1.38 (t, 2H), 0.92 (s, 6H).

Example 382

4-(4-{[2-(4-chlorophenyl)-4,4-dimethylcyclohex-1-en-1-yl]methyl}piperazin-1-yl)-2-(1H-indol-5-yloxy)-N-{[4-(methylsulfonyl)phenyl]sulfonyl}benzamide This example was prepared by substituting 4-(methylamino)-3-nitrobenzenesulfonamide for EXAMPLE 1F in EXAMPLE 177. $^1$H NMR (500 MHz, dimethylsulfoxide-$d_6$) δ 11.17 (s, 1H), 8.05 (m, 4H), 7.51 (d, 1H), 7.38 (m, 4H), 7.14 (m, 1H), 7.04 (d, 2H), 6.85 (d, 1H), 6.64 (dd, 1H), 6.40 (m, 1H), 6.17 (d, 1H), 3.27 (s, 3H), 3.05 (m, 4H), 2.79 (m, 2H), 2.21 (m, 6H), 1.96 (s, 2H), 1.39 (t, 2H), 0.92 (s, 6H).

Example 383

4-(4-{[2-(4-chlorophenyl)-4,4-dimethylcyclohex-1-en-1-yl]methyl}piperazin-1-yl)-2-(1H-indol-4-yloxy)-N-{[4-(methylsulfonyl)phenyl]sulfonyl}benzamide This example was prepared by substituting 4-(methylamino)-3-nitrobenzenesulfonamide for EXAMPLE 1F and EXAMPLE 55B for EXAMPLE 26C in EXAMPLE 177. $^1$H NMR (500 MHz, dimethylsulfoxide-$d_6$) δ 11.26 (s, 1H), 7.96 (m, 4H), 7.54 (d, 1H), 7.35 (d, 2H), 7.30 (m, 1H), 7.18 (d, 1H), 7.05 (d, 2H), 6.97 (t, 1H), 6.70 (dd, 1H), 6.37 (d, 1H), 6.30 (m, 2H), 3.25 (s, 3H), 3.08 (m, 4H), 2.84 (m, 2H), 2.26 (m, 6H), 1.97 (s, 2H), 1.40 (t, 2H), 0.93 (s, 6H).

Example 384

4-(4-{[2-(4-chlorophenyl)-4,4-dimethylcyclohex-1-en-1-yl]methyl}piperazin-1-yl)-N-({4-[(2,2-dimethyltetrahydro-2H-pyran-4-yl)methoxy]-3-nitrophenyl}sulfonyl)-2-(1H-indol-5-yloxy)benzamide

Example 384A

The title compound was prepared as described in EXAMPLE 297A by replacing (1,4-dioxan-2-yl)methanol with (2,2-dimethyltetrahydro-2H-pyran-4-yl)methanol.

Example 384B 4-(4-{[2-(4-chlorophenyl)-4,4-dimethylcyclohex-1-en-1-yl]methyl}piperazin-1-yl)-N-({4-[(2,2-dimethyltetrahydro-2H-pyran-4-yl)methoxy]-3-nitrophenyl}sulfonyl)-2-(1H-indol-5-yloxy)benzamide The title compound was prepared as described in EXAMPLE 175F by replacing EXAMPLE 175E and EXAMPLE 1F with EXAMPLE 26C and EXAMPLE 384A, respectively. $^1$H NMR (400 MHz, dimethylsulfoxide-$d_6$) δ 11.17 (s, 2H), 8.38 (d, 1H), 8.05 (dd, 1H), 7.51 (d, 1H), 7.31-7.43 (m, 5H), 7.15 (d, 1H), 7.04 (d, 2H), 6.85 (dd, 1H), 6.65 (dd, 1H), 6.40 (s, 1H), 6.15 (d, 1H), 3.98-4.07 (m, 2H), 3.54-3.67 (m, 2H), 3.05 (s, 4H), 2.78 (m, 2H), 2.09-2.31 (m, 7H), 1.95 (s, 2H), 1.56-1.68 (m, 2H), 1.38 (t, 2H), 1.08-1.27 (m, 8H), 0.92 (s, 6H).

Example 385

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-5-yloxy)benzamide

Example 385A 5-bromo-6-((4-fluorotetrahydro-2H-pyran-4-yl)methoxy)pyridine-3-sulfonamide This example was prepared by substituting EXAMPLE 306C for (tetrahydro-2H-pyran-4-yl)methanol in EXAMPLE 329B.

Example 385B 5-cyano-6-((4-fluorotetrahydro-2H-pyran-4-yl)methoxy)pyridine-3-sulfonamide This example was prepared by substituting EXAMPLE 385A for EXAMPLE 329B in EXAMPLE 333A.

Example 385C 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-5-yloxy)benzamide This example was prepared by substituting EXAMPLE 385B for EXAMPLE 1F in EXAMPLE 177. $^1$H NMR (500 MHz, dimethylsulfoxide-$d_6$) δ 11.10 (s, 1H). 8.79 (s, 1H), 8.59 (s, 1H), 7.54 (d, 1H), 7.34-7.38 (m, 4H), 7.04-7.06 (m, 3H), 6.79 (dd, 1H), 6.62 (dd, 1H), 6.35 (s, 1H), 6.17 (d, 1H), 4.28 (d, 2H), 3.76-3.79 (m, 2H), 3.56-3.62 (m, 2H), 3.07 (br s, 4H), 2.12-2.17 (m, 4H), 1.96 (s, 2H), 1.80-1.84 (m, 2H), 1.40 (t, 2H), 0.94 (s, 6H).

Example 386

4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-indol-4-yloxy)benzamide This example was prepared by substituting EXAMPLE 55B for EXAMPLE 26C and EXAMPLE 335A for EXAMPLE 1F in EXAMPLE 177. $^1$H NMR (500 MHz, dimethylsulfoxide-$d_6$) δ 11.20 (s, 1H), 8.67 (d, 1H), 8.35 (d, 1H), 7.57 (d, 1H), 7.36 (d, 2H), 7.26 (t, 1H), 7.11 (d, 1H), 7.05 (d, 2H), 6.90 (t, 1H), 6.70 (dd, 1H), 6.31 (d, 1H), 6.30 (d, 1H), 6.27 (s, 1H), 4.30 (d, 2H), 3.88 (dd, 2H), 3.35 (m, 2H), 3.12 (br s, 4H), 2.96 (br s, 2H), 2.40 (br s, 4H), 2.16 (br m, 2H), 2.06 (m, 1H), 1.98 (s, 2H), 1.65 (d, 2H), 1.41 (t, 2H), 1.36 (m, 2H), 0.93 (s, 6H).

Example 387

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-indol-4-yloxy)benzamide

Example 387A 5,6-dichloropyridine-3-sulfonamide

This example was prepared by substituting 5,6-dichloropyridine-3-sulfonyl chloride for 5-bromo-6-chloropyridine-3-sulfonyl chloride in EXAMPLE 329A.

Example 387B 5-chloro-6-((tetrahydro-2H-pyran-4-yl)methoxy)pyridine-3-sulfonamide This example was prepared by substituting EXAMPLE 387A for EXAMPLE 329A in EXAMPLE 329B.

Example 387C 4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-indol-4-yloxy)benzamide This example was prepared by substituting EXAMPLE 55B for EXAMPLE 26C and EXAMPLE 387B for EXAMPLE 1F in EXAMPLE 177. $^1$H NMR (500 MHz, dimethylsulfoxide-$d_6$) δ 11.24 (s, 1H), 8.45 (d, 1H), 8.05 (d, 1H), 7.56 (d, 1H), 7.36 (d, 2H), 7.28 (t, 1H), 7.15 (d, 1H), 7.05 (d, 2H), 6.95 (t, 1H), 6.71 (dd, 1H), 6.39 (d, 1H), 6.30 (d, 1H), 6.27 (s, 1H), 4.26 (d, 2H), 3.88 (dd, 2H), 3.35 (m, 2H), 3.09 (br s, 4H), 2.85 (br s, 2H), 2.30 (br s, 4H), 2.15 (br m, 2H), 2.07 (m, 1H), 1.96 (s, 2H), 1.65 (d, 2H), 1.41 (t, 2H), 1.35 (m, 2H), 0.93 (s, 6H).

Example 388

4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-indol-5-yloxy)benzamide

Example 388A 5-bromo-6-(2-morpholinoethoxy)pyridine-3-sulfonamide

This example was prepared by substituting 2-morpholinoethanol for (tetrahydro-2H-pyran-4-yl)methanol in EXAMPLE 329B.

Example 388B 5-cyano-6-(2-morpholinoethoxy)pyridine-3-sulfonamide

This example was prepared by substituting EXAMPLE 388A for EXAMPLE 329B in EXAMPLE 335A.

Example 388C 4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(H-indol-5-yloxy)benzamide This example was prepared by substituting EXAMPLE 388B for EXAMPLE 1F in EXAMPLE 177. $^1$H NMR (500 MHz, dimethylsulfoxide-$d_6$) δ 11.09 (s, 1H), 8.77 (s, 1H), 8.55 (s, 1H), 7.55 (d, 1H), 7.34-7.36 (m, 4H), 7.04-7.06 (m, 3H), 6.78 (dd, 1H), 6.63 (d, 1H), 6.35 (s, 1H), 6.16 (s, 1H), 4.61 (t, 2H), 3.58 (m, 4H), 3.05 (br s, 4H), 2.89 (br s, 4H), 2.65 (br s, 4H), 2.32-2 (br s, 2H), 2.15 (br s, 2H), 1.96 (s, 2H), 1.39 (t, 2H), 0.92 (s, 6H).

Example 389

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)oxy]phenyl}sulfonyl)benzamide

Example 389A 1-(tetrahydro-2H-pyran-4-yl)piperidin-4-ol

Piperidin-4-ol (7.8 g) and dihydro-2H-pyran-4(3H)-one (5.0 g) were dissolved in titanium(IV) isopropoxide (30 mL) and the reaction was stirred at room temperature overnight. Methanol (40 mL) was added and the reaction was cooled to 0°. NaBH$_4$ (3.8 g) was added in several portions over one hour. After two hours 1N aqueous NaOH was added, followed by ethyl acetate addition. After filtration through celite, the layers were separated, the aqueous layer was extracted with ethyl acetate, and the combined organic layers were dried over Na$_2$SO$_4$. The crude material was purified by column chromatography using CH$_2$Cl$_2$ with 5-10% 7N NH$_3$ in methanol.

Example 389B 3-nitro-4-(1-(tetrahydro-2H-pyran-4-yl)piperidin-4-yloxy)benzenesulfonamide EXAMPLE 389A (370 mg) was dissolved in tetrahydrofuran (10 mL), and 95% NaH (200 mg) was added. After stirring for 10 minutes, 4-fluoro-3-nitrobenzenesulfonamide (420 mg) was added and the reaction was stirred at room temperature overnight. The reaction was purified by column chromatography using CH$_2$Cl$_2$ with 6-10% 7N NH$_3$ in methanol, followed by slurrying in diethyl ether and filtering off the solid product.

Example 389C 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)oxy]phenyl}sulfonyl)benzamide This example was prepared by substituting EXAMPLE 26C for EXAMPLE 1E and EXAMPLE 389B for EXAMPLE 1F in EXAMPLE 1G, except here 5-7% methanol in CH$_2$Cl$_2$ was used for the chromatography. $^1$H NMR (400 MHz, dimethylsulfoxide-$d_6$) δ 11.07 (br s, 1H), 8.27 (s, 1H), 7.92 (d, 1H), 7.55 (d, 1H), 7.33 (m, 5H), 7.04 (m, 3H), 6.77 (dd, 1H), 6.58 (d, 1H), 6.35 (s, 1H), 6.14 (s, 1H), 4.85 (s, 1H), 3.93 (dd, 2H), 3.27 (m, 4H), 2.98 (br m, 7H), 2.72 (s, 2H), 2.16 (m, 6H), 2.04 (m, 2H), 1.95 (s, 2H), 1.84 (m, 4H), 1.55 (m, 2H), 1.38 (t, 2H), 0.92 (s, 6H).

Example 390

4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylbut-2-ynyl)oxy]-3-nitrophenyl}sulfonyl)benzamide Example 390A 4-morpholinobut-2-yn-1-ol To a mixture of morpholine (4.36 g) in toluene (15 mL) was added 4-chlorobut-2-yn-1-ol (2.09 g) in toluene (5 mL). The mixture was stirred at 85° C. for three hours. After cooling, the solid was filtered off. The filtrate was subjected to vacuum distillation to give the title compound.

Example 390B 4-(4-morpholinobut-2-ynyloxy)-3-nitrobenzene-sulfonamide

This example was prepared by substituting EXAMPLE 390A for (tetrahydro-2H-pyran-4-yl)methanol in EXAMPLE 279A.

Example 390C 4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylbut-2-ynyl)oxy]-3-nitrophenyl}sulfonyl)benzamide This example was prepared by substituting EXAMPLE 390B for EXAMPLE 1F in EXAMPLE 177. $^1$H NMR (500 MHz, dimethylsulfoxide-$d_6$) δ 11.17 (s, 1H), 8.40 (d, 1H), 8.11 (dd, 1H), 7.49-7.53 (m, 2H), 7.39-7.42 (m, 4H), 7.34 (d, 2H), 7.17 (d, 1H), 7.04 (d, J=8.54 Hz, 2H), 6.85 (dd, 1H), 6.64 (dd, 1H), 6.40 (s, 1H), 6.14 (d, 1H), 5.15 (s, 2H), 3.52-3.54 (m, 4H), 3.04 (br s, 4H), 2.78 (br s, 2H), 2.37-2.39 (m, 4H), 2.12-2.20 (br s, 6H), 1.95 (s, 2H), 1.38 (t, 2H), 0.92 (s, 6H).

Example 391

4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-(1H-indol-4-yloxy)benzamide Example 391A 6-((tetrahydro-2H-pyran-4-yl)methoxy)-5-((triiso-propylsilyl)ethynyl)pyridine-3-sulfonamide EXAMPLE 329B (0.176 g), bis(triphenylphosphine)palladium(II) chloride (0.176 g), copper(I) iodide (0.010 g), dimethylacetamide (2.5 ml) and triethylamine (0.105 ml) were combined, flushed with nitrogen and stirred for 2 minutes. (Triisopropyl)acetylene (0.135 ml) was added and the reaction mixture was flushed with nitrogen again, heated at 60° C. overnight, diluted with ethyl acetate, washed with water and brine, dried (MgSO$_4$), filtered, concentrated and chromatographed on silica gel with 10-30% ethyl acetate in hexanes as the eluent to give the title compound.

Example 391B 5-ethynyl-6-((tetrahydro-2H-pyran-4-yl)methoxy)pyridine-3-sulfonamide EXAMPLE 391A (0.205 g) in tetrahydrofuran (3 ml) at ambient temperature was treated with tetrabutyl ammonium fluoride (1 M in tetrahydrofuran) (0.906 ml) and stirred at ambient temperature for 4 hours. Additional tetrabutyl ammonium fluoride (1 M in tetrahydrofuran) (1.8 mL) was added and the mixture was heated at 40° C. for 45 minutes. Solid tetrabutyl ammonium fluoride (0.253 g) was added and heating was continued for 30 minutes. The reaction mixture was concentrated and then chromatographed on silica gel using 0-2% methanol in dichloromethane as the eluent to give the title compound.

Example 391C 4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-(1H-indol-4-yloxy)benzamide This example was prepared by substituting EXAMPLE 55B for EXAMPLE 26C and EXAMPLE 391B for EXAMPLE 1F in EXAMPLE 177. $^1$H NMR (300 MHz, dimethylsulfoxide-$d_6$) δ ppm 11.23 (s, 1H), 8.50 (d, 1H), 8.09 (d, 1H), 7.56 (d, 1H), 7.34 (m, 2H), 7.28 (m, 1H), 7.18 (d, 1H), 7.04 (m, 2H), 6.98 (t, 1H), 6.70 (dd, 1H), 6.44 (d, 1H), 6.27 (m, 2H), 4.55 (s, 1H), 4.25 (d, 2H), 3.87 (dd, 2H), 3.34 (m, 2H), 3.06 (m, 4H), 2.81 (m, 1H), 2.20 (m, 6H), 2.04 (m, 1H), 1.96 (m, 2H), 1.65 (dd, 2H), 1.35 (m, 5H), 0.92 (m, 6H).

Example 392

4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-indol-4-yloxy)benzamide This example was prepared by substituting EXAMPLE 55B for EXAMPLE 26C and EXAMPLE 388B for EXAMPLE 1F in EXAMPLE 177. $^1$H NMR (400 MHz, dimethylsulfoxide-$d_6$) δ 11.15 (s, 1H), 10.99 (s, 1H), 8.64 (d, 1H), 8.33 (d, 1H), 7.58 (d, 1H), 7.35 (d, 2H), 7.24 (m, 1H), 7.07 (m, 3H), 6.89 (m, 1H), 6.66 (dd, 1H), 6.26 (m, 3H), 4.59 (t, 2H), 3.58 (m, 4H), 3.05 (m, 4H), 2.87 (m, 4H), 2.62 (m, 4H), 2.24 (m, 6H), 1.98 (m, 2H), 1.40 (t, 2H), 0.93 (s, 6H).

Example 393

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indol-4-yloxy)benzamide This example was prepared by substituting EXAMPLE 55B for EXAMPLE 26C and EXAMPLE 385B for EXAMPLE 1F in EXAMPLE 177. $^1$H NMR (400 MHz, dimethylsulfoxide-$d_6$) δ 11.17 (s, 1H), 8.66 (s, 1H), 8.36 (s, 1H), 7.58 (d, 1H), 7.36 (d, 2H), 7.25 (s, 1H), 7.07 (m, 3H), 6.89 (m, 1H), 6.68 (m, 1H), 6.27 (m, 3H), 4.60 (s, 1H), 4.54 (s, 1H), 3.78 (m, 2H), 3.60 (m, 2H), 3.33 (m, 2H), 3.09 (m, 4H), 2.92 (m, 2H), 2.36 (m, 2H), 2.16 (m, 2H), 1.97 (s, 2H), 1.87 (m, 4H), 1.40 (t, 2H), 0.93 (s, 6H).

Example 394

4-(4-{[2-(4-chlorophenyl)-4,4-dimethylcyclohex-1-en-1-yl]methyl}piperazin-1-yl)-N-({4-[(3-hydroxy-4-methoxyphenyl)amino]-3-nitrophenyl}sulfonyl)-2-(1H-indol-5-yloxy)benzamide This example was prepared by substituting 5-amino-2-methoxyphenol for 1-(2-methoxy-ethyl)-piperidin-4-ylamine and EXAMPLE 187A for 4-chloro-3-nitrobenzenesulfonamide in EXAMPLE 189A.

Example 395

4-(4-{[2-(4-chlorophenyl)-4,4-dimethylcyclohex-1-en-1-yl]methyl}piperazin-1-yl)-2-(2,3-dihydro-1H-indol-4-yloxy)-N-({4-[(1-methylpiperidin-4-yl)amino]-3-nitrophenyl}sulfonyl)benzamide EXAMPLE 103 (676 mg) and NaCNBH$_3$ (49 mg) were combined in acetic acid (10 mL) and stirred at room temperature overnight. The reaction was diluted with water and extracted with 95/5 CH$_2$Cl$_2$/methanol. The organic layer was concentrated and the crude material was purified by preparative HPLC using a C18 column, 250×50 mm, 10μ, and eluting with a gradient of 20-100% CH$_3$CN vs. 0.1% trifluoroacetic acid in water, giving the title compound as a bistrifluoroacetate salt. $^1$H NMR (300 MHz, dimethylsulfoxide-d$_6$) δ 11.57 (br s, 1H), 9.70, 9.50 (both v br s, total 2H), 8.57 (d, 1H), 8.20 (br d, 1H), 7.85 (dd, 1H), 7.50 (d, 1H), 7.40 (d, 2H), 7.26 (d, 1H), 7.10 (d, 2H), 6.82 (dd, 1H), 6.75 (dd, 1H), 6.40 (d, 1H), 6.27 (d, 1H), 5.94 (d, 1H), 4.00, 3.70 (both v br m, total 8H), 3.55 (v br m, 3H), 3.42 (t, 2H), 3.37 (v br m, 1H), 3.10 (br m, 2H), 2.80 (m, 6H), 2.20 (br m, 4H), 2.03 (s, 2H), 1.82 (br m, 2H), 1.46 (t, 2H), 0.96 (s, 6H).

Example 396

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(pyridin-3-ylamino)benzamide Example 396A Methyl 4-(4-((2-(4-chlorophenyl)-4,4-dimethylcyclohex-1-enyl)methyl)piperazin-1-yl)-2-(pyridin-3-ylamino)benzoate A solution of EXAMPLE 18E (500 mg), cesium carbonate (429 mg), palladium (11) acetate (21 mg), rac-2,2'-bis(diphenylphosphino)-1,1'-binaphthyl (58.5 mg) and toluene (6.4 mL) was degassed with N$_2$. The mixture was stirred at 115° C. for 5 minutes. After cooling to room temperature, pyridin-3-amine (106 mg) was added and the reaction mixture was degassed again with N$_2$ and was stirred at 115° C. for 45 minutes. The mixture was cooled to room temperature, diluted with ethyl acetate and was washed with H$_2$O, brine, dried (MgSO$_4$), filtered and concentrated. The crude product was purified by flash chromatography on silica gel, eluting with CH$_2$Cl$_2$/1% methanol to afford the title compound.

Example 396B 4-(4-((2-(4-chlorophenyl)-4,4-dimethylcyclohex-1-enyl)methyl)piperazin-1-yl)-2-(pyridin-3-ylamino)benzoic acid, 2 Hydrochloric Acid This example was prepared by substituting EXAMPLE 396A for EXAMPLE 224C in EXAMPLE 224D.

Example 396C 4-(4-((2-(4-chlorophenyl)-4,4-dimethylcyclohex-1-enyl)methyl)piperazin-1-yl)-N-(4-(1-methylpiperidin-4-ylamino)-3-nitrophenylsulfonyl)-2-(pyridin-3-ylamino)benzamide This example was prepared by substituting EXAMPLE 396B for EXAMPLE 26C and EXAMPLE 21A for EXAMPLE 1F in EXAMPLE 177. $^1$H NMR (300 MHz, dimethylsulfoxide-d$_6$) δ 11.32-11.40 (br s, 1H), 9.21-9.39 (br s, 1H), 8.51 (d, 1H), 8.33 (d, 1H), 8.09 (dd, 1H), 7.98-8.07 (m, 1H), 7.94 (dd, 1H), 7.81 (d, 1H), 7.52-7.58 (m, 1H), 7.36 (d, 2H), 7.24-7.30 (m, 1H), 7.15 (d, 1H), 7.08 (d, 2H), 6.53 (d, 1H), 6.33 (dd, 1H), 3.81-3.96 (br s, 2H), 3.02-3.12 (br s, 6H), 2.67-2.80 (m, 5H), 2.07-2.32 (m, 8H), 1.98 (s, 3H), 1.70-1.85 (br s, 1H), 1.41 (t, 3H), 0.95 (s, 6H).

Example 397

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(pyridin-3-ylamino)benzamide This example was prepared by substituting EXAMPLE 396B for EXAMPLE 26C and EXAMPLE 173C for EXAMPLE 1F in EXAMPLE 177. $^1$H NMR (300 MHz, dimethylsulfoxide-d$_6$) δ 9.10-9.33 (br s, 1H), 8.53 (d, 1H), 8.36 (d, 1H), 8.12 (dd, 1H), 8.00-8.07 (m, 1H), 7.96 (dd, 1H), 7.80 (d, 1H), 7.53-7.59 (m, 1H), 7.38 (d, 2H), 7.25-7.31 (m, 1H), 7.20 (d, 1H), 7.09 (d, 2H), 6.53 (s, 1H), 6.36 (m, 1H), 4.28-4.75 (br s, 1H), 3.90-4.09 (m, 8H), 3.51-3.61 (m, 2H), 3.35 (m, 8H), 3.01-3.18 (br s, 4H), 2.15-2.26 (m, 1H), 1.88-2.09 (m, 5H), 1.56-1.86 (m, 4H), 1.44 (t, 2H), 0.96 (s, 6H).

Example 398

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(pyridin-3-yloxy)benzamide Example 398A 4-Fluoro-2-(pyridin-3-yloxy)-benzoic acid methyl ester This example was prepared by substituting methyl 2,4-difluorobenzoate for ethyl 2,4-difluorobenzote and 3-hydroxypyridine for 5-hydroxyindazole in EXAMPLE 20A.

Example 398B

4-{4-[2-(4-Chloro-phenyl)-4,4-dimethyl-cyclohex-1-enylmethyl]-piperazin-1-yl}-2-(pyridin-3-yloxy)-benzoic acid methyl ester This example was prepared by substituting EXAMPLE 398A for EXAMPLE 20A in EXAMPLE 20D.

Example 398C

4-{4-[2-(4-Chloro-phenyl)-4,4-dimethyl-cyclohex-1-enylmethyl]-piperazin-1-yl}-2-(pyridin-3-yloxy)-benzoic acid This example was prepared by substituting EXAMPLE 398B for EXAMPLE 1D in EXAMPLE 1E.

Example 398D 4-(4-{[2-(4-chlorophenyl)-4,4-dimethylcyclohex-1-en-1-yl]methyl}piperazin-1-yl)-2-(pyridin-3-yloxy)-N-({3-nitro-4-[(1-tetrahydro-2H-pyran-4-ylpiperidin-4-yl)amino]phenyl}sulfonyl)benzamide This example was prepared by substituting EXAMPLE 398C for EXAMPLE 1E and EXAMPLE 173C for EXAMPLE 1F in EXAMPLE 1G. $^1$H NMR (300 MHz, dimethylsulfoxide-$d_6$) δ 8.36 (d, 1H), 8.11 (t, 1H), 8.08 (t, 2H), 7.70 (dd, 1H), 7.60 (d, 1H), 7.37 (d, 2H), 7.15 (dd,), 7.10-7.03 (m 3H), 7 (dd, H), 6.73 (d, 6.43 (d, 1H), 3.99-3.93 (m, 3H), 3.86 (m, 1H), 3.13 (m, 6H), 2.78 (br s, 2H), 2.30-2.05 (m, 10H), 1.98 (br s, 2H), 1.92-1.67 (m, 6H), 1.57 (m, 2H), 1.41 (t, 2H), 0.94 (s, 6H).

Example 399

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1,2,3,4-tetrahydroisoquinolin-5-yloxy)benzamide

Example 399A tert-butyl 5-hydroxy-3,4-dihydroisoquinoline-2(1H)-carboxylate

A mixture of 1,2,3,4-tetrahydroisoquinolin-5-ol hydrochloric acid (1.0 g), di-tert-butyl dicarbonate (1.27 g) and 1.0 N NaOH (14.5 mL) in dioxane (20 mL) was stirred at room temperature for 16 hours. The reaction mixture was partitioned between water and ethyl acetate. The aqueous layer was neutralized with 5% HCl. The combined organic layers were washed with brine, dried (MgSO$_4$), filtered, and concentrated. The residue was purified by flash chromatography on silica gel to give the title compound.

Example 399B tert-butyl 5-(2-(ethoxycarbonyl)-5-fluorophenoxy)-3,4-dihydroisoquinoline-2(1H)-carboxylate This example was prepared by substituting EXAMPLE 399A for 5-hydroxyindazole in EXAMPLE 20A.

Example 399C tert-butyl 5-(5-(4-((2-(4-chlorophenyl)-4,4-dimethyl-cyclohex-1-enyl)methyl)piperazin-1-yl)-2-(ethoxycarbonyl)phenoxy)-3,4-dihydroisoquinoline-2(1H)-carboxylate This example was prepared by substituting EXAMPLE 399B for EXAMPLE 20A in EXAMPLE 20D.

Example 399D 2-(2-(tert-butoxycarbonyl)-1,2,3,4-tetrahydroisoquinolin-5-yloxy)-4-(4-((2-(4-chlorophenyl)-4,4-dimethylcyclohex-1-enyl)methyl)piperazin-1-yl)benzoic acid This example was prepared by substituting EXAMPLE 399C for EXAMPLE 1D in EXAMPLE 1E.

Example 399E 2-(2-(tert-butoxycarbonyl)-1,2,3,4-tetrahydroisoquinolin-5-yloxy)-4-(4-((2-(4-chlorophenyl)-4,4-dimethylcyclohex-1-enyl)methyl)piperazin-1-yl)benzoic 3-nitro-4-((tetrahydro-2H-pyran-4-yl)methylamino)benzenesulfonic anhydride This example was prepared by substituting EXAMPLE 399D for EXAMPLE 26C in EXAMPLE 177.

Example 399F 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1,2,3,4-tetrahydroisoquinolin-5-yloxy)benzamide A mixture of EXAMPLE 399E (0.058 g) and trifluoroacetic acid (1 mL) in dichloromethane (10 mL) was stirred for 2 hours. The solvent was removed, and the residue was taken into ethyl acetate. It was then washed with saturated NaHCO$_3$, brine, dried over MgSO$_4$, filtered, and concentrated to give the title compound. $^1$H NMR (500 MHz, dimethylsulfoxide-$d_6$) δ 8.36 (t, 1H), 8.27 (d, 1H), 7.65 (d, 1H), 7.36 (d, 2H), 7.07 (d, 2H) 6.93-6.97 (m, 2H), 6.73 (d 1H), 6.69 (dd, 1H), 6.33 (d, 1H), 6.26 (d, 1H), 4.19 (s, 2H), 3.85 (dd, 2H), 3.05-3.09 (m, 6H), 2.77 (s, 2H), 2.17-2.24 (m, 6H), 1.98-1.99 (m, 2H), 1.60-1.63 (m, 2H0, 1.41 (t, 2H), 0.94 (s, 6H).

Example 400

4-(4-{[2-(4-chlorophenyl)-4,4-dimethylcyclohex-1-en-1-yl]methyl}piperazin-1-yl)-2-(1H-indazol-4-yloxy)-N-({3-nitro-4-[(tetrahydro-2H-pyran-4-ylmethyl)amino]phenyl}sulfonyl)benzamide

Example 400A

4-Hydroxy-indazole-1-carboxylic acid tert-butyl ester and 4-hydroxy-indazole-2-carboxylic acid tert-butyl ester 4-Hydroxyindazole (3.94 g) was added to tetrahydrofuran (250 mL) and cooled to 0° C. using an ice bath. Sodium hydride (60% dispersion in mineral oil, 1.23 g) was added, and the mixture was stirred at 0° C. for five minutes. The mixture was allowed to warm to room temperature and stirred for an additional 20 minutes. The mixture was again cooled to 0° C. using an ice bath, and tert-butyldimethylchlorosilane (4.65 g) was added. The mixture was allowed to warm to room temperature and stirred for 16 hours. Solvent volume was reduced under vacuum, the residue vacuum filtered over a pad of silica gel and washed with ethyl acetate, and the solvent was removed under vacuum. To the residue was added acetonitrile (200 mL), di-tert-butyl dicarbonate (7.06 g), and 4-(dimethylamino)pyridine (0.359 g). The mixture was stirred at room temperature for three hours, and the solvent was removed under vacuum. To the residue was added tetrahydrofuran (200 mL) and tetrabutylammonium fluoride (1M in tetrahydrofuran, 82 mL). The mixture was stirred at room temperature for four days, the solvent removed under vacuum, and the residue taken up in ethyl acetate. The mixture was extracted with saturated aqueous ammonium chloride, extracted with brine, and dried on anhydrous sodium sulfate. The mixture was vacuum filtered over silica gel, and the solvent removed under vacuum to give a mixture of the two products, which was used in the next step without further purification.

Example 400B

4-Fluoro-2-(1H-indazol-4-yloxy)-benzoic acid methyl ester

EXAMPLE 400A (5.56 g) was added to diglyme (200 mL), and potassium tert-butoxide (1M in tetrahydrofuran, 30.8 mL) was added. The mixture was mixed at room temperature for 15 minutes, methyl 2,4-difluorobenzoate was added, and the mixture was heated at 115° C. for 16 hours. The mixture was cooled, the solvent was removed under vacuum, the residue was taken up in dichloromethane (100 mL), and trifluoroacetic acid (22.6 mL) was added. The mixture was stirred at room temperature for 16 hours, the solvent was removed under vacuum, the residue was taken up in ethyl acetate and washed with a saturated aqueous sodium bicarbonate mixture, and the organic layer was dried with anhydrous sodium sulfate. The material was purified by flash column chromatography on silica gel using 30% ethyl acetate (in hexanes) increasing to 40% ethyl acetate (in hexanes).

Example 400C 2-(1H-Indazol-4-yloxy)-4-piperazin-1-yl-benzoic acid methyl ester

EXAMPLE 400B (2.00 g) and piperazine (2.71 g) were added to dimethylsulfoxide (60 mL) and heated to 100° C. for one hour. The mixture was cooled, added to dichloromethane, washed with water twice, washed with a saturated aqueous sodium bicarbonate mixture, and dried on anhydrous sodium sulfate. After filtration, the solvent was removed under vacuum.

Example 400D

4-{4-[2-(4-Chloro-phenyl)-4,4-dimethyl-cyclohex-1-enylmethyl]-piperazin-1-yl}-2-(1H-indazol-4-yloxy)-benzoic acid methyl ester This example was prepared by substituting EXAMPLE 218A for 4'-chlorobiphenyl-2-carboxaldehyde and EXAMPLE 400C for tert-butyl piperazine-1-carboxylate in EXAMPLE 1A.

Example 400E

4-{4-[2-(4-Chloro-phenyl)-4,4-dimethyl-cyclohex-1-enylmethyl]-piperazin-1-yl}-2-(1H-indazol-4-yloxy)-benzoic acid This example was prepared by substituting EXAMPLE 400D for EXAMPLE 1D in EXAMPLE 1E.

Example 400F 4-(4-{[2-(4-chlorophenyl)-4,4-dimethylcyclohex-1-en-1-yl]methyl}piperazin-1-yl)-2-(1H-indazol-4-yloxy)-N-({3-nitro-4-[(tetrahydro-2H-pyran-4-ylmethyl)amino]phenyl}sulfonyl)benzamide This example was prepared by substituting EXAMPLE 400E for EXAMPLE 1E in EXAMPLE 1G. $^1$H NMR (300 MHz, dimethylsulfoxide-$d_6$) δ 13.09 (s, 1H), 8.56 (t, 1H), 8.38 (d, 1H), 7.80 (s, 1H), 7.56 (dd, 1H), 7.53 (d, 1H), 7.36 (d, 2H), 7.16-7.05 (m, 4H), 6.99 (d, 1H), 6.80 (dd, 1H), 6.52 (d, 1H), 6.19 (dd, 1H), 3.87 (dd, 2H), 3.25-3.12 (m, 6H), 2.78 (m, 2H), 2.30-2.16 (m, 6H), 1.97 (br s, 2H), 1.90 (m, 1H), 1.63 (m, 2H), 1.53 (m, 1H), 1.40 (t, 2H), 1.29 (m, 3H), 0.94 (s, 6H).

Example 401

4-(4-{[2-(4-chlorophenyl)-4,4-dimethylcyclohex-1-en-1-yl]methyl}piperazin-1-yl)-2-(1H-indazol-4-yloxy)-N-({3-nitro-4-[(1-tetrahydro-2H-pyran-4-ylpiperidin-4-yl)amino]phenyl}sulfonyl)benzamide Example 401A N-[(4-chloro-3-nitrophenyl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide This example was prepared by substituting EXAMPLE 400E for EXAMPLE 1E and 4-chloro-3-nitrobenzenesulfonamide for EXAMPLE 1F in EXAMPLE 1G. $^1$H NMR (300 MHz, dimethylsulfoxide-$d_6$) δ 13.04 (s, 1H), 8.17 (br s, 1H), 7.75 (s, 1H), 7.73 (d, 1H), 7.66-7.61 (m, 2H), 7.38 (d, 2H), 7.11-7.01 (m, 4H), 6.79 (dd, 1H), 6.54 (d, 1H), 6.10 (dd, 1H), 3.38-3.05 (m, 8H), 2.73 (br s, 2H), 2.19 (m, 2H), 2.00 (br s, 2H), 1.44 (t, 2H), 0.95 (s, 6H).

Example 401B 4-(4-{[2-(4-chlorophenyl)-4,4-dimethylcyclohex-1-en-1-yl]methyl}piperazin-1-yl)-2-(1H-indazol-4-yloxy)-N-({3-nitro-4-[(1-tetrahydro-2H-pyran-4-ylpiperidin-4-yl)amino]phenyl}sulfonyl)benzamide This example was prepared by substituting EXAMPLE 173B for 1-(2-methoxy-ethyl)-piperidin-4-ylamine and EXAMPLE 401A for 4-chloro-3-nitrobenzenesulfonamide in EXAMPLE 189A. $^1$H NMR (300 MHz, dimethylsulfoxide-d$_6$) δ 13.05 (br s, 1H), 8.35 (d, 1H), 8.13 (d, 1H), 7.78 (s, 1H), 7.61-7.52 (m, 2H), 7.35 (d, 2H), 7.11-7.03 (m, 4H), 6.98 (d, 1H), 6.77 (dd, 1H), 6.48 (d, 1H), 6.18 (m, 1H), 3.69-3.52 (m, 4H), 3.12 (m, 6H), 2.76 (br s, 2H), 2.67 (m, 4H), 2.28-2.16 (m, 6H), 2.09-2.01 (m, 2H), 1.97 (br s, 2H), 1.95 (m, 2H), 1.50-1.38 (m, 6H), 0.93 (s, 6H).

Example 402

Trans-4-(4-{[2-(4-chlorophenyl)-4,4-dimethylcyclohex-1-en-1-yl]methyl}piperazin-1-yl)-2-(1H-indazol-4-yloxy)-N-({4-[(4-morpholin-4-ylcyclohexyl)amino]-3-nitrophenyl}sulfonyl)benzamide This example was prepared by substituting trans-4-morpholin-4-yl-cyclohexylamine for 1-(2-methoxy-ethyl)-piperidin-4-ylamine and EXAMPLE 401A for 4-chloro-3-nitrobenzenesulfonamide in EXAMPLE 189A. $^1$H NMR (300 MHz, dimethylsulfoxide-d$_6$) δ 13.02 (br s, 1H), 8.35 (d, 1H), 8.12 (m, 1H), 7.75 (s, 1H), 7.65-7.55 (m, 2H), 7.35 (d, 2H), 7.10-7.03 (m, 4H), 6.97 (m, 1H), 6.76 (dd, 1H), 0.4 (m, 1H), 6.17 (t, 1H), 3.95 (m, 2H), 3.77 (m, 1H), 3.62 (m, 1H), 3.10 (m, 6H), 2.75 (br s, 2H), 2.28-2.14 (m, 8H), 2.06 (m, 2H), 1.97 (br s, 2H), 1.85 (m, 2H), 1.71 (m, 2H), 1.55 (m, 4H), 1.40 (t, 2H), 0.93 (s, 6H).

Example 403

2-(1H-benzimidazol-4-yloxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide

Example 403A methy 4-fluoro-2-(3-fluoro-2-nitrophenoxy)benzoate

To a solution of methyl 4-fluoro-2-hydroxybenzoate (3.0 g) in tetrahydrofuran (65 mL) was added potassium t-butoxide (1.979 g) portion wise. The resulting solution was stirred at ambient temperature for 30 minutes and a solution of 1,3-difluoro-2-nitrobenzene (2.338 g) in tetrahydrofuran (15 mL) was added dropwise. After 1 hour, the reaction was heated at reflux for 18 hours. The reaction was quenched with water (10 mL), diluted with brine (75 mL) and extracted with methylene chloride (2×75 mL). The crude product was isolated by concentration and purified on silica gel, eluted with a 10, 20, 50% ethyl acetate in hexane step gradient to provide the title compound.

Example 403B methyl 2(3-(bis(4-methoxyphenyl)methylamino)-2-nitrophenoxy)-4-fluorobenzoate To a solution of EXAMPLE 403A (3.82 g) and bis(4-methoxyphenyl)methanamine (4.51 g) in N-methyl-2-pyrrolidinone (65 mL) was added N-ethyl-N-isopropylpropan-2-amine (4.30 mL) and the mixture was heated at 100° C. for 24 hours. The crude product, isolated by concentration, was purified on silica gel, and was eluted with a 10, 25, and 65% ethyl acetate in hexane step gradient to provide the title compound.

Example 403C methyl 2-(2-amino-3-(bis(4-methoxyphenyl)methylamino)phenoxy)-4-fluorobenzoate To a solution of EXAMPLE 403B (2.76 g) in tetrahydrofuran (125 mL) in a stainless steel pressure bottle was added nickel catalyst (2.76 g). The mixture was stirred for 1 hour under hydrogen at 30 psi and ambient temperature. The mixture was filtered though a nylon membrane to remove the catalyst, and concentrated to give the product.

Example 403D methyl 2-(1-(bis(4-methoxyphenyl)methyl)-1H-benzo[d]imidazol-4-yloxy)-4-fluorobenzoate To a solution EXAMPLE 403C (1.25 g) in triethyl orthoformate (30 mL) was added concentrated hydrochloric acid (0.75 mL). The mixture was stirred for 18 hours, quenched by the slow addition of 50% saturated aqueous sodium carbonate solution (100 mL) and extracted with ethyl acetate (2×100 mL). The crude product was isolated by concentration and purified on silica gel, and was eluted with a 25, 50, and 70% ethyl acetate in hexane step gradient to provide title compound.

Example 403E methyl 2-(1-(bis(4-methoxyphenyl)methyl)-1H-benzo[d]imidazol-4-yloxy)-4-(piperazin-1-yl)benzoate A solution of EXAMPLE 403D (500 mg), and piperazine (420 mg) in dimethylsulfoxide (9 mL) was heated at 100° C. for 3 hours. The crude product was isolated by concentration and, following an aqueous work up, it was purified on silica gel, and was eluted with a 5 and 10% methanol in methylene chloride step gradient to provide the title compound.

Example 403F methyl 2-(1-(bis(4-methoxyphenyl)methyl)-1H-benzo[d]imidazol-4-yloxy)-4-(4-((2-(4-chlorophenyl)-4,4-dimethylcyclohex-1-enyl)methyl)piperazin-1-yl)benzoate To a solution of EXAMPLE 403E (430 mg) and EXAMPLE 218A (259 mg) in dichloromethane (13 mL) was added sodium triacetoxyborohydride (323 mg) portionwise. After stirring 42 hours, the reaction was quenched slowly with saturated aqueous sodium bicarbonate solution (80 mL) and extracted with methylene chloride (2×70 mL). The crude product was isolated by concentration and purified on silica gel, and was eluted with a 0, 2, 10% methanol in methylene chloride step gradient to provide the title compound.

Example 403G 2-(1-(bis(4-methoxyphenyl)methyl)-1H-benzo[d]imidazol-4-yloxy)-4-(4-((2-(4-chlorophenyl)-4,4-dimethylcyclohex-1-enyl)methyl)piperazin-1-yl)benzoic acid To a solution of EXAMPLE 403F (545 mg) in a mixture of methanol (7.50 mL) and tetrahydrofuran (7.50 mL) was added a solution of sodium hydroxide (269 mg) in water (3.0 mL). The reaction mixture was heated at 50° C. for 18 hours and then concentrated. The residue was mixed with water (100 mL) and the pH was adjusted to ca. 7 with 1M aqueous hydrochloric acid. The mixture was extracted with 10% methanol in methylene chloride (10×50 mL), and the combined organic layers were concentrated to provide the title compound.

Example 403H 2-(1-(bis(4-methoxyphenyl)methyl)-1H-benzo[d]imidazol-4-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide To a solution of EXAMPLE 403G (200 mg), EXAMPLE 1F (99 mg), triethylamine (0.122 mL), N,N-dimethylpyridin-4-amine (77 mg) in a mixture of dichloromethane (8 mL) and N,N-dimethylformamide (1 mL) was added $N^1$-((ethylimino)methylene)-$N^3$,$N^3$-dimethylpropane-1,3-diamine hydrochloric acid (96 mg). The reaction mixture was stirred 18 hours and then concentrated. The crude product was purified on silica gel eluted with an 80 and 100% ethyl acetate in hexane step gradient to provide the title compound.

Example 403I 2-(1H-benzimidazol-4-yloxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide A solution of EXAMPLE 403H (174 mg) and dichloromethane (25 mL) was cooled in an ice bath and 2,2,2-trifluoroacetic acid (25 mL) was added slowly dropwise. The reaction mixture was stirred 30 minutes under nitrogen and the ice bath was removed. The reaction was stirred 18 hours and then concentrated. The crude product was purified by reverse phase chromatography with ammonium acetate buffer in acetonitrile to give the title compound. $^1$H NMR (400 MHz, pyridine-$d_5$) δ 9.30 (d, 1H), 8.69 (t, 1H), 8.59 (s, 1H), 8.42 (dd, 1H), 7.99 (d, 1H), 7.53 (d, 1H), 7.43 (d, 2H), 7.26 (m, 1H), 7.18 (m, 1H), 7.06 (d, 2H), 6.94 (d, 1H), 6.72-6.66 (m, 2H), 5.53 (m, 2H), 3.98 (m, 2H), 3.32 (m, 2H), 3.18 (t, 2H), 2.03 (m, 4H), 2.76 (s, 2H), 2.25 (m, 2H), 2.13 (m, 4H), 1.97 (s, 2H), 1.83 (m, 1H), 1.60 (m, 2H), 1.40-1.29 (m, 4H), 0.94 (s, 6H).

Example 404

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide Example 404A 5-chloro-6-((4-fluorotetrahydro-2H-pyran-4-yl)methoxy)pyridine-3-sulfonamide The title compound was prepared by substituting EXAMPLE 387A for EXAMPLE 329A and EXAMPLE 306C for (tetrahydro-2H-pyran-4-yl)methanol in EXAMPLE 329B.

Example 404B

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide The title compound was prepared by substituting EXAMPLE 404A for EXAMPLE 1F and EXAMPLE 400E for EXAMPLE 26C in EXAMPLE 177. $^1$H NMR (500 MHz, dimethylsulfoxide-$d_6$) δ 13.09 (s, 1H), 8.27 (d, 1H), 7.88 (d, 1H), 7.80 (s, 1H), 7.60 (d, 1H), 7.37 (d, 2H), 7.03-7.10 (m, 4H), 6.79 (dd, 1H), 6.53 (d, 1H), 6.13 (d, 1H), 4.50 (d, 2H), 3.76-3.81 (m, 2H), 3.57-3.63 (m, 2H), 3.04 (br s, 4H), 2.84 (br s, 2H), 2.18 (m, 2H), 1.82-1.92 (m, 4H), 1.42 (t, 2H), 0.94 (s, 6H).

Example 405

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indol-4-yloxy)benzamide The title compound was prepared by substituting EXAMPLE 404A for EXAMPLE 1F and EXAMPLE 55B for EXAMPLE 26C in EXAMPLE 177. $^1$H NMR (500 MHz, dimethylsulfoxide-$d_6$) δ 11.21 (s, 1H), 8.43 (d, 1H), 8.06 (d, 1H), 7.55 (d, 1H), 7.34 (d, 2H), 7.27 (t, 1H), 7.13 (d, 1H), 7.04 (d, 2H), 6.93 (t, 2H), 6.69 (dd, 1H), 6.36 (d, 1H), 6.28 (d, 1H), 6.26 (d, 1H), 4.51 (d, 2H), 3.73-3.79 (m, 2H), 3.55-3.61 (m, 2H), 3.08 (br s, 4H), 2.86 (br s, 2H), 2.31 (br s, 2H), 2.18 (m, 2H), 1.95 (s, 2H), 1.79-1.90 (m, 4H), 1.36 (t, 2H), 0.92 (s, 6H).

Example 406

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-indazol-4-yloxy)benzamide The title compound was prepared by substituting EXAMPLE 385B for EXAMPLE 1F and EXAMPLE 400E for EXAMPLE 26C in EXAMPLE 177. $^1$H NMR (500 MHz, dimethylsulfoxide-$d_6$) δ 13.03 (s, 1H), 8.48 (d, 1H), 8.17 (s, 1H), 7.74 (s, 1H), 7.63 (d, 1H), 7.37 (d, 2H), 7.00-7.08 (m, 4H), 6.77 (dd, 1H), 6.51 (s, 1H), 6.07 (d, 1H), 4.55 (d, 2H), 3.77-3.81 (m, 2H), 3.58-3.63 (m, 2H), 3.20 (br s, 4H), 2.19 (br s, 2H), 1.99 (s, 2H), 1.85-1.92 (m, 4H), 1.42 (t, 2H), 0.94 (s, 6H).

Example 407

2-(H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide Example 407A (R)-tert-butyl 1-(2,2-difluoroethyl)pyrrolidin-3-ylcarbamate To a solution of (R)-tert-butyl pyrrolidin-3-ylcarbamate (500 mg), 1,1-difluoro-2-iodoethane (618 mg) in N,N-dimethylformamide (6 mL) was added N-ethyl-N-isopropylpropan-2-amine (1.403 mL) and the reaction stirred for 72 hours at 70° C. The reaction mixture was concentrated and the crude product was purified on a silica gel and was eluted with a 0, 2, and 5% methanol in methylene chloride step gradient to provide the title compound.

Example 407B (R)-1-(2,2-difluoroethyl)pyrrolidin-3-amine

To a solution of EXAMPLE 407A (525 mg) in a mixture of dichloromethane (3 mL) and methanol (2.0 mL) was added hydrogen chloride, 4M in dioxane (5.24 mL). The reaction was stirred for 3 hours, and concentrated to provide the title compound.

Example 407C (R)-4-(1-(2,2-difluoroethyl)pyrrolidin-3-ylamino)-3-nitrobenzenesulfonamide To a solution of EXAMPLE 407B (468 mg) in tetrahydrofuran (20 mL), N-ethyl-N-isopropylpropan-2-amine (2.193 mL) and N,N-dimethylformamide (2 mL) was added 4-fluoro-3-nitrobenzenesulfonamide (473 mg) and the reaction mixture was stirred 72 hours.

The crude product was isolated by concentration and was purified on silica gel, and was eluted with a 0.5, 2.5, and 5% methanol in methylene chloride step gradient to obtain the title compound.

Example 407D (R)-2-(1-(bis(4-methoxyphenyl)methyl)-1H-benzo[d]imidazol-4-yloxy)-4-(4-((2-(4-chlorophenyl)-4,4-dimethylcyclohex-1-enyl)methyl)piperazin-1-nitrophenylsulfonyl)benzamide The title compound was prepared by substituting EXAMPLE 407C for EXAMPLE 1F in EXAMPLE 403H.

Example 407E 2-(1H-benzimidazol-4-yloxy)-4-(4-({[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide The title compound was prepared by substituting EXAMPLE 407D for EXAMPLE 403H in EXAMPLE 403I.
$^1$H NMR (400 MHz, pyridine-$d_5$) δ 9.26 (d, 1H), 8.60-8.55 (m, 2H), 8.39 (m, 1H), 7.99 (d, 1H), 7.53 (d, 1H), 7.43 (d, 2H), 7.25 (m, 1H), 7.17 (m, 1H), 7.06 (d, 2H), 6.86 (d, 1H), 6.72-6.69 (m, 2H), 6.00-6.33 (m, 1H), 5.27 (m, 2H), 4.09 (m, 1H), 3.03 (m, 4H), 2.96-2.86 (m, 4H), 2.81-2.74 (m, 3H), 2.48 (m, 1H), 2.26 (m, 3H), 2.13 (m, 4H), 1.97 (s, 2H), 1.67 (m, 1H), 1.38 (t, 2H), 0.94 (s, 6H).

Example 408

2-(1H-benzimidazol-4-yloxy)-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)benzamide Example 408A 2-(1-(bis(4-methoxyphenyl)methyl)-1H-benzo[d]imidazol-4-yloxy)-4-(4-((2-(4-chlorophenyl)-4,4-dimethylcyclohex-1-enyl)methyl)piperazin-1-yl)-N-(4-((4-fluorotetrahydro-2H-pyran-4-yl)methoxy)-3-nitrophenylsulfonyl)benzamide The title compound was prepared by substituting EXAMPLE 306D for EXAMPLE 1F in EXAMPLE 403H.

Example 408B 2-(1H-benzimidazol-4-yloxy)-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)benzamide The title compound was prepared by substituting EXAMPLE 408A for EXAMPLE 403H in EXAMPLE 403I.
$^1$H NMR (400 MHz, pyridine-$d_5$) δ 9.01 (d, 1H), 8.57 (m, 2H), 7.99 (d, 1H), 7.53 (d, 1H), 7.44 (d, 2H), 7.25 (m, 1H), 7.21 (m, 1H), 7.12 (d, 1H), 7.07 (d, 2H), 6.73-6.70 (m, 2H), 5.35 (m, 2H), 4.36 (s, 1H), 4.31 (s, 1H), 3.88 (m, 2H), 3.78 (m, 2H), 3.05 (m, 4H), 2.77 (s, 2H), 2.26 (m, 2H), 2.15 (m, 4H), 2.07-192 (m, 6H), 1.39 (t, 2H), 0.94 (s, 6H).

Example 409

4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-indazol-4-yloxy)benzamide Example 409A (4-fluorotetrahydro-2H-pyran-4-yl)methyl methanesulfonate A mixture of EXAMPLE 306C (1.4 g), methanesulfonyl chloride (1.054 mL), triethylamine (2.99 mL), and 4-(dimethylamino)pyridine (0.051 g) in CH$_2$Cl$_2$ (20 mL) was stirred at 0° C. for 2 hours, concentrated and chromatographed on silica gel with 30% ethyl acetate in hexanes as eluent to give the product.

Example 409B 2-((4-fluorotetrahydro-2H-pyran-4-yl)methyl)isoindoline-1,3-dione

A mixture of EXAMPLE 409A (1.8 g) and potassium phthalimide (2.356 g) in N,N-dimethylformamide (30 mL) was heated at 150° C. overnight, diluted with ethyl acetate, washed with water and brine, dried (MgSO$_4$), filtered, concentrated and chromatographed on silica gel with 30% ethyl acetate in hexanes as eluent to give the product.

Example 409C (4-fluorotetrahydro-2H-pyran-4-yl)methanamine

A mixture of EXAMPLE 409B (1.4 g) and hydrazine (1.548 mL) in ethanol (40 mL) was heated at 70° C. overnight, cooled to room temperature, slurried with $CH_2C_{12}$ (200 mL) and the solid removed by filtration. The filtrate was concentrated and chromatographed on silica gel with 100:5:1 ethyl acetate/methanol/$NH_4OH$ as eluent to give the product.

Example 409D 4-((4-fluorotetrahydro-2H-pyran-4-yl)methylamino)-3-nitrobenzenesulfonamide A mixture of 4-fluoro-3-nitrobenzenesulfonamide (0.44 g), EXAMPLE 409C (0.266 g), and triethylamine (1.11 mL) in tetrahydrofuran (10 mL) was heated at 70 OC overnight, diluted with ethyl acetate, washed with water and brine, dried ($MgSO_4$), filtered, concentrated and chromatographed on silica gel with 50% ethyl acetate in hexanes as eluent to give the product.

Example 409E 4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-indazol-4-yloxy)benzamide The title compound was prepared by substituting EXAMPLE 409D for EXAMPLE 1F and EXAMPLE 400E for EXAMPLE 26C in EXAMPLE 177. $^1$H NMR (500 MHz, dimethylsulfoxide-$d_6$) δ 13.09 (s, 1H), 8.59 (t, 1H), 8.37 (d, 1H), 7.80 (s, 1H), 7.59 (dd, 1H), 7.37 (d, 2H), 7.04-7.13 (m, 5H), 6.79 (dd, 1H), 6.51 (d, 1H), 6.18 (d, 1H), 3.70-3.79 (m, 4H), 3.50-3.56 (m, 2H), 3.15 (br s, 4H), 2.78 (br s, 2H), 2.32 (br s, 4H), 2.17 (br s, 2H), 1.97 (s, 2H), 1.75-1.83 (m, 4H), 1.40 (t, 2H), 0.93 (s, 6H).

Example 410

4-(4-{[2-(4-chlorophenyl)-4,4-dimethylcyclohex-1-en-1-yl]methyl}piperazin-1-yl)-N-{6-[(4-fluorotetrahydro-2H-pyran-4-yl)methoxy]-5-(trifluoromethyl)pyridin-3-yl]sulfonyl}-2-(1H-indazol-4-yloxy)benzamide

Example 410A 5-nitro-3-(trifluoromethyl)pyridin-2-ol 3-(Trifluoromethyl)pyridin-2-ol (2.3 g) was added to concentrated sulfuric acid (15 mL) at 0° C. The mixture was stirred at 0° C. for 5 minutes. To this solution was added nitric acid (fuming) (6 mL) dropwise over 5 minutes. The reaction mixture was stirred at room temperature for 2 hours, and was heated at 50° C. for 3 hours. After cooling, the reaction mixture was poured into ice (200 g), and the mixture was extracted with ethyl acetate three times. The combined organic layers were washed with brine, dried over $MgSO_4$, filtered, and concentrated under reduced pressure to give the title compound.

Example 410B 2-chloro-5-nitro-3-(trifluoromethyl)pyridine

A mixture of EXAMPLE 410A (1.69 g), phosphorus pentachloride (2.03 g), and phosphoryl trichloride (0.97 mL) was heated at 90° C. for 3 hours. After cooling, the reaction mixture was poured into ice, and extracted with ethyl acetate three times. The extract was washed with brine, dried over $MgSO_4$, filtered, and concentrated under reduced pressure. The residue was purified by flash column chromatography on silica gel eluting with 1:9 ethyl acetate\hexanes to give the title compound.

Example 410C

A mixture of iron (1.5 g) and ammonium chloride (2.38 g) in water (40 mL) was stirred at room temperature for 5 minutes. To this suspension was added EXAMPLE 410B in methanol (40 mL). The reaction mixture was stirred at room temperature for 1 hour. Additional iron (1.8 g) was added to the reaction mixture, and it was stirred for another 3 hours. The solid from the reaction mixture was filtered off, and the filtrate was partitioned between water and ethyl acetate. The combined organic layers were washed with brine, dried over $MgSO_4$, filtered, and concentrated under reduced pressure. The residue was purified by flash column chromatography on silica gel eluting with 1:4 ethyl acetate\hexanes to give the title compound.

Example 410D 6-chloro-5-(trifluoromethyl)pyridine-3-sulfonyl chloride

Under ice-cooling, thionyl chloride (4 mL) was added dropwise over 20 minutes to water (27 mL). The mixture was stirred overnight for 12 hours to give a $SO_2$ containing solution. Separately, EXAMPLE 410C (1.14 g) in dioxane (5 mL) was added to concentrated HCl (20 mL) at 0° C. The solution was stirred for 5 minutes. To this mixture was added sodium nitrite (0.44 g) in water (6 mL) dropwise at 0° C. The solution stirred at 0° C. for three hours. During this time, any solids formed were crushed with a glass rod to make sure that EXAMPLE 410C was completely reacted. To the $SO_2$ containing solution was added copper(I) chloride (0.115 g). Then, to this solution was added the diazotized EXAMPLE 410C at 0° C. The solution was stirred for 30 minutes. The reaction mixture was extracted with ethyl acetate. The combined organic layers were washed with brine, dried over $MgSO_4$, filtered, and concentrated under reduced pressure. The residue was purified by flash column chromatography on silica gel eluting with 1:20 ethyl acetate\hexanes to give the title compound.

Example 410E 6-chloro-5-(trifluoromethyl)pyridine-3-sulfonamide

The title compound was prepared by substituting EXAMPLE 410D for 5-bromo-6-chloropyridine-3-sulfonyl chloride in EXAMPLE 329A.

Example 410F

The title compound was prepared by substituting EXAMPLE 410E for EXAMPLE 329A and EXAMPLE 306C for (tetrahydro-2H-pyran-4-yl)methanol in EXAMPLE 329B.

Example 410G 4-(4-{[2-(4-chlorophenyl)-4,4-dimethylcyclohex-1-en-1-yl]methyl}piperazin-1-yl)-N-{[6-[(4-fluorotetrahydro-2H-pyran-4-yl)methoxy]-5-(trifluoromethyl)pyridin-3-yl]sulfonyl}-2-(1H-indazol-4-yloxy)benzamide The title compound was prepared by substituting EXAMPLE 410F for EXAMPLE 1F and EXAMPLE 400E for EXAMPLE 26C in EXAMPLE 177. $^1$H NMR (500 MHz dimethylsulfoxide-d$_6$) 13.05 (s 1H), 8.59 (s, 1H), 8.17 (d, 1H) 776 (s, 1H), 7.62 (d, 1H), 7.37 (d, 2H), 7.00-7.08 (m, 4H), 6.78 (dd, 1H), 6.51 (s, 1H), 6.11 (d, 1H), 4.56 (d, 2H), 3.77-3.80 (m, 2H), 3.57-3.62 (m, 2H), 3.18 (br s, 2H), 2.32 (br s, 4H), 2.18 (br s, 2H), 1.99 (s, 2H), 1.81-1.90 (m, 4H), 1.42 (t, 2H), 0.94 (s, 6H).

Example 411

4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]-2-(1H-indazol-4-yloxy)benzamide The title compound was prepared by substituting EXAMPLE 400E for EXAMPLE 1E and EXAMPLE 432A for EXAMPLE 1F in EXAMPLE 1G. $^1$H NMR (300 MHz, dimethylsulfoxide-d$_6$) δ 13.09 (s, 1H), 8.57 (m, 1H), 8.37 (d, 1H), 7.81 (s, 1H), 7.56 (dd, 1H), 7.52 (d, 1H), 7.38-7.31 (m, 3H), 7.11-7.07 (m, 3H), 6.97 (d, 1H), 6.80 (dd, 1H), 6.52 (d, 1H), 6.17 (d, 1H), 3.84 (d, 1H), 3.24-3.10 (m, 6H), 2.93 (d, 2H), 2.76 (m, 2H), 2.73 (s, 2H), 2.34-2.10 (m, 8H), 1.97 (bs, 2H), 1.67 (m, 1H), 1.40 (t, 2H), 0.93 (s, 6H), 0.47-0.26 (m, 4H).

Example 412

4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-indazol-4-yloxy)benzamide

Example 412A tert-butyl(4,4-difluorocyclohexyl)methylcarbamate

Tert-butyl(4-oxocyclohexyl)methylcarbamate (5 g) and diethylaminosulfur trifluoride (7.45 g) were stirred in dichloromethane (100 mL) for 24 hours. The mixture was quenched with pH 7 buffer (100 mL), and poured into ether (400 mL). The resulting solution was separated, and the organic layer was washed twice with water, and once with brine, and then concentrated to give the crude product and fluoroolefin in a 3:2 ratio. The crude product was taken up in tetrahydrofuran (70 mL) and water (30 mL), and N-methylmorpholine-N-oxide (1.75 g), and OsO$_4$ (2.5 wt % solution in t-butanol) were added, and the mixture was stirred for 24 hours. Na$_2$S$_2$O$_3$ (10 g) was then added, and the mixture was stirred for 30 minutes. The mixture was then diluted with ether (300 mL), and the resulting solution was separated, and rinsed twice with water, and once with brine, and concentrated. The crude product was chromatographed on silica gel using 5-10% ethyl acetate in hexanes to give the title compound.

Example 412B (4,4-difluorocyclohexyl)methanamine

A solution of EXAMPLE 412A (3 g) in dichloromethane (35 mL), trifluroacetic acid (15 mL), and triethylsilane (1 mL) was stirred for 2 hours. The solution was concentrated, then concentrated from toluene, and left on high vacuum for 24 hours. The semi-solid was taken up in ether/hexane and filtered to give the product as its trifluroacetic acid salt.

Example 412C 4-((4,4-difluorocyclohexyl)methylamino)-3-nitrobenzenesulfonamide The title compound was prepared by substituting EXAMPLE 412B for 1-(2-methoxy-ethyl)-piperidin-4-ylamine in EXAMPLE 189A.

Example 412D 4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-indazol-4-yloxy)benzamide The title compound was prepared by substituting EXAMPLE 400E for EXAMPLE 1E and EXAMPLE 412C for EXAMPLE 1F in EXAMPLE 1G. $^1$H NMR (300 MHz, dimethylsulfoxide-d$_6$) δ 13.16 (s, 1H), 11.70 (br s, 1H), 8.65 (m, 1H), 8.44 (d, 1H), 7.87 (d, 1H), 7.61 (dd, 2H), 7.41 (d, 2H), 7.02-7.20 (m, 4H), 6.88 (dd, 1H), 6.58 (d, 1H), 6.26 (dd, 1H), 3.22 (m, 4H), 2.86 (m, 2H), 2.20-2.35 (m, 7H), 2.14 (s, 2H), 2.10 (m, 2H), 2.03 (m, 2H), 1.91 (m, 2H), 1.87 (m, 2H), 1.46 (m, 2H), 1.27-1.39 (m, 3H), 1.00 (s, 6H).

Example 413

N-[(5-chloro-6-{[(4-fluorotetrahydro-2H-pyran-4-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide

Example 413A

The title compound was prepared by substituting EXAMPLE 387A for 4-fluoro-3-nitrobenzenesulfonamide and EXAMPLE 409C for (tetrahydropyran-4-yl)methylamine in EXAMPLE 1F.

Example 413B

N-[(5-chloro-6-{[(4-fluorotetrahydro-2H-pyran-4-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide The title compound was prepared by substituting EXAMPLE 413A for EXAMPLE 1F and EXAMPLE 400E for EXAMPLE 26C in EXAMPLE 177. $^1$H NMR (500 MHz, dimethylsulfoxide-$d_6$) δ 13.14 (s, 1H), 8.19 (d, 1H), 7.87 (s, 1H), 7.60 (d, 1H), 7.56 (d, 1H), 7.36 (d, 2H), 7.31 (br s, 1H), 7.08-7.17 (m, 2H), 7.06 (d, 2H), 6.80 (dd, 1H), 6.53 (d, 1H), 6.20 (d, 1H), 3.70-3.78 (m, 4H), 3.43-3.54 (m, 2H), 3.18 (br s, 4H), 2.81 (s, 2H), 2.26 (br s, 4H), 2.17 (br s, 2H), 1.97 (s, 2H), 1.64-1.80 (m, 4H), 1.40 (t, 2H), 0.94 (s, 6H).

Example 414

Trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide Example 414A Cis-(4-methoxycyclohexyl)methanol and Trans-(4-methoxycyclohexyl)methanol Ethyl 4-methoxycyclohexanecarboxylate (1 g) in tetrahydrofuran (10 mL) was treated with 1.0 N LiAlH$_4$ in THF (2 mL) at 0° C. The mixture was stirred for 2 hours. The reaction was quenched with water (0.6 mL) followed by 2.0 N aqueous NaOH (0.2 mL). The mixture was stirred for another 20 minutes, and the solid was filtered off. The filtrate was taken up in ethyl acetate, washed with brine, dried over MgSO$_4$, filtered, and concentrated to give the title compound as a mixture of cis and trans isomers.

Example 414B 5-chloro-6-((trans-4-methoxycyclohexyl)methoxy)pyridine-3-sulfonamide The title compound was prepared by substituting EXAMPLE 387A for EXAMPLE 329A and EXAMPLE 414A for (tetrahydro-2H-pyran-4-yl)methanol in EXAMPLE 329B.

The trans isomer was isolated by flash column chromatography on silica gel.

Example 414C

Trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide The title compound was prepared by substituting EXAMPLE 414B for EXAMPLE 1F and EXAMPLE 400E for EXAMPLE 26C in EXAMPLE 177. $^1$H NMR (500 MHz, dimethylsulfoxide-$d_6$) δ 13.10 (s, 1H), 8.27 (d, 1H), 7.85 (d, 1H), 7.80 (s, 1H), 7.59 (d, 1H), 7.36 (d, 2H), 7.03-7.10 (m, 4H), 6.79 (dd, 1H), 6.53 (d, 1H), 6.14 (d, 1H), 4.19 (d, 2H), 3.24 (s, 3H), 3.20 (m, 4H), 3.07-3.10 (m, 2H), 2.93 (br s, 2H), 2.39 (s, 4H), 2.18 (s, 2H), 1.98-2.02 (m, 4H), 1.70-1.86 (m, 3H), 1.42 (t, 2H), 1.08-1.17 (m, 4H), 0.94 (s, 6H).

Example 415

2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(2,2-difluoroethyl)morpholin-2-yl]methyl}amino)-3-nitrophenyl]sulfonyl}benzamide Example 415A tert-Butyl 2-((2-nitro-4-sulfamoylphenylamino)methyl)morpholine-4-carboxylate This EXAMPLE was prepared by substituting tert-butyl 2-(aminomethyl)morpholine-4-carboxylate for (tetrahydropyran-4-yl)methylamine in EXAMPLE 1F.

Example 415B 4-(morpholin-2-ylmethylamino)-3-nitrobenzenesulfonamide

A solution of EXAMPLE 415A (0.8 g) in methylene chloride (10 mL) and trifluoroacetic acid (10 mL) was stirred at room temperature for 2 hours. The solvents were evaporated and the residue was triturated with diethyl ether. The resulting solid was dissolved in 5% aqueous sodium carbonate solution (20 mL). The solution was evaporated to dryness and the resulting solid was triturated with a solution of 10% methanol in dichloromethane several times. Evaporation of the organic solution gave the title compound.

Example 415C 4-((4-(2,2-difluoroethyl)morpholin-2-yl)methylamino)-3-nitrobenzenesulfonamide To a solution of EXAMPLE 415B (633 mg) in anhydrous N,N-dimethylformamide (10 mL) was added sodium carbonate (254 mg) and 2, 2-difluoroethyl iodide (422 mg). After stirring at 110° C. for 48 hours, the mixture was concentrated. The residue was mixed with water (20 mL) and extracted with ethyl acetate. The crude product was purified on a silica gel column eluting with 10% methanol in methylene chloride to give the title compound.

Example 415D 2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(2,2-difluoroethyl)morpholin-2-yl]methyl}amino)-3-nitrophenyl]sulfonyl}benzamide This EXAMPLE was prepared by substituting EXAMPLE 415C for EXAMPLE 428D in EXAMPLE 428E. $^1$H NMR (500 MHz, pyridine-$d_5$) δ 9.26 (d, 1H), 8.87 (t, 1H), 8.57 (s, 1H), 8.37 (dd, 1H), 7.99 (d, 1H), 7.53 (d, 1H), 7.43 (d, 2H), 7.25 (m, 2H), 7.17 (d, 1H), 7.06 (d, 2H), 6.96 (d, 1H), 6.72-6.69 (m, 2H), 6.31, 6.20, 6.09 (tt, 1H), 3.90 (m, 1H), 3.86 (d, 1H), 3.68 (dt, 1H), 3.54-3.41 (m, 2H), 3.03 (m, 4H), 2.97 (d, 1H), 2.83-2.75 (m, 4H), 2.69 (d, 1H), 2.35 (dt, 1H), 2.27-2.23 (m, 3H), 2.14 (m, 4H), 1.97 (s, 2H), 1.38 (t, 2H), 0.94 (s, 6H).

Example 416

4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-indazol-4-yloxy)benzamide Example 416A 5-bromo-3-fluoro-2-((4-fluorotetrahydro-2H-pyran-4-yl)methoxy)pyridine The title compound was prepared by substituting EXAMPLE 306C for (tetrahydro-2H-pyran-4-yl)methanol and 5-bromo-2,3-difluoropyridine for 4-fluoro-3-nitrobenzenesulfonamide in EXAMPLE 279A.

Example 416B tert-butyl 5-fluoro-6-((4-fluorotetrahydro-2H-pyran-4-yl)methoxy)pyridin-3-ylcarbamate EXAMPLE 416A (0.658 g), tert-butyl carbamate (0.300 g), palladium(II) acetate (0.024 g), 4,5-bis(diphenylphosphino)-9,9-dimethylxanthene (0.093 g) and cesium carbonate (1.044 g) were combined in a 20-mL vial with dioxane (10.7 ml). The vial was flushed with nitrogen, capped and stirred at 100° C. overnight. The reaction mixture was diluted with ethyl acetate, washed with water and brine, dried (MgSO$_4$), filtered, concentrated and chromatographed on silica gel with 20% ethyl acetate in hexanes as eluent.

Example 416C 5-fluoro-6-((4-fluorotetrahydro-2H-pyran-4-yl)methoxy)pyridine-3-sulfonyl chloride Under ice-cooling, thionyl chloride (1.563 mL) was added dropwise over 20 minutes to water (9 mL). The mixture was stirred for 12 hours to give a SO$_2$-containing solution. Separately, EXAMPLE 416B (0.295 g) was added to a mixture of dioxane (3.2 mL) and concentrated HCl (8 ml) at 0 OC. The solution was stirred for 15 minutes, treated with a solution of sodium nitrite (0.065 g) in water (2 mL) dropwise at 0° C. and stirred at 0° C. for three hours. The SO$_2$-containing solution was cooled to 0° C., treated sequentially with copper(I) chloride (0.042 g) and the diazotized mixture, and stirred for 30 minutes. The reaction mixture was then extracted with ethyl acetate and the organic layer was dried (MgSO$_4$), filtered and concentrated. The concentrate was chromatographed on silica gel with 5-10% ethyl acetate in hexanes as eluent.

Example 416D 5-fluoro-6-((4-fluorotetrahydro-2H-pyran-4-yl)methoxy)pyridine-3-sulfonamide EXAMPLE 416C (0.08 g,) in isopropanol (2 mL) at 0° C. was treated with ammonium hydroxide (1.70 mL) and stirred overnight. The reaction mixture was concentrated to dryness, slurried in water, filtered, rinsed with water and dried under vacuum to provide the title compound.

Example 416E 4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-indazol-4-yloxy)benzamide The title compound was prepared by substituting EXAMPLE 400E for EXAMPLE 26C and EXAMPLE 416D for EXAMPLE 1F in EXAMPLE 177. $^1$H NMR (400 MHz, PYRIDINE-d$_5$) δ 14.67 (s, 1H), 8.84 (d, 1H), 8.38 (d, 1H), 8.06 (d, 1H), 8.00 (dd, 1H), 7.46 (m, 2H), 7.35 (d, 1H), 7.12 (m, 3H), 6.87 (m, 2H), 6.47 (d, 1H), 4.56 (d, 2H), 3.80 (m, 4H), 3.18 (m, 4H), 2.83 (s, 2H), 2.31 (t, 2H), 2.24 (m, 4H), 1.99 (s, 2H), 1.86 (m, 4H), 1.41 (t, 2H), 0.96 (s, 6H).

Example 417

2-(1H-benzimidazol-4-yloxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide Example 417A 2-(1-(bis(4-methoxyphenyl)methyl)-1H-benzo[d]imidazol-4-yloxy)-4-(4-((2-(4-chlorophenyl)-4,4-dimethylcyclohex-1-enyl)methyl)piperazin-1-yl)-N-(3-nitro-4-(1-(tetrahydro-2H-pyran-4-yl)piperidin-4-ylamino)phenylsulfonyl)benzamide The title compound was prepared by substituting EXAMPLE 173C for EXAMPLE 1F in EXAMPLE 403H.

Example 417B 2-(1H-benzimidazol-4-yloxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide The title compound was prepared by substituting EXAMPLE 417A for EXAMPLE 403H in EXAMPLE 403I. $^1$H NMR (500 MHz, pyridine-d$_5$) δ 9.27 (m, 1H), 8.59 (s, 1H), 8.47 (d, 1H), 8.43 (d, 1H), 8.01 (d, 1H), 7.53 (d, 1H), 7.43 (d, 2H), 7.24 (m, 1H), 7.18 (m, 1H), 7.07 (d, 2H), 6.96 (d, 1H), 6.70 (m, 2H), 5.34 (m, 2H), 4.03 (m, 2H), 3.53 (m, 1H), 3.31 (m, 2H), 3.03 (m, 4H), 2.82 (m, 2H), 2.76 (s, 2H), 2.42 (m, 1H), 2.32 (m, 2H), 2.26-2.19 (m, 2H), 2.14 (m, 4H), 1.98 (m, 4H), 1.67-1.52 (m, 6H), 1.38 (m, 2H), 0.94 (s, 6H).

387

Example 418

2-(1H-benzimidazol-4-yloxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide

Example 418A 2-(1-(bis(4-methoxyphenyl)methyl)-1H-benzo[d]imidazol-4-yloxy)-4-(4-((2-(4-chlorophenyl)-4,4-dimethylcyclohex-1-enyl)methyl)piperazin-1-yl)-N-(4-(1-methylpiperidin-4-ylamino)-3-nitrophenylsulfonyl)benzamide The title compound was prepared by substituting EXAMPLE 21A for EXAMPLE 1F in EXAMPLE 403H.

Example 418B 2-(1H-benzimidazol-4-yloxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide The title compound was prepared by substituting EXAMPLE 418A for EXAMPLE 403H in EXAMPLE 403I. $^1$H NMR (500 MHz, pyridine-$d_5$) δ 9.25 (m, 1H), 8.58 (s, 1H), 8.42 (m, 2H), 8.02 (d, 1H), 7.52 (d, 1H), 7.43 (d, 2H), 7.23 (m, 1H), 7.14 (d, 1H), 7.07 (d, 2H), 6.92 (d, 1H), 6.70 (m, 2H), 5.52 (m, 2H), 3.50 (m, 1H), 3.03 (m, 4H), 2.77 (s, 2H), 2.68 (m, 2H), 2.25 (m, 2H), 2.20 (s, 3H), 2.14 (m, 6H), 1.97-1.90 (m, 4H), 1.67 (m, 2H), 1.38 (t, 2H), 0.94 (s, 6H).

Example 419

N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1 1H-indazol-4-yloxy)benzamide

Example 419A tert-butyl 4-fluoro-4-(hydroxymethyl)piperidine-1-carboxylate

1-Tert-butyl 4-ethyl 4-fluoropiperidine-1,4-dicarboxylate (1.0 g) in tetrahydrofuran (10 mL) at 0° C. was treated with a 1 N solution of LiAlH$_4$ in tetrahydrofuran (2.54 mL), stirred for 2 hours at room temperature, treated sequentially dropwise with water (0.2 mL) and a 2 N aqueous solution of NaOH (0.6 mL), and stirred for 1 hour. The solid was removed by filtration through a pad of diatomaceous earth rinsing with ethyl acetate. The filtrate was washed with water and brine, dried (MgSO$_4$), filtered and concentrated to give the title compound.

Example 419B tert-butyl 4-((3-chloro-5-sulfamoylpyridin-2-yloxy)methyl)-4-fluoropiperidine-1-carboxylate The title compound was prepared by substituting EXAMPLE 419A for (tetrahydro-2H-pyran-4-yl)methanol and EXAMPLE 387A for 4-fluoro-3-nitrobenzenesulfonamide in EXAMPLE 279A.

388

Example 419C 5-chloro-6-((4-fluoropiperidin-4-yl)methoxy)pyridine-3-sulfonamide, 2*trifluoroacetic acid salt The title compound was prepared by substituting EXAMPLE 419B for EXAMPLE 1A in EXAMPLE 1B.

Example 419D 5-chloro-6-((1-(cyanomethyl)-4-fluoropiperidin-4-yl)methoxy)pyridine-3-sulfonamide EXAMPLE 419C (0.166 g) in acetonitrile (3.00 mL) was treated with 2-chloroacetonitrile (0.027 g) and sodium carbonate (0.064 g), heated at 60 OC overnight, cooled to room temperature and chromatographed on silica gel with 0 to 3% methanol in CH$_2$C$_1$, as eluent. The obtained solid was slurried in water, filtered, rinsed with water and diethyl ether, and dried in a vacuum oven at 80 OC to provide the title compound

Example 419E

N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide The title compound was prepared by substituting EXAMPLE 400E for EXAMPLE 26C and EXAMPLE 419D for EXAMPLE 1F in EXAMPLE 177. $^1$H NMR (400 MHz, PYRIDINE-$d_5$) 14.70 (s, 1H), 8.91 (d, 1H), 8.39 (d, 2H), 8.10 (d, 1H), 7.46 (m, 2H), 7.35 (d, 1H), 7.11 (m, 3H), 6.87 (m, 2H), 6.50 (d, 1H), 4.49 (d, 2H), 3.72 (s, 2H), 3.17 (m, 4H), 2.82 (s, 2H), 2.72 (m, 4H), 2.31 (m, 2H), 2.23 (m, 4H), 2.06 (m, 2H), 1.99 (s, 2H), 1.89 (m, 2H), 1.41 (t, 2H), 0.96 (s, 6H).

Example 420

4-(4-{[2-(4-chlorophenyl)-4,4-dimethylcyclohex-1-en-1-yl]methyl}piperazin-1-yl)-N-{[5-chloro-6-(tetrahydrofuran-3-ylmethoxy)pyridin-3-yl]sulfonyl}-2-(1H-indazol-4-yloxy)benzamide

Example 420A 5-chloro-6-((tetrahydrofuran-3-yl)methoxy)pyridine-3-sulfonamide The title compound was prepared by substituting EXAMPLE 387A for EXAMPLE 329A and (tetrahydrofuran-3-yl)methanol for (tetrahydro-2H-pyran-4-yl)methanol in EXAMPLE 329B.

Example 420B 4-(4-{[2-(4-chlorophenyl)-4,4-dimethylcyclohex-1-en-1-yl]methyl}piperazin-1-yl)-N-{[5-chloro-6-(tetrahydrofuran-3-ylmethoxy)pyridin-3-yl]sulfonyl}-2-(1H-indazol-4-yloxy)benzamide The title compound was prepared by substituting EXAMPLE 420B for EXAMPLE 1F and EXAMPLE 400E for EXAMPLE 26C in EXAMPLE 177. $^1$H NMR (500 MHz, dimethylsulfoxide-$d_6$) δ 13.07 (s, 1H), 8.25 (d, 1H), 7.85 (d, 1H), 7.79 (s, 1H), 7.60 (d, 1H), 7.36 (d, 2H), 7.03-7.09 (m, 4H), 6.78 (dd, 1H), 6.51 (d, 1H), 6.13 (dd, 1H), 4.25-4.37 (m, 2H), 3.77-3.81 (m, 2H), 3.64-3.70 (m, 2H), 3.54-3.57 (m, 2H), 3.17 (br s, 4H), 2.89 (br s, 2H), 2.68-2.71 (m, 1H), 2.33 (m, 3H), 2.16-2.18 (m, 2H), 1.98-2.01 (m, 3H), 1.66-1.71 (m, 1H), 1.41 (t, 2H), 0.94 (s, 6H).

Example 421

Trans-N-({5-chloro-6-[(4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide Example 421A 6-((trans-4-(tert-butyldimethylsilyloxy)cyclohexyl)methoxy)-5-chloropyridine-3-sulfonamide The title compound was prepared by substituting EXAMPLE 387A for EXAMPLE 329A and trans-4-(tert-butyldimethylsilyloxy)cyclohexylmethanol, synthesized according to the procedure reported in WO 2008/124878 (Page 100), for (tetrahydro-2H-pyran-4-yl)methanol in EXAMPLE 329B.

Example 421B

Trans-N-({5-chloro-6-[(4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide The title compound was prepared by substituting EXAMPLE 421A for EXAMPLE 1F and EXAMPLE 400E for EXAMPLE 26C in EXAMPLE 177, after removal of the tert-butyldimethylsilyl group with trifluoroacetic acid. $^1$H NMR (500 MHz, dimethylsulfoxide-$d_6$) δ 13.12 (s, 1H), 8.29 (d, 1H), 7.88 (d, 1H), 7.84 (s, 1H), 7.40 (d, 2H), 7.07-7.13 (m, 4H), 6.83 (dd, 1H), 6.56 (s, 1H), 6.17 (d, 1H), 4.58 (d, 1H), 4.21 (d, 2H), 3.22 (br s, 4H), 2.36-2.40 (m, 3H), 2.20-2.24 (m, 2H), 2.02-2.03 (m, 2H), 1.75-1.89 (m, 5H), 1.45 (t, 2H), 1.11-1.21 (m, 4H), 0.98 (s, 6H).

Example 422

N-[(5-chloro-6-{[(3R)-1-(2,2-difluoroethyl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide Example 422A (R)-tert-butyl 3-(3-chloro-5-sulfamoylpyridin-2-yloxy)pyrrolidine-1-carboxylate The title compound was prepared by substituting (R)-tert-butyl 3-hydroxypyrrolidine-1-carboxylate for (tetrahydro-2H-pyran-4-yl)methanol in EXAMPLE 387B.

Example 422B (R)-5-chloro-6-(pyrrolidin-3-yloxy)pyridine-3-sulfonamideHydrochloride salt Example 422A 480 mg) was dissolved in anhydrous tetrahydrofuran (10 mL followed by addition of hydrogen chloride in dioxane solution (4M, 2.5 mL). The reaction mixture was stirred at room temperature overnight. The solvent was removed under vacuum to provide the title compound.

Example 422C (R)-5-chloro-6-(1-(2,2-difluoroethyl)pyrrolidin-3-yloxy)pyridine-3-sulfonamide A reaction mixture of EXAMPLE 422B (353 mg), 1,1-difluoro-2-iodoethane (268 mg) and $Na_2CO_3$ (283 mg) in N,N-dimethylformamide (10 mL) was heated at 80° C. overnight. The reaction mixture was cooled to room temperature and diluted with ethyl acetate. The organic phase was washed with water and brine, dried over anhydrous sodium sulfate, and concentrated. The crude material was purified with 2.5-3% methanol/dichloromethane to afford the title compound.

Example 422D

N-[(5-chloro-6-{[(3R)-1-(2,2-difluoroethyl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide The title compound was prepared by substituting EXAMPLE 400E for EXAMPLE 26C and EXAMPLE 422C for EXAMPLE 1F in EXAMPLE 177. $^1$H NMR (400 MHz, dimethylsulfoxide-$d_6$) δ 12.98 (s, 1H), 8.17 (d, 1H), 7.80 (d, 1H), 7.73 (s, 1H), 7.66 (d, 1H), 7.35 (d, 2H), 7.05 (m, 4H), 6.73 (m, 1H), 6.41 (d, 1H), 6.10 (m, 2H), 5.37 (m, 1H), 2.92 (m, 11H), 2.56 (m, 2H), 2.24 (m, 7H), 1.99 (m, 2H), 1.82 (m, 1H), 1.39 (m, 2H), 0.93 (s, 6H).

Example 423

2-(1H-benzimidazol-4-yloxy)-N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)benzamide Example 423A (S)-tert-Butyl 2-((3-chloro-5-sulfamoylpyridin-2-yloxy)methyl)morpholine-4-carboxylate This EXAMPLE was prepared by substituting (S)-tert-butyl 2-(hydroxymethyl)morpholine-4-carboxylate for 4-hydroxymethyl-tetrahydropyran in EXAMPLE 387B.

Example 423B (S)-5-chloro-6-(morpholin-2-ylmethoxy)pyridine-3-sulfonamide

This EXAMPLE was prepared by substituting EXAMPLE 423A for EXAMPLE 415A in EXAMPLE 415B.

Example 423C (S)-5-chloro-6-((4-(2-(dimethylamino)acetyl)morpholin-2-yl)methoxy)pyridine-3-sulfonamide To a solution of EXAMPLE 423B (0.32 g) in anhydrous N,N-dimethylformamide (10 mL) was added sodium carbonate (0.165 g) and 2-(dimethylamino)acetyl chloride hydrochloride (0.40 g). After stirred at ambient temperature overnight, the mixture was concentrated to dryness. The residue was mixed with 5% aqueous $Na_2CO_3$ (20 mL) and extracted with ethyl acetate. The crude product was purified on a silica gel column eluting with 10% methanol in dichloromethane saturated with ammonia to give the title compound.

Example 423D 2-(1H-benzimidazol-4-yloxy)-N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)benzamide This EXAMPLE was prepared by substituting EXAMPLE 423C for EXAMPLE 428D in EXAMPLE 428E. $^1$H NMR (500 MHz, pyridine-$d_5$) δ 9.08 (d, 1H), 8.60 (t, 1H), 8.57 (s, 1H), 8.01 (d, 1H), 7.53 (d, 1H), 7.43 (d, 2H), 7.25 (m, 2H), 7.15 (m, 1H), 7.07 (d, 2H), 6.73-6.69 (m, 2H), 4.86-4.36 (m, 4H), 4.05-3.90 (m, 1H), 3.88 (d, 1H), 3.62-3.18 (m, 4H), 3.04 (m, 4H), 2.87 (t, 1H), 2.77 (s, 2H), 2.33 (m, 6H), 2.26 (m, 2H), 2.15 (m, 4H), 1.97 (s, 2H), 1.39 (t, 2H), 0.94 (s, 6H).

Example 424

2-(1H-benzimidazol-4-yloxy)-N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)benzamide

Example 424A (R)-tert-butyl 2-((3-chloro-5-sulfamoylpyridin-2-yloxy)methyl)morpholine-4-carboxylate This EXAMPLE was prepared by substituting (R)-tert-butyl 2-(hydroxymethyl)morpholine-4-carboxylate for 4-hydroxymethyl-tetrahydropyran in EXAMPLE 387B.

Example 424B (R)-5-chloro-6-(morpholin-2-ylmethoxy)pyridine-3-sulfonamide

This EXAMPLE was prepared by substituting EXAMPLE 424A for EXAMPLE 415A in EXAMPLE 415B.

Example 424C (R)-5-chloro-6-((4-(2-(dimethylamino)acetyl)morpholin-2-yl)methoxy)pyridine-3-sulfonamide This EXAMPLE was prepared by substituting EXAMPLE 424B for EXAMPLE 423B in EXAMPLE 423C.

Example 424D 2-(1H-benzimidazol-4-yloxy)-N-[(5-chloro-6-{[(2R)-4-(N, N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)benzamide This EXAMPLE was prepared by substituting EXAMPLE 424C for EXAMPLE 428D in EXAMPLE 428E. $^1$H NMR (500 MHz, pyridine-$d_5$) δ 9.08 (d, 1H), 8.60 (t, 1H), 8.57 (s, 1H), 8.01 (d, 1H), 7.53 (d, 1H), 7.43 (d, 2H), 7.25 (m, 2H), 7.15 (m, 1H), 7.07 (d, 2H), 6.73-6.69 (m, 2H), 4.86-4.36 (m, 4H), 4.05-3.90 (m, 1H), 3.88 (d, 1H), 3.62-3.18 (m, 4H), 3.04 (m, 4H), 2.87 (t, 1H), 2.77 (s, 2H), 2.33 (m, 6H), 2.26 (m, 2H), 2.15 (m, 4H), 1.97 (s, 2H), 1.39 (t, 2H), 0.94 (s, 6H).

Example 425

N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide This EXAMPLE was prepared by substituting EXAMPLE 400E for EXAMPLE 1E and EXAMPLE 423C for EXAMPLE 1F in EXAMPLE 1G, and was purified by reverse-phase HPLC using a Waters Preparative LC4000 system with Phenomenex Luna C18 column and a water-acetonitrile mobile phase buffered with ammonium acetate. $^1$H NMR (500 MHz, pyridine-$d_5$) δ 8.87 (dd, 1H), 8.40 (t, 2H), 8.13 (dd, 1H), 7.46 (d, 2H), 7.35 (d, 1H), 7.15-7.10 (m, 3H) 6.87 (d, 1H), 6.85 (s, 1H), 6.50 (dd, 1H), 4.84-4.46 (m, 4H), 4.02-3.90 (m, 1H), 3.88 (m, 1H), 3.60-3.33 (m, 2H), 3.25-3.15 (m, 6H), 2.89-2.84 (m, 1H), 2.83 (s, 2H), 2.32-2.23 (m, 12H), 1.99 (s, 2H), 1.41 (t, 2H), 0.96 (s, 6H).

Example 426

Gary Wang

N-[(5-chloro-6-({[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide This EXAMPLE was prepared by substituting EXAMPLE 400E for EXAMPLE 1E and EXAMPLE 424C for EXAMPLE 1F in EXAMPLE 1G, and was purified by reverse-phase HPLC using a Waters Preparative LC4000 system with Phenomenex Luna C18 column and a water-acetonitrile mobile phase buffered with ammonium acetate. $^1$H NMR (500 MHz, pyridine-$d_5$) δ 8.87 (dd, 1H), 8.40 (t, 2H), 8.13 (dd, 1H), 7.46 (d, 2H), 7.35 (d, 1H), 7.15-7.10 (m, 3H), 6.87 (d, 1H), 6.85 (s, 1H), 6.50 (dd, 1H), 4.84-4.46 (m, 4H), 4.02-3.90 (m, 1H), 3.88 (m, 1H), 3.60-3.33 (m, 2H), 3.25-

3.15 (m, 6H), 2.89-2.84 (m, 1H), 2.83 (s, 2H), 2.32-2.23 (m, 12H), 1.99 (s, 2H), 1.41 (t, 2H), 0.96 (s, 6H).

Example 427

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-indazol-4-yloxy)benzamide The title compound was prepared by substituting EXAMPLE 387B for EXAMPLE 1F and EXAMPLE 400E for EXAMPLE 26C in EXAMPLE 177. $^1$H NMR (500 MHz, dimethylsulfoxide-d$_6$) δ 13.09 (s, 1H), 8.27 (d, 1H), 7.85 (d, 1H), 7.80 (s, 1H), 7.59 (d, 1H), 7.36 (d, 2H), 7.03-7.10 (m, 4H), 6.79 (dd, 1H), 6.52 (d, 1H), 6.13 (d, 1H), 4.27 (d, 2H), 3.88 (dd, 2H), 3.19 (br s, 4H), 2.91 (br s, 2H), 2.36-2.40 (br, 3H), 2.18 (m, 2H), 2.05 (m, 1H), 1.98 (s, 2H), 1.64-1.68 (m, 2H), 1.34-1.43 (m, 4H), 1.11-1.21 (m, 4H), 0.94 (s, 6H).

Example 428

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(cyanomethyl)pyrrolidin-3-yl]amino}-3-nitrophenyl)sulfonyl]benzamide

Example 428A

8-{4-[2-(4-chlorophenyl)-4,4-dimethylcyclohex-1-enylmethyl]piperazin-1-yl}-6-oxa-2, 11a-diaza-dibenzo[c,d,g]azulen-11-one A solution of EXAMPLE 403G (4.5 g) in anhydrous dichloromethane (100 mL) was cooled in an ice bath and catalytic N,N-dimethylformamide was added. This was followed by the dropwise addition of a solution of oxalyl dichloride (1.231 mL) in anhydrous methylene chloride (5 mL). The ice bath was removed and the reaction stirred for 1 hour while warming to ambient temperature. The reaction was quenched by the addition of ice (150 mL) and saturated sodium bicarbonate solution (100 mL). The mixture was further diluted with saturated sodium bicarbonate solution (200 mL) and methylene chloride (200 mL). The organic layer was purified on silica gel, and was eluted with a 0, 10, 25, and 100% ethyl acetate in methylene chloride step gradient to provide the title compound.

Example 428B (R)-tert-butyl 3-(2-nitro-4-sulfamoylphenylamino)pyrrolidine-1-carboxylate To a solution of (R)-tert-butyl 3-aminopyrrolidine-1-carboxylate (1.0 g), tetrahydrofuran (50 ml), N-ethyl-N-isopropylpropan-2-amine (5.61 mL) and N,N-dimethylformamide (10 mL) was added 4-fluoro-3-nitrobenzenesulfonamide (1.212 g) and the mixture was stirred for 18 hours. The crude product was isolated by concentration and was the material was purified on silica gel, and was eluted with a 30, 50, and 75% ethyl acetate in hexane step gradient to provide the title compound.

Example 428C (R)-3-nitro-4-(pyrrolidin-3-ylamino)benzenesulfonamide

A suspension of EXAMPLE 428B (2.018 g) in anhydrous dichloromethane (25 mL) was cooled in an ice bath and 2,2,2-trifluoroacetic acid (20 mL) was added. After stirring 15 minutes, the ice bath was removed and the reaction was allowed to come to ambient temperature over 2 hours. The reaction mixture was concentrated and the residue was dissolved in water and basified with aqueous sodium carbonate solution. The mixture was extracted repeatedly with 10% methanol in methylene chloride and the organics were concentrated to provide the title compound.

Example 428D (R)-4-(1-(cyanomethyl)pyrrolidin-3-ylamino)-3-nitrobenzenesulfonamide To a solution of EXAMPLE 428C (440 mg) in anhydrous N,N-dimethylformamide (10 mL) was added sodium carbonate (132 mg). To the resulting suspension was added 2-bromoacetonitrile (0.077 mL) and the mixture was heated at 60° C. for 18 hours. The crude material was isolated by concentration and was purified on silica gel, and was eluted with a 0.5, 2.5, and 5% methanol in methylene chloride step gradient to provide the title compound.

Example 428E 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(cyanomethyl)pyrrolidin-3-yl]amino}-3-nitrophenyl)sulfonyl]benzamide To a solution of EXAMPLE 428D (82.6 mg) in tetrahydrofuran (7 mL) was added 2,3,4,6,7,8,9,10-octahydropyrimido[1,2-a]azepine (0.063 mL). This mixture was stirred at ambient temperature for 45 minutes and a solution of EXAMPLE 428A (117 mg) in tetrahydrofuran (3 mL) was added. After stirring 18 hours, the crude product was isolated by concentration and was purified by reverse phase chromatography with ammonium acetate buffer in acetonitrile to give the title compound. $^1$H NMR (400 MHz, pyridine-d$_5$) δ 9.27 (d, 1H), 8.59 (s, 1H), 8.55 (d, 1H), 8.40 (dd, 1H), 7.99 (d, 1H), 7.54 (m, 1H), 7.43 (d, 2H), 7.25 (m, 1H), 7.16 (m, 1H), 7.07 (d, 2H), 6.86 (d, 1H), 6.69 (m, 2H), 5.73 (m, 2H), 4.15 (m, 1H), 3.90 (s, 2H), 3.03 (m, 4H), 2.96-287. (m, 2H), 2.81-2.76 (m. 3H), 2.58 (m, 1H), 2.32-2.23 (m, 3H), 2.14 (m, 4H), 1.97 (s, 2H), 1.73 (m, 1H), 1.38 (t, 2H), 0.94 (s, 6H).

Example 429

2-(1H-benzimidazol-4-yloxy)-4-(4-{[2-(4-chlorophenyl)-4,4-dimethylcyclohex-1-en-1-yl]methyl}piperazin-1-yl)-N-{[4-({(3R)-1-[2-(2-methoxyethoxy)ethyl]pyrrolidin-3-yl}amino)-3-nitrophenyl]sulfonyl}benzamide

Example 429A (R)-4-(1-(2-(2-methoxyethoxy)ethyl)pyrrolidin-3-ylamino)-3-nitrobenzenesulfonamide The title compound was prepared by substituting 1-bromo-2-(2-methoxyethoxy)ethane for 2-bromoacetonitrile in EXAMPLE 428D.

Example 429B 2-(1H-benzimidazol-4-yloxy)-4-(4-{[2-(4-chlorophenyl)-4,4-dimethylcyclohex-1-en-1-yl]methyl}piperazin-1-yl)-N-{[4-({(3R)-1-[2-(2-methoxyethoxy)ethyl]pyrrolidin-3-yl}amino)-3-nitrophenyl]sulfonyl}benzamide The title compound was prepared by substituting EXAMPLE 429A for EXAMPLE 428D in EXAMPLE 428E. $^1$H NMR (400 MHz, pyridine-$d_5$) δ 9.26 (d, 1H), 8.58 (m, 2H), 8.38 (dd, 1H), 8.01 (d, 1H), 7.53 (d, 1H), 7.43 (d, 2H), 7.25 (d, 1H), 7.16 (d, 1H), 7.07 (d, 2H), 6.85 (d, 1H), 6.71-6.69 (m, 2H), 5.33 (m, 2H), 4.05 (m, 1H), 3.63 (m, 4H), 3.54 (m, 2H), 3.29 (s, 3H), 3.03 (m, 4H), 2.86 (m, 1H), 2.77 (m, 4H), 2.70 (t, 2H), 2.38 (m, 1H), 2.27-2.18 (m, 3H), 2.14 (m, 4H), 1.97 (s, 2H), 1.64 (m, 1H), 1.38 (t, 2H), 0.94 (s, 6H).

Example 430

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(N,N-dimethylglycyl)pyrrolidin-3-yl]amino}-3-nitrophenyl)sulfonyl]benzamide

Example 430A

R)-4-(1-(2-(dimethylamino)acetyl)pyrrolidin-3-ylamino)-3-nitrobenzenesulfonamide The title compound was prepared by substituting 2-(dimethylamino)acetyl chloride for 2-bromoacetonitrile in EXAMPLE 428D.

Example 430B 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(3R)-1-(N,N-dimethylglycyl)pyrrolidin-3-yl]amino}-3-nitrophenyl)sulfonyl]benzamide The title compound was prepared by substituting EXAMPLE 430A for EXAMPLE 428D in EXAMPLE 428E. $^1$H NMR (400 MHz, pyridine-$d_5$) δ 9.25 (m, 1H), 8.59 (d, 1H), 8.47-8.35 (m, 2H), 8.01 (d, 1H), 7.54 (d, 1H), 7.44 (d, 2H), 7.25-7.20 (m, 2H), 7.16-6.92 (m, 4H), 6.71 (m, 2H), 5.55 (m, 1H), 4.34-4.18 (m, 1H), 4.03 (m, 1H), 3.84-3.63 (m, 3H), 3.44-3.34 (m, 2H), 3.03 (m, 4H), 2.77 (s, 2H), 2.43 (m, 6H), 2.25 (m, 3H), 2.14 (m, 4H), 2.03-1.83 (m, 3H), 1.38 (t, 2H), 0.94 (s, 6H).

Example 431

2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(cyanomethyl)morpholin-2-yl]methyl}amino)-3-nitrophenyl]sulfonyl}benzamide

Example 431A 4-((4-(cyanomethyl)morpholin-2-yl)methylamino)-3-nitrobenzenesulfonamide This EXAMPLE was prepared by substituting 2-bromoacetonitrile for 2, 2-difluoroethyl iodide in EXAMPLE 415C at ambient temperature.

Example 431B 2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(cyanomethyl)morpholin-2-yl]methyl}amino)-3-nitrophenyl]sulfonyl}benzamide This EXAMPLE was prepared by substituting EXAMPLE 431A for EXAMPLE 428D in EXAMPLE 428E. $^1$H NMR (500 MHz, pyridine-$d_5$) δ 9.25 (d, 1H), 8.87 (t, 1H), 8.58 (s, 1H), 8.38 (dd, 1H), 8.00 (d, 1H), 7.53 (d, 1H), 7.43 (d, 2H), 7.25 (m, 2H), 7.16 (d, 1H), 7.07 (d, 2H), 6.97 (d, 1H), 6.73-6.68 (m, 2H), 3.96-3.85 (m, 2H), 3.78 (s, 2H), 3.66 (dt, 1H), 3.53-3.42 (m, 2H), 3.03 (m, 4H), 2.90 (d, 1H), 2.76 (s, 2H), 2.61 (d, 1H), 2.51 (dt, 1H), 2.40 (t, 1H), 2.25 (m, 2H), 2.14 (m, 4H), 1.97 (s, 2H), 1.38 (t, 2H), 0.94 (s, 6H).

Example 432

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]benzamide

Example 432A 4-((4-cyclopropylmorpholin-2-yl)methylamino)-3-nitrobenzenesulfonamide A solution of EXAMPLE 415B (0.633 g) and (1-ethoxycyclopropoxy)trimethylsilane (1.601 ml) in anhydrous methanol (15 mL) and acetic acid (1.7 ml) was refluxed for 30 minutes and allowed to cool to room temperature. Sodium cyanoborohydride (0.377 g) was then added and the mixture was stirred at ambient temperature overnight. The reaction mixture was concentrated to dryness. The residue was mixed with 5% aqueous $Na_2CO_3$ solution (25 mL) and extracted with ethyl acetate. The crude product was purified on a silica gel column eluting with 5% and 10% methanol in dichloromethane to provide the title compound.

Example 432B 2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]benzamide This EXAMPLE was prepared by substituting EXAMPLE 432A for EXAMPLE 428D in EXAMPLE 428E. $^1$H NMR (500 MHz, pyridine-$d_5$) δ 9.25 (d, 1H), 8.89 (t, 1H), 8.57 (s, 1H), 8.38 (dd, 1H), 8.00 (d, 1H), 7.53 (d, 1H), 7.43 (d, 2H), 7.25 (m, 2H), 7.16 (d, 1H), 7.07 (d, 2H), 6.98 (d, 1H), 6.73-6.68 (m, 2H), 3.90-3.83 (m, 2H), 3.60 (dt, 1H), 3.55-3.41 (m, 2H), 3.03 (m, 4H), 2.96 (d, 1H), 2.76 (s, 2H), 2.69 (d, 1H), 2.35 (dt, 1H), 2.26-2.20 (m, 3H), 2.14 (m, 4H), 1.97 (s, 2H), 1.59 (m, 1H), 1.38 (t, 2H), 0.94 (s, 6H), 0.47-0.37 (m, 4H).

Example 433

2-(1H-benzimidazol-4-yloxy)-4-(4-{[2-(4-chlorophenyl)-4,4-dimethylcyclohex-1-en-1-yl]methyl}piperazin-1-yl)-N-[(3-nitro-4-{[(4-oxetan-3-ylmorpholin-2-yl)methyl]amino}phenyl)sulfonyl]benzamide Example 433A 3-nitro-4-((4-(oxetan-3-yl)morpholin-2-yl)methylamino)benzenesulfonamide This EXAMPLE was prepared by substituting oxetan-3-one for (1-ethoxycyclopropoxy)-trimethylsilane in EXAMPLE 432A.

Example 433B 2-(1H-benzimidazol-4-yloxy)-4-(4-{[2-(4-chlorophenyl)-4,4-dimethylcyclohex-1-en-1-yl]methyl}piperazin-1-yl)-N-[(3-nitro-4-{[(4-oxetan-3-ylmorpholin-2-yl)methyl]amino}phenyl)sulfonyl]benzamide This EXAMPLE was prepared by substituting EXAMPLE 433A for EXAMPLE 428D in EXAMPLE 428E. $^1$H NMR (500 MHz, pyridine-$d_5$) δ 9.25 (d, 1H), 8.87 (t, 1H), 8.57 (s, 1H), 8.38 (dd, 1H), 8.02 (d, 1H), 7.53 (d, 1H), 7.44 (d, 2H), 7.24 (m, 2H), 7.13 (d, 1H), 7.07 (d, 2H), 6.98 (d, 1H), 6.73-6.68 (m, 2H), 4.69-4.62 (m, 4H), 3.98-3.88 (m, 2H), 3.69 (dt, 1H), 3.55-3.35 (m, 3H), 3.03 (m, 4H), 2.77 (s, 2H), 2.74 (d, 1H), 2.44 (d, 1H), 2.25 (m, 2H), 2.14 (m, 4H), 1.97 (s, 2H), 1.94 (m, 1H), 1.87 (t, 1H), 1.38 (t, 2H), 0.94 (s, 6H).

Example 434

N-{[5-chloro-6-({(3R)-1-[2-fluoro-1-(fluoromethyl)ethyl]pyrrolidin-3-yl}oxy)pyridin-3-yl]sulfonyl}-4-(4-{[2-(4-chlorophenyl)-4,4-dimethylcyclohex-1-en-1-yl]methyl}piperazin-1-yl)-2-(1H-indazol-4-yloxy)benzamide Example 434A (R)-5-chloro-6-(1-(1,3-difluoropropan-2-yl)pyrrolidin-3-yloxy)pyridine-3-sulfonamide EXAMPLE 422B (278 mg) and 1,3-difluoropropan-2-one (94 mg) were suspended in dichloroethane (10 ml). N,N-dimethylformamide (1.5 mL) was added drop wise until a white milky suspension formed. The reaction mixture was stirred at room temperature for 15 minutes followed by the addition of sodium triacetoxyborohydride (424 mg). The reaction mixture was stirred at room temperature overnight. The solvent was removed under vacuum, and the crude material was purified with 2.5-5% methanol/dichloromethane to afford the title compound.

Example 434B

N-{[5-chloro-6-({(3R)-1-[2-fluoro-1-(fluoromethyl)ethyl]pyrrolidin-3-yl}oxy)pyridin-3-yl]sulfonyl}-4-(4-{[2-(4-chlorophenyl)-4,4-dimethylcyclohex-1-en-1-yl]methyl}piperazin-1-yl)-2-(1H-indazol-4-yloxy)benzamide The title compound was prepared by substituting EXAMPLE 400E for EXAMPLE 26C and EXAMPLE 434A for EXAMPLE 1F in EXAMPLE 177. $^1$H NMR (400 MHz, dimethylsulfoxide-$d_6$) δ 12.96 (s, 1H), 8.16 (d, 1H), 7.79 (m, 1H), 7.69 (m, 2H), 7.35 (d, 2H), 7.05 (m, 4H), 6.72 (m, 1H), 6.39 (d, 1H), 6.09 (dd, 3.05 Hz, 1H), 5.37 (m, 1H), 4.66 (t, 2H), 4.54 (t, 2H), 2.91 (m, 12H), 2.23 (m, 7H), 1.97 (s, 2H), 1.82 (m, 1H), 1.40 (t, 2H), 0.93 (s, 6H).

Example 435

4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-indazol-4-yloxy)benzamide Example 435A (R)-1-(1,3-difluoropropan-2-yl)pyrrolidin-3-amine To a solution of (R)-tert-butyl pyrrolidin-3-ylcarbamate (0.500 g) and 1,3-difluoropropan-2-one (0.278 g) in dichloromethane (5 mL) was added sodium triacetoxyborohydride (0.853 g). After stirring for one hour, the reaction was quenched with saturated aqueous NaHCO$_3$ solution (5 mL). The mixture was extracted with dichloromethane (25 mL), and the organic layer was dried over anhydrous magnesium sulfate, filtered, and concentrated. The resulting residue was treated with HCl (4.0M in 1,4-dioxane, 4 mL) and methanol (1 mL) and stirred for one hour. The mixture was concentrated to give the title compound.

Example 435B (R)-4-(1-(1,3-difluoropropan-2-yl)pyrrolidin-3-ylamino)-3-nitrobenzenesulfonamide To 4-fluoro-3-nitrobenzenesulfonamide (0.272 g) and EXAMPLE 435A (0.195 g) in tetrahydrofuran (3.0 mL) was added N-ethyl-N-isopropylpropan-2-amine (0.512 mL) and the reaction stirred at room temperature. After stirring for six hours, the reaction was concentrated, loaded onto silica gel (Reveleris 40 g) and the product eluted using a gradient of 25-100% ethyl acetate/hexanes over 30 minutes to give the title compound.

Example 435C

4-{4-[2-(4-Chloro-phenyl)-4,4-dimethyl-cyclohex-1-enylmethyl]-piperazin-1-yl}-2-[1-(2-trimethylsilanyl-ethoxymethyl)-1H-indazol-4-yloxy]-benzoic acid methyl ester EXAMPLE 400D (1000 mg) was dissolved in N,N-dimethylformamide (12 mL) and sodium hydride (60% in mineral oil, 45 mg) was added. The solution was stirred at room temperature for 15 minutes, 2-(trimethylsilyl)ethoxymethyl chloride (299 mg) was added, and the solution was stirred at room temperature for 45 minutes. The solution was added to water and extracted with ethyl acetate. The extract was washed with brine, dried on anhydrous sodium sulfate, filtered, concentrated and purified by flash column chromatography on silica gel using 30-50% ethyl acetate in hexanes.

Example 435D

4-{4-[2-(4-Chloro-phenyl)-4,4-dimethyl-cyclohex-1-enylmethyl]-piperazin-1-yl}-2-[1-(2-trimethylsilanyl-ethoxymethyl)-1H-indazol-4-yloxy]-benzoic acid This example was prepared by substituting EXAMPLE 435C for EXAMPLE 1D in EXAMPLE 1E.

Example 435E

N-{4-{4-[2-(4-Chloro-phenyl)-4,4-dimethyl-cyclohex-1-enylmethyl]-piperazin-1-yl}-2-[1-(2-trimethylsilanyl-ethoxymethyl)-1H-indazol-4-yloxy]-benzoyl}-4-[(R)-1-(2-fluoro-1-fluoromethyl-ethyl)-pyrrolidin-3-ylamino]-3-nitro-benzenesulfonamide This example was prepared by substituting EXAMPLE 435D for EXAMPLE 1E and EXAMPLE 435B for EXAMPLE 1F in EXAMPLE 1G.

Example 435F 4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-indazol-4-yloxy)benzamide EXAMPLE 435E (103 mg) was dissolved in trifluoroacetic acid (1.8 mL) and water (0.2 mL) and stirred at room temperature for 90 minutes. The solvents were removed under vacuum, the residue dissolved in 1,4-dioxane (2 mL) and treated with 1M sodium hydroxide (1 mL), and the solution stirred at room temperature for 30 minutes. The solution was added to a saturated aqueous sodium bicarbonate solution and extracted with dichloromethane. The extract was washed with brine, dried on anhydrous sodium sulfate, filtered, and the solvent removed under vacuum. $^1$H NMR (300 MHz, dimethylsulfoxide-$d_6$) δ 13.09 (bs, 1H), 8.37 (m, 2H), 7.84 (d, 1H), 7.58-7.45 (m, 2H), 7.36 (d, 2H), 7.17-7.03 (m, 4H), 6.95 (dd, 1H), 6.84-6.76 (m, 1H), 6.53 (dd, 1H), 6.17 (t, 1H), 4.72 (d, 2H), 4.56 (d, 2H), 4.23 (m, 1H), 3.17 (m, 4H), 3.12-3.03 (m, 2H), 3.02-2.91 (m, 2H), 2.86-2.73 (m, 4H), 2.40-2.14 (m, 6H), 1.97 (bs, 2H), 1.70 (m, 1H), 1.40 (t, 2H), 0.94 (s, 6H).

Example 436

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(1H-indazol-4-yloxy)benzamide

Example 436A 4-(1-cyclopropyl-piperidin-4-ylamino)-3-nitro-benzenesulfonamide This example was prepared by substituting 1-cyclopropyl-piperidin-4-ylamine for 1-(2-methoxy-ethyl)-piperidin-4-ylamine in EXAMPLE 189A.

Example 436B

N-{4-{4-[2-(4-chlorophenyl)-4,4-dimethyl-cyclohex-1-enylmethyl]-piperazin-1-yl}-2-[1-(2-trimethylsilanyl-ethoxymethyl)-1H-indazol-4-yloxy]-benzoyl}-4-(1-cyclopropyl-piperidin-4-ylamino)-3-nitro-benzenesulfonamide This example was prepared by substituting EXAMPLE 435D for EXAMPLE 1E and EXAMPLE 436A for EXAMPLE 1F in EXAMPLE 1G.

Example 436C 4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(1H-indazol-4-yloxy)benzamide This example was prepared by substituting EXAMPLE 436B for EXAMPLE 435E in EXAMPLE 435F. $^1$H NMR (300 MHz, dimethylsulfoxide-$d_6$) δ 13.05 (bs, 1H), 8.35 (d, 1H), 8.17 (d, 1H), 7.77 (bs, 1H), 7.57 (td, 2H), 7.35 (d, 2H), 7.09-7.03 (m, 4H), 6.98 (d, 1H), 6.77 (dd, 1H), 6.48 (bs, 1H), 6.17 (m, 1H), 3.66 (m, 1H), 3.12 (bs, 4H), 2.92 (m, 2H), 2.76 (bs, 2H), 2.21 (m, 8H), 1.97 (bs, 2H), 1.94 (m, 2H), 1.73 (m, 1H), 1.55 (m, 2H), 1.40 (t, 2H), 0.93 (s, 6H), 0.46 (d, 2H), 0.35 (bs, 2H).

Example 437

2-(1H-benzimidazol-4-yloxy)-4-(4-{[2-(4-chlorophenyl)-4,4-dimethylcyclohex-1-en-1-yl]methyl}piperazin-1-yl)-N-{[4-({[(2R)-4-(N,N-dimethylglycyl)morpholin-2-yl]methyl}amino)-3-nitrophenyl]sulfonyl}benzamide

Example 437A (R)-tert-butyl 2-((2-nitro-4-sulfamoylphenylamino)methyl)morpholine-4-carboxylate This example was prepared by substituting (R)-tert-butyl 2-(aminomethyl)morpholine-4-carboxylate for (tetrahydropyran-4-yl)methylamine in EXAMPLE 1F.

Example 437B (S)-4-(morpholin-2-ylmethylamino)-3-nitrobenzene-sulfonamide

This example was prepared by substituting EXAMPLE 437A for EXAMPLE 415A in EXAMPLE 415B.

Example 437C (R)-4-((4-(2-(dimethylamino)acetyl)morpholin-2-yl) methylamino)-3-nitrobenzenesulfonamide This example was prepared by substituting EXAMPLE 437B for EXAMPLE 423B in EXAMPLE 423C.

Example 437D 2-(1H-benzimidazol-4-yloxy)-4-(4-{[2-(4-chlorophenyl)-4,4-dimethylcyclohex-1-en-1-yl] methyl}piperazin-1-yl)-N-{[4-({[(2R)-4-(N,N-dimethylglycyl)morpholin-2-yl]methyl}amino)-3-nitrophenyl]sulfonyl}benzamide This example was prepared by substituting EXAMPLE 437C for EXAMPLE 428D in EXAMPLE 428E. $^1$H NMR (500 MHz, pyridine-$d_5$) δ 9.25 (s, 1H), 8.86 (t, 1H), 8.57 (s, 1H), 8.38 (t, 1H), 8.02 (d, 1H), 7.53 (d, 1H), 7.44 (d, 2H), 7.24 (m, 2H), 7.13 (d, 1H), 7.07 (d, 2H), 6.97 (dd, 1H), 6.73-6.68 (m, 2H), 4.75, 4.50 (dd, 1H), 4.33, 4.02 (dd, 1H), 3.93 (m, 1H), 3.85-3.70 (m, 1H), 3.65-3.40 (m, 3H), 3.33 (dd, 1H), 3.25-3.10 (m, 2H), 3.03 (m, 4H), 2.90 (m, 1H), 2.77 (s, 2H), 2.27-2.25 (m, 8H), 2.14 (m, 4H), 1.97 (s, 2H), 1.38 (t, 2H), 0.94 (s, 6H).

Example 438

2-(1H-benzimidazol-4-yloxy)-4-(4-{[2-(4-chlorophenyl)-4,4-dimethylcyclohex-1-en-1-yl] methyl}piperazin-1-yl)-N-{[4-({[(2S)-4-(N,N-dimethylglycyl)morpholin-2-yl]methyl}amino)-3-nitrophenyl]sulfonyl}benzamide

Example 438A (S)-tert-butyl 2-((2-nitro-4-sulfamoylphenylamino) methyl)morpholine-4-carboxylate This example was prepared by substituting (S)-tert-butyl 2-(aminomethyl)morpholine-4-carboxylate for (tetrahydropyran-4-yl)methylamine in EXAMPLE 1F.

Example 438B (R)-4-(morpholin-2-ylmethylamino)-3-nitrobenzene-sulfonamide

This example was prepared by substituting EXAMPLE 438A for EXAMPLE 415A in EXAMPLE 415B.

Example 438C (S)-4-((4-(2-(dimethylamino)acetyl)morpholin-2-yl) methylamino)-3-nitrobenzenesulfonamide This example was prepared by substituting EXAMPLE 438B for EXAMPLE 423B in EXAMPLE 423C.

Example 438D 2-(1H-benzimidazol-4-yloxy)-4-(4-{[2-(4-chlorophenyl)-4,4-dimethylcyclohex-1-en-1-yl] methyl}piperazin-1-yl)-N-{[4-({[(2S)-4-(N,N-dimethylglycyl)morpholin-2-yl]methyl}amino)-3-nitrophenyl]sulfonyl}benzamide This example was prepared by substituting EXAMPLE 438C for EXAMPLE 428D in EXAMPLE 428E. $^1$H NMR (500 MHz, pyridine-$d_5$) δ 9.25 (s, 1H), 8.86 (t, 1H), 8.57 (s, 1H), 8.38 (t, 1H), 8.02 (d, 1H), 7.53 (d, 1H), 7.44 (d, 2H), 7.24 (m, 2H), 7.13 (d, 1H), 7.07 (d, 2H), 6.97 (dd, 1H), 6.73-6.68 (m, 2H), 4.75, 4.50 (dd, 1H), 4.33, 4.02 (dd, 1H), 3.93 (m, 1H), 3.85-3.70 (m, 1H), 3.65-3.40 (m, 3H), 3.33 (dd, 1H), 3.25-3.10 (m, 2H), 3.03 (m, 4H), 2.90 (m, 1H), 2.77 (s, 2H), 2.27-2.25 (m, 8H), 2.14 (m, 4H), 1.97 (s, 2H), 1.38 (t, 2H), 0.94 (s, 6H).

Example 439

2-(1H-benzimidazol-4-yloxy)-4-(4-{[2-(4-chlorophenyl)-4,4-dimethylcyclohex-1-en-1-yl] methyl}piperazin-1-yl)-N-({3-nitro-4-[(tetrahydrofuran-3-ylmethyl)amino]phenyl}sulfonyl)benzamide

Example 439A 3-nitro-4-((tetrahydrofuran-3-yl)methylamino)benzenesulfonamide This example was prepared by substituting (tetrahydrofuran-3-yl)methylamine for (tetrahydropyran-4-yl)methylamine in EXAMPLE 1F.

Example 439B 2-(1H-benzimidazol-4-yloxy)-4-(4-{[2-(4-chlorophenyl)-4,4-dimethylcyclohex-1-en-1-yl] methyl}piperazin-1-yl)-N-({3-nitro-4-[(tetrahydrofuran-3-ylmethyl)amino]phenyl}sulfonyl)benzamide This example was prepared by substituting EXAMPLE 439A for EXAMPLE 428D in EXAMPLE 428E. $^1$H NMR (500 MHz, pyridine-$d_5$) δ 9.26 (d, 1H), 8.70 (t, 1H), 8.57 (s, 1H), 8.40 (dd, 1H), 8.01 (d, 1H), 7.51 (d, 1H), 7.44 (d, 2H), 7.24 (m, 2H), 7.14 (d, 1H), 7.07 (d, 2H), 6.89 (d, 1H), 6.73-6.68 (m, 2H), 3.93-3.89 (m, 1H), 3.83 (dd, 1H), 3.83-3.68 (m, 2H), 3.33-3.23 (m, 2H), 3.03 (m, 4H), 2.77 (s, 2H), 2.55-2.50 (m, 1H), 2.25 (m, 2H), 2.14 (m, 4H), 2.00-1.93 (m, 3H), 1.65-1.58 (m, 1H), 1.38 (t, 2H), 0.94 (s, 6H).

Example 440

Trans-2-(1H-benzimidazol-4-yloxy)-4-(4-{[2-(4-chlorophenyl)-4,4-dimethylcyclohex-1-en-1-yl] methyl}piperazin-1-yl)-N-[(4-{[(4-methoxycyclohexyl)methyl]amino}-3-nitrophenyl)sulfonyl] benzamide This example was prepared by substituting EXAMPLE 311B for EXAMPLE 428D in EXAMPLE 428E. $^1$H NMR (500 MHz, pyridine-$d_5$) δ 9.29 (d, 1H), 8.67 (t, 1H), 8.59 (s, 1H), 8.41 (dd, 1H), 7.99 (d, 1H), 7.52 (d, 1H), 7.43 (d, 2H), 7.24 (m, 1H), 7.17 (m, 1H), 7.07 (d, 2H), 6.90 (d, 1H), 6.72-6.68 (m, 2H), 5.97 (m, 2H), 3.29 (s, 3H), 3.14 (t, 2H), 3.02 (m, 5H), 2.76 (s, 2H), 2.25 (m, 2H), 2.13 (m, 4H), 2.07

(m, 2H), 1.97 (s, 2H), 1.82 (m, 2H), 1.57 (m, 1H), 1.38 (t, 2H), 1.22 (m, 2H), 1.01 (m, 2H), 0.94 (s, 6H).

Example 441

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]benzamide This example was prepared by substituting EXAMPLE 409D for EXAMPLE 428D in EXAMPLE 428E. $^1$H NMR (500 MHz, pyridine-$d_5$) δ 9.27 (d, 1H), 8.84 (t, 1H), 8.57 (s, 1H), 8.41 (dd, 1H), 7.99 (d, 1H), 7.52 (d, 1H), 7.43 (d, 2H), 7.23 (m, 1H), 7.15 (m, 1H), 7.14-7.02 (m, 3H), 6.70 (m, 2H), 6.49 (m, 2H), 3.86 (m, 2H), 3.76-3.69 (m, 3H), 3.65 (d, 1H), 3.03 (m, 4H), 2.76 (s, 2H), 2.25 (m, 2H), 2.14 (m, 4H), 1.97 (s, 2H), 1.92-1.76 (m, 4H), 1.38 (t, 2H), 0.94 (s, 6H).

Example 442

2-(1H-benzimidazol-4-yloxy)-4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)benzamide This example was prepared by substituting EXAMPLE 416D for EXAMPLE 428D in EXAMPLE 428E. $^1$H NMR (500 MHz, pyridine-$d_5$) δ 9.02 (d, 1H), 8.59 (s, 1H), 8.35 (m, 1H), 8.01 (d, 1H), 7.51 (d, 1H), 7.44 (d, 2H), 7.22 (m, 2H), 7.12 (d, 1H), 7.07 (d, 2H), 6.84 (m, 1H), 6.73 (m, 2H), 4.59 (s, 1H), 4.54 (s, 1H), 3.89-3.74 (m, 4H), 3.05 (m, 4H), 2.78 (s, 2H), 2.26 (m, 2H), 2.16 (m, 4H), 2.02-1.81 (m, 6H), 1.39 (t, 2H), 0.94 (s, 6H).

Example 443

2-(1H-benzimidazol-4-yloxy)-N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)benzamide This example was prepared by substituting EXAMPLE 404A for EXAMPLE 428D in EXAMPLE 428E. $^1$H NMR (500 MHz, pyridine-$d_5$) δ 9.12 (d, 1H), 8.68 (d, 1H), 8.59 (s, 1H), 7.99 (d, 1H), 7.52 (d, 1H), 7.44 (d, 2H), 7.24 (d, 1H), 7.15 (d, 1H), 7.07 (d, 2H), 6.73-6.69 (m, 3H), 6.56 (m, 1H), 4.56 (s, 1H), 4.51 (s, 1H), 3.91-3.76 (m, 4H), 3.04 (m, 4H), 2.77 (s, 2H), 2.26 (m, 2H), 2.15 (m, 4H), 1.99-1.85 (m, 6H), 1.39 (t, 2H), 0.94 (s, 6H).

Example 444

N-{[5-chloro-6-({(3R)-1-[2-fluoro-1-(fluoromethyl)ethyl]pyrrolidin-3-yl}methoxy)pyridin-3-yl]sulfonyl}-4-(4-{[2-(4-chlorophenyl)-4,4-dimethylcyclohex-1-en-1-yl]methyl}piperazin-1-yl)-2-(1H-indazol-4-yloxy)benzamide

Example 444A (R)-5-chloro-6-((1-(1,3-difluoropropan-2-yl)pyrrolidin-3-yl)methoxy)pyridine-3-sulfonamide This example was prepared by substituting EXAMPLE 445B for EXAMPLE 422B in EXAMPLE 434A.

Example 444B

N-{[5-chloro-6-({(3R)-1-[2-fluoro-1-(fluoromethyl)ethyl]pyrrolidin-3-yl}methoxy)pyridin-3-yl]sulfonyl}-4-(4-{[2-(4-chlorophenyl)-4,4-dimethylcyclohex-1-en-1-yl]methyl}piperazin-1-yl)-2-(1H-indazol-4-yloxy)benzamide This example was prepared by substituting EXAMPLE 400E for EXAMPLE 26C and EXAMPLE 444A for EXAMPLE 1F in EXAMPLE 177. $^1$H NMR (400 MHz, dimethylsulfoxide-$d_6$) δ 12.98 (s, 1H), 8.19 (d, 1H), 7.81 (d, 1H), 7.73 (s, 1H), 7.66 (d, 1H), 7.35 (d, 2H), 7.05 (m, 4H), 6.73 (dd, 1H), 6.42 (d, 1H), 6.10 (m, 1H), 4.64 (s, 2H), 4.54 (d, 2H), 4.24 (m, 2H), 3.07 (s, 4H), 2.89 (s, 2H), 2.74 (m, 4H), 2.56 (m, 2H), 2.20 (m, 6H), 1.98 (m, 4H), 1.54 (m, 1H), 1.40 (t, 2H), 0.91 (s, 6H).

Example 445

N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide

Example 445A (R)-tert-butyl 3-((3-chloro-5-sulfamoylpyridin-2-yloxy)methyl)pyrrolidine-1-carboxylate This example was prepared by substituting (R)-tert-butyl 3-(hydroxymethyl)pyrrolidine-1-carboxylate for (tetrahydro-2H-pyran-4-yl)methanol in EXAMPLE 387B.

Example 445B (R)-5-chloro-6-(pyrrolidin-3-ylmethoxy)pyridine-3-sulfonamide

This example was prepared by substituting EXAMPLE 445A for EXAMPLE 422A in EXAMPLE 422B.

Example 445C (R)-5-chloro-6-((1-(2,2-difluoroethyl)pyrrolidin-3-yl)methoxy)pyridine-3-sulfonamide This example was prepared by substituting EXAMPLE 445B for EXAMPLE 422B in EXAMPLE 422C.

Example 445D

N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-indazol-4-yloxy)benzamide This example was prepared by substituting EXAMPLE 400E for EXAMPLE 26C and EXAMPLE 445C for EXAMPLE 1F in EXAMPLE 177. $^1$H NMR (400 MHz, dimethylsulfoxide-$d_6$) δ 12.98 (s, 1H), 8.19 (d, 1H), 7.81 (d, 1H), 7.73 (s, 1H), 7.66 (d, 1H), 7.35 (d, 2H), 7.05 (m, 4H), 6.72 (dd, 1H), 6.41 (d, 1H), 6.10 (m, 2H), 4.23 (m, 2H), 3.07

(s, 4H), 2.82 (m, 5H), 2.62 (m, 3H), 2.24 (s, 4H), 2.17 (s, 2H), 1.94 (m, 3H), 1.53 (m, 1H), 1.40 (t, 2H), 0.93 (s, 6H).

Example 446

Trans-4-(4-{[2-(4-chlorophenyl)-4,4-dimethylcyclohex-1-en-1-yl]methyl}piperazin-1-yl)-2-(1H-indazol-4-yloxy)-N-[(4-{[(4-methoxycyclohexyl)methyl]amino}-3-nitrophenyl)sulfonyl]benzamide Example 446A 2-[1-(2-trimethylsilanyl-ethoxymethyl)-1H-indazol-4-yloxy]-4-(4-((2-(4-chlorophenyl)-4,4-dimethylcyclohex-1-enyl)methyl)piperazin-1-yl)-N-(4-((trans-4-methoxycyclohexyl)methylamino)-3-nitrophenylsulfonyl)benzamide This example was prepared by substituting EXAMPLE 435D for EXAMPLE 1E and EXAMPLE 311B for EXAMPLE 1F in EXAMPLE 1G.

Example 446B

Trans-4-(4-{[2-(4-chlorophenyl)-4,4-dimethylcyclohex-1-en-1-yl]methyl}piperazin-1-yl)-2-(1H-indazol-4-yloxy)-N-[(4-{[(4-methoxycyclohexyl)methyl]amino}-3-nitrophenyl)sulfonyl]benzamide This example was prepared by substituting EXAMPLE 446A for EXAMPLE 435E in EXAMPLE 435F. $^1$H NMR (300 MHz, dimethylsulfoxide-$d_6$) δ 13.08 (bs, 1H), 8.53 (t, 1H), 8.37 (d, 1H), 7.84 (d, 1H), 7.53 (m, 2H), 7.35 (d, 2H), 7.09 (d, 2H), 7.05 (d, 2H), 6.94 (d, 1H), 6.79 (m, 1H), 6.51 (dd, 1H), 6.18 (m, 1H), 3.23 (s, 3H), 3.17-3.00 (m, 5H), 2.78 (bs, 2H), 2.30-2.13 (m, 8H), 2.02 (m, 2H), 1.97, (bs, 2H), 1.80 (m, 2H), 1.60 (m, 1H), 1.40 (t, 2H), 1.07 (m, 4H), 0.93 (s, 6H).

Example 447

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indazol-4-yloxy)benzamide Example 447A N-{4-{4-[2-(4-Chloro-phenyl)-4,4-dimethyl-cyclohex-1-enylmethyl]-piperazin-1-yl}-2-[1-(2-trimethylsilanyl-ethoxymethyl)-1H-indazol-4-yloxy]-benzoyl}-4-([1,4]dioxan-2-ylmethoxy)-3-nitrobenzenesulfonamide This example was prepared by substituting EXAMPLE 435D for EXAMPLE 1E and EXAMPLE 297A for EXAMPLE 1F in EXAMPLE 1G.

Example 447B 4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indazol-4-yloxy)benzamide This example was prepared by substituting EXAMPLE 447A for EXAMPLE 435E in EXAMPLE 435F. $^1$H NMR (300 MHz, dimethylsulfoxide-$d_6$) δ 13.04 (bs, 1H), 8.07 (bs, 1H), 7.78 (t, 2H), 7.59 (d, 1H), 7.36 (d, 2H), 7.25 (d, 1H), 7.08 (d, 2H), 7.06 (d, 2H), 6.77 (d, 1H), 6.48 (bs, 1H), 6.15 (m, 1H), 4.20 (t, 2H), 3.92-3.76 (m, 3H), 3.65 (m, 2H), 3.48 (td, 2H), 3.14 (bs, 4H), 2.80 (m, 2H), 2.38-2.13 (m, 6H), 1.97 (bs, 2H), 1.40 (t, 2H), 0.94 (s, 6H).

Example 448

N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide Example 448A 5-chloro-6-(1-cyclopropyl-piperidin-4-ylamino)-pyridine-3-sulfonic acid amide This example was prepared by substituting 1-cyclopropyl-piperidin-4-ylamine for 1-(2-methoxy-ethyl)-piperidin-4-ylamine and EXAMPLE 387A for 4-chloro-3-nitrobenzenesulfonamide in EXAMPLE 189A.

Example 448B

5-Chloro-6-(1-cyclopropyl-piperidin-4-ylamino)-pyridine-3-sulfonic acid 4-{4-[2-(4-chloro-phenyl)-4,4-dimethyl-cyclohex-1-enylmethyl]-piperazin-1-yl}-2-[1-(2-trimethylsilanyl-ethoxymethyl)-1H-indazol-4-yloxy]-benzoylamide This example was prepared by substituting EXAMPLE 435D for EXAMPLE 1E and EXAMPLE 448A for EXAMPLE 1F in EXAMPLE 1G.

Example 448C

N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide This example was prepared by substituting EXAMPLE 448B for EXAMPLE 435E in EXAMPLE 435F. $^1$H NMR (300 MHz, dimethylsulfoxide-$d_6$) δ 13.03 (bs, 1H), 8.18 (d, 1H), 7.79 (bs, 1H), 7.65-7.58 (m, 2H), 7.36 (d, 2H), 7.33 (m, 1H), 7.10 (d, 2H), 7.06 (d, 2H), 6.74 (dd, 1H), 6.43 (bs, 1H), 6.19 (m, 1H), 3.95 (m, 1H), 3.08 (m, 4H), 2.96 (m, 2H), 2.75 (bs, 2H), 2.37-2.10 (m, 9H), 1.97 (bs, 2H), 1.78 (m, 2H), 1.56 (m, 2H), 1.40 (t, 2H), 0.93 (s, 6H), 0.42 (d, 2H), 0.33 (bs, 2H).

Example 449

2-(1H-benzimidazol-4-yloxy)-N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)benzamide Example 449A 5-chloro-6-(1-cyclopropylpiperidin-4-ylamino)pyridine-3-sulfonamide A mixture of EXAMPLE 387A (0.4 g), 1-cyclopropylpiperidin-4-amine (0.3 g) and N,N-diisopropylethylamine (0.37 mL) in dioxane (3 mL) was heated at 100° C. for 18 hours. The crude product was isolated by concentration and was purified on silica gel, which was eluted with ethyl acetate to give the title compound.

Example 449B 2-(1H-benzimidazol-4-yloxy)-N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)benzamide This example was prepared by substituting EXAMPLE 449A for EXAMPLE 428D in EXAMPLE 428E. $^1$H NMR (500 MHz, pyridine-d$_5$) δ 9.22 (m, 1H), 8.55 (s, 1H), 8.47 (s, 1H), 8.00 (d, 1H), 7.54 (d, 1H), 7.44 (d, 2H), 7.25 (m, 1H), 7.19 (m, 1H), 7.07 (d, 2H), 7.01 (m, 1H), 6.68 (m, 2H), 5.35 (m, 2H), 4.22 (m, 1H), 3.04-2.95 (m, 6H), 2.77 (s, 2H), 2.29-2.24 (m, 4H), 2.14 (m, 4H), 2.03 (m, 2H), 1.97 (s, 2H), 1.70 (m, 2H), 1.52 (m, 1H), 1.38 (t, 2H), 0.94 (s, 6H), 0.35 (m, 4H).

Example 450

2-(1H-benzimidazol-4-yloxy)-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide This example was prepared by substituting EXAMPLE 336A for EXAMPLE 428D in EXAMPLE 428E. $^1$H NMR (500 MHz, pyridine-d$_5$5) δ 9.24 (m, 1H), 8.81 (m, 1H), 8.56 (s, 1H), 8.37 (dd, 1H), 8.03 (d, 1H), 7.52 (d, 1H), 7.44 (d, 2H), 7.21 (m, 1H), 7.11 (m, 1H), 7.07 (d, 2H), 6.92 (d, 1H), 6.71 (m, 2H), 5.33 (m, 2H), 3.94 (m, 2H), 3.78 (m, 1H), 3.73-3.66 (m, 2H), 3.58 (m, 1H), 3.51-3.36 (m, 3H), 3.03 (m, 4H), 2.77 (s, 2H), 2.26 (m, 2H), 2.15 (m, 4H), 1.97 (s, 2H), 1.39 (t, 2H), 0.94 (s, 6H).

Example 451

2-(1H-benzimidazol-4-yloxy)-4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)benzamide

Example 451A 4-(1-cyclopropylpiperidin-4-ylamino)-3-nitrobenzenesulfonamide

To a solution of 4-fluoro-3-nitrobenzenesulfonamide (1.26 g) and 1-cyclopropylpiperidin-4-amine (0.802 g) in tetrahydrofuran (20 mL) was added N,N-diisopropylethylamine (2.22 g) and 4-dimethylaminopyridine (35 mg). The mixture was heated at reflux for 18 hours and upon cooling was diluted with ethyl acetate (200 mL) and aqueous NaHCO$_3$. The crude product was isolated by concentration of the organic layer and was purified on silica gel, which was eluted with 5% methanolic ammonia in methylene chloride to give the title compound.

Example 451B 2-(1H-benzimidazol-4-yloxy)-4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)benzamide This example was prepared by substituting EXAMPLE 451A for EXAMPLE 428D in EXAMPLE 428E. $^1$H NMR (500 MHz, pyridine-d$_5$) δ 9.26 (m, 1H), 8.59 (s, 1H), 8.46 (d, 1H), 8.42 (dd, 1H), 8.01 (d, 1H), 7.53 (d, 1H), 7.43 (d, 2H), 7.25 (d, 1H), 7.17 (d, 1H), 7.07 (d, 2H), 6.96 (d, 1H), 6.72-6.67 (m, 2H), 5.48 (m, 2H), 3.54 (m, 1H), 3.03 (m, 4H), 2.90 (m, 2H), 2.76 (s, 2H), 2.37 (m, 2H), 2.25 (m, 2H), 2.14 (m, 4H), 1.98-1.91 (m, 4H), 1.56 (m, 3H), 1.38 (t, 2H), 0.94 (s, 6H), 0.42 (m, 4H).

Example 452

Trans-2-(1H-benzimidazol-4-yloxy)-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide This example was prepared by substituting EXAMPLE 204A for EXAMPLE 428D in EXAMPLE 428E. $^1$H NMR (500 MHz, pyridine-d$_5$) δ 9.27 (m, 1H), 8.59 (s, 1H), 8.42 (dd, 1H), 8.36 (d, 1H), 8.01 (d, 1H), 7.53 (d, 1H), 7.43 (d, 2H), 7.25 (m, 1H), 7.17 (m, 1H), 7.07 (d, 2H), 6.95 (d, 1H), 6.71 (d, 2H), 6.33 (m, 2H), 3.76 (m, 4H), 3.40 (m, 1H), 3.03 (m, 4H), 2.76 (s, 2H), 2.52 (m, 4H), 2.25 (m, 3H), 2.14 (m, 4H), 2.07 (m, 2H), 1.97 (m, 2H), 1.89 (m, 2H), 1.42-1.21 (m, 6H), 0.94 (s, 6H).

Example 453

2-(1H-benzimidazol-4-yloxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide This example was prepared by substituting EXAMPLE 174A for EXAMPLE 428D in EXAMPLE 428E. $^1$H NMR (500 MHz, pyridine-d$_5$) δ 9.25 (m, 2H), 8.59 (s, 1H), 8.44 (m, 1H), 8.00 (d, 1H), 7.68 (d, 1H), 7.53 (d, 1H), 7.43 (d, 2H), 7.25 (m, 1H), 7.17 (m, 1H), 7.06 (d, 2H), 6.72-6.67 (m, 2H), 6.36 (m, 1H), 2.02 (m, 4H), 2.93 (m, 4H), 2.76 (s, 2H), 2.74-2.61 (m, 2H), 2.35-2.22 (m, 5H), 2.19 (s, 3H), 2.16-2.10 (m, 4H), 1.97 (m, 2H), 1.38 (t, 2H), 0.94 (s, 6H).

Example 454

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]benzamide This example was prepared by substituting EXAMPLE 88A for EXAMPLE 428D in EXAMPLE 428E. $^1$H NMR (500 MHz, pyridine-d$_5$) δ 9.28 (m, 1H), 8.66 (m, 1H), 8.58 (s, 1H), 8.40 (dd, 1H), 8.02 (d, 1H), 7.53 (d, 1H), 7.44 (d, 2H), 7.24 (m, 1H), 7.15 (m, 1H), 7.07 (d, 2H), 6.89 (d, 1H), 6.73-6.69 (m, 2H), 5.86 (m, 2H), 3.17 (t, 2H), 3.01-3.04 (m, 4H), 2.86 (m, 2H), 2.77 (s, 2H), 2.25 (m, 5H), 2.14 (m, 4H), 1.96-1.97 (s, 2H), 1.92 (m, 2H), 1.70 (m, 2H), 1.60 (m, 1H), 1.48-1.37 (m, 4H), 0.94 (s, 6H).

Example 455

2-(1H-benzimidazol-4-yloxy)-4-(4-{[2-(4-chlorophenyl)-4,4-dimethylcyclohex-1-en-1-yl]methyl}piperazin-1-yl)-N-({4-[({(2R)-4-[2-(2-methoxyethoxy)ethyl]morpholin-2-yl}methyl)amino]-3-nitrophenyl}sulfonyl)benzamide

Example 455A (R)-4-((4-(2-(2-methoxyethoxy)ethyl)morpholin-2-yl)methylamino)-3-nitrobenzenesulfonamide This example was prepared by substituting EXAMPLE 437B for EXAMPLE 415B and 2-(2-methoxyethoxy)ethyl bromide for 2,2-difluoroethyl iodide in EXAMPLE 415C.

Example 455B 2-(1H-benzimidazol-4-yloxy)-4-(4-{[2-(4-chlorophenyl)-4,4-dimethylcyclohex-1-en-1-yl]methyl}piperazin-1-yl)-N-({4-[({(2R)-4-[2-(2-methoxyethoxy)ethyl]morpholin-2-yl}methyl)amino]-3-nitrophenyl}sulfonyl)benzamide This example was prepared by substituting EXAMPLE 455A for EXAMPLE 428D in EXAMPLE 428E. $^1$H NMR (500 MHz, pyridine-$d_5$) δ 9.24 (d, 1H), 8.85 (t, 1H), 8.56 (s, 1H), 8.36 (dd, 1H), 8.03 (d, 1H), 7.51 (d, 1H), 7.44 (d, 2H), 7.24 (m, 2H), 7.12 (d, 1H), 7.07 (d, 2H), 6.91 (d, 1H), 6.73-6.68 (m, 2H), 3.93-3.86 (m, 2H), 3.72-3.61 (m, 5H), 3.53 (m, 2H), 3.48-3.40 (m, 2H), 3.28 (s, 3H), 3.03 (m, 4H), 2.95 (d, 1H), 2.77 (s, 2H), 2.70 (d, 1H), 2.69 (t, 2H), 2.27-2.10 (m, 8H), 1.97 (s, 2H), 1.38 (t, 2H), 0.94 (s, 6H).

Example 456

2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]benzamide This example was prepared by substituting EXAMPLE 412C for EXAMPLE 428D in EXAMPLE 428E. $^1$H NMR (500 MHz, pyridine-$d_5$) δ 9.29 (d, 1H), 8.73 (t, 1H), 8.58 (s, 1H), 8.42 (dd, 1H), 7.99 (d, 1H), 7.52 (d, 1H), 7.43 (d, 2H), 7.24 (m, 2H), 7.17 (d, 1H), 7.07 (d, 2H), 6.94 (d, 1H), 6.72 (d, 1H), 6.69 (dd, 1H), 3.22 (t, 2H), 3.03 (m, 4H), 2.76 (s, 2H), 2.25 (m, 2H), 2.13 (m, 6H), 1.97 (s, 2H), 1.85-1.70 (m, 5H), 1.38 (t, 2H), 1.36-1.33 (m, 2H), 0.94 (s, 6H).

Example 457

N-[(4-{[(4-acetylmorpholin-2-yl)methyl]amino}-3-nitrophenyl)sulfonyl]-2-(1H-benzimidazol-4-yloxy)-4-(4-{[2-(4-chlorophenyl)-4,4-dimethylcyclohex-1-en-1-yl]methyl}piperazin-1-yl)benzamide

Example 457A 4-((4-acetylmorpholin-2-yl)methylamino)-3-nitrobenzenesulfonamide A solution of EXAMPLE 415B (145 mg) and N-ethyl-N-isopropylpropan-2-amine (120 μl) in anhydrous dichloromethane (5 mL) and N,N-dimethylformamide (2 mL) was cooled with an ice bath and acetic anhydride (56 μl) was added dropwise. The mixture was stirred at room temperature for 3 hours and concentrated to dryness. The residue was triturated with water. The resulting solid was dried under vacuum to give the title compound.

Example 457B

N-[(4-{[(4-acetylmorpholin-2-yl)methyl]amino}-3-nitrophenyl)sulfonyl]-2-(1H-benzimidazol-4-yloxy)-4-(4-{[2-(4-chlorophenyl)-4,4-dimethylcyclohex-1-en-1-yl]methyl}piperazin-1-yl)benzamide This example was prepared by substituting EXAMPLE 457A for EXAMPLE 428D in EXAMPLE 428E. $^1$H NMR (500 MHz, pyridine-$d_5$) δ 9.24 (d, 1H), 8.83 (t, 1H), 8.56 (s, 1H), 8.38 (dd, 1H), 8.03 (d, 1H), 7.51 (d, 1H), 7.43 (d, 2H), 7.24 (m, 2H), 7.09 (d, 1H), 7.07 (d, 2H), 6.91 (dd, 1H), 6.72 (m, 2H), 3.89 (m, 1H), 3.80-3.70 (m, 1H), 3.60-3.40 (m, 4H), 3.06 (m, 1H), 3.03 (m, 4H), 2.77 (s, 2H), 2.70 (m, 1H), 2.26 (m, 2H), 2.18-2.13 (m, 5H), 2.09 (s, 3H), 1.97 (s, 2H), 1.38 (t, 2H), 0.94 (s, 6H).

Example 458

2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(methylsulfonyl)morpholin-2-yl]methyl}amino)-3-nitrophenyl]sulfonyl}benzamide

Example 458A 4-((4-(methylsulfonyl)morpholin-2-yl)methylamino)-3-nitrobenzenesulfonamide This example was prepared by substituting methanesulfonyl chloride for acetic anhydride in EXAMPLE 457A.

Example 458B 2-(1H-benzimidazol-4-yloxy)-4-(4-{[2-(4-chlorophenyl)-4,4-dimethylcyclohex-1-en-1-yl]methyl}piperazin-1-yl)-N-{[4-({[4-(methylsulfonyl)morpholin-2-yl]methyl}amino)-3-nitrophenyl]sulfonyl}benzamide This example was prepared by substituting EXAMPLE 458A for EXAMPLE 428D in EXAMPLE 428E. $^1$H NMR (500 MHz, pyridine-$d_5$) δ 9.23 (d, 1H), 8.85 (t, 1H), 8.57 (s, 1H), 8.37 (dd, 1H), 8.01 (d, 1H), 7.52 (d, 1H), 7.43 (d, 2H), 7.24 (m, 2H), 7.15 (m, 1H), 7.07 (d, 2H), 6.97 (d, 1H), 6.72 (m, 2H), 4.00-3.90 (m, 3H), 3.68-3.59 (m, 3H), 3.58-3.48 (m, 1H), 3.06-3.02 (m, 7H), 2.98-2.89 (m, 2H), 2.77 (s, 2H), 2.25 (m, 2H), 2.14 (m, 4H), 1.97 (s, 2H), 1.38 (t, 2H), 0.94 (s, 6H).

Example 459

4-(4-{[2-(4-chlorophenyl)-4,4-dimethylcyclohex-1-en-1-yl]methyl}piperazin-1-yl)-N-{[6-({4-fluoro-1-[2-fluoro-1-(fluoromethyl)ethyl]piperidin-4-yl}methoxy)-5-(trifluoromethyl)pyridin-3-yl]sulfonyl}-2-(1H-indazol-4-yloxy)benzamide

Example 459A tert-butyl 4-fluoro-4-((5-sulfamoyl-3-(trifluoromethyl)pyridin-2-yloxy)methyl)piperidine-1-carboxylate This example was prepared by substituting EXAMPLE 410E for EXAMPLE 329A and EXAMPLE 419A for (tetrahydro-2H-pyran-4-yl)methanol in EXAMPLE 329B.

Example 459B 6-((4-fluoropiperidin-4-yl)methoxy)-5-(trifluoromethyl)pyridine-3-sulfonamide This example was prepared by substituting EXAMPLE 459A for EXAMPLE 422A in EXAMPLE 422B.

Example 459C 6-((1-(1,3-difluoropropan-2-yl)-4-fluoropiperidin-4-yl)methoxy)-5-(trifluoromethyl)pyridine-3-sulfonamide This example was prepared by substituting EXAMPLE 459B for EXAMPLE 422B in EXAMPLE 434A.

Example 459D 4-(4-{[2-(4-chlorophenyl)-4,4-dimethylcyclohex-1-en-1-yl]methyl}piperazin-1-yl)-N-{[6-({4-fluoro-1-[2-fluoro-1-(fluoromethyl)ethyl]piperidin-4-yl}methoxy)-5-(trifluoromethyl)pyridin-3-yl]sulfonyl}-2-(1H-indazol-4-yloxy)benzamide This example was prepared by substituting EXAMPLE 400E for EXAMPLE 26C and EXAMPLE 459C for EXAMPLE 1F in EXAMPLE 177. $^1$H NMR (400 MHz, dimethylsulfoxide-$d_6$) δ 12.94 (d, 1H), 8.40 (d, 1H), 8.11 (d, 1H), 7.68 (m, 2H), 7.35 (d, 2H), 7.06 (d, 2H), 6.99 (d, 2H), 6.71 (dd, 1H), 6.39 (d, 1H), 6.06 (t, 1H), 4.67 (d, 2H), 4.55 (d, 2H), 4.47 (d, 2H), 3.07 (m, 5H), 2.74 (m, 6H), 2.19 (m, 6H), 1.90 (m, 6H), 1.40 (t, 2H), 0.93 (s, 6H).

Example 460

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-phenoxybenzamide The title compound was prepared as described in EXAMPLE 177 by replacing EXAMPLE 26C with EXAMPLE 18G. $^1$H NMR (400 MHz, dimethylsulfoxide-$d_6$) δ 12.87 (s, 1H), 11.60 (s, 1H), 8.58 (s, 1H), 8.47 (d, 1H), 8.11 (s, 1H), 7.81-7.91 (m, 1H), 7.76 (dd, 1H), 7.59-7.66 (m, 1H), 7.48 (d, 1H), 7.34 (d, 2H) 7.00-7.11 (m, 5H), 6.73 (dd, 1H) 6.67 (dd, 1H), 6.08 (d, 1H), 3.85 (dd, 2H), 3.20-3.30 (m, 4H), 3.04 (s, 4H), 2.77 (s, 2H), 2.17 (d, 6H), 1.96 (s, 2H), 1.81-1.92 (m, 1H), 1.55-1.66 (m, 2H), 1.39 (t, 2H), 1.17-1.32 (m, 2H), 0.93 (s, 6H).

Example 461

4-(4-{[2-(4-chlorophenyl)-4,4-dimethylcyclohex-1-en-1-yl]methyl}piperazin-1-yl)-N-{[5-chloro-6-(2-tetrahydrofuran-2-ylethoxy)pyridin-3-yl]sulfonyl}-2-(1H-indazol-4-yloxy)benzamide

Example 461A 5-chloro-6-(2-(tetrahydrofuran-2-yl)ethoxy)pyridine-3-sulfonamide This example was prepared by substituting EXAMPLE 387A for EXAMPLE 329A and 2-(tetrahydrofuran-2-yl)ethanol for (tetrahydro-2H-pyran-4-yl)methanol in EXAMPLE 329B.

Example 461B 4-(4-{[2-(4-chlorophenyl)-4,4-dimethylcyclohex-1-en-1-yl]methyl}piperazin-1-yl)-N-{[5-chloro-6-(2-tetrahydrofuran-2-ylethoxy)pyridin-3-yl]sulfonyl}-2-(1H-indazol-4-yloxy)benzamide This example was prepared by substituting EXAMPLE 461A for EXAMPLE 1F and EXAMPLE 400E for EXAMPLE 26C in EXAMPLE 177C. $^1$H NMR (500 MHz, dimethylsulfoxide-$d_6$) δ 13.08 (s, 1H), 8.27 (d, J=2.17 Hz, 1H), 7.83 (d, J=1.83 Hz, 1H), 7.80 (s, 1H), 7.58 (d, J=8.85 Hz, 1H), 7.36 (d, J=8.54 Hz, 2H), 7.03-7.10 (m, 4H), 6.79 (dd, J=9, 2.29 Hz, 1H), 6.54 (d, J=1.53 Hz, 1H), 6.13 (d, J=7.02 Hz, 1H), 4.41-4.47 (m, 2H), 3.91-3.94 (m, 1H), 3.71-3.80 (m, 1H), 3.56-3.63 (m, 2H), 3.25 (br s, 2H), 2.33 (br s, 2H), 2.16-2.18 (m, 2H), 1.92-2.01 (m, 5H), 1.80-1.86 (m, 2H), 1.47-1.53 (m, 1H), 1.42 (t, J=6.26 Hz, 2H), 0.94 (s, 6H).

Example 462

Trans-2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide

Example 462A 2-(trans-4-(aminomethyl)cyclohexyl)acetonitrile

To a solution of tert-butyl (trans-4-(cyanomethyl)cyclohexyl)methylcarbamate (500 mg) in dichloromethane (5 mL) was slowly added trifluoroacetic acid (3 mL) at 0° C. The mixture was warmed to room temperature, stirred for 1 hour. The title compound was obtained by concentration.

Example 462B 4-((trans-4-cyanocyclohexyl)methylamino)-3-nitrobenzenesulfonamide This example was prepared by substituting EXAMPLE 462A for (tetrahydropyran-4-yl)methylamine in EXAMPLE 1F.

Example 462C

Trans-2-(1H-benzimidazol-4-yloxy)-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide This example was prepared by substituting EXAMPLE 462B for EXAMPLE 428D in EXAMPLE 428E. $^1$H NMR (500 MHz, pyridine-$d_5$) δ 9.29 (d, 1H), 8.67 (t, 1H), 8.59 (s, 1H), 8.41 (dd, 1H), 7.98 (d, 1H), 7.53 (d, 1H), 7.43 (d, 2H), 7.25 (m, 1H), 7.19 (m, 1H), 7.07 (d, 2H), 6.91 (d, 1H), 6.73-6.68 (m, 2H), 5.24 (m, 2H), 3.13 (t, 2H), 3.03 (m, 4H), 2.76 (s, 2H), 2.43 (m, 1H), 2.25 (m, 2H), 2.13 (m, 4H), 1.99-1.94 (m, 4H), 1.77 (m, H), 1.59 (m, 1H), 1.46 (m, 2H), 1.38 (t, 2H), 0.99-0.90 (m, 8H).

Example 463

2-(1H-benzimidazol-4-yloxy)-N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)benzamide

Example 463A (4,4-difluorocyclohexyl)methanol

To a slurry of lithium aluminum hydride (0.24 g) in diethyl ether (15 mL) was added dropwise ethyl 4,4-difluorocyclohexanecarboxylate (1.0 g) in diethyl ether (2 mL). The reaction heated at reflux under nitrogen for 4 hours. The reaction was cooled to 0° C., followed by the careful addition of water (0.24 mL), 4N aqueous NaOH (0.24 mL), and water (0.72 mL). The reaction was diluted with diethyl ether (40 mL) and stirred with sodium sulfate for 30 minutes. The mixture was filtered though diatomaceous earth and the filtrate was concentrated to provide the title compound.

Example 463B 5-chloro-6-((4,4-difluorocyclohexyl)methoxy)pyridine-3-sulfonamide This example was prepared by substituting EXAMPLE 463A for (tetrahydro-2H-pyran-4-yl)methanol and EXAMPLE 387A for EXAMPLE 329A in EXAMPLE 329B.

Example 463C 2-(1H-benzimidazol-4-yloxy)-N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)benzamide This example was prepared by substituting EXAMPLE 463B for EXAMPLE 428D in EXAMPLE 428E. $^1$H NMR (500 MHz, pyridine-$d_5$) δ 9.15 (d, 1H), 8.69 (m, 1H), 8.59 (s, 1H), 7.99 (d, 1H), 7.53 (d, 1H), 7.44 (d, 2H), 7.24 (m, 1H), 7.16 (m, 1H), 7.07 (d, 2H), 6.70 (m, 2H), 5.45 (m, 2H), 4.22 (d, 2H), 3.04 (m, 4H), 2.77 (s, 2H), 2.26 (m, 2H), 2.16-2.08 (m, 6H), 1.97 (s, 2H), 1.86-1.68 (m, 5H), 1.47-1.36 (m, 4H), 0.94 (m, 6H).

Example 464

N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide

Example 464A 3-chloro-4-((4-fluorotetrahydro-2H-pyran-4-yl)methoxy)benzenesulfonamide This example was prepared by substituting 3,4-dichlorobenzenesulfonamide for EXAMPLE 329A and EXAMPLE 306C for (tetrahydro-2H-pyran-4-yl)methanol in EXAMPLE 329B.

Example 464B

N-(3-chloro-4-((4-fluorotetrahydro-2H-pyran-4-yl)methoxy)phenylsulfonyl)-4-(4-((2-(4-chlorophenyl)-4,4-dimethylcyclohex-1-enyl)methyl)piperazin-1-yl)-2-(1-((2-(trimethylsilyl)ethoxy)methyl)-1H-indazol-4-yloxy)benzamide This example was prepared by substituting EXAMPLE 435D for EXAMPLE 1E and EXAMPLE 464A for EXAMPLE 1F in EXAMPLE 1G.

Example 464C

N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-indazol-4-yloxy)benzamide This example was prepared by substituting EXAMPLE 464B for EXAMPLE 435E in EXAMPLE 435F. $^1$H NMR (300 MHz, dimethylsulfoxide-$d_6$) δ 13.15 (s, 1H), 11.74-11.31 (m, 1H), 7.85 (s, 1H), 7.67 (d, 1H), 7.62-7.49 (m, 2H), 7.35 (d, 2H), 7.22-7.09 (m, 3H), 7.05 (d, 2H), 6.80 (d, 1H), 6.53 (s, 1H), 6.23 (d, 1H), 4.26 (d, 2H), 3.79 (d, 2H), 3.62 (dd, 2H), 3.17 (s, 4H), 2.77 (d, 2H), 2.22 (d, 6H), 1.88 (dd, 6H), 1.40 (t, 2H), 0.94 (s, 6H).

Example 465

N-({5-chloro-6-[(4-fluorotetrahydro-2H-pyran-4-yl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)-2-(1H-indazol-4-yloxy)benzamide

Example 465A methyl 2-(1H-indazol-4-yloxy)-4-(4-((4-(4-chlorophenyl)-6,6-dimethyl-5,6-dihydro-2H-pyran-3-yl)methyl)piperazin-1-yl)benzoate This example was prepared by substituting EXAMPLE 400C for tert-butyl piperazine-1-carboxylate and EXAMPLE 145E for EXAMPLE 27C in EXAMPLE 1A.

Example 465B methyl 4-(4-((4-(4-chlorophenyl)-6,6-dimethyl-5,6-dihydro-2H-pyran-3-yl)methyl)piperazin-1-yl)-2-(1-((2-(trimethylsilyl)ethoxy)methyl)-1H-indazol-4-yloxy)benzoate This example was prepared by substituting EXAMPLE 465A for EXAMPLE 400D in EXAMPLE 435C.

Example 465C 4-(4-((4-(4-chlorophenyl)-6,6-dimethyl-5,6-dihydro-2H-pyran-3-yl)methyl)piperazin-1-yl)-2-(1-((2-(trimethylsilyl)ethoxy)methyl)-1H-indazol-4-yloxy)benzoic acid This example was prepared by substituting EXAMPLE 465B for EXAMPLE 175D in EXAMPLE 175E.

Example 465D

N-(5-chloro-6-((4-fluorotetrahydro-2H-pyran-4-yl)methoxy)pyridin-3-ylsulfonyl)-4-(4-((4-(4-chlorophenyl)-6,6-dimethyl-5,6-dihydro-2H-pyran-3-yl)methyl)piperazin-1-yl)-2-(1-((2-(trimethylsilyl)ethoxy)methyl)-1H-indazol-4-yloxy)benzamide This example was prepared by substituting EXAMPLE 465C for EXAMPLE 27G and EXAMPLE 404A for EXAMPLE 1F in EXAMPLE 27H.

Example 465E

N-({5-chloro-6-[(4-fluorotetrahydro-2H-pyran-4-yl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)-2-(1H-indazol-4-yloxy)benzamide This example was prepared by substituting EXAMPLE 465D for EXAMPLE 435E in EXAMPLE 435F, except here the final compound was purified by preparative HPLC using a C18 column, 250×50 mm, 10, and eluting with a gradient of 20-100% $CH_3CN$ vs. 0.1% trifluoroacetic acid in water, followed by column chromatography eluting with 98/2 dichloromethane/methanol. $^1$H NMR (400 MHz, dimethylsulfoxide-$d_6$) δ 13.13 (s, 1H), 8.28 (d, 1H), 7.90 (d, 1H), 7.83 (s, 1H), 7.58 (d, 1H), 7.39 (d, 2H), 7.17 (d, 2H), 7.08 (m, 2H), 6.82 (dd, 1H), 6.57 (d, 1H), 6.14 (d, 1H), 4.52 (d, 2H), 4.15 (s, 2H), 3.80 (m, 2H), 3.60 (m, 2H), 3.20 (v br m, 4H), 2.98 (v br s, 2H), 2.35 (v br m, 4H), 2.18 (s, 2H), 1.87 (m, 4H), 1.20 (s, 6H).

Example 466

4-(4-{[2-(4-chlorophenyl)-4,4-dimethylcyclohex-1-en-1-yl]methyl}piperazin-1-yl)-N-{[5-cyano-6-(2-tetrahydro-2H-pyran-4-ylethoxy)pyridin-3-yl]sulfonyl}-2-(1H-indazol-4-yloxy)benzamide

Example 466A 5-bromo-6-(2-(tetrahydro-2H-pyran-4-yl)ethoxy)pyridine-3-sulfonamide This example was prepared by substituting 2-(tetrahydro-2H-pyran-4-yl)ethanol for (tetrahydro-2H-pyran-4-yl)methanol in EXAMPLE 329B.

Example 466B 5-cyano-6-(2-(tetrahydro-2H-pyran-4-yl)ethoxy)pyridine-3-sulfonamide This example was prepared by substituting EXAMPLE 466A for EXAMPLE 329A in EXAMPLE 333A.

Example 466C 4-(4-{[2-(4-chlorophenyl)-4,4-dimethylcyclohex-1-en-1-yl]methyl}piperazin-1-yl)-N-{[5-cyano-6-(2-tetrahydro-2H-pyran-4-ylethoxy)pyridin-3-yl]sulfonyl}-2-(1H-indazol-4-yloxy)benzamide This example was prepared by substituting EXAMPLE 466B for EXAMPLE 1F and EXAMPLE 400E for EXAMPLE 26C in EXAMPLE 177C. $^1$H NMR (500 MHz, dimethylsulfoxide-$d_6$) δ 13.04 (s, 1H), 8.48 (d, 1H), 8.13 (s, 1H), 7.75 (s, 1H), 7.62 (d, 1H), 7.37 (d, 2H), 7.01-7.08 (m, 4H), 6.76 (dd, 1H), 6.51 (d, 1H), 6.08 (d, 1H), 4.47 (t, 2H), 3.81-3.85 (m, 2H), 3.71-3.80 (m, 1H), 2.18 (m, 2H), 1.99 (m, 2H), 1.62-1.72 (m, 5H), 1.42 (t, 2H), 1.23 (m, 2H), 0.94 (s, 6H).

Example 467

4-(4-{[2-(4-chlorophenyl)-4,4-dimethylcyclohex-1-en-1-yl]methyl}piperazin-1-yl)-2-(1H-indol-5-yloxy)-N-[(4-{[(1R,5S)-8-methyl-8-azabicyclo[3.2.1]oct-3-yl]amino}-3-nitrophenyl)sulfonyl]benzamide

Example 467A 4-(((1R,3R,5S)-8-methyl-8-azabicyclo[3.2.1]octan-3-ylamino)-3-nitrobenzenesulfonamide This EXAMPLE was prepared by substituting (1R,3R,5S)-8-methyl-8-azabicyclo[3.2.1]octan-3-amine for 1-(2-methoxy-ethyl)-piperidin-4-ylamine in EXAMPLE 189A.

Example 467B 4-(4-{[2-(4-chlorophenyl)-4,4-dimethylcyclohex-1-en-1-yl]methyl}piperazin-1-yl)-2-(1H-indol-5-yloxy)-N-[(4-{[(1R,5S)-8-methyl-8-azabicyclo[3.2.1]oct-3-yl]amino}-3-nitrophenyl)sulfonyl]benzamide This EXAMPLE was prepared by substituting EXAMPLE 26C for EXAMPLE 1E and EXAMPLE 467A for EXAMPLE 1F in EXAMPLE 1G. $^1$H NMR (500 MHz, dimethylsulfoxide-$d_6$) δ 11.47 (br s, 1H), 11.17 (s, 1H), 9.43 (br s, 1H), 8.69 (d, 1H), 8.62 (d, 1H), 7.90 (dd, 1H), 7.52 (d, 1H), 7.40 (m, 3H), 7.15 (d, 1H), 7.06 (m, 3H), 6.85 (dd, 1H), 6.68 (m, 1H), 6.39 (t, 1H), 6.19 (br s, 1H), 4.01 (m, 1H), 3.91 (m, 2H), 3.58 (m, 3H), 3.01 (m, 3H), 2.73 (m, 5H), 2.32 (m, 6H), 2.16 (m, 6H), 2.0 (m, 2H), 1.45 (m, 2H), 0.94 (s, 6H).

Example 468

N-({3-nitro-4-[(tetrahydro-2H-pyran-4-ylmethyl)
amino]phenyl}sulfonyl)-2-phenoxy-4-(4-{(3-phenyl-
propanoyl)[(1S,2S,3S,5R)-2,6,6-trimethylbicyclo
[3.1.1]hept-3-yl]amino}piperidin-1-yl)benzamide

Example 468A methyl 2-phenoxy-4-(1,4-dioxa-8-azaspiro[4.5]de-
can-8-yl)benzoate 1,4-dioxa-8-azaspiro[4.5]decane (1.18 g), methyl 4-fluoro-2-phenoxybenzoate (1.85 g), and $K_2CO_3$ (1.14 g) was stirred at 125° C. in dimethylsulfoxide (25 mL) for 24 hours. The mixture was cooled, poured into 300 mL water, extracted three times with ether, and the ether extracts were combined, rinsed three times with water, and brine, and concentrated. The residue was chromatographed on silica gel using 10-30% ethyl acetate in hexanes as eluent to give the title compound.

Example 468B methyl 4-(4-oxopiperidin-1-yl)-2-phenoxybenzoate

EXAMPLE 468A (23.7 g) was heated to 80° C. in a mixture of acetic acid (30 mL), tetrahydrofuran (40 mL) and water (30 mL) for 24 hours. The mixture was cooled and concentrated. The crude product was chromatographed on silica gel using 25% ethyl acetate in hexanes as the eluent to give the title compound.

Example 468C methyl 2-phenoxy-4-(4-((1S,2S,3S,5R)-2,6,6-trim-
ethylbicyclo[3.1.1]heptan-3-ylamino)piperidin-1-yl)
benzoate EXAMPLE 468B (0.99 g) and (1S,2S,3S,5R)-2,6,6-trimethylbicyclo[3.1.1]heptan-3-amine (0.51 mL) were refluxed in 200 mL methanol under a Dean-Stark trap for 24 hours. The solvent was boiled off to a volume of 75 mL, and the mixture was cooled to room temperature. $NaBH_4$ (0.115 g) was added and the mixture was stirred for 30 minutes. The reaction was quenched with 10 mL water, partially concentrated, and chromatographed on silica gel using 1% triethylamine in ethyl acetate as eluent to give the title compound.

Example 468D methyl 2-phenoxy-4-(4-(3-phenyl-N-((1S,2S,3S,5R)-
2,6,6-trimethylbicyclo[3.1.1]heptan-3-yl)propana-
mido)piperidin-1-yl)benzoate EXAMPLE 468C (320 mg), 3-phenylpropanoyl chloride (0.113 mL), and triethylamine (0.116 mL) were stirred in dichloromethane (15 mL) for 24 hours. The reaction mixture was partially concentrated and the residue was chromatographed on silica gel using 20% ethyl acetate in hexanes as eluent to give the title compound.

Example 468E 2-phenoxy-4-(4-(3-phenyl-N-((1S,2S,3S,5R)-2,6,6-
trimethylbicyclo[3.1.1]heptan-3-yl)propanamido)
piperidin-1-yl)benzoic acid This EXAMPLE was prepared by substituting EXAMPLE 468D for EXAMPLE 1D in EXAMPLE 1E.

Example 468F

N-({3-nitro-4-[(tetrahydro-2H-pyran-4-ylmethyl)
amino]phenyl}sulfonyl)-2-phenoxy-4-(4-{(3-phenyl-
propanoyl)[(1S,2S,3S,5R)-2,6,6-trimethylbicyclo
[3.1.1]hept-3-yl]amino}piperidin-1-yl)benzamide This EXAMPLE was prepared by substituting EXAMPLE 468E for EXAMPLE 1E in EXAMPLE 1G. $^1$H NMR (300 MHz, dimethylsulfoxide-$d_6$) δ 8.32 (m, 2H), 7.64 (m, 2H), 7.11-7.29 (m, 6H), 6.95 (dd, 1H), 6.89 (dd, 1H), 6.70 (m, 3H), 6.32 (m, 1H), 3.85 (m, 3H), 3.70 (m, 3H), 2.91 (m, 6H), 2.65-2.80 (m, 6H), 1.91 (s, 6H), 1.61 (m, 4H), 1.16-1.36 (m, 4H), 1.11 (m, 6H), 0.95 (m, 4H), 0.87 (d, 2H).

Example 469

N-({4-[(3-morpholin-4-ylpropyl)amino]-3-
nitrophenyl}sulfonyl)-2-phenoxy-4-(4-{(3-phenyl-
propanoyl)[(1S,2S,3S,5R)-2,6,6-trimethylbicyclo
[3.1.1]hept-3-yl]amino}piperidin-1-yl)benzamide This EXAMPLE was prepared by substituting EXAMPLE 468E for EXAMPLE 1E and EXAMPLE 7A for EXAMPLE 1F in EXAMPLE 1G. $^1$H NMR (300 MHz, dimethylsulfoxide-$d_6$) δ 8.72 (m, 1H), 8.44 (d, 1H), 7.73 (dd, 1H), 7.54 (m, 1H), 7.12-7.28 (m, 6H), 7.05 (dd, 1H), 6.95 (dd, 1H), 6.82 (d, 1H), 6.74 (m, 2H), 6.34 (m, 1H), 3.77 (m, 2H), 3.63 (m, 4H), 3.10 (m, 4H), 3.05 (m, 4H), 2.78 (m, 6H), 1.75-2.10 (m, 8H), 1.55 (m, 2H), 1.40 (m, 2H), 1.19 (m, 6H), 1.01 (m, 2H), 0.95 (m, 2H), 0.88 (d, 2H).

Example 470

N-({3-nitro-4-[(tetrahydro-2H-pyran-4-ylmethyl)
amino]phenyl}sulfonyl)-2-phenoxy-4-(4-{(3-phenyl-
propyl)[(1S,2S,3S,5R)-2,6,6-trimethylbicyclo[3.1.1]
hept-3-yl]amino}piperidin-1-yl)benzamide

Example 470A methyl 2-phenoxy-4-(4-((3-phenylpropyl)((1S,2S,
3S,5R)-2,6,6-trimethylbicyclo[3.1.1]heptan-3-yl)
amino)piperidin-1-yl)benzoate EXAMPLE 468C 320 mg), 3-phenylpropanal (111 mg), and $NaBH(OAc)_3$ (205 mg) were stirred in dichloromethane (15 mL) for 24 hours. The reaction mixture was chromatographed on silica gel using 20% ethyl acetate in hexanes as eluent to give the title compound.

Example 470B 2-phenoxy-4-(4-((3-phenylpropyl)((1S,2S,3S,5R)-2,
6,6-trimethylbicyclo[3.1.1]heptan-3-yl)amino)piperi-
din-1-yl)benzoic acid This EXAMPLE was prepared by substituting EXAMPLE 470A for EXAMPLE 1D in EXAMPLE 1E.

Example 470C

N-({3-nitro-4-[(tetrahydro-2H-pyran-4-ylmethyl) amino]phenyl}sulfonyl)-2-phenoxy-4-(4-{(3-phenyl-propyl)[(1S,2S,3S,5R)-2,6,6-trimethylbicyclo[3.1.1] hept-3-yl]amino}piperidin-1-yl)benzamide This EXAMPLE was prepared by substituting EXAMPLE 470B for EXAMPLE 1E in EXAMPLE 1G. $^1$H NMR (300 MHz, dimethylsulfoxide-$d_6$) δ 8.57 (m, 1H), 8.47 (d, 1H), 7.50 (m, 1H), 7.32 (m, 1H), 7.12-7.31 (m, 7H), 6.99 (dd, 1H), 6.81 (m, 3H), 6.37 (d, 1H), 4.44 (t, 1H), 3.84 (m, 4H), 3.37 (m, 2H), 3.25 (m, 2H), 3.06 (m, 2H), 2.70 (m, 4H), 2.57 (m, 4H), 1.82 (m, 2H), 1.77 (m, 4H), 1.52-1.71 (m, 8H), 1.25 (m, 3H), 1.15 (s, 3H), 0.95 (d, 2H), 0.93 (s, 3H), 0.74 (d, 2H).

Example 471

N-({4-[(3-morpholin-4-ylpropyl)amino]-3-nitrophenyl}sulfonyl)-2-phenoxy-4-(4-{(3-phenyl-propyl)[(1S,2S,3S,5R)-2,6,6-trimethylbicyclo[3.1.1] hept-3-yl]amino}piperidin-1-yl)benzamide This EXAMPLE was prepared by substituting EXAMPLE 470B for EXAMPLE 1E and EXAMPLE 7A for EXAMPLE 1F in EXAMPLE 1G. $^1$H NMR (300 MHz, dimethylsulfoxide-$d_6$) δ 8.68 (m, 1H), 8.40 (d, 1H), 7.70 (dd, 1H), 7.55 (d, 1H), 7.11-7.29 (m, 7H), 7.01 (dd, 1H), 6.95 (dd, 1H), 6.76 (d, 2H), 6.34 (m, 1H), 3.75 (m, 2H), 3.61 (m, 4H), 3.43 (m, 4H), 3.05 (m, 6H), 2.75 (m, 2H), 2.60 (m, 2H), 2.41 (m, 4H), 2.15 (m, 1H), 1.82 (m, 4H), 1.69 (m, 2H), 1.51 (m, 1H), 1.18 (m, 8H), 0.96 (m, 1H), 0.94 (s, 3H).

Example 472

4-[4-(2-{[(1R,5S)-8-methyl-8-azabicyclo[3.2.1]oct-3-yl]amino}benzyl)piperazin-1-yl]-N-({4-[(3-morpholin-4-ylpropyl)amino]-3-nitrophenyl}sulfonyl)-2-phenoxybenzamide

Example 472A

Ethyl 4-fluoro-2-phenoxybenzoate (600 mg) and piperazine (596 mg) were dissolved in anhydrous dimethyl sulfoxide and heated at 130° C. overnight. The reaction mixture was cooled to room temperature and diluted with ethyl acetate. The organic phase was washed with water and brine, dried over anhydrous sodium sulfate, filtered, and concentrated to afford the title compound.

Example 472B

EXAMPLE 472A (400 mg), 1-(bromomethyl)-2-nitrobenzene (277 mg) and sodium carbonate (408 mg) were suspended in anhydrous N,N-dimethylformamide (20 mL). The reaction mixture was stirred at room temperature for 4 hours. The reaction mixture was diluted with ethyl acetate. The organic phase was washed with water and brine, dried over anhydrous sodium sulfate, filtered, and concentrated. Flash column purification with 10-40% ethyl acetate/hexane to afford the title compound.

Example 472C

A solution of EXAMPLE 472B (0.6 g) in methanol (20 ml) was added to Ra—Ni, solvent washed (0.480 g) in a 250 mL pressure bottle and stirred for 3 hours at 30 psi at room temperature. The mixture was filtered through a nylon membrane and concentrated to afford the product.

Example 472D

This EXAMPLE was prepared by substituting (1R,5S)-8-methyl-8-azabicyclo[3.2.1]octan-3-one for 4'-chlorobiphenyl-2-carboxaldehyde and EXAMPLE 472C for tert-butyl piperazine-1-carboxylate in EXAMPLE 1A.

Example 472E

This EXAMPLE was prepared by substituting EXAMPLE 472D for EXAMPLE 175D in EXAMPLE 175E.

Example 472F

4-[4-(2-{[(1R,5S)-8-methyl-8-azabicyclo[3.2.1]oct-3-yl]amino}benzyl)piperazin-1-yl]-N-({4-[(3-morpholin-4-ylpropyl)amino]-3-nitrophenyl}sulfonyl)-2-phenoxybenzamide This EXAMPLE was prepared by substituting EXAMPLE 472E for EXAMPLE 27G and EXAMPLE 7A for EXAMPLE 1F in EXAMPLE 27H. $^1$H NMR (400 MHz, dimethylsulfoxide-$d_6$) δ 11.66 (bs, 1H), 9.90 (bs, 1H), 9.56 (s, 1H), 8.69 (t, 1H), 8.50 (d, 1H), 7.81 (dd, 1H), 7.54 (d, 1H), 7.22 (m, 5H), 7.01 (m, 1H), 6.83 (m, 3H), 6.47 (s, 1H), 3.84 (m, 4H), 3.65 (d, 6H), 3.54 (m, 4H), 3.43 (m, 2H), 3.19 (m, 8H), 2.68 (d, 3H), 2.34 (m, 2H), 2.25 (m, 4H), 1.99 (m, 4H).

Example 473

4-[4-(2-{[(1R,5S)-8-methyl-8-azabicyclo[3.2.1]oct-3-yl]amino}benzyl)piperazin-1-yl]-N-({3-nitro-4-[(tetrahydro-2H-pyran-4-ylmethyl)amino] phenyl}sulfonyl)-2-phenoxybenzamide This EXAMPLE was prepared by substituting EXAMPLE 472E for EXAMPLE 27G in EXAMPLE 27H. $^1$H NMR (400 MHz, dimethylsulfoxide-$d_6$) δ 11.61 (bs, 1H), 9.38 (bs, 1H), 8.64 (s, 1H), 8.47 (d, 1H), 7.75 (dd, 1H), 7.55 (d, 1H), 7.23 (t, 3H), 7.15 (d, 2H), 6.98 (t, 1H), 6.82 (d, 3H), 6.47 (s, 2H), 3.85 (m, 6H), 3.31 (m, 12H), 2.68 (d, 3H), 2.06 (m, 9H), 1.62 (m, 2H), 1.29 (m, 2H).

Example 474

4-{4-[2-(3-azabicyclo[3.2.2]non-3-yl)benzyl]piperazin-1-yl}-N-({3-nitro-4-[(tetrahydro-2H-pyran-4-ylmethyl)amino]phenyl}sulfonyl)-2-phenoxybenzamide

Example 474A

2-Fluorobenzaldehyde (264 mg), (1S,5S)-3-azabicyclo [3.2.2]nonane (500 mg) and sodium carbonate (846 mg) were suspended in anhydrous dimethylsulfoxide (3 mL). The reaction mixture was heated at 135° C. overnight. The reaction mixture was cooled to room temperature and diluted with ethyl acetate. The organic phase was washed with water and brine, dried over anhydrous sodium sulfate, filtered, and concentrated. Flash column purification with 0-10% ethyl acetate/hexane provided the title compound.

Example 474B

This EXAMPLE was prepared by substituting EXAMPLE 474A for 4'-chlorobiphenyl-2-carboxaldehyde and EXAMPLE 113A for tert-butyl piperazine-1-carboxylate in EXAMPLE 1A.

Example 474C

This EXAMPLE was prepared by substituting EXAMPLE 474B for EXAMPLE 175D in EXAMPLE 175E.

Example 474D

4-{4-[2-(3-azabicyclo[3.2.2]non-3-yl)benzyl]piperazin-1-yl}-N-({3-nitro-4-[(tetrahydro-2H-pyran-4-ylmethyl)amino]phenyl}sulfonyl)-2-phenoxybenzamide This EXAMPLE was prepared by substituting EXAMPLE 474C for EXAMPLE 27G in EXAMPLE 27H. $^1$H NMR (400 MHz, dimethylsulfoxide-$d_6$) δ 11.74 (bs, 1H), 8.64 (t, 1H), 8.47 (d, 1H), 7.76 (dd, 1H), 7.54 (m, 2H), 7.43 (d, 2H), 7.23 (m, 3H), 7.15 (d, 1H), 6.98 (t, 1H), 6.83 (m, 3H), 6.53 (d, 1H), 4.45 (bs, 2H), 3.87 (m, 4H), 3.30 (m, 6H), 3.06 (m, 8H), 1.89 (m, 7H), 1.64 (m, 6H), 1.29 (m, 2H).

Example 475

4-{4-[2-(3-azabicyclo[3.2.2]non-3-yl)benzyl]piperazin-1-yl}-2-phenoxy-N-({4-[(tetrahydro-2H-pyran-4-ylmethyl)amino]-3-[(trifluoromethyl)sulfonyl]phenyl}sulfonyl)benzamide This EXAMPLE was prepared by substituting EXAMPLE 474C for EXAMPLE 27G and EXAMPLE 163A for EXAMPLE 1F in EXAMPLE 27H. $^1$H NMR (400 MHz, dimethylsulfoxide-$d_6$) δ 11.78 (bs, 1H), 8.11 (d, 1H), 7.86 (dd, 1H), 7.54 (d, 2H), 7.44 (d, 2H), 7.28 (m, 4H), 7.11 (d, 1H), 7.04 (m, 1H), 6.85 (m, 3H), 6.53 (d, 1H), 4.46 (m, 2H), 3.86 (m, 4H), 3.28 (m, 6H), 3.10 (m, 4H), 2.98 (d, 4H), 1.97 (s, 2H), 1.84 (m, 5H), 1.64 (m, 6H), 1.26 (m, 2H).

Example 476

4-{4-[2-(3-azabicyclo[3.2.2]non-3-yl)benzyl]piperazin-1-yl}-2-phenoxy-N-({4-[(tetrahydro-2H-pyran-4-ylmethyl)amino]phenyl}sulfonyl)benzamide This EXAMPLE was prepared by substituting EXAMPLE 474C for EXAMPLE 27G and EXAMPLE 2A for EXAMPLE 1F in EXAMPLE 27H. $^1$H NMR (400 MHz, dimethylsulfoxide-$d_6$) δ 11.19 (bs, 1H), 9.83 (bs, 1H), 7.52 (m, 6H), 7.33 (m, 3H), 7.12 (t, 1H), 6.93 (d, 2H), 6.83 (m, 1H), 6.56 (d, 2H), 6.47 (d, 1H), 4.47 (s, 2H), 3.85 (m, 4H), 3.26 (m, 2H), 3.11 (m, 4H), 2.96 (m, 6H), 1.97 (s, 2H), 1.81 (m, 6H), 1.64 (m, 7H), 1.22 (m, 2H).

Example 477

4-{4-[2-(3-azabicyclo[3.2.2]non-3-yl)benzyl]piperazin-1-yl}-N-({4-[(3-morpholin-4-ylpropyl)amino]-3-nitrophenyl}sulfonyl)-2-phenoxybenzamide This EXAMPLE was prepared by substituting EXAMPLE 474C for EXAMPLE 27G and EXAMPLE 7A for EXAMPLE 1F in EXAMPLE 27H. $^1$H NMR (400 MHz, dimethylsulfoxide-$d_6$) δ 11.77 (bs, 1H), 10.04 (bs, 1H), 8.69 (t, 1H), 8.50 (d, 1H), 7.81 (dd, 1H), 7.55 (d, 2H), 7.43 (d, 2H), 7.24 (m, 3H), 7.15 (d, 1H), 7.01 (t, 1H), 6.84 (m, 3H), 6.52 (d, 1H), 4.44 (s, 2H), 3.97 (s, 2H), 3.54 (m, 6H), 3.39 (m, 4H), 3.19 (m, 8H), 2.97 (d, 4H), 1.99 (m, 4H), 1.83 (m, 4H), 1.64 (m, 4H).

Example 478

4-(4-{2-[(4R,7S)-2,3,3a,4,7,7a-hexahydro-1H-4,7-methanoinden-5-yl]benzyl}piperazin-1-yl)-N-({3-nitro-4-[(tetrahydro-2H-pyran-4-ylmethyl)amino]phenyl}sulfonyl)-2-phenoxybenzamide

Example 478A 4-(4-Methoxycarbonyl-3-phenoxy-phenyl)-piperazine-1-carboxylic acid tert-butyl ester This EXAMPLE was prepared by substituting piperazine-1-carboxylic acid tert-butyl ester for EXAMPLE 1B in EXAMPLE 1D.

Example 478B 4-(4-Carboxy-3-phenoxy-phenyl)-piperazine-1-carboxylic acid tert-butyl ester This EXAMPLE was prepared by substituting EXAMPLE 478A for EXAMPLE 1D in EXAMPLE 1E.

Example 478C 4-(4-{3-Nitro-4-[(tetrahydro-pyran-4-ylmethyl)-amino]-benzenesulfonylaminocarbonyl}-3-phenoxy-phenyl)-piperazine-1-carboxylic acid tert-butyl ester This EXAMPLE was prepared by substituting EXAMPLE 478B for EXAMPLE 1E in EXAMPLE 1G.

Example 478D

3-Nitro-N-(2-phenoxy-4-piperazin-1-yl-benzoyl)-4-[(tetrahydro-pyran-4-ylmethyl)-amino]-benzenesulfonamide This EXAMPLE was prepared by substituting EXAMPLE 478C for EXAMPLE 1A in EXAMPLE LB to isolate the title compound as the mono trifluoroacetic acid salt.

Example 478E

Trifluoromethanesulfonic acid (4R,7S)-(2,3,3a,4,7,7a-hexahydro-1H-4,7-methano-inden-5-yl) ester (4R,7R)-octahydro-4,7-methano-inden-5-one (2.00 g) was dissolved in tetrahydrofuran (25 mL) and cooled to −78° C. using an isopropyl alcohol/dry ice bath. Sodium bis(trimethylsilyl)-amide (1M in tetrahydrofuran, 14.65 mL) was added slowly. The solution was allowed to warm to room temperature, stirred for one hour, cooled to −78° C. using an isopropyl alcohol/dry ice bath, and N-phenyltrifluoromethanesulfonimide (5.23 g) was added. The solution was allowed to warm to room temperature and stir for 16 hours.

Hexane was added and the solution was stirred at room temperature for one hour, filtered, and the solvent removed under vacuum.

Example 478F (4R,7S)-2-(2,3,3a,4,7,7a-Hexahydro-1H-4,7-methano-inden-5-yl)-benzaldehyde EXAMPLE 478E (941 mg), 2-formylphenylboronic acid (600 mg), and potassium phosphate tribasic (1416 mg) were added to tetrahydrofuran (20 mL). The solution was degasses and flushed with nitrogen three times. Tetrakis(triphenylphosphine)palladium(O) (244 mg) was added and the solution was heated at 60° C. for 16 hours. The solution was cooled, added to water, and extracted with 50% ethyl acetate (hexanes). The extract was washed with brine, dried on anhydrous sodium sulfate, concentrated and purified by flash column chromatography on silica gel using 10% ethyl acetate (hexanes).

Example 478G 4-(4-{2-[(4R,7S)-2,3,3a,4,7,7a-hexahydro-1H-4,7-methanoinden-5-yl]benzyl}piperazin-1-yl)-N-({3-nitro-4-[(tetrahydro-2H-pyran-4-ylmethyl)amino]phenyl}sulfonyl)-2-phenoxybenzamide EXAMPLE 478D (200 mg), EXAMPLE 478F (74 mg), and sodium cyanoborohydride resin (2.15 mmol/g, 144 mg) were added to tetrahydrofuran (3 mL) and acetic acid (0.7 mL) and stirred at room temperature for 16 hours. The solution was concentrated on vacuum and purified by flash column chromatography on silica gel using 5% methanol (dichloromethane) to provide the title compound as the mono acetic acid salt. $^1$H NMR (300 MHz, dimethylsulfoxide-$d_6$) δ 11.94 (bs, 1H), 8.64 (t, 1H), 8.48 (d, 1H), 7.76 (dd, 1H), 7.51 (d, 1H), 7.40 (m, 1H), 7.27-7.18 (m, 5H), 7.16 (d, 1H), 6.99 (tt, 1H), 6.83 (dt, 2H), 6.78 (dd, 1H), 6.41 (d, 1H), 6.23 (d, 1H), 3.87 (dd, 2H), 3.50 (m, 2H), 3.34 (t, 2H), 3.21 (bs, 4H), 2.73 (bs, 1H), 2.63 (bs, 1H), 2.46 (m, 4H), 2.11 (m, 2H), 1.95-1.75 (m, 4H), 1.91 (s, 3H), 1.66-1.52 (m, 6H), 1.28 (m, 2H), 1.02 (m, 2H), 0.85 (m, 1H).

Example 479

4-[4-(2-{5-[(1R,5S)-8-azabicyclo[3.2.1]oct-8-ylmethyl]thien-2-yl}benzyl)piperazin-1-yl]-N-({3-nitro-4-[(tetrahydro-2H-pyran-4-ylmethyl)amino]phenyl}sulfonyl)-2-phenoxybenzamide

Example 479A tert-butyl 4-(4-(methoxycarbonyl)-3-phenoxyphenyl)piperazine-1-carboxylate This EXAMPLE was prepared by substituting tert-butyl piperazine-1-carboxylate for EXAMPLE 1B in EXAMPLE 1D.

Example 479B 4-(4-(tert-butoxycarbonyl)piperazin-1-yl)-2-phenoxybenzoic acid This EXAMPLE was prepared by substituting EXAMPLE 479A for EXAMPLE 1D in EXAMPLE 1E.

Example 479C tert-butyl 4-(4-(3-nitro-4-((tetrahydro-2H-pyran-4-yl)methylamino)phenylsulfonylcarbamoyl)-3-phenoxyphenyl)piperazine-1-carboxylate This EXAMPLE was prepared by substituting EXAMPLE 479B for EXAMPLE 1E in EXAMPLE 1G.

Example 479D

N-(3-nitro-4-((tetrahydro-2H-pyran-4-yl)methylamino)phenylsulfonyl)-2-phenoxy-4-(piperazin-1-yl)benzamide This EXAMPLE was prepared by substituting EXAMPLE 479C for EXAMPLE 1A in EXAMPLE 1B.

Example 479E 2-((4-(4-(3-nitro-4-((tetrahydro-2H-pyran-4-yl)methylamino)phenylsulfonylcarbamoyl)-3-phenoxyphenyl)piperazin-1-yl)methyl)phenylboronic acid EXAMPLE 479D (213 mg), 2-formylphenylboronic acid (54 mg), and sodium cyanoborohydride resin (2.38 mmol/g, 252 mg) were added to tetrahydrofuran (3.5 mL) and acetic acid (1.1 mL), and the solution was stirred at room temperature for 16 hours. The solution was purified by flash column chromatography on silica gel with 1% acetic acid and 10% methanol in dichloromethane.

Example 479F 8-((5-bromothiophen-2-yl)methyl)-8-azabicyclo[3.2.1]octane hydrochloride This EXAMPLE was prepared by substituting 5-bromothiophene-2-carbaldehyde for 4'-chlorobiphenyl-2-carboxaldehyde and 8-azabicyclo[3.2.1]octane hydrochloride for tert-butyl piperazine-1-carboxylate in EXAMPLE 1A.

Example 479G 4-(4-(2-(5-(8-azabicyclo[3.2.1]octan-8-ylmethyl)thiophen-2-yl)benzyl)piperazin-1-yl)-N-(3-nitro-4-((tetrahydro-2H-pyran-4-yl)methylamino)phenylsulfonyl)-2-phenoxybenzamide EXAMPLE 479E (80 mg), EXAMPLE 479F (42.5 mg), bis(triphenylphosphine)palladium(II) dichloride (7.7 mg), and lithium hydroxide (10.5 mg) were combined in a mixture of dimethoxyethane (1.6 mL), methanol (0.5 mL) and water (0.7 mL) in a microwave vial. The reaction mixture was heated in a CEM Discover microwave reactor at 150° C. for 15 minutes. The crude material was purified by flash chromatography eluting with a gradient of 1% methanol/dichloromethane to 5% methanol/dichloromethane. $^1$H NMR (500 MHz, dimethylsulfoxide-$d_6$) δ 8.33 (m, 2H), 7.64 (m, 2H), 7.44 (m, 1H), 7.39 (m, 1H), 7.32 (m, 2H), 7.12 (m, 3H), 6.90 (m, 2H), 6.85 (t, 1H), 6.68 (m, 3H), 6.30 (d, 1H), 3.83 (dd, 2H), 3.65 (s, 2H), 3.51 (s, 2H), 3.17 (m, 4H), 3.08 (m, 4H), 2.45 (m, 6H), 1.92 (m, 2H), 1.62 (m, 4H), 1.54 (m, 3H), 1.28 (m, 6H).

Example 480

4-[4-(2-{5-[(1R,5S)-8-azabicyclo[3.2.1]oct-8-ylmethyl]thien-2-yl}benzylidene)piperidin-1-yl]-N-({3-nitro-4-[(tetrahydro-2H-pyran-4-ylmethyl)amino]phenyl}sulfonyl)-2-phenoxybenzamide

Example 480A methyl 2-phenoxy-4-(1,4-dioxa-8-azaspiro[4.5]decan-8-yl)benzoate Methyl 4-fluoro-2-phenoxybenzoate (2 g) and 1,4-dioxa-8-azaspiro[4.5]decane (1.279 g) were combined in dimethylsulfoxideO (12 mL) in a 250 mL round-bottom flask. Sodium carbonate (1.291 g) was added. The reaction flask was sealed and heated to 130° C. overnight. The reaction mixture was diluted with ethyl acetate, washed thoroughly with water and with brine, and dried over MgSO$_4$, filtered and concentrated to obtain the desired product.

Example 480B methyl 4-(4-oxopiperidin-1-yl)-2-phenoxybenzoate

EXAMPLE 480A was taken up in acetic acid (30%, 20 mL) and tetrahydrofuran (10 mL). The reaction mixture was heated to 75° C. overnight. The volume was reduced under vacuum and the residue was neutralized with sodium hydroxide solution, and extracted with ethyl acetate. The extracts were washed with water and with brine, dried over MgSO$_4$, filtered and concentrated under vacuum to obtain the desired product.

Example 480C methyl 4-(4-(2-bromobenzylidene)piperidin-1-yl)-2-phenoxybenzoate Dimethylsulfoxide (22.88 mL) with sodium hydride (0.332 g) was heated to 70 OC for 1 hour, then cooled to room temperature and (2-bromobenzyl)triphenylphosphonium bromide (3.40 g) was added in several portions, and stirred at room temperature for 1 hour. A solution of methyl 4-(4-oxopiperidin-1-yl)-2-phenoxybenzoate (1.8 g) in dimethylsulfoxide (5.20 mL) was then added and the reaction was heated to 70° C. over the weekend. The reaction was acidified with 1M aqueous HCl solution and extracted with ether. The combined extracts were washed thoroughly with water and brine, dried over MgSO$_4$, filtered and concentrated under vacuum. The residue was purified by flash chromatography eluting with 0-20% ethyl acetate in hexanes.

Example 480D methyl 2-phenoxy-4-(4-(2-(4,4,5,5-tetramethyl-1,3,2-dioxaborolan-2-yl)benzylidene)piperidin-1-yl)benzoate EXAMPLE 480C (259 mg), bis(pinacolato)diboron (206 mg), [1,1'-bis(diphenylphosphino)ferrocene]dichloropalladium(II) dichloromethane (22 mg), and potassium acetate (159 mg) were combined in dimethyl sulfoxide (2.7 mL). The reaction was heated to 90° C. for 36 hours. The reaction mixture was diluted with ethyl acetate, washed thoroughly with water and with brine, and dried over MgSO$_4$, filtered and concentrated under vacuum. The crude solid was washed with hexanes and with hexanes/ether (2:1) to obtain the desired product.

Example 480E 4-(4-(2-(5-(8-azabicyclo[3.2.1]octan-8-ylmethyl)thiophen-2-yl)benzylidene)piperidin-1-yl)-2-phenoxybenzoic acid This EXAMPLE was prepared by substituting EXAMPLE 480D for EXAMPLE 479E in EXAMPLE 479G.

Example 480F 4-(4-(2-(5-(8-azabicyclo[3.2.1]octan-8-ylmethyl)thiophen-2-yl)benzylidene)piperidin-1-yl)-N-(3-nitro-4-((tetrahydro-2H-pyran-4-yl)methylamino)phenylsulfonyl)-2-phenoxybenzamide This EXAMPLE was prepared by substituting EXAMPLE 480E for EXAMPLE 1E in EXAMPLE 1G. $^1$H NMR (500 MHz, dimethylsulfoxide-d$_6$) δ 11.54 (s, 1H), 9.36 (br s, 1H), 8.48 (d, 1H), 7.76 (dd, 1H), 7.53 (m, 2H), 7.34 (m, 3H), 7.25 (m, 4H), 7.16 (d, 1H), 7.00 (t, 1H), 6.84 (d, 2H), 6.81 (dd, 1H), 6.44 (d, 1H), 6.37 (br s, 1H), 4.36 (d, 2H), 3.85 (m, 3H), 3.44 (m, 2H), 3.28 (m, 6H), 2.36 (m, 3H), 2.23 (m, 4H), 1.90 (m, 3H), 1.81 (m, 2H), 1.62 (m, 5H), 1.47 (m, 1H), 1.29 (m, 2H).

Example 481

4-[4-(3-{5-[(1R,5S)-8-azabicyclo[3.2.1]oct-8-ylmethyl]thien-2-yl}benzyl)piperazin-1-yl]-N-({3-nitro-4-[(tetrahydro-2H-pyran-4-ylmethyl)amino]phenyl}sulfonyl)-2-phenoxybenzamide

Example 481A 3-((4-(4-(3-nitro-4-((tetrahydro-2H-pyran-4-yl)methylamino)phenylsulfonylcarbamoyl)-3-phenoxyphenyl)piperazin-1-yl)methyl)phenylboronic acid This EXAMPLE was prepared by substituting 3-formylphenylboronic acid for 2-formylphenylboronic acid in EXAMPLE 479E.

Example 481B 4-(4-(3-(5-(8-azabicyclo[3.2.1]octan-8-ylmethyl)thiophen-2-yl)benzyl)piperazin-1-yl)-N-(3-nitro-4-((tetrahydro-2H-pyran-4-yl)methylamino)phenylsulfonyl)-2-phenoxybenzamide This EXAMPLE was prepared by substituting EXAMPLE 481A for EXAMPLE 479E in EXAMPLE 479G. $^1$H NMR (500 MHz, dimethylsulfoxide-d$_6$) δ 11.76 (br s, 1H), 9.55 (br s, 1H), 8.55 (t, 1H), 8.46 (d, 1H), 7.75 (m, 2H), 7.54 (m, 2H), 7.40 (m, 1H), 7.20 (m, 4H), 6.97 (m, 1H), 6.86 (m, 1H), 6.82 (m, 3H), 6.55 (m, 1H), 4.41 (d, 2H), 3.88 (m, 6H), 3.43 (m, 3H), 3.30 (m, 6H), 3.06 (m, 6H), 1.90 (m, 4H), 1.65 (m, 5H), 1.30 (m, 3H).

What is claimed is:

1. A compound, or a therapeutically acceptable salt thereof, wherein the compound is selected from the group consisting of:

2-(benzyloxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(2-phenylethoxy)benzamide;

2-benzyl-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

2-benzyl-4-(4-((4'-chloro-1,1'-biphenyl-2-yl)methyl)piperazin-1-yl)-N-((4-((tetrahydro-2H-pyran-4-ylmethyl)amino)phenyl)sulfonyl)benzamide;

2-benzyl-4-(4-((4'-chloro-1,1'-biphenyl-2-yl)methyl)piperazin-1-yl)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(2-phenylethyl)benzamide;

2-(benzylamino)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-methoxy-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(1H-indol-6-yloxy)benzamide;

N-[(3-{[chloro(difluoro)methyl]sulfonyl}-4-{[3-(dimethylamino)propyl]amino}phenyl)sulfonyl]-4-(4-{[2-(4-chlorophenyl)-4,4-dimethylcyclohex-1-en-1-yl]methyl}piperazin-1-yl)-2-(1H-indol-4-yloxy)benzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-(phenoxymethyl)benzamide;

4-(4-((4'-chloro-1,1'-biphenyl-2-yl)methyl)piperazin-1-yl)-N-((4-((3-morpholin-4-ylpropyl)amino)phenyl)sulfonyl)-2-phenoxybenzamide;

5-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-1,1'-biphenyl-2-carboxamide;

5-(4-((4'-chloro-1,1'-biphenyl-2-yl)methyl)piperazin-1-yl)-N-((4-((3-(dimethylamino)propyl)amino)-3-nitrophenyl)sulfonyl)-1,1'-biphenyl-2-carboxamide;

4-(4-((4'-chloro-4-(2-(dimethylamino)ethoxy)-1,1'-biphenyl-2-yl)methyl)piperazin-1-yl)-N-((4-((1-methylpiperidin-4-yl)amino)-3-nitrophenyl)sulfonyl)-2-phenoxybenzamide;

4-{4-[1-(4'-chloro-1,1'-biphenyl-2-yl)ethyl]piperazin-1-yl}-2-(1H-indol-4-yloxy)-N-({4-[(1-methylpiperidin-4-yl)amino]-3-nitrophenyl}sulfonyl)benzamide;

4-{4-[1-(4'-chloro-1,1'-biphenyl-2-yl)ethyl]piperazin-1-yl}-2-(1H-indol-4-yloxy)-N-({4-[(4-methylpiperazin-1-yl)amino]-3-nitrophenyl}sulfonyl)benzamide;

4-{4-[1-(4'-chloro-1,14'-biphenyl-2-yl)ethyl]piperazin-1-yl}-2-(1H-indol-4-yloxy)-N-({4-[(3-morpholin-4-ylpropyl)amino]-3-nitrophenyl}sulfonyl)benzamide;

4-{4-[(1R)-1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide;

4-{4-[(1S)-1-(4'-chloro-1,1'-biphenyl-2-yl)ethyl]piperazin-1-yl}-2-(1H-indol-4-yloxy)-N-({3-nitro-4-[(tetrahydro-2H-pyran-4-ylmethyl)amino]phenyl}sulfonyl)benzamide; and 4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(pyridin-3-ylamino)benzamide.

2. A pharmaceutical composition comprising an excipient and a therapeutically effective amount of the compound or therapeutically acceptable salt of claim 1.

* * * * *

UNITED STATES PATENT AND TRADEMARK OFFICE
CERTIFICATE OF CORRECTION

Page 1 of 2

PATENT NO. : 9,315,488 B2
APPLICATION NO. : 14/726337
DATED : April 19, 2016
INVENTOR(S) : Hong Ding et al.

It is certified that error appears in the above-identified patent and that said Letters Patent is hereby corrected as shown below:

In the Specification

Column 2, Line 35, "NHSO$_7$NHR$^1$" should read -- NHSO$_2$NHR$^1$ --; and Line 51, "S(O)R$^1$," should read -- S(O)R$^7$ --.

Column 3, Line 9, "CH/moieties" should read -- CH$_2$ moieties --.

Column 8, Line 9, "R$^2$ is" should read -- R$^{20}$ is --.

Column 10, Line 54, "N(R$^1$)$_2$," should read -- N(R$^{17}$)$_2$, --.

Column 11, Line 45, "N(R$^1$)$_2$," should read -- N(R$^{12}$)$_2$, --; and Line 46, "C(O)N(R$^2$)$_2$" should read -- C(O)N(R$^{12}$)$_2$ --.

Column 12, Line 8, "R$^2$" should read -- R$^{21}$ --; and Line 14, "R$^3$," should read -- R$^{23}$ --.

Column 17, Line 52, "NHC(O)NHR$^{15}$" should read -- NHC(O)NHR$^{55}$ --.

Column 18, Line 36, "N(R$^1$)$_2$," should read -- N(R$^{17}$)$_2$, --.

Column 19, Line 28, "C(O)NHR$^2$," should read -- C(O)NHR$^{12}$ --.

Column 58, Line 52, "R$^1$," should read -- R$^{12}$, --.

Column 59, Line 17, "OR$^{11}$," should read -- OR$^{22}$, --.

Column 61, Line 20, "NH$_1$" should read -- NH$_2$ --.

Column 110, Line 63, "OR$^1$," should read -- OR$^{12}$, --.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,315,488 B2

Column 122, Line 53, "$R^1$ is" should read -- $R^{11}$ is --.

In the Claims

Claim 1:
Column 428, Line 47, "-chloro-1,14'-biphenyl-2-yl)" should read -- -chloro-1,1'-biphenyl-2-yl) --.

SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Probe Peptide
<220> FEATURE:
<221> NAME/KEY: MOD_RES
<222> LOCATION: 1
<223> OTHER INFORMATION: Gly is modified with acetyl
<220> FEATURE:
<221> NAME/KEY: MOD_RES
<222> LOCATION: 13
<223> OTHER INFORMATION: Lys is modified with 6-FAM
<220> FEATURE:
<221> NAME/KEY: MOD_RES
<222> LOCATION: 16
<223> OTHER INFORMATION: Arg is modified with NH2

<400> SEQUENCE: 1

Gly Gln Val Gly Arg Gln Leu Ala Ile Ile Gly Asp Lys Ile Asn Arg
1               5                   10                  15